(12) United States Patent
Kimura et al.

(10) Patent No.: US 7,091,352 B2
(45) Date of Patent: Aug. 15, 2006

(54) COMPOUNDS SUBSTITUTED WITH BICYCLIC AMINO GROUPS

(75) Inventors: Tomio Kimura, Tokyo (JP); Akira Nakao, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 83 days.

(21) Appl. No.: 10/625,024

(22) Filed: Jul. 22, 2003

(65) Prior Publication Data

US 2004/0147525 A1    Jul. 29, 2004

Related U.S. Application Data

(63) Continuation-in-part of application No. PCT/JP02/00402, filed on Jan. 22, 2002.

(30) Foreign Application Priority Data

Jan. 22, 2001  (JP)  ............................. 2001-012881
Jan. 22, 2001  (JP)  ............................. 2001-013590

(51) Int. Cl.
  *C07D 221/02*  (2006.01)
(52) U.S. Cl. ............ 546/112; 546/94; 546/275.4; 546/121; 546/138; 546/183; 540/593; 544/333
(58) Field of Classification Search ............... 546/112, 546/138, 121, 94, 183, 275.4; 544/333; 540/593; 514/299, 300, 306, 294, 339, 214.01, 256
See application file for complete search history.

(56) References Cited

U.S. PATENT DOCUMENTS

| 4,213,983 A | 7/1980 | Hadley et al. |
| 4,559,346 A | 12/1985 | King |
| 2004/0054173 A1 | 3/2004 | Kimura et al. |

FOREIGN PATENT DOCUMENTS

| EP | 1 070 711 A2 | 1/2001 |
| EP | 1 243 589 A1 | 9/2002 |
| JP | 7-206863 | 8/1995 |
| WO | WO 93/14081 A1 | 7/1993 |
| WO | WO 96/21452 A1 | 7/1996 |
| WO | WO 97/23479 A1 | 7/1997 |
| WO | WO 98/52937 A1 | 11/1998 |
| WO | WO 00/00490 A2 | 1/2000 |
| WO | WO 00/31063 A1 | 6/2000 |

OTHER PUBLICATIONS

Cohen et al. American Journal of Clinical Pathology (1996), 105(5): 589-598, abstract.*
Steven et al. Chest (2000), 117(4): 1162-1172.*
Justin R. Harrison et al., "Studies Towards the Preparation of Sparteine-like Diamines For Asymmetric Synthesis", *J. Chem. Soc., Perkin Trans., 1*, 3623-3631 (1999).
Choon-Hong Tan et al., "Stereoselective Synthesis of the Indolizidene Core of the Allopumiliotoxins", *Tetrahedron Letters, 40*, 1397-1400 (1999).
Pierre Chalard et al., "Enantioseletive Synehtsis of (-)-Indolizidine 167B", *Tetrahedron Letters, 40*, 1661-1664 (1999).
A.H. Beckett et al., Bridgehead Nitrogen Compounds of Potential Analgetics, *Journal of Medicinal Chemistry*, 12 (4), 563-568 (1969).
U.S. Appl. No. 11/039,423 filed Jan. 19, 2005.
U.S. Appl. No. 10/411,061 filed Apr. 10, 2003.

* cited by examiner

*Primary Examiner*—Amelia A. Owens
(74) *Attorney, Agent, or Firm*—Frishauf, Holtz, Goodman & Chick, P.C.

(57) ABSTRACT

Compounds of the formula (I) below, or pharmacologically acceptable salts, esters or other derivatives thereof:

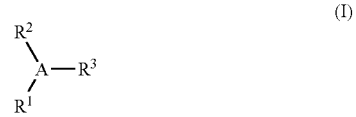

wherein A is furan, thiophene, pyrazole, imidazole, isoxazole or isothiazole; $R^1$ is a substituted or unsubstituted aryl or a substituted or unsubstituted heteroaryl; $R^2$ is a substituted or unsubstituted heteroaryl; and $R^3$ is a bicyclic amino group; provided that the substituents $R^1$ and $R^2$ are bonded to the two atoms of the cyclic group A which are adjacent to the atom of the cyclic group A to which the substituent $R^2$ is bonded. The compounds inhibit the production of inflammatory cytokines.

18 Claims, No Drawings

COMPOUNDS SUBSTITUTED WITH BICYCLIC AMINO GROUPS

CROSS REFERENCE TO RELATED APPLICATION

This application is a continuation-in-part application of International application PCT/JP02/00402 filed Jan. 22, 2002, the entire contents of which are hereby incorporated by reference herein.

BACKGROUND OF THE INVENTION

The present invention relates to heteroaryl-substituted pyrrole derivatives which are useful as a medicament. In detail, the present invention relates to compounds substituted with bicyclic amino groups which have excellent inhibitory activity against the production of inflammatory cytokines such as interleukin (IL)-1, IL-6 and IL-8 and tumor necrosis factor (TNF) and synthetic intermediates thereof. As a consequence, the compounds of the present invention have valuable anti-pyretic, analgesic and anti-inflammatory activity and are useful in the treatment of autoimmune diseases such as chronic rheumatism, bone diseases such as osteoporosis and other diseases in which the above-described inflammatory cytokines take part.

BACKGROUND ART

Non-steroidal anti-inflammatory drugs (NSAIDs) have been widely used for the treatment and prophylaxis of various inflammatory diseases and in pain relief because they have, as their main pharmacological activity, antipyretic, analgesic, and anti-inflammatory activity which is based on their ability to inhibit the biosynthesis of prostaglandin (PG) through the inhibition of cyclooxygenase activity.

For the treatment of chronic rheumatism, NSAIDs are used nosotropically and disease-modifying anti-rheumatic drugs (DMARDs) are used etiotropically.

There are a number of problems associated with these classes of drugs. Conventional NSAIDs can induce undesirable side effects including gastrointestinal disorders such as gastric ulcers, resulting in difficulties for any patient who has to take such a drug for an extended period of time. DMARDs have not yet been clearly shown to exhibit a stable, long-lasting effect.

A class of active substances generally called cytokines, which are produced in the body by immunocytes, has recently been found. One group of cytokines is known as the inflammatory cytokines and it includes interleukin (IL)-1, IL-6 and IL-8 and tumor necrosis factor (TNF). The inflammatory cytokines have been demonstrated to play a major role in a number of biological processes. These include action as an inflammatory mediator through the stimulation of the arachidonic acid metabolic pathway leading to the production of PG, the migration of leukocytes, the production of acute phase protein, and activation of osteoclasts.

Due to their mechanism of action, which is different from that of conventional drugs such as those described above, compounds which are able to inhibit the production of inflammatory cytokines are expected to provide an improved new generation of anti-pyretic, analgesic and anti-inflammatory drugs and medicaments for the treatment of autoimmune diseases such as chronic rheumatism, bone diseases such as osteoporosis and other diseases in which the above-described inflammatory cytokines are believed to take part.

As to heteroaryl compounds having an inhibitory activity against the production of inflammatory cytokines, the followings, for example, have been disclosed.

There is, however, a need for further compounds having improved activity, pharmacokinetics and safety.

Compounds having the characteristic bicyclic amino group of the compounds of the present invention have been neither disclosed nor suggested in the prior art.

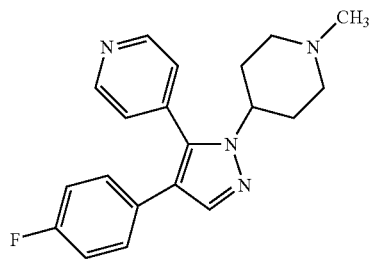

Compound of Example 17

WO 9852937

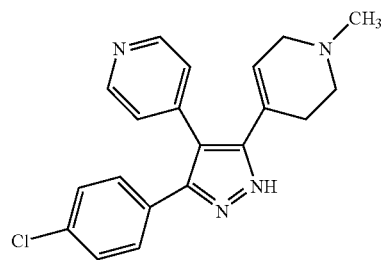

C-170

WO 0031063

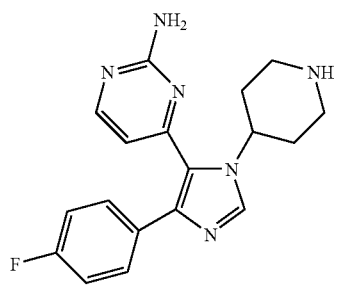

Compound of Example 6

WO97/23479

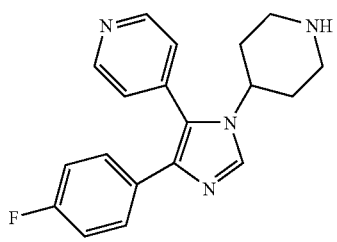

Compound of Example 23

WO96/21452

On the other hand, as to cyclic aminoketone compounds which are used as synthetic intermediates of the compounds substituted with bicyclic amino groups of the present invention, a racemate of 7-octahydroindolizinone is disclosed in "Preparation 15" of WO 00/00490. In "Preparation 16" of the said prior art document, an attempt was made to improve the purity of the optically active substance by converting it to a salt thereof. However, the purity of the compound obtained was about 30%.

Synthesis of octahydroindolizine-5,7-dione by using N-ethoxycarbonylacetylpyrrolidine-2-acetate as a starting material, was disclosed in Japanese Patent Application Publication Number Hei7-206863, but it does not refer to optical isomers.

Alternatively, synthesis of 7-octahydroindolizinone by using (2S)-methyl 3-[2-(2-methoxy-2-oxoethyl)pyrrolidino] propionic acid (the structure is shown below) as a starting material, was disclosed in Justin R. Harrison et al., J. Chem. Soc., Perkin Trans. 1, 3623–3631 (1999); however, the purity of the compound obtained was about 90% ee.

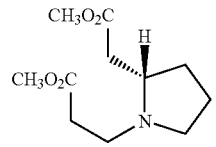

SUMMARY OF THE INVENTION

The inventors have made great efforts to study the synthesis of compounds which may inhibit the production of inflammatory cytokines described above, and pharmacological action thereof for many years and have found that compounds substituted with bicyclic amino groups exhibit excellent inhibitory activity against the production of inflammatory cytokines. Furthermore, the inventors have made great efforts to study the preparation of cyclic aminoketones having high optical purity, and then have found that by using monoester derivatives thereof as starting materials, the cyclic aminoketones having high optical purity can be synthesized, thereby leading to completion of the present invention.

The present invention relates to (1) compounds of the following formula (I), or pharmacologically acceptable salts, esters or other derivatives thereof:

wherein:

A represents a trivalent group selected from the group consisting of a benzene ring having three substituents $R^4$, a pyridine ring having two substituents $R^4$, a pyridazine ring having one substituent $R^4$, a pyrimidine ring having one substituent $R^4$, a furan ring having one substituent $R^4$, a thiophene ring having one substituent $R^4$, a pyrazole ring having one substituent $R^4$, an imidazole ring having one substituent $R^4$, an isoxazole ring and an isothiazole ring;

$R^1$ represents an aryl group; an aryl group which is substituted with one or more substituents selected from Substituent group α and Substituent group β; a heteroaryl group; or a heteroaryl group which is substituted with one or more substituents selected from Substituent group α and Substituent group β;

$R^2$ represents a heteroaryl group which has at least one ring nitrogen atom; or a heteroaryl group which has at least one ring nitrogen atom, wherein said heteroaryl group is substituted with one or more substituents selected from Substituent group α and Substituent group β; and $R^3$ represents a group of general formula (IIa), (IIb) or (IIc) shown below:

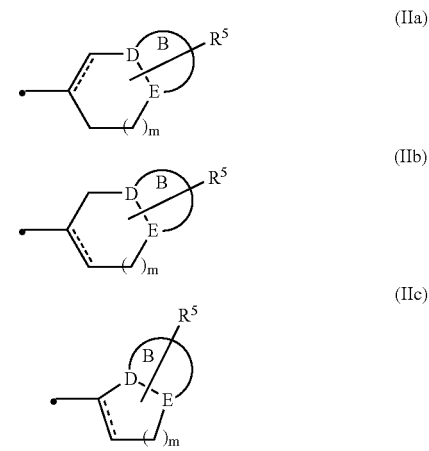

[wherein
a bond including a dotted line represents a single bond or a double bond,
m represents 1 or 2,
$R^5$ represents from 1 to 3 substituents which are independently selected from the group consisting of hydrogen atoms, Substituent group α, Substituent group β and Substituent group γ,
one of D and E represents a nitrogen atom and the other represents a group of formula >C($R^6$)— (wherein $R^6$ is a substituent selected from the group consisting of hydrogen atoms, Substituent group α and Substituent group β), and
B represents a 4- to 7-membered heterocyclic ring (said ring may be saturated or unsaturated, and may be fused with a group selected from aryl groups, heteroaryl groups, cycloalkyl groups and heterocyclyl groups)], and
$R^4$ represents a hydrogen atom; a substituent selected from Substituent group β; a cycloalkyl group substituted with one or more substituents selected from Substituent group α, Substituent group β and Substituent group γ; an aryl group; an aryl group substituted with one or more substituents selected from Substituent group α, Substituent group β and Substituent group γ; a heteroaryl group; a heteroaryl group substituted with one or more substituents selected from Substituent group α, Substituent group β and Substituent group γ; a heterocyclyl group; or a heterocyclyl group substituted with one or more substituents selected from Substituent group α, Substituent group β and Substituent group γ;

PROVIDED THAT said substituents $R^1$ and $R^3$ are bonded to the two atoms of said cyclic group A which are adjacent to the atom of the cyclic group A to which said substituent $R^2$ is bonded;

[Substituent Group α]
hydroxyl groups, nitro groups, cyano groups, halogen atoms, lower alkoxy groups, halogeno lower alkoxy groups, lower alkylthio groups, halogeno lower alkylthio groups and groups of formula —$NR^aR^b$ (wherein $R^a$ and $R^b$ are the same or different from each other and each represents a hydrogen atom, a lower alkyl group, a lower alkenyl group, a lower alkynyl group, an aralkyl group or a lower alkylsulfonyl group, or $R^a$ and $R^b$, taken together with the nitrogen atom to which they are attached, form a heterocyclyl group);

[Substituent Group β]

lower alkyl groups, lower alkenyl groups, lower alkynyl groups, aralkyl groups, cycloalkyl groups, lower alkyl groups which are substituted with one or more substituents selected from Substituent group α, lower alkenyl groups which are substituted with one or more substituents selected from Substituent group α and lower alkynyl groups which are substituted with one or more substituents selected from Substituent group α;

[Substituents Group γ]

oxo groups, hydroxyimino groups, lower alkoxyimino groups, lower alkylene groups, lower alkylenedioxy groups, lower alkylsulfinyl groups, lower alkylsulfonyl groups, aryl groups, aryl groups which are substituted with one or more substituents selected from Substituent group α and Substituent group β, aryloxy groups, aryloxy groups which are substituted with one or more substituents selected from Substituent group α and Substituent group β, lower alkylidenyl groups and aralkylidenyl groups.

DETAILED DESCRIPTION OF THE INVENTION

Of these, preferred compounds are those compounds of formula (I) and pharmacologically acceptable salts, esters and other derivatives thereof wherein:

(2) compounds wherein $R^1$ is an aryl group; or an aryl group which is substituted with one or more substituents selected from Substituent group α and Substituent group β;

(3) compounds wherein $R^1$ is a phenyl or naphthyl group; or a phenyl or naphthyl group in which said group is substituted with one or more substituents selected from Substituent group α and Substituent group β;

(4) compounds wherein $R^1$ is a phenyl group; or a phenyl group which is substituted with one or more substituents selected from Substituent group $α^1$ and Substituent group $β^1$;

(5) compounds wherein $R^1$ is a phenyl group; or a phenyl group which is substituted with one or more substituents selected from the substituent groups below, (the substituent groups: a halogen atom, a halogeno lower alkyl group and a halogeno lower alkoxy group), (6) compounds wherein $R^1$ is a phenyl, 4-fluorophenyl, 3-fluorophenyl, 3-chlorophenyl, 3,4-difluorophenyl, 3,4,5-trifluorophenyl, 3-chloro-4-fluorophenyl, 3-difluoromethoxyphenyl or 3-trifluoromethylphenyl group;

(7) compounds wherein $R^2$ is a 5- or 6-membered heteroaryl group which has one or two nitrogen atoms; or a 5- or 6-membered heteroaryl group which has one or two nitrogen atoms in which said group is substituted with one or more substituents selected from Substituent group α and Substituent group β;

(8) compounds wherein $R^2$ is a pyridyl or pyrimidinyl group; or a pyridyl or pyrimidinyl group in which said group is substituted with one or more substituents selected from Substituent group α and Substituent group β;

(9) compounds wherein $R^2$ is a 4-pyridyl or 4-pyrimidinyl group; or a 4-pyridyl or 4-pyrimidinyl group in which said group is substituted with one or more substituents selected from Substituent group α and Substituent group β;

(10) compounds wherein $R^2$ is a 4-pyridyl or 4-pyrimidinyl group; or a 4-pyridyl or 4-pyrimidinyl group in which said group is substituted at the 2-position thereof with one substituent selected from Substituent group α and Substituent group β;

(11) compounds wherein $R^2$ is a 4-pyridyl or 4-pyrimidinyl group; or a 4-pyridyl or 4-pyrimidinyl group which is substituted at the 2-position thereof with one substituent selected from the substituent groups below, (the substituent groups: methoxy, amino, methylamino, benzylamino and α-methylbenzylamino);

(12) compounds wherein $R^3$ is a group of general formula (IIa) or general formula (IIb); and B is a 5- or 6-membered heterocyclic ring which has one ring nitrogen atom and optionally has one further ring heteroatom or ring group selected from a nitrogen atom, an oxygen atom, a sulfur atom, an >SO group and an >$SO_2$ group (said ring may be saturated or unsaturated and may be fused with a group selected from aryl groups, heteroaryl groups, cycloalkyl groups and heterocyclyl groups);

(13) compounds wherein $R^3$ is a group of general formula (IIa) or general formula (IIb); and B is a 5- or 6-membered heterocyclic ring which consists of the group D, the group E and three or four carbon atoms (said ring may be saturated or unsaturated and may be fused with a group selected from aryl groups, heteroaryl groups, cycloalkyl groups and heterocyclyl groups);

(14) compounds wherein $R^3$ is a group of general formula (IIa);

(15) compounds wherein B is a pyrrolidine ring or a pyrroline ring;

(16) compounds wherein m is 1;

(17) compounds wherein $R^5$ is one or two substituents which are independently selected from hydrogen atoms, Substituent group α, Substituent group β and Substituent group $γ^1$;

(18) compounds wherein $R^5$ is one or two groups which are independently selected from hydrogen atoms, hydroxy groups, halogen atoms, lower alkoxy groups, lower alkylthio groups, halogeno lower alkoxy groups, lower alkyl groups, halogeno lower alkyl groups, oxo groups, aryl groups, aryl groups which are substituted with one or more substituents selected from Substituent group α and Substituent group β, lower alkylene groups, lower alkylenedioxy groups and lower alkylsulfonyl groups;

(19) compounds wherein $R^5$ is one or two groups which are independently selected from hydrogen atoms, hydroxy groups, fluorine atoms, chlorine atoms, methoxy groups, ethoxy groups, propoxy groups, methyl groups, ethyl groups, propyl groups, phenyl groups and phenyl groups which are substituted with one or more substituents selected from Substituent group α and Substituent group β;

(20) compounds wherein $R^5$ is one substituent which is independently selected from hydrogen atoms, methoxy groups, methyl groups, ethyl groups, propyl groups and phenyl groups;

(21) compounds wherein $R^4$ is a hydrogen atom; a lower alkyl group; a lower alkyl group which is substituted with one or more substituents selected from Substituent group α; an aryl group substituted with one or more substituents selected from Substituent group α, Substituent group β and Substituent group γ; a heterocyclyl group; or a heterocyclyl group substituted with one or more substituents selected from Substituent group α, Substituent group β and Substituent group γ;

(22) compounds wherein $R^4$ is a hydrogen atom; a lower alkyl group; a halogeno lower alkyl group; or a phenyl group substituted with one or more substituents selected from Substituent group α, Substituent group β and Substituent group γ;

(23) compounds wherein A is a pyrazole ring having one substituent $R^4$ or an imidazole ring having one substituent $R^4$;

(24) compounds wherein A is a pyrazole ring having one substituent $R^4$;

[Substituent Group $α^1$]

halogen atoms, lower alkoxy groups, halogeno lower alkoxy groups and groups of formula —$NR^aR^b$ (wherein one of $R^a$ and $R^b$ represents a hydrogen atom or a lower alkyl group, and the other represents a hydrogen atom, a lower alkyl group or an aralkyl group),

[Substituent Group $β^1$]

lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups,

[Substituent Group $γ^1$]

oxo groups, hydroxyimino groups, lower alkoxyimino groups, lower alkylene groups, lower alkylenedioxy groups, lower alkylsulfinyl groups, lower alkylsulfonyl groups, aryl groups, and aryl groups which are substituted with one or more substituents selected from Substituent group α and Substituent group β.

Compounds of formula (I) which comprise any combination of the factors selected freely from the nine groups consisting of (2) to (6); (7) to (11); (12) and (13); (14); (15); (16); (17) to (20); (21) and (22); and (23) and (24) are preferred.

Of the above, especially preferred compounds of the present invention are compounds from (25) of formula (I) selected from the following group of compounds, and pharmacologically acceptable salts, esters and other derivatives thereof:

3-(1,2,3,5,6,8a-hexahydroindolizin-7-yl)-5-phenyl-4-(pyridin-4-yl)pyrazole, 5-(3-fluorophenyl)-3-(1,2,3,5,6,8a-hexahydroindolizin-7-yl)-4-(pyridin-4-yl)pyrazole, 5-(4-fluorophenyl)-3-(1,2,3,5,6,8a-hexahydroindolizin-7-yl)-4-(pyridin-4-yl)pyrazole, 5-(4-fluorophenyl)-3-(2-methyl-1,2,3,5,6,8a-hexahydroindolizin-7-yl)-4-(pyridin-4-yl)pyrazole, 5-(4-fluorophenyl)-3-(2-phenyl-1,2,3,5,6,8a-hexahydroindolizin-7-yl)-4-(pyridin-4-yl)pyrazole, 5-(4-fluorophenyl)-3-(2-hydroxy-1,2,3,5,6,8a-hexahydroindolizin-7-yl)-4-(pyridin-4-yl)pyrazole, 5-(4-fluorophenyl)-3-(2-methoxy-1,2,3,5,6,8a-hexahydroindolizin-7-yl)-4-(pyridin-4-yl)pyrazole, 3-(2-fluoro-1,2,3,5,6,8a-hexahydroindolizin-7-yl)-5-(4-fluorophenyl)-4-(pyridin-4-yl)pyrazole, 3-(2,2-difluoro-1,2,3,5,6,8a-hexahydroindolizin-7-yl)-5-(4-fluorophenyl)-4-(pyridin-4-yl)pyrazole, 5-(4-fluorophenyl)-3-(8-methyl-1,2,3,5,6,8a-hexahydroindolizin-7-yl)-4-(pyridin-4-yl)pyrazole, 5-(3-chlorophenyl)-3-(1,2,3,5,6,8a-hexahydroindolizin-7-yl)-4-(pyridin-4-yl)pyrazole, 3-(1,2,3,5,6,8a-hexahydroindolizin-7-yl)-4-(pyridin-4-yl)-5-(3-trifluoromethylphenyl)pyrazole, 5-(3,4-difluorophenyl)-3-(1,2,3,5,6,8a-hexahydroindolizin-7-yl)-4-(pyridin-4-yl)pyrazole, 5-(4-fluorophenyl)-3-(1,2,3,5,6,8a-hexahydroindolizin-7-yl)-1-methyl-4-(pyridin-4-yl)pyrazole, 3-(4-fluorophenyl)-5-(1,2,3,5,6,8a-hexahydroindolizin-7-yl)-1-methyl-4-(pyridin-4-yl)pyrazole, 3-(4-fluorophenyl)-1-methyl-5-(2-methyl-1,2,3,5,6,8a-hexahydroindolizin-7-yl)-4-(pyridin-4-yl)pyrazole, 3-(4-fluorophenyl)-1-methyl-5-(2-phenyl-1,2,3,5,6,8a-hexahydroindolizin-7-yl)-4-(pyridin-4-yl)pyrazole, 3-(4-fluorophenyl)-5-(2-hydroxy-1,2,3,5,6,8a-hexahydroindolizin-7-yl)-1-methyl-4-(pyridin-4-yl)pyrazole, 3-(4-fluorophenyl)-5-(2-methoxy-1,2,3,5,6,8a-hexahydroindolizin-7-yl)-1-methyl-4-(pyridin-4-yl)pyrazole, 5-(2-fluoro-1,2,3,5,6,8a-hexahydroindolizin-7-yl)-3-(4-fluorophenyl)-1-methyl-4-(pyridin-4-yl)pyrazole, 5-(2,2-difluoro-1,2,3,5,6,8a-hexahydroindolizin-7-yl)-3-(4-fluorophenyl)-1-methyl-4-(pyridin-4-yl)pyrazole, 3-(4-fluorophenyl)-1-methyl-5-(8-methyl-1,2,3,5,6,8a-hexahydroindolizin-7-yl)-4-(pyridin-4-yl)pyrazole, 5-(4-fluorophenyl)-4-(pyridin-4-yl)-3-(3,5,6,8a-tetrahydroindolizin-7-yl)pyrazole, 5-(4-fluorophenyl)-3-(1,2,3,5,8,8a-hexahydroindolizin-7-yl)-4-(pyridin-4-yl)pyrazole, 5-(4-fluorophenyl)-3-(7-hydroxy-1,2,3,5,6,7,8,8a-octahydroindolizin-7-yl)-4-(pyridin-4-yl)pyrazole, 5-(4-fluorophenyl)-3-(1,2,3,5,6,7,8,8a-octahydroindolizin-7-yl)-4-(pyridin-4-yl)pyrazole, 4-(4-fluorophenyl)-1-(1,2,3,5,6,7,8,8a-octahydroindolizin-7-yl)-5-(pyridin-4-yl)imidazole, 5-(4-chlorophenyl)-3-(1,2,3,5,6,8a-hexahydroindolizin-7-yl)-4-(pyridin-4-yl)pyrazole, 3-(2-ethyl-1,2,3,5,6,8a-hexahydroindolizin-7-yl)-5-(4-fluorophenyl)-4-(pyridin-4-yl)pyrazole, 5-(4-fluorophenyl)-3-(2-propyl-1,2,3,5,6,8a-hexahydroindolizin-7-yl)-4-(pyridin-4-yl)pyrazole, 5-(4-fluorophenyl)-3-(2-methyliden-1,2,3,5,6,8a-hexahydroindolizin-7-yl)-4-(pyridin-4-yl)pyrazole, 3-(2-ethyliden-1,2,3,5,6,8a-hexahydroindolizin-7-yl)-5-(4-fluorophenyl)-4-(pyridin-4-yl)pyrazole, 5-(4-fluorophenyl)-3-(2-propyliden-1,2,3,5,6,8a-hexahydroindolizin-7-yl)-4-(pyridin-4-yl)pyrazole, 5-(4-fluorophenyl)-1-methyl-3-(2-methyl-1,2,3,5,6,8a-hexahydroindolizin-7-yl)-4-(pyridin-4-yl)pyrazole, 5-(4-fluorophenyl)-1-methyl-3-(2-phenyl-1,2,3,5,6,8a-hexahydroindolizin-7-yl)-4-(pyridin-4-yl)pyrazole, 5-(4-fluorophenyl)-3-(2-hydroxy-1,2,3,5,6,8a-hexahydroindolizin-7-yl)-1-methyl-4-(pyridin-4-yl)pyrazole, 5-(4-fluorophenyl)-3-(2-methoxy-1,2,3,5,6,8a-hexahydroindolizin-7-yl)-1-methyl-4-(pyridin-4-yl)pyrazole, 3-(2-fluoro-1,2,3,5,6,8a-hexahydroindolizin-7-yl)-5-(4-fluorophenyl)-1-methyl-4-(pyridin-4-yl)pyrazole, 5-(4-fluorophenyl)-1-methyl-3-(8-methyl-1,2,3,5,6,8a-hexahydroindolizin-7-yl)-4-(pyridin-4-yl)pyrazole, 5-(4-fluorophenyl)-3-(2-methyl-3,5,6,8a-tetrahydroindolizin-7-yl)-4-(pyridin-4-yl)pyrazole, 3-(2-ethyl-3,5,6,8a-tetrahydroindolizin-7-yl)-5-(4-fluorophenyl)-4-(pyridin-4-yl)pyrazole, 5-(4-fluorophenyl)-3-(2-propyl-3,5,6,8a-tetrahydroindolizin-7-yl)-4-(pyridin-4-yl)pyrazole, and 5-(4-fluorophenyl)-3-(2-phenyl-3,5,6,8a-tetrahydroindolizin-7-yl)-4-(pyridin-4-yl)pyrazole.

The other objects of the present invention are to provide a pharmaceutical composition comprising an effective amount of a compound selected from any one of (1) to (25) or a pharmacologically acceptable salt, ester or other derivative thereof; and a method for inhibiting the production of inflammatory cytokines in a mammal which comprises administering to said mammal (preferably human) an effective amount of a compound selected from any one of (1) to (25) or a pharmacologically acceptable salt, ester or other derivative thereof (more preferably a method for the treatment or relief of pain and/or inflammation; a method for the prophylaxis or treatment of chronic rheumatoid arthritis; or a method for the prophylaxis or treatment of osteoarthritis).

Furthermore, the present invention provides (a) a method for the preparation of a compound of general formula (53) below which substantially consists of Step A, Step B and Step C shown below

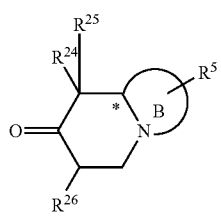
(53)

[wherein,

B represents a 4- to 7-membered heterocyclic ring (said ring may be saturated or unsaturated, and may be fused with a group selected from aryl groups, heteroaryl groups, cycloalkyl groups and heterocyclyl groups), $R^5$ represents from 1 to 3 substituents which are independently selected from the group consisting of hydrogen atoms, Substituent group α, Substituent group β and Substituent group γ, $R^{24}$, $R^{25}$ and $R^{26}$ are the same or different from each other and each represents one group selected from the groups defined for $R^5$, and the configuration based on the carbon atom which is marked by * represents S or R], <Step A> in Step A, a compound of general formula (48) below or a reactive derivative thereof

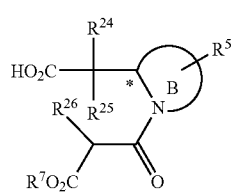
(48)

[wherein, B, $R^5$, $R^{24}$, $R^{25}$ and $R^{26}$ have the same meanings as defined above, $R^7$ represents a carboxyl protecting group and the configuration based on the carbon atom which is marked by * represents the same configuration as the compound of general formula (53)] is subjected to a ring closure reaction to give a compound of general formula (49) below

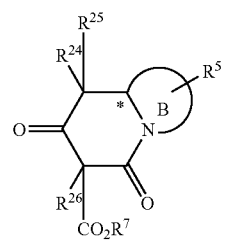
(49)

[wherein, B, $R^5$, $R^{24}$, $R^{25}$, $R^{26}$ and $R^7$ have the same meanings as defined above, and the configuration based on the carbon atom which is marked by * represents the same configuration as the compound of general formula (53)];

<Step B> in Step B, a compound of general formula (50) below is prepared by subjecting the compound of general formula (49) to a hydrolysis reaction and a decarboxylation reaction,

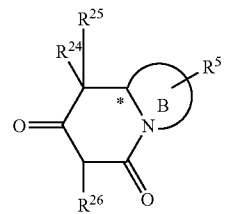
(50)

[wherein, B, $R^5$, $R^{24}$, $R^{25}$ and $R^{26}$ have the same meanings as defined above and the configuration based on the carbon atom which is marked by * represents the same configuration as the compound of general formula (53)];

<Step C> in Step C, a compound of general formula (53) is prepared by reducing the amido moiety of the compound of general formula (50);

(b) Step C described in (a) substantially consists of Step C1, Step C2 and Step C3 shown below, <Step C1> in Step C1, a compound of general formula (50) is reacted with a compound of general formula: $R^{14}$—NH—$R^{15}$

[wherein, $R^{14}$ and $R^{15}$ are the same or different from each other and each independently represents a hydrogen atom, a lower alkyl group or an aralkyl group, or $R^{14}$ and $R^{15}$, taken together with the nitrogen atom to which they are attached, form a heterocyclyl group] to prepare a compound of general formula (51) below

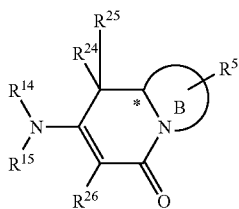

(51)

[wherein, B, $R^5$, $R^{24}$, $R^{25}$, $R^{26}$, $R^{14}$ and $R^{15}$ have the same meanings as defined above and the configuration based on the carbon atom which is marked by * represents the same configuration of the compound of general formula (53)];

<Step C2> in Step C2, a compound of general formula (52) below is prepared by reducing the amido moiety of the compound of general formula (51)

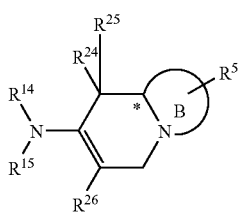

(52)

[wherein, B, $R^5$, $R^{24}$, $R^{25}$, $R^{26}$, $R^{14}$ and $R^{15}$ have the same meanings as defined above and the configuration based on the carbon atom which is marked by * represents the same configuration as the compound of general formula (53)];

<Step C3> in Step C3, a compound of general formula (53) is prepared by subjecting the compound of general formula (52) to a hydrolysis reaction;

(c) a method for the preparation of a compound of general formula (49) which comprises subjecting a compound of general formula (48) below or a reactive derivative thereof

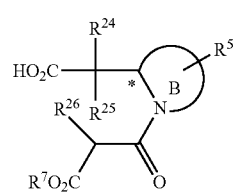

(48)

[wherein,

B represents a 4- to 7-membered heterocyclic ring (said ring may be saturated or unsaturated, and may be fused with a group selected from aryl groups, heteroaryl groups, cycloalkyl groups and heterocyclyl groups), $R^5$ represents from 1 to 3 substituents which are independently selected from the group consisting of hydrogen atoms, Substituent group α, Substituent group β and Substituent group γ, $R^7$ represents carboxyl protecting group, $R^{24}$, $R^{25}$ and $R^{26}$ are the same or different from each other and each represents one substituent selected from the groups defined in $R^5$, and the configuration based on the carbon atom which is marked by * represents S or R] subjected to a ring closure reaction to give a compound of general formula (49) below

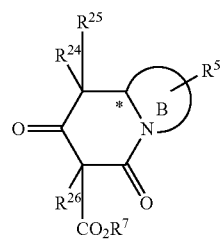

(49)

[wherein, B, $R^5$, $R^{24}$, $R^{25}$, $R^{26}$ and $R^7$ have the same meanings as defined above, and the configuration based on the carbon atom which is marked by * represents the same configuration as the compound of general formula (48)]; and (d) a substantially pure optically active substance of general formula (53) below

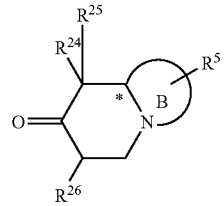

(53)

[wherein,

B represents a 4- to 7-membered heterocyclic ring (said ring may be saturated or unsaturated, and may be fused with a group selected from aryl groups, heteroaryl groups, cycloalkyl groups and heterocyclyl groups), $R^5$ represents from 1 to 3 substituents which are independently selected from the group consisting of hydrogen atoms, Substituent group α, Substituent group β and Substituent group γ, $R^{24}$, $R^{25}$ and $R^{26}$ are the same or different from each other and each represents one substituent selected from the groups defined in $R^5$, and the configuration based on the carbon atom which is marked by * represents S or R].

The compound of general formula (I) above is represented by any one of the followings:

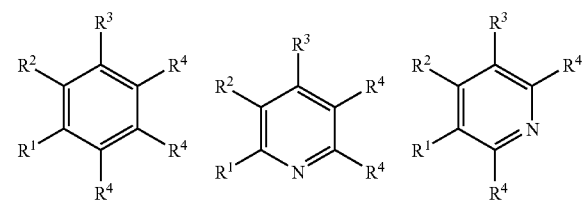

-continued

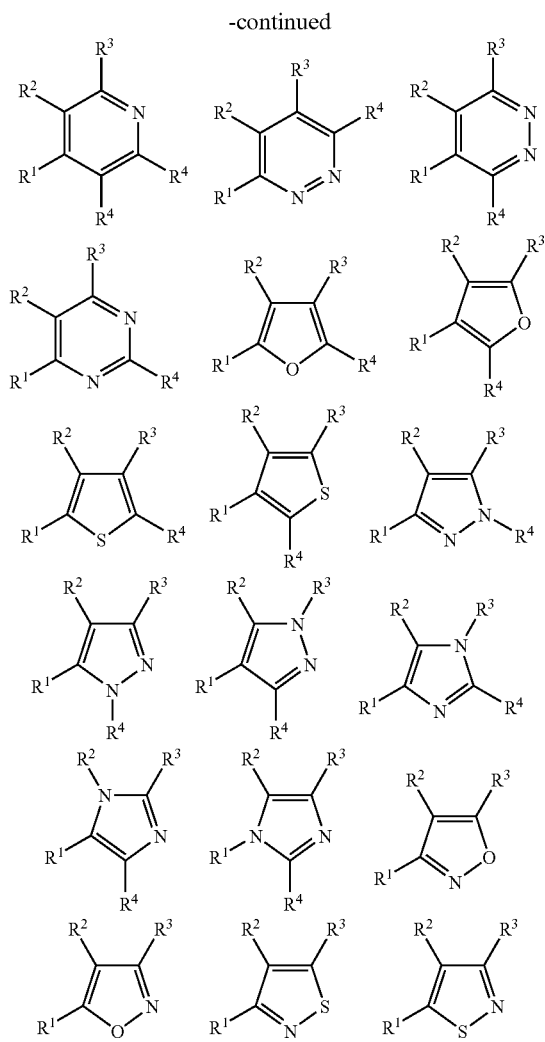

[wherein, $R^1$, $R^2$, $R^3$ and $R^4$ have the same meanings as defined above].

In the above formula (I), where $R^1$, $R^4$ or Substituent group γ represents an aryl group; where $R^1$ or Substituent group γ represents an aryl group which is substituted with one or more substituents selected from Substituent group α and Substituent group β; or where $R^4$ represents an aryl group which is substituted with one or more substituents selected from Substituent group α, Substituent group β and Substituent group γ, said aryl group is an aromatic hydrocarbon group having from 6 to 14 carbon atoms, and examples include phenyl, naphthyl, phenanthryl and anthracenyl groups. Of these, we prefer phenyl and naphthyl groups, most preferably a phenyl group.

The aryl group defined and exemplified above may be fused with a cycloalkyl group having from 3 to 10 carbon atoms. Examples of such a fused ring group include a 5-indanyl group.

Where $R^1$ or Substituent group γ represents an aryl group which is substituted with one or more substituents selected from Substituent group α and Substituent group β, it is preferably an aryl group substituted with from 1 to 4 substituents selected from Substituent group α and Substituent group β, and more preferably it is an aryl group substituted with from 1 to 3 substituents selected from Substituent group α and Substituent group β.

Examples of such substituted aryl groups include 4-fluorophenyl, 3-fluorophenyl, 4-chlorophenyl, 3-chlorophenyl, 3,4-difluorophenyl, 3,4-dichlorophenyl, 3,4,5-trifluorophenyl, 3-chloro-4-fluorophenyl, 3-difluoromethoxyphenyl, 3-trifluoromethoxyphenyl and 3-trifluoromethylphenyl groups.

Where $R^4$ represents an aryl group which is substituted with one or more substituents selected from Substituent group α, Substituent group β and Substituent group γ, it is preferably an aryl group substituted with from 1 to 4 substituents selected from Substituent group α, Substituent group β and Substituent group γ, and more preferably it is an aryl group substituted with from 1 to 3 substituents selected from Substituent group α, Substituent group β and Substituent group γ, and still more preferably it is an aryl group substituted with one group selected from lower alkylthio groups, halogeno lower alkylthio groups, lower alkylsulfinyl groups and lower alkylsulfonyl groups.

Examples of such substituted aryl groups include 4-methylthiophenyl, 4-ethylthiophenyl, 4-propylthiophenyl, 4-methylsulfinylphenyl, 4-ethylsulfinylphenyl, 4-propylsulfinylphenyl, 4-methylsulfonylphenyl, 4-ethylsulfonylphenyl and 4-propylsulfonylphenyl groups.

Where $R^1$ or $R^4$ represents a heteroaryl group; where $R^1$ represents a heteroaryl group which is substituted with one or more substituents selected from Substituent group α and Substituent group β; or where $R^4$ represents a heteroaryl group which is substituted with one or more substituents selected from Substituent group α, Substituent group β and Substituent group γ, said heteroaryl group is 5- to 7-membered heteroaryl group containing from 1 to 3 heteroatoms selected from the group consisting of sulfur atoms, oxygen atoms and nitrogen atoms. Examples of such heteroaryl groups include furyl, thienyl, pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl groups. We prefer 5- or 6-membered heteroaryl groups containing one or two heteroatoms selected from the group consisting of sulfur atoms, oxygen atoms and nitrogen atoms, examples of which include furyl, thienyl, pyrrolyl, pyrazolyl, imidazolyl, oxazolyl, isoxazolyl, thiazolyl, isothiazolyl, pyridyl, pyridazinyl, pyrimidinyl and pyrazinyl groups. Of these, furyl, thienyl, pyridyl and pyrimidinyl groups are particularly preferred.

The heteroaryl groups defined and exemplified above may be fused with another cyclic group (for example, a cyclic group such as an aryl group or a cycloalkyl group having from 3 to 10 carbon atoms). Examples of such a group include indolyl, benzofuranyl, benzothienyl, quinolyl, isoquinolyl, quinazolyl, tetrahydroquinolyl and tetrahydroisoquinolyl groups.

Where $R^1$ represents a heteroaryl group which is substituted with one or more substituents selected from Substituent group α and Substituent group β, said heteroaryl group is preferably a heteroaryl group substituted with from 1 to 3 substituents selected from Substituent group α and Substituent group 1, and more preferably it is a heteroaryl group substituted with one or two substituents selected from Substituent group α and Substituent group β.

Examples of such substituted heteroaryl groups include 5-fluoro-2-furyl, 4-chloro-2-thienyl, 5-difluoromethoxy-3-furyl, 5-trifluoromethyl-3-thienyl and 5-fluoro-2-oxazolyl groups.

Where $R^4$ represents a heteroaryl group which is substituted with substituents selected from Substituent group α, Substituent group β and Substituent group γ, it is preferably a heteroaryl group substituted with from 1 to 3 substituents selected from Substituent group α, Substituent group β and Substituent group γ, and more preferably it is a heteroaryl group substituted with one or two substituents selected from Substituent group α, Substituent group β and Substituent group γ.

Examples of such substituted heteroaryl groups include a 2-methylthio-5-pyridyl, 3-methylthio-6-pyridazinyl, 2-methylthio-5-pyrimidinyl, 2-methylsulfinyl-5-pyridyl, 3-methylsulfinyl-6-pyridazinyl, 2-methylsulfinyl-5-pyrimidinyl, 2-methylsulfonyl-5-pyridyl, 3-methylsulfonyl-6-pyridazinyl and 2-methylsulfonyl-5-pyrimidinyl groups.

Where $R^2$ represents a heteroaryl group having at least one ring nitrogen atom or a heteroaryl group having at least one ring nitrogen atom in which said heteroaryl group is substituted with one or more substituents selected from Substituent group α and Substituent group β, said heteroaryl groups having at least one ring nitrogen atom are 5- to 7-membered heteroaryl groups containing at least one nitrogen atom and optionally containing one or two further heteroatoms selected from the group consisting of sulfur atoms, oxygen atoms and nitrogen atoms. Examples of such groups include pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl groups. Of these, we prefer 5- or 6-membered heteroaryl groups containing one nitrogen atom and optionally containing one further heteroatom selected from the group consisting of sulfur atoms, oxygen atoms and nitrogen atoms, examples of which include pyrrolyl, pyrazolyl, imidazolyl, oxazolyl, isoxazolyl, thiazolyl, isothiazolyl, pyridyl, pyridazinyl, pyrimidinyl and pyrazinyl groups. 5- or 6-membered heteroaryl groups containing one or two nitrogen atoms, such as imidazolyl, pyridyl, pyridazinyl, pyrimidinyl and pyrazinyl groups are more preferred and pyridyl and pyrimidinyl groups are particularly preferred and 4-pyridyl and 4-pyrimidinyl groups are most preferred.

Where $R^2$ represents a heteroaryl group having at least one ring nitrogen atom in which said heteroaryl group is substituted with groups selected from Substituent group α and Substituent group β, said heteroaryl group is preferably a group substituted with from 1 to 3 substituents selected from Substituent group α and Substituent group β, more preferably it is a heteroaryl group substituted with one or two substituents selected from Substituent group α and Substituent group β, still more preferably it is a heteroaryl group substituted with one substituent selected from Substituent group α and Substituent group β, and particularly preferably it is a 4-pyridyl or 4-pyrimidinyl group which is substituted at the 2-position of said group with one substituent selected from Substituent group α and Substituent group β. Most preferably, said heteroaryl group is a 4-pyridyl or 4-pyrimidinyl group which is substituted at the 2-position with a group of formula —$NR^aR^b$ (wherein $R^a$ and $R^b$ are the same or different from each other and each independently represents a hydrogen atom, a lower alkyl group, a lower alkenyl group, a lower alkynyl group, an aralkyl group or a lower alkylsulfonyl group, or $R^a$ and $R^b$, taken together with the nitrogen atom to which they are attached, form a heterocyclyl group) or a lower alkyl group substituted with a group of formula —$NR^aR^b$ (wherein $R^a$ and $R^b$ have the same meaning as defined above). Preferred examples of such a group include 2-amino-4-pyridyl, 2-amino-4-pyrimidinyl, 2-methylamino-4-pyridyl, 2-methylamino-4-pyrimidinyl, 2-methoxy-4-pyridyl, 2-methoxy-4-pyrimidinyl, 2-benzylamino-4-pyridyl, 2-benzylamino-4-pyrimidinyl, 2-(α-methylbenzylamino)-4-pyridyl and 2-(α-methylbenzylamino)-4-pyrimidinyl.

The cyclic group B is defined as a "4- to 7-membered heterocyclic ring", by which we mean a 4- to 7-membered heterocyclic ring which consists of group D, group E, and 2 to 5 atoms or groups selected from carbon atoms, nitrogen atoms, oxygen atoms, sulfur atoms, >SO groups and >$SO_2$ groups, said heterocyclic ring containing at least one ring nitrogen atom (that is, a saturated heterocyclic ring or an unsaturated heterocyclic ring). Preferably, the cyclic group B is a 5- or 6-membered heterocyclic ring which contains one nitrogen atom and which may optionally contain one further ring heteroatom or ring group selected from nitrogen atoms, oxygen atoms, sulfur atoms, >SO groups and >$SO_2$ groups; more preferably it is pyrrolidine, pyrroline, imidazolidine, imidazoline, pyrazolidine, pyrazoline, oxazolidine, thiazolidine, piperidine, tetrahydropyridine, dihydropyridine, piperazine, morpholine or thiomorpholine; still more preferably it is pyrrolidine, pyrroline or imidazoline; and most preferably it is pyrrolidine or pyrroline.

The heterocyclic ring defined and exemplified above may optionally be fused with an aryl group as defined above, a heteroaryl group as defined above, a cycloalkyl group or a heterocyclyl group, and examples of such a fused ring system include tetrahydroquinoline, octahydroquinoline, decahydroquinoline, tetrahydroisoquinoline, octahydroisoquinoline, decahydroisoquinoline, indoline, octahydroindole, isoindoline and octahydroisoindole.

[said cycloalkyl groups are cycloalkyl groups having from 3 to 7 carbon atoms, such as cyclopropyl, cyclobutyl, cyclopentyl, cyclohexyl and cycloheptyl groups, of which we prefer cycloalkyl groups having from 3 to 6 carbon atoms. Said heterocyclyl groups are 4- to 7-membered heterocyclyl groups which have from 1 to 3 ring sulfur atoms, oxygen atoms and/or nitrogen atoms, and preferably 4- to 7-membered heterocyclyl groups which have one or two heteroatoms selected from the group consisting of sulfur atoms, oxygen atoms and nitrogen atoms. Of these, 5- or 6-membered heterocyclyl groups which contain one ring nitrogen atom and which may optionally contain one further oxygen atom, sulfur atom or nitrogen atom are preferred, and examples of such groups include azetidinyl, pyrrolidinyl, pyrrolinyl, imidazolidinyl, imidazolinyl, pyrazolidinyl, pyrazolinyl, oxazolidinyl, thiazolidinyl, piperidyl, tetrahydropyridyl, dihydropyridyl, piperazinyl, morpholinyl, thiomorpholinyl and homopiperidyl].

The cycloalkyl groups in the definition of Substituent group β, and the cycloalkyl moiety of the cycloalkyl groups which are substituted with one or more substituents selected from Substituent group α, Substituent group β, and Substituent group γ in the definition of $R^4$, are cycloalkyl groups having from 3 to 7 carbon atoms, such as cyclopropyl, cyclobutyl, cyclopentyl, cyclohexyl and cycloheptyl groups, of which more preferred are cycloalkyl groups having from 3 to 6 carbon atoms and still more preferred are cyclopentyl or cyclohexyl groups.

The heterocyclyl group in the definition of $R^4$, and the heterocyclyl moiety of the heterocyclyl groups which are substituted with one or more substituents selected from Substituent group α, Substituent group β and Substituent group 7, are 4- to 7-membered heterocyclyl groups which have from 1 to 3 ring sulfur atoms, oxygen atoms and/or nitrogen atoms, and preferably are 4- to 7-membered heterocyclyl groups which have one or two heteroatoms selected from the group consisting of sulfur atoms, oxygen atoms and nitrogen atoms. Of these, 5- or 6-membered heterocyclyl groups which contain one ring nitrogen atom and which may optionally contain one further oxygen atom, sulfur atom or nitrogen atom are preferred, and examples of such groups include azetidinyl, pyrrolidinyl, pyrrolinyl, imidazolidinyl, imidazolinyl, pyrazolidinyl, pyrazolinyl, oxazolidinyl, thiazolidinyl, piperidyl, tetrahydropyridyl, dihydropyridyl, piperazinyl, morpholinyl, thiomorpholinyl and homopiperidyl.

The lower alkyl groups in the definitions of $R^a$, $R^b$ and Substituent group β, and the lower alkyl moiety of the lower alkyl groups which are substituted with Substituent group α in the definition of Substituent group β are straight or branched chain alkyl groups having from 1 to 6 carbon atoms. Examples of said lower alkyl groups include methyl, ethyl, propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Alkyl groups having from 1 to 4 carbon atoms are preferred, methyl, ethyl, propyl, isopropyl and butyl groups are more preferred, and methyl, ethyl and propyl groups are most preferred.

The lower alkenyl groups in the definitions of $R^a$, $R^b$ and Substituent group β, and the lower alkenyl moiety of the lower alkenyl groups which are substituted with Substituent group α in the definition of Substituent group β are straight or branched chain alkenyl groups having from 2 to 6 carbon atoms. Examples of said lower alkenyl groups include vinyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl and 5-hexenyl groups. Alkenyl groups having from 2 to 4 carbon atoms are preferred, and alkenyl groups having 2 or 3 carbon atoms are most preferred.

The lower alkynyl groups in the definitions of $R^a$, $R^b$ and Substituent group β, and the lower alkynyl moiety of the lower alkynyl groups which are substituted with Substituent group α in the definition of Substituent group β are straight or branched chain alkynyl groups having from 2 to 6 carbon atoms. Examples of said lower alkynyl groups include ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups. Alkynyl groups having from 2 to 4 carbon atoms are preferred, and alkynyl groups having 2 or 3 carbon atoms are most preferred.

The aralkyl group in the definitions of $R^a$, $R^b$ and Substituent group β is a lower alkyl group as defined above which is substituted with an aryl group as defined above. Examples of such a group include benzyl, indenylmethyl, phenanthrenylmethyl, anthracenylmethyl, α-naphthylmethyl, β-naphthylmethyl, diphenylmethyl, triphenylmethyl, α-naphthyldiphenylmethyl, 9-anthrylmethyl, piperonyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl. Of these, benzyl, phenanthrenylmethyl, anthracenylmethyl, α-naphthylmethyl, β-naphthylmethyl, diphenylmethyl, triphenylmethyl, 9-anthrylmethyl, piperonyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl are preferred.

As noted above, the aryl moiety of the aralkyl groups may optionally be substituted with from 1 to 3 substituents selected from Substituent group α and Substituent group β, defined above. Examples of such a substituted aralkyl group include aralkyl groups substituted with halogen atoms such as 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3,5-difluorobenzyl, 2,5-difluorophenethyl, 2,6-difluorophenethyl, 2,4-difluorophenethyl, 3,5-dibromobenzyl, 2,5-dibromophenethyl, 2,6-dichlorobenzyl, 2,4-dichlorophenethyl, 2,3,6-trifluorobenzyl, 2,3,4-trifluorophenethyl, 3,4,5-trifluorobenzyl, 2,5,6-trifluorophenethyl, 2,4,6-trifluorobenzyl, 2,3,6-tribromophenethyl, 2,3,4-tribromobenzyl, 3,4,5-tribromophenethyl, 2,5,6-trichlorobenzyl, 2,4,6-trichlorophenethyl, 1-fluoro-2-naphthylmethyl, 2-fluoro-1-naphthylethyl, 3-fluoro-1-naphthylmethyl, 1-chloro-2-naphthylethyl, 2-chloro-1-naphthylmethyl, 3-bromo-1-naphthylethyl, 3,8-difluoro-1-naphthylmethyl, 2,3-difluoro-1-naphthylethyl, 4,8-difluoro-1-naphthylmethyl, 5,6-difluoro-1-naphthylethyl, 3,8-dichloro-1-naphthylmethyl, 2,3-dichloro-1-naphthylethyl, 4,8-dibromo-1-naphthylmethyl, 5,6-dibromo-1-naphthylethyl, 2,3,6-trifluoro-1-naphthylmethyl, 2,3,4-trifluoro-1-naphthylethyl, 3,4,5-trifluoro-1-naphthylmethyl, 4,5,6-trifluoro-1-naphthylethyl, 2,4,8-trifluoro-1-naphthylmethyl, bis(2-fluorophenyl)methyl, (3-fluorophenyl)(phenyl)methyl, bis(4-fluorophenyl)methyl, (4-fluorophenyl)(phenyl)methyl, bis(2-chlorophenyl)methyl, bis(3-chlorophenyl)methyl, bis(4-chlorophenyl)methyl, (4-chlorophenyl)(phenyl) methyl, (2-bromophenyl)(phenyl)methyl, (3-bromophenyl)(phenyl)methyl, bis(4-bromophenyl)methyl, bis(3,5-difluorophenyl)methyl, bis(2,5-difluorophenyl)methyl, bis(2,6-difluorophenyl)methyl, (2,4-difluorophenyl)(phenyl)methyl, bis(3,5-dibromophenyl)methyl, (2,5-dibromophenyl)(phenyl)methyl, (2,6-dichlorophenyl)(phenyl)methyl, bis(2,4-dichlorophenyl)methyl and bis(2,3,6-trifluorophenyl)methyl; aralkyl groups substituted with halogeno lower alkyl groups such as 2-trifluoromethylbenzyl, 3-trifluoromethylphenethyl, 4-trifluoromethylbenzyl, 2-trichloromethylphenethyl, 3-dichloromethylbenzyl, 4-trichloromethylphenethyl, 2-tribromomethylbenzyl, 3-dibromomethylphenethyl, 4-dibromomethylbenzyl, 3,5-bistrifluoromethylphenethyl, 2,5-bistrifluoromethylbenzyl, 2,6-bistrifluoromethylphenethyl, 2,4-bistrifluoromethylbenzyl, 3,5-bisdibromomethylphenethyl, 2,5-bisdibromomethylbenzyl, (2,6-bisdichloromethyl)(methyl)phenethyl, 2,4-bisdichloromethylbenzyl, 2,3,6-tristrifluoromethylphenethyl, 2,3,4-tristrifluoromethylbenzyl, 3,4,5-tristrifluoromethylphenethyl, 2,5,6-tristrifluoromethylbenzyl, 2,4,6-tristrifluoromethylphenethyl, 2,3,6-tristribromomethylbenzyl, 2,3,4-trisdibromomethylphenethyl, 3,4,5-tristribromomethylbenzyl, (2,5,6-trisdichloromethyl)

(methyl)phenethyl, 2,4,6-trisdichloromethylbenzyl, 1-trifluoromethyl-2-naphthylethyl, 2-trifluoromethyl-1-naphthylmethyl, 3-trifluoromethyl-1-naphthylethyl, 1-trichloromethyl-2-naphthylmethyl, 2-dichloromethyl-1-naphthylethyl, 3-tribromomethyl-1-naphthylmethyl, 3,8-bistrifluoromethyl-1-naphthylethyl, 2,3-bistrifluoromethyl-1-naphthylmethyl, 4,8-bistrifluoromethyl-1-naphthylethyl, 5,6-bistrifluoromethyl-1-naphthylmethyl, 3,8-bistrichloromethyl-1-naphthylethyl, 2,3-bisdichloromethyl-1-naphthylmethyl, 4,8-bisdibromomethyl-1-naphthylethyl, 5,6-bistribromomethyl-1-naphthylmethyl, 2,3,6-tristrifluoromethyl-1-naphthylethyl, 2,3,4-tristrifluoromethyl-1-naphthylmethyl, 3,4,5-tristrifluoromethyl-1-naphthylethyl, 4,5,6-tristrifluoromethyl-1-naphthylmethyl, 2,4,8-tristrifluoromethyl-1-naphthylmethyl, bis(4-trifluoromethylphenyl)methyl, (4-trifluoromethylphenyl)(phenyl)methyl, bis(2-trichloromethylphenyl)methyl, bis(3-trichloromethylphenyl)methyl, bis(4-trichloromethylphenyl)methyl, (2-tribromomethyl(phenyl)phenylmethyl, (3-tribromomethylphenyl)(phenyl)methyl, bis(4-tribromomethylphenyl)methyl, bis(3,5-bistrifluoromethylphenyl)methyl, bis(2,5-bistrifluoromethylphenyl)methyl, bis(2,6-bistrifluoromethylphenyl)methyl, (2,4-bistrifluoromethylphenyl)(phenyl)methyl, bis(3,5-bistribromomethylphenyl)methyl, (2,5-bistribromomethylphenyl)(phenyl)methyl, (2,6-bistrichloromethylphenyl)(phenyl)methyl, bis(2,4-bistrichloromethylphenyl)methyl and bis(2,3,6-tristrifluoromethylphenyl)methyl; aralkyl groups substituted with lower alkyl groups such as 2-methylbenzyl, 3-methylbenzyl, 4-methylbenzyl, 2-methylphenethyl, 4-methylphenethyl, 2-ethylbenzyl, 3-propylphenethyl, 4-ethylbenzyl, 2-butylphenethyl, 3-pentylbenzyl, 4-pentylphenethyl, 3,5-dimethylbenzyl, 2,5-dimethylphenethyl, 2,6-dimethylbenzyl, 2,4-dimethylphenethyl, 3,5-dibutylbenzyl, 2,5-dipentylphenethyl, 2,6-dipropylbenzyl, 2,4-dipropylphenethyl, 2,3,6-trimethylbenzyl, 2,3,4-trimethylphenethyl, 3,4,5-trimethylbenzyl, 2,4,6-trimethylbenzyl, 2,5,6-trimethylphenethyl, 2,3,6-tributylphenethyl, 2,3,4-tripentylbenzyl, 3,4,5-tributylphenethyl, 2,5,6-tripropylbenzyl, 2,4,6-tripropylphenethyl, 1-methyl-2-naphthylmethyl, 2-methyl-1-naphthylethyl, 3-methyl-1-naphthylmethyl, 1-ethyl-2-naphthylethyl, 2-propyl-1-naphthylmethyl, 3-butyl-1-naphthylethyl, 3,8-dimethyl-1-naphthylmethyl, 2,3-dimethyl-1-naphthylethyl, 4,8-dimethyl-1-naphthylmethyl, 5,6-dimethyl-1-naphthylethyl, 3,8-diethyl-1-naphthylmethyl, 2,3-dipropyl-1-naphthylmethyl, 4,8-dipentyl-1-naphthylethyl, 5,6-dibutyl-1-naphthylmethyl, 2,3,6-trimethyl-1-naphthylmethyl, 2,3,4-trimethyl-1-naphthylethyl, 3,4,5-trimethyl-1-naphthylmethyl, 4,5,6-trimethyl-1-naphthylmethyl, 2,4,8-trimethyl-1-naphthylmethyl, bis(2-methylphenyl)methyl, (3-methylphenyl)(phenyl)methyl, bis(4-methylphenyl)methyl, (4-methylphenyl)(phenyl)methyl, bis(2-ethylphenyl)methyl, bis(3-ethylphenyl)methyl, bis(4-ethylphenyl)methyl, (2-propylphenyl)(phenyl)methyl, (3-propylphenyl)(phenyl)methyl, bis(4-propylphenyl)methyl, bis(3,5-dimethylphenyl)methyl, bis(2,5-dimethylphenyl)methyl, bis(2,6-dimethylphenyl)methyl, (2,4-dimethylphenyl)(phenyl)methyl, bis(3,5-dipropylphenyl)methyl, (2,5-dipropylphenyl)(phenyl)methyl, (2,6-diethylphenyl)(phenyl)methyl, bis(2,4-diethylphenyl)methyl and bis(2,3,6-trimethylphenyl)methyl; aralkyl groups substituted with lower alkoxy groups such as 2-methoxybenzyl, 3-methoxybenzyl, 4-methoxybenzyl, 3-methoxyphenethyl, 2-ethoxyphenethyl, 3-propoxybenzyl, 4-ethoxyphenethyl, 2-butoxybenzyl, 3-pentoxyphenethyl, 4-pentoxybenzyl, 3,5-dimethoxyphenethyl, 2,5-dimethoxybenzyl, 2,6-dimethoxyphenethyl, 2,4-dimethoxybenzyl, 3,5-dibutoxyphenethyl, 2,5-dipentoxybenzyl, 2,6-dipropoxyphenethyl, 2,4-dipropoxybenzyl, 2,3,6-trimethoxyphenethyl, 2,3,4-trimethoxybenzyl, 3,4,5-trimethoxyphenethyl, 2,5,6-trimethoxybenzyl, 2,4,6-trimethoxyphenethyl, 2,3,6-tributoxybenzyl, 2,3,4-tripentoxyphenethyl, 3,4,5-tributoxybenzyl, 2,5,6-tripropoxyphenethyl, 2,4,6-tripropoxybenzyl, 1-methoxy-2-naphthylmethyl, 2-methoxy-1-naphthylmethyl, 3-methoxy-1-naphthylethyl, 1-ethoxy-2-naphthylmethyl, 2-propoxy-1-naphthylmethyl, 3-butoxy-1-naphthylethyl, 3,8-dimethoxy-1-naphthylmethyl, 2,3-dimethoxy-1-naphthylmethyl, 4,8-dimethoxy-1-naphthylethyl, 5,6-dimethoxy-1-naphthylmethyl, 3,8-diethoxy-1-naphthylmethyl, 2,3-dipropoxy-1-naphthylethyl, 4,8-dipentoxy-1-naphthylmethyl, 5,6-dibutoxy-1-naphthylmethyl, 2,3,6-trimethoxy-1-naphthylethyl, 2,3,4-trimethoxy-1-naphthylmethyl, 3,4,5-trimethoxy-1-naphthylmethyl, 4,5,6-trimethoxy-1-naphthylethyl, 2,4,8-trimethoxy-1-naphthylmethyl, bis(2-methoxyphenyl)methyl, (3-methoxyphenyl)(phenyl)methyl, bis(4-methoxyphenyl)methyl, (4-methoxyphenyl)(phenyl)methyl, bis(2-ethoxyphenyl)methyl, bis(3-ethoxyphenyl)methyl, bis(4-ethoxyphenyl)methyl, (2-propoxyphenyl)(phenyl)methyl, (3-propoxyphenyl)(phenyl)methyl, bis(4-propoxyphenyl)methyl, bis(3,5-dimethoxyphenyl)methyl, bis(2,5-dimethoxyphenyl)methyl, bis(2,6-dimethoxyphenyl)methyl, (2,4-dimethoxyphenyl)(phenyl)methyl, bis(3,5-dipropoxyphenyl)methyl, (2,5-dipropoxyphenyl)(phenyl)methyl, (2,6-diethoxyphenyl)(phenyl)methyl, bis(2,4-diethoxyphenyl)methyl and bis(2,3,6-trimethoxyphenyl)methyl; aralkyl groups substituted with amino groups such as 2-aminophenethyl, 3-aminobenzyl, 4-aminophenethyl, 3,5-diaminobenzyl, 2,5-diaminophenethyl, 2,6-diaminobenzyl, 2,4-diaminophenethyl, 2,3,6-triaminobenzyl, 2,3,4-triaminophenethyl, 3,4,5-triaminobenzyl, 2,5,6-triaminophenethyl, 2,4,6-triaminobenzyl, 1-amino-2-naphthylmethyl, 2-amino-1-naphthylethyl, 3-amino-1-naphthylmethyl, 3,8-diamino-1-naphthylmethyl, 2,3-diamino-1-naphthylethyl, 4,8-diamino-1-naphthylmethyl, 5,6-diamino-1-naphthylmethyl, 2,3,6-triamino-1-naphthylethyl, 2,3,4-triamino-1-naphthylmethyl, 3,4,5-triamino-1-naphthylmethyl, 4,5,6-triamino-1-naphthylethyl, 2,4,8-triamino-1-naphthylmethyl, bis(2-aminophenyl)methyl, (3-aminophenyl)(phenyl)methyl, bis(4-aminophenyl)methyl, (4-aminophenyl)(phenyl)methyl, bis(3,5-diaminophenyl)methyl, bis(2,5-diaminophenyl)methyl, bis(2,6-diaminophenyl)methyl, (2,4-diaminophenyl)(phenyl)methyl and bis(2,3,6-triaminophenyl)methyl; aralkyl groups substituted with nitro groups such as 2-nitrophenethyl, 3-nitrobenzyl, 4-nitrobenzyl, 4-nitrophenethyl, 3,5-dinitrobenzyl, 2,5-dinitrophenethyl, 2,6-dinitrobenzyl, 2,4-dinitrophenethyl, 2,3,6-trinitrobenzyl, 2,3,4-trinitrophenethyl, 3,4,5-trinitrobenzyl, 2,5,6-trinitrophenethyl, 2,4,6-trinitrobenzyl, 1-nitro-2-naphthylmethyl, 2-nitro-1-naphthylethyl, 3-nitro-1-naphthylmethyl, 3,8-dinitro-1-naphthylmethyl, 2,3-dinitro-1-naphthylethyl, 4,8-dinitro-1-naphthyhnethyl, 5,6-dinitro-1-naphthylmethyl, 2,3,6-trinitro-1-naphthylethyl, 2,3,4-trinitro-1-naphthylmethyl, 3,4,5-trinitro-1-naphthyhnethyl, 4,5,6-trinitro-1-naphthylmethyl, 2,4,8-trinitro-1-naphthylmethyl, bis(2-nitrophenyl)methyl, (3-nitrophenyl)(phenyl)methyl, bis(4-nitrophenyl)methyl, (4-nitrophenyl)(phenyl)methyl, bis(3,5-dinitrophenyl)methyl, bis(2,5-dinitrophenyl)methyl, bis(2,6-dinitrophenyl)methyl, (2,4-dinitrophenyl)(phenyl)methyl and bis(2,3,6-trinitrophenyl)methyl; and aralkyl groups substituted with cyano groups such as 2-cyanophenethyl, 3-cyanobenzyl, 4-cyanobenzyl, (4-cyanobenzyl)(diphenyl)methyl, 4-cyanophenethyl, 3,5-dicyanobenzyl, 2,5-dicyanophenethyl, 2,6-dicyanobenzyl, 2,4-dicyanophenethyl, 2,3,6-tricyanobenzyl, 2,3,4-tricyanophenethyl, 3,4,5-tricyanobenzyl, 2,5,6-tricyanophenethyl, 2,4,6-tricyanobenzyl, 1-cyano-2-naphthylmethyl, 3-cyano-1-naphthylmethyl, 3,8-dicyano-1-naphthylmethyl, 2,3-dicyano-1-naphthylethyl, 4,8-dicyano-1-naphthylmethyl, 5,6-dicyano-1-naphthylmethyl, 2,3,6-tricyano-1-naphthylethyl, 2,3,4-tricyano-1-naphthylmethyl, 3,4,5-tricyano-1-naphthylmethyl, 4,5,6-tricyano-1-naphthylethyl, 2,4,8-tricyano-1-naphthylmethyl, bis(2-cyanophenyl)methyl, (3-cyanophenyl)(phenyl)methyl, bis(4-cyanophenyl)methyl, (4-cyanophenyl)(phenyl)methyl, bis(3,5-dicyanophenyl)methyl, bis(2,5-dicyanophenyl)methyl, bis(2,6-dicyanophenyl)methyl, (2,4-dicyanophenyl)(phenyl)methyl and bis(2,3,6-tricyanophenyl)methyl.

Of the above, unsubstituted aralkyl groups and aralkyl groups substituted with one or more substituents selected from the group consisting of halogen atoms, lower alkyl groups and lower alkoxy groups are preferred, unsubstituted aralkyl groups and aralkyl groups substituted with one or more substituents selected from the group consisting of halogen atoms and lower alkyl groups are more preferred, and unsubstituted aralkyl groups are most preferred.

Where $R^a$, $R^b$ or Substituent 7 represent a lower alkylsulfonyl group, this is a group in which a lower alkyl group defined and exemplified above, is bonded to a sulfonyl group ($-SO_2-$). The lower alkylsulfonyl group is preferably a straight or branched chain alkylsulfonyl group having from 1 to 4 carbon atoms, more preferably a methylsulfonyl, ethylsulfonyl, propylsulfonyl, isopropylsulfonyl or butylsulfonyl group, and most preferably a methylsulfonyl, ethylsulfonyl or propylsulfonyl group.

Where $R^a$ and $R^b$ together with the nitrogen atom to which they are attached represent a heterocyclyl group, said heterocyclyl group is a 4- to 7-membered heterocyclyl group which contains one nitrogen atom and which optionally contains one further heteroatom selected from the group consisting of oxygen atoms, sulfur atoms and nitrogen atoms. Examples of such heterocyclyl groups include 1-azetidinyl, 1-pyrrolidinyl, 1-pyrrolinyl, 1-imidazolidinyl, 1-imidazolinyl, 1-pyrazolidinyl, 1-pyrazolinyl, 3-oxazolidinyl, 3-thiazolidinyl, 1-piperidyl, tetrahydropyridin-1-yl, dihydropyridin-1-yl, 1-piperazinyl, 4-morpholinyl, 4-thiomorpholinyl, 1-homopiperidyl, 8-azabicyclo[3.2.1]octan-8-yl, 8-azabicyclo[3.2.1]octen-8-yl, 9-azabicyclo[3.3.1]nonan-9-yl and 9-azabicyclo[3.3.1]nonen-9-yl.

Of the above, the heterocyclyl groups defined and exemplified above may be fused with an aryl group or a heteroaryl group. Examples of such fused heterocyclyl groups include tetrahydroquinolin-1-yl and tetrahydroisoquinolin-2-yl.

The halogen atoms in the definition of Substituent group α include fluorine, chlorine, bromine and iodine atoms, of which fluorine and chlorine atoms are preferred.

Where the substituent in the definition of Substituent group α is a lower alkoxy group, this is a group in which an oxygen atom is bonded to a lower alkyl group as defined and exemplified above. The alkoxy groups are preferably straight or branched chain alkoxy groups having from 1 to 4 carbon atoms, more preferably methoxy, ethoxy, propoxy, isopropoxy or butoxy groups, and particularly preferably methoxy, ethoxy or propoxy groups.

Where the substituent in the definition of Substituent group α is a halogeno lower alkoxy group, this is a group in which one or more hydrogen atoms of a lower alkoxy group as defined above are substituted with a halogen atom (s) as exemplified above. The halogeno lower alkoxy groups preferably have from 1 to 4 carbon atoms, and more preferably a difluoromethoxy, trifluoromethoxy or 2,2,2-trifluoroethoxy group. Difluoromethoxy groups are most preferred.

Where the substituent in the definition of Substituent group α is a lower alkylthio group, this is a group in which a sulfur atom is bonded to a lower alkyl group as defined and exemplified above. The lower alkylthio groups are preferably straight or branched chain alkylthio groups having from 1 to 4 carbon atoms, more preferably a methylthio, ethylthio, propylthio, isopropylthio or butylthio group, and particularly preferably a methylthio, ethylthio or propylthio group.

Where the substituent in the definition of Substituent group α is a halogeno lower alkylthio group, this is a group in which one or more hydrogen atoms of a lower alkylthio group as defined above are substituted with a halogen atom (s) as exemplified above. The halogeno lower alkylthio groups preferably have from 1 to 4 carbon atoms, and are more preferably a difluoromethylthio, trifluoromethylthio or 2,2,2-trifluoroethylthio group.

Where the substituent in the definition of Substituent group γ represents a lower alkoxyimino group, this is a group wherein the hydrogen atom of a hydroxyimino group is replaced by a lower alkyl group as defined and exemplified above. It is preferably an alkoxyimino group having from 1 to 4 carbon atoms, and more preferably a methoxyimino, ethoxyimino or propoxyimino group.

Where the substituent in the definition of Substituent group γ represents a lower alkylene group, it is a straight or branched chain alkylene group having from 2 to 6 carbon atoms, examples of which include ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene and hexamethylene groups. It is preferably a straight or branched chain alkylene group having from 2 to 4 carbon atoms, and more preferably it is an ethylene, trimethylene, propylene or tetramethylene group. It will be appreciated that the lower alkylene group together with the atom of the cyclic group B to which it is attached form a spiro group.

Where the substituent in the definition of Substituent group γ represents a lower alkylenedioxy group, this is a group wherein the alkylene moiety, which is a straight or branched chain alkylene group having from 1 to 6 carbon atoms, such as a methylene, ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene and hexamethylene, has two oxygen atoms attached to two separate carbon atoms thereof. Preferably, the alkylenedioxy group is a straight or branched chain alkylenedioxy group having from 1 to 4 carbon atoms, and more preferably it is a methylenedioxy, ethylenedioxy, trimethylenedioxy, propylenedioxy or tetramethylenedioxy group. It will be appreciated that the lower alkylenedioxy group together with the atom of the cyclic group B to which it is attached form a spiro group.

Where the substituent in the definition of Substituent group γ represents a lower alkylsulfinyl group, this is a group in which a lower alkyl group, defined and exemplified above, is bonded to a sulfinyl group ($-SO-$). The lower alkylsulfinyl group is preferably a straight or branched chain alkylsulfinyl group having from 1 to 4 carbon atoms, more preferably a methylsulfinyl, ethylsulfinyl, propylsulfinyl, isopropylsulfinyl or butylsulfinyl group, and most preferably a methylsulfinyl, ethylsulfinyl or propylsulfinyl group.

The aryloxy groups in the definitions of Substituent γ, and the aryloxy moiety of the aryloxy groups which are substituted with one or more substituents selected from Substituent group α and Substituent group β, are groups in which an oxygen atom is attached to an aryl group as defined and exemplified above, and examples include phenoxy, naphthyloxy, phenanthryloxy and anthracenyloxy groups. Of these, we prefer phenoxy and naphthyloxy groups, most preferably phenoxy groups.

Where the substituent in the definition of Substituent group γ represents a lower alkylidenyl group, this is a straight or branched chain alkylidenyl group having from 1 to 6 carbon atoms, examples of which include methylidenyl, ethylidenyl, propylidenyl, 1-methylethylidenyl, butylidenyl and 1-methylpropylidenyl groups. The lower alkylidenyl group is preferably a straight or branched alkylidenyl group having from 1 to 4 carbon atoms, and most preferably it is a methylidenyl, ethylidenyl or propylidenyl group.

Where the substituent in the definition of Substituent group γ represents an aralkylidenyl group, this is a group in which from 1 to 3 hydrogen atoms of an alkylidenyl group as defined and exemplified above are substituted with aryl groups as defined and exemplified above. Examples of these aralkylidenyl groups include benzylidenyl, phenylethylidenyl, phenylpropylidenyl and naphthylmethylidenyl groups. The aralkylidenyl group is preferably a straight or branched chain alkylidenyl group having from 1 to 4 carbon atoms which is substituted with a phenyl group or a naphthyl group, and most preferably it is a benzylidenyl or phenylethylidenyl group.

A preferred group of substituents of Substituent group α is Substituent group $α^1$ which consists of halogen atoms, lower alkoxy groups, halogeno lower alkoxy groups and groups of formula —$NR^aR^b$ (wherein one of $R^a$ and $R^b$ represents a hydrogen atom or a lower alkyl group, and the other represents a hydrogen atom, a lower alkyl group or an aralkyl group).

A preferred group of substituents of Substituent group β is Substituent group $β^1$ which consists of lower alkyl groups, halogeno lower alkyl groups, hydroxyl lower alkyl groups, nitro lower alkyl groups, amino lower alkyl groups, lower alkylamino lower alkyl groups, di(lower alkyl)amino lower alkyl groups and aralkylamino lower alkyl groups.

Where the substituent in the definition of Substituent group $β^1$ represents a halogeno lower alkyl group, this is a group in which one or more hydrogen atoms of a lower alkyl group as defined and exemplified above are substituted with a halogen atom (s) as defined and exemplified above. It is preferably a halogenoalkyl group having from 1 to 4 carbon atoms; more preferably it is a trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl or 2,2-dibromoethyl group; still more preferably it is a trifluoromethyl, trichloromethyl, difluoromethyl or fluoromethyl group; and most preferably it is a trifluoromethyl group.

Where the substituent in the definition of Substituent group $β^1$ represents a hydroxy lower alkyl group, this is a group in which one or more hydrogen atoms of a lower alkyl group as defined and exemplified above are substituted with a hydroxy group (s) as defined above. It is preferably a hydroxyalkyl group having from 1 to 4 carbon atoms, and most preferably it is a hydroxymethyl, 2-hydroxyethyl or 3-hydroxypropyl group.

Where the substituent in the definition of Substituent group $β^1$ represents a nitro lower alkyl group, this is a group in which one or more hydrogen atoms of a lower alkyl group as defined and exemplified above are substituted with a nitro group(s). It is preferably a nitroalkyl group having from 1 to 4 carbon atoms, and most preferably it is a nitromethyl, 2-nitroethyl or 3-nitropropyl group.

Where the substituent in the definition of Substituent group $β^1$ represents an amino lower alkyl group, a lower alkylamino lower alkyl group, a di(lower alkyl)amino lower alkyl group or an aralkylamino lower alkyl group, this is a group in which one or more hydrogen atoms of a lower alkyl group as defined and exemplified above are substituted with a group (s) of formula —$NR^aR^b$ (wherein one of $R^a$ and $R^b$ represents a hydrogen atom or a lower alkyl group, and the other represents a hydrogen atom, a lower alkyl group or an aralkyl group) in the definition of $α^1$. Of these, substituents in which the alkyl moiety which is substituted with the group of formula —$NR^aR^b$ has from 1 to 4 carbon atoms are preferred. Aminomethyl, 2-aminoethyl, 3-aminopropyl, methylaminomethyl, 2-(methylamino)ethyl, 3-(methylamino)propyl, ethylaminomethyl, 2-(ethylamino)ethyl, 3-(ethylamino)propyl, dimethylaminomethyl, 2-(dimethylamino)ethyl, 3-(dimethylamino)propyl, diethylaminomethyl, 2-(diethylamino)ethyl, 3-(diethylamino)propyl, benzylaminomethyl, 2-(benzylamino)ethyl and 3-(benzylamino)propyl groups are more preferred.

A preferred group of substituents of Substituent group γ is Substituent group $γ^1$ which consists of oxo groups, hydroxyimino groups, lower alkoxyimino groups, lower alkylene groups, lower alkylenedioxy groups, lower alkylsulfinyl groups, lower alkylsulfonyl groups, aryl groups and aryl groups which are substituted with one or more substituents selected from Substituent group α and Substituent group β.

The "esters and other derivatives" are compounds in which a functional group (for example, a hydroxyl group, an amino group, an imino group or a sulfonamide group) of said compound of the present invention is modified by the addition of a protecting group using conventional techniques well-known in the art.

In cases where the compound of the present invention includes, for example, a hydroxy group therein, such "esters and other derivatives" can be obtained by protecting said hydroxy group with a general protecting group or a protecting group which is capable of being removed by a metabolic process (e.g. hydrolysis) in vivo.

The general protecting group referred to above is a protecting group which is removable by a chemical process such as hydrogenolysis, hydrolysis, electrolysis or photolysis. Preferred examples of such a general protecting group include the following:

(i) aliphatic acyl groups (preferably lower aliphatic acyl groups having from 1 to 6 carbon atoms), examples of which include alkanoyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl groups, halogenated alkylcarbonyl groups such as chloroacetyl, dichloroacetyl, trichloroacetyl and trifluoroacetyl groups, lower alkoxyalkylcarbonyl groups such as methoxyacetyl groups, and unsaturated alkylcarbonyl groups such as acryloyl, propioloyl, methacryloyl, crotonoyl, isocrotonoyl and (E)-2-methyl-2-butenoyl groups;
(ii) aromatic acyl groups, examples of which include
arylcarbonyl groups such as benzoyl, α-naphthoyl and β-naphthoyl groups,
halogenated arylcarbonyl groups such as 2-bromobenzoyl, 4-chlorobenzoyl and 2,4,6-trifluorobenzoyl groups,
lower alkylated arylcarbonyl groups such as 2,4,6-trimethylbenzoyl and 4-toluoyl groups,
lower alkoxylated arylcarbonyl groups such as 4-anisoyl groups,
nitrated arylcarbonyl groups such as 4-nitrobenzoyl and 2-nitrobenzoyl groups,
lower alkoxycarbonylated arylcarbonyl groups such as 2-(methoxycarbonyl)benzoyl groups, and
arylated arylcarbonyl groups such as 4-phenylbenzoyl groups;
(iii) alkoxycarbonyl groups, examples of which include
lower alkoxycarbonyl groups such as methoxycarbonyl, ethoxycarbonyl, propoxycarbonyl, butoxycarbonyl, s-butoxycarbonyl, t-butoxycarbonyl and isobutoxycarbonyl groups, and
lower alkoxycarbonyl groups which are substituted with halogen atoms or tri(lower alkyl)silyl groups such as 2,2,2-trichloroethoxycarbonyl and 2-trimethylsilylethoxycarbonyl groups;
(iv) tetrahydropyranyl or tetrahydrothiopyranyl groups such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups;
(v) tetrahydrofuranyl or tetrahydrothiofuranyl groups such as tetrahydrofuran-2-yl and tetrahydrothiofuran-2-yl groups;
(vi) silyl groups, examples of which include
tri(lower alkyl)silyl groups such as trimethylsilyl, triethylsilyl, isopropyldimethylsilyl, t-butyldimethylsilyl, methyldiisopropylsilyl, methyl-di-t-butylsilyl and triisopropylsilyl groups, and
tri(lower alkyl)silyl groups which are substituted with one or two aryl groups such as diphenylmethylsilyl, diphenylbutylsilyl, diphenylisopropylsilyl and phenyldiisopropylsilyl groups;
(vii) alkoxymethyl groups, examples of which include
lower alkoxymethyl groups such as methoxymethyl, 1,1-dimethyl-1-methoxymethyl, ethoxymethyl, propoxymethyl, isopropoxymethyl, butoxymethyl and t-butoxymethyl groups,
lower alkoxylated lower alkoxymethyl groups such as 2-methoxyethoxymethyl groups, and
halogeno lower alkoxymethyl groups such as 2,2,2-trichloroethoxymethyl and bis(2-chloroethoxy)methyl groups;
(viii) substituted ethyl groups, examples of which include
lower alkoxylated ethyl groups such as 1-ethoxyethyl and 1-(isopropoxy)ethyl groups, and
halogenated ethyl groups such as 2,2,2-trichloroethyl groups;
(ix) aralkyl groups, examples of which include
lower alkyl groups which are substituted with from 1 to 3 aryl groups, examples of which include benzyl, α-naphthylmethyl, β-naphthylmethyl, diphenylmethyl, triphenylmethyl, α-naphthyldiphenylmethyl and 9-anthrylmethyl groups, and
lower alkyl groups which are substituted with from 1 to 3 aryl groups in which said aryl moiety is substituted with one or more substituents selected from the group consisting of lower alkyl, lower alkoxy, nitro, halogen and cyano, examples of which include 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups;
(x) alkenyloxycarbonyl groups, examples of which include vinyloxycarbonyl and allyloxycarbonyl groups; and
(xi) aralkyloxycarbonyl groups in which the aryl moiety may be substituted with one or two substituents selected from lower alkoxy groups and nitro groups, examples of which include benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The protecting group which is capable of being removed by a metabolic process (e.g. hydrolysis) in vivo is one, which on administration to the body of a live mammal is removable by a metabolic process (e.g. hydrolysis) to give the unprotected compound or a salt thereof. Whether an ester or other derivative of a compound has such a protecting group can be easily determined. The compound under investigation is intravenously administered to an experimental animal such as a rat or mouse and the body fluids of the animal are thereafter studied. If the unprotected compound or a pharmacologically acceptable salt thereof can be detected in the body fluids, the compound under investigation is judged to be a pharmacologically acceptable ester or other derivative.

Preferred examples of such a protecting group which is capable of being removed by a metabolic process (e.g. hydrolysis) in vivo include the following:
(i) 1-(acyloxy) lower alkyl groups, examples of which include 1-(lower aliphatic acyloxy) lower alkyl groups, examples of which include formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups,
1-(cycloalkylcarbonyloxy) lower alkyl groups, examples of which include cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl groups, and
1-(aromatic acyloxy) lower alkyl groups, examples of which include benzoyloxymethyl groups;
(ii) carbonyloxyalkyl groups, examples of which include
(lower alkoxycarbonyloxy)alkyl groups, examples of which include methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl groups, and oxodioxolenylmethyl groups, examples of which include (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups;

(iii) phthalidyl groups, examples of which include phthalidyl, dimethylphthalidyl and dimethoxyphthalidyl groups;
(iv) lower aliphatic acyl groups as defined and exemplified above;
(v) aromatic acyl groups as defined and exemplified above;
(vi) half-ester salt residues of succinic acid;
(vii) phosphate ester salt residues;
(viii) ester-forming residues of an amino acid;
(ix) carbamoyl groups;
(x) carbamoyl groups which are substituted with one or two lower alkyl groups; and
(xi) 1-(acyloxy)alkyloxycarbonyl groups, examples of which include pivaloyloxymethyloxycarbonyl groups.

Of the above protecting groups, carbonyloxyalkyl groups are preferred.

In the case where the compound of formula (I) of the present invention has an amino group, an imino group and/or a sulfonamide group, the compound can be converted to a derivative by modifying said functional groups.

Example of such derivatives include an amide derivative in which an aliphatic acyl group as defined and exemplified above or an aromatic acyl group as defined and exemplified above is bonded to a nitrogen atom of an amino group, imino group and/or sulfonamide group present in said compound of formula (I).

Where the compound of formula (I) of the present invention or a pharmacologically acceptable ester or other derivative thereof has a basic group, such as an amino group, the compound can be converted to a salt by reacting it with an acid, and in the case where the compound of formula (I) of the present invention or a pharmacologically acceptable ester or other derivative thereof has an acidic group, such as a sulfonamide group, the compound can be converted to a salt by reacting it with a base.

Preferred examples of the salts formed with a basic group include inorganic acid salts such as hydrohalogenated acid salts (e.g. hydrochlorides, hydrobromides and hydroiodides), nitrates, perchlorates, sulfates and phosphates; organic acid salts such as lower alkanesulfonates (e.g. methanesulfonates, trifluoromethanesulfonates and ethanesulfonates), arylsulfonates (e.g. benzenesulfonate or p-toluenesulfonate), acetates, malates, fumarates, succinates, citrates, ascorbates, tartrates, oxalates and maleates; and amino acid salts such as glycine salts, lysine salts, arginine salts, ornithine salts, glutamates and aspartates.

Preferred example of the salts formed with an acidic group include metal salts such as alkali metal salts (e.g. sodium salts, potassium salts and lithium salts), alkaline earth metal salts (e.g. calcium salts and magnesium salts), aluminum salts and iron salts; amine salts such as inorganic amine salts (e.g. ammonium salts) and organic amine salts (e.g. t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates.

The compound of formula (I) of the present invention or a pharmacologically acceptable salt or a pharmacologically acceptable ester or other derivative thereof can sometimes take up water upon exposure to the atmosphere or when recrystallized to absorb water or to form a hydrate and such hydrates are also included within the scope of the present invention.

The compounds of formula (I) of the present invention can sometimes exist in the form of geometrical isomers (cis and trans isomers or Z- and E-isomers) and, where said compounds contain one or more asymmetric centres, optical isomers. For the compounds of the present invention, each of said isomers and mixture of said isomers are depicted by a single formula, i.e. the formula (I). Accordingly, the present invention covers both the individual isomers and mixtures thereof in any proportion.

Specific examples of compounds of formula (I) of the present invention include the following compounds in Tables 1 to 13 below.

TABLE 1

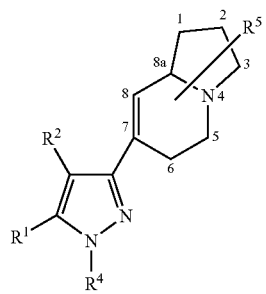

| Compound No. | $R^1$ | $R^2$ | $R^4$ | $R^5$ |
|---|---|---|---|---|
| 1-1 | Ph | 4-Pyr | H | — |
| 1-2 | Ph | 4-Pyr | H | 1-Me |
| 1-3 | Ph | 4-Pyr | H | 1-Et |
| 1-4 | Ph | 4-Pyr | H | 1-Pr |
| 1-5 | Ph | 4-Pyr | H | 1,1-diMe |
| 1-6 | Ph | 4-Pyr | H | 2-Me |
| 1-7 | Ph | 4-Pyr | H | 2-Et |

TABLE 1-continued

| Compound No. | R¹ | R² | R⁴ | R⁵ |
|---|---|---|---|---|
| 1-8 | Ph | 4-Pyr | H | 2-Pr |
| 1-9 | Ph | 4-Pyr | H | 2-Bu |
| 1-10 | Ph | 4-Pyr | H | 2-Allyl |
| 1-11 | Ph | 4-Pyr | H | 2-Ph |
| 1-12 | Ph | 4-Pyr | H | 2-Bn |
| 1-13 | Ph | 4-Pyr | H | 2-Phet |
| 1-14 | Ph | 4-Pyr | H | 2,2-diMe |
| 1-15 | Ph | 4-Pyr | H | 2-OH |
| 1-16 | Ph | 4-Pyr | H | 2-MeO |
| 1-17 | Ph | 4-Pyr | H | 2-EtO |
| 1-18 | Ph | 4-Pyr | H | 2-PrO |
| 1-19 | Ph | 4-Pyr | H | 2,2-di(MeO) |
| 1-20 | Ph | 4-Pyr | H | 2,2-di(EtO) |
| 1-21 | Ph | 4-Pyr | H | 2,2-OCH$_2$CH$_2$O— |
| 1-22 | Ph | 4-Pyr | H | 2-Oxo |
| 1-23 | Ph | 4-Pyr | H | 2-F |
| 1-24 | Ph | 4-Pyr | H | 2-Cl |
| 1-25 | Ph | 4-Pyr | H | 2-Br |
| 1-26 | Ph | 4-Pyr | H | 2-I |
| 1-27 | Ph | 4-Pyr | H | 2,2-diF |
| 1-28 | Ph | 4-Pyr | H | 2,2-diCl |
| 1-29 | Ph | 4-Pyr | H | 2,2-diBr |
| 1-30 | Ph | 4-Pyr | H | 3-Me |
| 1-31 | Ph | 4-Pyr | H | 3-Et |
| 1-32 | Ph | 4-Pyr | H | 3-Pr |
| 1-33 | Ph | 4-Pyr | H | 3,3-diMe |
| 1-34 | Ph | 4-Pyr | H | 5-Me |
| 1-35 | Ph | 4-Pyr | H | 5-Et |
| 1-36 | Ph | 4-Pyr | H | 5-Pr |
| 1-37 | Ph | 4-Pyr | H | 5,5-diMe |
| 1-38 | Ph | 4-Pyr | H | 6-Me |
| 1-39 | Ph | 4-Pyr | H | 6-Et |
| 1-40 | Ph | 4-Pyr | H | 6-Pr |
| 1-41 | Ph | 4-Pyr | H | 6,6-diMe |
| 1-42 | Ph | 4-Pyr | H | 6,6-diF |
| 1-43 | Ph | 4-Pyr | H | 6,6-CH$_2$CH$_2$— |
| 1-44 | Ph | 4-Pyr | H | 6-Oxo |
| 1-45 | Ph | 4-Pyr | H | 8-Me |
| 1-46 | Ph | 4-Pyr | H | 8-Et |
| 1-47 | Ph | 4-Pyr | H | 8-Pr |
| 1-48 | Ph | 4-Pyr | H | 8-Ph |
| 1-49 | Ph | 4-Pyr | H | 8a-Me |
| 1-50 | Ph | 4-Pyr | H | 8a-Et |
| 1-51 | Ph | 4-Pyr | H | 8a-Pr |
| 1-52 | Ph | 2-NH$_2$-4-Pym | H | — |
| 1-53 | Ph | 2-NH$_2$-4-Pym | H | 1-Me |
| 1-54 | Ph | 2-NH$_2$-4-Pym | H | 1-Et |
| 1-55 | Ph | 2-NH$_2$-4-Pym | H | 1-Pr |
| 1-56 | Ph | 2-NH$_2$-4-Pym | H | 1,1-diMe |
| 1-57 | Ph | 2-NH$_2$-4-Pym | H | 2-Me |
| 1-58 | Ph | 2-NH$_2$-4-Pym | H | 2-Et |
| 1-59 | Ph | 2-NH$_2$-4-Pym | H | 2-Pr |
| 1-60 | Ph | 2-NH$_2$-4-Pym | H | 2-Bu |
| 1-61 | Ph | 2-NH$_2$-4-Pym | H | 2-Allyl |
| 1-62 | Ph | 2-NH$_2$-4-Pym | H | 2-Ph |
| 1-63 | Ph | 2-NH$_2$-4-Pym | H | 2-Bn |
| 1-64 | Ph | 2-NH$_2$-4-Pym | H | 2-Phet |
| 1-65 | Ph | 2-NH$_2$-4-Pym | H | 2,2-diMe |
| 1-66 | Ph | 2-NH$_2$-4-Pym | H | 2-OH |
| 1-67 | Ph | 2-NH$_2$-4-Pym | H | 2-MeO |
| 1-68 | Ph | 2-NH$_2$-4-Pym | H | 2-EtO |
| 1-69 | Ph | 2-NH$_2$-4-Pym | H | 2-PrO |
| 1-70 | Ph | 2-NH$_2$-4-Pym | H | 2,2-di(MeO) |
| 1-71 | Ph | 2-NH$_2$-4-Pym | H | 2,2-di(EtO) |
| 1-72 | Ph | 2-NH$_2$-4-Pym | H | 2,2-OCH$_2$CH$_2$O— |
| 1-73 | Ph | 2-NH$_2$-4-Pym | H | 2-Oxo |
| 1-74 | Ph | 2-NH$_2$-4-Pym | H | 2-F |
| 1-75 | Ph | 2-NH$_2$-4-Pym | H | 2-Cl |
| 1-76 | Ph | 2-NH$_2$-4-Pym | H | 2-Br |
| 1-77 | Ph | 2-NH$_2$-4-Pym | H | 2-I |
| 1-78 | Ph | 2-NH$_2$-4-Pym | H | 2,2-diF |
| 1-79 | Ph | 2-NH$_2$-4-Pym | H | 2,2-diCl |
| 1-80 | Ph | 2-NH$_2$-4-Pym | H | 2,2-diBr |
| 1-81 | Ph | 2-NH$_2$-4-Pym | H | 3-Me |
| 1-82 | Ph | 2-NH$_2$-4-Pym | H | 3-Et |
| 1-83 | Ph | 2-NH$_2$-4-Pym | H | 3-Pr |
| 1-84 | Ph | 2-NH$_2$-4-Pym | H | 3,3-diMe |
| 1-85 | Ph | 2-NH$_2$-4-Pym | H | 5-Me |
| 1-86 | Ph | 2-NH$_2$-4-Pym | H | 5-Et |
| 1-87 | Ph | 2-NH$_2$-4-Pym | H | 5-Pr |
| 1-88 | Ph | 2-NH$_2$-4-Pym | H | 5,5-diMe |
| 1-89 | Ph | 2-NH$_2$-4-Pym | H | 6-Me |
| 1-90 | Ph | 2-NH$_2$-4-Pym | H | 6-Et |
| 1-91 | Ph | 2-NH$_2$-4-Pym | H | 6-Pr |
| 1-92 | Ph | 2-NH$_2$-4-Pym | H | 6,6-diMe |
| 1-93 | Ph | 2-NH$_2$-4-Pym | H | 6,6-diF |
| 1-94 | Ph | 2-NH$_2$-4-Pym | H | 6,6-CH$_2$CH$_2$— |
| 1-95 | Ph | 2-NH$_2$-4-Pym | H | 6-Oxo |
| 1-96 | Ph | 2-NH$_2$-4-Pym | H | 8-Me |
| 1-97 | Ph | 2-NH$_2$-4-Pym | H | 8-Et |
| 1-98 | Ph | 2-NH$_2$-4-Pym | H | 8-Pr |
| 1-99 | Ph | 2-NH$_2$-4-Pym | H | 8-Ph |
| 1-100 | Ph | 2-NH$_2$-4-Pym | H | 8a-Me |
| 1-101 | Ph | 2-NH$_2$-4-Pym | H | 8a-Et |
| 1-102 | Ph | 2-NH$_2$-4-Pym | H | 8a-Pr |
| 1-103 | Ph | 2-MeNH-4-Pym | H | — |
| 1-104 | Ph | 2-MeNH-4-Pym | H | 1-Me |
| 1-105 | Ph | 2-MeNH-4-Pym | H | 1-Et |
| 1-106 | Ph | 2-MeNH-4-Pym | H | 1-Pr |
| 1-107 | Ph | 2-MeNH-4-Pym | H | 1,1-diMe |
| 1-108 | Ph | 2-MeNH-4-Pym | H | 2-Me |
| 1-109 | Ph | 2-MeNH-4-Pym | H | 2-Et |
| 1-110 | Ph | 2-MeNH-4-Pym | H | 2-Pr |
| 1-111 | Ph | 2-MeNH-4-Pym | H | 2-Bu |
| 1-112 | Ph | 2-MeNH-4-Pym | H | 2-Allyl |
| 1-113 | Ph | 2-MeNH-4-Pym | H | 2-Ph |
| 1-114 | Ph | 2-MeNH-4-Pym | H | 2-Bn |
| 1-115 | Ph | 2-MeNH-4-Pym | H | 2-Phet |
| 1-116 | Ph | 2-MeNH-4-Pym | H | 2,2-diMe |
| 1-117 | Ph | 2-MeNH-4-Pym | H | 2-OH |
| 1-118 | Ph | 2-MeNH-4-Pym | H | 2-MeO |
| 1-119 | Ph | 2-MeNH-4-Pym | H | 2-EtO |
| 1-120 | Ph | 2-MeNH-4-Pym | H | 2-PrO |
| 1-121 | Ph | 2-MeNH-4-Pym | H | 2,2-di(MeO) |
| 1-122 | Ph | 2-MeNH-4-Pym | H | 2,2-di(EtO) |
| 1-123 | Ph | 2-MeNH-4-Pym | H | 2,2-OCH$_2$CH$_2$O— |
| 1-124 | Ph | 2-MeNH-4-Pym | H | 2-Oxo |
| 1-125 | Ph | 2-MeNH-4-Pym | H | 2-F |
| 1-126 | Ph | 2-MeNH-4-Pym | H | 2-Cl |
| 1-127 | Ph | 2-MeNH-4-Pym | H | 2-Br |

TABLE 1-continued

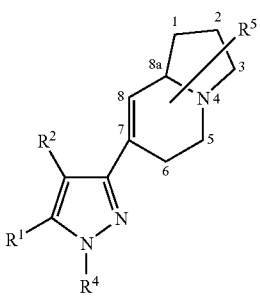

| Compound No. | R¹ | R² | R⁴ | R⁵ |
|---|---|---|---|---|
| 1-128 | Ph | 2-MeNH-4-Pym | H | 2-I |
| 1-129 | Ph | 2-MeNH-4-Pym | H | 2,2-diF |
| 1-130 | Ph | 2-MeNH-4-Pym | H | 2,2-diCl |
| 1-131 | Ph | 2-MeNH-4-Pym | H | 2,2-diBr |
| 1-132 | Ph | 2-MeNH-4-Pym | H | 3-Me |
| 1-133 | Ph | 2-MeNH-4-Pym | H | 3-Et |
| 1-134 | Ph | 2-MeNH-4-Pym | H | 3-Pr |
| 1-135 | Ph | 2-MeNH-4-Pym | H | 3,3-diMe |
| 1-136 | Ph | 2-MeNH-4-Pym | H | 5-Me |
| 1-137 | Ph | 2-MeNH-4-Pym | H | 5-Et |
| 1-138 | Ph | 2-MeNH-4-Pym | H | 5-Pr |
| 1-139 | Ph | 2-MeNH-4-Pym | H | 5,5-diMe |
| 1-140 | Ph | 2-MeNH-4-Pym | H | 6-Me |
| 1-141 | Ph | 2-MeNH-4-Pym | H | 6-Et |
| 1-142 | Ph | 2-MeNH-4-Pym | H | 6-Pr |
| 1-143 | Ph | 2-MeNH-4-Pym | H | 6,6-diMe |
| 1-144 | Ph | 2-MeNH-4-Pym | H | 6,6-diF |
| 1-145 | Ph | 2-MeNH-4-Pym | H | 6,6-CH₂CH₂— |
| 1-146 | Ph | 2-MeNH-4-Pym | H | 6-Oxo |
| 1-147 | Ph | 2-MeNH-4-Pym | H | 8-Me |
| 1-148 | Ph | 2-MeNH-4-Pym | H | 8-Et |
| 1-149 | Ph | 2-MeNH-4-Pym | H | 8-Pr |
| 1-150 | Ph | 2-MeNH-4-Pym | H | 8-Ph |
| 1-151 | Ph | 2-MeNH-4-Pym | H | 8a-Me |
| 1-152 | Ph | 2-MeNH-4-Pym | H | 8a-Et |
| 1-153 | Ph | 2-MeNH-4-Pym | H | 8a-Pr |
| 1-154 | 3-F-Ph | 4-Pyr | H | — |
| 1-155 | 3-F-Ph | 4-Pyr | H | 1-Me |
| 1-156 | 3-F-Ph | 4-Pyr | H | 1-Et |
| 1-157 | 3-F-Ph | 4-Pyr | H | 1-Pr |
| 1-158 | 3-F-Ph | 4-Pyr | H | 1,1-diMe |
| 1-159 | 3-F-Ph | 4-Pyr | H | 2-Me |
| 1-160 | 3-F-Ph | 4-Pyr | H | 2-Et |
| 1-161 | 3-F-Ph | 4-Pyr | H | 2-Pr |
| 1-162 | 3-F-Ph | 4-Pyr | H | 2-Bu |
| 1-163 | 3-F-Ph | 4-Pyr | H | 2-Allyl |
| 1-164 | 3-F-Ph | 4-Pyr | H | 2-Ph |
| 1-165 | 3-F-Ph | 4-Pyr | H | 2-Bn |
| 1-166 | 3-F-Ph | 4-Pyr | H | 2-Phet |
| 1-167 | 3-F-Ph | 4-Pyr | H | 2,2-diMe |
| 1-168 | 3-F-Ph | 4-Pyr | H | 2-OH |
| 1-169 | 3-F-Ph | 4-Pyr | H | 2-MeO |
| 1-170 | 3-F-Ph | 4-Pyr | H | 2-EtO |
| 1-171 | 3-F-Ph | 4-Pyr | H | 2-PrO |
| 1-172 | 3-F-Ph | 4-Pyr | H | 2,2-di(MeO) |
| 1-173 | 3-F-Ph | 4-Pyr | H | 2,2-di(EtO) |
| 1-174 | 3-F-Ph | 4-Pyr | H | 2,2-OCH₂CH₂O— |
| 1-175 | 3-F-Ph | 4-Pyr | H | 2-Oxo |
| 1-176 | 3-F-Ph | 4-Pyr | H | 2-F |
| 1-177 | 3-F-Ph | 4-Pyr | H | 2-Cl |
| 1-178 | 3-F-Ph | 4-Pyr | H | 2-Br |
| 1-179 | 3-F-Ph | 4-Pyr | H | 2-I |
| 1-180 | 3-F-Ph | 4-Pyr | H | 2,2-diF |
| 1-181 | 3-F-Ph | 4-Pyr | H | 2,2-diCl |
| 1-182 | 3-F-Ph | 4-Pyr | H | 2,2-diBr |
| 1-183 | 3-F-Ph | 4-Pyr | H | 3-Me |
| 1-184 | 3-F-Ph | 4-Pyr | H | 3-Et |
| 1-185 | 3-F-Ph | 4-Pyr | H | 3-Pr |
| 1-186 | 3-F-Ph | 4-Pyr | H | 3,3-diMe |
| 1-187 | 3-F-Ph | 4-Pyr | H | 5-Me |

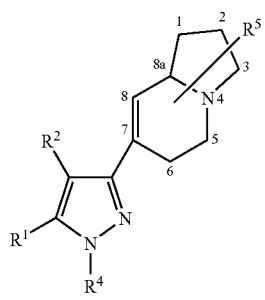

| Compound No. | R¹ | R² | R⁴ | R⁵ |
|---|---|---|---|---|
| 1-188 | 3-F-Ph | 4-Pyr | H | 5-Et |
| 1-189 | 3-F-Ph | 4-Pyr | H | 5-Pr |
| 1-190 | 3-F-Ph | 4-Pyr | H | 5,5-diMe |
| 1-191 | 3-F-Ph | 4-Pyr | H | 6-Me |
| 1-192 | 3-F-Ph | 4-Pyr | H | 6-Et |
| 1-193 | 3-F-Ph | 4-Pyr | H | 6-Pr |
| 1-194 | 3-F-Ph | 4-Pyr | H | 6,6-diMe |
| 1-195 | 3-F-Ph | 4-Pyr | H | 6,6-diF |
| 1-196 | 3-F-Ph | 4-Pyr | H | 6,6-CH₂CH₂— |
| 1-197 | 3-F-Ph | 4-Pyr | H | 6-Oxo |
| 1-198 | 3-F-Ph | 4-Pyr | H | 8-Me |
| 1-199 | 3-F-Ph | 4-Pyr | H | 8-Et |
| 1-200 | 3-F-Ph | 4-Pyr | H | 8-Pr |
| 1-201 | 3-F-Ph | 4-Pyr | H | 8-Ph |
| 1-202 | 3-F-Ph | 4-Pyr | H | 8a-Me |
| 1-203 | 3-F-Ph | 4-Pyr | H | 8a-Et |
| 1-204 | 3-F-Ph | 4-Pyr | H | 8a-Pr |
| 1-205 | 3-F-Ph | 2-NH₂-4-Pym | H | — |
| 1-206 | 3-F-Ph | 2-NH₂-4-Pym | H | 1-Me |
| 1-207 | 3-F-Ph | 2-NH₂-4-Pym | H | 1-Et |
| 1-208 | 3-F-Ph | 2-NH₂-4-Pym | H | 1-Pr |
| 1-209 | 3-F-Ph | 2-NH₂-4-Pym | H | 1,1-diMe |
| 1-210 | 3-F-Ph | 2-NH₂-4-Pym | H | 2-Me |
| 1-211 | 3-F-Ph | 2-NH₂-4-Pym | H | 2-Et |
| 1-212 | 3-F-Ph | 2-NH₂-4-Pym | H | 2-Pr |
| 1-213 | 3-F-Ph | 2-NH₂-4-Pym | H | 2-Bu |
| 1-214 | 3-F-Ph | 2-NH₂-4-Pym | H | 2-Allyl |
| 1-215 | 3-F-Ph | 2-NH₂-4-Pym | H | 2-Ph |
| 1-216 | 3-F-Ph | 2-NH₂-4-Pym | H | 2-Bn |
| 1-217 | 3-F-Ph | 2-NH₂-4-Pym | H | 2-Phet |
| 1-218 | 3-F-Ph | 2-NH₂-4-Pym | H | 2,2-diMe |
| 1-219 | 3-F-Ph | 2-NH₂-4-Pym | H | 2-OH |
| 1-220 | 3-F-Ph | 2-NH₂-4-Pym | H | 2-MeO |
| 1-221 | 3-F-Ph | 2-NH₂-4-Pym | H | 2-EtO |
| 1-222 | 3-F-Ph | 2-NH₂-4-Pym | H | 2-PrO |
| 1-223 | 3-F-Ph | 2-NH₂-4-Pym | H | 2,2-di(MeO) |
| 1-224 | 3-F-Ph | 2-NH₂-4-Pym | H | 2,2-di(EtO) |
| 1-225 | 3-F-Ph | 2-NH₂-4-Pym | H | 2,2-OCH₂CH₂O— |
| 1-226 | 3-F-Ph | 2-NH₂-4-Pym | H | 2-Oxo |
| 1-227 | 3-F-Ph | 2-NH₂-4-Pym | H | 2-F |
| 1-228 | 3-F-Ph | 2-NH₂-4-Pym | H | 2-Cl |
| 1-229 | 3-F-Ph | 2-NH₂-4-Pym | H | 2-Br |
| 1-230 | 3-F-Ph | 2-NH₂-4-Pym | H | 2-I |
| 1-231 | 3-F-Ph | 2-NH₂-4-Pym | H | 2,2-diF |
| 1-232 | 3-F-Ph | 2-NH₂-4-Pym | H | 2,2-diCl |
| 1-233 | 3-F-Ph | 2-NH₂-4-Pym | H | 2,2-diBr |
| 1-234 | 3-F-Ph | 2-NH₂-4-Pym | H | 3-Me |
| 1-235 | 3-F-Ph | 2-NH₂-4-Pym | H | 3-Et |
| 1-236 | 3-F-Ph | 2-NH₂-4-Pym | H | 3-Pr |
| 1-237 | 3-F-Ph | 2-NH₂-4-Pym | H | 3,3-diMe |
| 1-238 | 3-F-Ph | 2-NH₂-4-Pym | H | 5-Me |
| 1-239 | 3-F-Ph | 2-NH₂-4-Pym | H | 5-Et |
| 1-240 | 3-F-Ph | 2-NH₂-4-Pym | H | 5-Pr |
| 1-241 | 3-F-Ph | 2-NH₂-4-Pym | H | 5,5-diMe |
| 1-242 | 3-F-Ph | 2-NH₂-4-Pym | H | 6-Me |
| 1-243 | 3-F-Ph | 2-NH₂-4-Pym | H | 6-Et |
| 1-244 | 3-F-Ph | 2-NH₂-4-Pym | H | 6-Pr |
| 1-245 | 3-F-Ph | 2-NH₂-4-Pym | H | 6,6-diMe |
| 1-246 | 3-F-Ph | 2-NH₂-4-Pym | H | 6,6-diF |
| 1-247 | 3-F-Ph | 2-NH₂-4-Pym | H | 6,6-CH₂CH₂— |

TABLE 1-continued

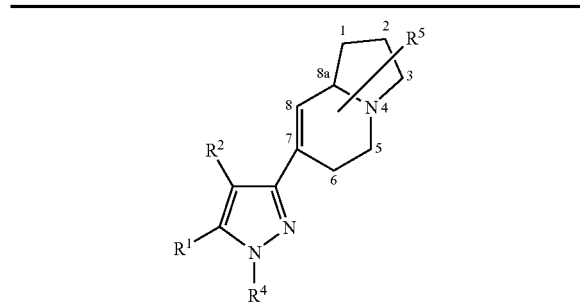

| Compound No. | R¹ | R² | R⁴ | R⁵ |
|---|---|---|---|---|
| 1-248 | 3-F-Ph | 2-NH₂-4-Pym | H | 6-Oxo |
| 1-249 | 3-F-Ph | 2-NH₂-4-Pym | H | 8-Me |
| 1-250 | 3-F-Ph | 2-NH₂-4-Pym | H | 8-Et |
| 1-251 | 3-F-Ph | 2-NH₂-4-Pym | H | 8-Pr |
| 1-252 | 3-F-Ph | 2-NH₂-4-Pym | H | 8-Ph |
| 1-253 | 3-F-Ph | 2-NH₂-4-Pym | H | 8a-Me |
| 1-254 | 3-F-Ph | 2-NH₂-4-Pym | H | 8a-Et |
| 1-255 | 3-F-Ph | 2-NH₂-4-Pym | H | 8a-Pr |
| 1-256 | 3-F-Ph | 2-MeNH-4-Pym | H | — |
| 1-257 | 3-F-Ph | 2-MeNH-4-Pym | H | 1-Me |
| 1-258 | 3-F-Ph | 2-MeNH-4-Pym | H | 1-Et |
| 1-259 | 3-F-Ph | 2-MeNH-4-Pym | H | 1-Pr |
| 1-260 | 3-F-Ph | 2-MeNH-4-Pym | H | 1,1-diMe |
| 1-261 | 3-F-Ph | 2-MeNH-4-Pym | H | 2-Me |
| 1-262 | 3-F-Ph | 2-MeNH-4-Pym | H | 2-Et |
| 1-263 | 3-F-Ph | 2-MeNH-4-Pym | H | 2-Pr |
| 1-264 | 3-F-Ph | 2-MeNH-4-Pym | H | 2-Bu |
| 1-265 | 3-F-Ph | 2-MeNH-4-Pym | H | 2-Allyl |
| 1-266 | 3-F-Ph | 2-MeNH-4-Pym | H | 2-Ph |
| 1-267 | 3-F-Ph | 2-MeNH-4-Pym | H | 2-Bn |
| 1-268 | 3-F-Ph | 2-MeNH-4-Pym | H | 2-Phet |
| 1-269 | 3-F-Ph | 2-MeNH-4-Pym | H | 2,2-diMe |
| 1-270 | 3-F-Ph | 2-MeNH-4-Pym | H | 2-OH |
| 1-271 | 3-F-Ph | 2-MeNH-4-Pym | H | 2-MeO |
| 1-272 | 3-F-Ph | 2-MeNH-4-Pym | H | 2-EtO |
| 1-273 | 3-F-Ph | 2-MeNH-4-Pym | H | 2-PrO |
| 1-274 | 3-F-Ph | 2-MeNH-4-Pym | H | 2,2-di(MeO) |
| 1-275 | 3-F-Ph | 2-MeNH-4-Pym | H | 2,2-di(EtO) |
| 1-276 | 3-F-Ph | 2-MeNH-4-Pym | H | 2,2-OCH₂CH₂O— |
| 1-277 | 3-F-Ph | 2-MeNH-4-Pym | H | 2-Oxo |
| 1-278 | 3-F-Ph | 2-MeNH-4-Pym | H | 2-F |
| 1-279 | 3-F-Ph | 2-MeNH-4-Pym | H | 2-Cl |
| 1-280 | 3-F-Ph | 2-MeNH-4-Pym | H | 2-Br |
| 1-281 | 3-F-Ph | 2-MeNH-4-Pym | H | 2-I |
| 1-282 | 3-F-Ph | 2-MeNH-4-Pym | H | 2,2-diF |
| 1-283 | 3-F-Ph | 2-MeNH-4-Pym | H | 2,2-diCl |
| 1-284 | 3-F-Ph | 2-MeNH-4-Pym | H | 2,2-diBr |
| 1-285 | 3-F-Ph | 2-MeNH-4-Pym | H | 3-Me |
| 1-286 | 3-F-Ph | 2-MeNH-4-Pym | H | 3-Et |
| 1-287 | 3-F-Ph | 2-MeNH-4-Pym | H | 3-Pr |
| 1-288 | 3-F-Ph | 2-MeNH-4-Pym | H | 3,3-diMe |
| 1-289 | 3-F-Ph | 2-MeNH-4-Pym | H | 5-Me |
| 1-290 | 3-F-Ph | 2-MeNH-4-Pym | H | 5-Et |
| 1-291 | 3-F-Ph | 2-MeNH-4-Pym | H | 5-Pr |
| 1-292 | 3-F-Ph | 2-MeNH-4-Pym | H | 5,5-diMe |
| 1-293 | 3-F-Ph | 2-MeNH-4-Pym | H | 6-Me |
| 1-294 | 3-F-Ph | 2-MeNH-4-Pym | H | 6-Et |
| 1-295 | 3-F-Ph | 2-MeNH-4-Pym | H | 6-Pr |
| 1-296 | 3-F-Ph | 2-MeNH-4-Pym | H | 6,6-diMe |
| 1-297 | 3-F-Ph | 2-MeNH-4-Pym | H | 6,6-diF |
| 1-298 | 3-F-Ph | 2-MeNH-4-Pym | H | 6,6-CH₂CH₂— |
| 1-299 | 3-F-Ph | 2-MeNH-4-Pym | H | 6-Oxo |
| 1-300 | 3-F-Ph | 2-MeNH-4-Pym | H | 8-Me |
| 1-301 | 3-F-Ph | 2-MeNH-4-Pym | H | 8-Et |
| 1-302 | 3-F-Ph | 2-MeNH-4-Pym | H | 8-Pr |
| 1-303 | 3-F-Ph | 2-MeNH-4-Pym | H | 8-Ph |
| 1-304 | 3-F-Ph | 2-MeNH-4-Pym | H | 8a-Me |
| 1-305 | 3-F-Ph | 2-MeNH-4-Pym | H | 8a-Et |
| 1-306 | 3-F-Ph | 2-MeNH-4-Pym | H | 8a-Pr |
| 1-307 | 4-F-Ph | 4-Pyr | H | — |
| 1-308 | 4-F-Ph | 4-Pyr | H | 1-Me |
| 1-309 | 4-F-Ph | 4-Pyr | H | 1-Et |
| 1-310 | 4-F-Ph | 4-Pyr | H | 1-Pr |
| 1-311 | 4-F-Ph | 4-Pyr | H | 1,1-diMe |
| 1-312 | 4-F-Ph | 4-Pyr | H | 2-Me |
| 1-313 | 4-F-Ph | 4-Pyr | H | 2-Et |
| 1-314 | 4-F-Ph | 4-Pyr | H | 2-Pr |
| 1-315 | 4-F-Ph | 4-Pyr | H | 2-Bu |
| 1-316 | 4-F-Ph | 4-Pyr | H | 2-Allyl |
| 1-317 | 4-F-Ph | 4-Pyr | H | 2-Ph |
| 1-318 | 4-F-Ph | 4-Pyr | H | 2-Bn |
| 1-319 | 4-F-Ph | 4-Pyr | H | 2-Phet |
| 1-320 | 4-F-Ph | 4-Pyr | H | 2,2-diMe |
| 1-321 | 4-F-Ph | 4-Pyr | H | 2-OH |
| 1-322 | 4-F-Ph | 4-Pyr | H | 2-MeO |
| 1-323 | 4-F-Ph | 4-Pyr | H | 2-EtO |
| 1-324 | 4-F-Ph | 4-Pyr | H | 2-PrO |
| 1-325 | 4-F-Ph | 4-Pyr | H | 2,2-di(MeO) |
| 1-326 | 4-F-Ph | 4-Pyr | H | 2,2-di(EtO) |
| 1-327 | 4-F-Ph | 4-Pyr | H | 2,2-OCH₂CH₂O— |
| 1-328 | 4-F-Ph | 4-Pyr | H | 2-Oxo |
| 1-329 | 4-F-Ph | 4-Pyr | H | 2-F |
| 1-330 | 4-F-Ph | 4-Pyr | H | 2-Cl |
| 1-331 | 4-F-Ph | 4-Pyr | H | 2-Br |
| 1-332 | 4-F-Ph | 4-Pyr | H | 2-I |
| 1-333 | 4-F-Ph | 4-Pyr | H | 2,2-diF |
| 1-334 | 4-F-Ph | 4-Pyr | H | 2,2-diCl |
| 1-335 | 4-F-Ph | 4-Pyr | H | 2,2-diBr |
| 1-336 | 4-F-Ph | 4-Pyr | H | 3-Me |
| 1-337 | 4-F-Ph | 4-Pyr | H | 3-Et |
| 1-338 | 4-F-Ph | 4-Pyr | H | 3-Pr |
| 1-339 | 4-F-Ph | 4-Pyr | H | 3,3-diMe |
| 1-340 | 4-F-Ph | 4-Pyr | H | 5-Me |
| 1-341 | 4-F-Ph | 4-Pyr | H | 5-Et |
| 1-342 | 4-F-Ph | 4-Pyr | H | 5-Pr |
| 1-343 | 4-F-Ph | 4-Pyr | H | 5,5-diMe |
| 1-344 | 4-F-Ph | 4-Pyr | H | 6-Me |
| 1-345 | 4-F-Ph | 4-Pyr | H | 6-Et |
| 1-346 | 4-F-Ph | 4-Pyr | H | 6-Pr |
| 1-347 | 4-F-Ph | 4-Pyr | H | 6,6-diMe |
| 1-348 | 4-F-Ph | 4-Pyr | H | 6,6-diF |
| 1-349 | 4-F-Ph | 4-Pyr | H | 6,6-CH₂CH₂— |
| 1-350 | 4-F-Ph | 4-Pyr | H | 6-Oxo |
| 1-351 | 4-F-Ph | 4-Pyr | H | 8-Me |
| 1-352 | 4-F-Ph | 4-Pyr | H | 8-Et |
| 1-353 | 4-F-Ph | 4-Pyr | H | 8-Pr |
| 1-354 | 4-F-Ph | 4-Pyr | H | 8-Ph |
| 1-355 | 4-F-Ph | 4-Pyr | H | 8a-Me |
| 1-356 | 4-F-Ph | 4-Pyr | H | 8a-Et |
| 1-357 | 4-F-Ph | 4-Pyr | H | 8a-Pr |
| 1-358 | 4-F-Ph | 2-NH₂-4-Pym | H | — |
| 1-359 | 4-F-Ph | 2-NH₂-4-Pym | H | 1-Me |
| 1-360 | 4-F-Ph | 2-NH₂-4-Pym | H | 1-Et |
| 1-361 | 4-F-Ph | 2-NH₂-4-Pym | H | 1-Pr |
| 1-362 | 4-F-Ph | 2-NH₂-4-Pym | H | 1,1-diMe |
| 1-363 | 4-F-Ph | 2-NH₂-4-Pym | H | 2-Me |
| 1-364 | 4-F-Ph | 2-NH₂-4-Pym | H | 2-Et |
| 1-365 | 4-F-Ph | 2-NH₂-4-Pym | H | 2-Pr |
| 1-366 | 4-F-Ph | 2-NH₂-4-Pym | H | 2-Bu |
| 1-367 | 4-F-Ph | 2-NH₂-4-Pym | H | 2-Allyl |

TABLE 1-continued

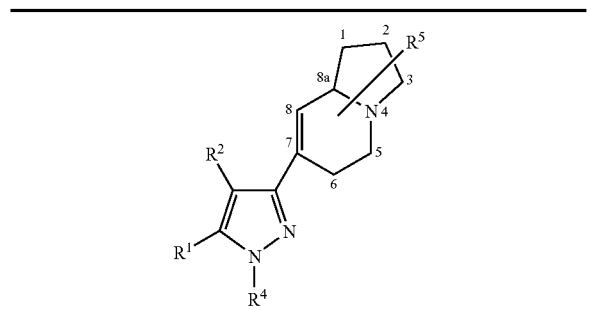

| Compound No. | R¹ | R² | R⁴ | R⁵ |
|---|---|---|---|---|
| 1-368 | 4-F-Ph | 2-NH₂-4-Pym | H | 2-Ph |
| 1-369 | 4-F-Ph | 2-NH₂-4-Pym | H | 2-Bn |
| 1-370 | 4-F-Ph | 2-NH₂-4-Pym | H | 2-Phet |
| 1-371 | 4-F-Ph | 2-NH₂-4-Pym | H | 2,2-diMe |
| 1-372 | 4-F-Ph | 2-NH₂-4-Pym | H | 2-OH |
| 1-373 | 4-F-Ph | 2-NH₂-4-Pym | H | 2-MeO |
| 1-374 | 4-F-Ph | 2-NH₂-4-Pym | H | 2-EtO |
| 1-375 | 4-F-Ph | 2-NH₂-4-Pym | H | 2-PrO |
| 1-376 | 4-F-Ph | 2-NH₂-4-Pym | H | 2,2-di(MeO) |
| 1-377 | 4-F-Ph | 2-NH₂-4-Pym | H | 2,2-di(EtO) |
| 1-378 | 4-F-Ph | 2-NH₂-4-Pym | H | 2,2-OCH₂CH₂O— |
| 1-379 | 4-F-Ph | 2-NH₂-4-Pym | H | 2-Oxo |
| 1-380 | 4-F-Ph | 2-NH₂-4-Pym | H | 2-F |
| 1-381 | 4-F-Ph | 2-NH₂-4-Pym | H | 2-Cl |
| 1-382 | 4-F-Ph | 2-NH₂-4-Pym | H | 2-Br |
| 1-383 | 4-F-Ph | 2-NH₂-4-Pym | H | 2-I |
| 1-384 | 4-F-Ph | 2-NH₂-4-Pym | H | 2,2-diF |
| 1-385 | 4-F-Ph | 2-NH₂-4-Pym | H | 2,2-diCl |
| 1-386 | 4-F-Ph | 2-NH₂-4-Pym | H | 2,2-diBr |
| 1-387 | 4-F-Ph | 2-NH₂-4-Pym | H | 3-Me |
| 1-388 | 4-F-Ph | 2-NH₂-4-Pym | H | 3-Et |
| 1-389 | 4-F-Ph | 2-NH₂-4-Pym | H | 3-Pr |
| 1-390 | 4-F-Ph | 2-NH₂-4-Pym | H | 3,3-diMe |
| 1-391 | 4-F-Ph | 2-NH₂-4-Pym | H | 5-Me |
| 1-392 | 4-F-Ph | 2-NH₂-4-Pym | H | 5-Et |
| 1-393 | 4-F-Ph | 2-NH₂-4-Pym | H | 5-Pr |
| 1-394 | 4-F-Ph | 2-NH₂-4-Pym | H | 5,5-diMe |
| 1-395 | 4-F-Ph | 2-NH₂-4-Pym | H | 6-Me |
| 1-396 | 4-F-Ph | 2-NH₂-4-Pym | H | 6-Et |
| 1-397 | 4-F-Ph | 2-NH₂-4-Pym | H | 6-Pr |
| 1-398 | 4-F-Ph | 2-NH₂-4-Pym | H | 6,6-diMe |
| 1-399 | 4-F-Ph | 2-NH₂-4-Pym | H | 6,6-diF |
| 1-400 | 4-F-Ph | 2-NH₂-4-Pym | H | 6,6-CH₂CH₂— |
| 1-401 | 4-F-Ph | 2-NH₂-4-Pym | H | 6-Oxo |
| 1-402 | 4-F-Ph | 2-NH₂-4-Pym | H | 8-Me |
| 1-403 | 4-F-Ph | 2-NH₂-4-Pym | H | 8-Et |
| 1-404 | 4-F-Ph | 2-NH₂-4-Pym | H | 8-Pr |
| 1-405 | 4-F-Ph | 2-NH₂-4-Pym | H | 8-Ph |
| 1-406 | 4-F-Ph | 2-NH₂-4-Pym | H | 8a-Me |
| 1-407 | 4-F-Ph | 2-NH₂-4-Pym | H | 8a-Et |
| 1-408 | 4-F-Ph | 2-NH₂-4-Pym | H | 8a-Pr |
| 1-409 | 4-F-Ph | 2-MeNH-4-Pym | H | — |
| 1-410 | 4-F-Ph | 2-MeNH-4-Pym | H | 1-Me |
| 1-411 | 4-F-Ph | 2-MeNH-4-Pym | H | 1-Et |
| 1-412 | 4-F-Ph | 2-MeNH-4-Pym | H | 1-Pr |
| 1-413 | 4-F-Ph | 2-MeNH-4-Pym | H | 1,1-diMe |
| 1-414 | 4-F-Ph | 2-MeNH-4-Pym | H | 2-Me |
| 1-415 | 4-F-Ph | 2-MeNH-4-Pym | H | 2-Et |
| 1-416 | 4-F-Ph | 2-MeNH-4-Pym | H | 2-Pr |
| 1-417 | 4-F-Ph | 2-MeNH-4-Pym | H | 2-Bu |
| 1-418 | 4-F-Ph | 2-MeNH-4-Pym | H | 2-Allyl |
| 1-419 | 4-F-Ph | 2-MeNH-4-Pym | H | 2-Ph |
| 1-420 | 4-F-Ph | 2-MeNH-4-Pym | H | 2-Bn |
| 1-421 | 4-F-Ph | 2-MeNH-4-Pym | H | 2-Phet |
| 1-422 | 4-F-Ph | 2-MeNH-4-Pym | H | 2,2-diMe |
| 1-423 | 4-F-Ph | 2-MeNH-4-Pym | H | 2-OH |
| 1-424 | 4-F-Ph | 2-MeNH-4-Pym | H | 2-MeO |
| 1-425 | 4-F-Ph | 2-MeNH-4-Pym | H | 2-EtO |
| 1-426 | 4-F-Ph | 2-MeNH-4-Pym | H | 2-PrO |
| 1-427 | 4-F-Ph | 2-MeNH-4-Pym | H | 2,2-di(MeO) |

TABLE 1-continued

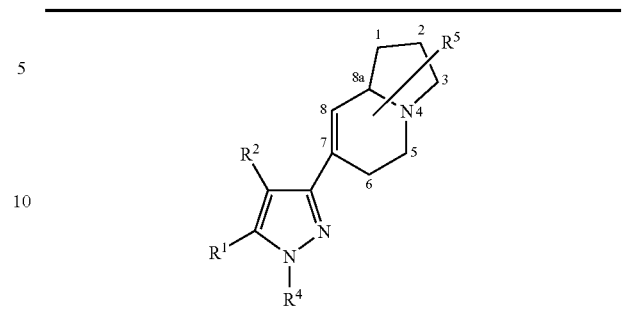

| Compound No. | R¹ | R² | R⁴ | R⁵ |
|---|---|---|---|---|
| 1-428 | 4-F-Ph | 2-MeNH-4-Pym | H | 2,2-di(EtO) |
| 1-429 | 4-F-Ph | 2-MeNH-4-Pym | H | 2,2-OCH₂CH₂O— |
| 1-430 | 4-F-Ph | 2-MeNH-4-Pym | H | 2-Oxo |
| 1-431 | 4-F-Ph | 2-MeNH-4-Pym | H | 2-F |
| 1-432 | 4-F-Ph | 2-MeNH-4-Pym | H | 2-Cl |
| 1-433 | 4-F-Ph | 2-MeNH-4-Pym | H | 2-Br |
| 1-434 | 4-F-Ph | 2-MeNH-4-Pym | H | 2-I |
| 1-435 | 4-F-Ph | 2-MeNH-4-Pym | H | 2,2-diF |
| 1-436 | 4-F-Ph | 2-MeNH-4-Pym | H | 2,2-diCl |
| 1-437 | 4-F-Ph | 2-MeNH-4-Pym | H | 2,2-diBr |
| 1-438 | 4-F-Ph | 2-MeNH-4-Pym | H | 3-Me |
| 1-439 | 4-F-Ph | 2-MeNH-4-Pym | H | 3-Et |
| 1-440 | 4-F-Ph | 2-MeNH-4-Pym | H | 3-Pr |
| 1-441 | 4-F-Ph | 2-MeNH-4-Pym | H | 3,3-diMe |
| 1-442 | 4-F-Ph | 2-MeNH-4-Pym | H | 5-Me |
| 1-443 | 4-F-Ph | 2-MeNH-4-Pym | H | 5-Et |
| 1-444 | 4-F-Ph | 2-MeNH-4-Pym | H | 5-Pr |
| 1-445 | 4-F-Ph | 2-MeNH-4-Pym | H | 5,5-diMe |
| 1-446 | 4-F-Ph | 2-MeNH-4-Pym | H | 6-Me |
| 1-447 | 4-F-Ph | 2-MeNH-4-Pym | H | 6-Et |
| 1-448 | 4-F-Ph | 2-MeNH-4-Pym | H | 6-Pr |
| 1-449 | 4-F-Ph | 2-MeNH-4-Pym | H | 6,6-diMe |
| 1-450 | 4-F-Ph | 2-MeNH-4-Pym | H | 6,6-diF |
| 1-451 | 4-F-Ph | 2-MeNH-4-Pym | H | 6,6-CH₂CH₂— |
| 1-452 | 4-F-Ph | 2-MeNH-4-Pym | H | 6-Oxo |
| 1-453 | 4-F-Ph | 2-MeNH-4-Pym | H | 8-Me |
| 1-454 | 4-F-Ph | 2-MeNH-4-Pym | H | 8-Et |
| 1-455 | 4-F-Ph | 2-MeNH-4-Pym | H | 8-Pr |
| 1-456 | 4-F-Ph | 2-MeNH-4-Pym | H | 8-Ph |
| 1-457 | 4-F-Ph | 2-MeNH-4-Pym | H | 8a-Me |
| 1-458 | 4-F-Ph | 2-MeNH-4-Pym | H | 8a-Et |
| 1-459 | 4-F-Ph | 2-MeNH-4-Pym | H | 8a-Pr |
| 1-460 | 3-Cl-Ph | 4-Pyr | H | — |
| 1-461 | 3-Cl-Ph | 4-Pyr | H | 1-Me |
| 1-462 | 3-Cl-Ph | 4-Pyr | H | 1-Et |
| 1-463 | 3-Cl-Ph | 4-Pyr | H | 1-Pr |
| 1-464 | 3-Cl-Ph | 4-Pyr | H | 1,1-diMe |
| 1-465 | 3-Cl-Ph | 4-Pyr | H | 2-Me |
| 1-466 | 3-Cl-Ph | 4-Pyr | H | 2-Et |
| 1-467 | 3-Cl-Ph | 4-Pyr | H | 2-Pr |
| 1-468 | 3-Cl-Ph | 4-Pyr | H | 2-Bu |
| 1-469 | 3-Cl-Ph | 4-Pyr | H | 2-Allyl |
| 1-470 | 3-Cl-Ph | 4-Pyr | H | 2-Ph |
| 1-471 | 3-Cl-Ph | 4-Pyr | H | 2-Bn |
| 1-472 | 3-Cl-Ph | 4-Pyr | H | 2-Phet |
| 1-473 | 3-Cl-Ph | 4-Pyr | H | 2,2-diMe |
| 1-474 | 3-Cl-Ph | 4-Pyr | H | 2-OH |
| 1-475 | 3-Cl-Ph | 4-Pyr | H | 2-MeO |
| 1-476 | 3-Cl-Ph | 4-Pyr | H | 2-EtO |
| 1-477 | 3-Cl-Ph | 4-Pyr | H | 2-PrO |
| 1-478 | 3-Cl-Ph | 4-Pyr | H | 2,2-di(MeO) |
| 1-479 | 3-Cl-Ph | 4-Pyr | H | 2,2-di(EtO) |
| 1-480 | 3-Cl-Ph | 4-Pyr | H | 2,2-OCH₂CH₂O— |
| 1-481 | 3-Cl-Ph | 4-Pyr | H | 2-Oxo |
| 1-482 | 3-Cl-Ph | 4-Pyr | H | 2-F |
| 1-483 | 3-Cl-Ph | 4-Pyr | H | 2-Cl |
| 1-484 | 3-Cl-Ph | 4-Pyr | H | 2-Br |
| 1-485 | 3-Cl-Ph | 4-Pyr | H | 2-I |
| 1-486 | 3-Cl-Ph | 4-Pyr | H | 2,2-diF |
| 1-487 | 3-Cl-Ph | 4-Pyr | H | 2,2-diCl |

TABLE 1-continued

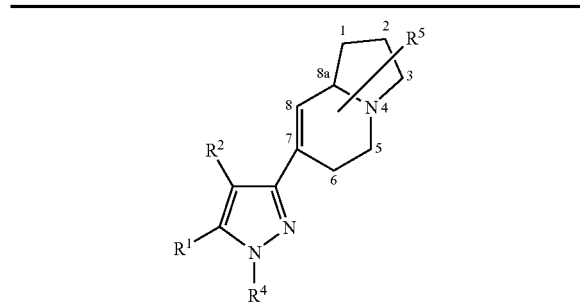

| Compound No. | R¹ | R² | R⁴ | R⁵ |
|---|---|---|---|---|
| 1-488 | 3-Cl-Ph | 4-Pyr | H | 2,2-diBr |
| 1-489 | 3-Cl-Ph | 4-Pyr | H | 3-Me |
| 1-490 | 3-Cl-Ph | 4-Pyr | H | 3-Et |
| 1-491 | 3-Cl-Ph | 4-Pyr | H | 3-Pr |
| 1-492 | 3-Cl-Ph | 4-Pyr | H | 3,3-diMe |
| 1-493 | 3-Cl-Ph | 4-Pyr | H | 5-Me |
| 1-494 | 3-Cl-Ph | 4-Pyr | H | 5-Et |
| 1-495 | 3-Cl-Ph | 4-Pyr | H | 5-Pr |
| 1-496 | 3-Cl-Ph | 4-Pyr | H | 5,5-diMe |
| 1-497 | 3-Cl-Ph | 4-Pyr | H | 6-Me |
| 1-498 | 3-Cl-Ph | 4-Pyr | H | 6-Et |
| 1-499 | 3-Cl-Ph | 4-Pyr | H | 6-Pr |
| 1-500 | 3-Cl-Ph | 4-Pyr | H | 6,6-diMe |
| 1-501 | 3-Cl-Ph | 4-Pyr | H | 6,6-diF |
| 1-502 | 3-Cl-Ph | 4-Pyr | H | 6,6-CH₂CH₂— |
| 1-503 | 3-Cl-Ph | 4-Pyr | H | 6-Oxo |
| 1-504 | 3-Cl-Ph | 4-Pyr | H | 8-Me |
| 1-505 | 3-Cl-Ph | 4-Pyr | H | 8-Et |
| 1-506 | 3-Cl-Ph | 4-Pyr | H | 8-Pr |
| 1-507 | 3-Cl-Ph | 4-Pyr | H | 8-Ph |
| 1-508 | 3-Cl-Ph | 4-Pyr | H | 8a-Me |
| 1-509 | 3-Cl-Ph | 4-Pyr | H | 8a-Et |
| 1-510 | 3-Cl-Ph | 4-Pyr | H | 8a-Pr |
| 1-511 | 3-Cl-Ph | 2-NH₂-4-Pym | H | — |
| 1-512 | 3-Cl-Ph | 2-NH₂-4-Pym | H | 1-Me |
| 1-513 | 3-Cl-Ph | 2-NH₂-4-Pym | H | 1-Et |
| 1-514 | 3-Cl-Ph | 2-NH₂-4-Pym | H | 1-Pr |
| 1-515 | 3-Cl-Ph | 2-NH₂-4-Pym | H | 1,1-diMe |
| 1-516 | 3-Cl-Ph | 2-NH₂-4-Pym | H | 2-Me |
| 1-517 | 3-Cl-Ph | 2-NH₂-4-Pym | H | 2-Et |
| 1-518 | 3-Cl-Ph | 2-NH₂-4-Pym | H | 2-Pr |
| 1-519 | 3-Cl-Ph | 2-NH₂-4-Pym | H | 2-Bu |
| 1-520 | 3-Cl-Ph | 2-NH₂-4-Pym | H | 2-Allyl |
| 1-521 | 3-Cl-Ph | 2-NH₂-4-Pym | H | 2-Ph |
| 1-522 | 3-Cl-Ph | 2-NH₂-4-Pym | H | 2-Bn |
| 1-523 | 3-Cl-Ph | 2-NH₂-4-Pym | H | 2-Phet |
| 1-524 | 3-Cl-Ph | 2-NH₂-4-Pym | H | 2,2-diMe |
| 1-525 | 3-Cl-Ph | 2-NH₂-4-Pym | H | 2-OH |
| 1-526 | 3-Cl-Ph | 2-NH₂-4-Pym | H | 2-MeO |
| 1-527 | 3-Cl-Ph | 2-NH₂-4-Pym | H | 2-EtO |
| 1-528 | 3-Cl-Ph | 2-NH₂-4-Pym | H | 2-PrO |
| 1-529 | 3-Cl-Ph | 2-NH₂-4-Pym | H | 2,2-di(MeO) |
| 1-530 | 3-Cl-Ph | 2-NH₂-4-Pym | H | 2,2-di(EtO) |
| 1-531 | 3-Cl-Ph | 2-NH₂-4-Pym | H | 2,2-OCH₂CH₂— |
| 1-532 | 3-Cl-Ph | 2-NH₂-4-Pym | H | 2-Oxo |
| 1-533 | 3-Cl-Ph | 2-NH₂-4-Pym | H | 2-F |
| 1-534 | 3-Cl-Ph | 2-NH₂-4-Pym | H | 2-Cl |
| 1-535 | 3-Cl-Ph | 2-NH₂-4-Pym | H | 2-Br |
| 1-536 | 3-Cl-Ph | 2-NH₂-4-Pym | H | 2-I |
| 1-537 | 3-Cl-Ph | 2-NH₂-4-Pym | H | 2,2-diF |
| 1-538 | 3-Cl-Ph | 2-NH₂-4-Pym | H | 2,2-diCl |
| 1-539 | 3-Cl-Ph | 2-NH₂-4-Pym | H | 2,2-diBr |
| 1-540 | 3-Cl-Ph | 2-NH₂-4-Pym | H | 3-Me |
| 1-541 | 3-Cl-Ph | 2-NH₂-4-Pym | H | 3-Et |
| 1-542 | 3-Cl-Ph | 2-NH₂-4-Pym | H | 3-Pr |
| 1-543 | 3-Cl-Ph | 2-NH₂-4-Pym | H | 3,3-diMe |
| 1-544 | 3-Cl-Ph | 2-NH₂-4-Pym | H | 5-Me |
| 1-545 | 3-Cl-Ph | 2-NH₂-4-Pym | H | 5-Et |
| 1-546 | 3-Cl-Ph | 2-NH₂-4-Pym | H | 5-Pr |
| 1-547 | 3-Cl-Ph | 2-NH₂-4-Pym | H | 5,5-diMe |
| 1-548 | 3-Cl-Ph | 2-NH₂-4-Pym | H | 6-Me |
| 1-549 | 3-Cl-Ph | 2-NH₂-4-Pym | H | 6-Et |
| 1-550 | 3-Cl-Ph | 2-NH₂-4-Pym | H | 6-Pr |
| 1-551 | 3-Cl-Ph | 2-NH₂-4-Pym | H | 6,6-diMe |
| 1-552 | 3-Cl-Ph | 2-NH₂-4-Pym | H | 6,6-diF |
| 1-553 | 3-Cl-Ph | 2-NH₂-4-Pym | H | 6,6-CH₂CH₂— |
| 1-554 | 3-Cl-Ph | 2-NH₂-4-Pym | H | 6-Oxo |
| 1-555 | 3-Cl-Ph | 2-NH₂-4-Pym | H | 8-Me |
| 1-556 | 3-Cl-Ph | 2-NH₂-4-Pym | H | 8-Et |
| 1-557 | 3-Cl-Ph | 2-NH₂-4-Pym | H | 8-Pr |
| 1-558 | 3-Cl-Ph | 2-NH₂-4-Pym | H | 8-Ph |
| 1-559 | 3-Cl-Ph | 2-NH₂-4-Pym | H | 8a-Me |
| 1-560 | 3-Cl-Ph | 2-NH₂-4-Pym | H | 8a-Et |
| 1-561 | 3-Cl-Ph | 2-NH₂-4-Pym | H | 8a-Pr |
| 1-562 | 3-Cl-Ph | 2-MeNH-4-Pym | H | — |
| 1-563 | 3-Cl-Ph | 2-MeNH-4-Pym | H | 1-Me |
| 1-564 | 3-Cl-Ph | 2-MeNH-4-Pym | H | 1-Et |
| 1-565 | 3-Cl-Ph | 2-MeNH-4-Pym | H | 1-Pr |
| 1-566 | 3-Cl-Ph | 2-MeNH-4-Pym | H | 1,1-diMe |
| 1-567 | 3-Cl-Ph | 2-MeNH-4-Pym | H | 2-Me |
| 1-568 | 3-Cl-Ph | 2-MeNH-4-Pym | H | 2-Et |
| 1-569 | 3-Cl-Ph | 2-MeNH-4-Pym | H | 2-Pr |
| 1-570 | 3-Cl-Ph | 2-MeNH-4-Pym | H | 2-Bu |
| 1-571 | 3-Cl-Ph | 2-MeNH-4-Pym | H | 2-Allyl |
| 1-572 | 3-Cl-Ph | 2-MeNH-4-Pym | H | 2-Ph |
| 1-573 | 3-Cl-Ph | 2-MeNH-4-Pym | H | 2-Bn |
| 1-574 | 3-Cl-Ph | 2-MeNH-4-Pym | H | 2-Phet |
| 1-575 | 3-Cl-Ph | 2-MeNH-4-Pym | H | 2,2-diMe |
| 1-576 | 3-Cl-Ph | 2-MeNH-4-Pym | H | 2-OH |
| 1-577 | 3-Cl-Ph | 2-MeNH-4-Pym | H | 2-MeO |
| 1-578 | 3-Cl-Ph | 2-MeNH-4-Pym | H | 2-EtO |
| 1-579 | 3-Cl-Ph | 2-MeNH-4-Pym | H | 2-PrO |
| 1-580 | 3-Cl-Ph | 2-MeNH-4-Pym | H | 2,2-di(MeO) |
| 1-581 | 3-Cl-Ph | 2-MeNH-4-Pym | H | 2,2-di(EtO) |
| 1-582 | 3-Cl-Ph | 2-MeNH-4-Pym | H | 2,2-OCH₂CH₂— |
| 1-583 | 3-Cl-Ph | 2-MeNH-4-Pym | H | 2-Oxo |
| 1-584 | 3-Cl-Ph | 2-MeNH-4-Pym | H | 2-F |
| 1-585 | 3-Cl-Ph | 2-MeNH-4-Pym | H | 2-Cl |
| 1-586 | 3-Cl-Ph | 2-MeNH-4-Pym | H | 2-Br |
| 1-587 | 3-Cl-Ph | 2-MeNH-4-Pym | H | 2-I |
| 1-588 | 3-Cl-Ph | 2-MeNH-4-Pym | H | 2,2-diF |
| 1-589 | 3-Cl-Ph | 2-MeNH-4-Pym | H | 2,2-diCl |
| 1-590 | 3-Cl-Ph | 2-MeNH-4-Pym | H | 2,2-diBr |
| 1-591 | 3-Cl-Ph | 2-MeNH-4-Pym | H | 3-Me |
| 1-592 | 3-Cl-Ph | 2-MeNH-4-Pym | H | 3-Et |
| 1-593 | 3-Cl-Ph | 2-MeNH-4-Pym | H | 3-Pr |
| 1-594 | 3-Cl-Ph | 2-MeNH-4-Pym | H | 3,3-diMe |
| 1-595 | 3-Cl-Ph | 2-MeNH-4-Pym | H | 5-Me |
| 1-596 | 3-Cl-Ph | 2-MeNH-4-Pym | H | 5-Et |
| 1-597 | 3-Cl-Ph | 2-MeNH-4-Pym | H | 5-Pr |
| 1-598 | 3-Cl-Ph | 2-MeNH-4-Pym | H | 5,5-diMe |
| 1-599 | 3-Cl-Ph | 2-MeNH-4-Pym | H | 6-Me |
| 1-600 | 3-Cl-Ph | 2-MeNH-4-Pym | H | 6-Et |
| 1-601 | 3-Cl-Ph | 2-MeNH-4-Pym | H | 6-Pr |
| 1-602 | 3-Cl-Ph | 2-MeNH-4-Pym | H | 6,6-diMe |
| 1-603 | 3-Cl-Ph | 2-MeNH-4-Pym | H | 6,6-diF |
| 1-604 | 3-Cl-Ph | 2-MeNH-4-Pym | H | 6,6-CH₂CH₂— |
| 1-605 | 3-Cl-Ph | 2-MeNH-4-Pym | H | 6-Oxo |
| 1-606 | 3-Cl-Ph | 2-MeNH-4-Pym | H | 8-Me |
| 1-607 | 3-Cl-Ph | 2-MeNH-4-Pym | H | 8-Et |

TABLE 1-continued

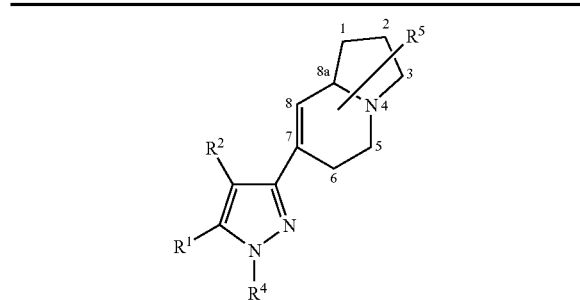

| Compound No. | R¹ | R² | R⁴ | R⁵ |
|---|---|---|---|---|
| 1-608 | 3-Cl-Ph | 2-MeNH-4-Pym | H | 8-Pr |
| 1-609 | 3-Cl-Ph | 2-MeNH-4-Pym | H | 8-Ph |
| 1-610 | 3-Cl-Ph | 2-MeNH-4-Pym | H | 8a-Me |
| 1-611 | 3-Cl-Ph | 2-MeNH-4-Pym | H | 8a-Et |
| 1-612 | 3-Cl-Ph | 2-MeNH-4-Pym | H | 8a-Pr |
| 1-613 | 3-CF₃-Ph | 4-Pyr | H | — |
| 1-614 | 3-CF₃-Ph | 4-Pyr | H | 1-Me |
| 1-615 | 3-CF₃-Ph | 4-Pyr | H | 1-Et |
| 1-616 | 3-CF₃-Ph | 4-Pyr | H | 1-Pr |
| 1-617 | 3-CF₃-Ph | 4-Pyr | H | 1,1-diMe |
| 1-618 | 3-CF₃-Ph | 4-Pyr | H | 2-Me |
| 1-619 | 3-CF₃-Ph | 4-Pyr | H | 2-Et |
| 1-620 | 3-CF₃-Ph | 4-Pyr | H | 2-Pr |
| 1-621 | 3-CF₃-Ph | 4-Pyr | H | 2-Bu |
| 1-622 | 3-CF₃-Ph | 4-Pyr | H | 2-Allyl |
| 1-623 | 3-CF₃-Ph | 4-Pyr | H | 2-Ph |
| 1-624 | 3-CF₃-Ph | 4-Pyr | H | 2-Bn |
| 1-625 | 3-CF₃-Ph | 4-Pyr | H | 2-Phet |
| 1-626 | 3-CF₃-Ph | 4-Pyr | H | 2,2-diMe |
| 1-627 | 3-CF₃-Ph | 4-Pyr | H | 2-OH |
| 1-628 | 3-CF₃-Ph | 4-Pyr | H | 2-MeO |
| 1-629 | 3-CF₃-Ph | 4-Pyr | H | 2-EtO |
| 1-630 | 3-CF₃-Ph | 4-Pyr | H | 2-PrO |
| 1-631 | 3-CF₃-Ph | 4-Pyr | H | 2,2-di(MeO) |
| 1-632 | 3-CF₃-Ph | 4-Pyr | H | 2,2-di(EtO) |
| 1-633 | 3-CF₃-Ph | 4-Pyr | H | 2,2-OCH₂CH₂O— |
| 1-634 | 3-CF₃-Ph | 4-Pyr | H | 2-Oxo |
| 1-635 | 3-CF₃-Ph | 4-Pyr | H | 2-F |
| 1-636 | 3-CF₃-Ph | 4-Pyr | H | 2-Cl |
| 1-637 | 3-CF₃-Ph | 4-Pyr | H | 2-Br |
| 1-638 | 3-CF₃-Ph | 4-Pyr | H | 2-I |
| 1-639 | 3-CF₃-Ph | 4-Pyr | H | 2,2-diF |
| 1-640 | 3-CF₃-Ph | 4-Pyr | H | 2,2-diCl |
| 1-641 | 3-CF₃-Ph | 4-Pyr | H | 2,2-diBr |
| 1-642 | 3-CF₃-Ph | 4-Pyr | H | 3-Me |
| 1-643 | 3-CF₃-Ph | 4-Pyr | H | 3-Et |
| 1-644 | 3-CF₃-Ph | 4-Pyr | H | 3-Pr |
| 1-645 | 3-CF₃-Ph | 4-Pyr | H | 3,3-diMe |
| 1-646 | 3-CF₃-Ph | 4-Pyr | H | 5-Me |
| 1-647 | 3-CF₃-Ph | 4-Pyr | H | 5-Et |
| 1-648 | 3-CF₃-Ph | 4-Pyr | H | 5-Pr |
| 1-649 | 3-CF₃-Ph | 4-Pyr | H | 5,5-diMe |
| 1-650 | 3-CF₃-Ph | 4-Pyr | H | 6-Me |
| 1-651 | 3-CF₃-Ph | 4-Pyr | H | 6-Et |
| 1-652 | 3-CF₃-Ph | 4-Pyr | H | 6-Pr |
| 1-653 | 3-CF₃-Ph | 4-Pyr | H | 6,6-diMe |
| 1-654 | 3-CF₃-Ph | 4-Pyr | H | 6,6-diF |
| 1-655 | 3-CF₃-Ph | 4-Pyr | H | 6,6-CH₂CH₂— |
| 1-656 | 3-CF₃-Ph | 4-Pyr | H | 6-Oxo |
| 1-657 | 3-CF₃-Ph | 4-Pyr | H | 8-Me |
| 1-658 | 3-CF₃-Ph | 4-Pyr | H | 8-Et |
| 1-659 | 3-CF₃-Ph | 4-Pyr | H | 8-Pr |
| 1-660 | 3-CF₃-Ph | 4-Pyr | H | 8-Ph |
| 1-661 | 3-CF₃-Ph | 4-Pyr | H | 8a-Me |
| 1-662 | 3-CF₃-Ph | 4-Pyr | H | 8a-Et |
| 1-663 | 3-CF₃-Ph | 4-Pyr | H | 8a-Pr |
| 1-664 | 3-CF₃-Ph | 2-NH₂-4-Pym | H | — |
| 1-665 | 3-CF₃-Ph | 2-NH₂-4-Pym | H | 1-Me |
| 1-666 | 3-CF₃-Ph | 2-NH₂-4-Pym | H | 1-Et |
| 1-667 | 3-CF₃-Ph | 2-NH₂-4-Pym | H | 1-Pr |
| 1-668 | 3-CF₃-Ph | 2-NH₂-4-Pym | H | 1,1-diMe |
| 1-669 | 3-CF₃-Ph | 2-NH₂-4-Pym | H | 2-Me |
| 1-670 | 3-CF₃-Ph | 2-NH₂-4-Pym | H | 2-Et |
| 1-671 | 3-CF₃-Ph | 2-NH₂-4-Pym | H | 2-Pr |
| 1-672 | 3-CF₃-Ph | 2-NH₂-4-Pym | H | 2-Bu |
| 1-673 | 3-CF₃-Ph | 2-NH₂-4-Pym | H | 2-Allyl |
| 1-674 | 3-CF₃-Ph | 2-NH₂-4-Pym | H | 2-Ph |
| 1-675 | 3-CF₃-Ph | 2-NH₂-4-Pym | H | 2-Bn |
| 1-676 | 3-CF₃-Ph | 2-NH₂-4-Pym | H | 2-Phet |
| 1-677 | 3-CF₃-Ph | 2-NH₂-4-Pym | H | 2,2-diMe |
| 1-678 | 3-CF₃-Ph | 2-NH₂-4-Pym | H | 2-OH |
| 1-679 | 3-CF₃-Ph | 2-NH₂-4-Pym | H | 2-MeO |
| 1-680 | 3-CF₃-Ph | 2-NH₂-4-Pym | H | 2-EtO |
| 1-681 | 3-CF₃-Ph | 2-NH₂-4-Pym | H | 2-PrO |
| 1-682 | 3-CF₃-Ph | 2-NH₂-4-Pym | H | 2,2-di(MeO) |
| 1-683 | 3-CF₃-Ph | 2-NH₂-4-Pym | H | 2,2-di(EtO) |
| 1-684 | 3-CF₃-Ph | 2-NH₂-4-Pym | H | 2,2-OCH₂CH₂O— |
| 1-685 | 3-CF₃-Ph | 2-NH₂-4-Pym | H | 2-Oxo |
| 1-686 | 3-CF₃-Ph | 2-NH₂-4-Pym | H | 2-F |
| 1-687 | 3-CF₃-Ph | 2-NH₂-4-Pym | H | 2-Cl |
| 1-688 | 3-CF₃-Ph | 2-NH₂-4-Pym | H | 2-Br |
| 1-689 | 3-CF₃-Ph | 2-NH₂-4-Pym | H | 2-I |
| 1-690 | 3-CF₃-Ph | 2-NH₂-4-Pym | H | 2,2-diF |
| 1-691 | 3-CF₃-Ph | 2-NH₂-4-Pym | H | 2,2-diCl |
| 1-692 | 3-CF₃-Ph | 2-NH₂-4-Pym | H | 2,2-diBr |
| 1-693 | 3-CF₃-Ph | 2-NH₂-4-Pym | H | 3-Me |
| 1-694 | 3-CF₃-Ph | 2-NH₂-4-Pym | H | 3-Et |
| 1-695 | 3-CF₃-Ph | 2-NH₂-4-Pym | H | 3-Pr |
| 1-696 | 3-CF₃-Ph | 2-NH₂-4-Pym | H | 3,3-diMe |
| 1-697 | 3-CF₃-Ph | 2-NH₂-4-Pym | H | 5-Me |
| 1-698 | 3-CF₃-Ph | 2-NH₂-4-Pym | H | 5-Et |
| 1-699 | 3-CF₃-Ph | 2-NH₂-4-Pym | H | 5-Pr |
| 1-700 | 3-CF₃-Ph | 2-NH₂-4-Pym | H | 5,5-diMe |
| 1-701 | 3-CF₃-Ph | 2-NH₂-4-Pym | H | 6-Me |
| 1-702 | 3-CF₃-Ph | 2-NH₂-4-Pym | H | 6-Et |
| 1-703 | 3-CF₃-Ph | 2-NH₂-4-Pym | H | 6-Pr |
| 1-704 | 3-CF₃-Ph | 2-NH₂-4-Pym | H | 6,6-diMe |
| 1-705 | 3-CF₃-Ph | 2-NH₂-4-Pym | H | 6,6-diF |
| 1-706 | 3-CF₃-Ph | 2-NH₂-4-Pym | H | 6,6-CH₂CH₂— |
| 1-707 | 3-CF₃-Ph | 2-NH₂-4-Pym | H | 6-Oxo |
| 1-708 | 3-CF₃-Ph | 2-NH₂-4-Pym | H | 8-Me |
| 1-709 | 3-CF₃-Ph | 2-NH₂-4-Pym | H | 8-Et |
| 1-710 | 3-CF₃-Ph | 2-NH₂-4-Pym | H | 8-Pr |
| 1-711 | 3-CF₃-Ph | 2-NH₂-4-Pym | H | 8-Ph |
| 1-712 | 3-CF₃-Ph | 2-NH₂-4-Pym | H | 8a-Me |
| 1-713 | 3-CF₃-Ph | 2-NH₂-4-Pym | H | 8a-Et |
| 1-714 | 3-CF₃-Ph | 2-NH₂-4-Pym | H | 8a-Pr |
| 1-715 | 3-CF₃-Ph | 2-MeNH-4-Pym | H | — |
| 1-716 | 3-CF₃-Ph | 2-MeNH-4-Pym | H | 1-Me |
| 1-717 | 3-CF₃-Ph | 2-MeNH-4-Pym | H | 1-Et |
| 1-718 | 3-CF₃-Ph | 2-MeNH-4-Pym | H | 1-Pr |
| 1-719 | 3-CF₃-Ph | 2-MeNH-4-Pym | H | 1,1-diMe |
| 1-720 | 3-CF₃-Ph | 2-MeNH-4-Pym | H | 2-Me |
| 1-721 | 3-CF₃-Ph | 2-MeNH-4-Pym | H | 2-Et |
| 1-722 | 3-CF₃-Ph | 2-MeNH-4-Pym | H | 2-Pr |
| 1-723 | 3-CF₃-Ph | 2-MeNH-4-Pym | H | 2-Bu |
| 1-724 | 3-CF₃-Ph | 2-MeNH-4-Pym | H | 2-Allyl |
| 1-725 | 3-CF₃-Ph | 2-MeNH-4-Pym | H | 2-Ph |
| 1-726 | 3-CF₃-Ph | 2-MeNH-4-Pym | H | 2-Bn |
| 1-727 | 3-CF₃-Ph | 2-MeNH-4-Pym | H | 2-Phet |

TABLE 1-continued

| Compound No. | R¹ | R² | R⁴ | R⁵ |
|---|---|---|---|---|
| 1-728 | 3-CF₃-Ph | 2-MeNH-4-Pym | H | 2,2-diMe |
| 1-729 | 3-CF₃-Ph | 2-MeNH-4-Pym | H | 2-OH |
| 1-730 | 3-CF₃-Ph | 2-MeNH-4-Pym | H | 2-MeO |
| 1-731 | 3-CF₃-Ph | 2-MeNH-4-Pym | H | 2-EtO |
| 1-732 | 3-CF₃-Ph | 2-MeNH-4-Pym | H | 2-PrO |
| 1-733 | 3-CF₃-Ph | 2-MeNH-4-Pym | H | 2,2-di(MeO) |
| 1-734 | 3-CF₃-Ph | 2-MeNH-4-Pym | H | 2,2-di(EtO) |
| 1-735 | 3-CF₃-Ph | 2-MeNH-4-Pym | H | 2,2-OCH₂CH₂O— |
| 1-736 | 3-CF₃-Ph | 2-MeNH-4-Pym | H | 2-Oxo |
| 1-737 | 3-CF₃-Ph | 2-MeNH-4-Pym | H | 2-F |
| 1-738 | 3-CF₃-Ph | 2-MeNH-4-Pym | H | 2-Cl |
| 1-739 | 3-CF₃-Ph | 2-MeNH-4-Pym | H | 2-Br |
| 1-740 | 3-CF₃-Ph | 2-MeNH-4-Pym | H | 2-I |
| 1-741 | 3-CF₃-Ph | 2-MeNH-4-Pym | H | 2,2-diF |
| 1-742 | 3-CF₃-Ph | 2-MeNH-4-Pym | H | 2,2-diCl |
| 1-743 | 3-CF₃-Ph | 2-MeNH-4-Pym | H | 2,2-diBr |
| 1-744 | 3-CF₃-Ph | 2-MeNH-4-Pym | H | 3-Me |
| 1-745 | 3-CF₃-Ph | 2-MeNH-4-Pym | H | 3-Et |
| 1-746 | 3-CF₃-Ph | 2-MeNH-4-Pym | H | 3-Pr |
| 1-747 | 3-CF₃-Ph | 2-MeNH-4-Pym | H | 3,3-diMe |
| 1-748 | 3-CF₃-Ph | 2-MeNH-4-Pym | H | 5-Me |
| 1-749 | 3-CF₃-Ph | 2-MeNH-4-Pym | H | 5-Et |
| 1-750 | 3-CF₃-Ph | 2-MeNH-4-Pym | H | 5-Pr |
| 1-751 | 3-CF₃-Ph | 2-MeNH-4-Pym | H | 5,5-diMe |
| 1-752 | 3-CF₃-Ph | 2-MeNH-4-Pym | H | 6-Me |
| 1-753 | 3-CF₃-Ph | 2-MeNH-4-Pym | H | 6-Et |
| 1-754 | 3-CF₃-Ph | 2-MeNH-4-Pym | H | 6-Pr |
| 1-755 | 3-CF₃-Ph | 2-MeNH-4-Pym | H | 6,6-diMe |
| 1-756 | 3-CF₃-Ph | 2-MeNH-4-Pym | H | 6,6-diF |
| 1-757 | 3-CF₃-Ph | 2-MeNH-4-Pym | H | 6,6-CH₂CH₂— |
| 1-758 | 3-CF₃-Ph | 2-MeNH-4-Pym | H | 6-Oxo |
| 1-759 | 3-CF₃-Ph | 2-MeNH-4-Pym | H | 8-Me |
| 1-760 | 3-CF₃-Ph | 2-MeNH-4-Pym | H | 8-Et |
| 1-761 | 3-CF₃-Ph | 2-MeNH-4-Pym | H | 8-Pr |
| 1-762 | 3-CF₃-Ph | 2-MeNH-4-Pym | H | 8-Ph |
| 1-763 | 3-CF₃-Ph | 2-MeNH-4-Pym | H | 8a-Me |
| 1-764 | 3-CF₃-Ph | 2-MeNH-4-Pym | H | 8a-Et |
| 1-765 | 3-CF₃-Ph | 2-MeNH-4-Pym | H | 8a-Pr |
| 1-766 | 3,4-diF-Ph | 4-Pyr | H | — |
| 1-767 | 3,4-diF-Ph | 4-Pyr | H | 1-Me |
| 1-768 | 3,4-diF-Ph | 4-Pyr | H | 1-Et |
| 1-769 | 3,4-diF-Ph | 4-Pyr | H | 1-Pr |
| 1-770 | 3,4-diF-Ph | 4-Pyr | H | 1,1-diMe |
| 1-771 | 3,4-diF-Ph | 4-Pyr | H | 2-Me |
| 1-772 | 3,4-diF-Ph | 4-Pyr | H | 2-Et |
| 1-773 | 3,4-diF-Ph | 4-Pyr | H | 2-Pr |
| 1-774 | 3,4-diF-Ph | 4-Pyr | H | 2-Bu |
| 1-775 | 3,4-diF-Ph | 4-Pyr | H | 2-Allyl |
| 1-776 | 3,4-diF-Ph | 4-Pyr | H | 2-Ph |
| 1-777 | 3,4-diF-Ph | 4-Pyr | H | 2-Bn |
| 1-778 | 3,4-diF-Ph | 4-Pyr | H | 2-Phet |
| 1-779 | 3,4-diF-Ph | 4-Pyr | H | 2,2-diMe |
| 1-780 | 3,4-diF-Ph | 4-Pyr | H | 2-OH |
| 1-781 | 3,4-diF-Ph | 4-Pyr | H | 2-MeO |
| 1-782 | 3,4-diF-Ph | 4-Pyr | H | 2-EtO |
| 1-783 | 3,4-diF-Ph | 4-Pyr | H | 2-PrO |
| 1-784 | 3,4-diF-Ph | 4-Pyr | H | 2,2-di(MeO) |
| 1-785 | 3,4-diF-Ph | 4-Pyr | H | 2,2-di(EtO) |
| 1-786 | 3,4-diF-Ph | 4-Pyr | H | 2,2-OCH₂CH₂O— |
| 1-787 | 3,4-diF-Ph | 4-Pyr | H | 2-Oxo |
| 1-788 | 3,4-diF-Ph | 4-Pyr | H | 2-F |
| 1-789 | 3,4-diF-Ph | 4-Pyr | H | 2-Cl |
| 1-790 | 3,4-diF-Ph | 4-Pyr | H | 2-Br |
| 1-791 | 3,4-diF-Ph | 4-Pyr | H | 2-I |
| 1-792 | 3,4-diF-Ph | 4-Pyr | H | 2,2-diF |
| 1-793 | 3,4-diF-Ph | 4-Pyr | H | 2,2-diCl |
| 1-794 | 3,4-diF-Ph | 4-Pyr | H | 2,2-diBr |
| 1-795 | 3,4-diF-Ph | 4-Pyr | H | 3-Me |
| 1-796 | 3,4-diF-Ph | 4-Pyr | H | 3-Et |
| 1-797 | 3,4-diF-Ph | 4-Pyr | H | 3-Pr |
| 1-798 | 3,4-diF-Ph | 4-Pyr | H | 3,3-diMe |
| 1-799 | 3,4-diF-Ph | 4-Pyr | H | 5-Me |
| 1-800 | 3,4-diF-Ph | 4-Pyr | H | 5-Et |
| 1-801 | 3,4-diF-Ph | 4-Pyr | H | 5-Pr |
| 1-802 | 3,4-diF-Ph | 4-Pyr | H | 5,5-diMe |
| 1-803 | 3,4-diF-Ph | 4-Pyr | H | 6-Me |
| 1-804 | 3,4-diF-Ph | 4-Pyr | H | 6-Et |
| 1-805 | 3,4-diF-Ph | 4-Pyr | H | 6-Pr |
| 1-806 | 3,4-diF-Ph | 4-Pyr | H | 6,6-diMe |
| 1-807 | 3,4-diF-Ph | 4-Pyr | H | 6,6-diF |
| 1-808 | 3,4-diF-Ph | 4-Pyr | H | 6,6-CH₂CH₂— |
| 1-809 | 3,4-diF-Ph | 4-Pyr | H | 6-Oxo |
| 1-810 | 3,4-diF-Ph | 4-Pyr | H | 8-Me |
| 1-811 | 3,4-diF-Ph | 4-Pyr | H | 8-Et |
| 1-812 | 3,4-diF-Ph | 4-Pyr | H | 8-Pr |
| 1-813 | 3,4-diF-Ph | 4-Pyr | H | 8-Ph |
| 1-814 | 3,4-diF-Ph | 4-Pyr | H | 8a-Me |
| 1-815 | 3,4-diF-Ph | 4-Pyr | H | 8a-Et |
| 1-816 | 3,4-diF-Ph | 4-Pyr | H | 8a-Pr |
| 1-817 | 3,4-diF-Ph | 2-NH₂-4-Pym | H | — |
| 1-818 | 3,4-diF-Ph | 2-NH₂-4-Pym | H | 1-Me |
| 1-819 | 3,4-diF-Ph | 2-NH₂-4-Pym | H | 1-Et |
| 1-820 | 3,4-diF-Ph | 2-NH₂-4-Pym | H | 1-Pr |
| 1-821 | 3,4-diF-Ph | 2-NH₂-4-Pym | H | 1,1-diMe |
| 1-822 | 3,4-diF-Ph | 2-NH₂-4-Pym | H | 2-Me |
| 1-823 | 3,4-diF-Ph | 2-NH₂-4-Pym | H | 2-Et |
| 1-824 | 3,4-diF-Ph | 2-NH₂-4-Pym | H | 2-Pr |
| 1-825 | 3,4-diF-Ph | 2-NH₂-4-Pym | H | 2-Bu |
| 1-826 | 3,4-diF-Ph | 2-NH₂-4-Pym | H | 2-Allyl |
| 1-827 | 3,4-diF-Ph | 2-NH₂-4-Pym | H | 2-Ph |
| 1-828 | 3,4-diF-Ph | 2-NH₂-4-Pym | H | 2-Bn |
| 1-829 | 3,4-diF-Ph | 2-NH₂-4-Pym | H | 2-Phet |
| 1-830 | 3,4-diF-Ph | 2-NH₂-4-Pym | H | 2,2-diMe |
| 1-831 | 3,4-diF-Ph | 2-NH₂-4-Pym | H | 2-OH |
| 1-832 | 3,4-diF-Ph | 2-NH₂-4-Pym | H | 2-MeO |
| 1-833 | 3,4-diF-Ph | 2-NH₂-4-Pym | H | 2-EtO |
| 1-834 | 3,4-diF-Ph | 2-NH₂-4-Pym | H | 2-PrO |
| 1-835 | 3,4-diF-Ph | 2-NH₂-4-Pym | H | 2,2-di(MeO) |
| 1-836 | 3,4-diF-Ph | 2-NH₂-4-Pym | H | 2,2-di(EtO) |
| 1-837 | 3,4-diF-Ph | 2-NH₂-4-Pym | H | 2,2-OCH₂CH₂O— |
| 1-838 | 3,4-diF-Ph | 2-NH₂-4-Pym | H | 2-Oxo |
| 1-839 | 3,4-diF-Ph | 2-NH₂-4-Pym | H | 2-F |
| 1-840 | 3,4-diF-Ph | 2-NH₂-4-Pym | H | 2-Cl |
| 1-841 | 3,4-diF-Ph | 2-NH₂-4-Pym | H | 2-Br |
| 1-842 | 3,4-diF-Ph | 2-NH₂-4-Pym | H | 2-I |
| 1-843 | 3,4-diF-Ph | 2-NH₂-4-Pym | H | 2,2-diF |
| 1-844 | 3,4-diF-Ph | 2-NH₂-4-Pym | H | 2,2-diCl |
| 1-845 | 3,4-diF-Ph | 2-NH₂-4-Pym | H | 2,2-diBr |
| 1-846 | 3,4-diF-Ph | 2-NH₂-4-Pym | H | 3-Me |
| 1-847 | 3,4-diF-Ph | 2-NH₂-4-Pym | H | 3-Et |

TABLE 1-continued

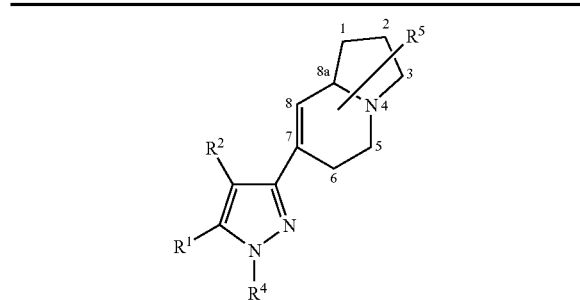

| Compound No. | R¹ | R² | R⁴ | R⁵ |
|---|---|---|---|---|
| 1-848 | 3,4-diF-Ph | 2-NH₂-4-Pym | H | 3-Pr |
| 1-849 | 3,4-diF-Ph | 2-NH₂-4-Pym | H | 3,3-diMe |
| 1-850 | 3,4-diF-Ph | 2-NH₂-4-Pym | H | 5-Me |
| 1-851 | 3,4-diF-Ph | 2-NH₂-4-Pym | H | 5-Et |
| 1-852 | 3,4-diF-Ph | 2-NH₂-4-Pym | H | 5-Pr |
| 1-853 | 3,4-diF-Ph | 2-NH₂-4-Pym | H | 5,5-diMe |
| 1-854 | 3,4-diF-Ph | 2-NH₂-4-Pym | H | 6-Me |
| 1-855 | 3,4-diF-Ph | 2-NH₂-4-Pym | H | 6-Et |
| 1-856 | 3,4-diF-Ph | 2-NH₂-4-Pym | H | 6-Pr |
| 1-857 | 3,4-diF-Ph | 2-NH₂-4-Pym | H | 6,6-diMe |
| 1-858 | 3,4-diF-Ph | 2-NH₂-4-Pym | H | 6,6-diF |
| 1-859 | 3,4-diF-Ph | 2-NH₂-4-Pym | H | 6,6-CH₂CH₂— |
| 1-860 | 3,4-diF-Ph | 2-NH₂-4-Pym | H | 6-Oxo |
| 1-861 | 3,4-diF-Ph | 2-NH₂-4-Pym | H | 8-Me |
| 1-862 | 3,4-diF-Ph | 2-NH₂-4-Pym | H | 8-Et |
| 1-863 | 3,4-diF-Ph | 2-NH₂-4-Pym | H | 8-Pr |
| 1-864 | 3,4-diF-Ph | 2-NH₂-4-Pym | H | 8-Ph |
| 1-865 | 3,4-diF-Ph | 2-NH₂-4-Pym | H | 8a-Me |
| 1-866 | 3,4-diF-Ph | 2-NH₂-4-Pym | H | 8a-Et |
| 1-867 | 3,4-diF-Ph | 2-NH₂-4-Pym | H | 8a-Pr |
| 1-868 | 3,4-diF-Ph | 2-MeNH-4-Pym | H | — |
| 1-869 | 3,4-diF-Ph | 2-MeNH-4-Pym | H | 1-Me |
| 1-870 | 3,4-diF-Ph | 2-MeNH-4-Pym | H | 1-Et |
| 1-871 | 3,4-diF-Ph | 2-MeNH-4-Pym | H | 1-Pr |
| 1-872 | 3,4-diF-Ph | 2-MeNH-4-Pym | H | 1,1-diMe |
| 1-873 | 3,4-diF-Ph | 2-MeNH-4-Pym | H | 2-Me |
| 1-874 | 3,4-diF-Ph | 2-MeNH-4-Pym | H | 2-Et |
| 1-875 | 3,4-diF-Ph | 2-MeNH-4-Pym | H | 2-Pr |
| 1-876 | 3,4-diF-Ph | 2-MeNH-4-Pym | H | 2-Bu |
| 1-877 | 3,4-diF-Ph | 2-MeNH-4-Pym | H | 2-Allyl |
| 1-878 | 3,4-diF-Ph | 2-MeNH-4-Pym | H | 2-Ph |
| 1-879 | 3,4-diF-Ph | 2-MeNH-4-Pym | H | 2-Bn |
| 1-880 | 3,4-diF-Ph | 2-MeNH-4-Pym | H | 2-Phet |
| 1-881 | 3,4-diF-Ph | 2-MeNH-4-Pym | H | 2,2-diMe |
| 1-882 | 3,4-diF-Ph | 2-MeNH-4-Pym | H | 2-OH |
| 1-883 | 3,4-diF-Ph | 2-MeNH-4-Pym | H | 2-MeO |
| 1-884 | 3,4-diF-Ph | 2-MeNH-4-Pym | H | 2-EtO |
| 1-885 | 3,4-diF-Ph | 2-MeNH-4-Pym | H | 2-PrO |
| 1-886 | 3,4-diF-Ph | 2-MeNH-4-Pym | H | 2,2-di(MeO) |
| 1-887 | 3,4-diF-Ph | 2-MeNH-4-Pym | H | 2,2-di(EtO) |
| 1-888 | 3,4-diF-Ph | 2-MeNH-4-Pym | H | 2,2-OCH₂CH₂— |
| 1-889 | 3,4-diF-Ph | 2-MeNH-4-Pym | H | 2-Oxo |
| 1-890 | 3,4-diF-Ph | 2-MeNH-4-Pym | H | 2-F |
| 1-891 | 3,4-diF-Ph | 2-MeNH-4-Pym | H | 2-Cl |
| 1-892 | 3,4-diF-Ph | 2-MeNH-4-Pym | H | 2-Br |
| 1-893 | 3,4-diF-Ph | 2-MeNH-4-Pym | H | 2-I |
| 1-894 | 3,4-diF-Ph | 2-MeNH-4-Pym | H | 2,2-diF |
| 1-895 | 3,4-diF-Ph | 2-MeNH-4-Pym | H | 2,2-diCl |
| 1-896 | 3,4-diF-Ph | 2-MeNH-4-Pym | H | 2,2-diBr |
| 1-897 | 3,4-diF-Ph | 2-MeNH-4-Pym | H | 3-Me |
| 1-898 | 3,4-diF-Ph | 2-MeNH-4-Pym | H | 3-Et |
| 1-899 | 3,4-diF-Ph | 2-MeNH-4-Pym | H | 3-Pr |
| 1-900 | 3,4-diF-Ph | 2-MeNH-4-Pym | H | 3,3-diMe |
| 1-901 | 3,4-diF-Ph | 2-MeNH-4-Pym | H | 5-Me |
| 1-902 | 3,4-diF-Ph | 2-MeNH-4-Pym | H | 5-Et |
| 1-903 | 3,4-diF-Ph | 2-MeNH-4-Pym | H | 5-Pr |
| 1-904 | 3,4-diF-Ph | 2-MeNH-4-Pym | H | 5,5-diMe |
| 1-905 | 3,4-diF-Ph | 2-MeNH-4-Pym | H | 6-Me |
| 1-906 | 3,4-diF-Ph | 2-MeNH-4-Pym | H | 6-Et |
| 1-907 | 3,4-diF-Ph | 2-MeNH-4-Pym | H | 6-Pr |
| 1-908 | 3,4-diF-Ph | 2-MeNH-4-Pym | H | 6,6-diMe |
| 1-909 | 3,4-diF-Ph | 2-MeNH-4-Pym | H | 6,6-diF |
| 1-910 | 3,4-diF-Ph | 2-MeNH-4-Pym | H | 6,6-CH₂CH₂— |
| 1-911 | 3,4-diF-Ph | 2-MeNH-4-Pym | H | 6-Oxo |
| 1-912 | 3,4-diF-Ph | 2-MeNH-4-Pym | H | 8-Me |
| 1-913 | 3,4-diF-Ph | 2-MeNH-4-Pym | H | 8-Et |
| 1-914 | 3,4-diF-Ph | 2-MeNH-4-Pym | H | 8-Pr |
| 1-915 | 3,4-diF-Ph | 2-MeNH-4-Pym | H | 8-Ph |
| 1-916 | 3,4-diF-Ph | 2-MeNH-4-Pym | H | 8a-Me |
| 1-917 | 3,4-diF-Ph | 2-MeNH-4-Pym | H | 8a-Et |
| 1-918 | 3,4-diF-Ph | 2-MeNH-4-Pym | H | 8a-Pr |
| 1-919 | 4-F-Ph | 4-Pyr | Me | — |
| 1-920 | 4-F-Ph | 4-Pyr | Me | 1-Me |
| 1-921 | 4-F-Ph | 4-Pyr | Me | 1-Et |
| 1-922 | 4-F-Ph | 4-Pyr | Me | 1-Pr |
| 1-923 | 4-F-Ph | 4-Pyr | Me | 1,1-diMe |
| 1-924 | 4-F-Ph | 4-Pyr | Me | 2-Me |
| 1-925 | 4-F-Ph | 4-Pyr | Me | 2-Et |
| 1-926 | 4-F-Ph | 4-Pyr | Me | 2-Pr |
| 1-927 | 4-F-Ph | 4-Pyr | Me | 2-Bu |
| 1-928 | 4-F-Ph | 4-Pyr | Me | 2-Allyl |
| 1-929 | 4-F-Ph | 4-Pyr | Me | 2-Ph |
| 1-930 | 4-F-Ph | 4-Pyr | Me | 2-Bn |
| 1-931 | 4-F-Ph | 4-Pyr | Me | 2-Phet |
| 1-932 | 4-F-Ph | 4-Pyr | Me | 2,2-diMe |
| 1-933 | 4-F-Ph | 4-Pyr | Me | 2-OH |
| 1-934 | 4-F-Ph | 4-Pyr | Me | 2-MeO |
| 1-935 | 4-F-Ph | 4-Pyr | Me | 2-EtO |
| 1-936 | 4-F-Ph | 4-Pyr | Me | 2-PrO |
| 1-937 | 4-F-Ph | 4-Pyr | Me | 2,2-di(MeO) |
| 1-938 | 4-F-Ph | 4-Pyr | Me | 2,2-di(EtO) |
| 1-939 | 4-F-Ph | 4-Pyr | Me | 2,2-OCH₂CH₂— |
| 1-940 | 4-F-Ph | 4-Pyr | Me | 2-Oxo |
| 1-941 | 4-F-Ph | 4-Pyr | Me | 2-F |
| 1-942 | 4-F-Ph | 4-Pyr | Me | 2-Cl |
| 1-943 | 4-F-Ph | 4-Pyr | Me | 2-Br |
| 1-944 | 4-F-Ph | 4-Pyr | Me | 2-I |
| 1-945 | 4-F-Ph | 4-Pyr | Me | 2,2-diF |
| 1-946 | 4-F-Ph | 4-Pyr | Me | 2,2-diCl |
| 1-947 | 4-F-Ph | 4-Pyr | Me | 2,2-diBr |
| 1-948 | 4-F-Ph | 4-Pyr | Me | 3-Me |
| 1-949 | 4-F-Ph | 4-Pyr | Me | 3-Et |
| 1-950 | 4-F-Ph | 4-Pyr | Me | 3-Pr |
| 1-951 | 4-F-Ph | 4-Pyr | Me | 3,3-diMe |
| 1-952 | 4-F-Ph | 4-Pyr | Me | 5-Me |
| 1-953 | 4-F-Ph | 4-Pyr | Me | 5-Et |
| 1-954 | 4-F-Ph | 4-Pyr | Me | 5-Pr |
| 1-955 | 4-F-Ph | 4-Pyr | Me | 5,5-diMe |
| 1-956 | 4-F-Ph | 4-Pyr | Me | 6-Me |
| 1-957 | 4-F-Ph | 4-Pyr | Me | 6-Et |
| 1-958 | 4-F-Ph | 4-Pyr | Me | 6-Pr |
| 1-959 | 4-F-Ph | 4-Pyr | Me | 6,6-diMe |
| 1-960 | 4-F-Ph | 4-Pyr | Me | 6,6-diF |
| 1-961 | 4-F-Ph | 4-Pyr | Me | 6,6-CH₂CH₂— |
| 1-962 | 4-F-Ph | 4-Pyr | Me | 6-Oxo |
| 1-963 | 4-F-Ph | 4-Pyr | Me | 8-Me |
| 1-964 | 4-F-Ph | 4-Pyr | Me | 8-Et |
| 1-965 | 4-F-Ph | 4-Pyr | Me | 8-Pr |
| 1-966 | 4-F-Ph | 4-Pyr | Me | 8-Ph |
| 1-967 | 4-F-Ph | 4-Pyr | Me | 8a-Me |

TABLE 1-continued

| Compound No. | R¹ | R² | R⁴ | R⁵ |
|---|---|---|---|---|
| 1-968 | 4-F-Ph | 4-Pyr | Me | 8a-Et |
| 1-969 | 4-F-Ph | 4-Pyr | Me | 8a-Pr |
| 1-970 | 4-F-Ph | 2-NH₂-4-Pym | Me | — |
| 1-971 | 4-F-Ph | 2-NH₂-4-Pym | Me | 1-Me |
| 1-972 | 4-F-Ph | 2-NH₂-4-Pym | Me | 1-Et |
| 1-973 | 4-F-Ph | 2-NH₂-4-Pym | Me | 1-Pr |
| 1-974 | 4-F-Ph | 2-NH₂-4-Pym | Me | 1,1-diMe |
| 1-975 | 4-F-Ph | 2-NH₂-4-Pym | Me | 2-Me |
| 1-976 | 4-F-Ph | 2-NH₂-4-Pym | Me | 2-Et |
| 1-977 | 4-F-Ph | 2-NH₂-4-Pym | Me | 2-Pr |
| 1-978 | 4-F-Ph | 2-NH₂-4-Pym | Me | 2-Bu |
| 1-979 | 4-F-Ph | 2-NH₂-4-Pym | Me | 2-Allyl |
| 1-980 | 4-F-Ph | 2-NH₂-4-Pym | Me | 2-Ph |
| 1-981 | 4-F-Ph | 2-NH₂-4-Pym | Me | 2-Bn |
| 1-982 | 4-F-Ph | 2-NH₂-4-Pym | Me | 2-Phet |
| 1-983 | 4-F-Ph | 2-NH₂-4-Pym | Me | 2,2-diMe |
| 1-984 | 4-F-Ph | 2-NH₂-4-Pym | Me | 2-OH |
| 1-985 | 4-F-Ph | 2-NH₂-4-Pym | Me | 2-MeO |
| 1-986 | 4-F-Ph | 2-NH₂-4-Pym | Me | 2-EtO |
| 1-987 | 4-F-Ph | 2-NH₂-4-Pym | Me | 2-PrO |
| 1-988 | 4-F-Ph | 2-NH₂-4-Pym | Me | 2,2-di(MeO) |
| 1-989 | 4-F-Ph | 2-NH₂-4-Pym | Me | 2,2-di(EtO) |
| 1-990 | 4-F-Ph | 2-NH₂-4-Pym | Me | 2,2-OCH₂CH₂O— |
| 1-991 | 4-F-Ph | 2-NH₂-4-Pym | Me | 2-Oxo |
| 1-992 | 4-F-Ph | 2-NH₂-4-Pym | Me | 2-F |
| 1-993 | 4-F-Ph | 2-NH₂-4-Pym | Me | 2-Cl |
| 1-994 | 4-F-Ph | 2-NH₂-4-Pym | Me | 2-Br |
| 1-995 | 4-F-Ph | 2-NH₂-4-Pym | Me | 2-I |
| 1-996 | 4-F-Ph | 2-NH₂-4-Pym | Me | 2,2-diF |
| 1-997 | 4-F-Ph | 2-NH₂-4-Pym | Me | 2,2-diCl |
| 1-998 | 4-F-Ph | 2-NH₂-4-Pym | Me | 2,2-diBr |
| 1-999 | 4-F-Ph | 2-NH₂-4-Pym | Me | 3-Me |
| 1-1000 | 4-F-Ph | 2-NH₂-4-Pym | Me | 3-Et |
| 1-1001 | 4-F-Ph | 2-NH₂-4-Pym | Me | 3-Pr |
| 1-1002 | 4-F-Ph | 2-NH₂-4-Pym | Me | 3,3-diMe |
| 1-1003 | 4-F-Ph | 2-NH₂-4-Pym | Me | 5-Me |
| 1-1004 | 4-F-Ph | 2-NH₂-4-Pym | Me | 5-Et |
| 1-1005 | 4-F-Ph | 2-NH₂-4-Pym | Me | 5-Pr |
| 1-1006 | 4-F-Ph | 2-NH₂-4-Pym | Me | 5,5-diMe |
| 1-1007 | 4-F-Ph | 2-NH₂-4-Pym | Me | 6-Me |
| 1-1008 | 4-F-Ph | 2-NH₂-4-Pym | Me | 6-Et |
| 1-1009 | 4-F-Ph | 2-NH₂-4-Pym | Me | 6-Pr |
| 1-1010 | 4-F-Ph | 2-NH₂-4-Pym | Me | 6,6-diMe |
| 1-1011 | 4-F-Ph | 2-NH₂-4-Pym | Me | 6,6-diF |
| 1-1012 | 4-F-Ph | 2-NH₂-4-Pym | Me | 6,6-CH₂CH₂— |
| 1-1013 | 4-F-Ph | 2-NH₂-4-Pym | Me | 6-Oxo |
| 1-1014 | 4-F-Ph | 2-NH₂-4-Pym | Me | 8-Me |
| 1-1015 | 4-F-Ph | 2-NH₂-4-Pym | Me | 8-Et |
| 1-1016 | 4-F-Ph | 2-NH₂-4-Pym | Me | 8-Pr |
| 1-1017 | 4-F-Ph | 2-NH₂-4-Pym | Me | 8-Ph |
| 1-1018 | 4-F-Ph | 2-NH₂-4-Pym | Me | 8a-Me |
| 1-1019 | 4-F-Ph | 2-NH₂-4-Pym | Me | 8a-Et |
| 1-1020 | 4-F-Ph | 2-NH₂-4-Pym | Me | 8a-Pr |
| 1-1021 | 4-F-Ph | 2-MeNH-4-Pym | Me | — |
| 1-1022 | 4-F-Ph | 2-MeNH-4-Pym | Me | 1-Me |
| 1-1023 | 4-F-Ph | 2-MeNH-4-Pym | Me | 1-Et |
| 1-1024 | 4-F-Ph | 2-MeNH-4-Pym | Me | 1-Pr |
| 1-1025 | 4-F-Ph | 2-MeNH-4-Pym | Me | 1,1-diMe |
| 1-1026 | 4-F-Ph | 2-MeNH-4-Pym | Me | 2-Me |
| 1-1027 | 4-F-Ph | 2-MeNH-4-Pym | Me | 2-Et |
| 1-1028 | 4-F-Ph | 2-MeNH-4-Pym | Me | 2-Pr |
| 1-1029 | 4-F-Ph | 2-MeNH-4-Pym | Me | 2-Bu |
| 1-1030 | 4-F-Ph | 2-MeNH-4-Pym | Me | 2-Allyl |
| 1-1031 | 4-F-Ph | 2-MeNH-4-Pym | Me | 2-Ph |
| 1-1032 | 4-F-Ph | 2-MeNH-4-Pym | Me | 2-Bn |
| 1-1033 | 4-F-Ph | 2-MeNH-4-Pym | Me | 2-Phet |
| 1-1034 | 4-F-Ph | 2-MeNH-4-Pym | Me | 2,2-diMe |
| 1-1035 | 4-F-Ph | 2-MeNH-4-Pym | Me | 2-OH |
| 1-1036 | 4-F-Ph | 2-MeNH-4-Pym | Me | 2-MeO |
| 1-1037 | 4-F-Ph | 2-MeNH-4-Pym | Me | 2-EtO |
| 1-1038 | 4-F-Ph | 2-MeNH-4-Pym | Me | 2-PrO |
| 1-1039 | 4-F-Ph | 2-MeNH-4-Pym | Me | 2,2-di(MeO) |
| 1-1040 | 4-F-Ph | 2-MeNH-4-Pym | Me | 2,2-di(EtO) |
| 1-1041 | 4-F-Ph | 2-MeNH-4-Pym | Me | 2,2-OCH₂CH₂O— |
| 1-1042 | 4-F-Ph | 2-MeNH-4-Pym | Me | 2-Oxo |
| 1-1043 | 4-F-Ph | 2-MeNH-4-Pym | Me | 2-F |
| 1-1044 | 4-F-Ph | 2-MeNH-4-Pym | Me | 2-Cl |
| 1-1045 | 4-F-Ph | 2-MeNH-4-Pym | Me | 2-Br |
| 1-1046 | 4-F-Ph | 2-MeNH-4-Pym | Me | 2-I |
| 1-1047 | 4-F-Ph | 2-MeNH-4-Pym | Me | 2,2-diF |
| 1-1048 | 4-F-Ph | 2-MeNH-4-Pym | Me | 2,2-diCl |
| 1-1049 | 4-F-Ph | 2-MeNH-4-Pym | Me | 2,2-diBr |
| 1-1050 | 4-F-Ph | 2-MeNH-4-Pym | Me | 3-Me |
| 1-1051 | 4-F-Ph | 2-MeNH-4-Pym | Me | 3-Et |
| 1-1052 | 4-F-Ph | 2-MeNH-4-Pym | Me | 3-Pr |
| 1-1053 | 4-F-Ph | 2-MeNH-4-Pym | Me | 3,3-diMe |
| 1-1054 | 4-F-Ph | 2-MeNH-4-Pym | Me | 5-Me |
| 1-1055 | 4-F-Ph | 2-MeNH-4-Pym | Me | 5-Et |
| 1-1056 | 4-F-Ph | 2-MeNH-4-Pym | Me | 5-Pr |
| 1-1057 | 4-F-Ph | 2-MeNH-4-Pym | Me | 5,5-diMe |
| 1-1058 | 4-F-Ph | 2-MeNH-4-Pym | Me | 6-Me |
| 1-1059 | 4-F-Ph | 2-MeNH-4-Pym | Me | 6-Et |
| 1-1060 | 4-F-Ph | 2-MeNH-4-Pym | Me | 6-Pr |
| 1-1061 | 4-F-Ph | 2-MeNH-4-Pym | Me | 6,6-diMe |
| 1-1062 | 4-F-Ph | 2-MeNH-4-Pym | Me | 6,6-diF |
| 1-1063 | 4-F-Ph | 2-MeNH-4-Pym | Me | 6,6-CH₂CH₂— |
| 1-1064 | 4-F-Ph | 2-MeNH-4-Pym | Me | 6-Oxo |
| 1-1065 | 4-F-Ph | 2-MeNH-4-Pym | Me | 8-Me |
| 1-1066 | 4-F-Ph | 2-MeNH-4-Pym | Me | 8-Et |
| 1-1067 | 4-F-Ph | 2-MeNH-4-Pym | Me | 8-Pr |
| 1-1068 | 4-F-Ph | 2-MeNH-4-Pym | Me | 8-Ph |
| 1-1069 | 4-F-Ph | 2-MeNH-4-Pym | Me | 8a-Me |
| 1-1070 | 4-F-Ph | 2-MeNH-4-Pym | Me | 8a-Et |
| 1-1071 | 4-F-Ph | 2-MeNH-4-Pym | Me | 8a-Pr |
| 1-1072 | 4-F-Ph | 2-MeO-4-Pyr | H | — |
| 1-1073 | 4-F-Ph | 2-MeO-4-Pyr | H | 2-OH |
| 1-1074 | 4-F-Ph | 2-MeO-4-Pyr | H | 2-MeO |
| 1-1075 | 4-F-Ph | 2-MeO-4-Pyr | H | 2-Ph |
| 1-1076 | 4-F-Ph | 2-MeO-4-Pyr | H | 8-Me |
| 1-1077 | 4-F-Ph | 2-MeO-4-Pyr | H | 2-F |
| 1-1078 | 4-F-Ph | 2-MeO-4-Pyr | H | 2-Cl |
| 1-1079 | 4-F-Ph | 2-MeO-4-Pyr | H | 2-Br |
| 1-1080 | 4-F-Ph | 2-MeO-4-Pyr | H | 2,2-diF |
| 1-1081 | 4-F-Ph | 2-MeO-4-Pyr | H | 2,2-diCl |
| 1-1082 | 4-F-Ph | 2-NH₂-4-Pyr | H | — |
| 1-1083 | 4-F-Ph | 2-NH₂-4-Pyr | H | 2-OH |
| 1-1084 | 4-F-Ph | 2-NH₂-4-Pyr | H | 2-MeO |
| 1-1085 | 4-F-Ph | 2-NH₂-4-Pyr | H | 2-Ph |
| 1-1086 | 4-F-Ph | 2-NH₂-4-Pyr | H | 8-Me |
| 1-1087 | 4-F-Ph | 2-NH₂-4-Pyr | H | 2-F |

TABLE 1-continued

| Compound No. | R¹ | R² | R⁴ | R⁵ |
|---|---|---|---|---|
| 1-1088 | 4-F-Ph | 2-NH$_2$-4-Pyr | H | 2-Cl |
| 1-1089 | 4-F-Ph | 2-NH$_2$-4-Pyr | H | 2-Br |
| 1-1090 | 4-F-Ph | 2-NH$_2$-4-Pyr | H | 2,2-diF |
| 1-1091 | 4-F-Ph | 2-NH$_2$-4-Pyr | H | 2,2-diCl |
| 1-1092 | 4-F-Ph | 2-MeNH-4-Pyr | H | — |
| 1-1093 | 4-F-Ph | 2-MeNH-4-Pyr | H | 2-OH |
| 1-1094 | 4-F-Ph | 2-MeNH-4-Pyr | H | 2-MeO |
| 1-1095 | 4-F-Ph | 2-MeNH-4-Pyr | H | 2-Ph |
| 1-1096 | 4-F-Ph | 2-MeNH-4-Pyr | H | 8-Me |
| 1-1097 | 4-F-Ph | 2-MeNH-4-Pyr | H | 2-F |
| 1-1098 | 4-F-Ph | 2-MeNH-4-Pyr | H | 2-Cl |
| 1-1099 | 4-F-Ph | 2-MeNH-4-Pyr | H | 2-Br |
| 1-1100 | 4-F-Ph | 2-MeNH-4-Pyr | H | 2,2-diF |
| 1-1101 | 4-F-Ph | 2-MeNH-4-Pyr | H | 2,2-diCl |
| 1-1102 | 4-F-Ph | 2-(α-Me-BnNH)-4-Pyr | H | — |
| 1-1103 | 4-F-Ph | 2-(α-Me-BnNH)-4-Pyr | H | 2-OH |
| 1-1104 | 4-F-Ph | 2-(α-Me-BnNH)-4-Pyr | H | 2-MeO |
| 1-1105 | 4-F-Ph | 2-(α-Me-BnNH)-4-Pyr | H | 2-Ph |
| 1-1106 | 4-F-Ph | 2-(α-Me-BnNH)-4-Pyr | H | 8-Me |
| 1-1107 | 4-F-Ph | 2-(α-Me-BnNH)-4-Pyr | H | 2-F |
| 1-1108 | 4-F-Ph | 2-(α-Me-BnNH)-4-Pyr | H | 2-Cl |
| 1-1109 | 4-F-Ph | 2-(α-Me-BnNH)-4-Pyr | H | 2-Br |
| 1-1110 | 4-F-Ph | 2-(α-Me-BnNH)-4-Pyr | H | 2,2-diF |
| 1-1111 | 4-F-Ph | 2-(α-Me-BnNH)-4-Pyr | H | 2,2-diCl |
| 1-1112 | 4-F-Ph | 2-BnNH-4-Pyr | H | — |
| 1-1113 | 4-F-Ph | 2-BnNH-4-Pyr | H | 2-OH |
| 1-1114 | 4-F-Ph | 2-BnNH-4-Pyr | H | 2-MeO |
| 1-1115 | 4-F-Ph | 2-BnNH-4-Pyr | H | 2-Ph |
| 1-1116 | 4-F-Ph | 2-BnNH-4-Pyr | H | 8-Me |
| 1-1117 | 4-F-Ph | 2-BnNH-4-Pyr | H | 2-F |
| 1-1118 | 4-F-Ph | 2-BnNH-4-Pyr | H | 2-Cl |
| 1-1119 | 4-F-Ph | 2-BnNH-4-Pyr | H | 2-Br |
| 1-1120 | 4-F-Ph | 2-BnNH-4-Pyr | H | 2,2-diF |
| 1-1121 | 4-F-Ph | 2-BnNH-4-Pyr | H | 2,2-diCl |
| 1-1122 | 4-F-Ph | 4-Pym | H | — |
| 1-1123 | 4-F-Ph | 4-Pym | H | 2-OH |
| 1-1124 | 4-F-Ph | 4-Pym | H | 2-MeO |
| 1-1125 | 4-F-Ph | 4-Pym | H | 2-Ph |
| 1-1126 | 4-F-Ph | 4-Pym | H | 8-Me |
| 1-1127 | 4-F-Ph | 4-Pym | H | 2-F |
| 1-1128 | 4-F-Ph | 4-Pym | H | 2-Cl |
| 1-1129 | 4-F-Ph | 4-Pym | H | 2-Br |
| 1-1130 | 4-F-Ph | 4-Pym | H | 2,2-diF |
| 1-1131 | 4-F-Ph | 4-Pym | H | 2,2-diCl |
| 1-1132 | 4-F-Ph | 2-MeO-4-Pym | H | — |
| 1-1133 | 4-F-Ph | 2-MeO-4-Pym | H | 2-OH |
| 1-1134 | 4-F-Ph | 2-MeO-4-Pym | H | 2-MeO |
| 1-1135 | 4-F-Ph | 2-MeO-4-Pym | H | 2-Ph |
| 1-1136 | 4-F-Ph | 2-MeO-4-Pym | H | 8-Me |
| 1-1137 | 4-F-Ph | 2-MeO-4-Pym | H | 2-F |
| 1-1138 | 4-F-Ph | 2-MeO-4-Pym | H | 2-Cl |
| 1-1139 | 4-F-Ph | 2-MeO-4-Pym | H | 2-Br |
| 1-1140 | 4-F-Ph | 2-MeO-4-Pym | H | 2,2-diF |
| 1-1141 | 4-F-Ph | 2-MeO-4-Pym | H | 2,2-diCl |
| 1-1142 | 4-F-Ph | 2-(α-Me-BnNH)-4-Pym | H | — |
| 1-1143 | 4-F-Ph | 2-(α-Me-BnNH)-4-Pym | H | 2-OH |
| 1-1144 | 4-F-Ph | 2-(α-Me-BnNH)-4-Pym | H | 2-MeO |
| 1-1145 | 4-F-Ph | 2-(α-Me-BnNH)-4-Pym | H | 2-Ph |
| 1-1146 | 4-F-Ph | 2-(α-Me-BnNH)-4-Pym | H | 8-Me |
| 1-1147 | 4-F-Ph | 2-(α-Me-BnNH)-4-Pym | H | 2-F |
| 1-1148 | 4-F-Ph | 2-(α-Me-BnNH)-4-Pym | H | 2-Cl |
| 1-1149 | 4-F-Ph | 2-(α-Me-BnNH)-4-Pym | H | 2-Br |
| 1-1150 | 4-F-Ph | 2-(α-Me-BnNH)-4-Pym | H | 2,2-diF |
| 1-1151 | 4-F-Ph | 2-(α-Me-BnNH)-4-Pym | H | 2,2-diCl |
| 1-1152 | 4-F-Ph | 2-BnNH-4-Pym | H | — |
| 1-1153 | 4-F-Ph | 2-BnNH-4-Pym | H | 2-OH |
| 1-1154 | 4-F-Ph | 2-BnNH-4-Pym | H | 2-MeO |
| 1-1155 | 4-F-Ph | 2-BnNH-4-Pym | H | 2-Ph |
| 1-1156 | 4-F-Ph | 2-BnNH-4-Pym | H | 8-Me |
| 1-1157 | 4-F-Ph | 2-BnNH-4-Pym | H | 2-F |
| 1-1158 | 4-F-Ph | 2-BnNH-4-Pym | H | 2-Cl |
| 1-1159 | 4-F-Ph | 2-BnNH-4-Pym | H | 2-Br |
| 1-1160 | 4-F-Ph | 2-BnNH-4-Pym | H | 2,2-diF |
| 1-1161 | 4-F-Ph | 2-BnNH-4-Pym | H | 2,2-diCl |
| 1-1162 | 4-F-Ph | 2-MeO-4-Pyr | Me | — |
| 1-1163 | 4-F-Ph | 2-MeO-4-Pyr | Me | 2-OH |
| 1-1164 | 4-F-Ph | 2-MeO-4-Pyr | Me | 2-MeO |
| 1-1165 | 4-F-Ph | 2-MeO-4-Pyr | Me | 2-Ph |
| 1-1166 | 4-F-Ph | 2-MeO-4-Pyr | Me | 8-Me |
| 1-1167 | 4-F-Ph | 2-MeO-4-Pyr | Me | 2-F |
| 1-1168 | 4-F-Ph | 2-MeO-4-Pyr | Me | 2-Cl |
| 1-1169 | 4-F-Ph | 2-MeO-4-Pyr | Me | 2-Br |
| 1-1170 | 4-F-Ph | 2-MeO-4-Pyr | Me | 2,2-diF |
| 1-1171 | 4-F-Ph | 2-MeO-4-Pyr | Me | 2,2-diCl |
| 1-1172 | 4-F-Ph | 2-NH$_2$-4-Pyr | Me | — |
| 1-1173 | 4-F-Ph | 2-NH$_2$-4-Pyr | Me | 2-OH |
| 1-1174 | 4-F-Ph | 2-NH$_2$-4-Pyr | Me | 2-MeO |
| 1-1175 | 4-F-Ph | 2-NH$_2$-4-Pyr | Me | 2-Ph |
| 1-1176 | 4-F-Ph | 2-NH$_2$-4-Pyr | Me | 8-Me |
| 1-1177 | 4-F-Ph | 2-NH$_2$-4-Pyr | Me | 2-F |
| 1-1178 | 4-F-Ph | 2-NH$_2$-4-Pyr | Me | 2-Cl |
| 1-1179 | 4-F-Ph | 2-NH$_2$-4-Pyr | Me | 2-Br |
| 1-1180 | 4-F-Ph | 2-NH$_2$-4-Pyr | Me | 2,2-diF |
| 1-1181 | 4-F-Ph | 2-NH$_2$-4-Pyr | Me | 2,2-diCl |
| 1-1182 | 4-F-Ph | 2-MeNH-4-Pyr | Me | — |
| 1-1183 | 4-F-Ph | 2-MeNH-4-Pyr | Me | 2-OH |
| 1-1184 | 4-F-Ph | 2-MeNH-4-Pyr | Me | 2-MeO |
| 1-1185 | 4-F-Ph | 2-MeNH-4-Pyr | Me | 2-Ph |
| 1-1186 | 4-F-Ph | 2-MeNH-4-Pyr | Me | 8-Me |
| 1-1187 | 4-F-Ph | 2-MeNH-4-Pyr | Me | 2-F |
| 1-1188 | 4-F-Ph | 2-MeNH-4-Pyr | Me | 2-Cl |
| 1-1189 | 4-F-Ph | 2-MeNH-4-Pyr | Me | 2-Br |
| 1-1190 | 4-F-Ph | 2-MeNH-4-Pyr | Me | 2,2-diF |
| 1-1191 | 4-F-Ph | 2-MeNH-4-Pyr | Me | 2,2-diCl |
| 1-1192 | 4-F-Ph | 2-(α-Me-BnNH)-4-Pyr | Me | — |
| 1-1193 | 4-F-Ph | 2-(α-Me-BnNH)-4-Pyr | Me | 2-OH |
| 1-1194 | 4-F-Ph | 2-(α-Me-BnNH)-4-Pyr | Me | 2-MeO |
| 1-1195 | 4-F-Ph | 2-(α-Me-BnNH)-4-Pyr | Me | 2-Ph |
| 1-1196 | 4-F-Ph | 2-(α-Me-BnNH)-4-Pyr | Me | 8-Me |
| 1-1197 | 4-F-Ph | 2-(α-Me-BnNH)-4-Pyr | Me | 2-F |

TABLE 1-continued

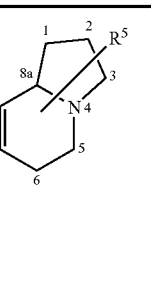

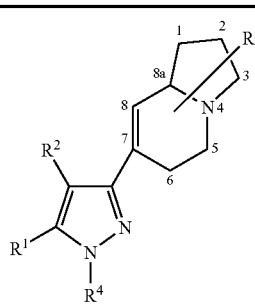

| Compound No. | R¹ | R² | R⁴ | R⁵ |
|---|---|---|---|---|
| 1-1198 | 4-F-Ph | 2-(α-Me-BnNH)-4-Pyr | Me | 2-Cl |
| 1-1199 | 4-F-Ph | 2-(α-Me-BnNH)-4-Pyr | Me | 2-Br |
| 1-1200 | 4-F-Ph | 2-(α-Me-BnNH)-4-Pyr | Me | 2,2-diF |
| 1-1201 | 4-F-Ph | 2-(α-Me-BnNH)-4-Pyr | Me | 2,2-diCl |
| 1-1202 | 4-F-Ph | 2-BnNH-4-Pyr | Me | — |
| 1-1203 | 4-F-Ph | 2-BnNH-4-Pyr | Me | 2-OH |
| 1-1204 | 4-F-Ph | 2-BnNH-4-Pyr | Me | 2-MeO |
| 1-1205 | 4-F-Ph | 2-BnNH-4-Pyr | Me | 2-Ph |
| 1-1206 | 4-F-Ph | 2-BnNH-4-Pyr | Me | 8-Me |
| 1-1207 | 4-F-Ph | 2-BnNH-4-Pyr | Me | 2-F |
| 1-1208 | 4-F-Ph | 2-BnNH-4-Pyr | Me | 2-Cl |
| 1-1209 | 4-F-Ph | 2-BnNH-4-Pyr | Me | 2-Br |
| 1-1210 | 4-F-Ph | 2-BnNH-4-Pyr | Me | 2,2-diF |
| 1-1211 | 4-F-Ph | 2-BnNH-4-Pyr | Me | 2,2-diCl |
| 1-1212 | 4-F-Ph | 4-Pym | Me | — |
| 1-1213 | 4-F-Ph | 4-Pym | Me | 2-OH |
| 1-1214 | 4-F-Ph | 4-Pym | Me | 2-MeO |
| 1-1215 | 4-F-Ph | 4-Pym | Me | 2-Ph |
| 1-1216 | 4-F-Ph | 4-Pym | Me | 8-Me |
| 1-1217 | 4-F-Ph | 4-Pym | Me | 2-F |
| 1-1218 | 4-F-Ph | 4-Pym | Me | 2-Cl |
| 1-1219 | 4-F-Ph | 4-Pym | Me | 2-Br |
| 1-1220 | 4-F-Ph | 4-Pym | Me | 2,2-diF |
| 1-1221 | 4-F-Ph | 4-Pym | Me | 2,2-diCl |
| 1-1222 | 4-F-Ph | 2-MeO-4-Pym | Me | — |
| 1-1223 | 4-F-Ph | 2-MeO-4-Pym | Me | 2-OH |
| 1-1224 | 4-F-Ph | 2-MeO-4-Pym | Me | 2-MeO |
| 1-1225 | 4-F-Ph | 2-MeO-4-Pym | Me | 2-Ph |
| 1-1226 | 4-F-Ph | 2-MeO-4-Pym | Me | 8-Me |
| 1-1227 | 4-F-Ph | 2-MeO-4-Pym | Me | 2-F |
| 1-1228 | 4-F-Ph | 2-MeO-4-Pym | Me | 2-Cl |
| 1-1229 | 4-F-Ph | 2-MeO-4-Pym | Me | 2-Br |
| 1-1230 | 4-F-Ph | 2-MeO-4-Pym | Me | 2,2-diF |
| 1-1231 | 4-F-Ph | 2-MeO-4-Pym | Me | 2,2-diCl |
| 1-1232 | 4-F-Ph | 2-(α-Me-BnNH)-4-Pym | Me | — |
| 1-1233 | 4-F-Ph | 2-(α-Me-BnNH)-4-Pym | Me | 2-OH |
| 1-1234 | 4-F-Ph | 2-(α-Me-BnNH)-4-Pym | Me | 2-MeO |
| 1-1235 | 4-F-Ph | 2-(α-Me-BnNH)-4-Pym | Me | 2-Ph |
| 1-1236 | 4-F-Ph | 2-(α-Me-BnNH)-4-Pym | Me | 8-Me |
| 1-1237 | 4-F-Ph | 2-(α-Me-BnNH)-4-Pym | Me | 2-F |
| 1-1238 | 4-F-Ph | 2-(α-Me-BnNH)-4-Pym | Me | 2-Cl |
| 1-1239 | 4-F-Ph | 2-(α-Me-BnNH)-4-Pym | Me | 2-Br |
| 1-1240 | 4-F-Ph | 2-(α-Me-BnNH)-4-Pym | Me | 2,2-diF |
| 1-1241 | 4-F-Ph | 2-(α-Me-BnNH)-4-Pym | Me | 2,2-diCl |
| 1-1242 | 4-F-Ph | 2-BnNH-4-Pym | Me | — |
| 1-1243 | 4-F-Ph | 2-BnNH-4-Pym | Me | 2-OH |
| 1-1244 | 4-F-Ph | 2-BnNH-4-Pym | Me | 2-MeO |
| 1-1245 | 4-F-Ph | 2-BnNH-4-Pym | Me | 2-Ph |
| 1-1246 | 4-F-Ph | 2-BnNH-4-Pym | Me | 8-Me |
| 1-1247 | 4-F-Ph | 2-BnNH-4-Pym | Me | 2-F |
| 1-1248 | 4-F-Ph | 2-BnNH-4-Pym | Me | 2-Cl |
| 1-1249 | 4-F-Ph | 2-BnNH-4-Pym | Me | 2-Br |
| 1-1250 | 4-F-Ph | 2-BnNH-4-Pym | Me | 2,2-diF |
| 1-1251 | 4-F-Ph | 2-BnNH-4-Pym | Me | 2,2-diCl |
| 1-1252 | 4-F-Ph | 4-Pyr | H | 2->CH₂ |
| 1-1253 | 4-F-Ph | 4-Pyr | H | 2->CHMe |
| 1-1254 | 4-F-Ph | 4-Pyr | H | 2->CHEt |
| 1-1255 | 4-F-Ph | 4-Pyr | H | 2->CHPr |
| 1-1256 | 4-F-Ph | 4-Pyr | H | 2->C(Me)₂ |
| 1-1257 | 4-F-Ph | 4-Pyr | H | 2->CHPh |
| 1-1258 | 4-F-Ph | 4-Pyr | H | 2,2-diPh |
| 1-1259 | 4-F-Ph | 4-Pyr | H | 2,2-O(CH₂)₃O— |
| 1-1260 | 4-F-Ph | 4-Pyr | H | 2,2-OCH₂C(Me)₂CH₂O— |
| 1-1261 | 4-F-Ph | 4-Pyr | H | 2,2-(CH₂)₂— |
| 1-1262 | 4-F-Ph | 4-Pyr | H | 2,2-(CH₂)₃— |
| 1-1263 | 4-F-Ph | 4-Pyr | H | 2,2-(CH₂)₄— |
| 1-1264 | 4-F-Ph | 4-Pyr | H | 2,2-(CH₂)₅— |
| 1-1265 | 4-F-Ph | 4-Pyr | H | 2-MeS |
| 1-1266 | 4-F-Ph | 4-Pyr | H | 2-EtS |
| 1-1267 | 4-F-Ph | 4-Pyr | H | 2-PrS |
| 1-1268 | 4-F-Ph | 4-Pyr | H | 2-BuS |
| 1-1269 | 4-F-Ph | 4-Pyr | H | 2-MeSO₂ |
| 1-1270 | 4-F-Ph | 4-Pyr | H | 2-PhO |
| 1-1271 | 4-Cl-Ph | 4-Pyr | H | 1-Me |
| 1-1272 | 4-Cl-Ph | 4-Pyr | H | 1-Et |
| 1-1273 | 4-Cl-Ph | 4-Pyr | H | 1-Pr |
| 1-1274 | 4-Cl-Ph | 4-Pyr | H | 1,1-diMe |
| 1-1275 | 4-Cl-Ph | 4-Pyr | H | 2-Me |
| 1-1276 | 4-Cl-Ph | 4-Pyr | H | 2-Et |
| 1-1277 | 4-Cl-Ph | 4-Pyr | H | 2-Pr |
| 1-1278 | 4-Cl-Ph | 4-Pyr | H | 2-Bu |
| 1-1279 | 4-Cl-Ph | 4-Pyr | H | 2-Allyl |
| 1-1280 | 4-Cl-Ph | 4-Pyr | H | 2-Ph |
| 1-1281 | 4-Cl-Ph | 4-Pyr | H | 2-Bn |
| 1-1282 | 4-Cl-Ph | 4-Pyr | H | 2-Phet |
| 1-1283 | 4-Cl-Ph | 4-Pyr | H | 2,2-diMe |
| 1-1284 | 4-Cl-Ph | 4-Pyr | H | 2-OH |
| 1-1285 | 4-Cl-Ph | 4-Pyr | H | 2-MeO |
| 1-1286 | 4-Cl-Ph | 4-Pyr | H | 2-EtO |
| 1-1287 | 4-Cl-Ph | 4-Pyr | H | 2-PrO |
| 1-1288 | 4-Cl-Ph | 4-Pyr | H | 2,2-di(MeO) |
| 1-1289 | 4-Cl-Ph | 4-Pyr | H | 2,2-di(EtO) |
| 1-1290 | 4-Cl-Ph | 4-Pyr | H | 2,2-OCH₂CH₂O— |
| 1-1291 | 4-Cl-Ph | 4-Pyr | H | 2-Oxo |
| 1-1292 | 4-Cl-Ph | 4-Pyr | H | 2-F |
| 1-1293 | 4-Cl-Ph | 4-Pyr | H | 2-Cl |
| 1-1294 | 4-Cl-Ph | 4-Pyr | H | 2-Br |
| 1-1295 | 4-Cl-Ph | 4-Pyr | H | 2-I |
| 1-1296 | 4-Cl-Ph | 4-Pyr | H | 2,2-diF |
| 1-1297 | 4-Cl-Ph | 4-Pyr | H | 2,2-diCl |
| 1-1298 | 4-Cl-Ph | 4-Pyr | H | 2,2-diBr |
| 1-1299 | 4-Cl-Ph | 4-Pyr | H | 3-Me |
| 1-1300 | 4-Cl-Ph | 4-Pyr | H | 3-Et |
| 1-1301 | 4-Cl-Ph | 4-Pyr | H | 3-Pr |
| 1-1302 | 4-Cl-Ph | 4-Pyr | H | 3,3-diMe |
| 1-1303 | 4-Cl-Ph | 4-Pyr | H | 5-Me |
| 1-1304 | 4-Cl-Ph | 4-Pyr | H | 5-Et |
| 1-1305 | 4-Cl-Ph | 4-Pyr | H | 5-Pr |
| 1-1306 | 4-Cl-Ph | 4-Pyr | H | 5,5-diMe |

TABLE 1-continued

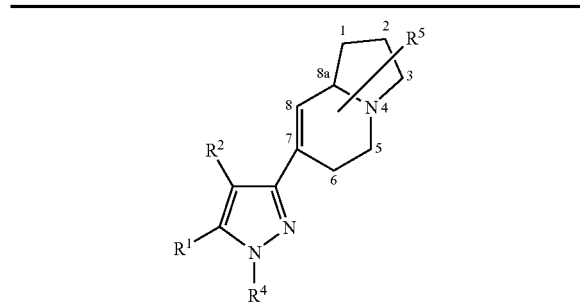

| Compound No. | R¹ | R² | R⁴ | R⁵ |
|---|---|---|---|---|
| 1-1307 | 4-Cl-Ph | 4-Pyr | H | 6-Me |
| 1-1308 | 4-Cl-Ph | 4-Pyr | H | 6-Et |
| 1-1309 | 4-Cl-Ph | 4-Pyr | H | 6-Pr |
| 1-1310 | 4-Cl-Ph | 4-Pyr | H | 6,6-diMe |
| 1-1311 | 4-Cl-Ph | 4-Pyr | H | 6-Oxo |
| 1-1312 | 4-Cl-Ph | 4-Pyr | H | 8-Me |
| 1-1313 | 4-Cl-Ph | 4-Pyr | H | 8-Et |
| 1-1314 | 4-Cl-Ph | 4-Pyr | H | 8-Pr |
| 1-1315 | 4-Cl-Ph | 4-Pyr | H | 8-Ph |
| 1-1316 | 4-Cl-Ph | 4-Pyr | H | 8a-Me |
| 1-1317 | 4-Cl-Ph | 4-Pyr | H | 8a-Et |
| 1-1318 | 4-Cl-Ph | 4-Pyr | H | 8a-Pr |
| 1-1319 | 4-Cl-Ph | 4-Pyr | H | 6,6-(CH$_2$)$_2$— |
| 1-1320 | 4-Cl-Ph | 4-Pyr | H | 6,6-diF |
| 1-1321 | 4-Cl-Ph | 4-Pyr | H | 2->CH$_2$ |
| 1-1322 | 4-Cl-Ph | 4-Pyr | H | 2->CHMe |
| 1-1323 | 4-Cl-Ph | 4-Pyr | H | 2->CHEt |
| 1-1324 | 4-Cl-Ph | 4-Pyr | H | 2->CHPr |
| 1-1325 | 4-Cl-Ph | 4-Pyr | H | 2->C(Me)$_2$ |
| 1-1326 | 4-Cl-Ph | 4-Pyr | H | 2->CHPh |
| 1-1327 | 4-Cl-Ph | 4-Pyr | H | 2,2-diPh |
| 1-1328 | 4-Cl-Ph | 4-Pyr | H | 2,2-O(CH$_2$)$_3$O— |
| 1-1329 | 4-Cl-Ph | 4-Pyr | H | 2,2-OCH$_2$C(Me)$_2$CH$_2$O— |
| 1-1330 | 4-Cl-Ph | 4-Pyr | H | 2,2-(CH$_2$)$_2$— |
| 1-1331 | 4-Cl-Ph | 4-Pyr | H | 2,2-(CH$_2$)$_3$— |
| 1-1332 | 4-Cl-Ph | 4-Pyr | H | 2,2-(CH$_2$)$_4$— |
| 1-1333 | 4-Cl-Ph | 4-Pyr | H | 2,2-(CH$_2$)$_5$— |
| 1-1334 | 4-Cl-Ph | 4-Pyr | H | 2-MeS |
| 1-1335 | 4-Cl-Ph | 4-Pyr | H | 2-EtS |
| 1-1336 | 4-Cl-Ph | 4-Pyr | H | 2-PrS |
| 1-1337 | 4-Cl-Ph | 4-Pyr | H | 2-BuS |
| 1-1338 | 4-Cl-Ph | 4-Pyr | H | 2-MeSO$_2$ |
| 1-1339 | 4-Cl-Ph | 4-Pyr | H | 2-PhO |
| 1-1340 | 4-F-Ph | 4-Pyr | H | 2-(4-MeO-Ph) |
| 1-1341 | 4-F-Ph | 4-Pyr | H | 2-(4-Me-Ph) |
| 1-1342 | 4-F-Ph | 4-Pyr | H | 2-(4-F-Ph) |
| 1-1343 | 4-F-Ph | 4-Pyr | H | 2-(4-CF$_3$-Ph) |
| 1-1344 | 4-F-Ph | 4-Pyr | H | 2-(4-Cl-Ph) |
| 1-1345 | 4-F-Ph | 4-Pyr | H | 2-(2,4-diF-Ph) |
| 1-1346 | 3-CF$_3$-Ph | 4-Pyr | H | 2-(4-MeO-Ph) |
| 1-1347 | 3-CF$_3$-Ph | 4-Pyr | H | 2-(4-Me-Ph) |
| 1-1348 | 3-CF$_3$-Ph | 4-Pyr | H | 2-(4-F-Ph) |
| 1-1349 | 3-CF$_3$-Ph | 4-Pyr | H | 2-(4-CF$_3$-Ph) |
| 1-1350 | 3-CF$_3$-Ph | 4-Pyr | H | 2-(4-Cl-Ph) |
| 1-1351 | 3-CF$_3$-Ph | 4-Pyr | H | 2-(2,4-diF-Ph) |
| 1-1352 | 4-F-Ph | 2-NH$_2$-4-Pym | H | 2->CH$_2$ |
| 1-1353 | 4-F-Ph | 2-NH$_2$-4-Pym | H | 2->CHMe |
| 1-1354 | 4-F-Ph | 2-NH$_2$-4-Pym | H | 2->CHEt |
| 1-1355 | 4-F-Ph | 2-NH$_2$-4-Pym | H | 2->CHPr |
| 1-1356 | 4-F-Ph | 2-NH$_2$-4-Pym | H | 2->C(Me)$_2$ |
| 1-1357 | 4-F-Ph | 2-NH$_2$-4-Pym | H | 2->CHPh |
| 1-1358 | 4-F-Ph | 2-NH$_2$-4-Pym | H | 2,2-diPh |
| 1-1359 | 4-F-Ph | 2-NH$_2$-4-Pym | H | 2,2-O(CH$_2$)$_3$O— |
| 1-1360 | 4-F-Ph | 2-NH$_2$-4-Pym | H | 2,2-OCH$_2$C(Me)$_2$CH$_2$O— |
| 1-1361 | 4-F-Ph | 2-NH$_2$-4-Pym | H | 2,2-(CH$_2$)$_2$— |
| 1-1362 | 4-F-Ph | 2-NH$_2$-4-Pym | H | 2,2-(CH$_2$)$_3$— |
| 1-1363 | 4-F-Ph | 2-NH$_2$-4-Pym | H | 2,2-(CH$_2$)$_4$— |
| 1-1364 | 4-F-Ph | 2-NH$_2$-4-Pym | H | 2,2-(CH$_2$)$_5$— |
| 1-1365 | 4-F-Ph | 2-NH$_2$-4-Pym | H | 2-MeS |
| 1-1366 | 4-F-Ph | 2-NH$_2$-4-Pym | H | 2-EtS |
| 1-1367 | 4-F-Ph | 2-NH$_2$-4-Pym | H | 2-PrS |
| 1-1368 | 4-F-Ph | 2-NH$_2$-4-Pym | H | 2-BuS |
| 1-1369 | 4-F-Ph | 2-NH$_2$-4-Pym | H | 2-MeSO$_2$ |
| 1-1370 | 4-F-Ph | 2-NH$_2$-4-Pym | H | 2-PhO |
| 1-1371 | 4-Cl-Ph | 2-NH$_2$-4-Pym | H | 1-Me |
| 1-1372 | 4-Cl-Ph | 2-NH$_2$-4-Pym | H | 1-Et |
| 1-1373 | 4-Cl-Ph | 2-NH$_2$-4-Pym | H | 1-Pr |
| 1-1374 | 4-Cl-Ph | 2-NH$_2$-4-Pym | H | 1,1-diMe |
| 1-1375 | 4-Cl-Ph | 2-NH$_2$-4-Pym | H | 2-Me |
| 1-1376 | 4-Cl-Ph | 2-NH$_2$-4-Pym | H | 2-Et |
| 1-1377 | 4-Cl-Ph | 2-NH$_2$-4-Pym | H | 2-Pr |
| 1-1378 | 4-Cl-Ph | 2-NH$_2$-4-Pym | H | 2-Bu |
| 1-1379 | 4-Cl-Ph | 2-NH$_2$-4-Pym | H | 2-Allyl |
| 1-1380 | 4-Cl-Ph | 2-NH$_2$-4-Pym | H | 2-Ph |
| 1-1381 | 4-Cl-Ph | 2-NH$_2$-4-Pym | H | 2-Bn |
| 1-1382 | 4-Cl-Ph | 2-NH$_2$-4-Pym | H | 2-Phet |
| 1-1383 | 4-Cl-Ph | 2-NH$_2$-4-Pym | H | 2,2-diMe |
| 1-1384 | 4-Cl-Ph | 2-NH$_2$-4-Pym | H | 2-OH |
| 1-1385 | 4-Cl-Ph | 2-NH$_2$-4-Pym | H | 2-MeO |
| 1-1386 | 4-Cl-Ph | 2-NH$_2$-4-Pym | H | 2-EtO |
| 1-1387 | 4-Cl-Ph | 2-NH$_2$-4-Pym | H | 2-PrO |
| 1-1388 | 4-Cl-Ph | 2-NH$_2$-4-Pym | H | 2,2-di(MeO) |
| 1-1389 | 4-Cl-Ph | 2-NH$_2$-4-Pym | H | 2,2-di(EtO) |
| 1-1390 | 4-Cl-Ph | 2-NH$_2$-4-Pym | H | 2,2-OCH$_2$CH$_2$O— |
| 1-1391 | 4-Cl-Ph | 2-NH$_2$-4-Pym | H | 2-Oxo |
| 1-1392 | 4-Cl-Ph | 2-NH$_2$-4-Pym | H | 2-F |
| 1-1393 | 4-Cl-Ph | 2-NH$_2$-4-Pym | H | 2-Cl |
| 1-1394 | 4-Cl-Ph | 2-NH$_2$-4-Pym | H | 2-Br |
| 1-1395 | 4-Cl-Ph | 2-NH$_2$-4-Pym | H | 2-I |
| 1-1396 | 4-Cl-Ph | 2-NH$_2$-4-Pym | H | 2,2-diF |
| 1-1397 | 4-Cl-Ph | 2-NH$_2$-4-Pym | H | 2,2-diCl |
| 1-1398 | 4-Cl-Ph | 2-NH$_2$-4-Pym | H | 2,2-diBr |
| 1-1399 | 4-Cl-Ph | 2-NH$_2$-4-Pym | H | 3-Me |
| 1-1400 | 4-Cl-Ph | 2-NH$_2$-4-Pym | H | 3-Et |
| 1-1401 | 4-Cl-Ph | 2-NH$_2$-4-Pym | H | 3-Pr |
| 1-1402 | 4-Cl-Ph | 2-NH$_2$-4-Pym | H | 3,3-diMe |
| 1-1403 | 4-Cl-Ph | 2-NH$_2$-4-Pym | H | 5-Me |
| 1-1404 | 4-Cl-Ph | 2-NH$_2$-4-Pym | H | 5-Et |
| 1-1405 | 4-Cl-Ph | 2-NH$_2$-4-Pym | H | 5-Pr |
| 1-1406 | 4-Cl-Ph | 2-NH$_2$-4-Pym | H | 5,5-diMe |
| 1-1407 | 4-Cl-Ph | 2-NH$_2$-4-Pym | H | 6-Me |
| 1-1408 | 4-Cl-Ph | 2-NH$_2$-4-Pym | H | 6-Et |
| 1-1409 | 4-Cl-Ph | 2-NH$_2$-4-Pym | H | 6-Pr |
| 1-1410 | 4-Cl-Ph | 2-NH$_2$-4-Pym | H | 6,6-diMe |
| 1-1411 | 4-Cl-Ph | 2-NH$_2$-4-Pym | H | 6-Oxo |
| 1-1412 | 4-Cl-Ph | 2-NH$_2$-4-Pym | H | 8-Me |
| 1-1413 | 4-Cl-Ph | 2-NH$_2$-4-Pym | H | 8-Et |
| 1-1414 | 4-Cl-Ph | 2-NH$_2$-4-Pym | H | 8-Pr |
| 1-1415 | 4-Cl-Ph | 2-NH$_2$-4-Pym | H | 8-Ph |
| 1-1416 | 4-Cl-Ph | 2-NH$_2$-4-Pym | H | 8a-Me |
| 1-1417 | 4-Cl-Ph | 2-NH$_2$-4-Pym | H | 8a-Et |
| 1-1418 | 4-Cl-Ph | 2-NH$_2$-4-Pym | H | 8a-Pr |
| 1-1419 | 4-Cl-Ph | 2-NH$_2$-4-Pym | H | 6,6-(CH$_2$)$_2$— |
| 1-1420 | 4-Cl-Ph | 2-NH$_2$-4-Pym | H | 6,6-diF |
| 1-1421 | 4-Cl-Ph | 2-NH$_2$-4-Pym | H | 2->CH$_2$ |
| 1-1422 | 4-Cl-Ph | 2-NH$_2$-4-Pym | H | 2->CHMe |
| 1-1423 | 4-Cl-Ph | 2-NH$_2$-4-Pym | H | 2->CHEt |
| 1-1424 | 4-Cl-Ph | 2-NH$_2$-4-Pym | H | 2->CHPr |

TABLE 1-continued

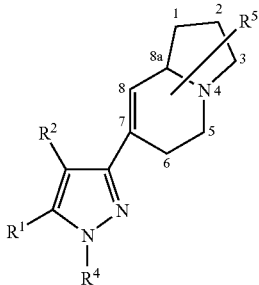

| Compound No. | R¹ | R² | R⁴ | R⁵ |
|---|---|---|---|---|
| 1-1425 | 4-Cl-Ph | 2-NH₂-4-Pym | H | 2->C(Me)₂ |
| 1-1426 | 4-Cl-Ph | 2-NH₂-4-Pym | H | 2->CHPh |
| 1-1427 | 4-Cl-Ph | 2-NH₂-4-Pym | H | 2,2-diPh |
| 1-1428 | 4-Cl-Ph | 2-NH₂-4-Pym | H | 2,2-O(CH₂)₃O— |
| 1-1429 | 4-Cl-Ph | 2-NH₂-4-Pym | H | 2,2-OCH₂C(Me)₂CH₂O— |
| 1-1430 | 4-Cl-Ph | 2-NH₂-4-Pym | H | 2,2-(CH₂)₂— |
| 1-1431 | 4-Cl-Ph | 2-NH₂-4-Pym | H | 2,2-(CH₂)₃— |
| 1-1432 | 4-Cl-Ph | 2-NH₂-4-Pym | H | 2,2-(CH₂)₄— |
| 1-1433 | 4-Cl-Ph | 2-NH₂-4-Pym | H | 2,2-(CH₂)₅— |
| 1-1434 | 4-Cl-Ph | 2-NH₂-4-Pym | H | 2-MeS |
| 1-1435 | 4-Cl-Ph | 2-NH₂-4-Pym | H | 2-EtS |
| 1-1436 | 4-Cl-Ph | 2-NH₂-4-Pym | H | 2-PrS |
| 1-1437 | 4-Cl-Ph | 2-NH₂-4-Pym | H | 2-BuS |
| 1-1438 | 4-Cl-Ph | 2-NH₂-4-Pym | H | 2-MeSO₂ |
| 1-1439 | 4-Cl-Ph | 2-NH₂-4-Pym | H | 2-PhO |
| 1-1440 | 4-F-Ph | 2-NH₂-4-Pym | H | 2-(4-MeO-Ph) |
| 1-1441 | 4-F-Ph | 2-NH₂-4-Pym | H | 2-(4-Me-Ph) |
| 1-1442 | 4-F-Ph | 2-NH₂-4-Pym | H | 2-(4-F-Ph) |
| 1-1443 | 4-F-Ph | 2-NH₂-4-Pym | H | 2-(4-CF₃-Ph) |
| 1-1444 | 4-F-Ph | 2-NH₂-4-Pym | H | 2-(4-Cl-Ph) |
| 1-1445 | 4-F-Ph | 2-NH₂-4-Pym | H | 2-(2,4-diF-Ph) |
| 1-1446 | 3-CF₃-Ph | 2-NH₂-4-Pym | H | 2-(4-MeO-Ph) |
| 1-1447 | 3-CF₃-Ph | 2-NH₂-4-Pym | H | 2-(4-Me-Ph) |
| 1-1448 | 3-CF₃-Ph | 2-NH₂-4-Pym | H | 2-(4-F-Ph) |
| 1-1449 | 3-CF₃-Ph | 2-NH₂-4-Pym | H | 2-(4-CF₃-Ph) |
| 1-1450 | 3-CF₃-Ph | 2-NH₂-4-Pym | H | 2-(4-Cl-Ph) |
| 1-1451 | 3-CF₃-Ph | 2-NH₂-4-Pym | H | 2-(2,4-diF-Ph) |
| 1-1452 | 4-F-Ph | 4-Pyr | Me | 2->CH₂ |
| 1-1453 | 4-F-Ph | 4-Pyr | Me | 2->CHMe |
| 1-1454 | 4-F-Ph | 4-Pyr | Me | 2->CHEt |
| 1-1455 | 4-F-Ph | 4-Pyr | Me | 2->CHPr |
| 1-1456 | 4-F-Ph | 4-Pyr | Me | 2->C(Me)₂ |
| 1-1457 | 4-F-Ph | 4-Pyr | Me | 2->CHPh |
| 1-1458 | 4-F-Ph | 4-Pyr | Me | 2,2-diPh |
| 1-1459 | 4-F-Ph | 4-Pyr | Me | 2,2-O(CH₂)₃O— |
| 1-1460 | 4-F-Ph | 4-Pyr | Me | 2,2-OCH₂C(Me)₂CH₂O— |
| 1-1461 | 4-F-Ph | 4-Pyr | Me | 2,2-(CH₂)₂— |
| 1-1462 | 4-F-Ph | 4-Pyr | Me | 2,2-(CH₂)₃— |
| 1-1463 | 4-F-Ph | 4-Pyr | Me | 2,2-(CH₂)₄— |
| 1-1464 | 4-F-Ph | 4-Pyr | Me | 2,2-(CH₂)₅— |
| 1-1465 | 4-F-Ph | 4-Pyr | Me | 2-MeS |
| 1-1466 | 4-F-Ph | 4-Pyr | Me | 2-EtS |
| 1-1467 | 4-F-Ph | 4-Pyr | Me | 2-PrS |
| 1-1468 | 4-F-Ph | 4-Pyr | Me | 2-BuS |
| 1-1469 | 4-F-Ph | 4-Pyr | Me | 2-MeSO₂ |
| 1-1470 | 4-F-Ph | 4-Pyr | Me | 2-PhO |
| 1-1471 | 4-Cl-Ph | 4-Pyr | Me | 1-Me |
| 1-1472 | 4-Cl-Ph | 4-Pyr | Me | 1-Et |
| 1-1473 | 4-Cl-Ph | 4-Pyr | Me | 1-Pr |
| 1-1474 | 4-Cl-Ph | 4-Pyr | Me | 1,1-diMe |
| 1-1475 | 4-Cl-Ph | 4-Pyr | Me | 2-Me |
| 1-1476 | 4-Cl-Ph | 4-Pyr | Me | 2-Et |
| 1-1477 | 4-Cl-Ph | 4-Pyr | Me | 2-Pr |
| 1-1478 | 4-Cl-Ph | 4-Pyr | Me | 2-Bu |
| 1-1479 | 4-Cl-Ph | 4-Pyr | Me | 2-Allyl |
| 1-1480 | 4-Cl-Ph | 4-Pyr | Me | 2-Ph |
| 1-1481 | 4-Cl-Ph | 4-Pyr | Me | 2-Bn |
| 1-1482 | 4-Cl-Ph | 4-Pyr | Me | 2-Phet |
| 1-1483 | 4-Cl-Ph | 4-Pyr | Me | 2,2-diMe |
| 1-1484 | 4-Cl-Ph | 4-Pyr | Me | 2-OH |
| 1-1485 | 4-Cl-Ph | 4-Pyr | Me | 2-MeO |
| 1-1486 | 4-Cl-Ph | 4-Pyr | Me | 2-EtO |
| 1-1487 | 4-Cl-Ph | 4-Pyr | Me | 2-PrO |
| 1-1488 | 4-Cl-Ph | 4-Pyr | Me | 2,2-di(MeO) |
| 1-1489 | 4-Cl-Ph | 4-Pyr | Me | 2,2-di(EtO) |
| 1-1490 | 4-Cl-Ph | 4-Pyr | Me | 2,2-OCH₂CH₂O— |
| 1-1491 | 4-Cl-Ph | 4-Pyr | Me | 2-Oxo |
| 1-1492 | 4-Cl-Ph | 4-Pyr | Me | 2-F |
| 1-1493 | 4-Cl-Ph | 4-Pyr | Me | 2-Cl |
| 1-1494 | 4-Cl-Ph | 4-Pyr | Me | 2-Br |
| 1-1495 | 4-Cl-Ph | 4-Pyr | Me | 2-I |
| 1-1496 | 4-Cl-Ph | 4-Pyr | Me | 2,2-diF |
| 1-1497 | 4-Cl-Ph | 4-Pyr | Me | 2,2-diCl |
| 1-1498 | 4-Cl-Ph | 4-Pyr | Me | 2,2-diBr |
| 1-1499 | 4-Cl-Ph | 4-Pyr | Me | 3-Me |
| 1-1500 | 4-Cl-Ph | 4-Pyr | Me | 3-Et |
| 1-1501 | 4-Cl-Ph | 4-Pyr | Me | 3-Pr |
| 1-1502 | 4-Cl-Ph | 4-Pyr | Me | 3,3-diMe |
| 1-1503 | 4-Cl-Ph | 4-Pyr | Me | 5-Me |
| 1-1504 | 4-Cl-Ph | 4-Pyr | Me | 5-Et |
| 1-1505 | 4-Cl-Ph | 4-Pyr | Me | 5-Pr |
| 1-1506 | 4-Cl-Ph | 4-Pyr | Me | 5,5-diMe |
| 1-1507 | 4-Cl-Ph | 4-Pyr | Me | 6-Me |
| 1-1508 | 4-Cl-Ph | 4-Pyr | Me | 6-Et |
| 1-1509 | 4-Cl-Ph | 4-Pyr | Me | 6-Pr |
| 1-1510 | 4-Cl-Ph | 4-Pyr | Me | 6,6-diMe |
| 1-1511 | 4-Cl-Ph | 4-Pyr | Me | 6-Oxo |
| 1-1512 | 4-Cl-Ph | 4-Pyr | Me | 8-Me |
| 1-1513 | 4-Cl-Ph | 4-Pyr | Me | 8-Et |
| 1-1514 | 4-Cl-Ph | 4-Pyr | Me | 8-Pr |
| 1-1515 | 4-Cl-Ph | 4-Pyr | Me | 8-Ph |
| 1-1516 | 4-Cl-Ph | 4-Pyr | Me | 8a-Me |
| 1-1517 | 4-Cl-Ph | 4-Pyr | Me | 8a-Et |
| 1-1518 | 4-Cl-Ph | 4-Pyr | Me | 8a-Pr |
| 1-1519 | 4-Cl-Ph | 4-Pyr | Me | 6,6-(CH₂)₂ |
| 1-1520 | 4-Cl-Ph | 4-Pyr | Me | 6,6-diF |
| 1-1521 | 4-Cl-Ph | 4-Pyr | Me | 2->CH₂ |
| 1-1522 | 4-Cl-Ph | 4-Pyr | Me | 2->CHMe |
| 1-1523 | 4-Cl-Ph | 4-Pyr | Me | 2->CHEt |
| 1-1524 | 4-Cl-Ph | 4-Pyr | Me | 2->CHPr |
| 1-1525 | 4-Cl-Ph | 4-Pyr | Me | 2->C(Me)₂ |
| 1-1526 | 4-Cl-Ph | 4-Pyr | Me | 2->CHPh |
| 1-1527 | 4-Cl-Ph | 4-Pyr | Me | 2,2-diPh |
| 1-1528 | 4-Cl-Ph | 4-Pyr | Me | 2,2-O(CH₂)₃O— |
| 1-1529 | 4-Cl-Ph | 4-Pyr | Me | 2,2-OCH₂C(Me)₂CH₂O— |
| 1-1530 | 4-Cl-Ph | 4-Pyr | Me | 2,2-(CH₂)₂— |
| 1-1531 | 4-Cl-Ph | 4-Pyr | Me | 2,2-(CH₂)₃— |
| 1-1532 | 4-Cl-Ph | 4-Pyr | Me | 2,2-(CH₂)₄— |
| 1-1533 | 4-Cl-Ph | 4-Pyr | Me | 2,2-(CH₂)₅— |
| 1-1534 | 4-Cl-Ph | 4-Pyr | Me | 2-MeS |
| 1-1535 | 4-Cl-Ph | 4-Pyr | Me | 2-EtS |
| 1-1536 | 4-Cl-Ph | 4-Pyr | Me | 2-PrS |
| 1-1537 | 4-Cl-Ph | 4-Pyr | Me | 2-BuS |
| 1-1538 | 4-Cl-Ph | 4-Pyr | Me | 2-MeSO₂ |
| 1-1539 | 4-Cl-Ph | 4-Pyr | Me | 2-PhO |
| 1-1540 | 4-F-Ph | 4-Pyr | Me | 2-(4-MeO-Ph) |
| 1-1541 | 4-F-Ph | 4-Pyr | Me | 2-(4-Me-Ph) |

TABLE 1-continued

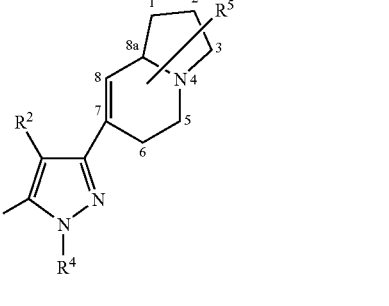

| Compound No. | R¹ | R² | R⁴ | R⁵ |
|---|---|---|---|---|
| 1-1542 | 4-F-Ph | 4-Pyr | Me | 2-(4-F-Ph) |
| 1-1543 | 4-F-Ph | 4-Pyr | Me | 2-(4-CF₃-Ph) |
| 1-1544 | 4-F-Ph | 4-Pyr | Me | 2-(4-Cl-Ph) |
| 1-1545 | 4-F-Ph | 4-Pyr | Me | 2-(2,4-diF-Ph) |
| 1-1546 | 3-CF₃-Ph | 4-Pyr | Me | 2-(4-MeO-Ph) |
| 1-1547 | 3-CF₃-Ph | 4-Pyr | Me | 2-(4-Me-Ph) |
| 1-1548 | 3-CF₃-Ph | 4-Pyr | Me | 2-(4-F-Ph) |
| 1-1549 | 3-CF₃-Ph | 4-Pyr | Me | 2-(4-CF₃-Ph) |
| 1-1550 | 3-CF₃-Ph | 4-Pyr | Me | 2-(4-Cl-Ph) |
| 1-1551 | 3-CF₃-Ph | 4-Pyr | Me | 2-(2,4-diF-Ph) |
| 1-1552 | 4-F-Ph | 2-NH₂-4-Pym | Me | 2->CH₂ |
| 1-1553 | 4-F-Ph | 2-NH₂-4-Pym | Me | 2->CHMe |
| 1-1554 | 4-F-Ph | 2-NH₂-4-Pym | Me | 2->CHEt |
| 1-1555 | 4-F-Ph | 2-NH₂-4-Pym | Me | 2->CHPr |
| 1-1556 | 4-F-Ph | 2-NH₂-4-Pym | Me | 2->C(Me)₂ |
| 1-1557 | 4-F-Ph | 2-NH₂-4-Pym | Me | 2->CHPh |
| 1-1558 | 4-F-Ph | 2-NH₂-4-Pym | Me | 2,2-diPh |
| 1-1559 | 4-F-Ph | 2-NH₂-4-Pym | Me | 2,2-O(CH₂)₃O— |
| 1-1560 | 4-F-Ph | 2-NH₂-4-Pym | Me | 2,2-OCH₂C(Me)₂CH₂O— |
| 1-1561 | 4-F-Ph | 2-NH₂-4-Pym | Me | 2,2-OCH₂C(Me)₂CH₂O— |
| 1-1562 | 4-F-Ph | 2-NH₂-4-Pym | Me | 2,2-(CH₂)₂— |
| 1-1563 | 4-F-Ph | 2-NH₂-4-Pym | Me | 2,2-(CH₂)₃— |
| 1-1564 | 4-F-Ph | 2-NH₂-4-Pym | Me | 2,2-(CH₂)₄— |
| 1-1565 | 4-F-Ph | 2-NH₂-4-Pym | Me | 2,2-(CH₂)₅— |
| 1-1566 | 4-F-Ph | 2-NH₂-4-Pym | Me | 2-MeS |
| 1-1567 | 4-F-Ph | 2-NH₂-4-Pym | Me | 2-EtS |
| 1-1568 | 4-F-Ph | 2-NH₂-4-Pym | Me | 2-PrS |
| 1-1569 | 4-F-Ph | 2-NH₂-4-Pym | Me | 2-BuS |
| 1-1570 | 4-F-Ph | 2-NH₂-4-Pym | Me | 2-MeSO₂ |
| 1-1571 | 4-Cl-Ph | 2-NH₂-4-Pym | Me | 2-PhO |
| 1-1572 | 4-Cl-Ph | 2-NH₂-4-Pym | Me | 1-Me |
| 1-1573 | 4-Cl-Ph | 2-NH₂-4-Pym | Me | 1-Et |
| 1-1574 | 4-Cl-Ph | 2-NH₂-4-Pym | Me | 1-Pr |
| 1-1575 | 4-Cl-Ph | 2-NH₂-4-Pym | Me | 1,1-diMe |
| 1-1576 | 4-Cl-Ph | 2-NH₂-4-Pym | Me | 2-Me |
| 1-1577 | 4-Cl-Ph | 2-NH₂-4-Pym | Me | 2-Et |
| 1-1578 | 4-Cl-Ph | 2-NH₂-4-Pym | Me | 2-Pr |
| 1-1579 | 4-Cl-Ph | 2-NH₂-4-Pym | Me | 2-Bu |
| 1-1580 | 4-Cl-Ph | 2-NH₂-4-Pym | Me | 2-Allyl |
| 1-1581 | 4-Cl-Ph | 2-NH₂-4-Pym | Me | 2-Ph |
| 1-1582 | 4-Cl-Ph | 2-NH₂-4-Pym | Me | 2-Bn |
| 1-1583 | 4-Cl-Ph | 2-NH₂-4-Pym | Me | 2-Phet |
| 1-1584 | 4-Cl-Ph | 2-NH₂-4-Pym | Me | 2,2-diMe |
| 1-1585 | 4-Cl-Ph | 2-NH₂-4-Pym | Me | 2-OH |
| 1-1586 | 4-Cl-Ph | 2-NH₂-4-Pym | Me | 2-MeO |
| 1-1587 | 4-Cl-Ph | 2-NH₂-4-Pym | Me | 2-EtO |
| 1-1588 | 4-Cl-Ph | 2-NH₂-4-Pym | Me | 2-PrO |
| 1-1589 | 4-Cl-Ph | 2-NH₂-4-Pym | Me | 2,2-di(MeO) |
| 1-1590 | 4-Cl-Ph | 2-NH₂-4-Pym | Me | 2,2-di(EtO) |
| 1-1591 | 4-Cl-Ph | 2-NH₂-4-Pym | Me | 2,2-OCH₂CH₂O— |
| 1-1592 | 4-Cl-Ph | 2-NH₂-4-Pym | Me | 2-Oxo |
| 1-1593 | 4-Cl-Ph | 2-NH₂-4-Pym | Me | 2-F |
| 1-1594 | 4-Cl-Ph | 2-NH₂-4-Pym | Me | 2-Cl |
| 1-1595 | 4-Cl-Ph | 2-NH₂-4-Pym | Me | 2-Br |
| 1-1596 | 4-Cl-Ph | 2-NH₂-4-Pym | Me | 2-I |
| 1-1597 | 4-Cl-Ph | 2-NH₂-4-Pym | Me | 2,2-diF |
| 1-1598 | 4-Cl-Ph | 2-NH₂-4-Pym | Me | 2,2-diCl |
| 1-1599 | 4-Cl-Ph | 2-NH₂-4-Pym | Me | 2,2-diBr |
| 1-1600 | 4-Cl-Ph | 2-NH₂-4-Pym | Me | 3-Me |

TABLE 1-continued

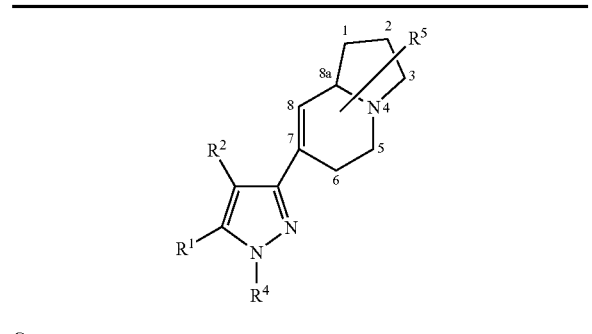

| Compound No. | R¹ | R² | R⁴ | R⁵ |
|---|---|---|---|---|
| 1-1601 | 4-Cl-Ph | 2-NH₂-4-Pym | Me | 3-Pr |
| 1-1602 | 4-Cl-Ph | 2-NH₂-4-Pym | Me | 3,3-diMe |
| 1-1603 | 4-Cl-Ph | 2-NH₂-4-Pym | Me | 5-Me |
| 1-1604 | 4-Cl-Ph | 2-NH₂-4-Pym | Me | 5-Et |
| 1-1605 | 4-Cl-Ph | 2-NH₂-4-Pym | Me | 5-Pr |
| 1-1606 | 4-Cl-Ph | 2-NH₂-4-Pym | Me | 5,5-diMe |
| 1-1607 | 4-Cl-Ph | 2-NH₂-4-Pym | Me | 6-Me |
| 1-1608 | 4-Cl-Ph | 2-NH₂-4-Pym | Me | 6-Et |
| 1-1609 | 4-Cl-Ph | 2-NH₂-4-Pym | Me | 6-Pr |
| 1-1610 | 4-Cl-Ph | 2-NH₂-4-Pym | Me | 6,6-diMe |
| 1-1611 | 4-Cl-Ph | 2-NH₂-4-Pym | Me | 6-Oxo |
| 1-1612 | 4-Cl-Ph | 2-NH₂-4-Pym | Me | 8-Me |
| 1-1613 | 4-Cl-Ph | 2-NH₂-4-Pym | Me | 8-Et |
| 1-1614 | 4-Cl-Ph | 2-NH₂-4-Pym | Me | 8-Pr |
| 1-1615 | 4-Cl-Ph | 2-NH₂-4-Pym | Me | 8-Ph |
| 1-1616 | 4-Cl-Ph | 2-NH₂-4-Pym | Me | 8a-Me |
| 1-1617 | 4-Cl-Ph | 2-NH₂-4-Pym | Me | 8a-Et |
| 1-1618 | 4-Cl-Ph | 2-NH₂-4-Pym | Me | 8a-Pr |
| 1-1619 | 4-Cl-Ph | 2-NH₂-4-Pym | Me | 6,6-(CH₂)₂— |
| 1-1620 | 4-Cl-Ph | 2-NH₂-4-Pym | Me | 6,6-diF |
| 1-1621 | 4-Cl-Ph | 2-NH₂-4-Pym | Me | 2->CH₂ |
| 1-1622 | 4-Cl-Ph | 2-NH₂-4-Pym | Me | 2->CHMe |
| 1-1623 | 4-Cl-Ph | 2-NH₂-4-Pym | Me | 2->CHEt |
| 1-1624 | 4-Cl-Ph | 2-NH₂-4-Pym | Me | 2->CHPr |
| 1-1625 | 4-Cl-Ph | 2-NH₂-4-Pym | Me | 2->C(Me)₂ |
| 1-1626 | 4-Cl-Ph | 2-NH₂-4-Pym | Me | 2->CHPh |
| 1-1627 | 4-Cl-Ph | 2-NH₂-4-Pym | Me | 2,2-diPh |
| 1-1628 | 4-Cl-Ph | 2-NH₂-4-Pym | Me | 2,2-O(CH₂)₃O— |
| 1-1629 | 4-Cl-Ph | 2-NH₂-4-Pym | Me | 2,2-OCH₂C(Me)₂CH₂O— |
| 1-1630 | 4-Cl-Ph | 2-NH₂-4-Pym | Me | 2,2-(CH₂)₂— |
| 1-1631 | 4-Cl-Ph | 2-NH₂-4-Pym | Me | 2,2-(CH₂)₃— |
| 1-1632 | 4-Cl-Ph | 2-NH₂-4-Pym | Me | 2,2-(CH₂)₄— |
| 1-1633 | 4-Cl-Ph | 2-NH₂-4-Pym | Me | 2,2-(CH₂)₅— |
| 1-1634 | 4-Cl-Ph | 2-NH₂-4-Pym | Me | 2-MeS |
| 1-1635 | 4-Cl-Ph | 2-NH₂-4-Pym | Me | 2-EtS |
| 1-1636 | 4-Cl-Ph | 2-NH₂-4-Pym | Me | 2-PrS |
| 1-1637 | 4-Cl-Ph | 2-NH₂-4-Pym | Me | 2-BuS |
| 1-1638 | 4-Cl-Ph | 2-NH₂-4-Pym | Me | 2-MeSO₂ |
| 1-1639 | 4-Cl-Ph | 2-NH₂-4-Pym | Me | 2-PhO |
| 1-1640 | 4-F-Ph | 2-NH₂-4-Pym | Me | 2-(4-MeO-Ph) |
| 1-1641 | 4-F-Ph | 2-NH₂-4-Pym | Me | 2-(4-Me-Ph) |
| 1-1642 | 4-F-Ph | 2-NH₂-4-Pym | Me | 2-(4-F-Ph) |
| 1-1643 | 4-F-Ph | 2-NH₂-4-Pym | Me | 2-(4-CF₃-Ph) |
| 1-1644 | 4-F-Ph | 2-NH₂-4-Pym | Me | 2-(4-Cl-Ph) |
| 1-1645 | 4-F-Ph | 2-NH₂-4-Pym | Me | 2-(2,4-diF-Ph) |
| 1-1646 | 3-CF₃-Ph | 2-NH₂-4-Pym | Me | 2-(4-MeO-Ph) |
| 1-1647 | 3-CF₃-Ph | 2-NH₂-4-Pym | Me | 2-(4-Me-Ph) |
| 1-1648 | 3-CF₃-Ph | 2-NH₂-4-Pym | Me | 2-(4-F-Ph) |
| 1-1649 | 3-CF₃-Ph | 2-NH₂-4-Pym | Me | 2-(4-CF₃-Ph) |
| 1-1650 | 3-CF₃-Ph | 2-NH₂-4-Pym | Me | 2-(4-Cl-Ph) |
| 1-1651 | 3-CF₃-Ph | 2-NH₂-4-Pym | Me | 2-(2,4-diF-Ph) |
| 1-1652 | 4-Cl-Ph | 4-Pyr | H | — |
| 1-1653 | 4-Cl-Ph | 4-Pyr | H | 2-(4-MeO-Ph) |
| 1-1654 | 4-Cl-Ph | 4-Pyr | H | 2-(4-Me-Ph) |
| 1-1656 | 4-Cl-Ph | 4-Pyr | H | 2-(4-F-Ph) |
| 1-1657 | 4-Cl-Ph | 4-Pyr | H | 2-(4-CF₃-Ph) |
| 1-1658 | 4-Cl-Ph | 4-Pyr | H | 2-(4-Cl-Ph) |
| 1-1659 | 4-Cl-Ph | 4-Pyr | H | 2-(2,4-diF-Ph) |
| 1-1660 | 4-Cl-Ph | 4-Pyr | Me | — |

TABLE 1-continued

[Structure diagram of pyrazole-fused bicyclic compound with positions 1, 2, 3, 4, 5, 6, 7, 8, 8a labeled; N at position 4; R¹, R², R⁴, R⁵ substituents]

| Compound No. | R¹ | R² | R⁴ | R⁵ |
|---|---|---|---|---|
| 1-1661 | 4-Cl-Ph | 4-Pyr | Me | 2-(4-MeO-Ph) |
| 1-1662 | 4-Cl-Ph | 4-Pyr | Me | 2-(4-Me-Ph) |
| 1-1663 | 4-Cl-Ph | 4-Pyr | Me | 2-(4-F-Ph) |
| 1-1664 | 4-Cl-Ph | 4-Pyr | Me | 2-(4-CF$_3$-Ph) |
| 1-1665 | 4-Cl-Ph | 4-Pyr | Me | 2-(4-Cl-Ph) |
| 1-1666 | 4-Cl-Ph | 4-Pyr | Me | 2-(2,4-diF-Ph) |
| 1-1667 | 4-Cl-Ph | 2-NH$_2$-4-Pym | H | — |
| 1-1668 | 4-Cl-Ph | 2-NH$_2$-4-Pym | Me | — |

TABLE 2

[Structure diagram of pyrazole-fused bicyclic compound with positions 1, 2, 3, 4, 5, 6, 7, 8, 8a labeled; N at position 4; R¹, R², R⁴, R⁵ substituents]

| Compound No. | R¹ | R² | R⁴ | R⁵ |
|---|---|---|---|---|
| 2-1 | 4-F-Ph | 4-Pyr | Me | — |
| 2-2 | 4-F-Ph | 4-Pyr | Me | 1-Me |
| 2-3 | 4-F-Ph | 4-Pyr | Me | 1-Et |
| 2-4 | 4-F-Ph | 4-Pyr | Me | 1-Pr |
| 2-5 | 4-F-Ph | 4-Pyr | Me | 1,1-diMe |
| 2-6 | 4-F-Ph | 4-Pyr | Me | 2-Me |
| 2-7 | 4-F-Ph | 4-Pyr | Me | 2-Et |
| 2-8 | 4-F-Ph | 4-Pyr | Me | 2-Pr |
| 2-9 | 4-F-Ph | 4-Pyr | Me | 2-Bu |
| 2-10 | 4-F-Ph | 4-Pyr | Me | 2-Allyl |
| 2-11 | 4-F-Ph | 4-Pyr | Me | 2-Ph |
| 2-12 | 4-F-Ph | 4-Pyr | Me | 2-Bn |
| 2-13 | 4-F-Ph | 4-Pyr | Me | 2-Phet |
| 2-14 | 4-F-Ph | 4-Pyr | Me | 2,2-diMe |
| 2-15 | 4-F-Ph | 4-Pyr | Me | 2-OH |
| 2-16 | 4-F-Ph | 4-Pyr | Me | 2-MeO |
| 2-17 | 4-F-Ph | 4-Pyr | Me | 2-EtO |
| 2-18 | 4-F-Ph | 4-Pyr | Me | 2-PrO |
| 2-19 | 4-F-Ph | 4-Pyr | Me | 2,2-di(MeO) |
| 2-20 | 4-F-Ph | 4-Pyr | Me | 2,2-di(EtO) |
| 2-21 | 4-F-Ph | 4-Pyr | Me | 2,2-OCH$_2$CH$_2$O— |
| 2-22 | 4-F-Ph | 4-Pyr | Me | 2-Oxo |
| 2-23 | 4-F-Ph | 4-Pyr | Me | 2-F |
| 2-24 | 4-F-Ph | 4-Pyr | Me | 2-Cl |
| 2-25 | 4-F-Ph | 4-Pyr | Me | 2-Br |
| 2-26 | 4-F-Ph | 4-Pyr | Me | 2-I |
| 2-27 | 4-F-Ph | 4-Pyr | Me | 2,2-diF |

TABLE 2-continued

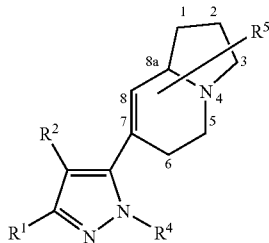

| Compound No. | R¹ | R² | R⁴ | R⁵ |
|---|---|---|---|---|
| 2-28 | 4-F-Ph | 4-Pyr | Me | 2,2-diCl |
| 2-29 | 4-F-Ph | 4-Pyr | Me | 2,2-diBr |
| 2-30 | 4-F-Ph | 4-Pyr | Me | 3-Me |
| 2-31 | 4-F-Ph | 4-Pyr | Me | 3-Et |
| 2-32 | 4-F-Ph | 4-Pyr | Me | 3-Pr |
| 2-33 | 4-F-Ph | 4-Pyr | Me | 3,3-diMe |
| 2-34 | 4-F-Ph | 4-Pyr | Me | 5-Me |
| 2-35 | 4-F-Ph | 4-Pyr | Me | 5-Et |
| 2-36 | 4-F-Ph | 4-Pyr | Me | 5-Pr |
| 2-37 | 4-F-Ph | 4-Pyr | Me | 5,5-diMe |
| 2-38 | 4-F-Ph | 4-Pyr | Me | 6-Me |
| 2-39 | 4-F-Ph | 4-Pyr | Me | 6-Et |
| 2-40 | 4-F-Ph | 4-Pyr | Me | 6-Pr |
| 2-41 | 4-F-Ph | 4-Pyr | Me | 6,6-diMe |
| 2-42 | 4-F-Ph | 4-Pyr | Me | 6,6-diF |
| 2-43 | 4-F-Ph | 4-Pyr | Me | 6,6-CH₂CH₂— |
| 2-44 | 4-F-Ph | 4-Pyr | Me | 6-Oxo |
| 2-45 | 4-F-Ph | 4-Pyr | Me | 8-Me |
| 2-46 | 4-F-Ph | 4-Pyr | Me | 8-Et |
| 2-47 | 4-F-Ph | 4-Pyr | Me | 8-Pr |
| 2-48 | 4-F-Ph | 4-Pyr | Me | 8-Ph |
| 2-49 | 4-F-Ph | 4-Pyr | Me | 8a-Me |
| 2-50 | 4-F-Ph | 4-Pyr | Me | 8a-Et |
| 2-51 | 4-F-Ph | 4-Pyr | Me | 8a-Pr |
| 2-52 | 4-F-Ph | 2-NH₂-4-Pym | Me | — |
| 2-53 | 4-F-Ph | 2-NH₂-4-Pym | Me | 1-Me |
| 2-54 | 4-F-Ph | 2-NH₂-4-Pym | Me | 1-Et |
| 2-55 | 4-F-Ph | 2-NH₂-4-Pym | Me | 1-Pr |
| 2-56 | 4-F-Ph | 2-NH₂-4-Pym | Me | 1,1-diMe |
| 2-57 | 4-F-Ph | 2-NH₂-4-Pym | Me | 2-Me |
| 2-58 | 4-F-Ph | 2-NH₂-4-Pym | Me | 2-Et |
| 2-59 | 4-F-Ph | 2-NH₂-4-Pym | Me | 2-Pr |
| 2-60 | 4-F-Ph | 2-NH₂-4-Pym | Me | 2-Bu |
| 2-61 | 4-F-Ph | 2-NH₂-4-Pym | Me | 2-Allyl |
| 2-62 | 4-F-Ph | 2-NH₂-4-Pym | Me | 2-Ph |
| 2-63 | 4-F-Ph | 2-NH₂-4-Pym | Me | 2-Bn |
| 2-64 | 4-F-Ph | 2-NH₂-4-Pym | Me | 2-Phet |
| 2-65 | 4-F-Ph | 2-NH₂-4-Pym | Me | 2,2-diMe |
| 2-66 | 4-F-Ph | 2-NH₂-4-Pym | Me | 2-OH |
| 2-67 | 4-F-Ph | 2-NH₂-4-Pym | Me | 2-MeO |
| 2-68 | 4-F-Ph | 2-NH₂-4-Pym | Me | 2-EtO |
| 2-69 | 4-F-Ph | 2-NH₂-4-Pym | Me | 2-PrO |
| 2-70 | 4-F-Ph | 2-NH₂-4-Pym | Me | 2,2-di(MeO) |
| 2-71 | 4-F-Ph | 2-NH₂-4-Pym | Me | 2,2-di(EtO) |
| 2-72 | 4-F-Ph | 2-NH₂-4-Pym | Me | 2,2-OCH₂CH₂O— |
| 2-73 | 4-F-Ph | 2-NH₂-4-Pym | Me | 2-Oxo |
| 2-74 | 4-F-Ph | 2-NH₂-4-Pym | Me | 2-F |
| 2-75 | 4-F-Ph | 2-NH₂-4-Pym | Me | 2-Cl |
| 2-76 | 4-F-Ph | 2-NH₂-4-Pym | Me | 2-Br |
| 2-77 | 4-F-Ph | 2-NH₂-4-Pym | Me | 2-I |
| 2-78 | 4-F-Ph | 2-NH₂-4-Pym | Me | 2,2-diF |
| 2-79 | 4-F-Ph | 2-NH₂-4-Pym | Me | 2,2-diCl |
| 2-80 | 4-F-Ph | 2-NH₂-4-Pym | Me | 2,2-diBr |
| 2-81 | 4-F-Ph | 2-NH₂-4-Pym | Me | 3-Me |
| 2-82 | 4-F-Ph | 2-NH₂-4-Pym | Me | 3-Et |
| 2-83 | 4-F-Ph | 2-NH₂-4-Pym | Me | 3-Pr |
| 2-84 | 4-F-Ph | 2-NH₂-4-Pym | Me | 3,3-diMe |
| 2-85 | 4-F-Ph | 2-NH₂-4-Pym | Me | 5-Me |
| 2-86 | 4-F-Ph | 2-NH₂-4-Pym | Me | 5-Et |
| 2-87 | 4-F-Ph | 2-NH₂-4-Pym | Me | 5-Pr |
| 2-88 | 4-F-Ph | 2-NH₂-4-Pym | Me | 5,5-diMe |
| 2-89 | 4-F-Ph | 2-NH₂-4-Pym | Me | 6-Me |
| 2-90 | 4-F-Ph | 2-NH₂-4-Pym | Me | 6-Et |

TABLE 2-continued

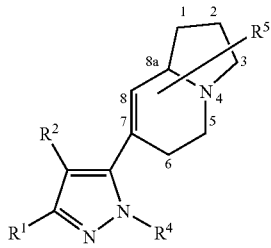

| Compound No. | R¹ | R² | R⁴ | R⁵ |
|---|---|---|---|---|
| 2-91 | 4-F-Ph | 2-NH₂-4-Pym | Me | 6-Pr |
| 2-92 | 4-F-Ph | 2-NH₂-4-Pym | Me | 6,6-diMe |
| 2-93 | 4-F-Ph | 2-NH₂-4-Pym | Me | 6,6-diF |
| 2-94 | 4-F-Ph | 2-NH₂-4-Pym | Me | 6,6-CH₂CH₂— |
| 2-95 | 4-F-Ph | 2-NH₂-4-Pym | Me | 6-Oxo |
| 2-96 | 4-F-Ph | 2-NH₂-4-Pym | Me | 8-Me |
| 2-97 | 4-F-Ph | 2-NH₂-4-Pym | Me | 8-Et |
| 2-98 | 4-F-Ph | 2-NH₂-4-Pym | Me | 8-Pr |
| 2-99 | 4-F-Ph | 2-NH₂-4-Pym | Me | 8-Ph |
| 2-100 | 4-F-Ph | 2-NH₂-4-Pym | Me | 8a-Me |
| 2-101 | 4-F-Ph | 2-NH₂-4-Pym | Me | 8a-Et |
| 2-102 | 4-F-Ph | 2-NH₂-4-Pym | Me | 8a-Pr |
| 2-103 | 4-F-Ph | 2-MeNH-4-Pym | Me | — |
| 2-104 | 4-F-Ph | 2-MeNH-4-Pym | Me | 1-Me |
| 2-105 | 4-F-Ph | 2-MeNH-4-Pym | Me | 1-Et |
| 2-106 | 4-F-Ph | 2-MeNH-4-Pym | Me | 1-Pr |
| 2-107 | 4-F-Ph | 2-MeNH-4-Pym | Me | 1,1-diMe |
| 2-108 | 4-F-Ph | 2-MeNH-4-Pym | Me | 2-Me |
| 2-109 | 4-F-Ph | 2-MeNH-4-Pym | Me | 2-Et |
| 2-110 | 4-F-Ph | 2-MeNH-4-Pym | Me | 2-Pr |
| 2-111 | 4-F-Ph | 2-MeNH-4-Pym | Me | 2-Bu |
| 2-112 | 4-F-Ph | 2-MeNH-4-Pym | Me | 2-Allyl |
| 2-113 | 4-F-Ph | 2-MeNH-4-Pym | Me | 2-Ph |
| 2-114 | 4-F-Ph | 2-MeNH-4-Pym | Me | 2-Bn |
| 2-115 | 4-F-Ph | 2-MeNH-4-Pym | Me | 2-Phet |
| 2-116 | 4-F-Ph | 2-MeNH-4-Pym | Me | 2,2-diMe |
| 2-117 | 4-F-Ph | 2-MeNH-4-Pym | Me | 2-OH |
| 2-118 | 4-F-Ph | 2-MeNH-4-Pym | Me | 2-MeO |
| 2-119 | 4-F-Ph | 2-MeNH-4-Pym | Me | 2-EtO |
| 2-120 | 4-F-Ph | 2-MeNH-4-Pym | Me | 2-PrO |
| 2-121 | 4-F-Ph | 2-MeNH-4-Pym | Me | 2,2-di(MeO) |
| 2-122 | 4-F-Ph | 2-MeNH-4-Pym | Me | 2,2-di(EtO) |
| 2-123 | 4-F-Ph | 2-MeNH-4-Pym | Me | 2,2-OCH₂CH₂O— |
| 2-124 | 4-F-Ph | 2-MeNH-4-Pym | Me | 2-Oxo |
| 2-125 | 4-F-Ph | 2-MeNH-4-Pym | Me | 2-F |
| 2-126 | 4-F-Ph | 2-MeNH-4-Pym | Me | 2-Cl |
| 2-127 | 4-F-Ph | 2-MeNH-4-Pym | Me | 2-Br |
| 2-128 | 4-F-Ph | 2-MeNH-4-Pym | Me | 2-I |
| 2-129 | 4-F-Ph | 2-MeNH-4-Pym | Me | 2,2-diF |
| 2-130 | 4-F-Ph | 2-MeNH-4-Pym | Me | 2,2-diCl |
| 2-131 | 4-F-Ph | 2-MeNH-4-Pym | Me | 2,2-diBr |
| 2-132 | 4-F-Ph | 2-MeNH-4-Pym | Me | 3-Me |
| 2-133 | 4-F-Ph | 2-MeNH-4-Pym | Me | 3-Et |
| 2-134 | 4-F-Ph | 2-MeNH-4-Pym | Me | 3-Pr |
| 2-135 | 4-F-Ph | 2-MeNH-4-Pym | Me | 3,3-diMe |
| 2-136 | 4-F-Ph | 2-MeNH-4-Pym | Me | 5-Me |
| 2-137 | 4-F-Ph | 2-MeNH-4-Pym | Me | 5-Et |
| 2-138 | 4-F-Ph | 2-MeNH-4-Pym | Me | 5-Pr |
| 2-139 | 4-F-Ph | 2-MeNH-4-Pym | Me | 5,5-diMe |
| 2-140 | 4-F-Ph | 2-MeNH-4-Pym | Me | 6-Me |
| 2-141 | 4-F-Ph | 2-MeNH-4-Pym | Me | 6-Et |
| 2-142 | 4-F-Ph | 2-MeNH-4-Pym | Me | 6-Pr |
| 2-143 | 4-F-Ph | 2-MeNH-4-Pym | Me | 6,6-diMe |
| 2-144 | 4-F-Ph | 2-MeNH-4-Pym | Me | 6,6-diF |
| 2-145 | 4-F-Ph | 2-MeNH-4-Pym | Me | 6,6-CH₂CH₂— |
| 2-146 | 4-F-Ph | 2-MeNH-4-Pym | Me | 6-Oxo |
| 2-147 | 4-F-Ph | 2-MeNH-4-Pym | Me | 8-Me |
| 2-148 | 4-F-Ph | 2-MeNH-4-Pym | Me | 8-Et |
| 2-149 | 4-F-Ph | 2-MeNH-4-Pym | Me | 8-Pr |
| 2-150 | 4-F-Ph | 2-MeNH-4-Pym | Me | 8-Ph |
| 2-151 | 4-F-Ph | 2-MeNH-4-Pym | Me | 8a-Me |
| 2-152 | 4-F-Ph | 2-MeNH-4-Pym | Me | 8a-Et |
| 2-153 | 4-F-Ph | 2-MeNH-4-Pym | Me | 8a-Pr |

TABLE 2-continued

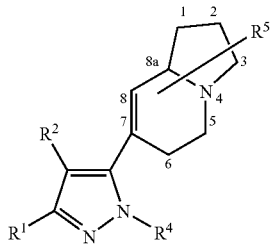

| Compound No. | R¹ | R² | R⁴ | R⁵ |
|---|---|---|---|---|
| 2-154 | 4-F-Ph | 2-MeO-4-Pyr | Me | — |
| 2-155 | 4-F-Ph | 2-MeO-4-Pyr | Me | 2-OH |
| 2-156 | 4-F-Ph | 2-MeO-4-Pyr | Me | 2-MeO |
| 2-157 | 4-F-Ph | 2-MeO-4-Pyr | Me | 2-Ph |
| 2-158 | 4-F-Ph | 2-MeO-4-Pyr | Me | 8-Me |
| 2-159 | 4-F-Ph | 2-MeO-4-Pyr | Me | 2-F |
| 2-160 | 4-F-Ph | 2-MeO-4-Pyr | Me | 2-Cl |
| 2-161 | 4-F-Ph | 2-MeO-4-Pyr | Me | 2-Br |
| 2-162 | 4-F-Ph | 2-MeO-4-Pyr | Me | 2,2-diF |
| 2-163 | 4-F-Ph | 2-MeO-4-Pyr | Me | 2,2-diCl |
| 2-164 | 4-F-Ph | 2-NH₂-4-Pyr | Me | — |
| 2-165 | 4-F-Ph | 2-NH₂-4-Pyr | Me | 2-OH |
| 2-166 | 4-F-Ph | 2-NH₂-4-Pyr | Me | 2-MeO |
| 2-167 | 4-F-Ph | 2-NH₂-4-Pyr | Me | 2-Ph |
| 2-168 | 4-F-Ph | 2-NH₂-4-Pyr | Me | 8-Me |
| 2-169 | 4-F-Ph | 2-NH₂-4-Pyr | Me | 2-F |
| 2-170 | 4-F-Ph | 2-NH₂-4-Pyr | Me | 2-Cl |
| 2-171 | 4-F-Ph | 2-NH₂-4-Pyr | Me | 2-Br |
| 2-172 | 4-F-Ph | 2-NH₂-4-Pyr | Me | 2,2-diF |
| 2-173 | 4-F-Ph | 2-NH₂-4-Pyr | Me | 2,2-diCl |
| 2-174 | 4-F-Ph | 2-MeNH-4-Pyr | Me | — |
| 2-175 | 4-F-Ph | 2-MeNH-4-Pyr | Me | 2-OH |
| 2-176 | 4-F-Ph | 2-MeNH-4-Pyr | Me | 2-MeO |
| 2-177 | 4-F-Ph | 2-MeNH-4-Pyr | Me | 2-Ph |
| 2-178 | 4-F-Ph | 2-MeNH-4-Pyr | Me | 8-Me |
| 2-179 | 4-F-Ph | 2-MeNH-4-Pyr | Me | 2-F |
| 2-180 | 4-F-Ph | 2-MeNH-4-Pyr | Me | 2-Cl |
| 2-181 | 4-F-Ph | 2-MeNH-4-Pyr | Me | 2-Br |
| 2-182 | 4-F-Ph | 2-MeNH-4-Pyr | Me | 2,2-diF |
| 2-183 | 4-F-Ph | 2-MeNH-4-Pyr | Me | 2,2-diCl |
| 2-184 | 4-F-Ph | 2-(α-Me-BnNH)-4-Pyr | Me | — |
| 2-185 | 4-F-Ph | 2-(α-Me-BnNH)-4-Pyr | Me | 2-OH |
| 2-186 | 4-F-Ph | 2-(α-Me-BnNH)-4-Pyr | Me | 2-MeO |
| 2-187 | 4-F-Ph | 2-(α-Me-BnNH)-4-Pyr | Me | 2-Ph |
| 2-188 | 4-F-Ph | 2-(α-Me-BnNH)-4-Pyr | Me | 8-Me |
| 2-189 | 4-F-Ph | 2-(α-Me-BnNH)-4-Pyr | Me | 2-F |
| 2-190 | 4-F-Ph | 2-(α-Me-BnNH)-4-Pyr | Me | 2-Cl |
| 2-191 | 4-F-Ph | 2-(α-Me-BnNH)-4-Pyr | Me | 2-Br |
| 2-192 | 4-F-Ph | 2-(α-Me-BnNH)-4-Pyr | Me | 2,2-diF |
| 2-193 | 4-F-Ph | 2-(α-Me-BnNH)-4-Pyr | Me | 2,2-diCl |
| 2-194 | 4-F-Ph | 2-BnNH-4-Pyr | Me | — |
| 2-195 | 4-F-Ph | 2-BnNH-4-Pyr | Me | 2-OH |
| 2-196 | 4-F-Ph | 2-BnNH-4-Pyr | Me | 2-MeO |
| 2-197 | 4-F-Ph | 2-BnNH-4-Pyr | Me | 2-Ph |
| 2-198 | 4-F-Ph | 2-BnNH-4-Pyr | Me | 8-Me |
| 2-199 | 4-F-Ph | 2-BnNH-4-Pyr | Me | 2-F |
| 2-200 | 4-F-Ph | 2-BnNH-4-Pyr | Me | 2-Cl |
| 2-201 | 4-F-Ph | 2-BnNH-4-Pyr | Me | 2-Br |
| 2-202 | 4-F-Ph | 2-BnNH-4-Pyr | Me | 2,2-diF |
| 2-203 | 4-F-Ph | 2-BnNH-4-Pyr | Me | 2,2-diCl |
| 2-204 | 4-F-Ph | 4-Pym | Me | — |
| 2-205 | 4-F-Ph | 4-Pym | Me | 2-OH |
| 2-206 | 4-F-Ph | 4-Pym | Me | 2-OH |
| 2-207 | 4-F-Ph | 4-Pym | Me | 2-Ph |
| 2-208 | 4-F-Ph | 4-Pym | Me | 8-Me |
| 2-209 | 4-F-Ph | 4-Pym | Me | 2-F |
| 2-210 | 4-F-Ph | 4-Pym | Me | 2-Cl |
| 2-211 | 4-F-Ph | 4-Pym | Me | 2-Br |
| 2-212 | 4-F-Ph | 4-Pym | Me | 2,2-diF |
| 2-213 | 4-F-Ph | 4-Pym | Me | 2,2-diCl |
| 2-214 | 4-F-Ph | 2-MeO-4-Pym | Me | — |
| 2-215 | 4-F-Ph | 2-MeO-4-Pym | Me | 2-OH |
| 2-216 | 4-F-Ph | 2-MeO-4-Pym | Me | 2-MeO |

TABLE 2-continued

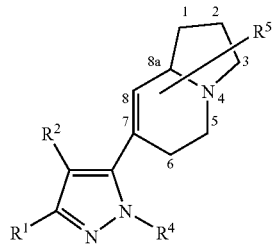

| Compound No. | R¹ | R² | R⁴ | R⁵ |
|---|---|---|---|---|
| 2-217 | 4-F-Ph | 2-MeO-4-Pym | Me | 2-Ph |
| 2-218 | 4-F-Ph | 2-MeO-4-Pym | Me | 8-Me |
| 2-219 | 4-F-Ph | 2-MeO-4-Pym | Me | 2-F |
| 2-220 | 4-F-Ph | 2-MeO-4-Pym | Me | 2-Cl |
| 2-221 | 4-F-Ph | 2-MeO-4-Pym | Me | 2-Br |
| 2-222 | 4-F-Ph | 2-MeO-4-Pym | Me | 2,2-diF |
| 2-223 | 4-F-Ph | 2-MeO-4-Pym | Me | 2,2-diCl |
| 2-224 | 4-F-Ph | 2-(α-Me-BnNH)-4-Pym | Me | — |
| 2-225 | 4-F-Ph | 2-(α-Me-BnNH)-4-Pym | Me | 2-OH |
| 2-226 | 4-F-Ph | 2-(α-Me-BnNH)-4-Pym | Me | 2-MeO |
| 2-227 | 4-F-Ph | 2-(α-Me-BnNH)-4-Pym | Me | 2-Ph |
| 2-228 | 4-F-Ph | 2-(α-Me-BnNH)-4-Pym | Me | 8-Me |
| 2-229 | 4-F-Ph | 2-(α-Me-BnNH)-4-Pym | Me | 2-F |
| 2-230 | 4-F-Ph | 2-(α-Me-BnNH)-4-Pym | Me | 2-Cl |
| 2-231 | 4-F-Ph | 2-(α-Me-BnNH)-4-Pym | Me | 2-Br |
| 2-232 | 4-F-Ph | 2-(α-Me-BnNH)-4-Pym | Me | 2,2-diF |
| 2-233 | 4-F-Ph | 2-(α-Me-BnNH)-4-Pym | Me | 2,2-diCl |
| 2-234 | 4-F-Ph | 2-BnNH-4-Pym | Me | — |
| 2-235 | 4-F-Ph | 2-BnNH-4-Pym | Me | 2-OH |
| 2-236 | 4-F-Ph | 2-BnNH-4-Pym | Me | 2-MeO |
| 2-237 | 4-F-Ph | 2-BnNH-4-Pym | Me | 2-Ph |
| 2-238 | 4-F-Ph | 2-BnNH-4-Pym | Me | 8-Me |
| 2-239 | 4-F-Ph | 2-BnNH-4-Pym | Me | 2-F |
| 2-240 | 4-F-Ph | 2-BnNH-4-Pym | Me | 2-Cl |
| 2-241 | 4-F-Ph | 2-BnNH-4-Pym | Me | 2-Br |
| 2-242 | 4-F-Ph | 2-BnNH-4-Pym | Me | 2,2-diF |
| 2-243 | 4-F-Ph | 2-BnNH-4-Pym | Me | 2,2-diCl |
| 2-244 | 4-F-Ph | 4-Pyr | Me | 2->CH₂ |
| 2-245 | 4-F-Ph | 4-Pyr | Me | 2->CHMe |
| 2-246 | 4-F-Ph | 4-Pyr | Me | 2->CHEt |
| 2-247 | 4-F-Ph | 4-Pyr | Me | 2->CHPr |
| 2-248 | 4-F-Ph | 4-Pyr | Me | 2->C(Me)₂ |
| 2-249 | 4-F-Ph | 4-Pyr | Me | 2->CHPh |
| 2-250 | 4-F-Ph | 4-Pyr | Me | 2,2-diPh |
| 2-251 | 4-F-Ph | 4-Pyr | Me | 2,2-O(CH₂)₃O— |
| 2-252 | 4-F-Ph | 4-Pyr | Me | 2,2-OCH₂C(Me)₂CH₂O— |
| 2-253 | 4-F-Ph | 4-Pyr | Me | 2,2-(CH₂)₂— |
| 2-254 | 4-F-Ph | 4-Pyr | Me | 2,2-(CH₂)₃— |
| 2-255 | 4-F-Ph | 4-Pyr | Me | 2,2-(CH₂)₄— |
| 2-256 | 4-F-Ph | 4-Pyr | Me | 2,2-(CH₂)₅— |
| 2-257 | 4-F-Ph | 4-Pyr | Me | 2-MeS |
| 2-258 | 4-F-Ph | 4-Pyr | Me | 2-EtS |
| 2-259 | 4-F-Ph | 4-Pyr | Me | 2-PrS |
| 2-260 | 4-F-Ph | 4-Pyr | Me | 2-BuS |
| 2-261 | 4-F-Ph | 4-Pyr | Me | 2-MeSO₂ |
| 2-262 | 4-F-Ph | 4-Pyr | Me | 2-PhO |
| 2-263 | 4-Cl-Ph | 4-Pyr | Me | 1-Me |
| 2-264 | 4-Cl-Ph | 4-Pyr | Me | 1-Et |
| 2-265 | 4-Cl-Ph | 4-Pyr | Me | 1-Pr |
| 2-266 | 4-Cl-Ph | 4-Pyr | Me | 1,1-diMe |
| 2-267 | 4-Cl-Ph | 4-Pyr | Me | 2-Me |
| 2-268 | 4-Cl-Ph | 4-Pyr | Me | 2-Et |
| 2-269 | 4-Cl-Ph | 4-Pyr | Me | 2-Pr |
| 2-270 | 4-Cl-Ph | 4-Pyr | Me | 2-Bu |
| 2-271 | 4-Cl-Ph | 4-Pyr | Me | 2-Allyl |
| 2-272 | 4-Cl-Ph | 4-Pyr | Me | 2-Ph |
| 2-273 | 4-Cl-Ph | 4-Pyr | Me | 2-Bn |
| 2-274 | 4-Cl-Ph | 4-Pyr | Me | 2-Phet |
| 2-275 | 4-Cl-Ph | 4-Pyr | Me | 2,2-diMe |
| 2-276 | 4-Cl-Ph | 4-Pyr | Me | 2-OH |
| 2-277 | 4-Cl-Ph | 4-Pyr | Me | 2-MeO |
| 2-278 | 4-Cl-Ph | 4-Pyr | Me | 2-EtO |

TABLE 2-continued

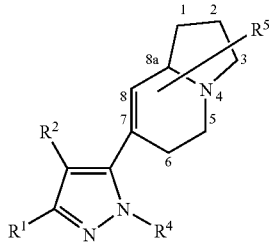

| Compound No. | R¹ | R² | R⁴ | R⁵ |
|---|---|---|---|---|
| 2-279 | 4-Cl-Ph | 4-Pyr | Me | 2-PrO |
| 2-280 | 4-Cl-Ph | 4-Pyr | Me | 2,2-di(MeO) |
| 2-281 | 4-Cl-Ph | 4-Pyr | Me | 2,2-di(EtO) |
| 2-282 | 4-Cl-Ph | 4-Pyr | Me | 2,2-OCH$_2$CH$_2$O— |
| 2-283 | 4-Cl-Ph | 4-Pyr | Me | 2-Oxo |
| 2-284 | 4-Cl-Ph | 4-Pyr | Me | 2-F |
| 2-285 | 4-Cl-Ph | 4-Pyr | Me | 2-Cl |
| 2-286 | 4-Cl-Ph | 4-Pyr | Me | 2-Br |
| 2-287 | 4-Cl-Ph | 4-Pyr | Me | 2-I |
| 2-288 | 4-Cl-Ph | 4-Pyr | Me | 2,2-diF |
| 2-289 | 4-Cl-Ph | 4-Pyr | Me | 2,2-diCl |
| 2-290 | 4-Cl-Ph | 4-Pyr | Me | 2,2-diBr |
| 2-291 | 4-Cl-Ph | 4-Pyr | Me | 3-Me |
| 2-292 | 4-Cl-Ph | 4-Pyr | Me | 3-Et |
| 2-293 | 4-Cl-Ph | 4-Pyr | Me | 3-Pr |
| 2-294 | 4-Cl-Ph | 4-Pyr | Me | 3,3-diMe |
| 2-295 | 4-Cl-Ph | 4-Pyr | Me | 5-Me |
| 2-296 | 4-Cl-Ph | 4-Pyr | Me | 5-Et |
| 2-297 | 4-Cl-Ph | 4-Pyr | Me | 5-Pr |
| 2-298 | 4-Cl-Ph | 4-Pyr | Me | 5,5-diMe |
| 2-299 | 4-Cl-Ph | 4-Pyr | Me | 6-Me |
| 2-300 | 4-Cl-Ph | 4-Pyr | Me | 6-Et |
| 2-301 | 4-Cl-Ph | 4-Pyr | Me | 6-Pr |
| 2-302 | 4-Cl-Ph | 4-Pyr | Me | 6,6-diMe |
| 2-303 | 4-Cl-Ph | 4-Pyr | Me | 6-Oxo |
| 2-304 | 4-Cl-Ph | 4-Pyr | Me | 8-Me |
| 2-305 | 4-Cl-Ph | 4-Pyr | Me | 8-Et |
| 2-306 | 4-Cl-Ph | 4-Pyr | Me | 8-Pr |
| 2-307 | 4-Cl-Ph | 4-Pyr | Me | 8-Ph |
| 2-308 | 4-Cl-Ph | 4-Pyr | Me | 8a-Me |
| 2-309 | 4-Cl-Ph | 4-Pyr | Me | 8a-Et |
| 2-310 | 4-Cl-Ph | 4-Pyr | Me | 8a-Pr |
| 2-311 | 4-Cl-Ph | 4-Pyr | Me | 6,6-(CH$_2$)$_2$— |
| 2-312 | 4-Cl-Ph | 4-Pyr | Me | 6,6-diF |
| 2-313 | 4-Cl-Ph | 4-Pyr | Me | 2->CH$_2$ |
| 2-314 | 4-Cl-Ph | 4-Pyr | Me | 2->CHMe |
| 2-315 | 4-Cl-Ph | 4-Pyr | Me | 2->CHEt |
| 2-316 | 4-Cl-Ph | 4-Pyr | Me | 2->CHPr |
| 2-317 | 4-Cl-Ph | 4-Pyr | Me | 2->C(Me)$_2$ |
| 2-318 | 4-Cl-Ph | 4-Pyr | Me | 2->CHPh |
| 2-319 | 4-Cl-Ph | 4-Pyr | Me | 2,2-diPh |
| 2-320 | 4-Cl-Ph | 4-Pyr | Me | 2,2-O(CH$_2$)$_3$O— |
| 2-321 | 4-Cl-Ph | 4-Pyr | Me | 2,2-OCH$_2$C(Me)$_2$CH$_2$O— |
| 2-322 | 4-Cl-Ph | 4-Pyr | Me | 2,2-(CH$_2$)$_2$— |
| 2-323 | 4-Cl-Ph | 4-Pyr | Me | 2,2-(CH$_2$)$_3$— |
| 2-324 | 4-Cl-Ph | 4-Pyr | Me | 2,2-(CH$_2$)$_4$— |
| 2-325 | 4-Cl-Ph | 4-Pyr | Me | 2,2-(CH$_2$)$_5$— |
| 2-326 | 4-Cl-Ph | 4-Pyr | Me | 2-MeS |
| 2-327 | 4-Cl-Ph | 4-Pyr | Me | 2-EtS |
| 2-328 | 4-Cl-Ph | 4-Pyr | Me | 2-PrS |
| 2-329 | 4-Cl-Ph | 4-Pyr | Me | 2-BuS |
| 2-330 | 4-Cl-Ph | 4-Pyr | Me | 2-MeSO$_2$ |
| 2-331 | 4-Cl-Ph | 4-Pyr | Me | 2-PhO |
| 2-332 | 4-F-Ph | 4-Pyr | Me | 2-(4-MeO-Ph) |
| 2-333 | 4-F-Ph | 4-Pyr | Me | 2-(4-Me-Ph) |
| 2-334 | 4-F-Ph | 4-Pyr | Me | 2-(4-F-Ph) |
| 2-335 | 4-F-Ph | 4-Pyr | Me | 2-(4-CF$_3$-Ph) |
| 2-336 | 4-F-Ph | 4-Pyr | Me | 2-(4-Cl-Ph) |
| 2-337 | 4-F-Ph | 4-Pyr | Me | 2-(2,4-diF-Ph) |
| 2-338 | 3-CF$_3$-Ph | 4-Pyr | Me | 2-(4-MeO-Ph) |
| 2-339 | 3-CF$_3$-Ph | 4-Pyr | Me | 2-(4-Me-Ph) |
| 2-340 | 3-CF$_3$-Ph | 4-Pyr | Me | 2-(4-F-Ph) |

TABLE 2-continued

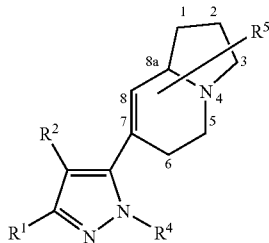

| Compound No. | $R^1$ | $R^2$ | $R^4$ | $R^5$ |
|---|---|---|---|---|
| 2-341 | 3-$CF_3$-Ph | 4-Pyr | Me | 2-(4-$CF_3$-Ph) |
| 2-342 | 3-$CF_3$-Ph | 4-Pyr | Me | 2-(4-Cl-Ph) |
| 2-343 | 3-$CF_3$-Ph | 4-Pyr | Me | 2-(2,4-diF-Ph) |
| 2-344 | 4-F-Ph | 2-$NH_2$-4-Pym | Me | 2->$CH_2$ |
| 2-345 | 4-F-Ph | 2-$NH_2$-4-Pym | Me | 2->CHMe |
| 2-346 | 4-F-Ph | 2-$NH_2$-4-Pym | Me | 2->CHEt |
| 2-347 | 4-F-Ph | 2-$NH_2$-4-Pym | Me | 2->CHPr |
| 2-348 | 4-F-Ph | 2-$NH_2$-4-Pym | Me | 2->$C(Me)_2$ |
| 2-349 | 4-F-Ph | 2-$NH_2$-4-Pym | Me | 2->CHPh |
| 2-350 | 4-F-Ph | 2-$NH_2$-4-Pym | Me | 2,2-diPh |
| 2-351 | 4-F-Ph | 2-$NH_2$-4-Pym | Me | 2,2-O$(CH_2)_3$O— |
| 2-352 | 4-F-Ph | 2-$NH_2$-4-Pym | Me | 2,2-O$CH_2$C$(Me)_2$C$H_2$O— |
| 2-353 | 4-F-Ph | 2-$NH_2$-4-Pym | Me | 2,2-$(CH_2)_2$— |
| 2-354 | 4-F-Ph | 2-$NH_2$-4-Pym | Me | 2,2-$(CH_2)_3$— |
| 2-355 | 4-F-Ph | 2-$NH_2$-4-Pym | Me | 2,2-$(CH_2)_4$— |
| 2-356 | 4-F-Ph | 2-$NH_2$-4-Pym | Me | 2,2-$(CH_2)_5$— |
| 2-357 | 4-F-Ph | 2-$NH_2$-4-Pym | Me | 2-MeS |
| 2-358 | 4-F-Ph | 2-$NH_2$-4-Pym | Me | 2-EtS |
| 2-359 | 4-F-Ph | 2-$NH_2$-4-Pym | Me | 2-PrS |
| 2-360 | 4-F-Ph | 2-$NH_2$-4-Pym | Me | 2-BuS |
| 2-361 | 4-F-Ph | 2-$NH_2$-4-Pym | Me | 2-MeS$O_2$ |
| 2-362 | 4-F-Ph | 2-$NH_2$-4-Pym | Me | 2-PhO |
| 2-363 | 4-Cl-Ph | 2-$NH_2$-4-Pym | Me | 1-Me |
| 2-364 | 4-Cl-Ph | 2-$NH_2$-4-Pym | Me | 1-Et |
| 2-365 | 4-Cl-Ph | 2-$NH_2$-4-Pym | Me | 1-Pr |
| 2-366 | 4-Cl-Ph | 2-$NH_2$-4-Pym | Me | 1,1-diMe |
| 2-367 | 4-Cl-Ph | 2-$NH_2$-4-Pym | Me | 2-Me |
| 2-368 | 4-Cl-Ph | 2-$NH_2$-4-Pym | Me | 2-Et |
| 2-369 | 4-Cl-Ph | 2-$NH_2$-4-Pym | Me | 2-Pr |
| 2-370 | 4-Cl-Ph | 2-$NH_2$-4-Pym | Me | 2-Bu |
| 2-371 | 4-Cl-Ph | 2-$NH_2$-4-Pym | Me | 2-Allyl |
| 2-372 | 4-Cl-Ph | 2-$NH_2$-4-Pym | Me | 2-Ph |
| 2-373 | 4-Cl-Ph | 2-$NH_2$-4-Pym | Me | 2-Bn |
| 2-374 | 4-Cl-Ph | 2-$NH_2$-4-Pym | Me | 2-Phet |
| 2-375 | 4-Cl-Ph | 2-$NH_2$-4-Pym | Me | 2m2-diMe |
| 2-376 | 4-Cl-Ph | 2-$NH_2$-4-Pym | Me | 2-OH |
| 2-377 | 4-Cl-Ph | 2-$NH_2$-4-Pym | Me | 2-MeO |
| 2-378 | 4-Cl-Ph | 2-$NH_2$-4-Pym | Me | 2-EtO |
| 2-379 | 4-Cl-Ph | 2-$NH_2$-4-Pym | Me | 2-PrO |
| 2-380 | 4-Cl-Ph | 2-$NH_2$-4-Pym | Me | 2,2-di(MeO) |
| 2-381 | 4-Cl-Ph | 2-$NH_2$-4-Pym | Me | 2,2-di(EtO) |
| 2-382 | 4-Cl-Ph | 2-$NH_2$-4-Pym | Me | 2,2-O$CH_2$C$H_2$O— |
| 2-383 | 4-Cl-Ph | 2-$NH_2$-4-Pym | Me | 2-Oxo |
| 2-384 | 4-Cl-Ph | 2-$NH_2$-4-Pym | Me | 2-F |
| 2-385 | 4-Cl-Ph | 2-$NH_2$-4-Pym | Me | 2-Cl |
| 2-386 | 4-Cl-Ph | 2-$NH_2$-4-Pym | Me | 2-Br |
| 2-387 | 4-Cl-Ph | 2-$NH_2$-4-Pym | Me | 2-I |
| 2-388 | 4-Cl-Ph | 2-$NH_2$-4-Pym | Me | 2,2-diF |
| 2-389 | 4-Cl-Ph | 2-$NH_2$-4-Pym | Me | 2,2-diCl |
| 2-390 | 4-Cl-Ph | 2-$NH_2$-4-Pym | Me | 2,2-diBr |
| 2-391 | 4-Cl-Ph | 2-$NH_2$-4-Pym | Me | 2-Me |
| 2-392 | 4-Cl-Ph | 2-$NH_2$-4-Pym | Me | 3-Et |
| 2-393 | 4-Cl-Ph | 2-$NH_2$-4-Pym | Me | 3-Pr |
| 2-394 | 4-Cl-Ph | 2-$NH_2$-4-Pym | Me | 3,3-diMe |
| 2-395 | 4-Cl-Ph | 2-$NH_2$-4-Pym | Me | 5-Me |
| 2-396 | 4-Cl-Ph | 2-$NH_2$-4-Pym | Me | 5-Et |
| 2-397 | 4-Cl-Ph | 2-$NH_2$-4-Pym | Me | 5-Pr |
| 2-398 | 4-Cl-Ph | 2-$NH_2$-4-Pym | Me | 5,5-diMe |
| 2-399 | 4-Cl-Ph | 2-$NH_2$-4-Pym | Me | 6-Me |
| 2-400 | 4-Cl-Ph | 2-$NH_2$-4-Pym | Me | 6-Et |
| 2-401 | 4-Cl-Ph | 2-$NH_2$-4-Pym | Me | 6-Pr |
| 2-402 | 4-Cl-Ph | 2-$NH_2$-4-Pym | Me | 6,6-diMe |

TABLE 2-continued

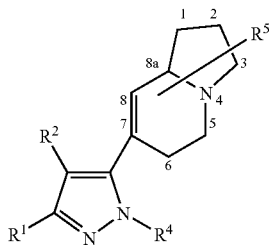

| Compound No. | R¹ | R² | R⁴ | R⁵ |
|---|---|---|---|---|
| 2-403 | 4-Cl-Ph | 2-NH₂-4-Pym | Me | 6-Oxo |
| 2-404 | 4-Cl-Ph | 2-NH₂-4-Pym | Me | 8-Me |
| 2-405 | 4-Cl-Ph | 2-NH₂-4-Pym | Me | 8-Et |
| 2-406 | 4-Cl-Ph | 2-NH₂-4-Pym | Me | 8-Pr |
| 2-407 | 4-Cl-Ph | 2-NH₂-4-Pym | Me | 8-Ph |
| 2-408 | 4-Cl-Ph | 2-NH₂-4-Pym | Me | 8a-Me |
| 2-409 | 4-Cl-Ph | 2-NH₂-4-Pym | Me | 8a-Et |
| 2-410 | 4-Cl-Ph | 2-NH₂-4-Pym | Me | 8a-Pr |
| 2-411 | 4-Cl-Ph | 2-NH₂-4-Pym | Me | 6,6-(CH₂)₂— |
| 2-412 | 4-Cl-Ph | 2-NH₂-4-Pym | Me | 6,6-diF |
| 2-413 | 4-Cl-Ph | 2-NH₂-4-Pym | Me | 2->CH₂ |
| 2-414 | 4-Cl-Ph | 2-NH₂-4-Pym | Me | 2->CHMe |
| 2-415 | 4-Cl-Ph | 2-NH₂-4-Pym | Me | 2->CHEt |
| 2-416 | 4-Cl-Ph | 2-NH₂-4-Pym | Me | 2->CHPr |
| 2-417 | 4-Cl-Ph | 2-NH₂-4-Pym | Me | 2->C(Me)₂ |
| 2-418 | 4-Cl-Ph | 2-NH₂-4-Pym | Me | 2->CHPh |
| 2-419 | 4-Cl-Ph | 2-NH₂-4-Pym | Me | 2,2-diPh |
| 2-420 | 4-Cl-Ph | 2-NH₂-4-Pym | Me | 2,2-O(CH₂)₃O— |
| 2-421 | 4-Cl-Ph | 2-NH₂-4-Pym | Me | 2,2-OCH₂C(Me)₂CH₂O— |
| 2-422 | 4-Cl-Ph | 2-NH₂-4-Pym | Me | 2,2-(CH₂)₂— |
| 2-423 | 4-Cl-Ph | 2-NH₂-4-Pym | Me | 2,2-(CH₂)₃— |
| 2-424 | 4-Cl-Ph | 2-NH₂-4-Pym | Me | 2,2-(CH₂)₄— |
| 2-425 | 4-Cl-Ph | 2-NH₂-4-Pym | Me | 2,2-(CH₂)₅— |
| 2-426 | 4-Cl-Ph | 2-NH₂-4-Pym | Me | 2-MeS |
| 2-427 | 4-Cl-Ph | 2-NH₂-4-Pym | Me | 2-EtS |
| 2-428 | 4-Cl-Ph | 2-NH₂-4-Pym | Me | 2-PrS |
| 2-429 | 4-Cl-Ph | 2-NH₂-4-Pym | Me | 2-BuS |
| 2-430 | 4-Cl-Ph | 2-NH₂-4-Pym | Me | 2-MeSO₂ |
| 2-431 | 4-Cl-Ph | 2-NH₂-4-Pym | Me | 2-PhO |
| 2-432 | 4-F-Ph | 2-NH₂-4-Pym | Me | 2-(4-MeO-Ph) |
| 2-433 | 4-F-Ph | 2-NH₂-4-Pym | Me | 2-(4-Me-Ph) |
| 2-434 | 4-F-Ph | 2-NH₂-4-Pym | Me | 2-(4-F-Ph) |
| 2-435 | 4-F-Ph | 2-NH₂-4-Pym | Me | 2-(4-CF₃-Ph) |
| 2-436 | 4-F-Ph | 2-NH₂-4-Pym | Me | 2-(4-Cl-Ph) |
| 2-437 | 4-F-Ph | 2-NH₂-4-Pym | Me | 2-(2,4-diF-Ph) |
| 2-438 | 3-CF₃-Ph | 2-NH₂-4-Pym | Me | 2-(4-MeO-Ph) |
| 2-439 | 3-CF₃-Ph | 2-NH₂-4-Pym | Me | 2-(4-Me-Ph) |
| 2-440 | 3-CF₃-Ph | 2-NH₂-4-Pym | Me | 2-(4-F-Ph) |
| 2-441 | 3-CF₃-Ph | 2-NH₂-4-Pym | Me | 2-(4-CF₃-Ph) |
| 2-442 | 3-CF₃-Ph | 2-NH₂-4-Pym | Me | 2-(4-Cl-Ph) |
| 2-443 | 3-CF₃-Ph | 2-NH₂-4-Pym | Me | 2-(2,4-diF-Ph) |
| 2-444 | 4-Cl-Ph | 4-Pyr | Me | — |
| 2-445 | 4-Cl-Ph | 4-Pyr | Me | 2-(4-MeO-Ph) |
| 2-446 | 4-Cl-Ph | 4-Pyr | Me | 2-(4-Me-Ph) |
| 2-447 | 4-Cl-Ph | 4-Pyr | Me | 2-(4-F-Ph) |
| 2-448 | 4-Cl-Ph | 4-Pyr | Me | 2-(4-CF₃-Ph) |
| 2-449 | 4-Cl-Ph | 4-Pyr | Me | 2-(4-Cl-Ph) |
| 2-450 | 4-Cl-Ph | 4-Pyr | Me | 2-(2,4-diF-Ph) |
| 2-451 | 4-Cl-Ph | 2-NH₂-4-Pym | Me | — |

TABLE 3

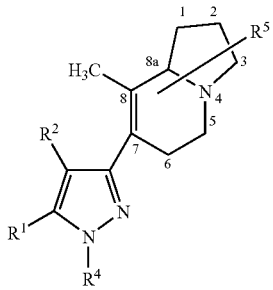

| Compound No. | R¹ | R² | R⁴ | R⁵ |
|---|---|---|---|---|
| 3-1 | 4-F-Ph | 4-Pyr | H | 1-Me |
| 3-2 | 4-F-Ph | 4-Pyr | H | 1-Et |
| 3-3 | 4-F-Ph | 4-Pyr | H | 1-Pr |
| 3-4 | 4-F-Ph | 4-Pyr | H | 1,1-diMe |
| 3-5 | 4-F-Ph | 4-Pyr | H | 2-Me |
| 3-6 | 4-F-Ph | 4-Pyr | H | 2-Et |
| 3-7 | 4-F-Ph | 4-Pyr | H | 2-Pr |
| 3-8 | 4-F-Ph | 4-Pyr | H | 2-Bu |
| 3-9 | 4-F-Ph | 4-Pyr | H | 2-Allyl |
| 3-10 | 4-F-Ph | 4-Pyr | H | 2-Ph |
| 3-11 | 4-F-Ph | 4-Pyr | H | 2-Bn |
| 3-12 | 4-F-Ph | 4-Pyr | H | 2-Phet |
| 3-13 | 4-F-Ph | 4-Pyr | H | 2,2-diMe |
| 3-14 | 4-F-Ph | 4-Pyr | H | 2-OH |
| 3-15 | 4-F-Ph | 4-Pyr | H | 2-MeO |
| 3-16 | 4-F-Ph | 4-Pyr | H | 2-EtO |
| 3-17 | 4-F-Ph | 4-Pyr | H | 2-PrO |
| 3-18 | 4-F-Ph | 4-Pyr | H | 2,2-di(MeO) |
| 3-19 | 4-F-Ph | 4-Pyr | H | 2,2-di(EtO) |
| 3-20 | 4-F-Ph | 4-Pyr | H | 2,2-OCH₂CH₂O— |
| 3-21 | 4-F-Ph | 4-Pyr | H | 2-Oxo |
| 3-22 | 4-F-Ph | 4-Pyr | H | 2-F |
| 3-23 | 4-F-Ph | 4-Pyr | H | 2-Cl |
| 3-24 | 4-F-Ph | 4-Pyr | H | 2-Br |
| 3-25 | 4-F-Ph | 4-Pyr | H | 2-I |
| 3-26 | 4-F-Ph | 4-Pyr | H | 2,2-diF |
| 3-27 | 4-F-Ph | 4-Pyr | H | 2,2-diCl |
| 3-28 | 4-F-Ph | 4-Pyr | H | 2,2-diBr |
| 3-29 | 4-F-Ph | 4-Pyr | H | 3-Me |
| 3-30 | 4-F-Ph | 4-Pyr | H | 3-Et |
| 3-31 | 4-F-Ph | 4-Pyr | H | 3-Pr |
| 3-32 | 4-F-Ph | 4-Pyr | H | 3,3-diMe |
| 3-33 | 4-F-Ph | 4-Pyr | H | 5-Me |
| 3-34 | 4-F-Ph | 4-Pyr | H | 5-Et |
| 3-35 | 4-F-Ph | 4-Pyr | H | 5-Pr |
| 3-36 | 4-F-Ph | 4-Pyr | H | 5,5-diMe |
| 3-37 | 4-F-Ph | 4-Pyr | H | 6-Me |
| 3-38 | 4-F-Ph | 4-Pyr | H | 6-Et |
| 3-39 | 4-F-Ph | 4-Pyr | H | 6-Pr |
| 3-40 | 4-F-Ph | 4-Pyr | H | 6,6-diMe |
| 3-41 | 4-F-Ph | 4-Pyr | H | 6,6-diF |
| 3-42 | 4-F-Ph | 4-Pyr | H | 6,6-CH₂CH₂— |
| 3-43 | 4-F-Ph | 4-Pyr | H | 6-Oxo |
| 3-44 | 4-F-Ph | 4-Pyr | H | 8a-Me |
| 3-45 | 4-F-Ph | 4-Pyr | H | 8a-Et |
| 3-46 | 4-F-Ph | 4-Pyr | H | 8a-Pr |
| 3-47 | 4-F-Ph | 4-Pyr | Me | 1-Me |
| 3-48 | 4-F-Ph | 4-Pyr | Me | 1-Et |
| 3-49 | 4-F-Ph | 4-Pyr | Me | 1-Pr |
| 3-50 | 4-F-Ph | 4-Pyr | Me | 1,1-diMe |
| 3-51 | 4-F-Ph | 4-Pyr | Me | 2-Me |
| 3-52 | 4-F-Ph | 4-Pyr | Me | 2-Et |
| 3-53 | 4-F-Ph | 4-Pyr | Me | 2-Pr |
| 3-54 | 4-F-Ph | 4-Pyr | Me | 2-Bu |
| 3-55 | 4-F-Ph | 4-Pyr | Me | 2-Allyl |
| 3-56 | 4-F-Ph | 4-Pyr | Me | 2-Ph |
| 3-57 | 4-F-Ph | 4-Pyr | Me | 2-Bn |
| 3-58 | 4-F-Ph | 4-Pyr | Me | 2-Phet |
| 3-59 | 4-F-Ph | 4-Pyr | Me | 2,2-diMe |
| 3-60 | 4-F-Ph | 4-Pyr | Me | 2-OH |
| 3-61 | 4-F-Ph | 4-Pyr | Me | 2-MeO |

TABLE 3-continued

| Compound No. | R¹ | R² | R⁴ | R⁵ |
|---|---|---|---|---|
| 3-62 | 4-F-Ph | 4-Pyr | Me | 2-EtO |
| 3-63 | 4-F-Ph | 4-Pyr | Me | 2-PrO |
| 3-64 | 4-F-Ph | 4-Pyr | Me | 2,2-di(MeO) |
| 3-65 | 4-F-Ph | 4-Pyr | Me | 2,2-di(EtO) |
| 3-66 | 4-F-Ph | 4-Pyr | Me | 2,2-OCH₂CH₂O— |
| 3-67 | 4-F-Ph | 4-Pyr | Me | 2-Oxo |
| 3-68 | 4-F-Ph | 4-Pyr | Me | 2-F |
| 3-69 | 4-F-Ph | 4-Pyr | Me | 2-Cl |
| 3-70 | 4-F-Ph | 4-Pyr | Me | 2-Br |
| 3-71 | 4-F-Ph | 4-Pyr | Me | 2-I |
| 3-72 | 4-F-Ph | 4-Pyr | Me | 2,2-diF |
| 3-73 | 4-F-Ph | 4-Pyr | Me | 2,2-diCl |
| 3-74 | 4-F-Ph | 4-Pyr | Me | 2,2-diBr |
| 3-75 | 4-F-Ph | 4-Pyr | Me | 3-Me |
| 3-76 | 4-F-Ph | 4-Pyr | Me | 3-Et |
| 3-77 | 4-F-Ph | 4-Pyr | Me | 3-Pr |
| 3-78 | 4-F-Ph | 4-Pyr | Me | 3,3-diMe |
| 3-79 | 4-F-Ph | 4-Pyr | Me | 5-Me |
| 3-80 | 4-F-Ph | 4-Pyr | Me | 5-Et |
| 3-81 | 4-F-Ph | 4-Pyr | Me | 5-Pr |
| 3-82 | 4-F-Ph | 4-Pyr | Me | 5,5-diMe |
| 3-83 | 4-F-Ph | 4-Pyr | Me | 6-Me |
| 3-84 | 4-F-Ph | 4-Pyr | Me | 6-Et |
| 3-85 | 4-F-Ph | 4-Pyr | Me | 6-Pr |
| 3-86 | 4-F-Ph | 4-Pyr | Me | 6,6-diMe |
| 3-87 | 4-F-Ph | 4-Pyr | Me | 6,6-diF |
| 3-88 | 4-F-Ph | 4-Pyr | Me | 6,6-CH₂CH₂— |
| 3-89 | 4-F-Ph | 4-Pyr | Me | 6-Oxo |
| 3-90 | 4-F-Ph | 4-Pyr | Me | 8a-Me |
| 3-91 | 4-F-Ph | 4-Pyr | Me | 8a-Et |
| 3-92 | 4-F-Ph | 4-Pyr | Me | 8a-Pr |

TABLE 4

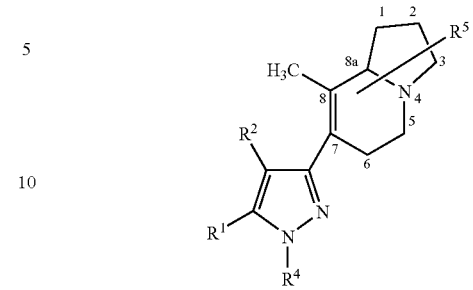

| Compound No. | R¹ | R² | R⁴ | R⁵ |
|---|---|---|---|---|
| 4-1 | 4-F-Ph | 4-Pyr | Me | 1-Me |
| 4-2 | 4-F-Ph | 4-Pyr | Me | 1-Et |
| 4-3 | 4-F-Ph | 4-Pyr | Me | 1-Pr |
| 4-4 | 4-F-Ph | 4-Pyr | Me | 1,1-diMe |
| 4-5 | 4-F-Ph | 4-Pyr | Me | 2-Me |
| 4-6 | 4-F-Ph | 4-Pyr | Me | 2-Et |
| 4-7 | 4-F-Ph | 4-Pyr | Me | 2-Pr |
| 4-8 | 4-F-Ph | 4-Pyr | Me | 2-Bu |
| 4-9 | 4-F-Ph | 4-Pyr | Me | 2-Allyl |

TABLE 4-continued

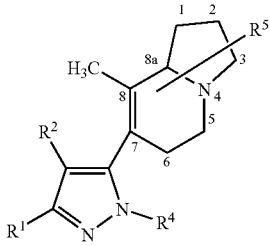

| Compound No. | R¹ | R² | R⁴ | R⁵ |
|---|---|---|---|---|
| 4-10 | 4-F-Ph | 4-Pyr | Me | 2-Ph |
| 4-11 | 4-F-Ph | 4-Pyr | Me | 2-Bn |
| 4-12 | 4-F-Ph | 4-Pyr | Me | 2-Phet |
| 4-13 | 4-F-Ph | 4-Pyr | Me | 2,2-diMe |
| 4-14 | 4-F-Ph | 4-Pyr | Me | 2-OH |
| 4-15 | 4-F-Ph | 4-Pyr | Me | 2-MeO |
| 4-16 | 4-F-Ph | 4-Pyr | Me | 2-EtO |
| 4-17 | 4-F-Ph | 4-Pyr | Me | 2-PrO |
| 4-18 | 4-F-Ph | 4-Pyr | Me | 2,2-di(MeO) |
| 4-19 | 4-F-Ph | 4-Pyr | Me | 2,2-di(EtO) |
| 4-20 | 4-F-Ph | 4-Pyr | Me | 2,2-OCH₂CH₂O— |
| 4-21 | 4-F-Ph | 4-Pyr | Me | 2-Oxo |
| 4-22 | 4-F-Ph | 4-Pyr | Me | 2-F |
| 4-23 | 4-F-Ph | 4-Pyr | Me | 2-Cl |
| 4-24 | 4-F-Ph | 4-Pyr | Me | 2-Br |
| 4-25 | 4-F-Ph | 4-Pyr | Me | 2-I |
| 4-26 | 4-F-Ph | 4-Pyr | Me | 2,2-diF |
| 4-27 | 4-F-Ph | 4-Pyr | Me | 2,2-diCl |
| 4-28 | 4-F-Ph | 4-Pyr | Me | 2,2-diBr |
| 4-29 | 4-F-Ph | 4-Pyr | Me | 3-Me |
| 4-30 | 4-F-Ph | 4-Pyr | Me | 3-Et |
| 4-31 | 4-F-Ph | 4-Pyr | Me | 3-Pr |
| 4-32 | 4-F-Ph | 4-Pyr | Me | 3,3-diMe |
| 4-33 | 4-F-Ph | 4-Pyr | Me | 5-Me |
| 4-34 | 4-F-Ph | 4-Pyr | Me | 5-Et |
| 4-35 | 4-F-Ph | 4-Pyr | Me | 5-Pr |
| 4-36 | 4-F-Ph | 4-Pyr | Me | 5,5-diMe |
| 4-37 | 4-F-Ph | 4-Pyr | Me | 6-Me |
| 4-38 | 4-F-Ph | 4-Pyr | Me | 6-Et |
| 4-39 | 4-F-Ph | 4-Pyr | Me | 6-Pr |
| 4-40 | 4-F-Ph | 4-Pyr | Me | 6,6-diMe |
| 4-41 | 4-F-Ph | 4-Pyr | Me | 6,6-diF |
| 4-42 | 4-F-Ph | 4-Pyr | Me | 6,6-CH₂CH₂— |
| 4-43 | 4-F-Ph | 4-Pyr | Me | 6-Oxo |
| 4-44 | 4-F-Ph | 4-Pyr | Me | 8a-Me |
| 4-45 | 4-F-Ph | 4-Pyr | Me | 8a-Et |
| 4-46 | 4-F-Ph | 4-Pyr | Me | 8a-Pr |

TABLE 5

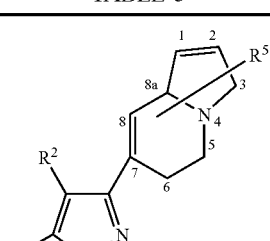

| Compound No. | R¹ | R² | R⁴ | R⁵ |
|---|---|---|---|---|
| 5-1 | 4-F-Ph | 4-Pyr | H | 1-Me |
| 5-2 | 4-F-Ph | 4-Pyr | H | 2-Me |
| 5-3 | 4-F-Ph | 4-Pyr | H | 2-Et |
| 5-4 | 4-F-Ph | 4-Pyr | H | 2-Pr |

TABLE 5-continued

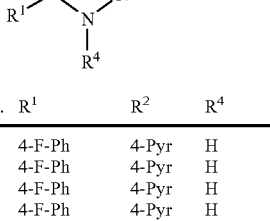

| Compound No. | R¹ | R² | R⁴ | R⁵ |
|---|---|---|---|---|
| 5-5 | 4-F-Ph | 4-Pyr | H | 2-Bu |
| 5-6 | 4-F-Ph | 4-Pyr | H | 2-Allyl |
| 5-7 | 4-F-Ph | 4-Pyr | H | 2-Ph |
| 5-8 | 4-F-Ph | 4-Pyr | H | 2-Bn |
| 5-9 | 4-F-Ph | 4-Pyr | H | 2-Phet |
| 5-10 | 4-F-Ph | 4-Pyr | H | 3-Me |
| 5-11 | 4-F-Ph | 4-Pyr | H | 3-Et |
| 5-12 | 4-F-Ph | 4-Pyr | H | 3-Pr |
| 5-13 | 4-F-Ph | 4-Pyr | H | 3,3-diMe |
| 5-14 | 4-F-Ph | 4-Pyr | H | 5-Me |
| 5-15 | 4-F-Ph | 4-Pyr | H | 5-Et |
| 5-16 | 4-F-Ph | 4-Pyr | H | 5-Pr |
| 5-17 | 4-F-Ph | 4-Pyr | H | 5,5-diMe |
| 5-18 | 4-F-Ph | 4-Pyr | H | 6-Me |
| 5-19 | 4-F-Ph | 4-Pyr | H | 6-Et |
| 5-20 | 4-F-Ph | 4-Pyr | H | 6-Pr |
| 5-21 | 4-F-Ph | 4-Pyr | H | 6,6-diMe |
| 5-22 | 4-F-Ph | 4-Pyr | H | 6,6-diF |
| 5-23 | 4-F-Ph | 4-Pyr | H | 6,6-CH₂CH₂— |
| 5-24 | 4-F-Ph | 4-Pyr | H | 6-Oxo |
| 5-25 | 4-F-Ph | 4-Pyr | H | 8-Me |
| 5-26 | 4-F-Ph | 4-Pyr | H | 8-Et |
| 5-27 | 4-F-Ph | 4-Pyr | H | 8-Pr |
| 5-28 | 4-F-Ph | 4-Pyr | H | 8-Ph |
| 5-29 | 4-F-Ph | 4-Pyr | H | 8a-Me |
| 5-30 | 4-F-Ph | 4-Pyr | H | 8a-Et |
| 5-31 | 4-F-Ph | 4-Pyr | H | 8a-Pr |
| 5-32 | 4-F-Ph | 4-Pyr | Me | 1-Me |
| 5-33 | 4-F-Ph | 4-Pyr | Me | 2-Me |
| 5-34 | 4-F-Ph | 4-Pyr | Me | 2-Et |
| 5-35 | 4-F-Ph | 4-Pyr | Me | 2-Pr |
| 5-36 | 4-F-Ph | 4-Pyr | Me | 2-Bu |
| 5-37 | 4-F-Ph | 4-Pyr | Me | 2-Allyl |
| 5-38 | 4-F-Ph | 4-Pyr | Me | 2-Ph |
| 5-39 | 4-F-Ph | 4-Pyr | Me | 2-Bn |
| 5-40 | 4-F-Ph | 4-Pyr | Me | 2-Phet |
| 5-41 | 4-F-Ph | 4-Pyr | Me | 3-Me |
| 5-42 | 4-F-Ph | 4-Pyr | Me | 3-Et |
| 5-43 | 4-F-Ph | 4-Pyr | Me | 3-Pr |
| 5-44 | 4-F-Ph | 4-Pyr | Me | 3,3-diMe |
| 5-45 | 4-F-Ph | 4-Pyr | Me | 5-Me |
| 5-46 | 4-F-Ph | 4-Pyr | Me | 5-Et |
| 5-47 | 4-F-Ph | 4-Pyr | Me | 5-Pr |
| 5-48 | 4-F-Ph | 4-Pyr | Me | 5,5-diMe |
| 5-49 | 4-F-Ph | 4-Pyr | Me | 6-Me |
| 5-50 | 4-F-Ph | 4-Pyr | Me | 6-Et |
| 5-51 | 4-F-Ph | 4-Pyr | Me | 6-Pr |
| 5-52 | 4-F-Ph | 4-Pyr | Me | 6,6-diMe |
| 5-53 | 4-F-Ph | 4-Pyr | Me | 6,6-diF |
| 5-54 | 4-F-Ph | 4-Pyr | Me | 6,6-CH₂CH₂— |
| 5-55 | 4-F-Ph | 4-Pyr | Me | 6-Oxo |
| 5-56 | 4-F-Ph | 4-Pyr | Me | 8-Me |
| 5-57 | 4-F-Ph | 4-Pyr | Me | 8-Et |
| 5-58 | 4-F-Ph | 4-Pyr | Me | 8-Pr |
| 5-59 | 4-F-Ph | 4-Pyr | Me | 8-Ph |
| 5-60 | 4-F-Ph | 4-Pyr | Me | 8a-Me |
| 5-61 | 4-F-Ph | 4-Pyr | Me | 8a-Et |
| 5-62 | 4-F-Ph | 4-Pyr | Me | 8a-Pr |
| 5-63 | 4-F-Ph | 4-Pyr | H | — |
| 5-64 | 4-F-Ph | 4-Pyr | Me | — |

TABLE 6

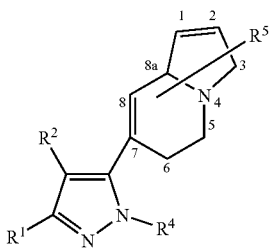

| Compound No. | R¹ | R² | R⁴ | R⁵ |
|---|---|---|---|---|
| 6-1 | 4-F-Ph | 4-Pyr | Me | 1-Me |
| 6-2 | 4-F-Ph | 4-Pyr | Me | 2-Me |
| 6-3 | 4-F-Ph | 4-Pyr | Me | 2-Et |
| 6-4 | 4-F-Ph | 4-Pyr | Me | 2-Pr |
| 6-5 | 4-F-Ph | 4-Pyr | Me | 2-Bu |
| 6-6 | 4-F-Ph | 4-Pyr | Me | 2-Allyl |
| 6-7 | 4-F-Ph | 4-Pyr | Me | 2-Ph |
| 6-8 | 4-F-Ph | 4-Pyr | Me | 2-Bn |
| 6-9 | 4-F-Ph | 4-Pyr | Me | 2-Phet |
| 6-10 | 4-F-Ph | 4-Pyr | Me | 2-Me |
| 6-11 | 4-F-Ph | 4-Pyr | Me | 3-Et |
| 6-12 | 4-F-Ph | 4-Pyr | Me | 3-Pr |
| 6-13 | 4-F-Ph | 4-Pyr | Me | 3,3-diMe |
| 6-14 | 4-F-Ph | 4-Pyr | Me | 5-Me |
| 6-15 | 4-F-Ph | 4-Pyr | Me | 5-Et |
| 6-16 | 4-F-Ph | 4-Pyr | Me | 5-Pr |
| 6-17 | 4-F-Ph | 4-Pyr | Me | 5,5-diMe |
| 6-18 | 4-F-Ph | 4-Pyr | Me | 6-Me |
| 6-19 | 4-F-Ph | 4-Pyr | Me | 6-Et |
| 6-20 | 4-F-Ph | 4-Pyr | Me | 6-Pr |
| 6-21 | 4-F-Ph | 4-Pyr | Me | 6,6-diMe |
| 6-22 | 4-F-Ph | 4-Pyr | Me | 6,6-diF |
| 6-23 | 4-F-Ph | 4-Pyr | Me | 6,6-CH₂CH₂— |
| 6-24 | 4-F-Ph | 4-Pyr | Me | 6-Oxo |
| 6-25 | 4-F-Ph | 4-Pyr | Me | 8-Me |
| 6-26 | 4-F-Ph | 4-Pyr | Me | 8-Et |
| 6-27 | 4-F-Ph | 4-Pyr | Me | 8-Pr |
| 6-28 | 4-F-Ph | 4-Pyr | Me | 8-Ph |
| 6-29 | 4-F-Ph | 4-Pyr | Me | 8a-Me |
| 6-30 | 4-F-Ph | 4-Pyr | Me | 8a-Et |
| 6-31 | 4-F-Ph | 4-Pyr | Me | 8a-Pr |
| 6-32 | 4-F-Ph | 4-Pyr | Me | — |

TABLE 7

| Compound No. | R¹ | R² | R⁴ | R⁵ |
|---|---|---|---|---|
| 7-1 | 4-F-Ph | 4-Pyr | H | — |
| 7-2 | 4-F-Ph | 4-Pyr | H | 1-Me |
| 7-3 | 4-F-Ph | 4-Pyr | H | 1-Et |
| 7-4 | 4-F-Ph | 4-Pyr | H | 1-Pr |
| 7-5 | 4-F-Ph | 4-Pyr | H | 1,1-diMe |
| 7-6 | 4-F-Ph | 4-Pyr | H | 2-Me |
| 7-7 | 4-F-Ph | 4-Pyr | H | 2-Et |
| 7-8 | 4-F-Ph | 4-Pyr | H | 2-Pr |
| 7-9 | 4-F-Ph | 4-Pyr | H | 2-Bu |
| 7-10 | 4-F-Ph | 4-Pyr | H | 2-Allyl |
| 7-11 | 4-F-Ph | 4-Pyr | H | 2-Ph |
| 7-12 | 4-F-Ph | 4-Pyr | H | 2-Bn |
| 7-13 | 4-F-Ph | 4-Pyr | H | 2-Phet |
| 7-14 | 4-F-Ph | 4-Pyr | H | 2,2-diMe |
| 7-15 | 4-F-Ph | 4-Pyr | H | 2-OH |
| 7-16 | 4-F-Ph | 4-Pyr | H | 2-MeO |
| 7-17 | 4-F-Ph | 4-Pyr | H | 2-EtO |
| 7-18 | 4-F-Ph | 4-Pyr | H | 2-PrO |
| 7-19 | 4-F-Ph | 4-Pyr | H | 2,2-di(MeO) |
| 7-20 | 4-F-Ph | 4-Pyr | H | 2,2-di(EtO) |
| 7-21 | 4-F-Ph | 4-Pyr | H | 2,2-OCH₂CH₂O— |
| 7-22 | 4-F-Ph | 4-Pyr | H | 2-Oxo |
| 7-23 | 4-F-Ph | 4-Pyr | H | 2-F |
| 7-24 | 4-F-Ph | 4-Pyr | H | 2-Cl |
| 7-25 | 4-F-Ph | 4-Pyr | H | 2-Br |
| 7-26 | 4-F-Ph | 4-Pyr | H | 2-I |
| 7-27 | 4-F-Ph | 4-Pyr | H | 2,2-diF |
| 7-28 | 4-F-Ph | 4-Pyr | H | 2,2-diCl |
| 7-29 | 4-F-Ph | 4-Pyr | H | 2,2-diBr |
| 7-30 | 4-F-Ph | 4-Pyr | H | 3-Me |
| 7-31 | 4-F-Ph | 4-Pyr | H | 3-Et |
| 7-32 | 4-F-Ph | 4-Pyr | H | 3-Pr |
| 7-33 | 4-F-Ph | 4-Pyr | H | 3,3-diMe |
| 7-34 | 4-F-Ph | 4-Pyr | H | 5-Me |
| 7-35 | 4-F-Ph | 4-Pyr | H | 5-Et |
| 7-36 | 4-F-Ph | 4-Pyr | H | 5-Pr |
| 7-37 | 4-F-Ph | 4-Pyr | H | 5,5-diMe |
| 7-38 | 4-F-Ph | 4-Pyr | H | 6-Me |
| 7-39 | 4-F-Ph | 4-Pyr | H | 6-Et |
| 7-40 | 4-F-Ph | 4-Pyr | H | 6-Pr |
| 7-41 | 4-F-Ph | 4-Pyr | H | 6-Ph |
| 7-42 | 4-F-Ph | 4-Pyr | H | 8-Me |
| 7-43 | 4-F-Ph | 4-Pyr | H | 8-Et |
| 7-44 | 4-F-Ph | 4-Pyr | H | 8-Pr |
| 7-45 | 4-F-Ph | 4-Pyr | H | 8,8-diMe |
| 7-46 | 4-F-Ph | 4-Pyr | H | 8,8-diF |
| 7-47 | 4-F-Ph | 4-Pyr | H | 8,8-CH₂CH₂— |
| 7-48 | 4-F-Ph | 4-Pyr | H | 8-Oxo |
| 7-49 | 4-F-Ph | 4-Pyr | H | 8a-Me |
| 7-50 | 4-F-Ph | 4-Pyr | H | 8a-Et |
| 7-51 | 4-F-Ph | 4-Pyr | H | 8a-Pr |
| 7-52 | 4-F-Ph | 4-Pyr | Me | — |
| 7-53 | 4-F-Ph | 4-Pyr | Me | 1-Me |
| 7-54 | 4-F-Ph | 4-Pyr | Me | 1-Et |
| 7-55 | 4-F-Ph | 4-Pyr | Me | 1-Pr |
| 7-56 | 4-F-Ph | 4-Pyr | Me | 1,1-diMe |
| 7-57 | 4-F-Ph | 4-Pyr | Me | 2-Me |
| 7-58 | 4-F-Ph | 4-Pyr | Me | 2-Et |
| 7-59 | 4-F-Ph | 4-Pyr | Me | 2-Pr |
| 7-60 | 4-F-Ph | 4-Pyr | Me | 2-Bu |
| 7-61 | 4-F-Ph | 4-Pyr | Me | 2-Allyl |
| 7-62 | 4-F-Ph | 4-Pyr | Me | 2-Ph |
| 7-63 | 4-F-Ph | 4-Pyr | Me | 2-Bn |
| 7-64 | 4-F-Ph | 4-Pyr | Me | 2-Phet |
| 7-65 | 4-F-Ph | 4-Pyr | Me | 2,2-diMe |
| 7-66 | 4-F-Ph | 4-Pyr | Me | 2-OH |
| 7-67 | 4-F-Ph | 4-Pyr | Me | 2-MeO |
| 7-68 | 4-F-Ph | 4-Pyr | Me | 2-EtO |
| 7-69 | 4-F-Ph | 4-Pyr | Me | 2-PrO |
| 7-70 | 4-F-Ph | 4-Pyr | Me | 2,2-di(MeO) |

TABLE 7-continued

| Compound No. | R¹ | R² | R⁴ | R⁵ |
|---|---|---|---|---|
| 7-71 | 4-F-Ph | 4-Pyr | Me | 2,2-di(EtO) |
| 7-72 | 4-F-Ph | 4-Pyr | Me | 2,2-OCH₂CH₂O— |
| 7-73 | 4-F-Ph | 4-Pyr | Me | 2-Oxo |
| 7-74 | 4-F-Ph | 4-Pyr | Me | 2-F |
| 7-75 | 4-F-Ph | 4-Pyr | Me | 2-Cl |
| 7-76 | 4-F-Ph | 4-Pyr | Me | 2-Br |
| 7-77 | 4-F-Ph | 4-Pyr | Me | 2-I |
| 7-78 | 4-F-Ph | 4-Pyr | Me | 2,2-diF |
| 7-79 | 4-F-Ph | 4-Pyr | Me | 2,2-diCl |
| 7-80 | 4-F-Ph | 4-Pyr | Me | 2,2-diBr |
| 7-81 | 4-F-Ph | 4-Pyr | Me | 3-Me |
| 7-82 | 4-F-Ph | 4-Pyr | Me | 3-Et |
| 7-83 | 4-F-Ph | 4-Pyr | Me | 3-Pr |
| 7-84 | 4-F-Ph | 4-Pyr | Me | 3,3-diMe |
| 7-85 | 4-F-Ph | 4-Pyr | Me | 5-Me |
| 7-86 | 4-F-Ph | 4-Pyr | Me | 5-Et |
| 7-87 | 4-F-Ph | 4-Pyr | Me | 5-Pr |
| 7-88 | 4-F-Ph | 4-Pyr | Me | 5,5-diMe |
| 7-89 | 4-F-Ph | 4-Pyr | Me | 6-Me |
| 7-90 | 4-F-Ph | 4-Pyr | Me | 6-Et |
| 7-91 | 4-F-Ph | 4-Pyr | Me | 6-Pr |
| 7-92 | 4-F-Ph | 4-Pyr | Me | 6-Ph |
| 7-93 | 4-F-Ph | 4-Pyr | Me | 8-Me |
| 7-94 | 4-F-Ph | 4-Pyr | Me | 8-Et |
| 7-95 | 4-F-Ph | 4-Pyr | Me | 8-Pr |
| 7-96 | 4-F-Ph | 4-Pyr | Me | 8,8-diMe |
| 7-97 | 4-F-Ph | 4-Pyr | Me | 8,8-diF |
| 7-98 | 4-F-Ph | 4-Pyr | Me | 8,8-CH₂CH₂— |
| 7-99 | 4-F-Ph | 4-Pyr | Me | 8-Oxo |
| 7-100 | 4-F-Ph | 4-Pyr | Me | 8a-Me |
| 7-101 | 4-F-Ph | 4-Pyr | Me | 8a-Et |
| 7-102 | 4-F-Ph | 4-Pyr | Me | 8a-Pr |
| 7-103 | 4-F-Ph | 4-Pyr | H | 2->CH₂ |
| 7-104 | 4-F-Ph | 4-Pyr | H | 2->CHMe |
| 7-105 | 4-F-Ph | 4-Pyr | H | 2->CHEt |
| 7-106 | 4-F-Ph | 4-Pyr | H | 2->CHPr |
| 7-107 | 4-F-Ph | 4-Pyr | H | 2->C(Me)₂ |
| 7-108 | 4-F-Ph | 4-Pyr | H | 2->CHPh |
| 7-109 | 4-F-Ph | 4-Pyr | H | 2,2-diPh |
| 7-110 | 4-F-Ph | 4-Pyr | H | 2,2-O(CH₂)₃O— |
| 7-111 | 4-F-Ph | 4-Pyr | H | 2,2-OCH₂C(Me)₂CH₂O— |
| 7-112 | 4-F-Ph | 4-Pyr | H | 2,2-(CH₂)₂— |
| 7-113 | 4-F-Ph | 4-Pyr | H | 2,2-(CH₂)₃— |
| 7-114 | 4-F-Ph | 4-Pyr | H | 2,2-(CH₂)₄— |
| 7-115 | 4-F-Ph | 4-Pyr | H | 2,2-(CH₂)₅— |
| 7-116 | 4-F-Ph | 4-Pyr | H | 2-MeS |
| 7-117 | 4-F-Ph | 4-Pyr | H | 2-EtS |
| 7-118 | 4-F-Ph | 4-Pyr | H | 2-PrS |
| 7-119 | 4-F-Ph | 4-Pyr | H | 2-BuS |
| 7-120 | 4-F-Ph | 4-Pyr | H | 2-MeSO₂ |
| 7-121 | 4-F-Ph | 4-Pyr | H | 2-PhO |
| 7-122 | 4-Cl-Ph | 4-Pyr | H | 1-Me |
| 7-123 | 4-Cl-Ph | 4-Pyr | H | 1-Et |
| 7-124 | 4-Cl-Ph | 4-Pyr | H | 1-Pr |
| 7-125 | 4-Cl-Ph | 4-Pyr | H | 1,1-diMe |
| 7-126 | 4-Cl-Ph | 4-Pyr | H | 2-Me |
| 7-127 | 4-Cl-Ph | 4-Pyr | H | 2-Et |
| 7-128 | 4-Cl-Ph | 4-Pyr | H | 2-Pr |
| 7-129 | 4-Cl-Ph | 4-Pyr | H | 2-Bu |
| 7-130 | 4-Cl-Ph | 4-Pyr | H | 2-Allyl |
| 7-131 | 4-Cl-Ph | 4-Pyr | H | 2-Ph |
| 7-132 | 4-Cl-Ph | 4-Pyr | H | 2-Bn |
| 7-133 | 4-Cl-Ph | 4-Pyr | H | 2-Phet |
| 7-134 | 4-Cl-Ph | 4-Pyr | H | 2,2-diMe |
| 7-135 | 4-Cl-Ph | 4-Pyr | H | 2-OH |
| 7-136 | 4-Cl-Ph | 4-Pyr | H | 2-MeO |
| 7-137 | 4-Cl-Ph | 4-Pyr | H | 2-EtO |
| 7-138 | 4-Cl-Ph | 4-Pyr | H | 2-PrO |
| 7-139 | 4-Cl-Ph | 4-Pyr | H | 2,2-di(MeO) |
| 7-140 | 4-Cl-Ph | 4-Pyr | H | 2,2-di(EtO) |
| 7-141 | 4-Cl-Ph | 4-Pyr | H | 2,2-OCH₂CH₂O— |
| 7-142 | 4-Cl-Ph | 4-Pyr | H | 2-Oxo |
| 7-143 | 4-Cl-Ph | 4-Pyr | H | 2-F |
| 7-144 | 4-Cl-Ph | 4-Pyr | H | 2-Cl |
| 7-145 | 4-Cl-Ph | 4-Pyr | H | 2-Br |
| 7-146 | 4-Cl-Ph | 4-Pyr | H | 2-I |
| 7-147 | 4-Cl-Ph | 4-Pyr | H | 2,2-diF |
| 7-148 | 4-Cl-Ph | 4-Pyr | H | 2,2-diCl |
| 7-149 | 4-Cl-Ph | 4-Pyr | H | 2,2-diBr |
| 7-150 | 4-Cl-Ph | 4-Pyr | H | 3-Me |
| 7-151 | 4-Cl-Ph | 4-Pyr | H | 3-Et |
| 7-152 | 4-Cl-Ph | 4-Pyr | H | 3-Pr |
| 7-153 | 4-Cl-Ph | 4-Pyr | H | 3,3-diMe |
| 7-154 | 4-Cl-Ph | 4-Pyr | H | 5-Me |
| 7-155 | 4-Cl-Ph | 4-Pyr | H | 5-Et |
| 7-156 | 4-Cl-Ph | 4-Pyr | H | 5-Pr |
| 7-157 | 4-Cl-Ph | 4-Pyr | H | 5,5-diMe |
| 7-158 | 4-Cl-Ph | 4-Pyr | H | 6-Me |
| 7-159 | 4-Cl-Ph | 4-Pyr | H | 6-Et |
| 7-160 | 4-Cl-Ph | 4-Pyr | H | 6-Pr |
| 7-161 | 4-Cl-Ph | 4-Pyr | H | 6,6-diMe |
| 7-162 | 4-Cl-Ph | 4-Pyr | H | 6-Oxo |
| 7-163 | 4-Cl-Ph | 4-Pyr | H | 8-Me |
| 7-164 | 4-Cl-Ph | 4-Pyr | H | 8-Et |
| 7-165 | 4-Cl-Ph | 4-Pyr | H | 8-Pr |
| 7-166 | 4-Cl-Ph | 4-Pyr | H | 8-Ph |
| 7-167 | 4-Cl-Ph | 4-Pyr | H | 8a-Me |
| 7-168 | 4-Cl-Ph | 4-Pyr | H | 8a-Et |
| 7-169 | 4-Cl-Ph | 4-Pyr | H | 8a-Pr |
| 7-170 | 4-Cl-Ph | 4-Pyr | H | 6,6-(CH₂)₂— |
| 7-171 | 4-Cl-Ph | 4-Pyr | H | 6,6-diF |
| 7-172 | 4-Cl-Ph | 4-Pyr | H | 2->CH₂ |
| 7-173 | 4-Cl-Ph | 4-Pyr | H | 2->CHMe |
| 7-174 | 4-Cl-Ph | 4-Pyr | H | 2->CHEt |
| 7-175 | 4-Cl-Ph | 4-Pyr | H | 2->CHPr |
| 7-176 | 4-Cl-Ph | 4-Pyr | H | 2->C(Me)₂ |
| 7-177 | 4-Cl-Ph | 4-Pyr | H | 2->CHPh |
| 7-178 | 4-Cl-Ph | 4-Pyr | H | 2,2-diPh |
| 7-179 | 4-Cl-Ph | 4-Pyr | H | 2,2-O(CH₂)₃O— |
| 7-180 | 4-Cl-Ph | 4-Pyr | H | 2,2-OCH₂C(Me)₂CH₂O— |
| 7-181 | 4-Cl-Ph | 4-Pyr | H | 2,2-(CH₂)₂— |
| 7-182 | 4-Cl-Ph | 4-Pyr | H | 2,2-(CH₂)₃— |
| 7-183 | 4-Cl-Ph | 4-Pyr | H | 2,2-(CH₂)₄— |
| 7-184 | 4-Cl-Ph | 4-Pyr | H | 2,2-(CH₂)₅— |
| 7-185 | 4-Cl-Ph | 4-Pyr | H | 2-MeS |
| 7-186 | 4-Cl-Ph | 4-Pyr | H | 2-EtS |
| 7-187 | 4-Cl-Ph | 4-Pyr | H | 2-PrS |
| 7-188 | 4-Cl-Ph | 4-Pyr | H | 2-BuS |
| 7-189 | 4-Cl-Ph | 4-Pyr | H | 2-MeSO₂ |
| 7-190 | 4-Cl-Ph | 4-Pyr | H | 2-PhO |

TABLE 7-continued

| Compound No. | R¹ | R² | R⁴ | R⁵ |
|---|---|---|---|---|
| 7-191 | 4-F-Ph | 4-Pyr | H | 2-(4-MeO-Ph) |
| 7-192 | 4-F-Ph | 4-Pyr | H | 2-(4-Me-Ph) |
| 7-193 | 4-F-Ph | 4-Pyr | H | 2-(4-F-Ph) |
| 7-194 | 4-F-Ph | 4-Pyr | H | 2-(4-CF₃-Ph) |
| 7-195 | 4-F-Ph | 4-Pyr | H | 2-(4-Cl-Ph) |
| 7-196 | 4-F-Ph | 4-Pyr | H | 2-(2,4-diF-Ph) |
| 7-197 | 3-CF₃-Ph | 4-Pyr | H | 2-(4-MeO-Ph) |
| 7-198 | 3-CF₃-Ph | 4-Pyr | H | 2-(4-Me-Ph) |
| 7-199 | 3-CF₃-Ph | 4-Pyr | H | 2-(4-F-Ph) |
| 7-200 | 3-CF₃-Ph | 4-Pyr | H | 2-(4-CF₃-Ph) |
| 7-201 | 3-CF₃-Ph | 4-Pyr | H | 2-(4-Cl-Ph) |
| 7-202 | 3-CF₃-Ph | 4-Pyr | H | 2-(2,4-diF-Ph) |
| 7-203 | 4-F-Ph | 2-NH₂-4-Pym | H | 2->CH₂ |
| 7-204 | 4-F-Ph | 2-NH₂-4-Pym | H | 2->CHMe |
| 7-205 | 4-F-Ph | 2-NH₂-4-Pym | H | 2->CHEt |
| 7-206 | 4-F-Ph | 2-NH₂-4-Pym | H | 2->CHPr |
| 7-207 | 4-F-Ph | 2-NH₂-4-Pym | H | 2->C(Me)₂ |
| 7-208 | 4-F-Ph | 2-NH₂-4-Pym | H | 2->CHPh |
| 7-209 | 4-F-Ph | 2-NH₂-4-Pym | H | 2,2-diPh |
| 7-210 | 4-F-Ph | 2-NH₂-4-Pym | H | 2,2-O(CH₂)₃O— |
| 7-211 | 4-F-Ph | 2-NH₂-4-Pym | H | 2,2-OCH₂C(Me)₂CH₂O— |
| 7-212 | 4-F-Ph | 2-NH₂-4-Pym | H | 2,2-(CH₂)₂— |
| 7-213 | 4-F-Ph | 2-NH₂-4-Pym | H | 2,2-(CH₂)₃— |
| 7-214 | 4-F-Ph | 2-NH₂-4-Pym | H | 2,2-(CH₂)₄— |
| 7-215 | 4-F-Ph | 2-NH₂-4-Pym | H | 2,2-(CH₂)₅— |
| 7-216 | 4-F-Ph | 2-NH₂-4-Pym | H | 2-MeS |
| 7-217 | 4-F-Ph | 2-NH₂-4-Pym | H | 2-EtS |
| 7-218 | 4-F-Ph | 2-NH₂-4-Pym | H | 2-PrS |
| 7-219 | 4-F-Ph | 2-NH₂-4-Pym | H | 2-BuS |
| 7-220 | 4-F-Ph | 2-NH₂-4-Pym | H | 2-MeSO₂ |
| 7-221 | 4-F-Ph | 2-NH₂-4-Pym | H | 2-PhO |
| 7-222 | 4-Cl-Ph | 2-NH₂-4-Pym | H | 1-Me |
| 7-223 | 4-Cl-Ph | 2-NH₂-4-Pym | H | 1-Et |
| 7-224 | 4-Cl-Ph | 2-NH₂-4-Pym | H | 1-Pr |
| 7-225 | 4-Cl-Ph | 2-NH₂-4-Pym | H | 1,1-diMe |
| 7-226 | 4-Cl-Ph | 2-NH₂-4-Pym | H | 2-Me |
| 7-227 | 4-Cl-Ph | 2-NH₂-4-Pym | H | 2-Et |
| 7-228 | 4-Cl-Ph | 2-NH₂-4-Pym | H | 2-Pr |
| 7-229 | 4-Cl-Ph | 2-NH₂-4-Pym | H | 2-Bu |
| 7-230 | 4-Cl-Ph | 2-NH₂-4-Pym | H | 2-Allyl |
| 7-231 | 4-Cl-Ph | 2-NH₂-4-Pym | H | 2-Ph |
| 7-232 | 4-Cl-Ph | 2-NH₂-4-Pym | H | 2-Bn |
| 7-233 | 4-Cl-Ph | 2-NH₂-4-Pym | H | 2-Phet |
| 7-234 | 4-Cl-Ph | 2-NH₂-4-Pym | H | 2,2-diMe |
| 7-235 | 4-Cl-Ph | 2-NH₂-4-Pym | H | 2-OH |
| 7-236 | 4-Cl-Ph | 2-NH₂-4-Pym | H | 2-MeO |
| 7-237 | 4-Cl-Ph | 2-NH₂-4-Pym | H | 2-EtO |
| 7-238 | 4-Cl-Ph | 2-NH₂-4-Pym | H | 2-PrO |
| 7-239 | 4-Cl-Ph | 2-NH₂-4-Pym | H | 2,2-di(MeO) |
| 7-240 | 4-Cl-Ph | 2-NH₂-4-Pym | H | 2,2-di(EtO) |
| 7-241 | 4-Cl-Ph | 2-NH₂-4-Pym | H | 2,2-OCH₂CH₂O— |
| 7-242 | 4-Cl-Ph | 2-NH₂-4-Pym | H | 2-Oxo |
| 7-243 | 4-Cl-Ph | 2-NH₂-4-Pym | H | 2-F |
| 7-244 | 4-Cl-Ph | 2-NH₂-4-Pym | H | 2-Cl |
| 7-245 | 4-Cl-Ph | 2-NH₂-4-Pym | H | 2-Br |
| 7-246 | 4-Cl-Ph | 2-NH₂-4-Pym | H | 2-I |
| 7-247 | 4-Cl-Ph | 2-NH₂-4-Pym | H | 2,2-diF |
| 7-248 | 4-Cl-Ph | 2-NH₂-4-Pym | H | 2,2-diCl |
| 7-249 | 4-Cl-Ph | 2-NH₂-4-Pym | H | 2,2-diBr |
| 7-250 | 4-Cl-Ph | 2-NH₂-4-Pym | H | 3-Me |
| 7-251 | 4-Cl-Ph | 2-NH₂-4-Pym | H | 3-Et |
| 7-252 | 4-Cl-Ph | 2-NH₂-4-Pym | H | 3-Pr |
| 7-253 | 4-Cl-Ph | 2-NH₂-4-Pym | H | 3,3-diMe |
| 7-254 | 4-Cl-Ph | 2-NH₂-4-Pym | H | 5-Me |
| 7-255 | 4-Cl-Ph | 2-NH₂-4-Pym | H | 5-Et |
| 7-256 | 4-Cl-Ph | 2-NH₂-4-Pym | H | 5-Pr |
| 7-257 | 4-Cl-Ph | 2-NH₂-4-Pym | H | 5,5-diMe |
| 7-258 | 4-Cl-Ph | 2-NH₂-4-Pym | H | 6-Me |
| 7-259 | 4-Cl-Ph | 2-NH₂-4-Pym | H | 6-Et |
| 7-260 | 4-Cl-Ph | 2-NH₂-4-Pym | H | 6-Pr |
| 7-261 | 4-Cl-Ph | 2-NH₂-4-Pym | H | 6,6-diMe |
| 7-262 | 4-Cl-Ph | 2-NH₂-4-Pym | H | 6-Oxo |
| 7-263 | 4-Cl-Ph | 2-NH₂-4-Pym | H | 8-Me |
| 7-264 | 4-Cl-Ph | 2-NH₂-4-Pym | H | 8-Et |
| 7-265 | 4-Cl-Ph | 2-NH₂-4-Pym | H | 8-Pr |
| 7-266 | 4-Cl-Ph | 2-NH₂-4-Pym | H | 8-Ph |
| 7-267 | 4-Cl-Ph | 2-NH₂-4-Pym | H | 8a-Me |
| 7-268 | 4-Cl-Ph | 2-NH₂-4-Pym | H | 8a-Et |
| 7-269 | 4-Cl-Ph | 2-NH₂-4-Pym | H | 8a-Pr |
| 7-270 | 4-Cl-Ph | 2-NH₂-4-Pym | H | 6,6-(CH₂)₂— |
| 7-271 | 4-Cl-Ph | 2-NH₂-4-Pym | H | 6,6-diF |
| 7-272 | 4-Cl-Ph | 2-NH₂-4-Pym | H | 2->CH₂ |
| 7-273 | 4-Cl-Ph | 2-NH₂-4-Pym | H | 2->CHMe |
| 7-274 | 4-Cl-Ph | 2-NH₂-4-Pym | H | 2->CHEt |
| 7-275 | 4-Cl-Ph | 2-NH₂-4-Pym | H | 2->CHPr |
| 7-276 | 4-Cl-Ph | 2-NH₂-4-Pym | H | 2->C(Me)₂ |
| 7-277 | 4-Cl-Ph | 2-NH₂-4-Pym | H | 2->CHPh |
| 7-278 | 4-Cl-Ph | 2-NH₂-4-Pym | H | 2,2-diPh |
| 7-279 | 4-Cl-Ph | 2-NH₂-4-Pym | H | 2,2-O(CH₂)₃O— |
| 7-280 | 4-Cl-Ph | 2-NH₂-4-Pym | H | 2,2-OCH₂C(Me)₂CH₂O— |
| 7-281 | 4-Cl-Ph | 2-NH₂-4-Pym | H | 2,2-(CH₂)₂— |
| 7-282 | 4-Cl-Ph | 2-NH₂-4-Pym | H | 2,2-(CH₂)₃— |
| 7-283 | 4-Cl-Ph | 2-NH₂-4-Pym | H | 2,2-(CH₂)₄— |
| 7-284 | 4-Cl-Ph | 2-NH₂-4-Pym | H | 2,2-(CH₂)₅— |
| 7-285 | 4-Cl-Ph | 2-NH₂-4-Pym | H | 2-MeS |
| 7-286 | 4-Cl-Ph | 2-NH₂-4-Pym | H | 2-EtS |
| 7-287 | 4-Cl-Ph | 2-NH₂-4-Pym | H | 2-PrS |
| 7-288 | 4-Cl-Ph | 2-NH₂-4-Pym | H | 2-BuS |
| 7-289 | 4-Cl-Ph | 2-NH₂-4-Pym | H | 2-MeSO₂ |
| 7-290 | 4-Cl-Ph | 2-NH₂-4-Pym | H | 2-PhO |
| 7-291 | 4-F-Ph | 2-NH₂-4-Pym | H | 2-(4-MeO-Ph) |
| 7-292 | 4-F-Ph | 2-NH₂-4-Pym | H | 2-(4-Me-Ph) |
| 7-293 | 4-F-Ph | 2-NH₂-4-Pym | H | 2-(4-F-Ph) |
| 7-294 | 4-F-Ph | 2-NH₂-4-Pym | H | 2-(4-CF₃-Ph) |
| 7-295 | 4-F-Ph | 2-NH₂-4-Pym | H | 2-(4-Cl-Ph) |
| 7-296 | 4-F-Ph | 2-NH₂-4-Pym | H | 2-(2,4-diF-Ph) |
| 7-297 | 3-CF₃-Ph | 2-NH₂-4-Pym | H | 2-(4-MeO-Ph) |
| 7-298 | 3-CF₃-Ph | 2-NH₂-4-Pym | H | 2-(4-Me-Ph) |
| 7-299 | 3-CF₃-Ph | 2-NH₂-4-Pym | H | 2-(4-F-Ph) |
| 7-300 | 3-CF₃-Ph | 2-NH₂-4-Pym | H | 2-(4-CF₃-Ph) |
| 7-301 | 3-CF₃-Ph | 2-NH₂-4-Pym | H | 2-(4-Cl-Ph) |
| 7-302 | 3-CF₃-Ph | 2-NH₂-4-Pym | H | 2-(2,4-diF-Ph) |
| 7-303 | 4-F-Ph | 4-Pyr | Me | 2->CH₂ |
| 7-304 | 4-F-Ph | 4-Pyr | Me | 2->CHMe |
| 7-305 | 4-F-Ph | 4-Pyr | Me | 2->CHEt |
| 7-306 | 4-F-Ph | 4-Pyr | Me | 2->CHPr |
| 7-307 | 4-F-Ph | 4-Pyr | Me | 2->C(Me)₂ |
| 7-308 | 4-F-Ph | 4-Pyr | Me | 2->CHPh |
| 7-309 | 4-F-Ph | 4-Pyr | Me | 2,2-diPh |
| 7-310 | 4-F-Ph | 4-Pyr | Me | 2,2-O(CH₂)₃O— |

TABLE 7-continued

| Compound No. | R¹ | R² | R⁴ | R⁵ |
|---|---|---|---|---|
| 7-311 | 4-F-Ph | 4-Pyr | Me | 2,2-OCH₂C(Me)₂CH₂O— |
| 7-312 | 4-F-Ph | 4-Pyr | Me | 2,2-(CH₂)₂— |
| 7-313 | 4-F-Ph | 4-Pyr | Me | 2,2-(CH₂)₃— |
| 7-314 | 4-F-Ph | 4-Pyr | Me | 2,2-(CH₂)₄— |
| 7-315 | 4-F-Ph | 4-Pyr | Me | 2,2-(CH₂)₅— |
| 7-316 | 4-F-Ph | 4-Pyr | Me | 2-MeS |
| 7-317 | 4-F-Ph | 4-Pyr | Me | 2-EtS |
| 7-318 | 4-F-Ph | 4-Pyr | Me | 2-PrS |
| 7-319 | 4-F-Ph | 4-Pyr | Me | 2-BuS |
| 7-320 | 4-F-Ph | 4-Pyr | Me | 2-MeSO₂ |
| 7-321 | 4-F-Ph | 4-Pyr | Me | 2-PhO |
| 7-322 | 4-Cl-Ph | 4-Pyr | Me | 1-Me |
| 7-323 | 4-Cl-Ph | 4-Pyr | Me | 1-Et |
| 7-324 | 4-Cl-Ph | 4-Pyr | Me | 1-Pr |
| 7-325 | 4-Cl-Ph | 4-Pyr | Me | 1,1-diMe |
| 7-326 | 4-Cl-Ph | 4-Pyr | Me | 2-Me |
| 7-327 | 4-Cl-Ph | 4-Pyr | Me | 2-Et |
| 7-328 | 4-Cl-Ph | 4-Pyr | Me | 2-Pr |
| 7-329 | 4-Cl-Ph | 4-Pyr | Me | 2-Bu |
| 7-330 | 4-Cl-Ph | 4-Pyr | Me | 2-Allyl |
| 7-331 | 4-Cl-Ph | 4-Pyr | Me | 2-Ph |
| 7-332 | 4-Cl-Ph | 4-Pyr | Me | 2-Bn |
| 7-333 | 4-Cl-Ph | 4-Pyr | Me | 2-Phet |
| 7-334 | 4-Cl-Ph | 4-Pyr | Me | 2,2-diMe |
| 7-335 | 4-Cl-Ph | 4-Pyr | Me | 2-OH |
| 7-336 | 4-Cl-Ph | 4-Pyr | Me | 2-MeO |
| 7-337 | 4-Cl-Ph | 4-Pyr | Me | 2-EtO |
| 7-338 | 4-Cl-Ph | 4-Pyr | Me | 2-PrO |
| 7-339 | 4-Cl-Ph | 4-Pyr | Me | 2,2-di(MeO) |
| 7-340 | 4-Cl-Ph | 4-Pyr | Me | 2,2-di(EtO) |
| 7-341 | 4-Cl-Ph | 4-Pyr | Me | 2,2-OCH₂CH₂O— |
| 7-342 | 4-Cl-Ph | 4-Pyr | Me | 2-Oxo |
| 7-343 | 4-Cl-Ph | 4-Pyr | Me | 2-F |
| 7-344 | 4-Cl-Ph | 4-Pyr | Me | 2-Cl |
| 7-345 | 4-Cl-Ph | 4-Pyr | Me | 2-Br |
| 7-346 | 4-Cl-Ph | 4-Pyr | Me | 2-I |
| 7-247 | 4-Cl-Ph | 4-Pyr | Me | 2,2-diF |
| 7-348 | 4-Cl-Ph | 4-Pyr | Me | 2,2-diCl |
| 7-349 | 4-Cl-Ph | 4-Pyr | Me | 2,2-diBr |
| 7-350 | 4-Cl-Ph | 4-Pyr | Me | 3-Me |
| 7-351 | 4-Cl-Ph | 4-Pyr | Me | 3-Et |
| 7-352 | 4-Cl-Ph | 4-Pyr | Me | 3-Pr |
| 7-353 | 4-Cl-Ph | 4-Pyr | Me | 3,3-diMe |
| 7-354 | 4-Cl-Ph | 4-Pyr | Me | 5-Me |
| 7-355 | 4-Cl-Ph | 4-Pyr | Me | 5-Et |
| 7-356 | 4-Cl-Ph | 4-Pyr | Me | 5-Pr |
| 7-357 | 4-Cl-Ph | 4-Pyr | Me | 5,5-diMe |
| 7-358 | 4-Cl-Ph | 4-Pyr | Me | 6-Me |
| 7-359 | 4-Cl-Ph | 4-Pyr | Me | 6-Et |
| 7-360 | 4-Cl-Ph | 4-Pyr | Me | 6-Pr |
| 7-361 | 4-Cl-Ph | 4-Pyr | Me | 6,6-diMe |
| 7-362 | 4-Cl-Ph | 4-Pyr | Me | 6-Oxo |
| 7-363 | 4-Cl-Ph | 4-Pyr | Me | 8-Me |
| 7-364 | 4-Cl-Ph | 4-Pyr | Me | 8-Et |
| 7-365 | 4-Cl-Ph | 4-Pyr | Me | 8-Pr |
| 7-366 | 4-Cl-Ph | 4-Pyr | Me | 8-Ph |
| 7-367 | 4-Cl-Ph | 4-Pyr | Me | 8a-Me |
| 7-368 | 4-Cl-Ph | 4-Pyr | Me | 8a-Et |
| 7-369 | 4-Cl-Ph | 4-Pyr | Me | 8a-Pr |
| 7-370 | 4-Cl-Ph | 4-Pyr | Me | 6,6-(CH₂)₂— |
| 7-371 | 4-Cl-Ph | 4-Pyr | Me | 6,6-diF |
| 7-372 | 4-Cl-Ph | 4-Pyr | Me | 2->CH₂ |
| 7-373 | 4-Cl-Ph | 4-Pyr | Me | 2->CHMe |
| 7-374 | 4-Cl-Ph | 4-Pyr | Me | 2->CHEt |
| 7-375 | 4-Cl-Ph | 4-Pyr | Me | 2->CHPr |
| 7-376 | 4-Cl-Ph | 4-Pyr | Me | 2->C(Me)₂ |
| 7-377 | 4-Cl-Ph | 4-Pyr | Me | 2->CHPh |
| 7-378 | 4-Cl-Ph | 4-Pyr | Me | 2,2-diPh |
| 7-379 | 4-Cl-Ph | 4-Pyr | Me | 2,2-O(CH₂)₃O— |
| 7-380 | 4-Cl-Ph | 4-Pyr | Me | 2,2-OCH₂C(Me)₂CH₂O— |
| 7-381 | 4-Cl-Ph | 4-Pyr | Me | 2,2-(CH₂)₂— |
| 7-382 | 4-Cl-Ph | 4-Pyr | Me | 2,2-(CH₂)₃— |
| 7-383 | 4-Cl-Ph | 4-Pyr | Me | 2,2-(CH₂)₄— |
| 7-384 | 4-Cl-Ph | 4-Pyr | Me | 2,2-(CH₂)₅— |
| 7-385 | 4-Cl-Ph | 4-Pyr | Me | 2-MeS |
| 7-386 | 4-Cl-Ph | 4-Pyr | Me | 2-EtS |
| 7-387 | 4-Cl-Ph | 4-Pyr | Me | 2-PrS |
| 7-388 | 4-Cl-Ph | 4-Pyr | Me | 2-BuS |
| 7-389 | 4-Cl-Ph | 4-Pyr | Me | 2-MeSO₂ |
| 7-390 | 4-Cl-Ph | 4-Pyr | Me | 2-PhO |
| 7-391 | 4-F-Ph | 4-Pyr | Me | 2-(4-MeO-Ph) |
| 7-392 | 4-F-Ph | 4-Pyr | Me | 2-(4-Me-Ph) |
| 7-393 | 4-F-Ph | 4-Pyr | Me | 2-(4-F-Ph) |
| 7-394 | 4-F-Ph | 4-Pyr | Me | 2-(4-CF₃-Ph) |
| 7-395 | 4-F-Ph | 4-Pyr | Me | 2-(4-Cl-Ph) |
| 7-396 | 4-F-Ph | 4-Pyr | Me | 2-(2,4-diF-Ph) |
| 7-397 | 3-CF₃-Ph | 4-Pyr | Me | 2-(4-MeO-Ph) |
| 7-398 | 3-CF₃-Ph | 4-Pyr | Me | 2-(4-Me-Ph) |
| 7-399 | 3-CF₃-Ph | 4-Pyr | Me | 2-(4-F-Ph) |
| 7-400 | 3-CF₃-Ph | 4-Pyr | Me | 2-(4-CF₃-Ph) |
| 7-401 | 3-CF₃-Ph | 4-Pyr | Me | 2-(4-Cl-Ph) |
| 7-402 | 3-CF₃-Ph | 4-Pyr | Me | 2-(2,4-diF-Ph) |
| 7-403 | 4-F-Ph | 2-NH₂-4-Pym | Me | 2->CH₂ |
| 7-404 | 4-F-Ph | 2-NH₂-4-Pym | Me | 2->CHMe |
| 7-405 | 4-F-Ph | 2-NH₂-4-Pym | Me | 2->CHEt |
| 7-406 | 4-F-Ph | 2-NH₂-4-Pym | Me | 2->CHPr |
| 7-407 | 4-F-Ph | 2-NH₂-4-Pym | Me | 2->C(Me)₂ |
| 7-408 | 4-F-Ph | 2-NH₂-4-Pym | Me | 2->CHPh |
| 7-409 | 4-F-Ph | 2-NH₂-4-Pym | Me | 2,2-diPh |
| 7-410 | 4-F-Ph | 2-NH₂-4-Pym | Me | 2,2-O(CH₂)₃O— |
| 7-411 | 4-F-Ph | 2-NH₂-4-Pym | Me | 2,2-OCH₂C(Me)₂CH₂O— |
| 7-412 | 4-F-Ph | 2-NH₂-4-Pym | Me | 2,2-(CH₂)₂— |
| 7-413 | 4-F-Ph | 2-NH₂-4-Pym | Me | 2,2-(CH₂)₃— |
| 7-414 | 4-F-Ph | 2-NH₂-4-Pym | Me | 2,2-(CH₂)₄— |
| 7-415 | 4-F-Ph | 2-NH₂-4-Pym | Me | 2,2-(CH₂)₅— |
| 7-416 | 4-F-Ph | 2-NH₂-4-Pym | Me | 2-MeS |
| 7-417 | 4-F-Ph | 2-NH₂-4-Pym | Me | 2-EtS |
| 7-418 | 4-F-Ph | 2-NH₂-4-Pym | Me | 2-PrS |
| 7-419 | 4-F-Ph | 2-NH₂-4-Pym | Me | 2-BuS |
| 7-420 | 4-F-Ph | 2-NH₂-4-Pym | Me | 2-MeSO₂ |
| 7-421 | 4-F-Ph | 2-NH₂-4-Pym | Me | 2-PhO |
| 7-422 | 4-Cl-Ph | 2-NH₂-4-Pym | Me | 1-Me |
| 7-423 | 4-Cl-Ph | 2-NH₂-4-Pym | Me | 1-Et |
| 7-424 | 4-Cl-Ph | 2-NH₂-4-Pym | Me | 1-Pr |
| 7-425 | 4-Cl-Ph | 2-NH₂-4-Pym | Me | 1,1-diMe |
| 7-426 | 4-Cl-Ph | 2-NH₂-4-Pym | Me | 2-Me |
| 7-427 | 4-Cl-Ph | 2-NH₂-4-Pym | Me | 2-Et |
| 7-428 | 4-Cl-Ph | 2-NH₂-4-Pym | Me | 2-Pr |
| 7-429 | 4-Cl-Ph | 2-NH₂-4-Pym | Me | 2-Bu |

TABLE 7-continued

[Structure diagram with pyrazole fused to bicyclic N-containing ring system, substituents R¹, R², R⁴, R⁵, numbered positions 1, 2, 3, 4, 5, 6, 7, 8, 8a]

| Compound No. | R¹ | R² | R⁴ | R⁵ |
|---|---|---|---|---|
| 7-430 | 4-Cl-Ph | 2-NH₂-4-Pym | Me | 2-Allyl |
| 7-431 | 4-Cl-Ph | 2-NH₂-4-Pym | Me | 2-Ph |
| 7-432 | 4-Cl-Ph | 2-NH₂-4-Pym | Me | 2-Bn |
| 7-433 | 4-Cl-Ph | 2-NH₂-4-Pym | Me | 2-Phet |
| 7-434 | 4-Cl-Ph | 2-NH₂-4-Pym | Me | 2,2-diMe |
| 7-435 | 4-Cl-Ph | 2-NH₂-4-Pym | Me | 2-OH |
| 7-436 | 4-Cl-Ph | 2-NH₂-4-Pym | Me | 2-MeO |
| 7-437 | 4-Cl-Ph | 2-NH₂-4-Pym | Me | 2-EtO |
| 7-438 | 4-Cl-Ph | 2-NH₂-4-Pym | Me | 2-PrO |
| 7-439 | 4-Cl-Ph | 2-NH₂-4-Pym | Me | 2,2-di(MeO) |
| 7-440 | 4-Cl-Ph | 2-NH₂-4-Pym | Me | 2,2-di(EtO) |
| 7-441 | 4-Cl-Ph | 2-NH₂-4-Pym | Me | 2,2-OCH₂CH₂O— |
| 7-442 | 4-Cl-Ph | 2-NH₂-4-Pym | Me | 2-Oxo |
| 7-443 | 4-Cl-Ph | 2-NH₂-4-Pym | Me | 2-F |
| 7-444 | 4-Cl-Ph | 2-NH₂-4-Pym | Me | 2-Cl |
| 7-445 | 4-Cl-Ph | 2-NH₂-4-Pym | Me | 2-Br |
| 7-446 | 4-Cl-Ph | 2-NH₂-4-Pym | Me | 2-I |
| 7-447 | 4-Cl-Ph | 2-NH₂-4-Pym | Me | 2,2-diF |
| 7-448 | 4-Cl-Ph | 2-NH₂-4-Pym | Me | 2,2-diCl |
| 7-449 | 4-Cl-Ph | 2-NH₂-4-Pym | Me | 2,2-diBr |
| 7-450 | 4-Cl-Ph | 2-NH₂-4-Pym | Me | 2-Me |
| 7-451 | 4-Cl-Ph | 2-NH₂-4-Pym | Me | 2-Et |
| 7-452 | 4-Cl-Ph | 2-NH₂-4-Pym | Me | 2-Pr |
| 7-453 | 4-Cl-Ph | 2-NH₂-4-Pym | Me | 2,2-diMe |
| 7-454 | 4-Cl-Ph | 2-NH₂-4-Pym | Me | 5-Me |
| 7-455 | 4-Cl-Ph | 2-NH₂-4-Pym | Me | 5-Et |
| 7-456 | 4-Cl-Ph | 2-NH₂-4-Pym | Me | 5-Pr |
| 7-457 | 4-Cl-Ph | 2-NH₂-4-Pym | Me | 5,5-diMe |
| 7-458 | 4-Cl-Ph | 2-NH₂-4-Pym | Me | 6-Me |
| 7-459 | 4-Cl-Ph | 2-NH₂-4-Pym | Me | 6-Et |
| 7-460 | 4-Cl-Ph | 2-NH₂-4-Pym | Me | 6-Pr |
| 7-461 | 4-Cl-Ph | 2-NH₂-4-Pym | Me | 6,6-diMe |
| 7-462 | 4-Cl-Ph | 2-NH₂-4-Pym | Me | 6-Oxo |
| 7-463 | 4-Cl-Ph | 2-NH₂-4-Pym | Me | 8-Me |
| 7-464 | 4-Cl-Ph | 2-NH₂-4-Pym | Me | 8-Et |
| 7-465 | 4-Cl-Ph | 2-NH₂-4-Pym | Me | 8-Pr |
| 7-466 | 4-Cl-Ph | 2-NH₂-4-Pym | Me | 8-Ph |
| 7-467 | 4-Cl-Ph | 2-NH₂-4-Pym | Me | 8a-Me |
| 7-468 | 4-Cl-Ph | 2-NH₂-4-Pym | Me | 8a-Et |
| 7-469 | 4-Cl-Ph | 2-NH₂-4-Pym | Me | 8a-Pr |
| 7-470 | 4-Cl-Ph | 2-NH₂-4-Pym | Me | 6,6-(CH₂)₂— |
| 7-471 | 4-Cl-Ph | 2-NH₂-4-Pym | Me | 6,6-diF |
| 7-472 | 4-Cl-Ph | 2-NH₂-4-Pym | Me | 2->CH₂ |
| 7-473 | 4-Cl-Ph | 2-NH₂-4-Pym | Me | 2->CHMe |
| 7-474 | 4-Cl-Ph | 2-NH₂-4-Pym | Me | 2->CHEt |
| 7-475 | 4-Cl-Ph | 2-NH₂-4-Pym | Me | 2->CHPr |
| 7-476 | 4-Cl-Ph | 2-NH₂-4-Pym | Me | 2->C(Me)₂ |
| 7-477 | 4-Cl-Ph | 2-NH₂-4-Pym | Me | 2->CHPh |
| 7-478 | 4-Cl-Ph | 2-NH₂-4-Pym | Me | 2,2-diPh |
| 7-479 | 4-Cl-Ph | 2-NH₂-4-Pym | Me | 2,2-O(CH₂)₃O— |
| 7-480 | 4-Cl-Ph | 2-NH₂-4-Pym | Me | 2,2-OCH₂C(Me)₂CH₂O— |
| 7-481 | 4-Cl-Ph | 2-NH₂-4-Pym | Me | 2,2-(CH₂)₂— |
| 7-482 | 4-Cl-Ph | 2-NH₂-4-Pym | Me | 2,2-(CH₂)₃— |
| 7-483 | 4-Cl-Ph | 2-NH₂-4-Pym | Me | 2,2-(CH₂)₄— |
| 7-484 | 4-Cl-Ph | 2-NH₂-4-Pym | Me | 2,2-(CH₂)₅— |
| 7-485 | 4-Cl-Ph | 2-NH₂-4-Pym | Me | 2-MeS |
| 7-486 | 4-Cl-Ph | 2-NH₂-4-Pym | Me | 2-EtS |
| 7-487 | 4-Cl-Ph | 2-NH₂-4-Pym | Me | 2-PrS |
| 7-488 | 4-Cl-Ph | 2-NH₂-4-Pym | Me | 2-BuS |
| 7-489 | 4-Cl-Ph | 2-NH₂-4-Pym | Me | 2-MeSO₂ |
| 7-490 | 4-Cl-Ph | 2-NH₂-4-Pym | Me | 2-PhO |
| 7-491 | 4-F-Ph | 2-NH₂-4-Pym | Me | 2-PhO |
| 7-492 | 4-F-Ph | 2-NH₂-4-Pym | Me | 2-(4-Me-Ph) |
| 7-493 | 4-F-Ph | 2-NH₂-4-Pym | Me | 2-(4-F-Ph) |
| 7-494 | 4-F-Ph | 2-NH₂-4-Pym | Me | 2-(4-CF₃-Ph) |
| 7-495 | 4-F-Ph | 2-NH₂-4-Pym | Me | 2-(4-Cl-Ph) |
| 7-496 | 4-F-Ph | 2-NH₂-4-Pym | Me | 2-(2,4-diF-Ph) |
| 7-497 | 3-CF₃-Ph | 2-NH₂-4-Pym | Me | 2-(4-MeO-Ph) |
| 7-498 | 3-CF₃-Ph | 2-NH₂-4-Pym | Me | 2-(4-Me-Ph) |
| 7-499 | 3-CF₃-Ph | 2-NH₂-4-Pym | Me | 2-(4-F-Ph) |
| 7-500 | 3-CF₃-Ph | 2-NH₂-4-Pym | Me | 2-(4-CF₃-Ph) |
| 7-501 | 3-CF₃-Ph | 2-NH₂-4-Pym | Me | 2-(4-Cl-Ph) |
| 7-502 | 3-CF₃-Ph | 2-NH₂-4-Pym | Me | 2-(2,4-diF-Ph) |
| 7-503 | 4-Cl-Ph | 4-Pyr | H | — |
| 7-504 | 4-Cl-Ph | 4-Pyr | H | 2-(4-MeO-Ph) |
| 7-505 | 4-Cl-Ph | 4-Pyr | H | 2-(4-Me-Ph) |
| 7-506 | 4-Cl-Ph | 4-Pyr | H | 2-(4-F-Ph) |
| 7-507 | 4-Cl-Ph | 4-Pyr | H | 2-(4-CF₃-Ph) |
| 7-508 | 4-Cl-Ph | 4-Pyr | H | 2-(4-Cl-Ph) |
| 7-509 | 4-Cl-Ph | 4-Pyr | H | 2-(2,4-diF-Ph) |
| 7-510 | 4-Cl-Ph | 4-Pyr | Me | — |
| 7-511 | 4-Cl-Ph | 4-Pyr | Me | 2-(4-MeO-Ph) |
| 7-512 | 4-Cl-Ph | 4-Pyr | Me | 2-(4-Me-Ph) |
| 7-513 | 4-Cl-Ph | 4-Pyr | Me | 2-(4-F-Ph) |
| 7-514 | 4-Cl-Ph | 4-Pyr | Me | 2-(4-CF₃-Ph) |
| 7-515 | 4-Cl-Ph | 4-Pyr | Me | 2-(4-Cl-Ph) |
| 7-516 | 4-Cl-Ph | 4-Pyr | Me | 2-(2,4-diF-Ph) |
| 7-517 | 4-Cl-Ph | 2-NH₂-4-Pym | H | — |
| 7-518 | 4-Cl-Ph | 2-NH₂-4-Pym | Me | — |

TABLE 8

[Structure diagram similar to above with pyrazole fused to bicyclic N-containing ring system, R¹, R², R⁴, R⁵ substituents]

| Compound No. | R¹ | R² | R⁴ | R⁵ |
|---|---|---|---|---|
| 8-1 | 4-F-Ph | 4-Pyr | Me | — |
| 8-2 | 4-F-Ph | 4-Pyr | Me | 1-Me |
| 8-3 | 4-F-Ph | 4-Pyr | Me | 1-Et |
| 8-4 | 4-F-Ph | 4-Pyr | Me | 1-Pr |
| 8-5 | 4-F-Ph | 4-Pyr | Me | 1,1-diMe |
| 8-6 | 4-F-Ph | 4-Pyr | Me | 2-Me |
| 8-7 | 4-F-Ph | 4-Pyr | Me | 2-Et |
| 8-8 | 4-F-Ph | 4-Pyr | Me | 2-Pr |
| 8-9 | 4-F-Ph | 4-Pyr | Me | 2-Bu |

TABLE 8-continued

| Compound No. | R¹ | R² | R⁴ | R⁵ |
|---|---|---|---|---|
| 8-10 | 4-F-Ph | 4-Pyr | Me | 2-Allyl |
| 8-11 | 4-F-Ph | 4-Pyr | Me | 2-Ph |
| 8-12 | 4-F-Ph | 4-Pyr | Me | 2-Bn |
| 8-13 | 4-F-Ph | 4-Pyr | Me | 2-Phet |
| 8-14 | 4-F-Ph | 4-Pyr | Me | 2,2-diMe |
| 8-15 | 4-F-Ph | 4-Pyr | Me | 2-OH |
| 8-16 | 4-F-Ph | 4-Pyr | Me | 2-MeO |
| 8-17 | 4-F-Ph | 4-Pyr | Me | 2-EtO |
| 8-18 | 4-F-Ph | 4-Pyr | Me | 2-PrO |
| 8-19 | 4-F-Ph | 4-Pyr | Me | 2,2-di(MeO) |
| 8-20 | 4-F-Ph | 4-Pyr | Me | 2,2-di(EtO) |
| 8-21 | 4-F-Ph | 4-Pyr | Me | 2,2-OCH$_2$CH$_2$O— |
| 8-22 | 4-F-Ph | 4-Pyr | Me | 2-Oxo |
| 8-23 | 4-F-Ph | 4-Pyr | Me | 2-F |
| 8-24 | 4-F-Ph | 4-Pyr | Me | 2-Cl |
| 8-25 | 4-F-Ph | 4-Pyr | Me | 2-Br |
| 8-26 | 4-F-Ph | 4-Pyr | Me | 2-I |
| 8-27 | 4-F-Ph | 4-Pyr | Me | 2,2-diF |
| 8-28 | 4-F-Ph | 4-Pyr | Me | 2,2-diCl |
| 8-29 | 4-F-Ph | 4-Pyr | Me | 2,2-diBr |
| 8-30 | 4-F-Ph | 4-Pyr | Me | 3-Me |
| 8-31 | 4-F-Ph | 4-Pyr | Me | 3-Et |
| 8-32 | 4-F-Ph | 4-Pyr | Me | 3-Pr |
| 8-33 | 4-F-Ph | 4-Pyr | Me | 3,3-diMe |
| 8-34 | 4-F-Ph | 4-Pyr | Me | 5-Me |
| 8-35 | 4-F-Ph | 4-Pyr | Me | 5-Et |
| 8-36 | 4-F-Ph | 4-Pyr | Me | 5-Pr |
| 8-37 | 4-F-Ph | 4-Pyr | Me | 5,5-diMe |
| 8-38 | 4-F-Ph | 4-Pyr | Me | 6-Me |
| 8-39 | 4-F-Ph | 4-Pyr | Me | 6-Et |
| 8-40 | 4-F-Ph | 4-Pyr | Me | 6-Pr |
| 8-41 | 4-F-Ph | 4-Pyr | Me | 6-Ph |
| 8-42 | 4-F-Ph | 4-Pyr | Me | 8-Me |
| 8-43 | 4-F-Ph | 4-Pyr | Me | 8-Et |
| 8-44 | 4-F-Ph | 4-Pyr | Me | 8-Pr |
| 8-45 | 4-F-Ph | 4-Pyr | Me | 8,8-diMe |
| 8-46 | 4-F-Ph | 4-Pyr | Me | 8,8-diF |
| 8-47 | 4-F-Ph | 4-Pyr | Me | 8,8-CH$_2$CH$_2$— |
| 8-48 | 4-F-Ph | 4-Pyr | Me | 8-Oxo |
| 8-49 | 4-F-Ph | 4-Pyr | Me | 8a-Me |
| 8-50 | 4-F-Ph | 4-Pyr | Me | 8a-Et |
| 8-51 | 4-F-Ph | 4-Pyr | Me | 8a-Pr |
| 8-52 | 4-F-Ph | 4-Pyr | Me | 2->CH$_2$ |
| 8-53 | 4-F-Ph | 4-Pyr | Me | 2->CHMe |
| 8-54 | 4-F-Ph | 4-Pyr | Me | 2->CHEt |
| 8-55 | 4-F-Ph | 4-Pyr | Me | 2->CHPr |
| 8-56 | 4-F-Ph | 4-Pyr | Me | 2->C(Me)$_2$ |
| 8-57 | 4-F-Ph | 4-Pyr | Me | 2->CHPh |
| 8-58 | 4-F-Ph | 4-Pyr | Me | 2,2-diPh |
| 8-59 | 4-F-Ph | 4-Pyr | Me | 2,2-O(CH$_2$)$_3$O— |
| 8-60 | 4-F-Ph | 4-Pyr | Me | 2,2-OCH$_2$C(Me)$_2$CH$_2$O— |
| 8-61 | 4-F-Ph | 4-Pyr | Me | 2,2-(CH$_2$)$_2$— |
| 8-62 | 4-F-Ph | 4-Pyr | Me | 2,2-(CH$_2$)$_3$— |
| 8-63 | 4-F-Ph | 4-Pyr | Me | 2,2-(CH$_2$)$_4$— |
| 8-64 | 4-F-Ph | 4-Pyr | Me | 2,2-(CH$_2$)$_5$— |
| 8-65 | 4-F-Ph | 4-Pyr | Me | 2-MeS |
| 8-66 | 4-F-Ph | 4-Pyr | Me | 2-EtS |
| 8-67 | 4-F-Ph | 4-Pyr | Me | 2-PrS |
| 8-68 | 4-F-Ph | 4-Pyr | Me | 2-BuS |
| 8-69 | 4-F-Ph | 4-Pyr | Me | 2-MeSO$_2$ |
| 8-70 | 4-F-Ph | 4-Pyr | Me | 2-PhO |
| 8-71 | 4-Cl-Ph | 4-Pyr | Me | 1-Me |
| 8-72 | 4-Cl-Ph | 4-Pyr | Me | 1-Et |
| 8-73 | 4-Cl-Ph | 4-Pyr | Me | 1-Pr |
| 8-74 | 4-Cl-Ph | 4-Pyr | Me | 1,1-diMe |
| 8-75 | 4-Cl-Ph | 4-Pyr | Me | 2-Me |
| 8-76 | 4-Cl-Ph | 4-Pyr | Me | 2-Et |
| 8-77 | 4-Cl-Ph | 4-Pyr | Me | 2-Pr |
| 8-78 | 4-Cl-Ph | 4-Pyr | Me | 2-Bu |
| 8-79 | 4-Cl-Ph | 4-Pyr | Me | 2-Allyl |
| 8-80 | 4-Cl-Ph | 4-Pyr | Me | 2-Ph |
| 8-81 | 4-Cl-Ph | 4-Pyr | Me | 2-Bn |
| 8-82 | 4-Cl-Ph | 4-Pyr | Me | 2-Phet |
| 8-83 | 4-Cl-Ph | 4-Pyr | Me | 2,2-diMe |
| 8-84 | 4-Cl-Ph | 4-Pyr | Me | 2-OH |
| 8-85 | 4-Cl-Ph | 4-Pyr | Me | 2-MeO |
| 8-86 | 4-Cl-Ph | 4-Pyr | Me | 2-EtO |
| 8-87 | 4-Cl-Ph | 4-Pyr | Me | 2-PrO |
| 8-88 | 4-Cl-Ph | 4-Pyr | Me | 2,2-di(MeO) |
| 8-89 | 4-Cl-Ph | 4-Pyr | Me | 2,2-di(EtO) |
| 8-90 | 4-Cl-Ph | 4-Pyr | Me | 2,2-OCH$_2$CH$_2$O— |
| 8-91 | 4-Cl-Ph | 4-Pyr | Me | 2-Oxo |
| 8-92 | 4-Cl-Ph | 4-Pyr | Me | 2-F |
| 8-93 | 4-Cl-Ph | 4-Pyr | Me | 2-Cl |
| 8-94 | 4-Cl-Ph | 4-Pyr | Me | 2-Br |
| 8-95 | 4-Cl-Ph | 4-Pyr | Me | 2-I |
| 8-96 | 4-Cl-Ph | 4-Pyr | Me | 2,2-diF |
| 8-97 | 4-Cl-Ph | 4-Pyr | Me | 2,2-diCl |
| 8-98 | 4-Cl-Ph | 4-Pyr | Me | 2,2-diBr |
| 8-99 | 4-Cl-Ph | 4-Pyr | Me | 2-Me |
| 8-100 | 4-Cl-Ph | 4-Pyr | Me | 3-Et |
| 8-101 | 4-Cl-Ph | 4-Pyr | Me | 3-Pr |
| 8-102 | 4-Cl-Ph | 4-Pyr | Me | 3,3-diMe |
| 8-103 | 4-Cl-Ph | 4-Pyr | Me | 5-Me |
| 8-104 | 4-Cl-Ph | 4-Pyr | Me | 5-Et |
| 8-105 | 4-Cl-Ph | 4-Pyr | Me | 5-Pr |
| 8-106 | 4-Cl-Ph | 4-Pyr | Me | 5,5-diMe |
| 8-107 | 4-Cl-Ph | 4-Pyr | Me | 6-Me |
| 8-108 | 4-Cl-Ph | 4-Pyr | Me | 6-Et |
| 8-109 | 4-Cl-Ph | 4-Pyr | Me | 6-Pr |
| 8-110 | 4-Cl-Ph | 4-Pyr | Me | 6,6-diMe |
| 8-111 | 4-Cl-Ph | 4-Pyr | Me | 6-Oxo |
| 8-112 | 4-Cl-Ph | 4-Pyr | Me | 8-Me |
| 8-113 | 4-Cl-Ph | 4-Pyr | Me | 8-Et |
| 8-114 | 4-Cl-Ph | 4-Pyr | Me | 8-Pr |
| 8-115 | 4-Cl-Ph | 4-Pyr | Me | 8-Ph |
| 8-116 | 4-Cl-Ph | 4-Pyr | Me | 8a-Me |
| 8-117 | 4-Cl-Ph | 4-Pyr | Me | 8a-Et |
| 8-118 | 4-Cl-Ph | 4-Pyr | Me | 8a-Pr |
| 8-119 | 4-Cl-Ph | 4-Pyr | Me | 6,6-(CH$_2$)$_2$— |
| 8-120 | 4-Cl-Ph | 4-Pyr | Me | 6,6-diF |
| 8-121 | 4-Cl-Ph | 4-Pyr | Me | 2->CH$_2$ |
| 8-122 | 4-Cl-Ph | 4-Pyr | Me | 2->CHMe |
| 8-123 | 4-Cl-Ph | 4-Pyr | Me | 2->CHEt |
| 8-124 | 4-Cl-Ph | 4-Pyr | Me | 2->CHPr |
| 8-125 | 4-Cl-Ph | 4-Pyr | Me | 2->C(Me)$_2$ |
| 8-126 | 4-Cl-Ph | 4-Pyr | Me | 2->CHPh |
| 8-127 | 4-Cl-Ph | 4-Pyr | Me | 2,2-diPh |
| 8-128 | 4-Cl-Ph | 4-Pyr | Me | 2,2-O(CH$_2$)$_3$O— |
| 8-129 | 4-Cl-Ph | 4-Pyr | Me | 2,2-OCH$_2$C(Me)$_2$CH$_2$O— |

TABLE 8-continued

| Compound No. | R¹ | R² | R⁴ | R⁵ |
|---|---|---|---|---|
| 8-130 | 4-Cl-Ph | 4-Pyr | Me | 2,2-(CH₂)₂— |
| 8-131 | 4-Cl-Ph | 4-Pyr | Me | 2,2-(CH₂)₃— |
| 8-132 | 4-Cl-Ph | 4-Pyr | Me | 2,2-(CH₂)₄— |
| 8-133 | 4-Cl-Ph | 4-Pyr | Me | 2,2-(CH₂)₅— |
| 8-134 | 4-Cl-Ph | 4-Pyr | Me | 2-MeS |
| 8-135 | 4-Cl-Ph | 4-Pyr | Me | 2-EtS |
| 8-136 | 4-Cl-Ph | 4-Pyr | Me | 2-PrS |
| 8-137 | 4-Cl-Ph | 4-Pyr | Me | 2-BuS |
| 8-138 | 4-Cl-Ph | 4-Pyr | Me | 2-MeSO₂ |
| 8-139 | 4-Cl-Ph | 4-Pyr | Me | 2-PhO |
| 8-140 | 4-F-Ph | 4-Pyr | Me | 2-(4-MeO-Ph) |
| 8-141 | 4-F-Ph | 4-Pyr | Me | 2-(4-Me-Ph) |
| 8-142 | 4-F-Ph | 4-Pyr | Me | 2-(4-F-Ph) |
| 8-143 | 4-F-Ph | 4-Pyr | Me | 2-(4-CF₃-Ph) |
| 8-144 | 4-F-Ph | 4-Pyr | Me | 2-(4-Cl-Ph) |
| 8-145 | 4-F-Ph | 4-Pyr | Me | 2-(2,4-diF-Ph) |
| 8-146 | 3-CF₃-Ph | 4-Pyr | Me | 2-(4-MeO-Ph) |
| 8-147 | 3-CF₃-Ph | 4-Pyr | Me | 2-(4-Me-Ph) |
| 8-148 | 3-CF₃-Ph | 4-Pyr | Me | 2-(4-F-Ph) |
| 8-149 | 3-CF₃-Ph | 4-Pyr | Me | 2-(4-CF₃-Ph) |
| 8-150 | 3-CF₃-Ph | 4-Pyr | Me | 2-(4-Cl-Ph) |
| 8-151 | 3-CF₃-Ph | 4-Pyr | Me | 2-(2,4-diF-Ph) |
| 8-152 | 4-F-Ph | 2-NH₂-4-Pym | Me | 2->CH₂ |
| 8-153 | 4-F-Ph | 2-NH₂-4-Pym | Me | 2->CHMe |
| 8-154 | 4-F-Ph | 2-NH₂-4-Pym | Me | 2->CHEt |
| 8-155 | 4-F-Ph | 2-NH₂-4-Pym | Me | 2->CHPr |
| 8-156 | 4-F-Ph | 2-NH₂-4-Pym | Me | 2->C(Me)₂ |
| 8-157 | 4-F-Ph | 2-NH₂-4-Pym | Me | 2->CHPh |
| 8-158 | 4-F-Ph | 2-NH₂-4-Pym | Me | 2,2-diPh |
| 8-159 | 4-F-Ph | 2-NH₂-4-Pym | Me | 2,2-O(CH₂)₃O— |
| 8-160 | 4-F-Ph | 2-NH₂-4-Pym | Me | 2,2-OCH₂C(Me)₂CH₂O— |
| 8-161 | 4-F-Ph | 2-NH₂-4-Pym | Me | 2,2-(CH₂)₂— |
| 8-162 | 4-F-Ph | 2-NH₂-4-Pym | Me | 2,2-(CH₂)₃— |
| 8-163 | 4-F-Ph | 2-NH₂-4-Pym | Me | 2,2-(CH₂)₄— |
| 8-164 | 4-F-Ph | 2-NH₂-4-Pym | Me | 2,2-(CH₂)₅— |
| 8-165 | 4-F-Ph | 2-NH₂-4-Pym | Me | 2-MeS |
| 8-166 | 4-F-Ph | 2-NH₂-4-Pym | Me | 2-EtS |
| 8-167 | 4-F-Ph | 2-NH₂-4-Pym | Me | 2-PrS |
| 8-168 | 4-F-Ph | 2-NH₂-4-Pym | Me | 2-BuS |
| 8-169 | 4-F-Ph | 2-NH₂-4-Pym | Me | 2-MeSO₂ |
| 8-170 | 4-F-Ph | 2-NH₂-4-Pym | Me | 2-PhO |
| 8-171 | 4-Cl-Ph | 2-NH₂-4-Pym | Me | 1-Me |
| 8-172 | 4-Cl-Ph | 2-NH₂-4-Pym | Me | 1-Et |
| 8-173 | 4-Cl-Ph | 2-NH₂-4-Pym | Me | 1-Pr |
| 8-174 | 4-Cl-Ph | 2-NH₂-4-Pym | Me | 2,2-diMe |
| 8-175 | 4-Cl-Ph | 2-NH₂-4-Pym | Me | 2-Me |
| 8-176 | 4-Cl-Ph | 2-NH₂-4-Pym | Me | 2-Et |
| 8-177 | 4-Cl-Ph | 2-NH₂-4-Pym | Me | 2-Pr |
| 8-178 | 4-Cl-Ph | 2-NH₂-4-Pym | Me | 2-Bu |
| 8-179 | 4-Cl-Ph | 2-NH₂-4-Pym | Me | 2-Allyl |
| 8-180 | 4-Cl-Ph | 2-NH₂-4-Pym | Me | 2-Ph |
| 8-181 | 4-Cl-Ph | 2-NH₂-4-Pym | Me | 2-Bn |
| 8-182 | 4-Cl-Ph | 2-NH₂-4-Pym | Me | 2-Phet |
| 8-183 | 4-Cl-Ph | 2-NH₂-4-Pym | Me | 2,2-diMe |
| 8-184 | 4-Cl-Ph | 2-NH₂-4-Pym | Me | 2-OH |
| 8-185 | 4-Cl-Ph | 2-NH₂-4-Pym | Me | 2-MeO |
| 8-186 | 4-Cl-Ph | 2-NH₂-4-Pym | Me | 2-EtO |
| 8-187 | 4-Cl-Ph | 2-NH₂-4-Pym | Me | 2-PrO |
| 8-188 | 4-Cl-Ph | 2-NH₂-4-Pym | Me | 2,2-di(MeO) |
| 8-189 | 4-Cl-Ph | 2-NH₂-4-Pym | Me | 2,2-di(EtO) |
| 8-190 | 4-Cl-Ph | 2-NH₂-4-Pym | Me | 2,2-OCH₂CH₂O— |
| 8-191 | 4-Cl-Ph | 2-NH₂-4-Pym | Me | 2,2-Oxo |
| 8-192 | 4-Cl-Ph | 2-NH₂-4-Pym | Me | 2-F |
| 8-193 | 4-Cl-Ph | 2-NH₂-4-Pym | Me | 2-Cl |
| 8-194 | 4-Cl-Ph | 2-NH₂-4-Pym | Me | 2-Br |
| 8-195 | 4-Cl-Ph | 2-NH₂-4-Pym | Me | 2-I |
| 8-196 | 4-Cl-Ph | 2-NH₂-4-Pym | Me | 2,2-diF |
| 8-197 | 4-Cl-Ph | 2-NH₂-4-Pym | Me | 2,2-diCl |
| 8-198 | 4-Cl-Ph | 2-NH₂-4-Pym | Me | 2,2-diBr |
| 8-199 | 4-Cl-Ph | 2-NH₂-4-Pym | Me | 3-Me |
| 8-200 | 4-Cl-Ph | 2-NH₂-4-Pym | Me | 3-Et |
| 8-201 | 4-Cl-Ph | 2-NH₂-4-Pym | Me | 3-Pr |
| 8-202 | 4-Cl-Ph | 2-NH₂-4-Pym | Me | 3,3-diMe |
| 8-203 | 4-Cl-Ph | 2-NH₂-4-Pym | Me | 5-Me |
| 8-204 | 4-Cl-Ph | 2-NH₂-4-Pym | Me | 5-Et |
| 8-205 | 4-Cl-Ph | 2-NH₂-4-Pym | Me | 5-Pr |
| 8-206 | 4-Cl-Ph | 2-NH₂-4-Pym | Me | 5,5-diMe |
| 8-207 | 4-Cl-Ph | 2-NH₂-4-Pym | Me | 6-Me |
| 8-208 | 4-Cl-Ph | 2-NH₂-4-Pym | Me | 6-Et |
| 8-209 | 4-Cl-Ph | 2-NH₂-4-Pym | Me | 6-Pr |
| 8-210 | 4-Cl-Ph | 2-NH₂-4-Pym | Me | 6,6-diMe |
| 8-211 | 4-Cl-Ph | 2-NH₂-4-Pym | Me | 6-Oxo |
| 8-212 | 4-Cl-Ph | 2-NH₂-4-Pym | Me | 8-Me |
| 8-213 | 4-Cl-Ph | 2-NH₂-4-Pym | Me | 8-Et |
| 8-214 | 4-Cl-Ph | 2-NH₂-4-Pym | Me | 8-Pr |
| 8-215 | 4-Cl-Ph | 2-NH₂-4-Pym | Me | 8-Ph |
| 8-216 | 4-Cl-Ph | 2-NH₂-4-Pym | Me | 8a-Me |
| 8-217 | 4-Cl-Ph | 2-NH₂-4-Pym | Me | 8a-Et |
| 8-218 | 4-Cl-Ph | 2-NH₂-4-Pym | Me | 8a-Pr |
| 8-219 | 4-Cl-Ph | 2-NH₂-4-Pym | Me | 6,6-(CH₂)₂— |
| 8-220 | 4-Cl-Ph | 2-NH₂-4-Pym | Me | 6,6-diF |
| 8-221 | 4-Cl-Ph | 2-NH₂-4-Pym | Me | 2->CH₂ |
| 8-222 | 4-Cl-Ph | 2-NH₂-4-Pym | Me | 2->CHMe |
| 8-223 | 4-Cl-Ph | 2-NH₂-4-Pym | Me | 2->CHEt |
| 8-224 | 4-Cl-Ph | 2-NH₂-4-Pym | Me | 2->CHPr |
| 8-225 | 4-Cl-Ph | 2-NH₂-4-Pym | Me | 2->C(Me)₂ |
| 8-226 | 4-Cl-Ph | 2-NH₂-4-Pym | Me | 2->CHPh |
| 8-227 | 4-Cl-Ph | 2-NH₂-4-Pym | Me | 2,2-diPh |
| 8-228 | 4-Cl-Ph | 2-NH₂-4-Pym | Me | 2,2-O(CH₂)₃O— |
| 8-229 | 4-Cl-Ph | 2-NH₂-4-Pym | Me | 2,2-OCH₂C(Me)₂CH₂O— |
| 8-230 | 4-Cl-Ph | 2-NH₂-4-Pym | Me | 2,2-(CH₂)₂— |
| 8-231 | 4-Cl-Ph | 2-NH₂-4-Pym | Me | 2,2-(CH₂)₃— |
| 8-232 | 4-Cl-Ph | 2-NH₂-4-Pym | Me | 2,2-(CH₂)₄— |
| 8-233 | 4-Cl-Ph | 2-NH₂-4-Pym | Me | 2,2-(CH₂)₅— |
| 8-234 | 4-Cl-Ph | 2-NH₂-4-Pym | Me | 2-MeS |
| 8-235 | 4-Cl-Ph | 2-NH₂-4-Pym | Me | 2-EtS |
| 8-236 | 4-Cl-Ph | 2-NH₂-4-Pym | Me | 2-PrS |
| 8-237 | 4-Cl-Ph | 2-NH₂-4-Pym | Me | 2-BuS |
| 8-238 | 4-Cl-Ph | 2-NH₂-4-Pym | Me | 2-MeSO₂ |
| 8-239 | 4-Cl-Ph | 2-NH₂-4-Pym | Me | 2-PhO |
| 8-240 | 4-F-Ph | 2-NH₂-4-Pym | Me | 2-(4-MeO-Ph) |
| 8-241 | 4-F-Ph | 2-NH₂-4-Pym | Me | 2-(4-Me-Ph) |
| 8-242 | 4-F-Ph | 2-NH₂-4-Pym | Me | 2-(4-F-Ph) |
| 8-243 | 4-F-Ph | 2-NH₂-4-Pym | Me | 2-(4-CF₃-Ph) |
| 8-244 | 4-F-Ph | 2-NH₂-4-Pym | Me | 2-(4-Cl-Ph) |
| 8-245 | 4-F-Ph | 2-NH₂-4-Pym | Me | 2-(2,4-diF-Ph) |
| 8-246 | 3-CF₃-Ph | 2-NH₂-4-Pym | Me | 2-(4-MeO-Ph) |
| 8-247 | 3-CF₃-Ph | 2-NH₂-4-Pym | Me | 2-(4-Me-Ph) |
| 8-248 | 3-CF₃-Ph | 2-NH₂-4-Pym | Me | 2-(4-F-Ph) |
| 8-249 | 3-CF₃-Ph | 2-NH₂-4-Pym | Me | 2-(4-CF₃-Ph) |

TABLE 8-continued

[Structure diagram: bicyclic amine substituted pyrazole with positions labeled 1, 2, 3 (R5), 4 (N), 5, 6, 7, 8, 8a; pyrazole ring with R1, R2, R4]

| Compound No. | R¹ | R² | R⁴ | R⁵ |
|---|---|---|---|---|
| 8-250 | 3-CF₃-Ph | 2-NH₂-4-Pym | Me | 2-(4-Cl-Ph) |
| 8-251 | 3-CF₃-Ph | 2-NH₂-4-Pym | Me | 2-(2,4-diF-Ph) |
| 8-252 | 4-Cl-Ph | 4-Pyr | Me | — |
| 8-253 | 4-Cl-Ph | 4-Pyr | Me | 2-(4-MeO-Ph) |
| 8-254 | 4-Cl-Ph | 4-Pyr | Me | 2-(4-Me-Ph) |
| 8-255 | 4-Cl-Ph | 4-Pyr | Me | 2-(4-F-Ph) |
| 8-256 | 4-Cl-Ph | 4-Pyr | Me | 2-(4-CF₃-Ph) |
| 8-257 | 4-Cl-Ph | 4-Pyr | Me | 2-(4-Cl-Ph) |
| 8-258 | 4-Cl-Ph | 4-Pyr | Me | 2-(2,4-diF-Ph) |
| 8-259 | 4-Cl-Ph | 2-NH₂-4-Pym | Me | — |

TABLE 9

[Structure diagram: pyrazole with R¹, R², R³, R⁴ substituents]

| Compound No. | R¹ | R² | R³ | R⁴ |
|---|---|---|---|---|
| 9-1 | 4-F-Ph | 4-Pyr | [pyrrolizidine group] | H |
| 9-2 | 4-F-Ph | 4-Pyr | [quinolizidine group] | H |
| 9-3 | 4-F-Ph | 4-Pyr | [methyl-substituted quinolizidine group] | H |
| 9-4 | 4-F-Ph | 4-Pyr | [methyl-substituted azabicyclic group] | H |

TABLE 9-continued
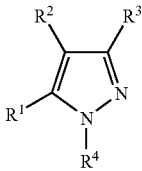
| Compound No. | R¹ | R² | R³ | R⁴ |
|---|---|---|---|---|
| 9-5 | 4-F-Ph | 4-Pyr | | H |
| 9-6 | 4-F-Ph | 4-Pyr | | H |
| 9-7 | 4-F-Ph | 4-Pyr | | H |
| 9-8 | 4-F-Ph | 4-Pyr | | H |
| 9-9 | 4-F-Ph | 4-Pyr | | H |
| 9-10 | 4-F-Ph | 4-Pyr | | H |
| 9-11 | 4-F-Ph | 4-Pyr | | H |
| 9-12 | 4-F-Ph | 4-Pyr | | Me |
| 9-13 | 4-F-Ph | 4-Pyr | | Me |

TABLE 9-continued

| Compound No. | R¹ | R² | R³ | R⁴ |
|---|---|---|---|---|
| 9-14 | 4-F-Ph | 4-Pyr | (structure) | Me |
| 9-15 | 4-F-Ph | 4-Pyr | (structure) | Me |
| 9-16 | 4-F-Ph | 4-Pyr | (structure) | Me |
| 9-17 | 4-F-Ph | 4-Pyr | (structure) | Me |
| 9-18 | 4-F-Ph | 4-Pyr | (structure) | Me |
| 9-19 | 4-F-Ph | 4-Pyr | (structure) | Me |
| 9-20 | 4-F-Ph | 4-Pyr | (structure) | Me |
| 9-21 | 4-F-Ph | 4-Pyr | (structure) | Me |

TABLE 9-continued
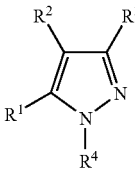
| Compound No. | R¹ | R² | R³ | R⁴ |
|---|---|---|---|---|
| 9-22 | 4-F-Ph | 4-Pyr | | Me |
| 9-23 | 4-F-Ph | 4-Pyr | | H |
| 9-24 | 4-F-Ph | 4-Pyr | | Me |
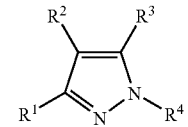
| Compound No. | R¹ | R² | R³ | R⁴ |
|---|---|---|---|---|
| 10-1 | 4-F-Ph | 4-Pyr | | Me |
| 10-2 | 4-F-Ph | 4-Pyr | | Me |
| 10-3 | 4-F-Ph | 4-Pyr | | Me |
| 10-4 | 4-F-Ph | 4-Pyr | | Me |
| 10-5 | 4-F-Ph | 4-Pyr | | Me |
| 10-6 | 4-F-Ph | 4-Pyr | | Me |
| 10-7 | 4-F-Ph | 4-Pyr | | Me |

TABLE 10-continued

R1, R2, R3 on pyrazole with N-R4

| Compound No. | R¹ | R² | R³ | R⁴ |
|---|---|---|---|---|
| 10-8 | 4-F-Ph | 4-Pyr | (indolizino-benzene group) | Me |
| 10-9 | 4-F-Ph | 4-Pyr | (imidazo[1,2-a]pyridine group) | Me |
| 10-10 | 4-F-Ph | 4-Pyr | (octahydroindolizine fused) | Me |
| 10-11 | 4-F-Ph | 4-Pyr | (quinolizidine group) | Me |
| 10-12 | 4-F-Ph | 4-Pyr | (hydroxy-indolizidine group, HO-) | Me |

TABLE 11

| Compound No. | R¹ | R² | A | R⁵ |
|---|---|---|---|---|
| 11-1 | 4-F-Ph | 4-Pyr | ring 1 | — |
| 11-2 | 4-F-Ph | 4-Pyr | ring 2 | — |
| 11-3 | 4-F-Ph | 4-Pyr | ring 3 | — |
| 11-4 | 4-F-Ph | 4-Pyr | ring 4 | — |
| 11-5 | 4-F-Ph | 4-Pyr | ring 5 | — |
| 11-6 | 4-F-Ph | 4-Pyr | ring 6 | — |
| 11-7 | 4-F-Ph | 4-Pyr | ring 7 | — |
| 11-8 | 4-F-Ph | 4-Pyr | ring 8 | — |
| 11-9 | 4-F-Ph | 4-Pyr | ring 9 | — |
| 11-10 | 4-F-Ph | 4-Pyr | ring 10 | — |
| 11-11 | 4-F-Ph | 4-Pyr | ring 11 | — |
| 11-12 | 4-F-Ph | 4-Pyr | ring 12 | — |
| 11-13 | 4-F-Ph | 4-Pyr | ring 13 | — |
| 11-14 | 4-F-Ph | 4-Pyr | ring 14 | — |
| 11-15 | 4-F-Ph | 4-Pyr | ring 15 | — |
| 11-46 | 4-F-Ph | 4-Pyr | ring 16 | — |
| 11-17 | 4-F-Ph | 4-Pyr | ring 17 | — |
| 11-18 | 4-F-Ph | 4-Pyr | ring 18 | — |
| 11-19 | 4-F-Ph | 4-Pyr | ring 19 | — |
| 11-20 | 4-F-Ph | 4-Pyr | ring 20 | — |
| 11-21 | 4-F-Ph | 4-Pyr | ring 21 | — |
| 11-22 | 4-F-Ph | 4-Pyr | ring 22 | — |
| 11-23 | 4-F-Ph | 4-Pyr | ring 23 | — |
| 11-24 | 4-F-Ph | 4-Pyr | ring 24 | — |
| 11-25 | 4-F-Ph | 4-Pyr | ring 25 | — |
| 11-26 | 4-F-Ph | 4-Pyr | ring 26 | — |
| 11-27 | 4-F-Ph | 4-Pyr | ring 27 | — |
| 11-28 | 4-F-Ph | 4-Pyr | ring 28 | — |
| 11-29 | 4-F-Ph | 4-Pyr | ring 29 | — |
| 11-30 | 4-F-Ph | 4-Pyr | ring 30 | — |
| 11-31 | 4-F-Ph | 4-Pyr | ring 31 | — |
| 11-32 | 4-F-Ph | 4-Pyr | ring 32 | — |
| 11-33 | 4-F-Ph | 4-Pyr | ring 33 | — |
| 11-34 | 4-F-Ph | 4-Pyr | ring 34 | — |
| 11-35 | 4-F-Ph | 4-Pyr | ring 35 | — |
| 11-36 | 4-F-Ph | 4-Pyr | ring 36 | — |
| 11-37 | 4-F-Ph | 4-Pyr | ring 37 | — |
| 11-38 | 4-F-Ph | 4-Pyr | ring 1 | 2-Me |
| 11-39 | 4-F-Ph | 4-Pyr | ring 2 | 2-Me |
| 11-40 | 4-F-Ph | 4-Pyr | ring 3 | 2-Me |
| 11-41 | 4-F-Ph | 4-Pyr | ring 4 | 2-Me |
| 11-42 | 4-F-Ph | 4-Pyr | ring 5 | 2-Me |
| 11-43 | 4-F-Ph | 4-Pyr | ring 6 | 2-Me |
| 11-44 | 4-F-Ph | 4-Pyr | ring 7 | 2-Me |
| 11-45 | 4-F-Ph | 4-Pyr | ring 8 | 2-Me |
| 11-46 | 4-F-Ph | 4-Pyr | ring 9 | 2-Me |
| 11-47 | 4-F-Ph | 4-Pyr | ring 10 | 2-Me |
| 11-48 | 4-F-Ph | 4-Pyr | ring 11 | 2-Me |
| 11-49 | 4-F-Ph | 4-Pyr | ring 12 | 2-Me |
| 11-50 | 4-F-Ph | 4-Pyr | ring 13 | 2-Me |
| 11-51 | 4-F-Ph | 4-Pyr | ring 14 | 2-Me |
| 11-52 | 4-F-Ph | 4-Pyr | ring 15 | 2-Me |
| 11-53 | 4-F-Ph | 4-Pyr | ring 16 | 2-Me |
| 11-54 | 4-F-Ph | 4-Pyr | ring 17 | 2-Me |
| 11-55 | 4-F-Ph | 4-Pyr | ring 18 | 2-Me |
| 11-56 | 4-F-Ph | 4-Pyr | ring 19 | 2-Me |
| 11-57 | 4-F-Ph | 4-Pyr | ring 20 | 2-Me |
| 11-58 | 4-F-Ph | 4-Pyr | ring 21 | 2-Me |
| 11-59 | 4-F-Ph | 4-Pyr | ring 22 | 2-Me |
| 11-60 | 4-F-Ph | 4-Pyr | ring 23 | 2-Me |
| 11-61 | 4-F-Ph | 4-Pyr | ring 24 | 2-Me |
| 11-62 | 4-F-Ph | 4-Pyr | ring 25 | 2-Me |
| 11-63 | 4-F-Ph | 4-Pyr | ring 26 | 2-Me |
| 11-64 | 4-F-Ph | 4-Pyr | ring 27 | 2-Me |
| 11-65 | 4-F-Ph | 4-Pyr | ring 28 | 2-Me |
| 11-66 | 4-F-Ph | 4-Pyr | ring 29 | 2-Me |
| 11-67 | 4-F-Ph | 4-Pyr | ring 30 | 2-Me |
| 11-68 | 4-F-Ph | 4-Pyr | ring 31 | 2-Me |
| 11-69 | 4-F-Ph | 4-Pyr | ring 32 | 2-Me |
| 11-70 | 4-F-Ph | 4-Pyr | ring 33 | 2-Me |
| 11-71 | 4-F-Ph | 4-Pyr | ring 34 | 2-Me |
| 11-72 | 4-F-Ph | 4-Pyr | ring 35 | 2-Me |
| 11-73 | 4-F-Ph | 4-Pyr | ring 36 | 2-Me |
| 11-74 | 4-F-Ph | 4-Pyr | ring 37 | 2-Me |
| 11-75 | 4-F-Ph | 4-Pyr | ring 1 | 2-OH |
| 11-76 | 4-F-Ph | 4-Pyr | ring 2 | 2-OH |
| 11-77 | 4-F-Ph | 4-Pyr | ring 3 | 2-OH |
| 11-78 | 4-F-Ph | 4-Pyr | ring 4 | 2-OH |

TABLE 11-continued

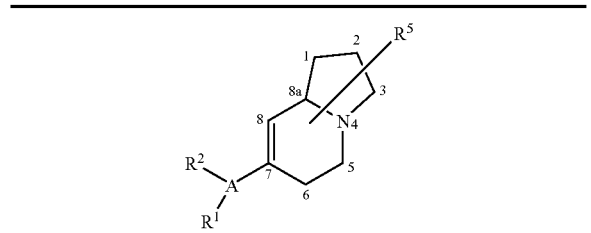

| Compound No. | R¹ | R² | A | R⁵ |
|---|---|---|---|---|
| 11-79 | 4-F-Ph | 4-Pyr | ring 5 | 2-OH |
| 11-80 | 4-F-Ph | 4-Pyr | ring 6 | 2-OH |
| 11-81 | 4-F-Ph | 4-Pyr | ring 7 | 2-OH |
| 11-82 | 4-F-Ph | 4-Pyr | ring 8 | 2-OH |
| 11-83 | 4-F-Ph | 4-Pyr | ring 9 | 2-OH |
| 11-84 | 4-F-Ph | 4-Pyr | ring 10 | 2-OH |
| 11-85 | 4-F-Ph | 4-Pyr | ring 11 | 2-OH |
| 11-86 | 4-F-Ph | 4-Pyr | ring 12 | 2-OH |
| 11-87 | 4-F-Ph | 4-Pyr | ring 13 | 2-OH |
| 11-88 | 4-F-Ph | 4-Pyr | ring 14 | 2-OH |
| 11-89 | 4-F-Ph | 4-Pyr | ring 15 | 2-OH |
| 11-90 | 4-F-Ph | 4-Pyr | ring 16 | 2-OH |
| 11-91 | 4-F-Ph | 4-Pyr | ring 17 | 2-OH |
| 11-92 | 4-F-Ph | 4-Pyr | ring 18 | 2-OH |
| 11-93 | 4-F-Ph | 4-Pyr | ring 19 | 2-OH |
| 11-94 | 4-F-Ph | 4-Pyr | ring 20 | 2-OH |
| 11-95 | 4-F-Ph | 4-Pyr | ring 21 | 2-OH |
| 11-96 | 4-F-Ph | 4-Pyr | ring 22 | 2-OH |
| 11-97 | 4-F-Ph | 4-Pyr | ring 23 | 2-OH |
| 11-98 | 4-F-Ph | 4-Pyr | ring 24 | 2-OH |
| 11-99 | 4-F-Ph | 4-Pyr | ring 25 | 2-OH |
| 11-100 | 4-F-Ph | 4-Pyr | ring 26 | 2-OH |
| 11-101 | 4-F-Ph | 4-Pyr | ring 27 | 2-OH |
| 11-102 | 4-F-Ph | 4-Pyr | ring 28 | 2-OH |
| 11-103 | 4-F-Ph | 4-Pyr | ring 29 | 2-OH |
| 11-104 | 4-F-Ph | 4-Pyr | ring 30 | 2-OH |
| 11-105 | 4-F-Ph | 4-Pyr | ring 31 | 2-OH |
| 11-106 | 4-F-Ph | 4-Pyr | ring 32 | 2-OH |
| 11-107 | 4-F-Ph | 4-Pyr | ring 33 | 2-OH |
| 11-108 | 4-F-Ph | 4-Pyr | ring 34 | 2-OH |
| 11-109 | 4-F-Ph | 4-Pyr | ring 35 | 2-OH |
| 11-110 | 4-F-Ph | 4-Pyr | ring 36 | 2-OH |
| 11-111 | 4-F-Ph | 4-Pyr | ring 37 | 2-OH |
| 11-112 | 4-F-Ph | 4-Pyr | ring 1 | 2-MeO |
| 11-113 | 4-F-Ph | 4-Pyr | ring 2 | 2-MeO |
| 11-114 | 4-F-Ph | 4-Pyr | ring 3 | 2-MeO |
| 11-115 | 4-F-Ph | 4-Pyr | ring 4 | 2-MeO |
| 11-116 | 4-F-Ph | 4-Pyr | ring 5 | 2-MeO |
| 11-117 | 4-F-Ph | 4-Pyr | ring 6 | 2-MeO |
| 11-118 | 4-F-Ph | 4-Pyr | ring 7 | 2-MeO |
| 11-119 | 4-F-Ph | 4-Pyr | ring 8 | 2-MeO |
| 11-120 | 4-F-Ph | 4-Pyr | ring 9 | 2-MeO |
| 11-121 | 4-F-Ph | 4-Pyr | ring 10 | 2-MeO |
| 11-122 | 4-F-Ph | 4-Pyr | ring 11 | 2-MeO |
| 11-123 | 4-F-Ph | 4-Pyr | ring 12 | 2-MeO |
| 11-124 | 4-F-Ph | 4-Pyr | ring 13 | 2-MeO |
| 11-125 | 4-F-Ph | 4-Pyr | ring 14 | 2-MeO |
| 11-126 | 4-F-Ph | 4-Pyr | ring 15 | 2-MeO |
| 11-127 | 4-F-Ph | 4-Pyr | ring 16 | 2-MeO |
| 11-128 | 4-F-Ph | 4-Pyr | ring 17 | 2-MeO |
| 11-129 | 4-F-Ph | 4-Pyr | ring 18 | 2-MeO |
| 11-130 | 4-F-Ph | 4-Pyr | ring 19 | 2-MeO |
| 11-131 | 4-F-Ph | 4-Pyr | ring 20 | 2-MeO |
| 11-132 | 4-F-Ph | 4-Pyr | ring 21 | 2-MeO |
| 11-133 | 4-F-Ph | 4-Pyr | ring 22 | 2-MeO |
| 11-134 | 4-F-Ph | 4-Pyr | ring 23 | 2-MeO |
| 11-135 | 4-F-Ph | 4-Pyr | ring 24 | 2-MeO |
| 11-136 | 4-F-Ph | 4-Pyr | ring 25 | 2-MeO |
| 11-137 | 4-F-Ph | 4-Pyr | ring 26 | 2-MeO |
| 11-138 | 4-F-Ph | 4-Pyr | ring 27 | 2-MeO |
| 11-139 | 4-F-Ph | 4-Pyr | ring 28 | 2-MeO |
| 11-140 | 4-F-Ph | 4-Pyr | ring 29 | 2-MeO |
| 11-141 | 4-F-Ph | 4-Pyr | ring 30 | 2-MeO |
| 11-142 | 4-F-Ph | 4-Pyr | ring 31 | 2-MeO |
| 11-143 | 4-F-Ph | 4-Pyr | ring 32 | 2-MeO |
| 11-144 | 4-F-Ph | 4-Pyr | ring 33 | 2-MeO |
| 11-145 | 4-F-Ph | 4-Pyr | ring 34 | 2-MeO |
| 11-146 | 4-F-Ph | 4-Pyr | ring 35 | 2-MeO |
| 11-147 | 4-F-Ph | 4-Pyr | ring 36 | 2-MeO |
| 11-148 | 4-F-Ph | 4-Pyr | ring 37 | 2-MeO |
| 11-149 | 4-F-Ph | 4-Pyr | ring 1 | 2-F |
| 11-150 | 4-F-Ph | 4-Pyr | ring 2 | 2-F |
| 11-151 | 4-F-Ph | 4-Pyr | ring 3 | 2-F |
| 11-152 | 4-F-Ph | 4-Pyr | ring 4 | 2-F |
| 11-153 | 4-F-Ph | 4-Pyr | ring 5 | 2-F |
| 11-154 | 4-F-Ph | 4-Pyr | ring 6 | 2-F |
| 11-155 | 4-F-Ph | 4-Pyr | ring 7 | 2-F |
| 11-156 | 4-F-Ph | 4-Pyr | ring 8 | 2-F |
| 11-157 | 4-F-Ph | 4-Pyr | ring 9 | 2-F |
| 11-158 | 4-F-Ph | 4-Pyr | ring 10 | 2-F |
| 11-159 | 4-F-Ph | 4-Pyr | ring 11 | 2-F |
| 11-160 | 4-F-Ph | 4-Pyr | ring 12 | 2-F |
| 11-161 | 4-F-Ph | 4-Pyr | ring 13 | 2-F |
| 11-162 | 4-F-Ph | 4-Pyr | ring 14 | 2-F |
| 11-163 | 4-F-Ph | 4-Pyr | ring 15 | 2-F |
| 11-164 | 4-F-Ph | 4-Pyr | ring 16 | 2-F |
| 11-165 | 4-F-Ph | 4-Pyr | ring 17 | 2-F |
| 11-166 | 4-F-Ph | 4-Pyr | ring 18 | 2-F |
| 11-167 | 4-F-Ph | 4-Pyr | ring 19 | 2-F |
| 11-168 | 4-F-Ph | 4-Pyr | ring 20 | 2-F |
| 11-169 | 4-F-Ph | 4-Pyr | ring 21 | 2-F |
| 11-170 | 4-F-Ph | 4-Pyr | ring 22 | 2-F |
| 11-171 | 4-F-Ph | 4-Pyr | ring 23 | 2-F |
| 11-172 | 4-F-Ph | 4-Pyr | ring 24 | 2-F |
| 11-173 | 4-F-Ph | 4-Pyr | ring 25 | 2-F |
| 11-174 | 4-F-Ph | 4-Pyr | ring 26 | 2-F |
| 11-175 | 4-F-Ph | 4-Pyr | ring 27 | 2-F |
| 11-176 | 4-F-Ph | 4-Pyr | ring 28 | 2-F |
| 11-177 | 4-F-Ph | 4-Pyr | ring 29 | 2-F |
| 11-178 | 4-F-Ph | 4-Pyr | ring 30 | 2-F |
| 11-179 | 4-F-Ph | 4-Pyr | ring 31 | 2-F |
| 11-180 | 4-F-Ph | 4-Pyr | ring 32 | 2-F |
| 11-181 | 4-F-Ph | 4-Pyr | ring 33 | 2-F |
| 11-182 | 4-F-Ph | 4-Pyr | ring 34 | 2-F |
| 11-183 | 4-F-Ph | 4-Pyr | ring 35 | 2-F |
| 11-184 | 4-F-Ph | 4-Pyr | ring 36 | 2-F |
| 11-185 | 4-F-Ph | 4-Pyr | ring 37 | 2-F |
| 11-186 | 4-F-Ph | 4-Pyr | ring 1 | 2-Cl |
| 11-187 | 4-F-Ph | 4-Pyr | ring 2 | 2-Cl |
| 11-188 | 4-F-Ph | 4-Pyr | ring 3 | 2-Cl |
| 11-189 | 4-F-Ph | 4-Pyr | ring4 | 2-Cl |
| 11-190 | 4-F-Ph | 4-Pyr | ring 5 | 2-Cl |
| 11-191 | 4-F-Ph | 4-Pyr | ring 6 | 2-Cl |
| 11-192 | 4-F-Ph | 4-Pyr | ring 7 | 2-Cl |
| 11-193 | 4-F-Ph | 4-Pyr | ring 8 | 2-Cl |
| 11-194 | 4-F-Ph | 4-Pyr | ring 9 | 2-Cl |
| 11-195 | 4-F-Ph | 4-Pyr | ring 10 | 2-Cl |
| 11-196 | 4-F-Ph | 4-Pyr | ring 11 | 2-Cl |
| 11-197 | 4-F-Ph | 4-Pyr | ring 12 | 2-Cl |
| 11-198 | 4-F-Ph | 4-Pyr | ring 13 | 2-Cl |
| 11-199 | 4-F-Ph | 4-Pyr | ring 14 | 2-Cl |
| 11-200 | 4-F-Ph | 4-Pyr | ring 15 | 2-Cl |
| 11-201 | 4-F-Ph | 4-Pyr | ring 16 | 2-Cl |
| 11-202 | 4-F-Ph | 4-Pyr | ring 17 | 2-Cl |
| 11-203 | 4-F-Ph | 4-Pyr | ring 18 | 2-Cl |
| 11-204 | 4-F-Ph | 4-Pyr | ring 19 | 2-Cl |
| 11-205 | 4-F-Ph | 4-Pyr | ring 20 | 2-Cl |
| 11-206 | 4-F-Ph | 4-Pyr | ring 21 | 2-Cl |
| 11-207 | 4-F-Ph | 4-Pyr | ring 22 | 2-Cl |
| 11-208 | 4-F-Ph | 4-Pyr | ring 23 | 2-Cl |

TABLE 11-continued

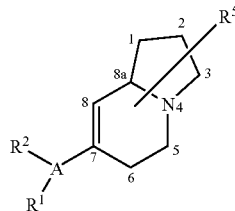

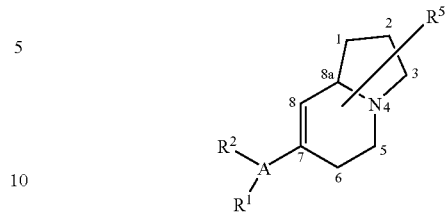

| Compound No. | R¹ | R² | A | R⁵ |
|---|---|---|---|---|
| 11-209 | 4-F-Ph | 4-Pyr | ring 24 | 2-Cl |
| 11-210 | 4-F-Ph | 4-Pyr | ring 25 | 2-Cl |
| 11-211 | 4-F-Ph | 4-Pyr | ring 26 | 2-Cl |
| 11-212 | 4-F-Ph | 4-Pyr | ring 27 | 2-Cl |
| 11-213 | 4-F-Ph | 4-Pyr | ring 28 | 2-Cl |
| 11-214 | 4-F-Ph | 4-Pyr | ring 29 | 2-Cl |
| 11-215 | 4-F-Ph | 4-Pyr | ring 30 | 2-Cl |
| 11-216 | 4-F-Ph | 4-Pyr | ring 31 | 2-Cl |
| 11-217 | 4-F-Ph | 4-Pyr | ring 32 | 2-Cl |
| 11-218 | 4-F-Ph | 4-Pyr | ring 33 | 2-Cl |
| 11-219 | 4-F-Ph | 4-Pyr | ring 34 | 2-Cl |
| 11-220 | 4-F-Ph | 4-Pyr | ring 35 | 2-Cl |
| 11-221 | 4-F-Ph | 4-Pyr | ring 36 | 2-Cl |
| 11-222 | 4-F-Ph | 4-Pyr | ring 37 | 2-Cl |
| 11-223 | 4-F-Ph | 4-Pyr | ring 1 | 2,2-diF |
| 11-224 | 4-F-Ph | 4-Pyr | ring 2 | 2,2-diF |
| 11-225 | 4-F-Ph | 4-Pyr | ring 3 | 2,2-diF |
| 11-226 | 4-F-Ph | 4-Pyr | ring 4 | 2,2-diF |
| 11-227 | 4-F-Ph | 4-Pyr | ring 5 | 2,2-diF |
| 11-228 | 4-F-Ph | 4-Pyr | ring 6 | 2,2-diF |
| 11-229 | 4-F-Ph | 4-Pyr | ring 7 | 2,2-diF |
| 11-230 | 4-F-Ph | 4-Pyr | ring 8 | 2,2-diF |
| 11-231 | 4-F-Ph | 4-Pyr | ring 9 | 2,2-diF |
| 11-232 | 4-F-Ph | 4-Pyr | ring 10 | 2,2-diF |
| 11-233 | 4-F-Ph | 4-Pyr | ring 11 | 2,2-diF |
| 11-234 | 4-F-Ph | 4-Pyr | ring 12 | 2,2-diF |
| 11-235 | 4-F-Ph | 4-Pyr | ring 13 | 2,2-diF |
| 11-236 | 4-F-Ph | 4-Pyr | ring 14 | 2,2-diF |
| 11-237 | 4-F-Ph | 4-Pyr | ring 15 | 2,2-diF |
| 11-238 | 4-F-Ph | 4-Pyr | ring 16 | 2,2-diF |
| 11-239 | 4-F-Ph | 4-Pyr | ring 17 | 2,2-diF |
| 11-240 | 4-F-Ph | 4-Pyr | ring 18 | 2,2-diF |
| 11-241 | 4-F-Ph | 4-Pyr | ring 19 | 2,2-diF |
| 11-242 | 4-F-Ph | 4-Pyr | ring 20 | 2,2-diF |
| 11-243 | 4-F-Ph | 4-Pyr | ring 21 | 2,2-diF |
| 11-244 | 4-F-Ph | 4-Pyr | ring 22 | 2,2-diF |
| 11-245 | 4-F-Ph | 4-Pyr | ring 23 | 2,2-diF |
| 11-246 | 4-F-Ph | 4-Pyr | ring 24 | 2,2-diF |
| 11-247 | 4-F-Ph | 4-Pyr | ring 25 | 2,2-diF |
| 11-248 | 4-F-Ph | 4-Pyr | ring 26 | 2,2-diF |
| 11-249 | 4-F-Ph | 4-Pyr | ring 27 | 2,2-diF |
| 11-250 | 4-F-Ph | 4-Pyr | ring 28 | 2,2-diF |
| 11-251 | 4-F-Ph | 4-Pyr | ring 29 | 2,2-diF |
| 11-252 | 4-F-Ph | 4-Pyr | ring 30 | 2,2-diF |
| 11-253 | 4-F-Ph | 4-Pyr | ring 31 | 2,2-diF |
| 11-254 | 4-F-Ph | 4-Pyr | ring 32 | 2,2-diF |
| 11-255 | 4-F-Ph | 4-Pyr | ring 33 | 2,2-diF |
| 11-256 | 4-F-Ph | 4-Pyr | ring 34 | 2,2-diF |
| 11-257 | 4-F-Ph | 4-Pyr | ring 35 | 2,2-diF |
| 11-258 | 4-F-Ph | 4-Pyr | ring 36 | 2,2-diF |
| 11-259 | 4-F-Ph | 4-Pyr | ring 37 | 2,2-diF |
| 11-260 | 4-F-Ph | 4-Pyr | ring 1 | 8-Me |
| 11-261 | 4-F-Ph | 4-Pyr | ring 2 | 8-Me |
| 11-262 | 4-F-Ph | 4-Pyr | ring 3 | 8-Me |
| 11-263 | 4-F-Ph | 4-Pyr | ring 4 | 8-Me |
| 11-264 | 4-F-Ph | 4-Pyr | ring 5 | 8-Me |
| 11-265 | 4-F-Ph | 4-Pyr | ring 6 | 8-Me |
| 11-266 | 4-F-Ph | 4-Pyr | ring 7 | 8-Me |
| 11-267 | 4-F-Ph | 4-Pyr | ring 8 | 8-Me |
| 11-268 | 4-F-Ph | 4-Pyr | ring 9 | 8-Me |
| 11-269 | 4-F-Ph | 4-Pyr | ring 10 | 8-Me |
| 11-270 | 4-F-Ph | 4-Pyr | ring 11 | 8-Me |
| 11-271 | 4-F-Ph | 4-Pyr | ring 12 | 8-Me |
| 11-272 | 4-F-Ph | 4-Pyr | ring 13 | 8-Me |
| 11-273 | 4-F-Ph | 4-Pyr | ring 14 | 8-Me |
| 11-274 | 4-F-Ph | 4-Pyr | ring 15 | 8-Me |
| 11-275 | 4-F-Ph | 4-Pyr | ring 16 | 8-Me |
| 11-276 | 4-F-Ph | 4-Pyr | ring 17 | 8-Me |
| 11-277 | 4-F-Ph | 4-Pyr | ring 18 | 8-Me |
| 11-278 | 4-F-Ph | 4-Pyr | ring 19 | 8-Me |
| 11-279 | 4-F-Ph | 4-Pyr | ring 20 | 8-Me |
| 11-280 | 4-F-Ph | 4-Pyr | ring 21 | 8-Me |
| 11-281 | 4-F-Ph | 4-Pyr | ring 22 | 8-Me |
| 11-282 | 4-F-Ph | 4-Pyr | ring 23 | 8-Me |
| 11-283 | 4-F-Ph | 4-Pyr | ring 24 | 8-Me |
| 11-284 | 4-F-Ph | 4-Pyr | ring 25 | 8-Me |
| 11-285 | 4-F-Ph | 4-Pyr | ring 26 | 8-Me |
| 11-286 | 4-F-Ph | 4-Pyr | ring 27 | 8-Me |
| 11-287 | 4-F-Ph | 4-Pyr | ring 28 | 8-Me |
| 11-288 | 4-F-Ph | 4-Pyr | ring 29 | 8-Me |
| 11-289 | 4-F-Ph | 4-Pyr | ring 30 | 8-Me |
| 11-290 | 4-F-Ph | 4-Pyr | ring 31 | 8-Me |
| 11-291 | 4-F-Ph | 4-Pyr | ring 32 | 8-Me |
| 11-292 | 4-F-Ph | 4-Pyr | ring 33 | 8-Me |
| 11-293 | 4-F-Ph | 4-Pyr | ring 34 | 8-Me |
| 11-294 | 4-F-Ph | 4-Pyr | ring 35 | 8-Me |
| 11-295 | 4-F-Ph | 4-Pyr | ring 36 | 8-Me |
| 11-296 | 4-F-Ph | 4-Pyr | ring 37 | 8-Me |
| 11-297 | 4-F-Ph | 2-NH₂-4-Pym | ring 1 | — |
| 11-298 | 4-F-Ph | 2-NH₂-4-Pym | ring 2 | — |
| 11-299 | 4-F-Ph | 2-NH₂-4-Pym | ring 3 | — |
| 11-300 | 4-F-Ph | 2-NH₂-4-Pym | ring 4 | — |
| 11-301 | 4-F-Ph | 2-NH₂-4-Pym | ring 5 | — |
| 11-302 | 4-F-Ph | 2-NH₂-4-Pym | ring 6 | — |
| 11-303 | 4-F-Ph | 2-NH₂-4-Pym | ring 7 | — |
| 11-304 | 4-F-Ph | 2-NH₂-4-Pym | ring 8 | — |
| 11-305 | 4-F-Ph | 2-NH₂-4-Pym | ring 9 | — |
| 11-306 | 4-F-Ph | 2-NH₂-4-Pym | ring 10 | — |
| 11-307 | 4-F-Ph | 2-NH₂-4-Pym | ring 11 | — |
| 11-308 | 4-F-Ph | 2-NH₂-4-Pym | ring 12 | — |
| 11-309 | 4-F-Ph | 2-NH₂-4-Pym | ring 13 | — |
| 11-310 | 4-F-Ph | 2-NH₂-4-Pym | ring 14 | — |
| 11-311 | 4-F-Ph | 2-NH₂-4-Pym | ring 15 | — |
| 11-312 | 4-F-Ph | 2-NH₂-4-Pym | ring 16 | — |
| 11-313 | 4-F-Ph | 2-NH₂-4-Pym | ring 17 | — |
| 11-314 | 4-F-Ph | 2-NH₂-4-Pym | ring 18 | — |
| 11-315 | 4-F-Ph | 2-NH₂-4-Pym | ring 19 | — |
| 11-316 | 4-F-Ph | 2-NH₂-4-Pym | ring 20 | — |
| 11-317 | 4-F-Ph | 2-NH₂-4-Pym | ring 21 | — |
| 11-318 | 4-F-Ph | 2-NH₂-4-Pym | ring 22 | — |
| 11-319 | 4-F-Ph | 2-NH₂-4-Pym | ring 23 | — |
| 11-320 | 4-F-Ph | 2-NH₂-4-Pym | ring 24 | — |
| 11-321 | 4-F-Ph | 2-NH₂-4-Pym | ring 25 | — |
| 11-322 | 4-F-Ph | 2-NH₂-4-Pym | ring 26 | — |
| 11-323 | 4-F-Ph | 2-NH₂-4-Pym | ring 27 | — |
| 11-324 | 4-F-Ph | 2-NH₂-4-Pym | ring 28 | — |
| 11-325 | 4-F-Ph | 2-NH₂-4-Pym | ring 29 | — |
| 11-326 | 4-F-Ph | 2-NH₂-4-Pym | ring 30 | — |
| 11-327 | 4-F-Ph | 2-NH₂-4-Pym | ring 31 | — |
| 11-328 | 4-F-Ph | 2-NH₂-4-Pym | ring 32 | — |
| 11-329 | 4-F-Ph | 2-NH₂-4-Pym | ring 33 | — |
| 11-330 | 4-F-Ph | 2-NH₂-4-Pym | ring 34 | — |
| 11-331 | 4-F-Ph | 2-NH₂-4-Pym | ring 35 | — |
| 11-332 | 4-F-Ph | 2-NH₂-4-Pym | ring 36 | — |
| 11-333 | 4-F-Ph | 2-NH₂-4-Pym | ring 37 | — |
| 11-334 | 4-F-Ph | 2-NH₂-4-Pym | ring 1 | 2-Me |
| 11-335 | 4-F-Ph | 2-NH₂-4-Pym | ring 2 | 2-Me |
| 11-336 | 4-F-Ph | 2-NH₂-4-Pym | ring 3 | 2-Me |
| 11-337 | 4-F-Ph | 2-NH₂-4-Pym | ring 4 | 2-Me |
| 11-338 | 4-F-Ph | 2-NH₂-4-Pym | ring 5 | 2-Me |

TABLE 11-continued

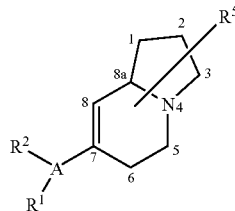

| Compound No. | R¹ | R² | A | R⁵ |
|---|---|---|---|---|
| 11-339 | 4-F-Ph | 2-NH$_2$-4-Pym | ring 6 | 2-Me |
| 11-340 | 4-F-Ph | 2-NH$_2$-4-Pym | ring 7 | 2-Me |
| 11-341 | 4-F-Ph | 2-NH$_2$-4-Pym | ring 8 | 2-Me |
| 11-342 | 4-F-Ph | 2-NH$_2$-4-Pym | ring 9 | 2-Me |
| 11-343 | 4-F-Ph | 2-NH$_2$-4-Pym | ring 10 | 2-Me |
| 11-344 | 4-F-Ph | 2-NH$_2$-4-Pym | ring 11 | 2-Me |
| 11-345 | 4-F-Ph | 2-NH$_2$-4-Pym | ring 12 | 2-Me |
| 11-346 | 4-F-Ph | 2-NH$_2$-4-Pym | ring 13 | 2-Me |
| 11-347 | 4-F-Ph | 2-NH$_2$-4-Pym | ring 14 | 2-Me |
| 11-348 | 4-F-Ph | 2-NH$_2$-4-Pym | ring 15 | 2-Me |
| 11-349 | 4-F-Ph | 2-NH$_2$-4-Pym | ring 16 | 2-Me |
| 11-350 | 4-F-Ph | 2-NH$_2$-4-Pym | ring 17 | 2-Me |
| 11-351 | 4-F-Ph | 2-NH$_2$-4-Pym | ring 18 | 2-Me |
| 11-352 | 4-F-Ph | 2-NH$_2$-4-Pym | ring 19 | 2-Me |
| 11-353 | 4-F-Ph | 2-NH$_2$-4-Pym | ring 20 | 2-Me |
| 11-354 | 4-F-Ph | 2-NH$_2$-4-Pym | ring 21 | 2-Me |
| 11-355 | 4-F-Ph | 2-NH$_2$-4-Pym | ring 22 | 2-Me |
| 11-356 | 4-F-Ph | 2-NH$_2$-4-Pym | ring 23 | 2-Me |
| 11-357 | 4-F-Ph | 2-NH$_2$-4-Pym | ring 24 | 2-Me |
| 11-358 | 4-F-Ph | 2-NH$_2$-4-Pym | ring 25 | 2-Me |
| 11-359 | 4-F-Ph | 2-NH$_2$-4-Pym | ring 26 | 2-Me |
| 11-360 | 4-F-Ph | 2-NH$_2$-4-Pym | ring 27 | 2-Me |
| 11-361 | 4-F-Ph | 2-NH$_2$-4-Pym | ring 28 | 2-Me |
| 11-362 | 4-F-Ph | 2-NH$_2$-4-Pym | ring 29 | 2-Me |
| 11-363 | 4-F-Ph | 2-NH$_2$-4-Pym | ring 30 | 2-Me |
| 11-364 | 4-F-Ph | 2-NH$_2$-4-Pym | ring 31 | 2-Me |
| 11-365 | 4-F-Ph | 2-NH$_2$-4-Pym | ring 32 | 2-Me |
| 11-366 | 4-F-Ph | 2-NH$_2$-4-Pym | ring 33 | 2-Me |
| 11-367 | 4-F-Ph | 2-NH$_2$-4-Pym | ring 34 | 2-Me |
| 11-368 | 4-F-Ph | 2-NH$_2$-4-Pym | ring 35 | 2-Me |
| 11-369 | 4-F-Ph | 2-NH$_2$-4-Pym | ring 36 | 2-Me |
| 11-370 | 4-F-Ph | 2-NH$_2$-4-Pym | ring 37 | 2-Me |
| 11-371 | 4-F-Ph | 2-NH$_2$-4-Pym | ring 1 | 2-OH |
| 11-372 | 4-F-Ph | 2-NH$_2$-4-Pym | ring 2 | 2-OH |
| 11-373 | 4-F-Ph | 2-NH$_2$-4-Pym | ring 3 | 2-OH |
| 11-374 | 4-F-Ph | 2-NH$_2$-4-Pym | ring 4 | 2-OH |
| 11-375 | 4-F-Ph | 2-NH$_2$-4-Pym | ring 5 | 2-OH |
| 11-376 | 4-F-Ph | 2-NH$_2$-4-Pym | ring 6 | 2-OH |
| 11-377 | 4-F-Ph | 2-NH$_2$-4-Pym | ring 7 | 2-OH |
| 11-378 | 4-F-Ph | 2-NH$_2$-4-Pym | ring 8 | 2-OH |
| 11-379 | 4-F-Ph | 2-NH$_2$-4-Pym | ring 9 | 2-OH |
| 11-380 | 4-F-Ph | 2-NH$_2$-4-Pym | ring 10 | 2-OH |
| 11-381 | 4-F-Ph | 2-NH$_2$-4-Pym | ring 11 | 2-OH |
| 11-382 | 4-F-Ph | 2-NH$_2$-4-Pym | ring 12 | 2-OH |
| 11-383 | 4-F-Ph | 2-NH$_2$-4-Pym | ring 13 | 2-OH |
| 11-384 | 4-F-Ph | 2-NH$_2$-4-Pym | ring 14 | 2-OH |
| 11-385 | 4-F-Ph | 2-NH$_2$-4-Pym | ring 15 | 2-OH |
| 11-386 | 4-F-Ph | 2-NH$_2$-4-Pym | ring 16 | 2-OH |
| 11-387 | 4-F-Ph | 2-NH$_2$-4-Pym | ring 17 | 2-OH |
| 11-388 | 4-F-Ph | 2-NH$_2$-4-Pym | ring 18 | 2-OH |
| 11-389 | 4-F-Ph | 2-NH$_2$-4-Pym | ring 19 | 2-OH |
| 11-390 | 4-F-Ph | 2-NH$_2$-4-Pym | ring 20 | 2-OH |
| 11-391 | 4-F-Ph | 2-NH$_2$-4-Pym | ring 21 | 2-OH |
| 11-392 | 4-F-Ph | 2-NH$_2$-4-Pym | ring 22 | 2-OH |
| 11-393 | 4-F-Ph | 2-NH$_2$-4-Pym | ring 23 | 2-OH |
| 11-394 | 4-F-Ph | 2-NH$_2$-4-Pym | ring 24 | 2-OH |
| 11-395 | 4-F-Ph | 2-NH$_2$-4-Pym | ring 25 | 2-OH |
| 11-396 | 4-F-Ph | 2-NH$_2$-4-Pym | ring 26 | 2-OH |
| 11-397 | 4-F-Ph | 2-NH$_2$-4-Pym | ring 27 | 2-OH |
| 11-398 | 4-F-Ph | 2-NH$_2$-4-Pym | ring 28 | 2-OH |
| 11-399 | 4-F-Ph | 2-NH$_2$-4-Pym | ring 29 | 2-OH |
| 11-400 | 4-F-Ph | 2-NH$_2$-4-Pym | ring 30 | 2-OH |
| 11-401 | 4-F-Ph | 2-NH$_2$-4-Pym | ring 31 | 2-OH |
| 11-402 | 4-F-Ph | 2-NH$_2$-4-Pym | ring 32 | 2-OH |
| 11-403 | 4-F-Ph | 2-NH$_2$-4-Pym | ring 33 | 2-OH |

TABLE 11-continued

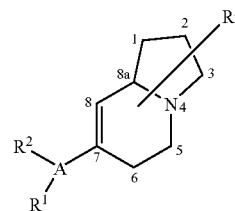

| Compound No. | R¹ | R² | A | R⁵ |
|---|---|---|---|---|
| 11-404 | 4-F-Ph | 2-NH$_2$-4-Pym | ring 34 | 2-OH |
| 11-405 | 4-F-Ph | 2-NH$_2$-4-Pym | ring 35 | 2-OH |
| 11-406 | 4-F-Ph | 2-NH$_2$-4-Pym | ring 36 | 2-OH |
| 11-407 | 4-F-Ph | 2-NH$_2$-4-Pym | ring 37 | 2-OH |
| 11-408 | 4-F-Ph | 2-NH$_2$-4-Pym | ring 1 | 2-MeO |
| 11-409 | 4-F-Ph | 2-NH$_2$-4-Pym | ring 2 | 2-MeO |
| 11-410 | 4-F-Ph | 2-NH$_2$-4-Pym | ring 3 | 2-MeO |
| 11-411 | 4-F-Ph | 2-NH$_2$-4-Pym | ring 4 | 2-MeO |
| 11-412 | 4-F-Ph | 2-NH$_2$-4-Pym | ring 5 | 2-MeO |
| 11-413 | 4-F-Ph | 2-NH$_2$-4-Pym | ring 6 | 2-MeO |
| 11-414 | 4-F-Ph | 2-NH$_2$-4-Pym | ring 7 | 2-MeO |
| 11-415 | 4-F-Ph | 2-NH$_2$-4-Pym | ring 8 | 2-MeO |
| 11-416 | 4-F-Ph | 2-NH$_2$-4-Pym | ring 9 | 2-MeO |
| 11-417 | 4-F-Ph | 2-NH$_2$-4-Pym | ring 10 | 2-MeO |
| 11-418 | 4-F-Ph | 2-NH$_2$-4-Pym | ring 11 | 2-MeO |
| 11-419 | 4-F-Ph | 2-NH$_2$-4-Pym | ring 12 | 2-MeO |
| 11-420 | 4-F-Ph | 2-NH$_2$-4-Pym | ring 13 | 2-MeO |
| 11-421 | 4-F-Ph | 2-NH$_2$-4-Pym | ring 14 | 2-MeO |
| 11-422 | 4-F-Ph | 2-NH$_2$-4-Pym | ring 15 | 2-MeO |
| 11-423 | 4-F-Ph | 2-NH$_2$-4-Pym | ring 16 | 2-MeO |
| 11-424 | 4-F-Ph | 2-NH$_2$-4-Pym | ring 17 | 2-MeO |
| 11-425 | 4-F-Ph | 2-NH$_2$-4-Pym | ring 18 | 2-MeO |
| 11-426 | 4-F-Ph | 2-NH$_2$-4-Pym | ring 19 | 2-MeO |
| 11-427 | 4-F-Ph | 2-NH$_2$-4-Pym | ring 20 | 2-MeO |
| 11-428 | 4-F-Ph | 2-NH$_2$-4-Pym | ring 21 | 2-MeO |
| 11-429 | 4-F-Ph | 2-NH$_2$-4-Pym | ring 22 | 2-MeO |
| 11-430 | 4-F-Ph | 2-NH$_2$-4-Pym | ring 23 | 2-MeO |
| 11-431 | 4-F-Ph | 2-NH$_2$-4-Pym | ring 24 | 2-MeO |
| 11-432 | 4-F-Ph | 2-NH$_2$-4-Pym | ring 25 | 2-MeO |
| 11-433 | 4-F-Ph | 2-NH$_2$-4-Pym | ring 26 | 2-MeO |
| 11-434 | 4-F-Ph | 2-NH$_2$-4-Pym | ring 27 | 2-MeO |
| 11-435 | 4-F-Ph | 2-NH$_2$-4-Pym | ring 28 | 2-MeO |
| 11-436 | 4-F-Ph | 2-NH$_2$-4-Pym | ring 29 | 2-MeO |
| 11-437 | 4-F-Ph | 2-NH$_2$-4-Pym | ring 30 | 2-MeO |
| 11-438 | 4-F-Ph | 2-NH$_2$-4-Pym | ring 31 | 2-MeO |
| 11-439 | 4-F-Ph | 2-NH$_2$-4-Pym | ring 32 | 2-MeO |
| 11-440 | 4-F-Ph | 2-NH$_2$-4-Pym | ring 33 | 2-MeO |
| 11-441 | 4-F-Ph | 2-NH$_2$-4-Pym | ring 34 | 2-MeO |
| 11-442 | 4-F-Ph | 2-NH$_2$-4-Pym | ring 35 | 2-MeO |
| 11-443 | 4-F-Ph | 2-NH$_2$-4-Pym | ring 36 | 2-MeO |
| 11-444 | 4-F-Ph | 2-NH$_2$-4-Pym | ring 37 | 2-MeO |
| 11-445 | 4-F-Ph | 2-NH$_2$-4-Pym | ring 1 | 2-F |
| 11-446 | 4-F-Ph | 2-NH$_2$-4-Pym | ring 2 | 2-F |
| 11-447 | 4-F-Ph | 2-NH$_2$-4-Pym | ring 3 | 2-F |
| 11-448 | 4-F-Ph | 2-NH$_2$-4-Pym | ring 4 | 2-F |
| 11-449 | 4-F-Ph | 2-NH$_2$-4-Pym | ring 5 | 2-F |
| 11-450 | 4-F-Ph | 2-NH$_2$-4-Pym | ring 6 | 2-F |
| 11-451 | 4-F-Ph | 2-NH$_2$-4-Pym | ring 7 | 2-F |
| 11-452 | 4-F-Ph | 2-NH$_2$-4-Pym | ring 8 | 2-F |
| 11-453 | 4-F-Ph | 2-NH$_2$-4-Pym | ring 9 | 2-F |
| 11-454 | 4-F-Ph | 2-NH$_2$-4-Pym | ring 10 | 2-F |
| 11-455 | 4-F-Ph | 2-NH$_2$-4-Pym | ring 11 | 2-F |
| 11-456 | 4-F-Ph | 2-NH$_2$-4-Pym | ring 12 | 2-F |
| 11-457 | 4-F-Ph | 2-NH$_2$-4-Pym | ring 13 | 2-F |
| 11-458 | 4-F-Ph | 2-NH$_2$-4-Pym | ring 14 | 2-F |
| 11-459 | 4-F-Ph | 2-NH$_2$-4-Pym | ring 15 | 2-F |
| 11-460 | 4-F-Ph | 2-NH$_2$-4-Pym | ring 16 | 2-F |
| 11-461 | 4-F-Ph | 2-NH$_2$-4-Pym | ring 17 | 2-F |
| 11-462 | 4-F-Ph | 2-NH$_2$-4-Pym | ring 18 | 2-F |
| 11-463 | 4-F-Ph | 2-NH$_2$-4-Pym | ring 19 | 2-F |
| 11-464 | 4-F-Ph | 2-NH$_2$-4-Pym | ring 20 | 2-F |
| 11-465 | 4-F-Ph | 2-NH$_2$-4-Pym | ring 21 | 2-F |
| 11-466 | 4-F-Ph | 2-NH$_2$-4-Pym | ring 22 | 2-F |
| 11-467 | 4-F-Ph | 2-NH$_2$-4-Pym | ring 23 | 2-F |
| 11-468 | 4-F-Ph | 2-NH$_2$-4-Pym | ring 24 | 2-F |

TABLE 11-continued

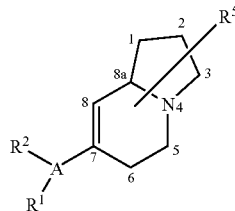

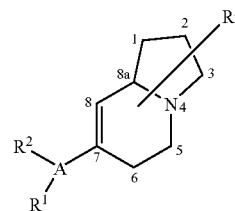

| Compound No. | R¹ | R² | A | R⁵ |
|---|---|---|---|---|
| 11-469 | 4-F-Ph | 2-NH$_2$-4-Pym | ring 25 | 2-F |
| 11-470 | 4-F-Ph | 2-NH$_2$-4-Pym | ring 26 | 2-F |
| 11-471 | 4-F-Ph | 2-NH$_2$-4-Pym | ring 27 | 2-F |
| 11-472 | 4-F-Ph | 2-NH$_2$-4-Pym | ring 28 | 2-F |
| 11-473 | 4-F-Ph | 2-NH$_2$-4-Pym | ring 29 | 2-F |
| 11-474 | 4-F-Ph | 2-NH$_2$-4-Pym | ring 30 | 2-F |
| 11-475 | 4-F-Ph | 2-NH$_2$-4-Pym | ring 31 | 2-F |
| 11-476 | 4-F-Ph | 2-NH$_2$-4-Pym | ring 32 | 2-F |
| 11-477 | 4-F-Ph | 2-NH$_2$-4-Pym | ring 33 | 2-F |
| 11-478 | 4-F-Ph | 2-NH$_2$-4-Pym | ring 34 | 2-F |
| 11-479 | 4-F-Ph | 2-NH$_2$-4-Pym | ring 35 | 2-F |
| 11-480 | 4-F-Ph | 2-NH$_2$-4-Pym | ring 36 | 2-F |
| 11-481 | 4-F-Ph | 2-NH$_2$-4-Pym | ring 37 | 2-F |
| 11-482 | 4-F-Ph | 2-NH$_2$-4-Pym | ring 1 | 2-Cl |
| 11-483 | 4-F-Ph | 2-NH$_2$-4-Pym | ring 2 | 2-Cl |
| 11-484 | 4-F-Ph | 2-NH$_2$-4-Pym | ring 3 | 2-Cl |
| 11-485 | 4-F-Ph | 2-NH$_2$-4-Pym | ring 4 | 2-Cl |
| 11-486 | 4-F-Ph | 2-NH$_2$-4-Pym | ring 5 | 2-Cl |
| 11-487 | 4-F-Ph | 2-NH$_2$-4-Pym | ring 6 | 2-Cl |
| 11-488 | 4-F-Ph | 2-NH$_2$-4-Pym | ring 7 | 2-Cl |
| 11-489 | 4-F-Ph | 2-NH$_2$-4-Pym | ring 8 | 2-Cl |
| 11-490 | 4-F-Ph | 2-NH$_2$-4-Pym | ring 9 | 2-Cl |
| 11-491 | 4-F-Ph | 2-NH$_2$-4-Pym | ring 10 | 2-Cl |
| 11-492 | 4-F-Ph | 2-NH$_2$-4-Pym | ring 11 | 2-Cl |
| 11-493 | 4-F-Ph | 2-NH$_2$-4-Pym | ring 12 | 2-Cl |
| 11-494 | 4-F-Ph | 2-NH$_2$-4-Pym | ring 13 | 2-Cl |
| 11-495 | 4-F-Ph | 2-NH$_2$-4-Pym | ring 14 | 2-Cl |
| 11-496 | 4-F-Ph | 2-NH$_2$-4-Pym | ring 15 | 2-Cl |
| 11-497 | 4-F-Ph | 2-NH$_2$-4-Pym | ring 16 | 2-Cl |
| 11-498 | 4-F-Ph | 2-NH$_2$-4-Pym | ring 17 | 2-Cl |
| 11-499 | 4-F-Ph | 2-NH$_2$-4-Pym | ring 18 | 2-Cl |
| 11-500 | 4-F-Ph | 2-NH$_2$-4-Pym | ring 19 | 2-Cl |
| 11-501 | 4-F-Ph | 2-NH$_2$-4-Pym | ring 20 | 2-Cl |
| 11-502 | 4-F-Ph | 2-NH$_2$-4-Pym | ring 21 | 2-Cl |
| 11-503 | 4-F-Ph | 2-NH$_2$-4-Pym | ring 22 | 2-Cl |
| 11-504 | 4-F-Ph | 2-NH$_2$-4-Pym | ring 23 | 2-Cl |
| 11-505 | 4-F-Ph | 2-NH$_2$-4-Pym | ring 24 | 2-Cl |
| 11-506 | 4-F-Ph | 2-NH$_2$-4-Pym | ring 25 | 2-Cl |
| 11-507 | 4-F-Ph | 2-NH$_2$-4-Pym | ring 26 | 2-Cl |
| 11-508 | 4-F-Ph | 2-NH$_2$-4-Pym | ring 27 | 2-Cl |
| 11-509 | 4-F-Ph | 2-NH$_2$-4-Pym | ring 28 | 2-Cl |
| 11-510 | 4-F-Ph | 2-NH$_2$-4-Pym | ring 29 | 2-Cl |
| 11-511 | 4-F-Ph | 2-NH$_2$-4-Pym | ring 30 | 2-Cl |
| 11-512 | 4-F-Ph | 2-NH$_2$-4-Pym | ring 31 | 2-Cl |
| 11-513 | 4-F-Ph | 2-NH$_2$-4-Pym | ring 32 | 2-Cl |
| 11-514 | 4-F-Ph | 2-NH$_2$-4-Pym | ring 33 | 2-Cl |
| 11-515 | 4-F-Ph | 2-NH$_2$-4-Pym | ring 34 | 2-Cl |
| 11-516 | 4-F-Ph | 2-NH$_2$-4-Pym | ring 35 | 2-Cl |
| 11-517 | 4-F-Ph | 2-NH$_2$-4-Pym | ring 36 | 2-Cl |
| 11-518 | 4-F-Ph | 2-NH$_2$-4-Pym | ring 37 | 2-Cl |
| 11-519 | 4-F-Ph | 2-NH$_2$-4-Pym | ring 1 | 2,2-diF |
| 11-520 | 4-F-Ph | 2-NH$_2$-4-Pym | ring 2 | 2,2-diF |
| 11-521 | 4-F-Ph | 2-NH$_2$-4-Pym | ring 3 | 2,2-diF |
| 11-522 | 4-F-Ph | 2-NH$_2$-4-Pym | ring 4 | 2,2-diF |
| 11-523 | 4-F-Ph | 2-NH$_2$-4-Pym | ring 5 | 2,2-diF |
| 11-524 | 4-F-Ph | 2-NH$_2$-4-Pym | ring 6 | 2,2-diF |
| 11-525 | 4-F-Ph | 2-NH$_2$-4-Pym | ring 7 | 2,2-diF |
| 11-526 | 4-F-Ph | 2-NH$_2$-4-Pym | ring 8 | 2,2-diF |
| 11-527 | 4-F-Ph | 2-NH$_2$-4-Pym | ring 9 | 2,2-diF |
| 11-528 | 4-F-Ph | 2-NH$_2$-4-Pym | ring 10 | 2,2-diF |
| 11-529 | 4-F-Ph | 2-NH$_2$-4-Pym | ring 11 | 2,2-diF |
| 11-530 | 4-F-Ph | 2-NH$_2$-4-Pym | ring 12 | 2,2-diF |
| 11-531 | 4-F-Ph | 2-NH$_2$-4-Pym | ring 13 | 2,2-diF |
| 11-532 | 4-F-Ph | 2-NH$_2$-4-Pym | ring 14 | 2,2-diF |
| 11-533 | 4-F-Ph | 2-NH$_2$-4-Pym | ring 15 | 2,2-diF |
| 11-534 | 4-F-Ph | 2-NH$_2$-4-Pym | ring 16 | 2,2-diF |
| 11-535 | 4-F-Ph | 2-NH$_2$-4-Pym | ring 17 | 2,2-diF |
| 11-536 | 4-F-Ph | 2-NH$_2$-4-Pym | ring 18 | 2,2-diF |
| 11-537 | 4-F-Ph | 2-NH$_2$-4-Pym | ring 19 | 2,2-diF |
| 11-538 | 4-F-Ph | 2-NH$_2$-4-Pym | ring 20 | 2,2-diF |
| 11-539 | 4-F-Ph | 2-NH$_2$-4-Pym | ring 21 | 2,2-diF |
| 11-540 | 4-F-Ph | 2-NH$_2$-4-Pym | ring 22 | 2,2-diF |
| 11-541 | 4-F-Ph | 2-NH$_2$-4-Pym | ring 23 | 2,2-diF |
| 11-542 | 4-F-Ph | 2-NH$_2$-4-Pym | ring 24 | 2,2-diF |
| 11-543 | 4-F-Ph | 2-NH$_2$-4-Pym | ring 25 | 2,2-diF |
| 11-544 | 4-F-Ph | 2-NH$_2$-4-Pym | ring 26 | 2,2-diF |
| 11-545 | 4-F-Ph | 2-NH$_2$-4-Pym | ring 27 | 2,2-diF |
| 11-546 | 4-F-Ph | 2-NH$_2$-4-Pym | ring 28 | 2,2-diF |
| 11-547 | 4-F-Ph | 2-NH$_2$-4-Pym | ring 29 | 2,2-diF |
| 11-548 | 4-F-Ph | 2-NH$_2$-4-Pym | ring 30 | 2,2-diF |
| 11-549 | 4-F-Ph | 2-NH$_2$-4-Pym | ring 31 | 2,2-diF |
| 11-550 | 4-F-Ph | 2-NH$_2$-4-Pym | ring 32 | 2,2-diF |
| 11-551 | 4-F-Ph | 2-NH$_2$-4-Pym | ring 33 | 2,2-diF |
| 11-552 | 4-F-Ph | 2-NH$_2$-4-Pym | ring 34 | 2,2-diF |
| 11-553 | 4-F-Ph | 2-NH$_2$-4-Pym | ring 35 | 2,2-diF |
| 11-554 | 4-F-Ph | 2-NH$_2$-4-Pym | ring 36 | 2,2-diF |
| 11-555 | 4-F-Ph | 2-NH$_2$-4-Pym | ring 37 | 2,2-diF |
| 11-556 | 4-F-Ph | 2-NH$_2$-4-Pym | ring 1 | 8-Me |
| 11-557 | 4-F-Ph | 2-NH$_2$-4-Pym | ring 2 | 8-Me |
| 11-558 | 4-F-Ph | 2-NH$_2$-4-Pym | ring 3 | 8-Me |
| 11-559 | 4-F-Ph | 2-NH$_2$-4-Pym | ring 4 | 8-Me |
| 11-560 | 4-F-Ph | 2-NH$_2$-4-Pym | ring 5 | 8-Me |
| 11-561 | 4-F-Ph | 2-NH$_2$-4-Pym | ring 6 | 8-Me |
| 11-562 | 4-F-Ph | 2-NH$_2$-4-Pym | ring 7 | 8-Me |
| 11-563 | 4-F-Ph | 2-NH$_2$-4-Pym | ring 8 | 8-Me |
| 11-564 | 4-F-Ph | 2-NH$_2$-4-Pym | ring 9 | 8-Me |
| 11-565 | 4-F-Ph | 2-NH$_2$-4-Pym | ring 10 | 8-Me |
| 11-566 | 4-F-Ph | 2-NH$_2$-4-Pym | ring 11 | 8-Me |
| 11-567 | 4-F-Ph | 2-NH$_2$-4-Pym | ring 12 | 8-Me |
| 11-568 | 4-F-Ph | 2-NH$_2$-4-Pym | ring 13 | 8-Me |
| 11-569 | 4-F-Ph | 2-NH$_2$-4-Pym | ring 14 | 8-Me |
| 11-570 | 4-F-Ph | 2-NH$_2$-4-Pym | ring 15 | 8-Me |
| 11-571 | 4-F-Ph | 2-NH$_2$-4-Pym | ring 16 | 8-Me |
| 11-572 | 4-F-Ph | 2-NH$_2$-4-Pym | ring 17 | 8-Me |
| 11-573 | 4-F-Ph | 2-NH$_2$-4-Pym | ring 18 | 8-Me |
| 11-574 | 4-F-Ph | 2-NH$_2$-4-Pym | ring 19 | 8-Me |
| 11-575 | 4-F-Ph | 2-NH$_2$-4-Pym | ring 20 | 8-Me |
| 11-576 | 4-F-Ph | 2-NH$_2$-4-Pym | ring 21 | 8-Me |
| 11-577 | 4-F-Ph | 2-NH$_2$-4-Pym | ring 22 | 8-Me |
| 11-578 | 4-F-Ph | 2-NH$_2$-4-Pym | ring 23 | 8-Me |
| 11-579 | 4-F-Ph | 2-NH$_2$-4-Pym | ring 24 | 8-Me |
| 11-580 | 4-F-Ph | 2-NH$_2$-4-Pym | ring 25 | 8-Me |
| 11-581 | 4-F-Ph | 2-NH$_2$-4-Pym | ring 26 | 8-Me |
| 11-582 | 4-F-Ph | 2-NH$_2$-4-Pym | ring 27 | 8-Me |
| 11-583 | 4-F-Ph | 2-NH$_2$-4-Pym | ring 28 | 8-Me |
| 11-584 | 4-F-Ph | 2-NH$_2$-4-Pym | ring 29 | 8-Me |
| 11-585 | 4-F-Ph | 2-NH$_2$-4-Pym | ring 30 | 8-Me |
| 11-586 | 4-F-Ph | 2-NH$_2$-4-Pym | ring 31 | 8-Me |
| 11-587 | 4-F-Ph | 2-NH$_2$-4-Pym | ring 32 | 8-Me |
| 11-588 | 4-F-Ph | 2-NH$_2$-4-Pym | ring 33 | 8-Me |
| 11-589 | 4-F-Ph | 2-NH$_2$-4-Pym | ring 34 | 8-Me |
| 11-590 | 4-F-Ph | 2-NH$_2$-4-Pym | ring 35 | 8-Me |
| 11-591 | 4-F-Ph | 2-NH$_2$-4-Pym | ring 36 | 8-Me |
| 11-592 | 4-F-Ph | 2-NH$_2$-4-Pym | ring 37 | 8-Me |
| 11-593 | 4-F-Ph | 2-MeNH-4-Pym | ring 1 | — |
| 11-594 | 4-F-Ph | 2-MeNH-4-Pym | ring 2 | — |
| 11-595 | 4-F-Ph | 2-MeNH-4-Pym | ring 3 | — |
| 11-596 | 4-F-Ph | 2-MeNH-4-Pym | ring 4 | — |
| 11-597 | 4-F-Ph | 2-MeNH-4-Pym | ring 5 | — |
| 11-598 | 4-F-Ph | 2-MeNH-4-Pym | ring 6 | — |

TABLE 11-continued

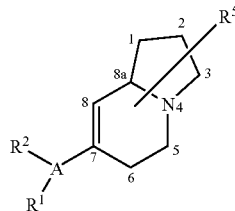

| Compound No. | R¹ | R² | A | R⁵ |
|---|---|---|---|---|
| 11-599 | 4-F-Ph | 2-MeNH-4-Pym | ring 7 | — |
| 11-600 | 4-F-Ph | 2-MeNH-4-Pym | ring 8 | — |
| 11-601 | 4-F-Ph | 2-MeNH-4-Pym | ring 9 | — |
| 11-602 | 4-F-Ph | 2-MeNH-4-Pym | ring 10 | — |
| 11-603 | 4-F-Ph | 2-MeNH-4-Pym | ring 11 | — |
| 11-604 | 4-F-Ph | 2-MeNH-4-Pym | ring 12 | — |
| 11-605 | 4-F-Ph | 2-MeNH-4-Pym | ring 13 | — |
| 11-606 | 4-F-Ph | 2-MeNH-4-Pym | ring 14 | — |
| 11-607 | 4-F-Ph | 2-MeNH-4-Pym | ring 15 | — |
| 11-608 | 4-F-Ph | 2-MeNH-4-Pym | ring 16 | — |
| 11-609 | 4-F-Ph | 2-MeNH-4-Pym | ring 17 | — |
| 11-610 | 4-F-Ph | 2-MeNH-4-Pym | ring 18 | — |
| 11-611 | 4-F-Ph | 2-MeNH-4-Pym | ring 19 | — |
| 11-612 | 4-F-Ph | 2-MeNH-4-Pym | ring 20 | — |
| 11-613 | 4-F-Ph | 2-MeNH-4-Pym | ring 21 | — |
| 11-614 | 4-F-Ph | 2-MeNH-4-Pym | ring 22 | — |
| 11-615 | 4-F-Ph | 2-MeNH-4-Pym | ring 23 | — |
| 11-616 | 4-F-Ph | 2-MeNH-4-Pym | ring 24 | — |
| 11-617 | 4-F-Ph | 2-MeNH-4-Pym | ring 25 | — |
| 11-618 | 4-F-Ph | 2-MeNH-4-Pym | ring 26 | — |
| 11-619 | 4-F-Ph | 2-MeNH-4-Pym | ring 27 | — |
| 11-620 | 4-F-Ph | 2-MeNH-4-Pym | ring 28 | — |
| 11-621 | 4-F-Ph | 2-MeNH-4-Pym | ring 29 | — |
| 11-622 | 4-F-Ph | 2-MeNH-4-Pym | ring 30 | — |
| 11-623 | 4-F-Ph | 2-MeNH-4-Pym | ring 31 | — |
| 11-624 | 4-F-Ph | 2-MeNH-4-Pym | ring 32 | — |
| 11-625 | 4-F-Ph | 2-MeNH-4-Pym | ring 33 | — |
| 11-626 | 4-F-Ph | 2-MeNH-4-Pym | ring 34 | — |
| 11-627 | 4-F-Ph | 2-MeNH-4-Pym | ring 35 | — |
| 11-628 | 4-F-Ph | 2-MeNH-4-Pym | ring 36 | — |
| 11-629 | 4-F-Ph | 2-MeNH-4-Pym | ring 37 | — |
| 11-630 | 4-F-Ph | 2-MeNH-4-Pym | ring 1 | 2-Me |
| 11-631 | 4-F-Ph | 2-MeNH-4-Pym | ring 2 | 2-Me |
| 11-632 | 4-F-Ph | 2-MeNH-4-Pym | ring 3 | 2-Me |
| 11-633 | 4-F-Ph | 2-MeNH-4-Pym | ring 4 | 2-Me |
| 11-634 | 4-F-Ph | 2-MeNH-4-Pym | ring 5 | 2-Me |
| 11-635 | 4-F-Ph | 2-MeNH-4-Pym | ring 6 | 2-Me |
| 11-636 | 4-F-Ph | 2-MeNH-4-Pym | ring 7 | 2-Me |
| 11-637 | 4-F-Ph | 2-MeNH-4-Pym | ring 8 | 2-Me |
| 11-638 | 4-F-Ph | 2-MeNH-4-Pym | ring 9 | 2-Me |
| 11-639 | 4-F-Ph | 2-MeNH-4-Pym | ring 10 | 2-Me |
| 11-640 | 4-F-Ph | 2-MeNH-4-Pym | ring 11 | 2-Me |
| 11-641 | 4-F-Ph | 2-MeNH-4-Pym | ring 12 | 2-Me |
| 11-642 | 4-F-Ph | 2-MeNH-4-Pym | ring 13 | 2-Me |
| 11-643 | 4-F-Ph | 2-MeNH-4-Pym | ring 14 | 2-Me |
| 11-644 | 4-F-Ph | 2-MeNH-4-Pym | ring 15 | 2-Me |
| 11-645 | 4-F-Ph | 2-MeNH-4-Pym | ring 16 | 2-Me |
| 11-646 | 4-F-Ph | 2-MeNH-4-Pym | ring 17 | 2-Me |
| 11-647 | 4-F-Ph | 2-MeNH-4-Pym | ring 18 | 2-Me |
| 11-648 | 4-F-Ph | 2-MeNH-4-Pym | ring 19 | 2-Me |
| 11-649 | 4-F-Ph | 2-MeNH-4-Pym | ring 20 | 2-Me |
| 11-650 | 4-F-Ph | 2-MeNH-4-Pym | ring 21 | 2-Me |
| 11-651 | 4-F-Ph | 2-MeNH-4-Pym | ring 22 | 2-Me |
| 11-652 | 4-F-Ph | 2-MeNH-4-Pym | ring 23 | 2-Me |
| 11-653 | 4-F-Ph | 2-MeNH-4-Pym | ring 24 | 2-Me |
| 11-654 | 4-F-Ph | 2-MeNH-4-Pym | ring 25 | 2-Me |
| 11-655 | 4-F-Ph | 2-MeNH-4-Pym | ring 26 | 2-Me |
| 11-656 | 4-F-Ph | 2-MeNH-4-Pym | ring 27 | 2-Me |
| 11-657 | 4-F-Ph | 2-MeNH-4-Pym | ring 28 | 2-Me |
| 11-658 | 4-F-Ph | 2-MeNH-4-Pym | ring 29 | 2-Me |
| 11-659 | 4-F-Ph | 2-MeNH-4-Pym | ring 30 | 2-Me |
| 11-660 | 4-F-Ph | 2-MeNH-4-Pym | ring 31 | 2-Me |
| 11-661 | 4-F-Ph | 2-MeNH-4-Pym | ring 32 | 2-Me |
| 11-662 | 4-F-Ph | 2-MeNH-4-Pym | ring 33 | 2-Me |
| 11-663 | 4-F-Ph | 2-MeNH-4-Pym | ring 34 | 2-Me |
| 11-664 | 4-F-Ph | 2-MeNH-4-Pym | ring 35 | 2-Me |
| 11-665 | 4-F-Ph | 2-MeNH-4-Pym | ring 36 | 2-Me |
| 11-666 | 4-F-Ph | 2-MeNH-4-Pym | ring 37 | 2-Me |
| 11-667 | 4-F-Ph | 2-MeNH-4-Pym | ring 1 | 2-OH |
| 11-668 | 4-F-Ph | 2-MeNH-4-Pym | ring 2 | 2-OH |
| 11-669 | 4-F-Ph | 2-MeNH-4-Pym | ring 3 | 2-OH |
| 11-670 | 4-F-Ph | 2-MeNH-4-Pym | ring 4 | 2-OH |
| 11-671 | 4-F-Ph | 2-MeNH-4-Pym | ring 5 | 2-OH |
| 11-672 | 4-F-Ph | 2-MeNH-4-Pym | ring 6 | 2-OH |
| 11-673 | 4-F-Ph | 2-MeNH-4-Pym | ring 7 | 2-OH |
| 11-674 | 4-F-Ph | 2-MeNH-4-Pym | ring 8 | 2-OH |
| 11-675 | 4-F-Ph | 2-MeNH-4-Pym | ring 9 | 2-OH |
| 11-676 | 4-F-Ph | 2-MeNH-4-Pym | ring 10 | 2-OH |
| 11-677 | 4-F-Ph | 2-MeNH-4-Pym | ring 11 | 2-OH |
| 11-678 | 4-F-Ph | 2-MeNH-4-Pym | ring 12 | 2-OH |
| 11-679 | 4-F-Ph | 2-MeNH-4-Pym | ring 13 | 2-OH |
| 11-680 | 4-F-Ph | 2-MeNH-4-Pym | ring 14 | 2-OH |
| 11-681 | 4-F-Ph | 2-MeNH-4-Pym | ring 15 | 2-OH |
| 11-682 | 4-F-Ph | 2-MeNH-4-Pym | ring 16 | 2-OH |
| 11-683 | 4-F-Ph | 2-MeNH-4-Pym | ring 17 | 2-OH |
| 11-684 | 4-F-Ph | 2-MeNH-4-Pym | ring 18 | 2-OH |
| 11-685 | 4-F-Ph | 2-MeNH-4-Pym | ring 19 | 2-OH |
| 11-686 | 4-F-Ph | 2-MeNH-4-Pym | ring 20 | 2-OH |
| 11-687 | 4-F-Ph | 2-MeNH-4-Pym | ring 21 | 2-OH |
| 11-688 | 4-F-Ph | 2-MeNH-4-Pym | ring 22 | 2-OH |
| 11-689 | 4-F-Ph | 2-MeNH-4-Pym | ring 23 | 2-OH |
| 11-690 | 4-F-Ph | 2-MeNH-4-Pym | ring 24 | 2-OH |
| 11-691 | 4-F-Ph | 2-MeNH-4-Pym | ring 25 | 2-OH |
| 11-692 | 4-F-Ph | 2-MeNH-4-Pym | ring 26 | 2-OH |
| 11-693 | 4-F-Ph | 2-MeNH-4-Pym | ring 27 | 2-OH |
| 11-694 | 4-F-Ph | 2-MeNH-4-Pym | ring 28 | 2-OH |
| 11-695 | 4-F-Ph | 2-MeNH-4-Pym | ring 29 | 2-OH |
| 11-696 | 4-F-Ph | 2-MeNH-4-Pym | ring 30 | 2-OH |
| 11-697 | 4-F-Ph | 2-MeNH-4-Pym | ring 31 | 2-OH |
| 11-698 | 4-F-Ph | 2-MeNH-4-Pym | ring 32 | 2-OH |
| 11-699 | 4-F-Ph | 2-MeNH-4-Pym | ring 33 | 2-OH |
| 11-700 | 4-F-Ph | 2-MeNH-4-Pym | ring 34 | 2-OH |
| 11-701 | 4-F-Ph | 2-MeNH-4-Pym | ring 35 | 2-OH |
| 11-702 | 4-F-Ph | 2-MeNH-4-Pym | ring 36 | 2-OH |
| 11-703 | 4-F-Ph | 2-MeNH-4-Pym | ring 37 | 2-OH |
| 11-704 | 4-F-Ph | 2-MeNH-4-Pym | ring 1 | 2-MeO |
| 11-705 | 4-F-Ph | 2-MeNH-4-Pym | ring 2 | 2-MeO |
| 11-706 | 4-F-Ph | 2-MeNH-4-Pym | ring 3 | 2-MeO |
| 11-707 | 4-F-Ph | 2-MeNH-4-Pym | ring 4 | 2-MeO |
| 11-708 | 4-F-Ph | 2-MeNH-4-Pym | ring 5 | 2-MeO |
| 11-709 | 4-F-Ph | 2-MeNH-4-Pym | ring 6 | 2-MeO |
| 11-710 | 4-F-Ph | 2-MeNH-4-Pym | ring 7 | 2-MeO |
| 11-711 | 4-F-Ph | 2-MeNH-4-Pym | ring 8 | 2-MeO |
| 11-712 | 4-F-Ph | 2-MeNH-4-Pyni | ring 9 | 2-MeO |
| 11-713 | 4-F-Ph | 2-MeNH-4-Pym | ring 10 | 2-MeO |
| 11-714 | 4-F-Ph | 2-MeNH-4-Pym | ring 11 | 2-MeO |
| 11-715 | 4-F-Ph | 2-MeNH-4-Pym | ring 12 | 2-MeO |
| 11-716 | 4-F-Ph | 2-MeNH-4-Pym | ring 13 | 2-MeO |
| 11-717 | 4-F-Ph | 2-MeNH-4-Pym | ring 14 | 2-MeO |
| 11-718 | 4-F-Ph | 2-MeNH-4-Pym | ring 15 | 2-MeO |
| 11-719 | 4-F-Ph | 2-MeNH-4-Pym | ring 16 | 2-MeO |
| 11-720 | 4-F-Ph | 2-MeNH-4-Pym | ring 17 | 2-MeO |
| 11-721 | 4-F-Ph | 2-MeNH-4-Pym | ring 18 | 2-MeO |
| 11-722 | 4-F-Ph | 2-MeNH-4-Pym | ring 19 | 2-MeO |
| 11-723 | 4-F-Ph | 2-MeNH-4-Pym | ring 20 | 2-MeO |
| 11-724 | 4-F-Ph | 2-MeNH-4-Pym | ring 21 | 2-MeO |
| 11-725 | 4-F-Ph | 2-MeNH-4-Pym | ring 22 | 2-MeO |
| 11-726 | 4-F-Ph | 2-MeNH-4-Pym | ring 23 | 2-MeO |
| 11-727 | 4-F-Ph | 2-MeNH-4-Pym | ring 24 | 2-MeO |
| 11-728 | 4-F-Ph | 2-MeNH-4-Pym | ring 25 | 2-MeO |

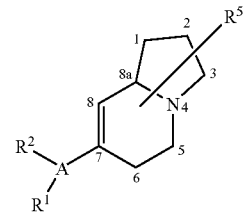

TABLE 11-continued

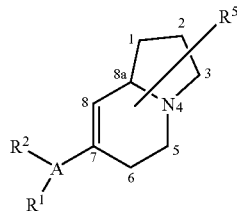

| Compound No. | R¹ | R² | A | R⁵ |
|---|---|---|---|---|
| 11-729 | 4-F-Ph | 2-MeNH-4-Pym | ring 26 | 2-MeO |
| 11-730 | 4-F-Ph | 2-MeNH-4-Pym | ring 27 | 2-MeO |
| 11-731 | 4-F-Ph | 2-MeNH-4-Pym | ring 28 | 2-MeO |
| 11-732 | 4-F-Ph | 2-MeNH-4-Pym | ring 29 | 2-MeO |
| 11-733 | 4-F-Ph | 2-MeNH-4-Pym | ring 30 | 2-MeO |
| 11-734 | 4-F-Ph | 2-MeNH-4-Pym | ring 31 | 2-MeO |
| 11-735 | 4-F-Ph | 2-MeNH-4-Pym | ring 32 | 2-MeO |
| 11-736 | 4-F-Ph | 2-MeNH-4-Pym | ring 33 | 2-MeO |
| 11-737 | 4-F-Ph | 2-MeNH-4-Pym | ring 34 | 2-MeO |
| 11-738 | 4-F-Ph | 2-MeNH-4-Pym | ring 35 | 2-MeO |
| 11-739 | 4-F-Ph | 2-MeNH-4-Pym | ring 36 | 2-MeO |
| 11-740 | 4-F-Ph | 2-MeNH-4-Pym | ring 37 | 2-MeO |
| 11-741 | 4-F-Ph | 2-MeNH-4-Pym | ring 1 | 2-F |
| 11-742 | 4-F-Ph | 2-MeNH-4-Pym | ring 2 | 2-F |
| 11-743 | 4-F-Ph | 2-MeNH-4-Pym | ring 3 | 2-F |
| 11-744 | 4-F-Ph | 2-MeNH-4-Pym | ring 4 | 2-F |
| 11-745 | 4-F-Ph | 2-MeNH-4-Pym | ring 5 | 2-F |
| 11-746 | 4-F-Ph | 2-MeNH-4-Pym | ring 6 | 2-F |
| 11-747 | 4-F-Ph | 2-MeNH-4-Pym | ring 7 | 2-F |
| 11-748 | 4-F-Ph | 2-MeNH-4-Pym | ring 8 | 2-F |
| 11-749 | 4-F-Ph | 2-MeNH-4-Pym | ring 9 | 2-F |
| 11-750 | 4-F-Ph | 2-MeNH-4-Pym | ring 10 | 2-F |
| 11-751 | 4-F-Ph | 2-MeNH-4-Pym | ring 11 | 2-F |
| 11-752 | 4-F-Ph | 2-MeNH-4-Pym | ring 12 | 2-F |
| 11-753 | 4-F-Ph | 2-MeNH-4-Pym | ring 13 | 2-F |
| 11-754 | 4-F-Ph | 2-MeNH-4-Pym | ring 14 | 2-F |
| 11-755 | 4-F-Ph | 2-MeNH-4-Pym | ring 15 | 2-F |
| 11-756 | 4-F-Ph | 2-MeNH-4-Pym | ring 16 | 2-F |
| 11-757 | 4-F-Ph | 2-MeNH-4-Pym | ring 17 | 2-F |
| 11-758 | 4-F-Ph | 2-MeNH-4-Pym | ring 18 | 2-F |
| 11-759 | 4-F-Ph | 2-MeNH-4-Pym | ring 19 | 2-F |
| 11-760 | 4-F-Ph | 2-MeNH-4-Pym | ring 20 | 2-F |
| 11-761 | 4-F-Ph | 2-MeNH-4-Pym | ring 21 | 2-F |
| 11-762 | 4-F-Ph | 2-MeNH-4-Pym | ring 22 | 2-F |
| 11-763 | 4-F-Ph | 2-MeNH-4-Pym | ring 23 | 2-F |
| 11-764 | 4-F-Ph | 2-MeNH-4-Pym | ring 24 | 2-F |
| 11-765 | 4-F-Ph | 2-MeNH-4-Pym | ring 25 | 2-F |
| 11-766 | 4-F-Ph | 2-MeNH-4-Pym | ring 26 | 2-F |
| 11-767 | 4-F-Ph | 2-MeNH-4-Pym | ring 27 | 2-F |
| 11-768 | 4-F-Ph | 2-MeNH-4-Pym | ring 28 | 2-F |
| 11-769 | 4-F-Ph | 2-MeNH-4-Pym | ring 29 | 2-F |
| 11-770 | 4-F-Ph | 2-MeNH-4-Pym | ring 30 | 2-F |
| 11-771 | 4-F-Ph | 2-MeNH-4-Pym | ring 31 | 2-F |
| 11-772 | 4-F-Ph | 2-MeNH-4-Pym | ring 32 | 2-F |
| 11-773 | 4-F-Ph | 2-MeNH-4-Pym | ring 33 | 2-F |
| 11-774 | 4-F-Ph | 2-MeNH-4-Pym | ring 34 | 2-F |
| 11-775 | 4-F-Ph | 2-MeNH-4-Pym | ring 35 | 2-F |
| 11-776 | 4-F-Ph | 2-MeNH-4-Pym | ring 36 | 2-F |
| 11-777 | 4-F-Ph | 2-MeNH-4-Pym | ring 37 | 2-F |
| 11-778 | 4-F-Ph | 2-MeNH-4-Pym | ring 1 | 2-Cl |
| 11-779 | 4-F-Ph | 2-MeNH-4-Pym | ring 2 | 2-Cl |
| 11-780 | 4-F-Ph | 2-MeNH-4-Pym | ring 3 | 2-Cl |
| 11-781 | 4-F-Ph | 2-MeNH-4-Pym | ring 4 | 2-Cl |
| 11-782 | 4-F-Ph | 2-MeNH-4-Pym | ring 5 | 2-Cl |
| 11-783 | 4-F-Ph | 2-MeNH-4-Pym | ring 6 | 2-Cl |
| 11-784 | 4-F-Ph | 2-MeNH-4-Pym | ring 7 | 2-Cl |
| 11-785 | 4-F-Ph | 2-MeNH-4-Pym | ring 8 | 2-Cl |
| 11-786 | 4-F-Ph | 2-MeNH-4-Pym | ring 9 | 2-Cl |
| 11-787 | 4-F-Ph | 2-MeNH-4-Pym | ring 10 | 2-Cl |
| 11-788 | 4-F-Ph | 2-MeNH-4-Pym | ring 11 | 2-Cl |
| 11-789 | 4-F-Ph | 2-MeNH-4-Pym | ring 12 | 2-Cl |
| 11-790 | 4-F-Ph | 2-MeNH-4-Pym | ring 13 | 2-Cl |
| 11-791 | 4-F-Ph | 2-MeNH-4-Pym | ring 14 | 2-Cl |
| 11-792 | 4-F-Ph | 2-MeNH-4-Pym | ring 15 | 2-Cl |
| 11-793 | 4-F-Ph | 2-MeNH-4-Pym | ring 16 | 2-Cl |

TABLE 11-continued

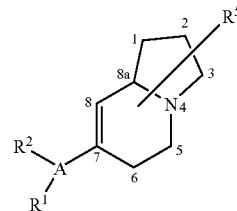

| Compound No. | R¹ | R² | A | R⁵ |
|---|---|---|---|---|
| 11-794 | 4-F-Ph | 2-MeNH-4-Pym | ring 17 | 2-Cl |
| 11-795 | 4-F-Ph | 2-MeNH-4-Pym | ring 18 | 2-Cl |
| 11-796 | 4-F-Ph | 2-MeNH-4-Pym | ring 19 | 2-Cl |
| 11-797 | 4-F-Ph | 2-MeNH-4-Pym | ring 20 | 2-Cl |
| 11-798 | 4-F-Ph | 2-MeNH-4-Pym | ring 21 | 2-Cl |
| 11-799 | 4-F-Ph | 2-MeNH-4-Pym | ring 22 | 2-Cl |
| 11-800 | 4-F-Ph | 2-MeNH-4-Pym | ring 23 | 2-Cl |
| 11-801 | 4-F-Ph | 2-MeNH-4-Pym | ring 24 | 2-Cl |
| 11-802 | 4-F-Ph | 2-MeNH-4-Pym | ring 25 | 2-Cl |
| 11-803 | 4-F-Ph | 2-MeNH-4-Pym | ring 26 | 2-Cl |
| 11-804 | 4-F-Ph | 2-MeNH-4-Pym | ring 27 | 2-Cl |
| 11-805 | 4-F-Ph | 2-MeKH-4-Pym | ring 28 | 2-Cl |
| 11-806 | 4-F-Ph | 2-MeNH-4-Pym | ring 29 | 2-Cl |
| 11-807 | 4-F-Ph | 2-MeNH-4-Pym | ring 30 | 2-Cl |
| 11-808 | 4-F-Ph | 2-MeNH-4-Pym | ring 31 | 2-Cl |
| 11-809 | 4-F-Ph | 2-MeNH-4-Pym | ring 32 | 2-Cl |
| 11-810 | 4-F-Ph | 2-MeNH-4-Pym | ring 33 | 2-Cl |
| 11-811 | 4-F-Ph | 2-MeNH-4-Pym | ring 34 | 2-Cl |
| 11-812 | 4-F-Ph | 2-MeNH-4-Pym | ring 35 | 2-Cl |
| 11-813 | 4-F-Ph | 2-MeNH-4-Pym | ring 36 | 2-Cl |
| 11-814 | 4-F-Ph | 2-MeNH-4-Pym | ring 37 | 2-Cl |
| 11-815 | 4-F-Ph | 2-MeNH-4-Pym | ring 1 | 2,2-diF |
| 11-816 | 4-F-Ph | 2-MeNH-4-Pym | ring 2 | 2,2-diF |
| 11-817 | 4-F-Ph | 2-MeNH-4-Pym | ring 3 | 2,2-diF |
| 11-818 | 4-F-Ph | 2-MeNH-4-Pym | ring 4 | 2,2-diF |
| 11-819 | 4-F-Ph | 2-MeNH-4-Pym | ring 5 | 2,2-diF |
| 11-820 | 4-F-Ph | 2-MeNH-4-Pym | ring 6 | 2,2-diF |
| 11-821 | 4-F-Ph | 2-MeNH-4-Pym | ring 7 | 2,2-diF |
| 11-822 | 4-F-Ph | 2-MeNH-4-Pym | ring 8 | 2,2-diF |
| 11-823 | 4-F-Ph | 2-MeNH-4-Pym | ring 9 | 2,2-diF |
| 11-824 | 4-F-Ph | 2-MeNH-4-Pym | ring 10 | 2,2-diF |
| 11-825 | 4-F-Ph | 2-MeNH-4-Pym | ring 11 | 2,2-diF |
| 11-826 | 4-F-Ph | 2-MeNH-4-Pym | ring 12 | 2,2-diF |
| 11-827 | 4-F-Ph | 2-MeNH-4-Pym | ring 13 | 2,2-diF |
| 11-828 | 4-F-Ph | 2-MeNH-4-Pym | ring 14 | 2,2-diF |
| 11-829 | 4-F-Ph | 2-MeNH-4-Pym | ring 15 | 2,2-diF |
| 11-830 | 4-F-Ph | 2-MeNH-4-Pym | ring 16 | 2,2-diF |
| 11-831 | 4-F-Ph | 2-MeNH-4-Pym | ring 17 | 2,2-diF |
| 11-832 | 4-F-Ph | 2-MeNH-4-Pym | ring 18 | 2,2-diF |
| 11-833 | 4-F-Ph | 2-MeNH-4-Pym | ring 19 | 2,2-diF |
| 11-834 | 4-F-Ph | 2-MeNH-4-Pym | ring 20 | 2,2-diF |
| 11-835 | 4-F-Ph | 2-MeNH-4-Pym | ring 21 | 2,2-diF |
| 11-836 | 4-F-Ph | 2-MeNH-4-Pym | ring 22 | 2,2-diF |
| 11-837 | 4-F-Ph | 2-MeNH-4-Pym | ring 23 | 2,2-diF |
| 11-838 | 4-F-Ph | 2-MeNH-4-Pym | ring 24 | 2,2-diF |
| 11-839 | 4-F-Ph | 2-MeNH-4-Pym | ring 25 | 2,2-diF |
| 11-840 | 4-F-Ph | 2-MeNH-4-Pym | ring 26 | 2,2-diF |
| 11-841 | 4-F-Ph | 2-MeNH-4-Pym | ring 27 | 2,2-diF |
| 11-842 | 4-F-Ph | 2-MeNH-4-Pym | ring 28 | 2,2-diF |
| 11-843 | 4-F-Ph | 2-MeNH-4-Pym | ring 29 | 2,2-diF |
| 11-844 | 4-F-Ph | 2-MeNH-4-Pym | ring 30 | 2,2-diF |
| 11-845 | 4-F-Ph | 2-MeNH-4-Pym | ring 31 | 2,2-diF |
| 11-846 | 4-F-Ph | 2-MeNH-4-Pym | ring 32 | 2,2-diF |
| 11-847 | 4-F-Ph | 2-MeNH-4-Pym | ring 33 | 2,2-diF |
| 11-848 | 4-F-Ph | 2-MeNH-4-Pym | ring 34 | 2,2-diF |
| 11-849 | 4-F-Ph | 2-MeNH-4-Pym | ring 35 | 2,2-diF |
| 11-850 | 4-F-Ph | 2-MeNH-4-Pym | ring 36 | 2,2-diF |
| 11-851 | 4-F-Ph | 2-MeNH-4-Pym | ring 37 | 2,2-diF |
| 11-852 | 4-F-Ph | 2-MeNR-4-Pym | ring 1 | 8-Me |
| 11-853 | 4-F-Ph | 2-MeNH-4-Pym | ring 2 | 8-Me |
| 11-854 | 4-F-Ph | 2-MeNH-4-Pym | ring 3 | 8-Me |
| 11-855 | 4-F-Ph | 2-MeNH-4-Pym | ring 4 | 8-Me |
| 11-856 | 4-F-Ph | 2-MeNH-4-Pym | ring 5 | 8-Me |
| 11-857 | 4-F-Ph | 2-MeNH-4-Pym | ring 6 | 8-Me |
| 11-858 | 4-F-Ph | 2-MeNH-4-Pym | ring 7 | 8-Me |

TABLE 11-continued

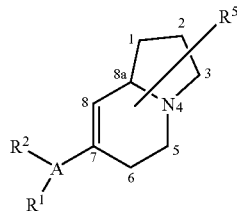

| Compound No. | R¹ | R² | A | R⁵ |
|---|---|---|---|---|
| 11-859 | 4-F-Ph | 2-MeNH-4-Pym | ring 8 | 8-Me |
| 11-860 | 4-F-Ph | 2-MeNH-4-Pym | ring 9 | 8-Me |
| 11-861 | 4-F-Ph | 2-MeNH-4-Pym | ring 10 | 8-Me |
| 11-862 | 4-F-Ph | 2-MeNH-4-Pym | ring 11 | 8-Me |
| 11-863 | 4-F-Ph | 2-MeNH-4-Pym | ring 12 | 8-Me |
| 11-864 | 4-F-Ph | 2-MeNH-4-Pym | ring 13 | 8-Me |
| 11-865 | 4-F-Ph | 2-MeNH-4-Pym | ring 14 | 8-Me |
| 11-866 | 4-F-Ph | 2-MeNH-4-Pym | ring 15 | 8-Me |
| 11-867 | 4-F-Ph | 2-MeNH-4-Pym | ring 16 | 8-Me |
| 11-868 | 4-F-Ph | 2-MeNH-4-Pym | ring 17 | 8-Me |
| 11-869 | 4-F-Ph | 2-MeNH-4-Pym | ring 18 | 8-Me |
| 11-870 | 4-F-Ph | 2-MeNH-4-Pym | ring 19 | 8-Me |
| 11-871 | 4-F-Ph | 2-MeNH-4-Pym | ring 20 | 8-Me |
| 11-872 | 4-F-Ph | 2-MeNH-4-Pym | ring 21 | 8-Me |
| 11-873 | 4-F-Ph | 2-MeNH-4-Pym | ring 22 | 8-Me |
| 11-874 | 4-F-Ph | 2-MeNH-4-Pym | ring 23 | 8-Me |
| 11-875 | 4-F-Ph | 2-MeNH-4-Pym | ring 24 | 8-Me |
| 11-876 | 4-F-Ph | 2-MeNH-4-Pym | ring 25 | 8-Me |
| 11-877 | 4-F-Ph | 2-MeNH-4-Pym | ring 26 | 8-Me |
| 11-878 | 4-F-Ph | 2-MeNH-4-Pym | ring 27 | 8-Me |
| 11-879 | 4-F-Ph | 2-MeNH-4-Pym | ring 28 | 8-Me |
| 11-880 | 4-F-Ph | 2-MeNH-4-Pym | ring 29 | 8-Me |
| 11-881 | 4-F-Ph | 2-MeNH-4-Pym | ring 30 | 8-Me |
| 11-882 | 4-F-Ph | 2-MeNH-4-Pym | ring 31 | 8-Me |
| 11-883 | 4-F-Ph | 2-MeNH-4-Pym | ring 32 | 8-Me |
| 11-884 | 4-F-Ph | 2-MeNH-4-Pym | ring 33 | 8-Me |
| 11-885 | 4-F-Ph | 2-MeNH-4-Pym | ring 34 | 8-Me |
| 11-886 | 4-F-Ph | 2-MeNR-4-Pym | ring 35 | 8-Me |
| 11-887 | 4-F-Ph | 2-MeNH-4-Pym | ring 36 | 8-Me |
| 11-888 | 4-F-Ph | 2-MeNH-4-Pym | ring 37 | 8-Me |
| 11-889 | 4-F-Ph | 2-(α-Me-BnNH)-4-Pym | ring 1 | — |
| 11-890 | 4-F-Ph | 2-(α-Me-BnNH)-4-Pym | ring 2 | — |
| 11-891 | 4-F-Ph | 2-(α-Me-BnNH)-4-Pym | ring 3 | — |
| 11-892 | 4-F-Ph | 2-(α-Me-BnNH)-4-Pym | ring 4 | — |
| 11-893 | 4-F-Ph | 2-(α-Me-BnNH)-4-Pym | ring 5 | — |
| 11-894 | 4-F-Ph | 2-(α-Me-BnNH)-4-Pym | ring 6 | — |
| 11-895 | 4-F-Ph | 2-(α-Me-BnNH)-4-Pym | ring 7 | — |
| 11-896 | 4-F-Ph | 2-(α-Me-BnNH)-4-Pym | ring 8 | — |
| 11-897 | 4-F-Ph | 2-(α-Me-BnNH)-4-Pym | ring 9 | — |
| 11-898 | 4-F-Ph | 2-(α-Me-BnNH)-4-Pym | ring 10 | — |
| 11-899 | 4-F-Ph | 2-(α-Me-BnNH)-4-Pym | ring 11 | — |
| 11-900 | 4-F-Ph | 2-(α-Me-BnNH)-4-Pym | ring 12 | — |
| 11-901 | 4-F-Ph | 2-(α-Me-BnNH)-4-Pym | ring 13 | — |
| 11-902 | 4-F-Ph | 2-(α-Me-BnNH)-4-Pym | ring 14 | — |
| 11-903 | 4-F-Ph | 2-(α-Me-BnNH)-4-Pym | ring 15 | — |
| 11-904 | 4-F-Ph | 2-(α-Me-BnNH)-4-Pym | ring 16 | — |
| 11-905 | 4-F-Ph | 2-(α-Me-BnNH)-4-Pym | ring 17 | — |
| 11-906 | 4-F-Ph | 2-(α-Me-BnNH)-4-Pym | ring 18 | — |
| 11-907 | 4-F-Ph | 2-(α-Me-BnNH)-4-Pym | ring 19 | — |
| 11-908 | 4-F-Ph | 2-(α-Me-BnNH)-4-Pym | ring 20 | — |
| 11-909 | 4-F-Ph | 2-(α-Me-BnNH)-4-Pym | ring 21 | — |
| 11-910 | 4-F-Ph | 2-(α-Me-BnNH)-4-Pym | ring 22 | — |
| 11-911 | 4-F-Ph | 2-(α-Me-BnNH)-4-Pym | ring 23 | — |
| 11-912 | 4-F-Ph | 2-(α-Me-BnNH)-4-Pym | ring 24 | — |
| 11-913 | 4-F-Ph | 2-(α-Me-BnNH)-4-Pym | ring 25 | — |
| 11-914 | 4-F-Ph | 2-(α-Me-BnNH)-4-Pym | ring 26 | — |
| 11-915 | 4-F-Ph | 2-(α-Me-BnNH)-4-Pym | ring 27 | — |
| 11-916 | 4-F-Ph | 2-(α-Me-BnNH)-4-Pym | ring 28 | — |
| 11-917 | 4-F-Ph | 2-(α-Me-BnNH)-4-Pym | ring 29 | — |
| 11-918 | 4-F-Ph | 2-(α-Me-BnNH)-4-Pym | ring 30 | — |
| 11-919 | 4-F-Ph | 2-(α-Me-BnNH)-4-Pym | ring 31 | — |
| 11-920 | 4-F-Ph | 2-(α-Me-BnNH)-4-Pym | ring 32 | — |
| 11-921 | 4-F-Ph | 2-(α-Me-BnNH)-4-Pym | ring 33 | — |
| 11-922 | 4-F-Ph | 2-(α-Me-BnNH)-4-Pym | ring 34 | — |
| 11-923 | 4-F-Ph | 2-(α-Me-BnNH)-4-Pym | ring 35 | — |

TABLE 11-continued

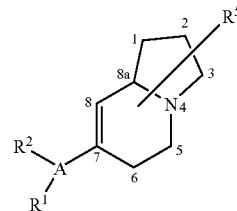

| Compound No. | R¹ | R² | A | R⁵ |
|---|---|---|---|---|
| 11-924 | 4-F-Ph | 2-(α-Me-BnNH)-4-Pym | ring 36 | — |
| 11-925 | 4-F-Ph | 2-(α-Me-BnNH)-4-Pym | ring 37 | — |
| 11-926 | 4-F-Ph | 2-(α-Me-BnNH)-4-Pym | ring 1 | 2-Me |
| 11-927 | 4-F-Ph | 2-(α-Me-BnNH)-4-Pym | ring 2 | 2-Me |
| 11-928 | 4-F-Ph | 2-(α-Me-BnNH)-4-Pym | ring 3 | 2-Me |
| 11-929 | 4-F-Ph | 2-(α-Me-BnNH)-4-Pym | ring 4 | 2-Me |
| 11-930 | 4-F-Ph | 2-(α-Me-BnNH)-4-Pym | ring 5 | 2-Me |
| 11-931 | 4-F-Ph | 2-(α-Me-BnNH)-4-Pym | ring 6 | 2-Me |
| 11-932 | 4-F-Ph | 2-(α-Me-BnNH)-4-Pym | ring 7 | 2-Me |
| 11-933 | 4-F-Ph | 2-(α-Me-BnNH)-4-Pym | ring 8 | 2-Me |
| 11-934 | 4-F-Ph | 2-(α-Me-BnNH)-4-Pym | ring 9 | 2-Me |
| 11-935 | 4-F-Ph | 2-(α-Me-BnNH)-4-Pym | ring 10 | 2-Me |
| 11-936 | 4-F-Ph | 2-(α-Me-BnNH)-4-Pym | ring 11 | 2-Me |
| 11-937 | 4-F-Ph | 2-(α-Me-BnNH)-4-Pym | ring 12 | 2-Me |
| 11-938 | 4-F-Ph | 2-(α-Me-BnNH)-4-Pym | ring 13 | 2-Me |
| 11-939 | 4-F-Ph | 2-(α-Me-BnNH)-4-Pym | ring 14 | 2-Me |
| 11-940 | 4-F-Ph | 2-(α-Me-BnNH)-4-Pym | ring 15 | 2-Me |
| 11-941 | 4-F-Ph | 2-(α-Me-BnNH)-4-Pym | ring 16 | 2-Me |
| 11-942 | 4-F-Ph | 2-(α-Me-BnNH)-4-Pym | ring 17 | 2-Me |
| 11-943 | 4-F-Ph | 2-(α-Me-BnNH)-4-Pym | ring 18 | 2-Me |
| 11-944 | 4-F-Ph | 2-(α-Me-BnNH)-4-Pym | ring 19 | 2-Me |
| 11-945 | 4-F-Ph | 2-(α-Me-BnNH)-4-Pym | ring 20 | 2-Me |
| 11-946 | 4-F-Ph | 2-(α-Me-BnNH)-4-Pym | ring 21 | 2-Me |
| 11-947 | 4-F-Ph | 2-(α-Me-BnNH)-4-Pym | ring 22 | 2-Me |
| 11-948 | 4-F-Ph | 2-(α-Me-BnNH)-4-Pym | ring 23 | 2-Me |
| 11-949 | 4-F-Ph | 2-(α-Me-BnNH)-4-Pym | ring 24 | 2-Me |
| 11-950 | 4-F-Ph | 2-(α-Me-BnNH)-4-Pym | ring 25 | 2-Me |
| 11-951 | 4-F-Ph | 2-(α-Me-BnNH)-4-Pym | ring 26 | 2-Me |
| 11-952 | 4-F-Ph | 2-(α-Me-BnNH)-4-Pym | ring 27 | 2-Me |
| 11-953 | 4-F-Ph | 2-(α-Me-BnNH)-4-Pym | ring 28 | 2-Me |
| 11-954 | 4-F-Ph | 2-(α-Me-BnNH)-4-Pym | ring 29 | 2-Me |
| 11-955 | 4-F-Ph | 2-(α-Me-BnNH)-4-Pym | ring 30 | 2-Me |
| 11-956 | 4-F-Ph | 2-(α-Me-BnNH)-4-Pym | ring 31 | 2-Me |
| 11-957 | 4-F-Ph | 2-(α-Me-BnNH)-4-Pym | ring 32 | 2-Me |
| 11-958 | 4-F-Ph | 2-(α-Me-BnNH)-4-Pym | ring 33 | 2-Me |
| 11-959 | 4-F-Ph | 2-(α-Me-BnNH)-4-Pym | ring 34 | 2-Me |
| 11-960 | 4-F-Ph | 2-(α-Me-BnNH)-4-Pym | ring 35 | 2-Me |
| 11-961 | 4-F-Ph | 2-(α-Me-BnNH)-4-Pym | ring 36 | 2-Me |
| 11-962 | 4-F-Ph | 2-(α-Me-BnNH)-4-Pym | ring 37 | 2-Me |
| 11-963 | 4-F-Ph | 2-(α-Me-BnNH)-4-Pym | ring 1 | 2-OH |
| 11-964 | 4-F-Ph | 2-(α-Me-BnNH)-4-Pym | ring 2 | 2-OH |
| 11-965 | 4-F-Ph | 2-(α-Me-BnNH)-4-Pym | ring 3 | 2-OH |
| 11-966 | 4-F-Ph | 2-(α-Me-BnNH)-4-Pym | ring 4 | 2-OH |
| 11-967 | 4-F-Ph | 2-(α-Me-BnNH)-4-Pym | ring 5 | 2-OH |
| 11-968 | 4-F-Ph | 2-(α-Me-BnNH)-4-Pym | ring 6 | 2-OH |
| 11-969 | 4-F-Ph | 2-(α-Me-BnNH)-4-Pym | ring 7 | 2-OH |
| 11-970 | 4-F-Ph | 2-(α-Me-BnNH)-4-Pym | ring 8 | 2-OH |
| 11-971 | 4-F-Ph | 2-(α-Me-BnNH)-4-Pym | ring 9 | 2-OH |
| 11-972 | 4-F-Ph | 2-(α-Me-BnNH)-4-Pym | ring 10 | 2-OH |
| 11-973 | 4-F-Ph | 2-(α-Me-BnNH)-4-Pym | ring 11 | 2-OH |
| 11-974 | 4-F-Ph | 2-(α-Me-BnNH)-4-Pym | ring 12 | 2-OH |
| 11-975 | 4-F-Ph | 2-(α-Me-BnNH)-4-Pym | ring 13 | 2-OH |
| 11-976 | 4-F-Ph | 2-(α-Me-BnNH)-4-Pym | ring 14 | 2-OH |
| 11-977 | 4-F-Ph | 2-(α-Me-BnNH)-4-Pym | ring 15 | 2-OH |
| 11-978 | 4-F-Ph | 2-(α-Me-BnNH)-4-Pym | ring 16 | 2-OH |
| 11-979 | 4-F-Ph | 2-(α-Me-BnNH)-4-Pym | ring 17 | 2-OH |
| 11-980 | 4-F-Ph | 2-(α-Me-BnNH)-4-Pym | ring 18 | 2-OH |
| 11-981 | 4-F-Ph | 2-(α-Me-BnNH)-4-Pym | ring 19 | 2-OH |
| 11-982 | 4-F-Ph | 2-(α-Me-BnNH)-4-Pym | ring 20 | 2-OH |
| 11-983 | 4-F-Ph | 2-(α-Me-BnNH)-4-Pym | ring 21 | 2-OH |
| 11-984 | 4-F-Ph | 2-(α-Me-BnNH)-4-Pym | ring 22 | 2-OH |
| 11-985 | 4-F-Ph | 2-(α-Me-BnNH)-4-Pym | ring 23 | 2-OH |
| 11-986 | 4-F-Ph | 2-(α-Me-BnNH)-4-Pym | ring 24 | 2-OH |
| 11-987 | 4-F-Ph | 2-(α-Me-BnNH)-4-Pym | ring 25 | 2-OH |
| 11-988 | 4-F-Ph | 2-(α-Me-BnNH)-4-Pym | ring 26 | 2-OH |

TABLE 11-continued

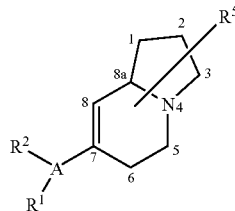

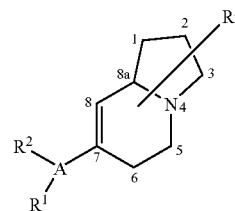

| Compound No. | R¹ | R² | A | R⁵ | Compound No. | R¹ | R² | A | R⁵ |
| --- | --- | --- | --- | --- | --- | --- | --- | --- | --- |
| 11-989 | 4-F-Ph | 2-(α-Me-BnNH)-4-Pym | ring 27 | 2-OH | 11-1054 | 4-F-Ph | 2-(α-Me-BnNH)-4-Pym | ring 18 | 2-F |
| 11-990 | 4-F-Ph | 2-(α-Me-BnNH)-4-Pym | ring 28 | 2-OH | 11-1055 | 4-F-Ph | 2-(α-Me-BnNH)-4-Pym | ring 19 | 2-F |
| 11-991 | 4-F-Ph | 2-(α-Me-BnNH)-4-Pym | ring 29 | 2-OH | 11-1056 | 4-F-Ph | 2-(α-Me-BnNH)-4-Pym | ring 20 | 2-F |
| 11-992 | 4-F-Ph | 2-(α-Me-BnNH)-4-Pym | ring 30 | 2-OH | 11-1057 | 4-F-Ph | 2-(α-Me-BnNH)-4-Pym | ring 21 | 2-F |
| 11-993 | 4-F-Ph | 2-(α-Me-BnNH)-4-Pym | ring 31 | 2-OH | 11-1058 | 4-F-Ph | 2-(α-Me-BnNH)-4-Pym | ring 22 | 2-F |
| 11-994 | 4-F-Ph | 2-(α-Me-BnNH)-4-Pym | ring 32 | 2-OH | 11-1059 | 4-F-Ph | 2-(α-Me-BnNH)-4-Pym | ring 23 | 2-F |
| 11-995 | 4-F-Ph | 2-(α-Me-BnNH)-4-Pym | ring 33 | 2-OH | 11-1060 | 4-F-Ph | 2-(α-Me-BnNH)-4-Pym | ring 24 | 2-F |
| 11-996 | 4-F-Ph | 2-(α-Me-BnNH)-4-Pym | ring 34 | 2-OH | 11-1061 | 4-F-Ph | 2-(α-Me-BnNH)-4-Pym | ring 25 | 2-F |
| 11-997 | 4-F-Ph | 2-(α-Me-BnNH)-4-Pym | ring 35 | 2-OH | 11-1062 | 4-F-Ph | 2-(α-Me-BnNH)-4-Pym | ring 26 | 2-F |
| 11-998 | 4-F-Ph | 2-(α-Me-BnNH)-4-Pym | ring 36 | 2-OH | 11-1063 | 4-F-Ph | 2-(α-Me-BnNH)-4-Pym | ring 27 | 2-F |
| 11-999 | 4-F-Ph | 2-(α-Me-BnNH)-4-Pym | ring 37 | 2-OH | 11-1064 | 4-F-Ph | 2-(α-Me-BnNH)-4-Pym | ring 28 | 2-F |
| 11-1000 | 4-F-Ph | 2-(α-Me-BnNH)-4-Pym | ring 1 | 2-MeO | 11-1065 | 4-F-Ph | 2-(α-Me-BnNH)-4-Pym | ring 29 | 2-F |
| 11-1001 | 4-F-Ph | 2-(α-Me-BnNH)-4-Pym | ring 2 | 2-MeO | 11-1066 | 4-F-Ph | 2-(α-Me-BnNH)-4-Pym | ring 30 | 2-F |
| 11-1002 | 4-F-Ph | 2-(α-Me-BnNH)-4-Pym | ring 3 | 2-MeO | 11-1067 | 4-F-Ph | 2-(α-Me-BnNH)-4-Pym | ring 31 | 2-F |
| 11-1003 | 4-F-Ph | 2-(α-Me-BnNH)-4-Pym | ring 4 | 2-MeO | 11-1068 | 4-F-Ph | 2-(α-Me-BnNH)-4-Pym | ring 32 | 2-F |
| 11-1004 | 4-F-Ph | 2-(α-Me-BnNH)-4-Pym | ring 5 | 2-MeO | 11-1069 | 4-F-Ph | 2-(α-Me-BnNH)-4-Pym | ring 33 | 2-F |
| 11-1005 | 4-F-Ph | 2-(α-Me-BnNH)-4-Pym | ring 6 | 2-MeO | 11-1070 | 4-F-Ph | 2-(α-Me-BnNH)-4-Pym | ring 34 | 2-F |
| 11-1006 | 4-F-Ph | 2-(α-Me-BnNH)-4-Pym | ring 7 | 2-MeO | 11-1071 | 4-F-Ph | 2-(α-Me-BnNH)-4-Pym | ring 35 | 2-F |
| 11-1007 | 4-F-Ph | 2-(α-Me-BnNH)-4-Pym | ring 8 | 2-MeO | 11-1072 | 4-F-Ph | 2-(α-Me-BnNH)-4-Pym | ring 36 | 2-F |
| 11-1008 | 4-F-Ph | 2-(α-Me-BnNH)-4-Pym | ring 9 | 2-MeO | 11-1073 | 4-F-Ph | 2-(α-Me-BnNH)-4-Pym | ring 37 | 2-F |
| 11-1009 | 4-F-Ph | 2-(α-Me-BnNH)-4-Pym | ring 10 | 2-MeO | 11-1074 | 4-F-Ph | 2-(α-Me-BnNH)-4-Pym | ring 1 | 2-Cl |
| 11-1010 | 4-F-Ph | 2-(α-Me-BnNH)-4-Pym | ring 11 | 2-MeO | 11-1075 | 4-F-Ph | 2-(α-Me-BnNH)-4-Pym | ring 2 | 2-Cl |
| 11-1011 | 4-F-Ph | 2-(α-Me-BnNH)-4-Pym | ring 12 | 2-MeO | 11-1076 | 4-F-Ph | 2-(α-Me-BnNH)-4-Pym | ring 3 | 2-Cl |
| 11-1012 | 4-F-Ph | 2-(α-Me-BnNH)-4-Pym | ring 13 | 2-MeO | 11-1077 | 4-F-Ph | 2-(α-Me-BnNH)-4-Pym | ring 4 | 2-Cl |
| 11-1013 | 4-F-Ph | 2-(α-Me-BnNH)-4-Pym | ring 14 | 2-MeO | 11-1078 | 4-F-Ph | 2-(α-Me-BnNH)-4-Pym | ring 5 | 2-Cl |
| 11-1014 | 4-F-Ph | 2-(α-Me-BnNH)-4-Pym | ring 15 | 2-MeO | 11-1079 | 4-F-Ph | 2-(α-Me-BnNH)-4-Pym | ring 6 | 2-Cl |
| 11-1015 | 4-F-Ph | 2-(α-Me-BnNH)-4-Pym | ring 16 | 2-MeO | 11-1080 | 4-F-Ph | 2-(α-Me-BnNH)-4-Pym | ring 7 | 2-Cl |
| 11-1016 | 4-F-Ph | 2-(α-Me-BnNH)-4-Pym | ring 17 | 2-MeO | 11-1081 | 4-F-Ph | 2-(α-Me-BnNH)-4-Pym | ring 8 | 2-Cl |
| 11-1017 | 4-F-Ph | 2-(α-Me-BnNH)-4-Pym | ring 18 | 2-MeO | 11-1082 | 4-F-Ph | 2-(α-Me-BnNH)-4-Pym | ring 9 | 2-Cl |
| 11-1018 | 4-F-Ph | 2-(α-Me-BnNH)-4-Pym | ring 19 | 2-MeO | 11-1083 | 4-F-Ph | 2-(α-Me-BnNH)-4-Pym | ring 10 | 2-Cl |
| 11-1019 | 4-F-Ph | 2-(α-Me-BnNH)-4-Pym | ring 20 | 2-MeO | 11-1084 | 4-F-Ph | 2-(α-Me-BnNH)-4-Pym | ring 11 | 2-Cl |
| 11-1020 | 4-F-Ph | 2-(α-Me-BnNH)-4-Pym | ring 21 | 2-MeO | 11-1085 | 4-F-Ph | 2-(α-Me-BnNH)-4-Pym | ring 12 | 2-Cl |
| 11-1021 | 4-F-Ph | 2-(α-Me-BnNH)-4-Pym | ring 22 | 2-MeO | 11-1086 | 4-F-Ph | 2-(α-Me-BnNH)-4-Pym | ring 13 | 2-Cl |
| 11-1022 | 4-F-Ph | 2-(α-Me-BnNR)-4-Pym | ring 23 | 2-MeO | 11-1087 | 4-F-Ph | 2-(α-Me-BnNH)-4-Pym | ring 14 | 2-Cl |
| 11-1023 | 4-F-Ph | 2-(α-Me-BnNH)-4-Pym | ring 24 | 2-MeO | 11-1088 | 4-F-Ph | 2-(α-Me-BnNH)-4-Pym | ring 15 | 2-Cl |
| 11-1024 | 4-F-Ph | 2-(α-Me-BnNH)-4-Pym | ring 25 | 2-MeO | 11-1089 | 4-F-Ph | 2-(α-Me-BnNH)-4-Pym | ring 16 | 2-Cl |
| 11-1025 | 4-F-Ph | 2-(α-Me-BnNH)-4-Pym | ring 26 | 2-MeO | 11-1090 | 4-F-Ph | 2-(α-Me-BnNH)-4-Pym | ring 17 | 2-Cl |
| 11-1026 | 4-F-Ph | 2-(α-Me-BnNH)-4-Pym | ring 27 | 2-MeO | 11-1091 | 4-F-Ph | 2-(α-Me-BnNH)-4-Pym | ring 18 | 2-Cl |
| 11-1027 | 4-F-Ph | 2-(α-Me-BnNH)-4-Pym | ring 28 | 2-MeO | 11-1092 | 4-F-Ph | 2-(α-Me-BnNH)-4-Pym | ring 19 | 2-Cl |
| 11-1028 | 4-F-Ph | 2-(α-Me-BnNH)-4-Pym | ring 29 | 2-MeO | 11-1093 | 4-F-Ph | 2-(α-Me-BnNH)-4-Pym | ring 20 | 2-Cl |
| 11-1029 | 4-F-Ph | 2-(α-Me-BnNH)-4-Pym | ring 30 | 2-MeO | 11-1094 | 4-F-Ph | 2-(α-Me-BnNH)-4-Pym | ring 21 | 2-Cl |
| 11-1030 | 4-F-Ph | 2-(α-Me-BnNH)-4-Pym | ring 31 | 2-MeO | 11-1095 | 4-F-Ph | 2-(α-Me-BnNH)-4-Pym | ring 22 | 2-Cl |
| 11-1031 | 4-F-Ph | 2-(α-Me-BnNH)-4-Pym | ring 32 | 2-MeO | 11-1096 | 4-F-Ph | 2-(α-Me-BnNH)-4-Pym | ring 23 | 2-Cl |
| 11-1032 | 4-F-Ph | 2-(α-Me-BnNH)-4-Pym | ring 33 | 2-MeO | 11-1097 | 4-F-Ph | 2-(α-Me-BnNH)-4-Pym | ring 24 | 2-Cl |
| 11-1033 | 4-F-Ph | 2-(α-Me-BnNH)-4-Pym | ring 34 | 2-MeO | 11-1098 | 4-F-Ph | 2-(α-Me-BnNH)-4-Pym | ring 25 | 2-Cl |
| 11-1034 | 4-F-Ph | 2-(α-Me-BnNH)-4-Pym | ring 35 | 2-MeO | 11-1099 | 4-F-Ph | 2-(α-Me-BnNH)-4-Pym | ring 26 | 2-Cl |
| 11-1035 | 4-F-Ph | 2-(α-Me-BnNH)-4-Pym | ring 36 | 2-MeO | 11-1100 | 4-F-Ph | 2-(α-Me-BnNH)-4-Pym | ring 27 | 2-Cl |
| 11-1036 | 4-F-Ph | 2-(α-Me-BnNH)-4-Pym | ring 37 | 2-MeO | 11-1101 | 4-F-Ph | 2-(α-Me-BnNH)-4-Pym | ring 28 | 2-Cl |
| 11-1037 | 4-F-Ph | 2-(α-Me-BnNH)-4-Pym | ring 1 | 2-F | 11-1102 | 4-F-Ph | 2-(α-Me-BnNH)-4-Pym | ring 29 | 2-Cl |
| 11-1038 | 4-F-Ph | 2-(α-Me-BnNH)-4-Pym | ring 2 | 2-F | 11-1103 | 4-F-Ph | 2-(α-Me-BnNH)-4-Pym | ring 30 | 2-Cl |
| 11-1039 | 4-F-Ph | 2-(α-Me-BnNH)-4-Pym | ring 3 | 2-F | 11-1104 | 4-F-Ph | 2-(α-Me-BnNH)-4-Pym | ring 31 | 2-Cl |
| 11-1040 | 4-F-Ph | 2-(α-Me-BnNH)-4-Pym | ring 4 | 2-F | 11-1105 | 4-F-Ph | 2-(α-Me-BnNH)-4-Pym | ring 32 | 2-Cl |
| 11-1041 | 4-F-Ph | 2-(α-Me-BnNH)-4-Pym | ring 5 | 2-F | 11-1106 | 4-F-Ph | 2-(α-Me-BnNH)-4-Pym | ring 33 | 2-Cl |
| 11-1042 | 4-F-Ph | 2-(α-Me-BnNH)-4-Pym | ring 6 | 2-F | 11-1107 | 4-F-Ph | 2-(α-Me-BnNH)-4-Pym | ring 34 | 2-Cl |
| 11-1043 | 4-F-Ph | 2-(α-Me-BnNH)-4-Pym | ring 7 | 2-F | 11-1108 | 4-F-Ph | 2-(α-Me-BnNH)-4-Pym | ring 35 | 2-Cl |
| 11-1044 | 4-F-Ph | 2-(α-Me-BnNH)-4-Pym | ring 8 | 2-F | 11-1109 | 4-F-Ph | 2-(α-Me-BnNH)-4-Pym | ring 36 | 2-Cl |
| 11-1045 | 4-F-Ph | 2-(α-Me-BnNH)-4-Pym | ring 9 | 2-F | 11-1110 | 4-F-Ph | 2-(α-Me-BnNH)-4-Pym | ring 37 | 2-Cl |
| 11-1046 | 4-F-Ph | 2-(α-Me-BnNH)-4-Pym | ring 10 | 2-F | 11-1111 | 4-F-Ph | 2-(α-Me-BnNH)-4-Pym | ring 1 | 2,2-diF |
| 11-1047 | 4-F-Ph | 2-(α-Me-BnNH)-4-Pym | ring 11 | 2-F | 11-1112 | 4-F-Ph | 2-(α-Me-BnNH)-4-Pym | ring 2 | 2,2-diF |
| 11-1048 | 4-F-Ph | 2-(α-Me-BnNH)-4-Pym | ring 12 | 2-F | 11-1113 | 4-F-Ph | 2-(α-Me-BnNH)-4-Pym | ring 3 | 2,2-diF |
| 11-1049 | 4-F-Ph | 2-(α-Me-BnNH)-4-Pym | ring 13 | 2-F | 11-1114 | 4-F-Ph | 2-(α-Me-BnNH)-4-Pym | ring 4 | 2,2-diF |
| 11-1050 | 4-F-Ph | 2-(α-Me-BnNH)-4-Pym | ring 14 | 2-F | 11-1115 | 4-F-Ph | 2-(α-Me-BnNH)-4-Pym | ring 5 | 2,2-diF |
| 11-1051 | 4-F-Ph | 2-(α-Me-BnNH)-4-Pym | ring 15 | 2-F | 11-1116 | 4-F-Ph | 2-(α-Me-BnNH)-4-Pym | ring 6 | 2,2-diF |
| 11-1052 | 4-F-Ph | 2-(α-Me-BnNH)-4-Pym | ring 16 | 2-F | 11-1117 | 4-F-Ph | 2-(α-Me-BnNH)-4-Pym | ring 7 | 2,2-diF |
| 11-1053 | 4-F-Ph | 2-(α-Me-BnNH)-4-Pym | ring 17 | 2-F | 11-1118 | 4-F-Ph | 2-(α-Me-BnNH)-4-Pym | ring 8 | 2,2-diF |

TABLE 11-continued

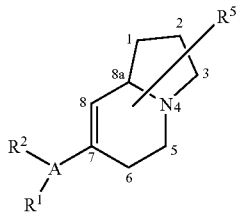

| Compound No. | R¹ | R² | A | R⁵ |
|---|---|---|---|---|
| 11-1119 | 4-F-Ph | 2-(α-Me-BnNH)-4-Pym | ring 9 | 2,2-diF |
| 11-1120 | 4-F-Ph | 2-(α-Me-BnNH)-4-Pym | ring 10 | 2,2-diF |
| 11-1121 | 4-F-Ph | 2-(α-Me-BnNH)-4-Pym | ring 11 | 2,2-diF |
| 11-1122 | 4-F-Ph | 2-(α-Me-BnNH)-4-Pym | ring 12 | 2,2-diF |
| 11-1123 | 4-F-Ph | 2-(α-Me-BnNH)-4-Pym | ring 13 | 2,2-diF |
| 11-1124 | 4-F-Ph | 2-(α-Me-BnNH)-4-Pym | ring 14 | 2,2-diF |
| 11-1125 | 4-F-Ph | 2-(α-Me-BnNH)-4-Pym | ring 15 | 2,2-diF |
| 11-1126 | 4-F-Ph | 2-(α-Me-BnNH)-4-Pym | ring 16 | 2,2-diF |
| 11-1127 | 4-F-Ph | 2-(α-Me-BnNH)-4-Pym | ring 17 | 2,2-diF |
| 11-1128 | 4-F-Ph | 2-(α-Me-BnNH)-4-Pym | ring 18 | 2,2-diF |
| 11-1129 | 4-F-Ph | 2-(α-Me-BnNH)-4-Pym | ring 19 | 2,2-diF |
| 11-1130 | 4-F-Ph | 2-(α-Me-BnNH)-4-Pym | ring 20 | 2,2-diF |
| 11-1131 | 4-F-Ph | 2-(α-Me-BnNH)-4-Pym | ring 21 | 2,2-diF |
| 11-1132 | 4-F-Ph | 2-(α-Me-BnNH)-4-Pym | ring 22 | 2,2-diF |
| 11-1133 | 4-F-Ph | 2-(α-Me-BnNH)-4-Pym | ring 23 | 2,2-diF |
| 11-1134 | 4-F-Ph | 2-(α-Me-BnNH)-4-Pym | ring 24 | 2,2-diF |
| 11-1135 | 4-F-Ph | 2-(α-Me-BnNH)-4-Pym | ring 25 | 2,2-diF |
| 11-1136 | 4-F-Ph | 2-(α-Me-BnNH)-4-Pym | ring 26 | 2,2-diF |
| 11-1137 | 4-F-Ph | 2-(α-Me-BnNH)-4-Pym | ring 27 | 2,2-diF |
| 11-1138 | 4-F-Ph | 2-(α-Me-BnNH)-4-Pym | ring 28 | 2,2-diF |
| 11-1139 | 4-F-Ph | 2-(α-Me-BnNH)-4-Pym | ring 29 | 2,2-diF |
| 11-1140 | 4-F-Ph | 2-(α-Me-BnNH)-4-Pym | ring 30 | 2,2-diF |
| 11-1141 | 4-F-Ph | 2-(α-Me-BnNH)-4-Pym | ring 31 | 2,2-diF |
| 11-1142 | 4-F-Ph | 2-(α-Me-BnNH)-4-Pym | ring 32 | 2,2-diF |
| 11-1143 | 4-F-Ph | 2-(α-Me-BnNH)-4-Pym | ring 33 | 2,2-diF |
| 11-1144 | 4-F-Ph | 2-(α-Me-BnNH)-4-Pym | ring 34 | 2,2-diF |
| 11-1145 | 4-F-Ph | 2-(α-Me-BnNH)-4-Pym | ring 35 | 2,2-diF |
| 11-1146 | 4-F-Ph | 2-(α-Me-BnNH)-4-Pym | ring 36 | 2,2-diF |
| 11-1147 | 4-F-Ph | 2-(α-Me-BnNH)-4-Pym | ring 37 | 2,2-diF |
| 11-1148 | 4-F-Ph | 2-(α-Me-BnNH)-4-Pym | ring 1 | 8-Me |
| 11-1149 | 4-F-Ph | 2-(α-Me-BnNH)-4-Pym | ring 2 | 8-Me |
| 11-1150 | 4-F-Ph | 2-(α-Me-BnNH)-4-Pym | ring 3 | 8-Me |
| 11-1151 | 4-F-Ph | 2-(α-Me-BnNH)-4-Pym | ring 4 | 8-Me |
| 11-1152 | 4-F-Ph | 2-(α-Me-BnNH)-4-Pym | ring 5 | 8-Me |
| 11-1153 | 4-F-Ph | 2-(α-Me-BnNH)-4-Pym | ring 6 | 8-Me |
| 11-1154 | 4-F-Ph | 2-(α-Me-BnNH)-4-Pym | ring 7 | 8-Me |
| 11-1155 | 4-F-Ph | 2-(α-Me-BnNH)-4-Pym | ring 8 | 8-Me |
| 11-1156 | 4-F-Ph | 2-(α-Me-BnNH)-4-Pym | ring 9 | 8-Me |
| 11-1157 | 4-F-Ph | 2-(α-Me-BnNH)-4-Pym | ring 10 | 8-Me |
| 11-1158 | 4-F-Ph | 2-(α-Me-BnNH)-4-Pym | ring 11 | 8-Me |
| 11-1159 | 4-F-Ph | 2-(α-Me-BnNH)-4-Pym | ring 12 | 8-Me |
| 11-1160 | 4-F-Ph | 2-(α-Me-BnNH)-4-Pym | ring 13 | 8-Me |
| 11-1161 | 4-F-Ph | 2-(α-Me-BnNH)-4-Pym | ring 14 | 8-Me |
| 11-1162 | 4-F-Ph | 2-(α-Me-BnNH)-4-Pym | ring 15 | 8-Me |
| 11-1163 | 4-F-Ph | 2-(α-Me-BnNH)-4-Pym | ring 16 | 8-Me |
| 11-1164 | 4-F-Ph | 2-(α-Me-BnNH)-4-Pym | ring 17 | 8-Me |
| 11-1165 | 4-F-Ph | 2-(α-Me-BnNH)-4-Pym | ring 18 | 8-Me |
| 11-1166 | 4-F-Ph | 2-(α-Me-BnNH)-4-Pym | ring 19 | 8-Me |
| 11-1167 | 4-F-Ph | 2-(α-Me-BnNH)-4-Pym | ring 20 | 8-Me |
| 11-1168 | 4-F-Ph | 2-(α-Me-BnNH)-4-Pym | ring 21 | 8-Me |
| 11-1169 | 4-F-Ph | 2-(α-Me-BnNH)-4-Pym | ring 22 | 8-Me |
| 11-1170 | 4-F-Ph | 2-(α-Me-BnNH)-4-Pym | ring 23 | 8-Me |
| 11-1171 | 4-F-Ph | 2-(α-Me-BnNH)-4-Pym | ring 24 | 8-Me |
| 11-1172 | 4-F-Ph | 2-(α-Me-BnNH)-4-Pym | ring 25 | 8-Me |
| 11-1173 | 4-F-Ph | 2-(α-Me-BnNH)-4-Pym | ring 26 | 8-Me |
| 11-1174 | 4-F-Ph | 2-(α-Me-BnNH)-4-Pym | ring 27 | 8-Me |
| 11-1175 | 4-F-Ph | 2-(α-Me-BnNH)-4-Pym | ring 28 | 8-Me |
| 11-1176 | 4-F-Ph | 2-(α-Me-BnNH)-4-Pym | ring 29 | 8-Me |
| 11-1177 | 4-F-Ph | 2-(α-Me-BnNH)-4-Pym | ring 30 | 8-Me |
| 11-1178 | 4-F-Ph | 2-(α-Me-BnNH)-4-Pym | ring 31 | 8-Me |
| 11-1179 | 4-F-Ph | 2-(α-Me-BnNH)-4-Pym | ring 32 | 8-Me |
| 11-1180 | 4-F-Ph | 2-(α-Me-BnNH)-4-Pym | ring 33 | 8-Me |
| 11-1181 | 4-F-Ph | 2-(α-Me-BnNH)-4-Pym | ring 34 | 8-Me |
| 11-1182 | 4-F-Ph | 2-(α-Me-BnNH)-4-Pym | ring 35 | 8-Me |
| 11-1183 | 4-F-Ph | 2-(α-Me-BnNH)-4-Pym | ring 36 | 8-Me |

TABLE 11-continued

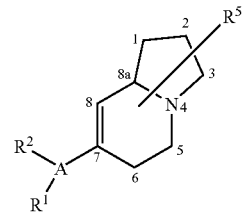

| Compound No. | R¹ | R² | A | R⁵ |
|---|---|---|---|---|
| 11-1184 | 4-F-Ph | 2-(α-Me-BnNH)-4-Pym | ring 37 | 8-Me |

TABLE 12

| Compound No. | R¹ | R² | A | R⁵ |
|---|---|---|---|---|
| 12-1 | 4-F-Ph | 4-Pyr | ring 1 | — |
| 12-2 | 4-F-Ph | 4-Pyr | ring 2 | — |
| 12-3 | 4-F-Ph | 4-Pyr | ring 3 | — |
| 12-4 | 4-F-Ph | 4-Pyr | ring 4 | — |
| 12-5 | 4-F-Ph | 4-Pyr | ring 5 | — |
| 12-6 | 4-F-Ph | 4-Pyr | ring 6 | — |
| 12-7 | 4-F-Ph | 4-Pyr | ring 7 | — |
| 12-8 | 4-F-Ph | 4-Pyr | ring 8 | — |
| 12-9 | 4-F-Ph | 4-Pyr | ring 9 | — |
| 12-10 | 4-F-Ph | 4-Pyr | ring 10 | — |
| 12-11 | 4-F-Ph | 4-Pyr | ring 11 | — |
| 12-12 | 4-F-Ph | 4-Pyr | ring 12 | — |
| 12-13 | 4-F-Ph | 4-Pyr | ring 13 | — |
| 12-14 | 4-F-Ph | 4-Pyr | ring 14 | — |
| 12-15 | 4-F-Ph | 4-Pyr | ring 15 | — |
| 12-16 | 4-F-Ph | 4-Pyr | ring 16 | — |
| 12-17 | 4-F-Ph | 4-Pyr | ring 17 | — |
| 12-18 | 4-F-Ph | 4-Pyr | ring 18 | — |
| 12-19 | 4-F-Ph | 4-Pyr | ring 19 | — |
| 12-20 | 4-F-Ph | 4-Pyr | ring 20 | — |
| 12-21 | 4-F-Ph | 4-Pyr | ring 21 | — |
| 12-22 | 4-F-Ph | 4-Pyr | ring 22 | — |
| 12-23 | 4-F-Ph | 4-Pyr | ring 23 | — |
| 12-24 | 4-F-Ph | 4-Pyr | ring 24 | — |
| 12-25 | 4-F-Ph | 4-Pyr | ring 25 | — |
| 12-26 | 4-F-Ph | 4-Pyr | ring 26 | — |
| 12-27 | 4-F-Ph | 4-Pyr | ring 27 | — |
| 12-28 | 4-F-Ph | 4-Pyr | ring 28 | — |
| 12-29 | 4-F-Ph | 4-Pyr | ring 29 | — |
| 12-30 | 4-F-Ph | 4-Pyr | ring 30 | — |
| 12-31 | 4-F-Ph | 4-Pyr | ring 31 | — |
| 12-32 | 4-F-Ph | 4-Pyr | ring 32 | — |
| 12-33 | 4-F-Ph | 4-Pyr | ring 33 | — |
| 12-34 | 4-F-Ph | 4-Pyr | ring 34 | — |
| 12-35 | 4-F-Ph | 4-Pyr | ring 35 | — |
| 12-36 | 4-F-Ph | 4-Pyr | ring 36 | — |
| 12-37 | 4-F-Ph | 4-Pyr | ring 37 | — |
| 12-38 | 4-F-Ph | 4-Pyr | ring 1 | 2-Me |
| 12-39 | 4-F-Ph | 4-Pyr | ring 2 | 2-Me |
| 12-40 | 4-F-Ph | 4-Pyr | ring 3 | 2-Me |
| 12-41 | 4-F-Ph | 4-Pyr | ring 4 | 2-Me |
| 12-42 | 4-F-Ph | 4-Pyr | ring 5 | 2-Me |
| 12-43 | 4-F-Ph | 4-Pyr | ring 6 | 2-Me |
| 12-44 | 4-F-Ph | 4-Pyr | ring 7 | 2-Me |
| 12-45 | 4-F-Ph | 4-Pyr | ring 8 | 2-Me |
| 12-46 | 4-F-Ph | 4-Pyr | ring 9 | 2-Me |
| 12-47 | 4-F-Ph | 4-Pyr | ring 10 | 2-Me |

TABLE 12-continued

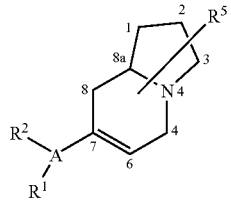

| Compound No. | R¹ | R² | A | R⁵ |
|---|---|---|---|---|
| 12-48 | 4-F-Ph | 4-Pyr | ring 11 | 2-Me |
| 12-49 | 4-F-Ph | 4-Pyr | ring 12 | 2-Me |
| 12-50 | 4-F-Ph | 4-Pyr | ring 13 | 2-Me |
| 12-51 | 4-F-Ph | 4-Pyr | ring 14 | 2-Me |
| 12-52 | 4-F-Ph | 4-Pyr | ring 15 | 2-Me |
| 12-53 | 4-F-Ph | 4-Pyr | ring 16 | 2-Me |
| 12-54 | 4-F-Ph | 4-Pyr | ring 17 | 2-Me |
| 12-55 | 4-F-Ph | 4-Pyr | ring 18 | 2-Me |
| 12-56 | 4-F-Ph | 4-Pyr | ring 19 | 2-Me |
| 12-57 | 4-F-Ph | 4-Pyr | ring 20 | 2-Me |
| 12-58 | 4-F-Ph | 4-Pyr | ring 21 | 2-Me |
| 12-59 | 4-F-Ph | 4-Pyr | ring 22 | 2-Me |
| 12-60 | 4-F-Ph | 4-Pyr | ring 23 | 2-Me |
| 12-61 | 4-F-Ph | 4-Pyr | ring 24 | 2-Me |
| 12-62 | 4-F-Ph | 4-Pyr | ring 25 | 2-Me |
| 12-63 | 4-F-Ph | 4-Pyr | ring 26 | 2-Me |
| 12-64 | 4-F-Ph | 4-Pyr | ring 27 | 2-Me |
| 12-65 | 4-F-Ph | 4-Pyr | ring 28 | 2-Me |
| 12-66 | 4-F-Ph | 4-Pyr | ring 29 | 2-Me |
| 12-67 | 4-F-Ph | 4-Pyr | ring 30 | 2-Me |
| 12-68 | 4-F-Ph | 4-Pyr | ring 31 | 2-Me |
| 12-69 | 4-F-Ph | 4-Pyr | ring 32 | 2-Me |
| 12-70 | 4-F-Ph | 4-Pyr | ring 33 | 2-Me |
| 12-71 | 4-F-Ph | 4-Pyr | ring 34 | 2-Me |
| 12-72 | 4-F-Ph | 4-Pyr | ring 35 | 2-Me |
| 12-73 | 4-F-Ph | 4-Pyr | ring 36 | 2-Me |
| 12-74 | 4-F-Ph | 4-Pyr | ring 37 | 2-Me |
| 12-75 | 4-F-Ph | 4-Pyr | ring 1 | 2-OH |
| 12-76 | 4-F-Ph | 4-Pyr | ring 2 | 2-OH |
| 12-77 | 4-F-Ph | 4-Pyr | ring 3 | 2-OH |
| 12-78 | 4-F-Ph | 4-Pyr | ring 4 | 2-OH |
| 12-79 | 4-F-Ph | 4-Pyr | ring 5 | 2-OH |
| 12-80 | 4-F-Ph | 4-Pyr | ring 6 | 2-OH |
| 12-81 | 4-F-Ph | 4-Pyr | ring 7 | 2-OH |
| 12-82 | 4-F-Ph | 4-Pyr | ring 8 | 2-OH |
| 12-83 | 4-F-Ph | 4-Pyr | ring 9 | 2-OH |
| 12-84 | 4-F-Ph | 4-Pyr | ring 10 | 2-OH |
| 12-85 | 4-F-Ph | 4-Pyr | ring 11 | 2-OH |
| 12-86 | 4-F-Ph | 4-Pyr | ring 12 | 2-OH |
| 12-87 | 4-F-Ph | 4-Pyr | ring 13 | 2-OH |
| 12-88 | 4-F-Ph | 4-Pyr | ring 14 | 2-OH |
| 12-89 | 4-F-Ph | 4-Pyr | ring 15 | 2-OH |
| 12-90 | 4-F-Ph | 4-Pyr | ring 16 | 2-OH |
| 12-91 | 4-F-Ph | 4-Pyr | ring 17 | 2-OH |
| 12-92 | 4-F-Ph | 4-Pyr | ring 18 | 2-OH |
| 12-93 | 4-F-Ph | 4-Pyr | ring 19 | 2-OH |
| 12-94 | 4-F-Ph | 4-Pyr | ring 20 | 2-OH |
| 12-95 | 4-F-Ph | 4-Pyr | ring 21 | 2-OH |
| 12-96 | 4-F-Ph | 4-Pyr | ring 22 | 2-OH |
| 12-97 | 4-F-Ph | 4-Pyr | ring 23 | 2-OH |
| 12-98 | 4-F-Ph | 4-Pyr | ring 24 | 2-OH |
| 12-99 | 4-F-Ph | 4-Pyr | ring 25 | 2-OH |
| 12-100 | 4-F-Ph | 4-Pyr | ring 26 | 2-OH |
| 12-101 | 4-F-Ph | 4-Pyr | ring 27 | 2-OH |
| 12-102 | 4-F-Ph | 4-Pyr | ring 28 | 2-OH |
| 12-103 | 4-F-Ph | 4-Pyr | ring 29 | 2-OH |
| 12-104 | 4-F-Ph | 4-Pyr | ring 30 | 2-OH |
| 12-105 | 4-F-Ph | 4-Pyr | ring 31 | 2-OH |
| 12-106 | 4-F-Ph | 4-Pyr | ring 32 | 2-OH |
| 12-107 | 4-F-Ph | 4-Pyr | ring 33 | 2-OH |
| 12-108 | 4-F-Ph | 4-Pyr | ring 34 | 2-OH |
| 12-109 | 4-F-Ph | 4-Pyr | ring 35 | 2-OH |
| 12-110 | 4-F-Ph | 4-Pyr | ring 36 | 2-OH |
| 12-111 | 4-F-Ph | 4-Pyr | ring 37 | 2-OH |
| 12-112 | 4-F-Ph | 4-Pyr | ring 1 | 2-MeO |
| 12-113 | 4-F-Ph | 4-Pyr | ring 2 | 2-MeO |

TABLE 12-continued

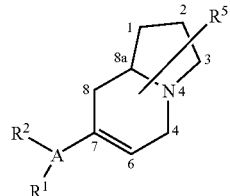

| Compound No. | R¹ | R² | A | R⁵ |
|---|---|---|---|---|
| 12-114 | 4-F-Ph | 4-Pyr | ring 3 | 2-MeO |
| 12-115 | 4-F-Ph | 4-Pyr | ring 4 | 2-MeO |
| 12-116 | 4-F-Ph | 4-Pyr | ring 5 | 2-MeO |
| 12-117 | 4-F-Ph | 4-Pyr | ring 6 | 2-MeO |
| 12-118 | 4-F-Ph | 4-Pyr | ring 7 | 2-MeO |
| 12-119 | 4-F-Ph | 4-Pyr | ring 8 | 2-MeO |
| 12-120 | 4-F-Ph | 4-Pyr | ring 9 | 2-MeO |
| 12-121 | 4-F-Ph | 4-Pyr | ring 10 | 2-MeO |
| 12-122 | 4-F-Ph | 4-Pyr | ring 11 | 2-MeO |
| 12-123 | 4-F-Ph | 4-Pyr | ring 12 | 2-MeO |
| 12-124 | 4-F-Ph | 4-Pyr | ring 13 | 2-MeO |
| 12-125 | 4-F-Ph | 4-Pyr | ring 14 | 2-MeO |
| 12-126 | 4-F-Ph | 4-Pyr | ring 15 | 2-MeO |
| 12-127 | 4-F-Ph | 4-Pyr | ring 16 | 2-MeO |
| 12-128 | 4-F-Ph | 4-Pyr | ring 17 | 2-MeO |
| 12-129 | 4-F-Ph | 4-Pyr | ring 18 | 2-MeO |
| 12-130 | 4-F-Ph | 4-Pyr | ring 19 | 2-MeO |
| 12-131 | 4-F-Ph | 4-Pyr | ring 20 | 2-MeO |
| 12-132 | 4-F-Ph | 4-Pyr | ring 21 | 2-MeO |
| 12-133 | 4-F-Ph | 4-Pyr | ring 22 | 2-MeO |
| 12-134 | 4-F-Ph | 4-Pyr | ring 23 | 2-MeO |
| 12-135 | 4-F-Ph | 4-Pyr | ring 24 | 2-MeO |
| 12-136 | 4-F-Ph | 4-Pyr | ring 25 | 2-MeO |
| 12-137 | 4-F-Ph | 4-Pyr | ring 26 | 2-MeO |
| 12-138 | 4-F-Ph | 4-Pyr | ring 27 | 2-MeO |
| 12-139 | 4-F-Ph | 4-Pyr | ring 28 | 2-MeO |
| 12-140 | 4-F-Ph | 4-Pyr | ring 29 | 2-MeO |
| 12-141 | 4-F-Ph | 4-Pyr | ring 30 | 2-MeO |
| 12-142 | 4-F-Ph | 4-Pyr | ring 31 | 2-MeO |
| 12-143 | 4-F-Ph | 4-Pyr | ring 32 | 2-MeO |
| 12-144 | 4-F-Ph | 4-Pyr | ring 33 | 2-MeO |
| 12-145 | 4-F-Ph | 4-Pyr | ring 34 | 2-MeO |
| 12-146 | 4-F-Ph | 4-Pyr | ring 35 | 2-MeO |
| 12-147 | 4-F-Ph | 4-Pyr | ring 36 | 2-MeO |
| 12-148 | 4-F-Ph | 4-Pyr | ring 37 | 2-MeO |
| 12-149 | 4-F-Ph | 4-Pyr | ring 1 | 2-F |
| 12-150 | 4-F-Ph | 4-Pyr | ring 2 | 2-F |
| 12-151 | 4-F-Ph | 4-Pyr | ring 3 | 2-F |
| 12-152 | 4-F-Ph | 4-Pyr | ring 4 | 2-F |
| 12-153 | 4-F-Ph | 4-Pyr | ring 5 | 2-F |
| 12-154 | 4-F-Ph | 4-Pyr | ring 6 | 2-F |
| 12-155 | 4-F-Ph | 4-Pyr | ring 7 | 2-F |
| 12-156 | 4-F-Ph | 4-Pyr | ring 8 | 2-F |
| 12-157 | 4-F-Ph | 4-Pyr | ring 9 | 2-F |
| 12-158 | 4-F-Ph | 4-Pyr | ring 10 | 2-F |
| 12-159 | 4-F-Ph | 4-Pyr | ring 11 | 2-F |
| 12-160 | 4-F-Ph | 4-Pyr | ring 12 | 2-F |
| 12-161 | 4-F-Ph | 4-Pyr | ring 13 | 2-F |
| 12-162 | 4-F-Ph | 4-Pyr | ring 14 | 2-F |
| 12-163 | 4-F-Ph | 4-Pyr | ring 15 | 2-F |
| 12-164 | 4-F-Ph | 4-Pyr | ring 16 | 2-F |
| 12-165 | 4-F-Ph | 4-Pyr | ring 17 | 2-F |
| 12-166 | 4-F-Ph | 4-Pyr | ring 18 | 2-F |
| 12-167 | 4-F-Ph | 4-Pyr | ring 19 | 2-F |
| 12-168 | 4-F-Ph | 4-Pyr | ring 20 | 2-F |
| 12-169 | 4-F-Ph | 4-Pyr | ring 21 | 2-F |
| 12-170 | 4-F-Ph | 4-Pyr | ring 22 | 2-F |
| 12-171 | 4-F-Ph | 4-Pyr | ring 23 | 2-F |
| 12-172 | 4-F-Ph | 4-Pyr | ring 24 | 2-F |
| 12-173 | 4-F-Ph | 4-Pyr | ring 25 | 2-F |
| 12-174 | 4-F-Ph | 4-Pyr | ring 26 | 2-F |
| 12-175 | 4-F-Ph | 4-Pyr | ring 27 | 2-F |
| 12-176 | 4-F-Ph | 4-Pyr | ring 28 | 2-F |
| 12-177 | 4-F-Ph | 4-Pyr | ring 29 | 2-F |
| 12-178 | 4-F-Ph | 4-Pyr | ring 30 | 2-F |
| 12-179 | 4-F-Ph | 4-Pyr | ring 31 | 2-F |

TABLE 12-continued

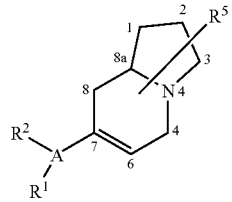

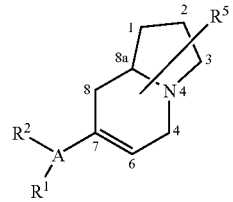

| Compound No. | $R^1$ | $R^2$ | A | $R^5$ |
|---|---|---|---|---|
| 12-180 | 4-F-Ph | 4-Pyr | ring 32 | 2-F |
| 12-181 | 4-F-Ph | 4-Pyr | ring 33 | 2-F |
| 12-182 | 4-F-Ph | 4-Pyr | ring 34 | 2-F |
| 12-183 | 4-F-Ph | 4-Pyr | ring 35 | 2-F |
| 12-184 | 4-F-Ph | 4-Pyr | ring 36 | 2-F |
| 12-185 | 4-F-Ph | 4-Pyr | ring 37 | 2-F |
| 12-186 | 4-F-Ph | 4-Pyr | ring 1 | 2-Cl |
| 12-187 | 4-F-Ph | 4-Pyr | ring 2 | 2-Cl |
| 12-188 | 4-F-Ph | 4-Pyr | ring 3 | 2-Cl |
| 12-189 | 4-F-Ph | 4-Pyr | ring 4 | 2-Cl |
| 12-190 | 4-F-Ph | 4-Pyr | ring 5 | 2-Cl |
| 12-191 | 4-F-Ph | 4-Pyr | ring 6 | 2-Cl |
| 12-192 | 4-F-Ph | 4-Pyr | ring 7 | 2-Cl |
| 12-193 | 4-F-Ph | 4-Pyr | ring 8 | 2-Cl |
| 12-194 | 4-F-Ph | 4-Pyr | ring 9 | 2-Cl |
| 12-195 | 4-F-Ph | 4-Pyr | ring 10 | 2-Cl |
| 12-196 | 4-F-Ph | 4-Pyr | ring 11 | 2-Cl |
| 12-197 | 4-F-Ph | 4-Pyr | ring 12 | 2-Cl |
| 12-198 | 4-F-Ph | 4-Pyr | ring 13 | 2-Cl |
| 12-199 | 4-F-Ph | 4-Pyr | ring 14 | 2-Cl |
| 12-200 | 4-F-Ph | 4-Pyr | ring 15 | 2-Cl |
| 12-201 | 4-F-Ph | 4-Pyr | ring 16 | 2-Cl |
| 12-202 | 4-F-Ph | 4-Pyr | ring 17 | 2-Cl |
| 12-203 | 4-F-Ph | 4-Pyr | ring 18 | 2-Cl |
| 12-204 | 4-F-Ph | 4-Pyr | ring 19 | 2-Cl |
| 12-205 | 4-F-Ph | 4-Pyr | ring 20 | 2-Cl |
| 12-206 | 4-F-Ph | 4-Pyr | ring 21 | 2-Cl |
| 12-207 | 4-F-Ph | 4-Pyr | ring 22 | 2-Cl |
| 12-208 | 4-F-Ph | 4-Pyr | ring 23 | 2-Cl |
| 12-209 | 4-F-Ph | 4-Pyr | ring 24 | 2-Cl |
| 12-210 | 4-F-Ph | 4-Pyr | ring 25 | 2-Cl |
| 12-211 | 4-F-Ph | 4-Pyr | ring 26 | 2-Cl |
| 12-212 | 4-F-Ph | 4-Pyr | ring 27 | 2-Cl |
| 12-213 | 4-F-Ph | 4-Pyr | ring 28 | 2-Cl |
| 12-214 | 4-F-Ph | 4-Pyr | ring 29 | 2-Cl |
| 12-215 | 4-F-Ph | 4-Pyr | ring 30 | 2-Cl |
| 12-216 | 4-F-Ph | 4-Pyr | ring 31 | 2-Cl |
| 12-217 | 4-F-Ph | 4-Pyr | ring 32 | 2-Cl |
| 12-218 | 4-F-Ph | 4-Pyr | ring 33 | 2-Cl |
| 12-219 | 4-F-Ph | 4-Pyr | ring 34 | 2-Cl |
| 12-220 | 4-F-Ph | 4-Pyr | ring 35 | 2-Cl |
| 12-221 | 4-F-Ph | 4-Pyr | ring 36 | 2-Cl |
| 12-222 | 4-F-Ph | 4-Pyr | ring 37 | 2-Cl |
| 12-223 | 4-F-Ph | 4-Pyr | ring 1 | 2,2-diF |
| 12-224 | 4-F-Ph | 4-Pyr | ring 2 | 2,2-diF |
| 12-225 | 4-F-Ph | 4-Pyr | ring 3 | 2,2-diF |
| 12-226 | 4-F-Ph | 4-Pyr | ring 4 | 2,2-diF |
| 12-227 | 4-F-Ph | 4-Pyr | ring 5 | 2,2-diF |
| 12-228 | 4-F-Ph | 4-Pyr | ring 6 | 2,2-diF |
| 12-229 | 4-F-Ph | 4-Pyr | ring 7 | 2,2-diF |
| 12-230 | 4-F-Ph | 4-Pyr | ring 8 | 2,2-diF |
| 12-231 | 4-F-Ph | 4-Pyr | ring 9 | 2,2-diF |
| 12-232 | 4-F-Ph | 4-Pyr | ring 10 | 2,2-diF |
| 12-233 | 4-F-Ph | 4-Pyr | ring 11 | 2,2-diF |
| 12-234 | 4-F-Ph | 4-Pyr | ring 12 | 2,2-diF |
| 12-235 | 4-F-Ph | 4-Pyr | ring 13 | 2,2-diF |
| 12-236 | 4-F-Ph | 4-Pyr | ring 14 | 2,2-diF |
| 12-237 | 4-F-Ph | 4-Pyr | ring 15 | 2,2-diF |
| 12-238 | 4-F-Ph | 4-Pyr | ring 16 | 2,2-diF |
| 12-239 | 4-F-Ph | 4-Pyr | ring 17 | 2,2-diF |
| 12-240 | 4-F-Ph | 4-Pyr | ring 18 | 2,2-diF |
| 12-241 | 4-F-Ph | 4-Pyr | ring 19 | 2,2-diF |
| 12-242 | 4-F-Ph | 4-Pyr | ring 20 | 2,2-diF |
| 12-243 | 4-F-Ph | 4-Pyr | ring 21 | 2,2-diF |
| 12-244 | 4-F-Ph | 4-Pyr | ring 22 | 2,2-diF |
| 12-245 | 4-F-Ph | 4-Pyr | ring 23 | 2,2-diF |
| 12-246 | 4-F-Ph | 4-Pyr | ring 24 | 2,2-diF |
| 12-247 | 4-F-Ph | 4-Pyr | ring 25 | 2,2-diF |
| 12-248 | 4-F-Ph | 4-Pyr | ring 26 | 2,2-diF |
| 12-249 | 4-F-Ph | 4-Pyr | ring 27 | 2,2-diF |
| 12-250 | 4-F-Ph | 4-Pyr | ring 28 | 2,2-diF |
| 12-251 | 4-F-Ph | 4-Pyr | ring 29 | 2,2-diF |
| 12-252 | 4-F-Ph | 4-Pyr | ring 30 | 2,2-diF |
| 12-253 | 4-F-Ph | 4-Pyr | ring 31 | 2,2-diF |
| 12-254 | 4-F-Ph | 4-Pyr | ring 32 | 2,2-diF |
| 12-255 | 4-F-Ph | 4-Pyr | ring 33 | 2,2-diF |
| 12-256 | 4-F-Ph | 4-Pyr | ring 34 | 2,2-diF |
| 12-257 | 4-F-Ph | 4-Pyr | ring 35 | 2,2-diF |
| 12-258 | 4-F-Ph | 4-Pyr | ring 36 | 2,2-diF |
| 12-259 | 4-F-Ph | 4-Pyr | ring 37 | 2,2-diF |
| 12-260 | 4-F-Ph | 4-Pyr | ring 1 | 8-Me |
| 12-261 | 4-F-Ph | 4-Pyr | ring 2 | 8-Me |
| 12-262 | 4-F-Ph | 4-Pyr | ring 3 | 8-Me |
| 12-263 | 4-F-Ph | 4-Pyr | ring 4 | 8-Me |
| 12-264 | 4-F-Ph | 4-Pyr | ring 5 | 8-Me |
| 12-265 | 4-F-Ph | 4-Pyr | ring 6 | 8-Me |
| 12-266 | 4-F-Ph | 4-Pyr | ring 7 | 8-Me |
| 12-267 | 4-F-Ph | 4-Pyr | ring 8 | 8-Me |
| 12-268 | 4-F-Ph | 4-Pyr | ring 9 | 8-Me |
| 12-269 | 4-F-Ph | 4-Pyr | ring 10 | 8-Me |
| 12-270 | 4-F-Ph | 4-Pyr | ring 11 | 8-Me |
| 12-271 | 4-F-Ph | 4-Pyr | ring 12 | 8-Me |
| 12-272 | 4-F-Ph | 4-Pyr | ring 13 | 8-Me |
| 12-273 | 4-F-Ph | 4-Pyr | ring 14 | 8-Me |
| 12-274 | 4-F-Ph | 4-Pyr | ring 15 | 8-Me |
| 12-275 | 4-F-Ph | 4-Pyr | ring 16 | 8-Me |
| 12-276 | 4-F-Ph | 4-Pyr | ring 17 | 8-Me |
| 12-277 | 4-F-Ph | 4-Pyr | ring 18 | 8-Me |
| 12-278 | 4-F-Ph | 4-Pyr | ring 19 | 8-Me |
| 12-279 | 4-F-Ph | 4-Pyr | ring 20 | 8-Me |
| 12-280 | 4-F-Ph | 4-Pyr | ring 21 | 8-Me |
| 12-281 | 4-F-Ph | 4-Pyr | ring 22 | 8-Me |
| 12-282 | 4-F-Ph | 4-Pyr | ring 23 | 8-Me |
| 12-283 | 4-F-Ph | 4-Pyr | ring 24 | 8-Me |
| 12-284 | 4-F-Ph | 4-Pyr | ring 25 | 8-Me |
| 12-285 | 4-F-Ph | 4-Pyr | ring 26 | 8-Me |
| 12-286 | 4-F-Ph | 4-Pyr | ring 27 | 8-Me |
| 12-287 | 4-F-Ph | 4-Pyr | ring 28 | 8-Me |
| 12-288 | 4-F-Ph | 4-Pyr | ring 29 | 8-Me |
| 12-289 | 4-F-Ph | 4-Pyr | ring 30 | 8-Me |
| 12-290 | 4-F-Ph | 4-Pyr | ring 31 | 8-Me |
| 12-291 | 4-F-Ph | 4-Pyr | ring 32 | 8-Me |
| 12-292 | 4-F-Ph | 4-Pyr | ring 33 | 8-Me |
| 12-293 | 4-F-Ph | 4-Pyr | ring 34 | 8-Me |
| 12-294 | 4-F-Ph | 4-Pyr | ring 35 | 8-Me |
| 12-295 | 4-F-Ph | 4-Pyr | ring 36 | 8-Me |
| 12-296 | 4-F-Ph | 4-Pyr | ring 37 | 8-Me |
| 12-297 | 4-F-Ph | 2-$NH_2$-4-Pym | ring 1 | — |
| 12-298 | 4-F-Ph | 2-$NH_2$-4-Pym | ring 2 | — |
| 12-299 | 4-F-Ph | 2-$NH_2$-4-Pym | ring 3 | — |
| 12-300 | 4-F-Ph | 2-$NH_2$-4-Pym | ring 4 | — |
| 12-301 | 4-F-Ph | 2-$NH_2$-4-Pym | ring 5 | — |
| 12-302 | 4-F-Ph | 2-$NH_2$-4-Pym | ring 6 | — |
| 12-303 | 4-F-Ph | 2-$NH_2$-4-Pym | ring 7 | — |
| 12-304 | 4-F-Ph | 2-$NH_2$-4-Pym | ring 8 | — |
| 12-305 | 4-F-Ph | 2-$NH_2$-4-Pym | ring 9 | — |
| 12-306 | 4-F-Ph | 2-$NH_2$-4-Pym | ring 10 | — |
| 12-307 | 4-F-Ph | 2-$NH_2$-4-Pym | ring 11 | — |
| 12-308 | 4-F-Ph | 2-$NH_2$-4-Pym | ring 12 | — |
| 12-309 | 4-F-Ph | 2-$NH_2$-4-Pym | ring 13 | — |
| 12-310 | 4-F-Ph | 2-$NH_2$-4-Pym | ring 14 | — |
| 12-311 | 4-F-Ph | 2-$NH_2$-4-Pym | ring 15 | — |

TABLE 12-continued

[Structure: bicyclic ring system with positions 1, 2, 3, 4, 6, 7, 8, 8a, N4, with R⁵ at position 2/3, R² and R¹ on A at position 7]

| Compound No. | R¹ | R² | A | R⁵ |
|---|---|---|---|---|
| 12-312 | 4-F-Ph | 2-NH₂-4-Pym | ring 16 | — |
| 12-313 | 4-F-Ph | 2-NH₂-4-Pym | ring 17 | — |
| 12-314 | 4-F-Ph | 2-NH₂-4-Pym | ring 18 | — |
| 12-315 | 4-F-Ph | 2-NH₂-4-Pym | ring 19 | — |
| 12-316 | 4-F-Ph | 2-NH₂-4-Pym | ring 20 | — |
| 12-317 | 4-F-Ph | 2-NH₂-4-Pym | ring 21 | — |
| 12-318 | 4-F-Ph | 2-NH₂-4-Pym | ring 22 | — |
| 12-319 | 4-F-Ph | 2-NH₂-4-Pym | ring 23 | — |
| 12-320 | 4-F-Ph | 2-NH₂-4-Pym | ring 24 | — |
| 12-321 | 4-F-Ph | 2-NH₂-4-Pym | ring 25 | — |
| 12-322 | 4-F-Ph | 2-NH₂-4-Pym | ring 26 | — |
| 12-323 | 4-F-Ph | 2-NH₂-4-Pym | ring 27 | — |
| 12-324 | 4-F-Ph | 2-NH₂-4-Pym | ring 28 | — |
| 12-325 | 4-F-Ph | 2-NH₂-4-Pym | ring 29 | — |
| 12-326 | 4-F-Ph | 2-NH₂-4-Pym | ring 30 | — |
| 12-327 | 4-F-Ph | 2-NH₂-4-Pym | ring 31 | — |
| 12-328 | 4-F-Ph | 2-NH₂-4-Pym | ring 32 | — |
| 12-329 | 4-F-Ph | 2-NH₂-4-Pym | ring 33 | — |
| 12-330 | 4-F-Ph | 2-NH₂-4-Pym | ring 34 | — |
| 12-331 | 4-F-Ph | 2-NH₂-4-Pym | ring 35 | — |
| 12-332 | 4-F-Ph | 2-NH₂-4-Pym | ring 36 | — |
| 12-333 | 4-F-Ph | 2-NH₂-4-Pym | ring 37 | — |
| 12-334 | 4-F-Ph | 2-NH₂-4-Pym | ring 1 | 2-Me |
| 12-335 | 4-F-Ph | 2-NH₂-4-Pym | ring 2 | 2-Me |
| 12-336 | 4-F-Ph | 2-NH₂-4-Pym | ring 3 | 2-Me |
| 12-337 | 4-F-Ph | 2-NH₂-4-Pym | ring 4 | 2-Me |
| 12-338 | 4-F-Ph | 2-NH₂-4-Pym | ring 5 | 2-Me |
| 12-339 | 4-F-Ph | 2-NH₂-4-Pym | ring 6 | 2-Me |
| 12-340 | 4-F-Ph | 2-NH₂-4-Pym | ring 7 | 2-Me |
| 12-341 | 4-F-Ph | 2-NH₂-4-Pym | ring 8 | 2-Me |
| 12-342 | 4-F-Ph | 2-NH₂-4-Pym | ring 9 | 2-Me |
| 12-343 | 4-F-Ph | 2-NH₂-4-Pym | ring 10 | 2-Me |
| 12-344 | 4-F-Ph | 2-NH₂-4-Pym | ring 11 | 2-Me |
| 12-345 | 4-F-Ph | 2-NH₂-4-Pym | ring 12 | 2-Me |
| 12-346 | 4-F-Ph | 2-NH₂-4-Pym | ring 13 | 2-Me |
| 12-347 | 4-F-Ph | 2-NH₂-4-Pym | ring 14 | 2-Me |
| 12-348 | 4-F-Ph | 2-NH₂-4-Pym | ring 15 | 2-Me |
| 12-349 | 4-F-Ph | 2-NH₂-4-Pym | ring 16 | 2-Me |
| 12-350 | 4-F-Ph | 2-NH₂-4-Pym | ring 17 | 2-Me |
| 12-351 | 4-F-Ph | 2-NH₂-4-Pym | ring 18 | 2-Me |
| 12-352 | 4-F-Ph | 2-NH₂-4-Pym | ring 19 | 2-Me |
| 12-353 | 4-F-Ph | 2-NH₂-4-Pym | ring 20 | 2-Me |
| 12-354 | 4-F-Ph | 2-NH₂-4-Pym | ring 21 | 2-Me |
| 12-355 | 4-F-Ph | 2-NH₂-4-Pym | ring 22 | 2-Me |
| 12-356 | 4-F-Ph | 2-NH₂-4-Pym | ring 23 | 2-Me |
| 12-357 | 4-F-Ph | 2-NH₂-4-Pym | ring 24 | 2-Me |
| 12-358 | 4-F-Ph | 2-NH₂-4-Pym | ring 25 | 2-Me |
| 12-359 | 4-F-Ph | 2-NH₂-4-Pym | ring 26 | 2-Me |
| 12-360 | 4-F-Ph | 2-NH₂-4-Pym | ring 27 | 2-Me |
| 12-361 | 4-F-Ph | 2-NH₂-4-Pym | ring 28 | 2-Me |
| 12-362 | 4-F-Ph | 2-NH₂-4-Pym | ring 29 | 2-Me |
| 12-363 | 4-F-Ph | 2-NH₂-4-Pym | ring 30 | 2-Me |
| 12-364 | 4-F-Ph | 2-NH₂-4-Pym | ring 31 | 2-Me |
| 12-365 | 4-F-Ph | 2-NH₂-4-Pym | ring 32 | 2-Me |
| 12-366 | 4-F-Ph | 2-NH₂-4-Pym | ring 33 | 2-Me |
| 12-367 | 4-F-Ph | 2-NH₂-4-Pym | ring 34 | 2-Me |
| 12-368 | 4-F-Ph | 2-NH₂-4-Pym | ring 35 | 2-Me |
| 12-369 | 4-F-Ph | 2-NH₂-4-Pym | ring 36 | 2-Me |
| 12-370 | 4-F-Ph | 2-NH₂-4-Pym | ring 37 | 2-Me |
| 12-371 | 4-F-Ph | 2-NH₂-4-Pym | ring 1 | 2-OH |
| 12-372 | 4-F-Ph | 2-NH₂-4-Pym | ring 2 | 2-OH |
| 12-373 | 4-F-Ph | 2-NH₂-4-Pym | ring 3 | 2-OH |
| 12-374 | 4-F-Ph | 2-NH₂-4-Pym | ring 4 | 2-OH |
| 12-375 | 4-F-Ph | 2-NH₂-4-Pym | ring 5 | 2-OH |
| 12-376 | 4-F-Ph | 2-NH₂-4-Pym | ring 6 | 2-OH |
| 12-377 | 4-F-Ph | 2-NH₂-4-Pym | ring 7 | 2-OH |
| 12-378 | 4-F-Ph | 2-NH₂-4-Pym | ring 8 | 2-OH |
| 12-379 | 4-F-Ph | 2-NH₂-4-Pym | ring 9 | 2-OH |
| 12-380 | 4-F-Ph | 2-NH₂-4-Pym | ring 10 | 2-OH |
| 12-381 | 4-F-Ph | 2-NH₂-4-Pym | ring 11 | 2-OH |
| 12-382 | 4-F-Ph | 2-NH₂-4-Pym | ring 12 | 2-OH |
| 12-383 | 4-F-Ph | 2-NH₂-4-Pym | ring 13 | 2-OH |
| 12-384 | 4-F-Ph | 2-NH₂-4-Pym | ring 14 | 2-OH |
| 12-385 | 4-F-Ph | 2-NH₂-4-Pym | ring 15 | 2-OH |
| 12-386 | 4-F-Ph | 2-NH₂-4-Pym | ring 16 | 2-OH |
| 12-387 | 4-F-Ph | 2-NH₂-4-Pym | ring 17 | 2-OH |
| 12-388 | 4-F-Ph | 2-NH₂-4-Pym | ring 18 | 2-OH |
| 12-389 | 4-F-Ph | 2-NH₂-4-Pym | ring 19 | 2-OH |
| 12-390 | 4-F-Ph | 2-NH₂-4-Pym | ring 20 | 2-OH |
| 12-391 | 4-F-Ph | 2-NH₂-4-Pym | ring 21 | 2-OH |
| 12-392 | 4-F-Ph | 2-NH₂-4-Pym | ring 22 | 2-OH |
| 12-393 | 4-F-Ph | 2-NH₂-4-Pym | ring 23 | 2-OH |
| 12-394 | 4-F-Ph | 2-NH₂-4-Pym | ring 24 | 2-OH |
| 12-395 | 4-F-Ph | 2-NH₂-4-Pym | ring 25 | 2-OH |
| 12-396 | 4-F-Ph | 2-NH₂-4-Pym | ring 26 | 2-OH |
| 12-397 | 4-F-Ph | 2-NH₂-4-Pym | ring 27 | 2-OH |
| 12-398 | 4-F-Ph | 2-NH₂-4-Pym | ring 28 | 2-OH |
| 12-399 | 4-F-Ph | 2-NH₂-4-Pym | ring 29 | 2-OH |
| 12-400 | 4-F-Ph | 2-NH₂-4-Pym | ring 30 | 2-OH |
| 12-401 | 4-F-Ph | 2-NH₂-4-Pym | ring 31 | 2-OH |
| 12-402 | 4-F-Ph | 2-NH₂-4-Pym | ring 32 | 2-OH |
| 12-403 | 4-F-Ph | 2-NH₂-4-Pym | ring 33 | 2-OH |
| 12-404 | 4-F-Ph | 2-NH₂-4-Pym | ring 34 | 2-OH |
| 12-405 | 4-F-Ph | 2-NH₂-4-Pym | ring 35 | 2-OH |
| 12-406 | 4-F-Ph | 2-NH₂-4-Pym | ring 36 | 2-OH |
| 12-407 | 4-F-Ph | 2-NH₂-4-Pym | ring 37 | 2-OH |
| 12-408 | 4-F-Ph | 2-NH₂-4-Pym | ring 1 | 2-MeO |
| 12-409 | 4-F-Ph | 2-NH₂-4-Pym | ring 2 | 2-MeO |
| 12-410 | 4-F-Ph | 2-NH₂-4-Pym | ring 3 | 2-MeO |
| 12-411 | 4-F-Ph | 2-NH₂-4-Pym | ring 4 | 2-MeO |
| 12-412 | 4-F-Ph | 2-NH₂-4-Pym | ring 5 | 2-MeO |
| 12-413 | 4-F-Ph | 2-NH₂-4-Pym | ring 6 | 2-MeO |
| 12-414 | 4-F-Ph | 2-NH₂-4-Pym | ring 7 | 2-MeO |
| 12-415 | 4-F-Ph | 2-NH₂-4-Pym | ring 8 | 2-MeO |
| 12-416 | 4-F-Ph | 2-NH₂-4-Pym | ring 9 | 2-MeO |
| 12-417 | 4-F-Ph | 2-NH₂-4-Pym | ring 10 | 2-MeO |
| 12-418 | 4-F-Ph | 2-NH₂-4-Pym | ring 11 | 2-MeO |
| 12-419 | 4-F-Ph | 2-NH₂-4-Pym | ring 12 | 2-MeO |
| 12-420 | 4-F-Ph | 2-NH₂-4-Pym | ring 13 | 2-MeO |
| 12-421 | 4-F-Ph | 2-NH₂-4-Pym | ring 14 | 2-MeO |
| 12-422 | 4-F-Ph | 2-NH₂-4-Pym | ring 15 | 2-MeO |
| 12-423 | 4-F-Ph | 2-NH₂-4-Pym | ring 16 | 2-MeO |
| 12-424 | 4-F-Ph | 2-NH₂-4-Pym | ring 17 | 2-MeO |
| 12-425 | 4-F-Ph | 2-NH₂-4-Pym | ring 18 | 2-MeO |
| 12-426 | 4-F-Ph | 2-NH₂-4-Pym | ring 19 | 2-MeO |
| 12-427 | 4-F-Ph | 2-NH₂-4-Pym | ring 20 | 2-MeO |
| 12-428 | 4-F-Ph | 2-NH₂-4-Pym | ring 21 | 2-MeO |
| 12-429 | 4-F-Ph | 2-NH₂-4-Pym | ring 22 | 2-MeO |
| 12-430 | 4-F-Ph | 2-NH₂-4-Pym | ring 23 | 2-MeO |
| 12-431 | 4-F-Ph | 2-NH₂-4-Pym | ring 24 | 2-MeO |
| 12-432 | 4-F-Ph | 2-NH₂-4-Pym | ring 25 | 2-MeO |
| 12-433 | 4-F-Ph | 2-NH₂-4-Pym | ring 26 | 2-MeO |
| 12-434 | 4-F-Ph | 2-NH₂-4-Pym | ring 27 | 2-MeO |
| 12-435 | 4-F-Ph | 2-NH₂-4-Pym | ring 28 | 2-MeO |
| 12-436 | 4-F-Ph | 2-NH₂-4-Pym | ring 29 | 2-MeO |
| 12-437 | 4-F-Ph | 2-NH₂-4-Pym | ring 30 | 2-MeO |
| 12-438 | 4-F-Ph | 2-NH₂-4-Pym | ring 31 | 2-MeO |
| 12-439 | 4-F-Ph | 2-NH₂-4-Pym | ring 32 | 2-MeO |
| 12-440 | 4-F-Ph | 2-NH₂-4-Pym | ring 33 | 2-MeO |
| 12-441 | 4-F-Ph | 2-NH₂-4-Pym | ring 34 | 2-MeO |
| 12-442 | 4-F-Ph | 2-NH₂-4-Pym | ring 35 | 2-MeO |
| 12-443 | 4-F-Ph | 2-NH₂-4-Pym | ring 36 | 2-MeO |

TABLE 12-continued

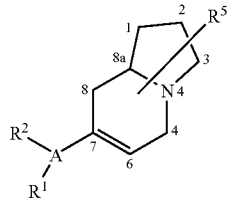

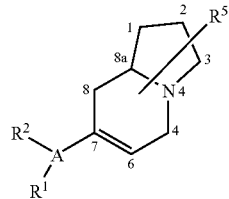

| Compound No. | R¹ | R² | A | R⁵ | Compound No. | R¹ | R² | A | R⁵ |
|---|---|---|---|---|---|---|---|---|---|
| 12-444 | 4-F-Ph | 2-NH₂-4-Pym | ring 37 | 2-MeO | 12-510 | 4-F-Ph | 2-NH₂-4-Pym | ring 29 | 2-Cl |
| 12-445 | 4-F-Ph | 2-NH₂-4-Pym | ring 1 | 2-F | 12-511 | 4-F-Ph | 2-NH₂-4-Pym | ring 30 | 2-Cl |
| 12-446 | 4-F-Ph | 2-NH₂-4-Pym | ring 2 | 2-F | 12-512 | 4-F-Ph | 2-NH₂-4-Pym | ring 31 | 2-Cl |
| 12-447 | 4-F-Ph | 2-NH₂-4-Pym | ring 3 | 2-F | 12-513 | 4-F-Ph | 2-NH₂-4-Pym | ring 32 | 2-Cl |
| 12-448 | 4-F-Ph | 2-NH₂-4-Pym | ring 4 | 2-F | 12-514 | 4-F-Ph | 2-NH₂-4-Pym | ring 33 | 2-Cl |
| 12-449 | 4-F-Ph | 2-NH₂-4-Pym | ring 5 | 2-F | 12-515 | 4-F-Ph | 2-NH₂-4-Pym | ring 34 | 2-Cl |
| 12-450 | 4-F-Ph | 2-NH₂-4-Pym | ring 6 | 2-F | 12-516 | 4-F-Ph | 2-NH₂-4-Pym | ring 35 | 2-Cl |
| 12-451 | 4-F-Ph | 2-NH₂-4-Pym | ring 7 | 2-F | 12-517 | 4-F-Ph | 2-NH₂-4-Pym | ring 36 | 2-Cl |
| 12-452 | 4-F-Ph | 2-NH₂-4-Pym | ring 8 | 2-F | 12-518 | 4-F-Ph | 2-NH₂-4-Pym | ring 37 | 2-Cl |
| 12-453 | 4-F-Ph | 2-NH₂-4-Pym | ring 9 | 2-F | 12-519 | 4-F-Ph | 2-NH₂-4-Pym | ring 1 | 2,2-diF |
| 12-454 | 4-F-Ph | 2-NH₂-4-Pym | ring 10 | 2-F | 12-520 | 4-F-Ph | 2-NH₂-4-Pym | ring 2 | 2,2-diF |
| 12-455 | 4-F-Ph | 2-NH₂-4-Pym | ring 11 | 2-F | 12-521 | 4-F-Ph | 2-NH₂-4-Pym | ring 3 | 2,2-diF |
| 12-456 | 4-F-Ph | 2-NH₂-4-Pym | ring 12 | 2-F | 12-522 | 4-F-Ph | 2-NH₂-4-Pym | ring 4 | 2,2-diF |
| 12-457 | 4-F-Ph | 2-NH₂-4-Pym | ring 13 | 2-F | 12-523 | 4-F-Ph | 2-NH₂-4-Pym | ring 5 | 2,2-diF |
| 12-458 | 4-F-Ph | 2-NH₂-4-Pym | ring 14 | 2-F | 12-524 | 4-F-Ph | 2-NH₂-4-Pym | ring 6 | 2,2-diF |
| 12-459 | 4-F-Ph | 2-NH₂-4-Pym | ring 15 | 2-F | 12-525 | 4-F-Ph | 2-NH₂-4-Pym | ring 7 | 2,2-diF |
| 12-460 | 4-F-Ph | 2-NH₂-4-Pym | ring 16 | 2-F | 12-526 | 4-F-Ph | 2-NH₂-4-Pym | ring 8 | 2,2-diF |
| 12-461 | 4-F-Ph | 2-NH₂-4-Pym | ring 17 | 2-F | 12-527 | 4-F-Ph | 2-NH₂-4-Pym | ring 9 | 2,2-diF |
| 12-462 | 4-F-Ph | 2-NH₂-4-Pym | ring 18 | 2-F | 12-528 | 4-F-Ph | 2-NH₂-4-Pym | ring 10 | 2,2-diF |
| 12-463 | 4-F-Ph | 2-NH₂-4-Pym | ring 19 | 2-F | 12-529 | 4-F-Ph | 2-NH₂-4-Pym | ring 11 | 2,2-diF |
| 12-464 | 4-F-Ph | 2-NH₂-4-Pym | ring 20 | 2-F | 12-530 | 4-F-Ph | 2-NH₂-4-Pym | ring 12 | 2,2-diF |
| 12-465 | 4-F-Ph | 2-NH₂-4-Pym | ring 21 | 2-F | 12-531 | 4-F-Ph | 2-NH₂-4-Pym | ring 13 | 2,2-diF |
| 12-466 | 4-F-Ph | 2-NH₂-4-Pym | ring 22 | 2-F | 12-532 | 4-F-Ph | 2-NH₂-4-Pym | ring 14 | 2,2-diF |
| 12-467 | 4-F-Ph | 2-NH₂-4-Pym | ring 23 | 2-F | 12-533 | 4-F-Ph | 2-NH₂-4-Pym | ring 15 | 2,2-diF |
| 12-468 | 4-F-Ph | 2-NH₂-4-Pym | ring 24 | 2-F | 12-534 | 4-F-Ph | 2-NH₂-4-Pym | ring 16 | 2,2-diF |
| 12-469 | 4-F-Ph | 2-NH₂-4-Pym | ring 25 | 2-F | 12-535 | 4-F-Ph | 2-NH₂-4-Pym | ring 17 | 2,2-diF |
| 12-470 | 4-F-Ph | 2-NH₂-4-Pym | ring 26 | 2-F | 12-536 | 4-F-Ph | 2-NH₂-4-Pym | ring 18 | 2,2-diF |
| 12-471 | 4-F-Ph | 2-NH₂-4-Pym | ring 27 | 2-F | 12-537 | 4-F-Ph | 2-NH₂-4-Pym | ring 19 | 2,2-diF |
| 12-472 | 4-F-Ph | 2-NH₂-4-Pym | ring 28 | 2-F | 12-538 | 4-F-Ph | 2-NH₂-4-Pym | ring 20 | 2,2-diF |
| 12-473 | 4-F-Ph | 2-NH₂-4-Pym | ring 29 | 2-F | 12-539 | 4-F-Ph | 2-NH₂-4-Pym | ring 21 | 2,2-diF |
| 12-474 | 4-F-Ph | 2-NH₂-4-Pym | ring 30 | 2-F | 12-540 | 4-F-Ph | 2-NH₂-4-Pym | ring 22 | 2,2-diF |
| 12-475 | 4-F-Ph | 2-NH₂-4-Pym | ring 31 | 2-F | 12-541 | 4-F-Ph | 2-NH₂-4-Pym | ring 23 | 2,2-diF |
| 12-476 | 4-F-Ph | 2-NH₂-4-Pym | ring 32 | 2-F | 12-542 | 4-F-Ph | 2-NH₂-4-Pym | ring 24 | 2,2-diF |
| 12-477 | 4-F-Ph | 2-NH₂-4-Pym | ring 33 | 2-F | 12-543 | 4-F-Ph | 2-NH₂-4-Pym | ring 25 | 2,2-diF |
| 12-478 | 4-F-Ph | 2-NH₂-4-Pym | ring 34 | 2-F | 12-544 | 4-F-Ph | 2-NH₂-4-Pym | ring 26 | 2,2-diF |
| 12-479 | 4-F-Ph | 2-NH₂-4-Pym | ring 35 | 2-F | 12-545 | 4-F-Ph | 2-NH₂-4-Pym | ring 27 | 2,2-diF |
| 12-480 | 4-F-Ph | 2-NH₂-4-Pym | ring 36 | 2-F | 12-546 | 4-F-Ph | 2-NH₂-4-Pym | ring 28 | 2,2-diF |
| 12-481 | 4-F-Ph | 2-NH₂-4-Pym | ring 37 | 2-F | 12-547 | 4-F-Ph | 2-NH₂-4-Pym | ring 29 | 2,2-diF |
| 12-482 | 4-F-Ph | 2-NH₂-4-Pym | ring 1 | 2-Cl | 12-548 | 4-F-Ph | 2-NH₂-4-Pym | ring 30 | 2,2-diF |
| 12-483 | 4-F-Ph | 2-NH₂-4-Pym | ring 2 | 2-Cl | 12-549 | 4-F-Ph | 2-NH₂-4-Pym | ring 31 | 2,2-diF |
| 12-484 | 4-F-Ph | 2-NH₂-4-Pym | ring 3 | 2-Cl | 12-550 | 4-F-Ph | 2-NH₂-4-Pym | ring 32 | 2,2-diF |
| 12-485 | 4-F-Ph | 2-NH₂-4-Pym | ring 4 | 2-Cl | 12-551 | 4-F-Ph | 2-NH₂-4-Pym | ring 33 | 2,2-diF |
| 12-486 | 4-F-Ph | 2-NH₂-4-Pym | ring 5 | 2-Cl | 12-552 | 4-F-Ph | 2-NH₂-4-Pym | ring 34 | 2,2-diF |
| 12-487 | 4-F-Ph | 2-NH₂-4-Pym | ring 6 | 2-Cl | 12-553 | 4-F-Ph | 2-NH₂-4-Pym | ring 35 | 2,2-diF |
| 42-488 | 4-F-Ph | 2-NH₂-4-Pym | ring 7 | 2-Cl | 12-554 | 4-F-Ph | 2-NH₂-4-Pym | ring 36 | 2,2-diF |
| 12-489 | 4-F-Ph | 2-NH₂-4-Pym | ring 8 | 2-Cl | 12-555 | 4-F-Ph | 2-NH₂-4-Pym | ring 37 | 2,2-diF |
| 12-490 | 4-F-Ph | 2-NH₂-4-Pym | ring 9 | 2-Cl | 12-556 | 4-F-Ph | 2-NH₂-4-Pym | ring 1 | 8-Me |
| 12-491 | 4-F-Ph | 2-NH₂-4-Pym | ring 10 | 2-Cl | 12-557 | 4-F-Ph | 2-NH₂-4-Pym | ring 2 | 8-Me |
| 12-492 | 4-F-Ph | 2-NH₂-4-Pym | ring 11 | 2-Cl | 12-558 | 4-F-Ph | 2-NH₂-4-Pym | ring 3 | 8-Me |
| 12-493 | 4-F-Ph | 2-NH₂-4-Pym | ring 12 | 2-Cl | 12-559 | 4-F-Ph | 2-NH₂-4-Pym | ring 4 | 8-Me |
| 12-494 | 4-F-Ph | 2-NH₂-4-Pym | ring 13 | 2-Cl | 12-560 | 4-F-Ph | 2-NH₂-4-Pym | ring 5 | 8-Me |
| 12-495 | 4-F-Ph | 2-NH₂-4-Pym | ring 14 | 2-Cl | 12-561 | 4-F-Ph | 2-NH₂-4-Pym | ring 6 | 8-Me |
| 12-496 | 4-F-Ph | 2-NH₂-4-Pym | ring 15 | 2-Cl | 12-562 | 4-F-Ph | 2-NH₂-4-Pym | ring 7 | 8-Me |
| 12-497 | 4-F-Ph | 2-NH₂-4-Pym | ring 16 | 2-Cl | 12-563 | 4-F-Ph | 2-NH₂-4-Pym | ring 8 | 8-Me |
| 12-498 | 4-F-Ph | 2-NH₂-4-Pym | ring 17 | 2-Cl | 12-564 | 4-F-Ph | 2-NH₂-4-Pym | ring 9 | 8-Me |
| 12-499 | 4-F-Ph | 2-NH₂-4-Pym | ring 18 | 2-Cl | 12-565 | 4-F-Ph | 2-NH₂-4-Pym | ring 10 | 8-Me |
| 12-500 | 4-F-Ph | 2-NH₂-4-Pym | ring 19 | 2-Cl | 12-566 | 4-F-Ph | 2-NH₂-4-Pym | ring 11 | 8-Me |
| 12-501 | 4-F-Ph | 2-NH₂-4-Pym | ring 20 | 2-Cl | 12-567 | 4-F-Ph | 2-NH₂-4-Pym | ring 12 | 8-Me |
| 12-502 | 4-F-Ph | 2-NH₂-4-Pym | ring 21 | 2-Cl | 12-568 | 4-F-Ph | 2-NH₂-4-Pym | ring 13 | 8-Me |
| 12-503 | 4-F-Ph | 2-NH₂-4-Pym | ring 22 | 2-Cl | 12-569 | 4-F-Ph | 2-NH₂-4-Pym | ring 14 | 8-Me |
| 12-504 | 4-F-Ph | 2-NH₂-4-Pym | ring 23 | 2-Cl | 12-570 | 4-F-Ph | 2-NH₂-4-Pym | ring 15 | 8-Me |
| 12-505 | 4-F-Ph | 2-NH₂-4-Pym | ring 24 | 2-Cl | 12-571 | 4-F-Ph | 2-NH₂-4-Pym | ring 16 | 8-Me |
| 12-506 | 4-F-Ph | 2-NH₂-4-Pym | ring 25 | 2-Cl | 12-572 | 4-F-Ph | 2-NH₂-4-Pym | ring 17 | 8-Me |
| 12-507 | 4-F-Ph | 2-NH₂-4-Pym | ring 26 | 2-Cl | 12-573 | 4-F-Ph | 2-NH₂-4-Pym | ring 18 | 8-Me |
| 12-508 | 4-F-Ph | 2-NH₂-4-Pym | ring 27 | 2-Cl | 12-574 | 4-F-Ph | 2-NH₂-4-Pym | ring 19 | 8-Me |
| 12-509 | 4-F-Ph | 2-NH₂-4-Pym | ring 28 | 2-Cl | 12-575 | 4-F-Ph | 2-NH₂-4-Pym | ring 20 | 8-Me |

TABLE 12-continued

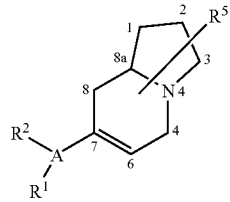

| Compound No. | R¹ | R² | A | R⁵ |
|---|---|---|---|---|
| 12-576 | 4-F-Ph | 2-NH₂-4-Pym | ring 21 | 8-Me |
| 12-577 | 4-F-Ph | 2-NH₂-4-Pym | ring 22 | 8-Me |
| 12-578 | 4-F-Ph | 2-NH₂-4-Pym | ring 23 | 8-Me |
| 12-579 | 4-F-Ph | 2-NH₂-4-Pym | ring 24 | 8-Me |
| 12-580 | 4-F-Ph | 2-NH₂-4-Pym | ring 25 | 8-Me |
| 12-581 | 4-F-Ph | 2-NH₂-4-Pym | ring 26 | 8-Me |
| 12-582 | 4-F-Ph | 2-NH₂-4-Pym | ring 27 | 8-Me |
| 12-583 | 4-F-Ph | 2-NH₂-4-Pym | ring 28 | 8-Me |
| 12-584 | 4-F-Ph | 2-NH₂-4-Pym | ring 29 | 8-Me |
| 12-585 | 4-F-Ph | 2-NH₂-4-Pym | ring 30 | 8-Me |
| 12-586 | 4-F-Ph | 2-NH₂-4-Pym | ring 31 | 8-Me |
| 12-587 | 4-F-Ph | 2-NH₂-4-Pym | ring 32 | 8-Me |
| 12-588 | 4-F-Ph | 2-NH₂-4-Pym | ring 33 | 8-Me |
| 12-589 | 4-F-Ph | 2-NH₂-4-Pym | ring 34 | 8-Me |
| 12-590 | 4-F-Ph | 2-NH₂-4-Pym | ring 35 | 8-Me |
| 12-591 | 4-F-Ph | 2-NH₂-4-Pym | ring 36 | 8-Me |
| 12-592 | 4-F-Ph | 2-NH₂-4-Pym | ring 37 | 8-Me |
| 12-593 | 4-F-Ph | 2-MeNH-4-Pym | ring 1 | — |
| 12-594 | 4-F-Ph | 2-MeNH-4-Pym | ring 2 | — |
| 12-595 | 4-F-Ph | 2-MeNH-4-Pym | ring 3 | — |
| 12-596 | 4-F-Ph | 2-MeNH-4-Pym | ring 4 | — |
| 12-597 | 4-F-Ph | 2-MeNH-4-Pym | ring 5 | — |
| 12-598 | 4-F-Ph | 2-MeNH-4-Pym | ring 6 | — |
| 12-599 | 4-F-Ph | 2-MeNH-4-Pym | ring 7 | — |
| 12-600 | 4-F-Ph | 2-MeNH-4-Pym | ring 8 | — |
| 12-601 | 4-F-Ph | 2-MeNH-4-Pym | ring 9 | — |
| 12-602 | 4-F-Ph | 2-MeNH-4-Pym | ring 10 | — |
| 12-603 | 4-F-Ph | 2-MeNH-4-Pym | ring 11 | — |
| 12-604 | 4-F-Ph | 2-MeNH-4-Pym | ring 12 | — |
| 12-605 | 4-F-Ph | 2-MeNH-4-Pym | ring 13 | — |
| 12-606 | 4-F-Ph | 2-MeNH-4-Pym | ring 14 | — |
| 12-607 | 4-F-Ph | 2-MeNH-4-Pym | ring 15 | — |
| 12-608 | 4-F-Ph | 2-MeNH-4-Pym | ring 16 | — |
| 12-609 | 4-F-Ph | 2-MeNH-4-Pym | ring 17 | — |
| 12-610 | 4-F-Ph | 2-MeNH-4-Pym | ring 18 | — |
| 12-611 | 4-F-Ph | 2-MeNH-4-Pym | ring 19 | — |
| 12-612 | 4-F-Ph | 2-MeNH-4-Pym | ring 20 | — |
| 12-613 | 4-F-Ph | 2-MeNH-4-Pym | ring 21 | — |
| 12-614 | 4-F-Ph | 2-MeNH-4-Pym | ring 22 | — |
| 12-615 | 4-F-Ph | 2-MeNH-4-Pym | ring 23 | — |
| 12-616 | 4-F-Ph | 2-MeNH-4-Pym | ring 24 | — |
| 12-617 | 4-F-Ph | 2-MeNH-4-Pym | ring 25 | — |
| 12-618 | 4-F-Ph | 2-MeNH-4-Pym | ring 26 | — |
| 12-619 | 4-F-Ph | 2-MeNH-4-Pym | ring 27 | — |
| 12-620 | 4-F-Ph | 2-MeNH-4-Pym | ring 28 | — |
| 12-621 | 4-F-Ph | 2-MeNH-4-Pym | ring 29 | — |
| 12-622 | 4-F-Ph | 2-MeNH-4-Pym | ring 30 | — |
| 12-623 | 4-F-Ph | 2-MeNH-4-Pym | ring 31 | — |
| 12-624 | 4-F-Ph | 2-MeNH-4-Pym | ring 32 | — |
| 12-625 | 4-F-Ph | 2-MeNH-4-Pym | ring 33 | — |
| 12-626 | 4-F-Ph | 2-MeNH-4-Pym | ring 34 | — |
| 12-627 | 4-F-Ph | 2-MeNH-4-Pym | ring 35 | — |
| 12-628 | 4-F-Ph | 2-MeNH-4-Pym | ring 36 | — |
| 12-629 | 4-F-Ph | 2-MeNH-4-Pym | ring 37 | — |
| 12-630 | 4-F-Ph | 2-MeNH-4-Pym | ring 1 | 2-Me |
| 12-631 | 4-F-Ph | 2-MeNH-4-Pym | ring 2 | 2-Me |
| 12-632 | 4-F-Ph | 2-MeNH-4-Pym | ring 3 | 2-Me |
| 12-633 | 4-F-Ph | 2-MeNH-4-Pym | ring 4 | 2-Me |
| 12-634 | 4-F-Ph | 2-MeNH-4-Pym | ring 5 | 2-Me |
| 12-635 | 4-F-Ph | 2-MeNH-4-Pym | ring 6 | 2-Me |
| 12-636 | 4-F-Ph | 2-MeNH-4-Pym | ring 7 | 2-Me |
| 12-637 | 4-F-Ph | 2-MeNH-4-Pym | ring 8 | 2-Me |
| 12-638 | 4-F-Ph | 2-MeNH-4-Pym | ring 9 | 2-Me |
| 12-639 | 4-F-Ph | 2-MeNH-4-Pym | ring 10 | 2-Me |
| 12-640 | 4-F-Ph | 2-MeNH-4-Pym | ring 11 | 2-Me |
| 12-641 | 4-F-Ph | 2-MeNH-4-Pym | ring 12 | 2-Me |

TABLE 12-continued

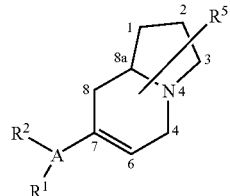

| Compound No. | R¹ | R² | A | R⁵ |
|---|---|---|---|---|
| 12-642 | 4-F-Ph | 2-MeNH-4-Pym | ring 13 | 2-Me |
| 12-643 | 4-F-Ph | 2-MeNH-4-Pym | ring 14 | 2-Me |
| 12-644 | 4-F-Ph | 2-MeNH-4-Pym | ring 15 | 2-Me |
| 12-645 | 4-F-Ph | 2-MeNH-4-Pym | ring 16 | 2-Me |
| 12-646 | 4-F-Ph | 2-MeNH-4-Pym | ring 17 | 2-Me |
| 12-647 | 4-F-Ph | 2-MeNH-4-Pym | ring 18 | 2-Me |
| 12-648 | 4-F-Ph | 2-MeNH-4-Pym | ring 19 | 2-Me |
| 12-649 | 4-F-Ph | 2-MeNH-4-Pym | ring 20 | 2-Me |
| 12-650 | 4-F-Ph | 2-MeNH-4-Pym | ring 21 | 2-Me |
| 12-651 | 4-F-Ph | 2-MeNH-4-Pym | ring 22 | 2-Me |
| 12-652 | 4-F-Ph | 2-MeNH-4-Pym | ring 23 | 2-Me |
| 12-653 | 4-F-Ph | 2-MeNH-4-Pym | ring 24 | 2-Me |
| 12-654 | 4-F-Ph | 2-MeNH-4-Pym | ring 25 | 2-Me |
| 12-655 | 4-F-Ph | 2-MeNH-4-Pym | ring 26 | 2-Me |
| 12-656 | 4-F-Ph | 2-MeNH-4-Pym | ring 27 | 2-Me |
| 12-657 | 4-F-Ph | 2-MeNH-4-Pym | ring 28 | 2-Me |
| 12-658 | 4-F-Ph | 2-MeNH-4-Pym | ring 29 | 2-Me |
| 12-659 | 4-F-Ph | 2-MeNH-4-Pym | ring 30 | 2-Me |
| 12-660 | 4-F-Ph | 2-MeNH-4-Pym | ring 31 | 2-Me |
| 12-661 | 4-F-Ph | 2-MeNH-4-Pym | ring 32 | 2-Me |
| 12-662 | 4-F-Ph | 2-MeNH-4-Pym | ring 33 | 2-Me |
| 12-663 | 4-F-Ph | 2-MeNH-4-Pym | ring 34 | 2-Me |
| 12-664 | 4-F-Ph | 2-MeNH-4-Pym | ring 35 | 2-Me |
| 12-665 | 4-F-Ph | 2-MeNH-4-Pym | ring 36 | 2-Me |
| 12-666 | 4-F-Ph | 2-MeNH-4-Pym | ring 37 | 2-Me |
| 12-667 | 4-F-Ph | 2-MeNH-4-Pym | ring 1 | 2-OH |
| 12-668 | 4-F-Ph | 2-MeNH-4-Pym | ring 2 | 2-OH |
| 12-669 | 4-F-Ph | 2-MeNH-4-Pym | ring 3 | 2-OH |
| 12-670 | 4-F-Ph | 2-MeNH-4-Pym | ring 4 | 2-OH |
| 12-671 | 4-F-Ph | 2-MeNH-4-Pym | ring 5 | 2-OH |
| 12-672 | 4-F-Ph | 2-MeNH-4-Pym | ring 6 | 2-OH |
| 12-673 | 4-F-Ph | 2-MeNH-4-Pym | ring 7 | 2-OH |
| 12-674 | 4-F-Ph | 2-MeNH-4-Pym | ring 8 | 2-OH |
| 12-675 | 4-F-Ph | 2-MeNH-4-Pym | ring 9 | 2-OH |
| 12-676 | 4-F-Ph | 2-MeNH-4-Pym | ring 10 | 2-OH |
| 12-677 | 4-F-Ph | 2-MeNH-4-Pym | ring 11 | 2-OH |
| 12-678 | 4-F-Ph | 2-MeNH-4-Pym | ring 12 | 2-OH |
| 12-679 | 4-F-Ph | 2-MeNH-4-Pym | ring 13 | 2-OH |
| 12-680 | 4-F-Ph | 2-MeNH-4-Pym | ring 14 | 2-OH |
| 12-681 | 4-F-Ph | 2-MeNH-4-Pym | ring 15 | 2-OH |
| 12-682 | 4-F-Ph | 2-MeNH-4-Pym | ring 16 | 2-OH |
| 12-683 | 4-F-Ph | 2-MeNH-4-Pym | ring 17 | 2-OH |
| 12-684 | 4-F-Ph | 2-MeNH-4-Pym | ring 18 | 2-OH |
| 12-685 | 4-F-Ph | 2-MeNH-4-Pym | ring 19 | 2-OH |
| 12-686 | 4-F-Ph | 2-MeNH-4-Pym | ring 20 | 2-OH |
| 12-687 | 4-F-Ph | 2-MeNH-4-Pym | ring 21 | 2-OH |
| 12-688 | 4-F-Ph | 2-MeNH-4-Pym | ring 22 | 2-OH |
| 12-689 | 4-F-Ph | 2-MeNH-4-Pym | ring 23 | 2-OH |
| 12-690 | 4-F-Ph | 2-MeNH-4-Pym | ring 24 | 2-OH |
| 12-691 | 4-F-Ph | 2-MeNH-4-Pym | ring 25 | 2-OH |
| 12-692 | 4-F-Ph | 2-MeNH-4-Pym | ring 26 | 2-OH |
| 12-693 | 4-F-Ph | 2-MeNH-4-Pym | ring 27 | 2-OH |
| 12-694 | 4-F-Ph | 2-MeNH-4-Pym | ring 28 | 2-OH |
| 12-695 | 4-F-Ph | 2-MeNH-4-Pym | ring 29 | 2-OH |
| 12-696 | 4-F-Ph | 2-MeNH-4-Pym | ring 30 | 2-OH |
| 12-697 | 4-F-Ph | 2-MeNH-4-Pym | ring 31 | 2-OH |
| 12-698 | 4-F-Ph | 2-MeNH-4-Pym | ring 32 | 2-OH |
| 12-699 | 4-F-Ph | 2-MeNH-4-Pym | ring 33 | 2-OH |
| 12-700 | 4-F-Ph | 2-MeNH-4-Pym | ring 34 | 2-OH |
| 12-701 | 4-F-Ph | 2-MeNH-4-Pym | ring 35 | 2-OH |
| 12-702 | 4-F-Ph | 2-MeNH-4-Pym | ring 36 | 2-OH |
| 12-703 | 4-F-Ph | 2-MeNH-4-Pym | ring 37 | 2-OH |
| 12-704 | 4-F-Ph | 2-MeNH-4-Pym | ring 1 | 2-MeO |
| 12-705 | 4-F-Ph | 2-MeNH-4-Pym | ring 2 | 2-MeO |
| 12-706 | 4-F-Ph | 2-MeNH-4-Pym | ring 3 | 2-MeO |
| 12-707 | 4-F-Ph | 2-MeNH-4-Pym | ring 4 | 2-MeO |

TABLE 12-continued

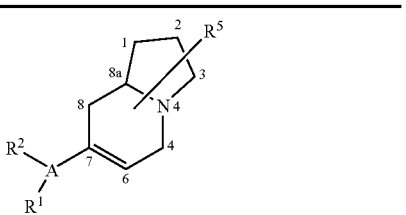

| Compound No. | R¹ | R² | A | R⁵ |
|---|---|---|---|---|
| 12-708 | 4-F-Ph | 2-MeNH-4-Pym | ring 5 | 2-MeO |
| 12-709 | 4-F-Ph | 2-MeNH-4-Pym | ring 6 | 2-MeO |
| 12-710 | 4-F-Ph | 2-MeNH-4-Pym | ring 7 | 2-MeO |
| 12-711 | 4-F-Ph | 2-MeNH-4-Pym | ring 8 | 2-MeO |
| 12-712 | 4-F-Ph | 2-MeNH-4-Pym | ring 9 | 2-MeO |
| 12-713 | 4-F-Ph | 2-MeNH-4-Pym | ring 10 | 2-MeO |
| 12-714 | 4-F-Ph | 2-MeNH-4-Pym | ring 11 | 2-MeO |
| 12-715 | 4-F-Ph | 2-MeNH-4-Pym | ring 12 | 2-MeO |
| 12-716 | 4-F-Ph | 2-MeNH-4-Pym | ring 13 | 2-MeO |
| 12-717 | 4-F-Ph | 2-MeNH-4-Pym | ring 14 | 2-MeO |
| 12-718 | 4-F-Ph | 2-MeNH-4-Pym | ring 15 | 2-MeO |
| 12-719 | 4-F-Ph | 2-MeNH-4-Pym | ring 16 | 2-MeO |
| 12-720 | 4-F-Ph | 2-MeNH-4-Pym | ring 17 | 2-MeO |
| 12-721 | 4-F-Ph | 2-MeNH-4-Pym | ring 18 | 2-MeO |
| 12-722 | 4-F-Ph | 2-MeNH-4-Pym | ring 19 | 2-MeO |
| 12-723 | 4-F-Ph | 2-MeNH-4-Pym | ring 20 | 2-MeO |
| 12-724 | 4-F-Ph | 2-MeNH-4-Pym | ring 21 | 2-MeO |
| 12-725 | 4-F-Ph | 2-MeNH-4-Pym | ring 22 | 2-MeO |
| 12-726 | 4-F-Ph | 2-MeNH-4-Pym | ring 23 | 2-MeO |
| 12-727 | 4-F-Ph | 2-MeNH-4-Pym | ring 24 | 2-MeO |
| 12-728 | 4-F-Ph | 2-MeNH-4-Pym | ring 25 | 2-MeO |
| 12-729 | 4-F-Ph | 2-MeNH-4-Pym | ring 26 | 2-MeO |
| 12-730 | 4-F-Ph | 2-MeNH-4-Pym | ring 27 | 2-MeO |
| 12-731 | 4-F-Ph | 2-MeNH-4-Pym | ring 28 | 2-MeO |
| 12-732 | 4-F-Ph | 2-MeNH-4-Pym | ring 29 | 2-MeO |
| 12-733 | 4-F-Ph | 2-MeNH-4-Pym | ring 30 | 2-MeO |
| 12-734 | 4-F-Ph | 2-MeNH-4-Pym | ring 31 | 2-MeO |
| 12-735 | 4-F-Ph | 2-MeNH-4-Pym | ring 32 | 2-MeO |
| 12-736 | 4-F-Ph | 2-MeNH-4-Pym | ring 33 | 2-MeO |
| 12-737 | 4-F-Ph | 2-MeNH-4-Pym | ring 34 | 2-MeO |
| 12-738 | 4-F-Ph | 2-MeNH-4-Pym | ring 35 | 2-MeO |
| 12-739 | 4-F-Ph | 2-MeNH-4-Pym | ring 36 | 2-MeO |
| 12-740 | 4-F-Ph | 2-MeNH-4-Pym | ring 37 | 2-MeO |
| 12-741 | 4-F-Ph | 2-MeNH-4-Pym | ring 1 | 2-F |
| 12-742 | 4-F-Ph | 2-MeNH-4-Pym | ring 2 | 2-F |
| 12-743 | 4-F-Ph | 2-MeNH-4-Pym | ring 3 | 2-F |
| 12-744 | 4-F-Ph | 2-MeNH-4-Pym | ring 4 | 2-F |
| 12-745 | 4-F-Ph | 2-MeNH-4-Pym | ring 5 | 2-F |
| 12-746 | 4-F-Ph | 2-MeNH-4-Pym | ring 6 | 2-F |
| 12-747 | 4-F-Ph | 2-MeNH-4-Pym | ring 7 | 2-F |
| 12-748 | 4-F-Ph | 2-MeNH-4-Pym | ring 8 | 2-F |
| 12-749 | 4-F-Ph | 2-MeNH-4-Pym | ring 9 | 2-F |
| 12-750 | 4-F-Ph | 2-MeNH-4-Pym | ring 10 | 2-F |
| 12-751 | 4-F-Ph | 2-MeNH-4-Pym | ring 11 | 2-F |
| 12-752 | 4-F-Ph | 2-MeNH-4-Pym | ring 12 | 2-F |
| 12-753 | 4-F-Ph | 2-MeNH-4-Pym | ring 13 | 2-F |
| 12-754 | 4-F-Ph | 2-MeNH-4-Pym | ring 14 | 2-F |
| 12-755 | 4-F-Ph | 2-MeNH-4-Pym | ring 15 | 2-F |
| 12-756 | 4-F-Ph | 2-MeNH-4-Pym | ring 16 | 2-F |
| 12-757 | 4-F-Ph | 2-MeNH-4-Pym | ring 17 | 2-F |
| 12-758 | 4-F-Ph | 2-MeNH-4-Pym | ring 18 | 2-F |
| 12-759 | 4-F-Ph | 2-MeNH-4-Pym | ring 19 | 2-F |
| 12-760 | 4-F-Ph | 2-MeNH-4-Pym | ring 20 | 2-F |
| 12-761 | 4-F-Ph | 2-MeNH-4-Pym | ring 21 | 2-F |
| 12-762 | 4-F-Ph | 2-MeNH-4-Pym | ring 22 | 2-F |
| 12-763 | 4-F-Ph | 2-MeNH-4-Pym | ring 23 | 2-F |
| 12-764 | 4-F-Ph | 2-MeNH-4-Pym | ring 24 | 2-F |
| 12-765 | 4-F-Ph | 2-MeNH-4-Pym | ring 25 | 2-F |
| 12-766 | 4-F-Ph | 2-MeNH-4-Pym | ring 26 | 2-F |
| 12-767 | 4-F-Ph | 2-MeNH-4-Pym | ring 27 | 2-F |
| 12-768 | 4-F-Ph | 2-MeNH-4-Pym | ring 28 | 2-F |
| 12-769 | 4-F-Ph | 2-MeNH-4-Pym | ring 29 | 2-F |
| 12-770 | 4-F-Ph | 2-MeNH-4-Pym | ring 30 | 2-F |
| 12-771 | 4-F-Ph | 2-MeNH-4-Pym | ring 31 | 2-F |
| 12-772 | 4-F-Ph | 2-MeNH-4-Pym | ring 32 | 2-F |
| 12-773 | 4-F-Ph | 2-MeNH-4-Pym | ring 33 | 2-F |

TABLE 12-continued

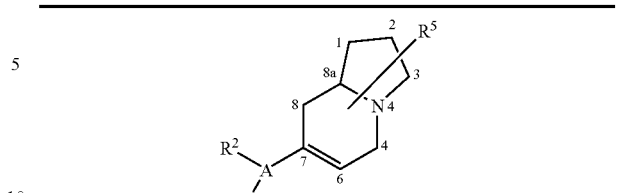

| Compound No. | R¹ | R² | A | R⁵ |
|---|---|---|---|---|
| 12-774 | 4-F-Ph | 2-MeNH-4-Pym | ring 34 | 2-F |
| 12-775 | 4-F-Ph | 2-MeNH-4-Pym | ring 35 | 2-F |
| 12-776 | 4-F-Ph | 2-MeNH-4-Pym | ring 36 | 2-F |
| 12-777 | 4-F-Ph | 2-MeNH-4-Pym | ring 37 | 2-F |
| 12-778 | 4-F-Ph | 2-MeNH-4-Pym | ring 1 | 2-Cl |
| 12-779 | 4-F-Ph | 2-MeNH-4-Pym | ring 2 | 2-Cl |
| 12-780 | 4-F-Ph | 2-MeNH-4-Pym | ring 3 | 2-Cl |
| 12-781 | 4-F-Ph | 2-MeNH-4-Pym | ring 4 | 2-Cl |
| 12-782 | 4-F-Ph | 2-MeNH-4-Pym | ring 5 | 2-Cl |
| 12-783 | 4-F-Ph | 2-MeNH-4-Pym | ring 6 | 2-Cl |
| 12-784 | 4-F-Ph | 2-MeNH-4-Pym | ring 7 | 2-Cl |
| 12-785 | 4-F-Ph | 2-MeNH-4-Pym | ring 8 | 2-Cl |
| 12-786 | 4-F-Ph | 2-MeNH-4-Pym | ring 9 | 2-Cl |
| 12-787 | 4-F-Ph | 2-MeNH-4-Pym | ring 10 | 2-Cl |
| 12-788 | 4-F-Ph | 2-MeNH-4-Pym | ring 11 | 2-Cl |
| 12-789 | 4-F-Ph | 2-MeNH-4-Pym | ring 12 | 2-Cl |
| 12-790 | 4-F-Ph | 2-MeNH-4-Pym | ring 13 | 2-Cl |
| 12-791 | 4-F-Ph | 2-MeNH-4-Pym | ring 14 | 2-Cl |
| 12-792 | 4-F-Ph | 2-MeNH-4-Pym | ring 15 | 2-Cl |
| 12-793 | 4-F-Ph | 2-MeNH-4-Pym | ring 16 | 2-Cl |
| 12-794 | 4-F-Ph | 2-MeNH-4-Pym | ring 17 | 2-Cl |
| 12-795 | 4-F-Ph | 2-MeNH-4-Pym | ring 18 | 2-Cl |
| 12-796 | 4-F-Ph | 2-MeNH-4-Pym | ring 19 | 2-Cl |
| 12-797 | 4-F-Ph | 2-MeNH-4-Pym | ring 20 | 2-Cl |
| 12-798 | 4-F-Ph | 2-MeNH-4-Pym | ring 21 | 2-Cl |
| 12-799 | 4-F-Ph | 2-MeNH-4-Pym | ring 22 | 2-Cl |
| 12-800 | 4-F-Ph | 2-MeNH-4-Pym | ring 23 | 2-Cl |
| 12-801 | 4-F-Ph | 2-MeNH-4-Pym | ring 24 | 2-Cl |
| 12-802 | 4-F-Ph | 2-MeNH-4-Pym | ring 25 | 2-Cl |
| 12-803 | 4-F-Ph | 2-MeNH-4-Pym | ring 26 | 2-Cl |
| 12-804 | 4-F-Ph | 2-MeNH-4-Pym | ring 27 | 2-Cl |
| 12-805 | 4-F-Ph | 2-MeNH-4-Pym | ring 28 | 2-Cl |
| 12-806 | 4-F-Ph | 2-MeNH-4-Pym | ring 29 | 2-Cl |
| 12-807 | 4-F-Ph | 2-MeNH-4-Pym | ring 30 | 2-Cl |
| 12-808 | 4-F-Ph | 2-MeNH-4-Pym | ring 31 | 2-Cl |
| 12-809 | 4-F-Ph | 2-MeNH-4-Pym | ring 32 | 2-Cl |
| 12-810 | 4-F-Ph | 2-MeNH-4-Pym | ring 33 | 2-Cl |
| 12-811 | 4-F-Ph | 2-MeNH-4-Pym | ring 34 | 2-Cl |
| 12-812 | 4-F-Ph | 2-MeNH-4-Pym | ring 35 | 2-Cl |
| 12-813 | 4-F-Ph | 2-MeNH-4-Pym | ring 36 | 2-Cl |
| 12-814 | 4-F-Ph | 2-MeNH-4-Pym | ring 37 | 2-Cl |
| 12-815 | 4-F-Ph | 2-MeNH-4-Pym | ring 1 | 2,2-diF |
| 12-816 | 4-F-Ph | 2-MeNH-4-Pym | ring 2 | 2,2-diF |
| 12-817 | 4-F-Ph | 2-MeNH-4-Pym | ring 3 | 2,2-diF |
| 12-818 | 4-F-Ph | 2-MeNH-4-Pym | ring 4 | 2,2-diF |
| 12-819 | 4-F-Ph | 2-MeNH-4-Pym | ring 5 | 2,2-diF |
| 12-820 | 4-F-Ph | 2-MeNH-4-Pym | ring 6 | 2,2-diF |
| 12-821 | 4-F-Ph | 2-MeNH-4-Pym | ring 7 | 2,2-diF |
| 12-822 | 4-F-Ph | 2-MeNH-4-Pym | ring 8 | 2,2-diF |
| 12-823 | 4-F-Ph | 2-MeNH-4-Pym | ring 9 | 2,2-diF |
| 12-824 | 4-F-Ph | 2-MeNH-4-Pym | ring 10 | 2,2-diF |
| 12-825 | 4-F-Ph | 2-MeNH-4-Pym | ring 11 | 2,2-diF |
| 12-826 | 4-F-Ph | 2-MeNH-4-Pym | ring 12 | 2,2-diF |
| 12-827 | 4-F-Ph | 2-MeNH-4-Pym | ring 13 | 2,2-diF |
| 12-828 | 4-F-Ph | 2-MeNH-4-Pym | ring 14 | 2,2-diF |
| 12-829 | 4-F-Ph | 2-MeNH-4-Pym | ring 15 | 2,2-diF |
| 12-830 | 4-F-Ph | 2-MeNH-4-Pym | ring 16 | 2,2-diF |
| 12-831 | 4-F-Ph | 2-MeNH-4-Pym | ring 17 | 2,2-diF |
| 12-832 | 4-F-Ph | 2-MeNH-4-Pym | ring 18 | 2,2-diF |
| 12-833 | 4-F-Ph | 2-MeNH-4-Pym | ring 19 | 2,2-diF |
| 12-834 | 4-F-Ph | 2-MeNH-4-Pym | ring 20 | 2,2-diF |
| 12-835 | 4-F-Ph | 2-MeNH-4-Pym | ring 21 | 2,2-diF |
| 12-836 | 4-F-Ph | 2-MeNH-4-Pym | ring 22 | 2,2-diF |
| 12-837 | 4-F-Ph | 2-MeNH-4-Pym | ring 23 | 2,2-diF |
| 12-838 | 4-F-Ph | 2-MeNH-4-Pym | ring 24 | 2,2-diF |
| 12-839 | 4-F-Ph | 2-MeNH-4-Pym | ring 25 | 2,2-diF |

TABLE 12-continued

| Compound No. | R¹ | R² | A | R⁵ |
|---|---|---|---|---|
| 12-840 | 4-F-Ph | 2-MeNH-4-Pym | ring 26 | 2,2-diF |
| 12-841 | 4-F-Ph | 2-MeNH-4-Pym | ring 27 | 2,2-diF |
| 12-842 | 4-F-Ph | 2-MeNH-4-Pym | ring 28 | 2,2-diF |
| 12-843 | 4-F-Ph | 2-MeNH-4-Pym | ring 29 | 2,2-diF |
| 12-844 | 4-F-Ph | 2-MeNH-4-Pym | ring 30 | 2,2-diF |
| 12-845 | 4-F-Ph | 2-MeNH-4-Pym | ring 31 | 2,2-diF |
| 12-846 | 4-F-Ph | 2-MeNH-4-Pym | ring 32 | 2,2-diF |
| 12-847 | 4-F-Ph | 2-MeNR-4-Pym | ring 33 | 2,2-diF |
| 12-848 | 4-F-Ph | 2-MeNH-4-Pym | ring 34 | 2,2-diF |
| 12-849 | 4-F-Ph | 2-MeNH-4-Pym | ring 35 | 2,2-diF |
| 12-850 | 4-F-Ph | 2-MeNH-4-Pym | ring 36 | 2,2-diF |
| 12-851 | 4-F-Ph | 2-MeNH-4-Pym | ring 37 | 2,2-diF |
| 12-852 | 4-F-Ph | 2-MeNH-4-Pym | ring 1 | 8-Me |
| 12-853 | 4-F-Ph | 2-MeNH-4-Pym | ring 2 | 8-Me |
| 12-854 | 4-F-Ph | 2-MeNH-4-Pym | ring 3 | 8-Me |
| 12-855 | 4-F-Ph | 2-MeNH-4-Pym | ring 4 | 8-Me |
| 12-856 | 4-F-Ph | 2-MeNH-4-Pym | ring 5 | 8-Me |
| 12-857 | 4-F-Ph | 2-MeNH-4-Pym | ring 6 | 8-Me |
| 12-858 | 4-F-Ph | 2-MeNH-4-Pym | ring 7 | 8-Me |
| 12-859 | 4-F-Ph | 2-MeNH-4-Pym | ring 8 | 8-Me |
| 12-860 | 4-F-Ph | 2-MeNH-4-Pym | ring 9 | 8-Me |
| 12-861 | 4-F-Ph | 2-MeNH-4-Pym | ring 10 | 8-Me |
| 12-862 | 4-F-Ph | 2-MeNH-4-Pym | ring 11 | 8-Me |
| 12-863 | 4-F-Ph | 2-MeNH-4-Pym | ring 12 | 8-Me |
| 12-864 | 4-F-Ph | 2-MeNH-4-Pym | ring 13 | 8-Me |
| 12-865 | 4-F-Ph | 2-MeNH-4-Pym | ring 14 | 8-Me |
| 12-866 | 4-F-Ph | 2-MeNH-4-Pym | ring 15 | 8-Me |
| 12-867 | 4-F-Ph | 2-MeNH-4-Pym | ring 16 | 8-Me |
| 12-868 | 4-F-Ph | 2-MeNH-4-Pym | ring 17 | 8-Me |
| 12-869 | 4-F-Ph | 2-MeNH-4-Pym | ring 18 | 8-Me |
| 12-870 | 4-F-Ph | 2-MeNH-4-Pym | ring 19 | 8-Me |
| 12-871 | 4-F-Ph | 2-MeNH-4-Pym | ring 20 | 8-Me |
| 12-872 | 4-F-Ph | 2-MeNH-4-Pym | ring 21 | 8-Me |
| 12-873 | 4-F-Ph | 2-MeNH-4-Pym | ring 22 | 8-Me |
| 12-874 | 4-F-Ph | 2-MeNH-4-Pym | ring 23 | 8-Me |
| 12-875 | 4-F-Ph | 2-MeNH-4-Pym | ring 24 | 8-Me |
| 12-876 | 4-F-Ph | 2-MeNH-4-Pym | ring 25 | 8-Me |
| 12-877 | 4-F-Ph | 2-MeNH-4-Pym | ring 26 | 8-Me |
| 12-878 | 4-F-Ph | 2-MeNH-4-Pym | ring 27 | 8-Me |
| 12-879 | 4-F-Ph | 2-MeNH-4-Pym | ring 28 | 8-Me |
| 12-880 | 4-F-Ph | 2-MeNH-4-Pym | ring 29 | 8-Me |
| 12-881 | 4-F-Ph | 2-MeNH-4-Pym | ring 30 | 8-Me |
| 12-882 | 4-F-Ph | 2-MeNH-4-Pym | ring 31 | 8-Me |
| 12-883 | 4-F-Ph | 2-MeNH-4-Pym | ring 32 | 8-Me |
| 12-884 | 4-F-Ph | 2-MeNH-4-Pym | ring 33 | 8-Me |
| 12-885 | 4-F-Ph | 2-MeNH-4-Pym | ring 34 | 8-Me |
| 12-886 | 4-F-Ph | 2-MeNH-4-Pym | ring 35 | 8-Me |
| 12-887 | 4-F-Ph | 2-MeNH-4-Pym | ring 36 | 8-Me |
| 12-888 | 4-F-Ph | 2-MeNH-4-Pym | ring 37 | 8-Me |
| 12-889 | 4-F-Ph | 2-(α-Me-BnNH)-4-Pym | ring 1 | — |
| 12-890 | 4-F-Ph | 2-(α-Me-BnNH)-4-Pym | ring 2 | — |
| 12-891 | 4-F-Ph | 2-(α-Me-BnNH)-4-Pym | ring 3 | — |
| 12-892 | 4-F-Ph | 2-(α-Me-BnNH)-4-Pym | ring 4 | — |
| 12-893 | 4-F-Ph | 2-(α-Me-BnNH)-4-Pym | ring 5 | — |
| 12-894 | 4-F-Ph | 2-(α-Me-BnNH)-4-Pym | ring 6 | — |
| 12-895 | 4-F-Ph | 2-(α-Me-BnNH)-4-Pym | ring 7 | — |
| 12-896 | 4-F-Ph | 2-(α-Me-BnNH)-4-Pym | ring 8 | — |
| 12-897 | 4-F-Ph | 2-(α-Me-BnNH)-4-Pym | ring 9 | — |
| 12-898 | 4-F-Ph | 2-(α-Me-BnNH)-4-Pym | ring 10 | — |
| 12-899 | 4-F-Ph | 2-(α-Me-BnNH)-4-Pym | ring 11 | — |
| 12-900 | 4-F-Ph | 2-(α-Me-BnNH)-4-Pym | ring 12 | — |
| 12-901 | 4-F-Ph | 2-(α-Me-BnNH)-4-Pym | ring 13 | — |
| 12-902 | 4-F-Ph | 2-(α-Me-BnNH)-4-Pym | ring 14 | — |
| 12-903 | 4-F-Ph | 2-(α-Me-BnNH)-4-Pym | ring 15 | — |
| 12-904 | 4-F-Ph | 2-(α-Me-BnNH)-4-Pym | ring 16 | — |
| 12-905 | 4-F-Ph | 2-(α-Me-BnNH)-4-Pym | ring 17 | — |
| 12-906 | 4-F-Ph | 2-(α-Me-BnNH)-4-Pym | ring 18 | — |
| 12-907 | 4-F-Ph | 2-(α-Me-BnNH)-4-Pym | ring 19 | — |
| 12-908 | 4-F-Ph | 2-(α-Me-BnNH)-4-Pym | ring 20 | — |
| 12-909 | 4-F-Ph | 2-(α-Me-BnNH)-4-Pym | ring 21 | — |
| 12-910 | 4-F-Ph | 2-(α-Me-BnNH)-4-Pym | ring 22 | — |
| 12-911 | 4-F-Ph | 2-(α-Me-BnNH)-4-Pym | ring 23 | — |
| 12-912 | 4-F-Ph | 2-(α-Me-BnNH)-4-Pym | ring 24 | — |
| 12-913 | 4-F-Ph | 2-(α-Me-BnNH)-4-Pym | ring 25 | — |
| 12-914 | 4-F-Ph | 2-(α-Me-BnNH)-4-Pym | ring 26 | — |
| 12-915 | 4-F-Ph | 2-(α-Me-BnNH)-4-Pym | ring 27 | — |
| 12-916 | 4-F-Ph | 2-(α-Me-BnNH)-4-Pym | ring 28 | — |
| 12-917 | 4-F-Ph | 2-(α-Me-BnNH)-4-Pym | ring 29 | — |
| 12-918 | 4-F-Ph | 2-(α-Me-BnNH)-4-Pym | ring 30 | — |
| 12-919 | 4-F-Ph | 2-(α-Me-BnNH)-4-Pym | ring 31 | — |
| 12-920 | 4-F-Ph | 2-(α-Me-BnNH)-4-Pym | ring 32 | — |
| 12-921 | 4-F-Ph | 2-(α-Me-BnNH)-4-Pym | ring 33 | — |
| 12-922 | 4-F-Ph | 2-(α-Me-BnNH)-4-Pym | ring 34 | — |
| 12-923 | 4-F-Ph | 2-(α-Me-BnNH)-4-Pym | ring 35 | — |
| 12-924 | 4-F-Ph | 2-(α-Me-BnNH)-4-Pym | ring 36 | — |
| 12-925 | 4-F-Ph | 2-(α-Me-BnNH)-4-Pym | ring 37 | — |
| 12-926 | 4-F-Ph | 2-(α-Me-BnNH)-4-Pym | ring 1 | 2-Me |
| 12-927 | 4-F-Ph | 2-(α-Me-BnNH)-4-Pym | ring 2 | 2-Me |
| 12-928 | 4-F-Ph | 2-(α-Me-BnNH)-4-Pym | ring 3 | 2-Me |
| 12-929 | 4-F-Ph | 2-(α-Me-BnNH)-4-Pym | ring 4 | 2-Me |
| 12-930 | 4-F-Ph | 2-(α-Me-BnNH)-4-Pym | ring 5 | 2-Me |
| 12-931 | 4-F-Ph | 2-(α-Me-BnNH)-4-Pym | ring 6 | 2-Me |
| 12-932 | 4-F-Ph | 2-(α-Me-BnNH)-4-Pym | ring 7 | 2-Me |
| 12-933 | 4-F-Ph | 2-(α-Me-BnNH)-4-Pym | ring 8 | 2-Me |
| 12-934 | 4-F-Ph | 2-(α-Me-BnNH)-4-Pym | ring 9 | 2-Me |
| 12-935 | 4-F-Ph | 2-(α-Me-BnNH)-4-Pym | ring 10 | 2-Me |
| 12-936 | 4-F-Ph | 2-(α-Me-BnNR)-4-Pym | ring 11 | 2-Me |
| 12-937 | 4-F-Ph | 2-(α-Me-BnNH)-4-Pym | ring 12 | 2-Me |
| 12-938 | 4-F-Ph | 2-(α-Me-BnNH)-4-Pym | ring 13 | 2-Me |
| 12-939 | 4-F-Ph | 2-(α-Me-BnNH)-4-Pym | ring 14 | 2-Me |
| 12-940 | 4-F-Ph | 2-(α-Me-BnNH)-4-Pym | ring 15 | 2-Me |
| 12-941 | 4-F-Ph | 2-(α-Me-BnNH)-4-Pym | ring 16 | 2-Me |
| 12-942 | 4-F-Ph | 2-(α-Me-BnNH)-4-Pym | ring 17 | 2-Me |
| 12-943 | 4-F-Ph | 2-(α-Me-BnNH)-4-Pym | ring 18 | 2-Me |
| 12-944 | 4-F-Ph | 2-(α-Me-BnNH)-4-Pym | ring 19 | 2-Me |
| 12-945 | 4-F-Ph | 2-(α-Me-BnNH)-4-Pym | ring 20 | 2-Me |
| 12-946 | 4-F-Ph | 2-(α-Me-BnNH)-4-Pym | ring 21 | 2-Me |
| 12-947 | 4-F-Ph | 2-(α-Me-BnNH)-4-Pym | ring 22 | 2-Me |
| 12-948 | 4-F-Ph | 2-(α-Me-BnNH)-4-Pym | ring 23 | 2-Me |
| 12-949 | 4-F-Ph | 2-(α-Me-BnNH)-4-Pym | ring 24 | 2-Me |
| 12-950 | 4-F-Ph | 2-(α-Me-BnNH)-4-Pym | ring 25 | 2-Me |
| 12-951 | 4-F-Ph | 2-(α-Me-BnNH)-4-Pym | ring 26 | 2-Me |
| 12-952 | 4-F-Ph | 2-(α-Me-BnNH)-4-Pym | ring 27 | 2-Me |
| 12-953 | 4-F-Ph | 2-(α-Me-BnNH)-4-Pym | ring 28 | 2-Me |
| 12-954 | 4-F-Ph | 2-(α-Me-BnNH)-4-Pym | ring 29 | 2-Me |
| 12-955 | 4-F-Ph | 2-(α-Me-BnNH)-4-Pym | ring 30 | 2-Me |
| 12-956 | 4-F-Ph | 2-(α-Me-BnNH)-4-Pym | ring 31 | 2-Me |
| 12-957 | 4-F-Ph | 2-(α-Me-BnNH)-4-Pym | ring 32 | 2-Me |
| 12-958 | 4-F-Ph | 2-(α-Me-BnNH)-4-Pym | ring 33 | 2-Me |
| 12-959 | 4-F-Ph | 2-(α-Me-BnNH)-4-Pym | ring 34 | 2-Me |
| 12-960 | 4-F-Ph | 2-(α-Me-BnNH)-4-Pym | ring 35 | 2-Me |
| 12-961 | 4-F-Ph | 2-(α-Me-BnNH)-4-Pym | ring 36 | 2-Me |
| 12-962 | 4-F-Ph | 2-(α-Me-BnNH)-4-Pym | ring 37 | 2-Me |
| 12-963 | 4-F-Ph | 2-(α-Me-BnNH)-4-Pym | ring 1 | 2-OH |
| 12-964 | 4-F-Ph | 2-(α-Me-BnNH)-4-Pym | ring 2 | 2-OH |
| 12-965 | 4-F-Ph | 2-(α-Me-BnNH)-4-Pym | ring 3 | 2-OH |
| 12-966 | 4-F-Ph | 2-(α-Me-BnNH)-4-Pym | ring 4 | 2-OH |
| 12-967 | 4-F-Ph | 2-(α-Me-BnNH)-4-Pym | ring 5 | 2-OH |
| 12-968 | 4-F-Ph | 2-(α-Me-BnNH)-4-Pym | ring 6 | 2-OH |
| 12-969 | 4-F-Ph | 2-(α-Me-BnNH)-4-Pym | ring 7 | 2-OH |
| 12-970 | 4-F-Ph | 2-(α-Me-BnNH)-4-Pym | ring 8 | 2-OH |
| 12-971 | 4-F-Ph | 2-(α-Me-BnNH)-4-Pym | ring 9 | 2-OH |

TABLE 12-continued

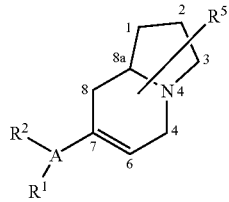

| Compound No. | R¹ | R² | A | R⁵ |
|---|---|---|---|---|
| 12-972 | 4-F-Ph | 2-(α-Me-BnNH)-4-Pym | ring 10 | 2-OH |
| 12-973 | 4-F-Ph | 2-(α-Me-BnNH)-4-Pym | ring 11 | 2-OH |
| 12-974 | 4-F-Ph | 2-(α-Me-BnNH)-4-Pym | ring 12 | 2-OH |
| 12-975 | 4-F-Ph | 2-(α-Me-BnNH)-4-Pym | ring 13 | 2-OH |
| 12-976 | 4-F-Ph | 2-(α-Me-BnNH)-4-Pym | ring 14 | 2-OH |
| 12-977 | 4-F-Ph | 2-(α-Me-BnNH)-4-Pym | ring 15 | 2-OH |
| 12-978 | 4-F-Ph | 2-(α-Me-BnNH)-4-Pym | ring 16 | 2-OH |
| 12-979 | 4-F-Ph | 2-(α-Me-BnNH)-4-Pym | ring 17 | 2-OH |
| 12-980 | 4-F-Ph | 2-(α-Me-BnNH)-4-Pym | ring 18 | 2-OH |
| 12-981 | 4-F-Ph | 2-(α-Me-BnMI)-4-Pym | ring 19 | 2-OH |
| 12-982 | 4-F-Ph | 2-(α-Me-BnNH)-4-Pym | ring 20 | 2-OH |
| 12-983 | 4-F-Ph | 2-(α-Me-BnNH)-4-Pym | ring 21 | 2-OH |
| 12-984 | 4-F-Ph | 2-(α-Me-BnNH)-4-Pym | ring 22 | 2-OH |
| 12-985 | 4-F-Ph | 2-(α-Me-BnNH)-4-Pym | ring 23 | 2-OH |
| 12-986 | 4-F-Ph | 2-(α-Me-BnNH)-4-Pym | ring 24 | 2-OH |
| 12-987 | 4-F-Ph | 2-(α-Me-BnNH)-4-Pym | ring 25 | 2-OH |
| 12-988 | 4-F-Ph | 2-(α-Me-BnNH)-4-Pym | ring 26 | 2-OH |
| 12-989 | 4-F-Ph | 2-(α-Me-BnNH)-4-Pym | ring 27 | 2-OH |
| 12-990 | 4-F-Ph | 2-(α-Me-BnNH)-4-Pym | ring 28 | 2-OH |
| 12-991 | 4-F-Ph | 2-(α-Me-BnNH)-4-Pym | ring 29 | 2-OH |
| 12-992 | 4-F-Ph | 2-(α-Me-BnNH)-4-Pym | ring 30 | 2-OH |
| 12-993 | 4-F-Ph | 2-(α-Me-BnNH)-4-Pym | ring 31 | 2-OH |
| 12-994 | 4-F-Ph | 2-(α-Me-BnNH)-4-Pym | ring 32 | 2-OH |
| 12-995 | 4-F-Ph | 2-(α-Me-BnNH)-4-Pym | ring 33 | 2-OH |
| 12-996 | 4-F-Ph | 2-(α-Me-BnNH)-4-Pym | ring 34 | 2-OH |
| 12-997 | 4-F-Ph | 2-(α-Me-BnNH)-4-Pym | ring 35 | 2-OH |
| 12-998 | 4-F-Ph | 2-(α-Me-BnNH)-4-Pym | ring 36 | 2-OH |
| 12-999 | 4-F-Ph | 2-(α-Me-BnNH)-4-Pym | ring 37 | 2-OH |
| 12-1000 | 4-F-Ph | 2-(α-Me-BnNH)-4-Pym | ring 1 | 2-MeO |
| 12-1001 | 4-F-Ph | 2-(α-Me-BnNH)-4-Pym | ring 2 | 2-MeO |
| 12-1002 | 4-F-Ph | 2-(α-Me-BnNH)-4-Pym | ring 3 | 2-MeO |
| 12-1003 | 4-F-Ph | 2-(α-Me-BnNH)-4-Pym | ring 4 | 2-MeO |
| 12-1004 | 4-F-Ph | 2-(α-Me-BnNH)-4-Pym | ring 5 | 2-MeO |
| 12-1005 | 4-F-Ph | 2-(α-Me-BnNH)-4-Pym | ring 6 | 2-MeO |
| 12-1006 | 4-F-Ph | 2-(α-Me-BnNH)-4-Pym | ring 7 | 2-MeO |
| 12-1007 | 4-F-Ph | 2-(α-Me-BnNH)-4-Pym | ring 8 | 2-MeO |
| 12-1008 | 4-F-Ph | 2-(α-Me-BnNH)-4-Pym | ring 9 | 2-MeO |
| 12-1009 | 4-F-Ph | 2-(α-Me-BnNH)-4-Pym | ring 10 | 2-MeO |
| 12-1010 | 4-F-Ph | 2-(α-Me-BnNH)-4-Pym | ring 11 | 2-MeO |
| 12-1011 | 4-F-Ph | 2-(α-Me-BnNH)-4-Pym | ring 12 | 2-MeO |
| 12-1012 | 4-F-Ph | 2-(α-Me-BnNH)-4-Pym | ring 13 | 2-MeO |
| 12-1013 | 4-F-Ph | 2-(α-Me-BnNH)-4-Pym | ring 14 | 2-MeO |
| 12-1014 | 4-F-Ph | 2-(α-Me-BnNH)-4-Pym | ring 15 | 2-MeO |
| 12-1015 | 4-F-Ph | 2-(α-Me-BnNH)-4-Pym | ring 16 | 2-MeO |
| 12-1016 | 4-F-Ph | 2-(α-Me-BnNH)-4-Pym | ring 17 | 2-MeO |
| 12-1017 | 4-F-Ph | 2-(α-Me-BnNH)-4-Pym | ring 18 | 2-MeO |
| 12-1018 | 4-F-Ph | 2-(α-Me-BnNH)-4-Pym | ring 19 | 2-MeO |
| 12-1019 | 4-F-Ph | 2-(α-Me-BnNH)-4-Pym | ring 20 | 2-MeO |
| 12-1020 | 4-F-Ph | 2-(α-Me-BnNH)-4-Pym | ring 21 | 2-MeO |
| 12-1021 | 4-F-Ph | 2-(α-Me-BnNH)-4-Pym | ring 22 | 2-MeO |
| 12-1022 | 4-F-Ph | 2-(α-Me-BnNH)-4-Pym | ring 23 | 2-MeO |
| 12-1023 | 4-F-Ph | 2-(α-Me-BnNH)-4-Pym | ring 24 | 2-MeO |
| 12-1024 | 4-F-Ph | 2-(α-Me-BnNH)-4-Pym | ring 25 | 2-MeO |
| 12-1025 | 4-F-Ph | 2-(α-Me-BnNH)-4-Pym | ring 26 | 2-MeO |
| 12-1026 | 4-F-Ph | 2-(α-Me-BnNH)-4-Pym | ring 27 | 2-MeO |
| 12-1027 | 4-F-Ph | 2-(α-Me-BnNH)-4-Pym | ring 28 | 2-MeO |
| 12-1028 | 4-F-Ph | 2-(α-Me-BnNH)-4-Pym | ring 29 | 2-MeO |
| 12-1029 | 4-F-Ph | 2-(α-Me-BnNH)-4-Pym | ring 30 | 2-MeO |
| 12-1030 | 4-F-Ph | 2-(α-Me-BnNH)-4-Pym | ring 31 | 2-MeO |
| 12-1031 | 4-F-Ph | 2-(α-Me-BnNH)-4-Pym | ring 32 | 2-MeO |
| 12-1032 | 4-F-Ph | 2-(α-Me-BnNH)-4-Pym | ring 33 | 2-MeO |
| 12-1033 | 4-F-Ph | 2-(α-Me-BnNH)-4-Pym | ring 34 | 2-MeO |
| 12-1034 | 4-F-Ph | 2-(α-Me-BnNH)-4-Pym | ring 35 | 2-MeO |
| 12-1035 | 4-F-Ph | 2-(α-Me-BnNH)-4-Pym | ring 36 | 2-MeO |
| 12-1036 | 4-F-Ph | 2-(α-Me-BnNH)-4-Pym | ring 37 | 2-MeO |
| 12-1037 | 4-F-Ph | 2-(α-Me-BnNH)-4-Pym | ring 1 | 2-F |

TABLE 12-continued

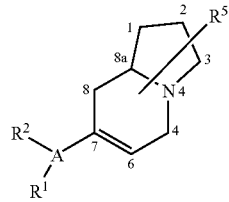

| Compound No. | R¹ | R² | A | R⁵ |
|---|---|---|---|---|
| 12-1038 | 4-F-Ph | 2-(α-Me-BnNH)-4-Pym | ring 2 | 2-F |
| 12-1039 | 4-F-Ph | 2-(α-Me-BnNH)-4-Pym | ring 3 | 2-F |
| 12-1040 | 4-F-Ph | 2-(α-Me-BnNH)-4-Pym | ring 4 | 2-F |
| 12-1041 | 4-F-Ph | 2-(α-Me-BnNH)-4-Pym | ring 5 | 2-F |
| 12-1042 | 4-F-Ph | 2-(α-Me-BnNH)-4-Pym | ring 6 | 2-F |
| 12-1043 | 4-F-Ph | 2-(α-Me-BnNH)-4-Pym | ring 7 | 2-F |
| 12-1044 | 4-F-Ph | 2-(α-Me-BnNH)-4-Pym | ring 8 | 2-F |
| 12-1045 | 4-F-Ph | 2-(α-Me-BnNH)-4-Pym | ring 9 | 2-F |
| 12-1046 | 4-F-Ph | 2-(α-Me-BnNH)-4-Pym | ring 10 | 2-F |
| 12-1047 | 4-F-Ph | 2-(α-Me-BnNH)-4-Pym | ring 11 | 2-F |
| 12-1048 | 4-F-Ph | 2-(α-Me-BnNH)-4-Pym | ring 12 | 2-F |
| 12-1049 | 4-F-Ph | 2-(α-Me-BnNH)-4-Pym | ring 13 | 2-F |
| 12-1050 | 4-F-Ph | 2-(α-Me-BnNH)-4-Pym | ring 14 | 2-F |
| 12-1051 | 4-F-Ph | 2-(α-Me-BnNH)-4-Pym | ring 15 | 2-F |
| 12-1052 | 4-F-Ph | 2-(α-Me-BnNH)-4-Pym | ring 16 | 2-F |
| 12-1053 | 4-F-Ph | 2-(α-Me-BnNH)-4-Pym | ring 17 | 2-F |
| 12-1054 | 4-F-Ph | 2-(α-Me-BnNH)-4-Pym | ring 18 | 2-F |
| 12-1055 | 4-F-Ph | 2-(α-Me-BnNH)-4-Pym | ring 19 | 2-F |
| 12-1056 | 4-F-Ph | 2-(α-Me-BnNH)-4-Pym | ring 20 | 2-F |
| 12-1057 | 4-F-Ph | 2-(α-Me-BnNH)-4-Pym | ring 21 | 2-F |
| 12-1058 | 4-F-Ph | 2-(α-Me-BnNH)-4-Pym | ring 22 | 2-F |
| 12-1059 | 4-F-Ph | 2-(α-Me-BnNH)-4-Pym | ring 23 | 2-F |
| 12-1060 | 4-F-Ph | 2-(α-Me-BnNH)-4-Pym | ring 24 | 2-F |
| 12-1061 | 4-F-Ph | 2-(α-Me-BnNH)-4-Pym | ring 25 | 2-F |
| 12-1062 | 4-F-Ph | 2-(α-Me-BnNH)-4-Pym | ring 26 | 2-F |
| 12-1063 | 4-F-Ph | 2-(α-Me-BnNH)-4-Pym | ring 27 | 2-F |
| 12-1064 | 4-F-Ph | 2-(α-Me-BnNH)-4-Pym | ring 28 | 2-F |
| 12-1065 | 4-F-Ph | 2-(α-Me-BnNH)-4-Pym | ring 29 | 2-F |
| 12-1066 | 4-F-Ph | 2-(α-Me-BnNH)-4-Pym | ring 30 | 2-F |
| 12-1067 | 4-F-Ph | 2-(α-Me-BnNH)-4-Pym | ring 31 | 2-F |
| 12-1068 | 4-F-Ph | 2-(α-Me-BnNH)-4-Pym | ring 32 | 2-F |
| 12-1069 | 4-F-Ph | 2-(α-Me-BnNH)-4-Pym | ring 33 | 2-F |
| 12-1070 | 4-F-Ph | 2-(α-Me-BnNH)-4-Pym | ring 34 | 2-F |
| 12-1071 | 4-F-Ph | 2-(α-Me-BnNH)-4-Pym | ring 35 | 2-F |
| 12-1072 | 4-F-Ph | 2-(α-Me-BnNH)-4-Pym | ring 36 | 2-F |
| 12-1073 | 4-F-Ph | 2-(α-Me-BnNH)-4-Pym | ring 37 | 2-F |
| 12-1074 | 4-F-Ph | 2-(α-Me-BnNH)-4-Pym | ring 1 | 2-Cl |
| 12-1075 | 4-F-Ph | 2-(α-Me-BnNH)-4-Pym | ring 2 | 2-Cl |
| 12-1076 | 4-F-Ph | 2-(α-Me-BnNH)-4-Pym | ring 3 | 2-Cl |
| 12-1077 | 4-F-Ph | 2-(α-Me-BnNH)-4-Pym | ring 4 | 2-Cl |
| 12-1078 | 4-F-Ph | 2-(α-Me-BnNH)-4-Pym | ring 5 | 2-Cl |
| 12-1079 | 4-F-Ph | 2-(α-Me-BnNH)-4-Pym | ring 6 | 2-Cl |
| 12-1080 | 4-F-Ph | 2-(α-Me-BnNH)-4-Pym | ring 7 | 2-Cl |
| 12-1081 | 4-F-Ph | 2-(α-Me-BnNH)-4-Pym | ring 8 | 2-Cl |
| 12-1082 | 4-F-Ph | 2-(α-Me-BnNH)-4-Pym | ring 9 | 2-Cl |
| 12-1083 | 4-F-Ph | 2-(α-Me-BnNH)-4-Pym | ring 10 | 2-Cl |
| 12-1084 | 4-F-Ph | 2-(α-Me-BnNH)-4-Pym | ring 11 | 2-Cl |
| 12-1085 | 4-F-Ph | 2-(α-Me-BnNH)-4-Pym | ring 12 | 2-Cl |
| 12-1086 | 4-F-Ph | 2-(α-Me-BnNH)-4-Pym | ring 13 | 2-Cl |
| 12-1087 | 4-F-Ph | 2-(α-Me-BnNH)-4-Pym | ring 14 | 2-Cl |
| 12-1088 | 4-F-Ph | 2-(α-Me-BnNH)-4-Pym | ring 15 | 2-Cl |
| 12-1089 | 4-F-Ph | 2-(α-Me-BnNH)-4-Pym | ring 16 | 2-Cl |
| 12-1090 | 4-F-Ph | 2-(α-Me-BnNH)-4-Pym | ring 17 | 2-Cl |
| 12-1091 | 4-F-Ph | 2-(α-Me-BnNH)-4-Pym | ring 18 | 2-Cl |
| 12-1092 | 4-F-Ph | 2-(α-Me-BnNH)-4-Pym | ring 19 | 2-Cl |
| 12-1093 | 4-F-Ph | 2-(α-Me-BnNH)-4-Pym | ring 20 | 2-Cl |
| 12-1094 | 4-F-Ph | 2-(α-Me-BnNH)-4-Pym | ring 21 | 2-Cl |
| 12-1095 | 4-F-Ph | 2-(α-Me-BnNH)-4-Pym | ring 22 | 2-Cl |
| 12-1096 | 4-F-Ph | 2-(α-Me-BnNH)-4-Pym | ring 23 | 2-Cl |
| 12-1097 | 4-F-Ph | 2-(α-Me-BnNH)-4-Pym | ring 24 | 2-Cl |
| 12-1098 | 4-F-Ph | 2-(α-Me-BnNH)-4-Pym | ring 25 | 2-Cl |
| 12-1099 | 4-F-Ph | 2-(α-Me-BnNH)-4-Pym | ring 26 | 2-Cl |
| 12-1100 | 4-F-Ph | 2-(α-Me-BnNH)-4-Pym | ring 27 | 2-Cl |
| 12-1101 | 4-F-Ph | 2-(α-Me-BnNH)-4-Pym | ring 28 | 2-Cl |
| 12-1102 | 4-F-Ph | 2-(α-Me-BnNH)-4-Pym | ring 29 | 2-Cl |
| 12-1103 | 4-F-Ph | 2-(α-Me-BnNH)-4-Pym | ring 30 | 2-Cl |

TABLE 12-continued

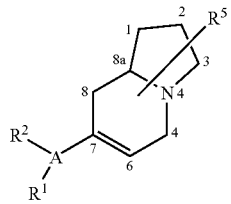

| Compound No. | R¹ | R² | A | R⁵ |
|---|---|---|---|---|
| 12-1104 | 4-F-Ph | 2-(α-Me-BnNH)-4-Pym | ring 31 | 2-Cl |
| 12-1105 | 4-F-Ph | 2-(α-Me-BnNH)-4-Pym | ring 32 | 2-Cl |
| 12-1106 | 4-F-Ph | 2-(α-Me-BnNH)-4-Pym | ring 33 | 2-Cl |
| 12-1107 | 4-F-Ph | 2-(α-Me-BnNH)-4-Pym | ring 34 | 2-Cl |
| 12-1108 | 4-F-Ph | 2-(α-Me-BnNH)-4-Pym | ring 35 | 2-Cl |
| 12-1109 | 4-F-Ph | 2-(α-Me-BnNH)-4-Pym | ring 36 | 2-Cl |
| 12-1110 | 4-F-Ph | 2-(α-Me-BnNH)-4-Pym | ring 37 | 2-Cl |
| 12-1111 | 4-F-Ph | 2-(α-Me-BnNH)-4-Pym | ring 1 | 2,2-diF |
| 12-1112 | 4-F-Ph | 2-(α-Me-BnNH)-4-Pym | ring 2 | 2,2-diF |
| 12-1113 | 4-F-Ph | 2-(α-Me-BnNH)-4-Pym | ring 3 | 2,2-diF |
| 12-1114 | 4-F-Ph | 2-(α-Me-BnNH)-4-Pym | ring 4 | 2,2-diF |
| 12-1115 | 4-F-Ph | 2-(α-Me-BnNH)-4-Pym | ring 5 | 2,2-diF |
| 12-1116 | 4-F-Ph | 2-(α-Me-BnNH)-4-Pym | ring 6 | 2,2-diF |
| 12-1117 | 4-F-Ph | 2-(α-Me-BnNH)-4-Pym | ring 7 | 2,2-diF |
| 12-1118 | 4-F-Ph | 2-(α-Me-BnNH)-4-Pym | ring 8 | 2,2-diF |
| 12-1119 | 4-F-Ph | 2-(α-Me-BnNH)-4-Pym | ring 9 | 2,2-diF |
| 12-1120 | 4-F-Ph | 2-(α-Me-BnNH)-4-Pym | ring 10 | 2,2-diF |
| 12-1121 | 4-F-Ph | 2-(α-Me-BnNH)-4-Pym | ring 11 | 2,2-diF |
| 12-1122 | 4-F-Ph | 2-(α-Me-BnNH)-4-Pym | ring 12 | 2,2-diF |
| 12-1123 | 4-F-Ph | 2-(α-Me-BnNH)-4-Pym | ring 13 | 2,2-diF |
| 12-1124 | 4-F-Ph | 2-(α-Me-BnNH)-4-Pym | ring 14 | 2,2-diF |
| 12-1125 | 4-F-Ph | 2-(α-Me-BnNH)-4-Pym | ring 15 | 2,2-diF |
| 12-1126 | 4-F-Ph | 2-(α-Me-BnNH)-4-Pym | ring 16 | 2,2-diF |
| 12-1127 | 4-F-Ph | 2-(α-Me-BnNH)-4-Pym | ring 17 | 2,2-diF |
| 12-1128 | 4-F-Ph | 2-(α-Me-BnNH)-4-Pym | ring 18 | 2,2-diF |
| 12-1129 | 4-F-Ph | 2-(α-Me-BnNH)-4-Pym | ring 19 | 2,2-diF |
| 12-1130 | 4-F-Ph | 2-(α-Me-BnNH)-4-Pym | ring 20 | 2,2-diF |
| 12-1131 | 4-F-Ph | 2-(α-Me-BnNH)-4-Pym | ring 21 | 2,2-diF |
| 12-1132 | 4-F-Ph | 2-(α-Me-BnNH)-4-Pym | ring 22 | 2,2-diF |
| 12-1133 | 4-F-Ph | 2-(α-Me-BnNH)-4-Pym | ring 23 | 2,2-diF |
| 12-1134 | 4-F-Ph | 2-(α-Me-BnNH)-4-Pym | ring 24 | 2,2-diF |
| 12-1135 | 4-F-Ph | 2-(α-Me-BnNH)-4-Pym | ring 25 | 2,2-diF |
| 12-1136 | 4-F-Ph | 2-(α-Me-BnNH)-4-Pym | ring 26 | 2,2-diF |
| 12-1137 | 4-F-Ph | 2-(α-Me-BnNH)-4-Pym | ring 27 | 2,2-diF |
| 12-1138 | 4-F-Ph | 2-(α-Me-BnNH)-4-Pym | ring 28 | 2,2-diF |
| 12-1139 | 4-F-Ph | 2-(α-Me-BnNH)-4-Pym | ring 29 | 2,2-diF |
| 12-1140 | 4-F-Ph | 2-(α-Me-BnNH)-4-Pym | ring 30 | 2,2-diF |
| 12-1141 | 4-F-Ph | 2-(α-Me-BnNH)-4-Pym | ring 31 | 2,2-diF |
| 12-1142 | 4-F-Ph | 2-(α-Me-BnNH)-4-Pym | ring 32 | 2,2-diF |
| 12-1143 | 4-F-Ph | 2-(α-Me-BnNH)-4-Pym | ring 33 | 2,2-diF |
| 12-1144 | 4-F-Ph | 2-(α-Me-BnNH)-4-Pym | ring 34 | 2,2-diF |
| 12-1145 | 4-F-Ph | 2-(α-Me-BnNH)-4-Pym | ring 35 | 2,2-diF |
| 12-1146 | 4-F-Ph | 2-(α-Me-BnNH)-4-Pym | ring 36 | 2,2-diF |
| 12-1147 | 4-F-Ph | 2-(α-Me-BnNH)-4-Pym | ring 37 | 2,2-diF |
| 12-1148 | 4-F-Ph | 2-(α-Me-BnNH)-4-Pym | ring 1 | 8-Me |
| 12-1149 | 4-F-Ph | 2-(α-Me-BnNH)-4-Pym | ring 2 | 8-Me |
| 12-1150 | 4-F-Ph | 2-(α-Me-BnNH)-4-Pym | ring 3 | 8-Me |
| 12-1151 | 4-F-Ph | 2-(α-Me-BnNH)-4-Pym | ring 4 | 8-Me |
| 12-1152 | 4-F-Ph | 2-(α-Me-BnNH)-4-Pym | ring 5 | 8-Me |
| 12-1153 | 4-F-Ph | 2-(α-Me-BnNH)-4-Pym | ring 6 | 8-Me |
| 12-1154 | 4-F-Ph | 2-(α-Me-BnNH)-4-Pym | ring 7 | 8-Me |
| 12-1155 | 4-F-Ph | 2-(α-Me-BnNH)-4-Pym | ring 8 | 8-Me |
| 12-1156 | 4-F-Ph | 2-(α-Me-BnNH)-4-Pym | ring 9 | 8-Me |
| 12-1157 | 4-F-Ph | 2-(α-Me-BnNH)-4-Pym | ring 10 | 8-Me |
| 12-1158 | 4-F-Ph | 2-(α-Me-BnNH)-4-Pym | ring 11 | 8-Me |
| 12-1159 | 4-F-Ph | 2-(α-Me-BnNH)-4-Pym | ring 12 | 8-Me |
| 12-1160 | 4-F-Ph | 2-(α-Me-BnNH)-4-Pym | ring 13 | 8-Me |
| 12-1161 | 4-F-Ph | 2-(α-Me-BnNH)-4-Pym | ring 14 | 8-Me |
| 12-1162 | 4-F-Ph | 2-(α-Me-BnNH)-4-Pym | ring 15 | 8-Me |
| 12-1163 | 4-F-Ph | 2-(α-Me-BnNH)-4-Pym | ring 16 | 8-Me |
| 12-1164 | 4-F-Ph | 2-(α-Me-BnNH)-4-Pym | ring 17 | 8-Me |
| 12-1165 | 4-F-Ph | 2-(α-Me-BnNH)-4-Pym | ring 18 | 8-Me |
| 12-1166 | 4-F-Ph | 2-(α-Me-BnNH)-4-Pym | ring 19 | 8-Me |
| 12-1167 | 4-F-Ph | 2-(α-Me-BnNH)-4-Pym | ring 20 | 8-Me |
| 12-1168 | 4-F-Ph | 2-(α-Me-BnNH)-4-Pym | ring 21 | 8-Me |
| 12-1169 | 4-F-Ph | 2-(α-Me-BnNH)-4-Pym | ring 22 | 8-Me |

TABLE 12-continued

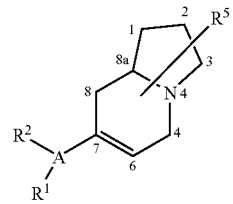

| Compound No. | R¹ | R² | A | R⁵ |
|---|---|---|---|---|
| 12-1170 | 4-F-Ph | 2-(α-Me-BnNH)-4-Pym | ring 23 | 8-Me |
| 12-1171 | 4-F-Ph | 2-(α-Me-BnNH)-4-Pym | ring 24 | 8-Me |
| 12-1172 | 4-F-Ph | 2-(α-Me-BnNH)-4-Pym | ring 25 | 8-Me |
| 12-1173 | 4-F-Ph | 2-(α-Me-BnNH)-4-Pym | ring 26 | 8-Me |
| 12-1174 | 4-F-Ph | 2-(α-Me-BnNH)-4-Pym | ring 27 | 8-Me |
| 12-1175 | 4-F-Ph | 2-(α-Me-BnNH)-4-Pym | ring 28 | 8-Me |
| 12-1176 | 4-F-Ph | 2-(α-Me-BnNH)-4-Pym | ring 29 | 8-Me |
| 12-1177 | 4-F-Ph | 2-(α-Me-BnNH)-4-Pym | ring 30 | 8-Me |
| 12-1178 | 4-F-Ph | 2-(α-Me-BnNH)-4-Pym | ring 31 | 8-Me |
| 12-1179 | 4-F-Ph | 2-(α-Me-BnNH)-4-Pym | ring 32 | 8-Me |
| 12-1180 | 4-F-Ph | 2-(α-Me-BnNH)-4-Pym | ring 33 | 8-Me |
| 12-1181 | 4-F-Ph | 2-(α-Me-BnNH)-4-Pym | ring 34 | 8-Me |
| 12-1182 | 4-F-Ph | 2-(α-Me-BnNH)-4-Pym | ring 35 | 8-Me |
| 12-1183 | 4-F-Ph | 2-(α-Me-BnNH)-4-Pym | ring 36 | 8-Me |
| 12-1184 | 4-F-Ph | 2-(α-Me-BnNH)-4-Pym | ring 37 | 8-Me |

TABLE 13

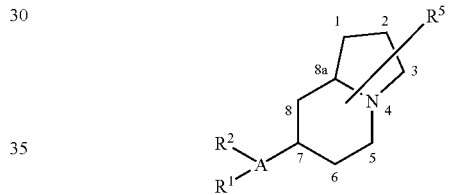

| Compound No. | R¹ | R² | A | R⁵ |
|---|---|---|---|---|
| 13-1 | 4-F-Ph | 4-Pyr | ring 1 | — |
| 13-2 | 4-F-Ph | 4-Pyr | ring 2 | — |
| 13-3 | 4-F-Ph | 4-Pyr | ring 3 | — |
| 13-4 | 4-F-Ph | 4-Pyr | ring 4 | — |
| 13-5 | 4-F-Ph | 4-Pyr | ring 5 | — |
| 13-6 | 4-F-Ph | 4-Pyr | ring 6 | — |
| 13-7 | 4-F-Ph | 4-Pyr | ring 7 | — |
| 13-8 | 4-F-Ph | 4-Pyr | ring 8 | — |
| 13-9 | 4-F-Ph | 4-Pyr | ring 9 | — |
| 13-10 | 4-F-Ph | 4-Pyr | ring 10 | — |
| 13-11 | 4-F-Ph | 4-Pyr | ring 11 | — |
| 13-12 | 4-F-Ph | 4-Pyr | ring 12 | — |
| 13-13 | 4-F-Ph | 4-Pyr | ring 13 | — |
| 13-14 | 4-F-Ph | 4-Pyr | ring 14 | — |
| 13-15 | 4-F-Ph | 4-Pyr | ring 15 | — |
| 13-16 | 4-F-Ph | 4-Pyr | ring 16 | — |
| 13-17 | 4-F-Ph | 4-Pyr | ring 17 | — |
| 13-18 | 4-F-Ph | 4-Pyr | ring 18 | — |
| 13-19 | 4-F-Ph | 4-Pyr | ring 19 | — |
| 13-20 | 4-F-Ph | 4-Pyr | ring 20 | — |
| 13-21 | 4-F-Ph | 4-Pyr | ring 21 | — |
| 13-22 | 4-F-Ph | 4-Pyr | ring 22 | — |
| 13-23 | 4-F-Ph | 4-Pyr | ring 23 | — |
| 13-24 | 4-F-Ph | 4-Pyr | ring 24 | — |
| 13-25 | 4-F-Ph | 4-Pyr | ring 25 | — |
| 13-26 | 4-F-Ph | 4-Pyr | ring 26 | — |
| 13-27 | 4-F-Ph | 4-Pyr | ring 27 | — |
| 13-28 | 4-F-Ph | 4-Pyr | ring 28 | — |
| 13-29 | 4-F-Ph | 4-Pyr | ring 29 | — |
| 13-30 | 4-F-Ph | 4-Pyr | ring 30 | — |
| 13-31 | 4-F-Ph | 4-Pyr | ring 31 | — |
| 13-32 | 4-F-Ph | 4-Pyr | ring 32 | — |
| 13-33 | 4-F-Ph | 4-Pyr | ring 33 | — |

TABLE 13-continued

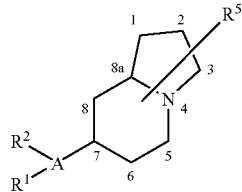

| Compound No. | R¹ | R² | A | R⁵ |
|---|---|---|---|---|
| 13-34 | 4-F-Ph | 4-Pyr | ring 34 | — |
| 13-35 | 4-F-Ph | 4-Pyr | ring 35 | — |
| 13-36 | 4-F-Ph | 4-Pyr | ring 36 | — |
| 13-37 | 4-F-Ph | 4-Pyr | ring 37 | — |
| 13-38 | 4-F-Ph | 4-Pyr | ring 1 | 2-Me |
| 13-39 | 4-F-Ph | 4-Pyr | ring 2 | 2-Me |
| 13-40 | 4-F-Ph | 4-Pyr | ring 3 | 2-Me |
| 13-41 | 4-F-Ph | 4-Pyr | ring 4 | 2-Me |
| 13-42 | 4-F-Ph | 4-Pyr | ring 5 | 2-Me |
| 13-43 | 4-F-Ph | 4-Pyr | ring 6 | 2-Me |
| 13-44 | 4-F-Ph | 4-Pyr | ring 7 | 2-Me |
| 13-45 | 4-F-Ph | 4-Pyr | ring 8 | 2-Me |
| 13-46 | 4-F-Ph | 4-Pyr | ring 9 | 2-Me |
| 13-47 | 4-F-Ph | 4-Pyr | ring 10 | 2-Me |
| 13-48 | 4-F-Ph | 4-Pyr | ring 11 | 2-Me |
| 13-49 | 4-F-Ph | 4-Pyr | ring 12 | 2-Me |
| 13-50 | 4-F-Ph | 4-Pyr | ring 13 | 2-Me |
| 13-51 | 4-F-Ph | 4-Pyr | ring 14 | 2-Me |
| 13-52 | 4-F-Ph | 4-Pyr | ring 15 | 2-Me |
| 13-53 | 4-F-Ph | 4-Pyr | ring 16 | 2-Me |
| 13-54 | 4-F-Ph | 4-Pyr | ring 17 | 2-Me |
| 13-55 | 4-F-Ph | 4-Pyr | ring 18 | 2-Me |
| 13-56 | 4-F-Ph | 4-Pyr | ring 19 | 2-Me |
| 13-57 | 4-F-Ph | 4-Pyr | ring 20 | 2-Me |
| 13-58 | 4-F-Ph | 4-Pyr | ring 21 | 2-Me |
| 13-59 | 4-F-Ph | 4-Pyr | ring 22 | 2-Me |
| 13-60 | 4-F-Ph | 4-Pyr | ring 23 | 2-Me |
| 13-61 | 4-F-Ph | 4-Pyr | ring 24 | 2-Me |
| 13-62 | 4-F-Ph | 4-Pyr | ring 25 | 2-Me |
| 13-63 | 4-F-Ph | 4-Pyr | ring 26 | 2-Me |
| 13-64 | 4-F-Ph | 4-Pyr | ring 27 | 2-Me |
| 13-65 | 4-F-Ph | 4-Pyr | ring 28 | 2-Me |
| 13-66 | 4-F-Ph | 4-Pyr | ring 29 | 2-Me |
| 13-67 | 4-F-Ph | 4-Pyr | ring 30 | 2-Me |
| 13-68 | 4-F-Ph | 4-Pyr | ring 31 | 2-Me |
| 13-69 | 4-F-Ph | 4-Pyr | ring 32 | 2-Me |
| 13-70 | 4-F-Ph | 4-Pyr | ring 33 | 2-Me |
| 13-71 | 4-F-Ph | 4-Pyr | ring 34 | 2-Me |
| 13-72 | 4-F-Ph | 4-Pyr | ring 35 | 2-Me |
| 13-73 | 4-F-Ph | 4-Pyr | ring 36 | 2-Me |
| 13-74 | 4-F-Ph | 4-Pyr | ring 37 | 2-Me |
| 13-75 | 4-F-Ph | 4-Pyr | ring 1 | 2-OH |
| 13-76 | 4-F-Ph | 4-Pyr | ring 2 | 2-OH |
| 13-77 | 4-F-Ph | 4-Pyr | ring 3 | 2-OH |
| 13-78 | 4-F-Ph | 4-Pyr | ring 4 | 2-OH |
| 13-79 | 4-F-Ph | 4-Pyr | ring 5 | 2-OH |
| 13-80 | 4-F-Ph | 4-Pyr | ring 6 | 2-OH |
| 13-81 | 4-F-Ph | 4-Pyr | ring 7 | 2-OH |
| 13-82 | 4-F-Ph | 4-Pyr | ring 8 | 2-OH |
| 13-83 | 4-F-Ph | 4-Pyr | ring 9 | 2-OH |
| 13-84 | 4-F-Ph | 4-Pyr | ring 10 | 2-OH |
| 13-85 | 4-F-Ph | 4-Pyr | ring 11 | 2-OH |
| 13-86 | 4-F-Ph | 4-Pyr | ring 12 | 2-OH |
| 13-87 | 4-F-Ph | 4-Pyr | ring 13 | 2-OH |
| 13-88 | 4-F-Ph | 4-Pyr | ring 14 | 2-OH |
| 13-89 | 4-F-Ph | 4-Pyr | ring 15 | 2-OH |
| 13-90 | 4-F-Ph | 4-Pyr | ring 16 | 2-OH |
| 13-91 | 4-F-Ph | 4-Pyr | ring 17 | 2-OH |
| 13-92 | 4-F-Ph | 4-Pyr | ring 18 | 2-OH |
| 13-93 | 4-F-Ph | 4-Pyr | ring 19 | 2-OH |
| 13-94 | 4-F-Ph | 4-Pyr | ring 20 | 2-OH |
| 13-95 | 4-F-Ph | 4-Pyr | ring 21 | 2-OH |
| 13-96 | 4-F-Ph | 4-Pyr | ring 22 | 2-OH |
| 13-97 | 4-F-Ph | 4-Pyr | ring 23 | 2-OH |
| 13-98 | 4-F-Ph | 4-Pyr | ring 24 | 2-OH |

TABLE 13-continued

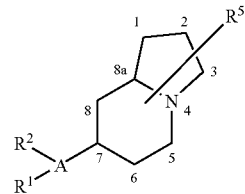

| Compound No. | R¹ | R² | A | R⁵ |
|---|---|---|---|---|
| 13-99 | 4-F-Ph | 4-Pyr | ring 25 | 2-OH |
| 13-100 | 4-F-Ph | 4-Pyr | ring 26 | 2-OH |
| 13-101 | 4-F-Ph | 4-Pyr | ring 27 | 2-OH |
| 13-102 | 4-F-Ph | 4-Pyr | ring 28 | 2-OH |
| 13-103 | 4-F-Ph | 4-Pyr | ring 29 | 2-OH |
| 13-104 | 4-F-Ph | 4-Pyr | ring 30 | 2-OH |
| 13-105 | 4-F-Ph | 4-Pyr | ring 31 | 2-OH |
| 13-106 | 4-F-Ph | 4-Pyr | ring 32 | 2-OH |
| 13-107 | 4-F-Ph | 4-Pyr | ring 33 | 2-OH |
| 13-108 | 4-F-Ph | 4-Pyr | ring 34 | 2-OH |
| 13-109 | 4-F-Ph | 4-Pyr | ring 35 | 2-OH |
| 13-110 | 4-F-Ph | 4-Pyr | ring 36 | 2-OH |
| 13-111 | 4-F-Ph | 4-Pyr | ring 37 | 2-OH |
| 13-112 | 4-F-Ph | 4-Pyr | ring 1 | 2-MeO |
| 13-113 | 4-F-Ph | 4-Pyr | ring 2 | 2-MeO |
| 13-114 | 4-F-Ph | 4-Pyr | ring 3 | 2-MeO |
| 13-115 | 4-F-Ph | 4-Pyr | ring 4 | 2-MeO |
| 13-116 | 4-F-Ph | 4-Pyr | ring 5 | 2-MeO |
| 13-117 | 4-F-Ph | 4-Pyr | ring 6 | 2-MeO |
| 13-118 | 4-F-Ph | 4-Pyr | ring 7 | 2-MeO |
| 13-119 | 4-F-Ph | 4-Pyr | ring 8 | 2-MeO |
| 13-120 | 4-F-Ph | 4-Pyr | ring 9 | 2-MeO |
| 13-121 | 4-F-Ph | 4-Pyr | ring 10 | 2-MeO |
| 13-122 | 4-F-Ph | 4-Pyr | ring 11 | 2-MeO |
| 13-123 | 4-F-Ph | 4-Pyr | ring 12 | 2-MeO |
| 13-124 | 4-F-Ph | 4-Pyr | ring 13 | 2-MeO |
| 13-125 | 4-F-Ph | 4-Pyr | ring 14 | 2-MeO |
| 13-126 | 4-F-Ph | 4-Pyr | ring 15 | 2-MeO |
| 13-127 | 4-F-Ph | 4-Pyr | ring 16 | 2-MeO |
| 13-128 | 4-F-Ph | 4-Pyr | ring 17 | 2-MeO |
| 13-129 | 4-F-Ph | 4-Pyr | ring 18 | 2-MeO |
| 13-130 | 4-F-Ph | 4-Pyr | ring 19 | 2-MeO |
| 13-131 | 4-F-Ph | 4-Pyr | ring 20 | 2-MeO |
| 13-132 | 4-F-Ph | 4-Pyr | ring 21 | 2-MeO |
| 13-133 | 4-F-Ph | 4-Pyr | ring 22 | 2-MeO |
| 13-134 | 4-F-Ph | 4-Pyr | ring 23 | 2-MeO |
| 13-135 | 4-F-Ph | 4-Pyr | ring 24 | 2-MeO |
| 13-136 | 4-F-Ph | 4-Pyr | ring 25 | 2-MeO |
| 13-137 | 4-F-Ph | 4-Pyr | ring 26 | 2-MeO |
| 13-138 | 4-F-Ph | 4-Pyr | ring 27 | 2-MeO |
| 13-139 | 4-F-Ph | 4-Pyr | ring 28 | 2-MeO |
| 13-140 | 4-F-Ph | 4-Pyr | ring 29 | 2-MeO |
| 13-141 | 4-F-Ph | 4-Pyr | ring 30 | 2-MeO |
| 13-142 | 4-F-Ph | 4-Pyr | ring 31 | 2-MeO |
| 13-143 | 4-F-Ph | 4-Pyr | ring 32 | 2-MeO |
| 13-144 | 4-F-Ph | 4-Pyr | ring 33 | 2-MeO |
| 13-145 | 4-F-Ph | 4-Pyr | ring 34 | 2-MeO |
| 13-146 | 4-F-Ph | 4-Pyr | ring 35 | 2-MeO |
| 13-147 | 4-F-Ph | 4-Pyr | ring 36 | 2-MeO |
| 13-148 | 4-F-Ph | 4-Pyr | ring 37 | 2-MeO |
| 13-149 | 4-F-Ph | 4-Pyr | ring 1 | 2-F |
| 13-150 | 4-F-Ph | 4-Pyr | ring 2 | 2-F |
| 13-151 | 4-F-Ph | 4-Pyr | ring 3 | 2-F |
| 13-152 | 4-F-Ph | 4-Pyr | ring 4 | 2-F |
| 13-153 | 4-F-Ph | 4-Pyr | ring 5 | 2-F |
| 13-154 | 4-F-Ph | 4-Pyr | ring 6 | 2-F |
| 13-155 | 4-F-Ph | 4-Pyr | ring 7 | 2-F |
| 13-156 | 4-F-Ph | 4-Pyr | ring 8 | 2-F |
| 13-157 | 4-F-Ph | 4-Pyr | ring 9 | 2-F |
| 13-158 | 4-F-Ph | 4-Pyr | ring 10 | 2-F |
| 13-159 | 4-F-Ph | 4-Pyr | ring 11 | 2-F |
| 13-160 | 4-F-Ph | 4-Pyr | ring 12 | 2-F |
| 13-161 | 4-F-Ph | 4-Pyr | ring 13 | 2-F |
| 13-162 | 4-F-Ph | 4-Pyr | ring 14 | 2-F |
| 13-163 | 4-F-Ph | 4-Pyr | ring 15 | 2-F |

TABLE 13-continued

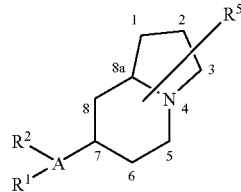

| Compound No. | $R^1$ | $R^2$ | A | $R^5$ |
|---|---|---|---|---|
| 13-164 | 4-F-Ph | 4-Pyr | ring 16 | 2-F |
| 13-165 | 4-F-Ph | 4-Pyr | ring 17 | 2-F |
| 13-166 | 4-F-Ph | 4-Pyr | ring 18 | 2-F |
| 13-167 | 4-F-Ph | 4-Pyr | ring 19 | 2-F |
| 13-168 | 4-F-Ph | 4-Pyr | ring 20 | 2-F |
| 13-169 | 4-F-Ph | 4-Pyr | ring 21 | 2-F |
| 13-170 | 4-F-Ph | 4-Pyr | ring 22 | 2-F |
| 13-171 | 4-F-Ph | 4-Pyr | ring 23 | 2-F |
| 13-172 | 4-F-Ph | 4-Pyr | ring 24 | 2-F |
| 13-173 | 4-F-Ph | 4-Pyr | ring 25 | 2-F |
| 13-174 | 4-F-Ph | 4-Pyr | ring 26 | 2-F |
| 13-175 | 4-F-Ph | 4-Pyr | ring 27 | 2-F |
| 13-176 | 4-F-Ph | 4-Pyr | ring 28 | 2-F |
| 13-177 | 4-F-Ph | 4-Pyr | ring 29 | 2-F |
| 13-178 | 4-F-Ph | 4-Pyr | ring 30 | 2-F |
| 13-179 | 4-F-Ph | 4-Pyr | ring 31 | 2-F |
| 13-180 | 4-F-Ph | 4-Pyr | ring 32 | 2-F |
| 13-181 | 4-F-Ph | 4-Pyr | ring 33 | 2-F |
| 13-182 | 4-F-Ph | 4-Pyr | ring 34 | 2-F |
| 13-183 | 4-F-Ph | 4-Pyr | ring 35 | 2-F |
| 13-184 | 4-F-Ph | 4-Pyr | ring 36 | 2-F |
| 13-185 | 4-F-Ph | 4-Pyr | ring 37 | 2-F |
| 13-186 | 4-F-Ph | 4-Pyr | ring 1 | 2-Cl |
| 13-187 | 4-F-Ph | 4-Pyr | ring 2 | 2-Cl |
| 13-188 | 4-F-Ph | 4-Pyr | ring 3 | 2-Cl |
| 13-189 | 4-F-Ph | 4-Pyr | ring 4 | 2-Cl |
| 13-190 | 4-F-Ph | 4-Pyr | ring 5 | 2-Cl |
| 13-191 | 4-F-Ph | 4-Pyr | ring 6 | 2-Cl |
| 13-192 | 4-F-Ph | 4-Pyr | ring 7 | 2-Cl |
| 13-193 | 4-F-Ph | 4-Pyr | ring 8 | 2-Cl |
| 13-194 | 4-F-Ph | 4-Pyr | ring 9 | 2-Cl |
| 13-195 | 4-F-Ph | 4-Pyr | ring 10 | 2-Cl |
| 13-196 | 4-F-Ph | 4-Pyr | ring 11 | 2-Cl |
| 13-197 | 4-F-Ph | 4-Pyr | ring 12 | 2-Cl |
| 13-198 | 4-F-Ph | 4-Pyr | ring 13 | 2-Cl |
| 13-199 | 4-F-Ph | 4-Pyr | ring 14 | 2-Cl |
| 13-200 | 4-F-Ph | 4-Pyr | ring 15 | 2-Cl |
| 13-201 | 4-F-Ph | 4-Pyr | ring 16 | 2-Cl |
| 13-202 | 4-F-Ph | 4-Pyr | ring 17 | 2-Cl |
| 13-203 | 4-F-Ph | 4-Pyr | ring 18 | 2-Cl |
| 13-204 | 4-F-Ph | 4-Pyr | ring 19 | 2-Cl |
| 13-205 | 4-F-Ph | 4-Pyr | ring 20 | 2-Cl |
| 13-206 | 4-F-Ph | 4-Pyr | ring 21 | 2-Cl |
| 13-207 | 4-F-Ph | 4-Pyr | ring 22 | 2-Cl |
| 13-208 | 4-F-Ph | 4-Pyr | ring 23 | 2-Cl |
| 13-209 | 4-F-Ph | 4-Pyr | ring 24 | 2-Cl |
| 13-210 | 4-F-Ph | 4-Pyr | ring 25 | 2-Cl |
| 13-211 | 4-F-Ph | 4-Pyr | ring 26 | 2-Cl |
| 13-212 | 4-F-Ph | 4-Pyr | ring 27 | 2-Cl |
| 13-213 | 4-F-Ph | 4-Pyr | ring 28 | 2-Cl |
| 13-214 | 4-F-Ph | 4-Pyr | ring 29 | 2-Cl |
| 13-215 | 4-F-Ph | 4-Pyr | ring 30 | 2-Cl |
| 13-216 | 4-F-Ph | 4-Pyr | ring 31 | 2-Cl |
| 13-217 | 4-F-Ph | 4-Pyr | ring 32 | 2-Cl |
| 13-218 | 4-F-Ph | 4-Pyr | ring 33 | 2-Cl |
| 13-219 | 4-F-Ph | 4-Pyr | ring 34 | 2-Cl |
| 13-220 | 4-F-Ph | 4-Pyr | ring 35 | 2-Cl |
| 13-221 | 4-F-Ph | 4-Pyr | ring 36 | 2-Cl |
| 13-222 | 4-F-Ph | 4-Pyr | ring 37 | 2-Cl |
| 13-223 | 4-F-Ph | 4-Pyr | ring 1 | 2,2-diF |
| 13-224 | 4-F-Ph | 4-Pyr | ring 2 | 2,2-diF |
| 13-225 | 4-F-Ph | 4-Pyr | ring 3 | 2,2-diF |
| 13-226 | 4-F-Ph | 4-Pyr | ring 4 | 2,2-diF |
| 13-227 | 4-F-Ph | 4-Pyr | ring 5 | 2,2-diF |
| 13-228 | 4-F-Ph | 4-Pyr | ring 6 | 2,2-diF |
| 13-229 | 4-F-Ph | 4-Pyr | ring 7 | 2,2-diF |
| 13-230 | 4-F-Ph | 4-Pyr | ring 8 | 2,2-diF |
| 13-231 | 4-F-Ph | 4-Pyr | ring 9 | 2,2-diF |
| 13-232 | 4-F-Ph | 4-Pyr | ring 10 | 2,2-diF |
| 13-233 | 4-F-Ph | 4-Pyr | ring 11 | 2,2-diF |
| 13-234 | 4-F-Ph | 4-Pyr | ring 12 | 2,2-diF |
| 13-235 | 4-F-Ph | 4-Pyr | ring 13 | 2,2-diF |
| 13-236 | 4-F-Ph | 4-Pyr | ring 14 | 2,2-diF |
| 13-237 | 4-F-Ph | 4-Pyr | ring 15 | 2,2-diF |
| 13-238 | 4-F-Ph | 4-Pyr | ring 16 | 2,2-diF |
| 13-239 | 4-F-Ph | 4-Pyr | ring 17 | 2,2-diF |
| 13-240 | 4-F-Ph | 4-Pyr | ring 18 | 2,2-diF |
| 13-241 | 4-F-Ph | 4-Pyr | ring 19 | 2,2-diF |
| 13-242 | 4-F-Ph | 4-Pyr | ring 20 | 2,2-diF |
| 13-243 | 4-F-Ph | 4-Pyr | ring 21 | 2,2-diF |
| 13-244 | 4-F-Ph | 4-Pyr | ring 22 | 2,2-diF |
| 13-245 | 4-F-Ph | 4-Pyr | ring 23 | 2,2-diF |
| 13-246 | 4-F-Ph | 4-Pyr | ring 24 | 2,2-diF |
| 13-247 | 4-F-Ph | 4-Pyr | ring 25 | 2,2-diF |
| 13-248 | 4-F-Ph | 4-Pyr | ring 26 | 2,2-diF |
| 13-249 | 4-F-Ph | 4-Pyr | ring 27 | 2,2-diF |
| 13-250 | 4-F-Ph | 4-Pyr | ring 28 | 2,2-diF |
| 13-251 | 4-F-Ph | 4-Pyr | ring 29 | 2,2-diF |
| 13-252 | 4-F-Ph | 4-Pyr | ring 30 | 2,2-diF |
| 13-253 | 4-F-Ph | 4-Pyr | ring 31 | 2,2-diF |
| 13-254 | 4-F-Ph | 4-Pyr | ring 32 | 2,2-diF |
| 13-255 | 4-F-Ph | 4-Pyr | ring 33 | 2,2-diF |
| 13-256 | 4-F-Ph | 4-Pyr | ring 34 | 2,2-diF |
| 13-257 | 4-F-Ph | 4-Pyr | ring 35 | 2,2-diF |
| 13-258 | 4-F-Ph | 4-Pyr | ring 36 | 2,2-diF |
| 13-259 | 4-F-Ph | 4-Pyr | ring 37 | 2,2-diF |
| 13-260 | 4-F-Ph | 4-Pyr | ring 1 | 8-Me |
| 13-261 | 4-F-Ph | 4-Pyr | ring 2 | 8-Me |
| 13-262 | 4-F-Ph | 4-Pyr | ring 3 | 8-Me |
| 13-263 | 4-F-Ph | 4-Pyr | ring 4 | 8-Me |
| 13-264 | 4-F-Ph | 4-Pyr | ring 5 | 8-Me |
| 13-265 | 4-F-Ph | 4-Pyr | ring 6 | 8-Me |
| 13-266 | 4-F-Ph | 4-Pyr | ring 7 | 8-Me |
| 13-267 | 4-F-Ph | 4-Pyr | ring 8 | 8-Me |
| 13-268 | 4-F-Ph | 4-Pyr | ring 9 | 8-Me |
| 13-269 | 4-F-Ph | 4-Pyr | ring 10 | 8-Me |
| 13-270 | 4-F-Ph | 4-Pyr | ring 11 | 8-Me |
| 13-271 | 4-F-Ph | 4-Pyr | ring 12 | 8-Me |
| 13-272 | 4-F-Ph | 4-Pyr | ring 13 | 8-Me |
| 13-273 | 4-F-Ph | 4-Pyr | ring 14 | 8-Me |
| 13-274 | 4-F-Ph | 4-Pyr | ring 15 | 8-Me |
| 13-275 | 4-F-Ph | 4-Pyr | ring 16 | 8-Me |
| 13-276 | 4-F-Ph | 4-Pyr | ring 17 | 8-Me |
| 13-277 | 4-F-Ph | 4-Pyr | ring 18 | 8-Me |
| 13-278 | 4-F-Ph | 4-Pyr | ring 19 | 8-Me |
| 13-279 | 4-F-Ph | 4-Pyr | ring 20 | 8-Me |
| 13-280 | 4-F-Ph | 4-Pyr | ring 21 | 8-Me |
| 13-281 | 4-F-Ph | 4-Pyr | ring 22 | 8-Me |
| 13-282 | 4-F-Ph | 4-Pyr | ring 23 | 8-Me |
| 13-283 | 4-F-Ph | 4-Pyr | ring 24 | 8-Me |
| 13-284 | 4-F-Ph | 4-Pyr | ring 25 | 8-Me |
| 13-285 | 4-F-Ph | 4-Pyr | ring 26 | 8-Me |
| 13-286 | 4-F-Ph | 4-Pyr | ring 27 | 8-Me |
| 13-287 | 4-F-Ph | 4-Pyr | ring 28 | 8-Me |
| 13-288 | 4-F-Ph | 4-Pyr | ring 29 | 8-Me |
| 13-289 | 4-F-Ph | 4-Pyr | ring 30 | 8-Me |
| 13-290 | 4-F-Ph | 4-Pyr | ring 31 | 8-Me |
| 13-291 | 4-F-Ph | 4-Pyr | ring 32 | 8-Me |
| 13-292 | 4-F-Ph | 4-Pyr | ring 33 | 8-Me |
| 13-293 | 4-F-Ph | 4-Pyr | ring 34 | 8-Me |

TABLE 13-continued

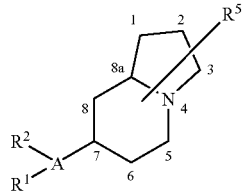

| Compound No. | R¹ | R² | A | R⁵ |
|---|---|---|---|---|
| 13-294 | 4-F-Ph | 4-Pyr | ring 35 | 8-Me |
| 13-295 | 4-F-Ph | 4-Pyr | ring 36 | 8-Me |
| 13-296 | 4-F-Ph | 4-Pyr | ring 37 | 8-Me |
| 13-297 | 4-F-Ph | 2-NH$_2$-4-Pym | ring 1 | — |
| 13-298 | 4-F-Ph | 2-NH$_2$-4-Pym | ring 2 | — |
| 13-299 | 4-F-Ph | 2-NH$_2$-4-Pym | ring 3 | — |
| 13-300 | 4-F-Ph | 2-NH$_2$-4-Pym | ring 4 | — |
| 13-301 | 4-F-Ph | 2-NH$_2$-4-Pym | ring 5 | — |
| 13-302 | 4-F-Ph | 2-NH$_2$-4-Pym | ring 6 | — |
| 13-303 | 4-F-Ph | 2-NH$_2$-4-Pym | ring 7 | — |
| 13-304 | 4-F-Ph | 2-NH$_2$-4-Pym | ring 8 | — |
| 13-305 | 4-F-Ph | 2-NH$_2$-4-Pym | ring 9 | — |
| 13-306 | 4-F-Ph | 2-NH$_2$-4-Pym | ring 10 | — |
| 13-307 | 4-F-Ph | 2-NH$_2$-4-Pym | ring 11 | — |
| 13-308 | 4-F-Ph | 2-NH$_2$-4-Pym | ring 12 | — |
| 13-309 | 4-F-Ph | 2-NH$_2$-4-Pym | ring 13 | — |
| 13-310 | 4-F-Ph | 2-NH$_2$-4-Pym | ring 14 | — |
| 13-311 | 4-F-Ph | 2-NH$_2$-4-Pym | ring 15 | — |
| 13-312 | 4-F-Ph | 2-NH$_2$-4-Pym | ring 16 | — |
| 13-313 | 4-F-Ph | 2-NH$_2$-4-Pym | ring 17 | — |
| 13-314 | 4-F-Ph | 2-NH$_2$-4-Pym | ring 18 | — |
| 13-315 | 4-F-Ph | 2-NH$_2$-4-Pym | ring 19 | — |
| 13-316 | 4-F-Ph | 2-NH$_2$-4-Pym | ring 20 | — |
| 13-317 | 4-F-Ph | 2-NH$_2$-4-Pym | ring 21 | — |
| 13-318 | 4-F-Ph | 2-NH$_2$-4-Pym | ring 22 | — |
| 13-319 | 4-F-Ph | 2-NH$_2$-4-Pym | ring 23 | — |
| 13-320 | 4-F-Ph | 2-NH$_2$-4-Pym | ring 24 | — |
| 13-321 | 4-F-Ph | 2-NH$_2$-4-Pym | ring 25 | — |
| 13-322 | 4-F-Ph | 2-NH$_2$-4-Pym | ring 26 | — |
| 13-323 | 4-F-Ph | 2-NH$_2$-4-Pym | ring 27 | — |
| 13-324 | 4-F-Ph | 2-NH$_2$-4-Pym | ring 28 | — |
| 13-325 | 4-F-Ph | 2-NH$_2$-4-Pym | ring 29 | — |
| 13-326 | 4-F-Ph | 2-NH$_2$-4-Pym | ring 30 | — |
| 13-327 | 4-F-Ph | 2-NH$_2$-4-Pym | ring 31 | — |
| 13-328 | 4-F-Ph | 2-NH$_2$-4-Pym | ring 32 | — |
| 13-329 | 4-F-Ph | 2-NH$_2$-4-Pym | ring 33 | — |
| 13-330 | 4-F-Ph | 2-NH$_2$-4-Pym | ring 34 | — |
| 13-331 | 4-F-Ph | 2-NH$_2$-4-Pym | ring 35 | — |
| 13-332 | 4-F-Ph | 2-NH$_2$-4-Pym | ring 36 | — |
| 13-333 | 4-F-Ph | 2-NH$_2$-4-Pym | ring 37 | — |
| 13-334 | 4-F-Ph | 2-NH$_2$-4-Pym | ring 1 | 2-Me |
| 13-335 | 4-F-Ph | 2-NH$_2$-4-Pym | ring 2 | 2-Me |
| 13-336 | 4-F-Ph | 2-NH$_2$-4-Pym | ring 3 | 2-Me |
| 13-337 | 4-F-Ph | 2-NH$_2$-4-Pym | ring 4 | 2-Me |
| 13-338 | 4-F-Ph | 2-NH$_2$-4-Pym | ring 5 | 2-Me |
| 13-339 | 4-F-Ph | 2-NH$_2$-4-Pym | ring 6 | 2-Me |
| 13-340 | 4-F-Ph | 2-NH$_2$-4-Pym | ring 7 | 2-Me |
| 13-341 | 4-F-Ph | 2-NH$_2$-4-Pym | ring 8 | 2-Me |
| 13-342 | 4-F-Ph | 2-NH$_2$-4-Pym | ring 9 | 2-Me |
| 13-343 | 4-F-Ph | 2-NH$_2$-4-Pym | ring 10 | 2-Me |
| 13-344 | 4-F-Ph | 2-NH$_2$-4-Pym | ring 11 | 2-Me |
| 13-345 | 4-F-Ph | 2-NH$_2$-4-Pym | ring 12 | 2-Me |
| 13-346 | 4-F-Ph | 2-NH$_2$-4-Pym | ring 13 | 2-Me |
| 13-347 | 4-F-Ph | 2-NH$_2$-4-Pym | ring 14 | 2-Me |
| 13-348 | 4-F-Ph | 2-NH$_2$-4-Pym | ring 15 | 2-Me |
| 13-349 | 4-F-Ph | 2-NH$_2$-4-Pym | ring 16 | 2-Me |
| 13-350 | 4-F-Ph | 2-NH$_2$-4-Pym | ring 17 | 2-Me |
| 13-351 | 4-F-Ph | 2-NH$_2$-4-Pym | ring 18 | 2-Me |
| 13-352 | 4-F-Ph | 2-NH$_2$-4-Pym | ring 19 | 2-Me |
| 13-353 | 4-F-Ph | 2-NH$_2$-4-Pym | ring 20 | 2-Me |
| 13-354 | 4-F-Ph | 2-NH$_2$-4-Pym | ring 21 | 2-Me |
| 13-355 | 4-F-Ph | 2-NH$_2$-4-Pym | ring 22 | 2-Me |
| 13-356 | 4-F-Ph | 2-NH$_2$-4-Pym | ring 23 | 2-Me |
| 13-357 | 4-F-Ph | 2-NH$_2$-4-Pym | ring 24 | 2-Me |
| 13-358 | 4-F-Ph | 2-NH$_2$-4-Pym | ring 25 | 2-Me |

TABLE 13-continued

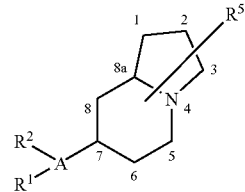

| Compound No. | R¹ | R² | A | R⁵ |
|---|---|---|---|---|
| 13-359 | 4-F-Ph | 2-NH$_2$-4-Pym | ring 26 | 2-Me |
| 13-360 | 4-F-Ph | 2-NH$_2$-4-Pym | ring 27 | 2-Me |
| 13-361 | 4-F-Ph | 2-NH$_2$-4-Pym | ring 28 | 2-Me |
| 13-362 | 4-F-Ph | 2-NH$_2$-4-Pym | ring 29 | 2-Me |
| 13-363 | 4-F-Ph | 2-NH$_2$-4-Pym | ring 30 | 2-Me |
| 13-364 | 4-F-Ph | 2-NH$_2$-4-Pym | ring 31 | 2-Me |
| 13-365 | 4-F-Ph | 2-NH$_2$-4-Pym | ring 32 | 2-Me |
| 13-366 | 4-F-Ph | 2-NH$_2$-4-Pym | ring 33 | 2-Me |
| 13-367 | 4-F-Ph | 2-NH$_2$-4-Pym | ring 34 | 2-Me |
| 13-368 | 4-F-Ph | 2-NH$_2$-4-Pym | ring 35 | 2-Me |
| 13-369 | 4-F-Ph | 2-NH$_2$-4-Pym | ring 36 | 2-Me |
| 13-370 | 4-F-Ph | 2-NH$_2$-4-Pym | ring 37 | 2-Me |
| 13-371 | 4-F-Ph | 2-NH$_2$-4-Pym | ring 1 | 2-OH |
| 13-372 | 4-F-Ph | 2-NH$_2$-4-Pym | ring 2 | 2-OH |
| 13-373 | 4-F-Ph | 2-NH$_2$-4-Pym | ring 3 | 2-OH |
| 13-374 | 4-F-Ph | 2-NH$_2$-4-Pym | ring 4 | 2-OH |
| 13-375 | 4-F-Ph | 2-NH$_2$-4-Pym | ring 5 | 2-OH |
| 13-376 | 4-F-Ph | 2-NH$_2$-4-Pym | ring 6 | 2-OH |
| 13-377 | 4-F-Ph | 2-NH$_2$-4-Pym | ring 7 | 2-OH |
| 13-378 | 4-F-Ph | 2-NH$_2$-4-Pym | ring 8 | 2-OH |
| 13-379 | 4-F-Ph | 2-NH$_2$-4-Pym | ring 9 | 2-OH |
| 13-380 | 4-F-Ph | 2-NH$_2$-4-Pym | ring 10 | 2-OH |
| 13-381 | 4-F-Ph | 2-NH$_2$-4-Pym | ring 11 | 2-OH |
| 13-382 | 4-F-Ph | 2-NH$_2$-4-Pym | ring 12 | 2-OH |
| 13-383 | 4-F-Ph | 2-NH$_2$-4-Pym | ring 13 | 2-OH |
| 13-384 | 4-F-Ph | 2-NH$_2$-4-Pym | ring 14 | 2-OH |
| 13-385 | 4-F-Ph | 2-NH$_2$-4-Pym | ring 15 | 2-OH |
| 13-386 | 4-F-Ph | 2-NH$_2$-4-Pym | ring 16 | 2-OH |
| 13-387 | 4-F-Ph | 2-NH$_2$-4-Pym | ring 17 | 2-OH |
| 13-388 | 4-F-Ph | 2-NH$_2$-4-Pym | ring 18 | 2-OH |
| 13-389 | 4-F-Ph | 2-NH$_2$-4-Pym | ring 19 | 2-OH |
| 13-390 | 4-F-Ph | 2-NH$_2$-4-Pym | ring 20 | 2-OH |
| 13-391 | 4-F-Ph | 2-NH$_2$-4-Pym | ring 21 | 2-OH |
| 13-392 | 4-F-Ph | 2-NH$_2$-4-Pym | ring 22 | 2-OH |
| 13-393 | 4-F-Ph | 2-NH$_2$-4-Pym | ring 23 | 2-OH |
| 13-394 | 4-F-Ph | 2-NH$_2$-4-Pym | ring 24 | 2-OH |
| 13-395 | 4-F-Ph | 2-NH$_2$-4-Pym | ring 25 | 2-OH |
| 13-396 | 4-F-Ph | 2-NH$_2$-4-Pym | ring 26 | 2-OH |
| 13-397 | 4-F-Ph | 2-NH$_2$-4-Pym | ring 27 | 2-OH |
| 13-398 | 4-F-Ph | 2-NH$_2$-4-Pym | ring 28 | 2-OH |
| 13-399 | 4-F-Ph | 2-NH$_2$-4-Pym | ring 29 | 2-OH |
| 13-400 | 4-F-Ph | 2-NH$_2$-4-Pym | ring 30 | 2-OH |
| 13-401 | 4-F-Ph | 2-NH$_2$-4-Pym | ring 31 | 2-OH |
| 13-402 | 4-F-Ph | 2-NH$_2$-4-Pym | ring 32 | 2-OH |
| 13-403 | 4-F-Ph | 2-NH$_2$-4-Pym | ring 33 | 2-OH |
| 13-404 | 4-F-Ph | 2-NH$_2$-4-Pym | ring 34 | 2-OH |
| 13-405 | 4-F-Ph | 2-NH$_2$-4-Pym | ring 35 | 2-OH |
| 13-406 | 4-F-Ph | 2-NH$_2$-4-Pym | ring 36 | 2-OH |
| 13-407 | 4-F-Ph | 2-NH$_2$-4-Pym | ring 37 | 2-OH |
| 13-408 | 4-F-Ph | 2-NH$_2$-4-Pym | ring 1 | 2-MeO |
| 13-409 | 4-F-Ph | 2-NH$_2$-4-Pym | ring 2 | 2-MeO |
| 13-410 | 4-F-Ph | 2-NH$_2$-4-Pym | ring 3 | 2-MeO |
| 13-411 | 4-F-Ph | 2-NH$_2$-4-Pym | ring 4 | 2-MeO |
| 13-412 | 4-F-Ph | 2-NH$_2$-4-Pym | ring 5 | 2-MeO |
| 13-413 | 4-F-Ph | 2-NH$_2$-4-Pym | ring 6 | 2-MeO |
| 13-414 | 4-F-Ph | 2-NH$_2$-4-Pym | ring 7 | 2-MeO |
| 13-415 | 4-F-Ph | 2-NH$_2$-4-Pym | ring 8 | 2-MeO |
| 13-416 | 4-F-Ph | 2-NH$_2$-4-Pym | ring 9 | 2-MeO |
| 13-417 | 4-F-Ph | 2-NH$_2$-4-Pym | ring 10 | 2-MeO |
| 13-418 | 4-F-Ph | 2-NH$_2$-4-Pym | ring 11 | 2-MeO |
| 13-419 | 4-F-Ph | 2-NH$_2$-4-Pym | ring 12 | 2-MeO |
| 13-420 | 4-F-Ph | 2-NH$_2$-4-Pym | ring 13 | 2-MeO |
| 13-421 | 4-F-Ph | 2-NH$_2$-4-Pym | ring 14 | 2-MeO |
| 13-422 | 4-F-Ph | 2-NH$_2$-4-Pym | ring 15 | 2-MeO |
| 13-423 | 4-F-Ph | 2-NH$_2$-4-Pym | ring 16 | 2-MeO |

TABLE 13-continued

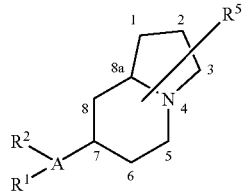

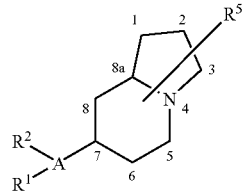

| Compound No. | $R^1$ | $R^2$ | A | $R^5$ |
|---|---|---|---|---|
| 13-424 | 4-F-Ph | 2-NH$_2$-4-Pym | ring 17 | 2-MeO |
| 13-425 | 4-F-Ph | 2-NH$_2$-4-Pym | ring 18 | 2-MeO |
| 13-426 | 4-F-Ph | 2-NH$_2$-4-Pym | ring 19 | 2-MeO |
| 13-427 | 4-F-Ph | 2-NH$_2$-4-Pym | ring 20 | 2-MeO |
| 13-428 | 4-F-Ph | 2-NH$_2$-4-Pym | ring 21 | 2-MeO |
| 13-429 | 4-F-Ph | 2-NH$_2$-4-Pym | ring 22 | 2-MeO |
| 13-430 | 4-F-Ph | 2-NH$_2$-4-Pym | ring 23 | 2-MeO |
| 13-431 | 4-F-Ph | 2-NH$_2$-4-Pym | ring 24 | 2-MeO |
| 13-432 | 4-F-Ph | 2-NH$_2$-4-Pym | ring 25 | 2-MeO |
| 13-433 | 4-F-Ph | 2-NH$_2$-4-Pym | ring 26 | 2-MeO |
| 13-434 | 4-F-Ph | 2-NH$_2$-4-Pym | ring 27 | 2-MeO |
| 13-435 | 4-F-Ph | 2-NH$_2$-4-Pym | ring 28 | 2-MeO |
| 13-436 | 4-F-Ph | 2-NH$_2$-4-Pym | ring 29 | 2-MeO |
| 13-437 | 4-F-Ph | 2-NH$_2$-4-Pym | ring 30 | 2-MeO |
| 13-438 | 4-F-Ph | 2-NH$_2$-4-Pym | ring 31 | 2-MeO |
| 13-439 | 4-F-Ph | 2-NH$_2$-4-Pym | ring 32 | 2-MeO |
| 13-440 | 4-F-Ph | 2-NH$_2$-4-Pym | ring 33 | 2-MeO |
| 13-441 | 4-F-Ph | 2-NH$_2$-4-Pym | ring 34 | 2-MeO |
| 13-442 | 4-F-Ph | 2-NH$_2$-4-Pym | ring 35 | 2-MeO |
| 13-443 | 4-F-Ph | 2-NH$_2$-4-Pym | ring 36 | 2-MeO |
| 13-444 | 4-F-Ph | 2-NH$_2$-4-Pym | ring 37 | 2-MeO |
| 13-445 | 4-F-Ph | 2-NH$_2$-4-Pym | ring 1 | 2-F |
| 13-446 | 4-F-Ph | 2-NH$_2$-4-Pym | ring 2 | 2-F |
| 13-447 | 4-F-Ph | 2-NH$_2$-4-Pym | ring 3 | 2-F |
| 13-448 | 4-F-Ph | 2-NH$_2$-4-Pym | ring 4 | 2-F |
| 13-449 | 4-F-Ph | 2-NH$_2$-4-Pym | ring 5 | 2-F |
| 13-450 | 4-F-Ph | 2-NH$_2$-4-Pym | ring 6 | 2-F |
| 13-451 | 4-F-Ph | 2-NH$_2$-4-Pym | ring 7 | 2-F |
| 13-452 | 4-F-Ph | 2-NH$_2$-4-Pym | ring 8 | 2-F |
| 13-453 | 4-F-Ph | 2-NH$_2$-4-Pym | ring 9 | 2-F |
| 13-454 | 4-F-Ph | 2-NH$_2$-4-Pym | ring 10 | 2-F |
| 13-455 | 4-F-Ph | 2-NH$_2$-4-Pym | ring 11 | 2-F |
| 13-456 | 4-F-Ph | 2-NH$_2$-4-Pym | ring 12 | 2-F |
| 13-457 | 4-F-Ph | 2-NH$_2$-4-Pym | ring 13 | 2-F |
| 13-458 | 4-F-Ph | 2-NH$_2$-4-Pym | ring 14 | 2-F |
| 13-459 | 4-F-Ph | 2-NH$_2$-4-Pym | ring 15 | 2-F |
| 13-460 | 4-F-Ph | 2-NH$_2$-4-Pym | ring 16 | 2-F |
| 13-461 | 4-F-Ph | 2-NH$_2$-4-Pym | ring 17 | 2-F |
| 13-462 | 4-F-Ph | 2-NH$_2$-4-Pym | ring 18 | 2-F |
| 13-463 | 4-F-Ph | 2-NH$_2$-4-Pym | ring 19 | 2-F |
| 13-464 | 4-F-Ph | 2-NH$_2$-4-Pym | ring 20 | 2-F |
| 13-465 | 4-F-Ph | 2-NH$_2$-4-Pym | ring 21 | 2-F |
| 13-466 | 4-F-Ph | 2-NH$_2$-4-Pym | ring 22 | 2-F |
| 13-467 | 4-F-Ph | 2-NH$_2$-4-Pym | ring 23 | 2-F |
| 13-468 | 4-F-Ph | 2-NH$_2$-4-Pym | ring 24 | 2-F |
| 13-469 | 4-F-Ph | 2-NH$_2$-4-Pym | ring 25 | 2-F |
| 13-470 | 4-F-Ph | 2-NH$_2$-4-Pym | ring 26 | 2-F |
| 13-471 | 4-F-Ph | 2-NH$_2$-4-Pym | ring 27 | 2-F |
| 13-472 | 4-F-Ph | 2-NH$_2$-4-Pym | ring 28 | 2-F |
| 13-473 | 4-F-Ph | 2-NH$_2$-4-Pym | ring 29 | 2-F |
| 13-474 | 4-F-Ph | 2-NH$_2$-4-Pym | ring 30 | 2-F |
| 13-475 | 4-F-Ph | 2-NH$_2$-4-Pym | ring 31 | 2-F |
| 13-476 | 4-F-Ph | 2-NH$_2$-4-Pym | ring 32 | 2-F |
| 13-477 | 4-F-Ph | 2-NH$_2$-4-Pym | ring 33 | 2-F |
| 13-478 | 4-F-Ph | 2-NH$_2$-4-Pym | ring 34 | 2-F |
| 13-479 | 4-F-Ph | 2-NH$_2$-4-Pym | ring 35 | 2-F |
| 13-480 | 4-F-Ph | 2-NH$_2$-4-Pym | ring 36 | 2-F |
| 13-481 | 4-F-Ph | 2-NH$_2$-4-Pym | ring 37 | 2-F |
| 13-482 | 4-F-Ph | 2-NH$_2$-4-Pym | ring 1 | 2-Cl |
| 13-483 | 4-F-Ph | 2-NH$_2$-4-Pym | ring 2 | 2-Cl |
| 13-484 | 4-F-Ph | 2-NH$_2$-4-Pym | ring 3 | 2-Cl |
| 13-485 | 4-F-Ph | 2-NH$_2$-4-Pym | ring 4 | 2-Cl |
| 13-486 | 4-F-Ph | 2-NH$_2$-4-Pym | ring 5 | 2-Cl |
| 13-487 | 4-F-Ph | 2-NH$_2$-4-Pym | ring 6 | 2-Cl |
| 13-488 | 4-F-Ph | 2-NH$_2$-4-Pym | ring 7 | 2-Cl |
| 13-489 | 4-F-Ph | 2-NH$_2$-4-Pym | ring 8 | 2-Cl |
| 13-490 | 4-F-Ph | 2-NH$_2$-4-Pym | ring 9 | 2-Cl |
| 13-491 | 4-F-Ph | 2-NH$_2$-4-Pym | ring 10 | 2-Cl |
| 13-492 | 4-F-Ph | 2-NH$_2$-4-Pym | ring 11 | 2-Cl |
| 13-493 | 4-F-Ph | 2-NH$_2$-4-Pym | ring 12 | 2-Cl |
| 13-494 | 4-F-Ph | 2-NH$_2$-4-Pym | ring 13 | 2-Cl |
| 13-495 | 4-F-Ph | 2-NH$_2$-4-Pym | ring 14 | 2-Cl |
| 13-496 | 4-F-Ph | 2-NH$_2$-4-Pym | ring 15 | 2-Cl |
| 13-497 | 4-F-Ph | 2-NH$_2$-4-Pym | ring 16 | 2-Cl |
| 13-498 | 4-F-Ph | 2-NH$_2$-4-Pym | ring 17 | 2-Cl |
| 13-499 | 4-F-Ph | 2-NH$_2$-4-Pym | ring 18 | 2-Cl |
| 13-500 | 4-F-Ph | 2-NH$_2$-4-Pym | ring 19 | 2-Cl |
| 13-501 | 4-F-Ph | 2-NH$_2$-4-Pym | ring 20 | 2-Cl |
| 13-502 | 4-F-Ph | 2-NH$_2$-4-Pym | ring 21 | 2-Cl |
| 13-503 | 4-F-Ph | 2-NH$_2$-4-Pym | ring 22 | 2-Cl |
| 13-504 | 4-F-Ph | 2-NH$_2$-4-Pym | ring 23 | 2-Cl |
| 13-505 | 4-F-Ph | 2-NH$_2$-4-Pym | ring 24 | 2-Cl |
| 13-506 | 4-F-Ph | 2-NH$_2$-4-Pym | ring 25 | 2-Cl |
| 13-507 | 4-F-Ph | 2-NH$_2$-4-Pym | ring 26 | 2-Cl |
| 13-508 | 4-F-Ph | 2-NH$_2$-4-Pym | ring 27 | 2-Cl |
| 13-509 | 4-F-Ph | 2-NH$_2$-4-Pym | ring 28 | 2-Cl |
| 13-510 | 4-F-Ph | 2-NH$_2$-4-Pym | ring 29 | 2-Cl |
| 13-511 | 4-F-Ph | 2-NH$_2$-4-Pym | ring 30 | 2-Cl |
| 13-512 | 4-F-Ph | 2-NH$_2$-4-Pym | ring 31 | 2-Cl |
| 13-513 | 4-F-Ph | 2-NH$_2$-4-Pym | ring 32 | 2-Cl |
| 13-514 | 4-F-Ph | 2-NH$_2$-4-Pym | ring 33 | 2-Cl |
| 13-515 | 4-F-Ph | 2-NH$_2$-4-Pym | ring 34 | 2-Cl |
| 13-516 | 4-F-Ph | 2-NH$_2$-4-Pym | ring 35 | 2-Cl |
| 13-517 | 4-F-Ph | 2-NH$_2$-4-Pym | ring 36 | 2-Cl |
| 13-518 | 4-F-Ph | 2-NH$_2$-4-Pym | ring 37 | 2-Cl |
| 13-519 | 4-F-Ph | 2-NH$_2$-4-Pym | ring 1 | 2,2-diF |
| 13-520 | 4-F-Ph | 2-NH$_2$-4-Pym | ring 2 | 2,2-diF |
| 13-521 | 4-F-Ph | 2-NH$_2$-4-Pym | ring 3 | 2,2-diF |
| 13-522 | 4-F-Ph | 2-NH$_2$-4-Pym | ring 4 | 2,2-diF |
| 13-523 | 4-F-Ph | 2-NH$_2$-4-Pym | ring S | 2,2-diF |
| 13-524 | 4-F-Ph | 2-NH$_2$-4-Pym | ring 6 | 2,2-diF |
| 13-525 | 4-F-Ph | 2-NH$_2$-4-Pym | ring 7 | 2,2-diF |
| 13-526 | 4-F-Ph | 2-NH$_2$-4-Pym | ring 8 | 2,2-diF |
| 13-527 | 4-F-Ph | 2-NH$_2$-4-Pym | ring 9 | 2,2-diF |
| 13-528 | 4-F-Ph | 2-NH$_2$-4-Pym | ring 10 | 2,2-diF |
| 13-529 | 4-F-Ph | 2-NH$_2$-4-Pym | ring 11 | 2,2-diF |
| 13-530 | 4-F-Ph | 2-NH$_2$-4-Pym | ring 12 | 2,2-diF |
| 13-531 | 4-F-Ph | 2-NH$_2$-4-Pym | ring 13 | 2,2-diF |
| 13-532 | 4-F-Ph | 2-NH$_2$-4-Pym | ring 14 | 2,2-diF |
| 13-533 | 4-F-Ph | 2-NH$_2$-4-Pym | ring 15 | 2,2-diF |
| 13-534 | 4-F-Ph | 2-NH$_2$-4-Pym | ring 16 | 2,2-diF |
| 13-535 | 4-F-Ph | 2-NH$_2$-4-Pym | ring 17 | 2,2-diF |
| 13-536 | 4-F-Ph | 2-NH$_2$-4-Pym | ring 18 | 2,2-diF |
| 13-537 | 4-F-Ph | 2-NH$_2$-4-Pym | ring 19 | 2,2-diF |
| 13-538 | 4-F-Ph | 2-NH$_2$-4-Pym | ring 20 | 2,2-diF |
| 13-539 | 4-F-Ph | 2-NH$_2$-4-Pym | ring 21 | 2,2-diF |
| 13-540 | 4-F-Ph | 2-NH$_2$-4-Pym | ring 22 | 2,2-diF |
| 13-541 | 4-F-Ph | 2-NH$_2$-4-Pym | ring 23 | 2,2-diF |
| 13-542 | 4-F-Ph | 2-NH$_2$-4-Pym | ring 24 | 2,2-diF |
| 13-543 | 4-F-Ph | 2-NH$_2$-4-Pym | ring 25 | 2,2-diF |
| 13-544 | 4-F-Ph | 2-NH$_2$-4-Pym | ring 26 | 2,2-diF |
| 13-545 | 4-F-Ph | 2-NH$_2$-4-Pym | ring 27 | 2,2-diF |
| 13-546 | 4-F-Ph | 2-NH$_2$-4-Pym | ring 28 | 2,2-diF |
| 13-547 | 4-F-Ph | 2-NH$_2$-4-Pym | ring 29 | 2,2-diF |
| 13-548 | 4-F-Ph | 2-NH$_2$-4-Pym | ring 30 | 2,2-diF |
| 13-549 | 4-F-Ph | 2-NH$_2$-4-Pym | ring 31 | 2,2-diF |
| 13-550 | 4-F-Ph | 2-NH$_2$-4-Pym | ring 32 | 2,2-diF |
| 13-551 | 4-F-Ph | 2-NH$_2$-4-Pym | ring 33 | 2,2-diF |
| 13-552 | 4-F-Ph | 2-NH$_2$-4-Pym | ring 34 | 2,2-diF |
| 13-553 | 4-F-Ph | 2-NH$_2$-4-Pym | ring 35 | 2,2-diF |

TABLE 13-continued

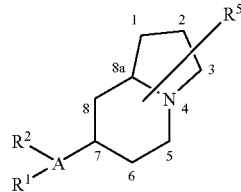 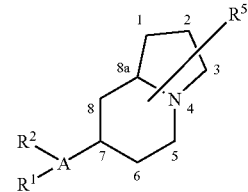

| Compound No. | R¹ | R² | A | R⁵ |
|---|---|---|---|---|
| 13-554 | 4-F-Ph | 2-NH₂-4-Pym | ring 36 | 2,2-diF |
| 13-555 | 4-F-Ph | 2-NH₂-4-Pym | ring 37 | 2,2-diF |
| 13-556 | 4-F-Ph | 2-NH₂-4-Pym | ring 1 | 8-Me |
| 13-557 | 4-F-Ph | 2-NH₂-4-Pym | ring 2 | 8-Me |
| 13-558 | 4-F-Ph | 2-NH₂-4-Pym | ring 3 | 8-Me |
| 13-559 | 4-F-Ph | 2-NH₂-4-Pym | ring 4 | 8-Me |
| 13-560 | 4-F-Ph | 2-NH₂-4-Pym | ring S | 8-Me |
| 13-561 | 4-F-Ph | 2-NH₂-4-Pym | ring 6 | 8-Me |
| 13-562 | 4-F-Ph | 2-NH₂-4-Pym | ring 7 | 8-Me |
| 13-563 | 4-F-Ph | 2-NH₂-4-Pym | ring 8 | 8-Me |
| 13-564 | 4-F-Ph | 2-NH₂-4-Pym | ring 9 | 8-Me |
| 13-565 | 4-F-Ph | 2-NH₂-4-Pym | ring 10 | 8-Me |
| 13-566 | 4-F-Ph | 2-NH₂-4-Pym | ring 11 | 8-Me |
| 13-567 | 4-F-Ph | 2-NH₂-4-Pym | ring 12 | 8-Me |
| 13-568 | 4-F-Ph | 2-NH₂-4-Pym | ring 13 | 8-Me |
| 13-569 | 4-F-Ph | 2-NH₂-4-Pym | ring 14 | 8-Me |
| 13-570 | 4-F-Ph | 2-NH₂-4-Pym | ring 15 | 8-Me |
| 13-571 | 4-F-Ph | 2-NH₂-4-Pym | ring 16 | 8-Me |
| 13-572 | 4-F-Ph | 2-NH₂-4-Pym | ring 17 | 8-Me |
| 13-573 | 4-F-Ph | 2-NH₂-4-Pym | ring 18 | 8-Me |
| 13-574 | 4-F-Ph | 2-NH₂-4-Pym | ring 19 | 8-Me |
| 13-575 | 4-F-Ph | 2-NH₂-4-Pym | ring 20 | 8-Me |
| 13-576 | 4-F-Ph | 2-NH₂-4-Pym | ring 21 | 8-Me |
| 13-577 | 4-F-Ph | 2-NH₂-4-Pym | ring 22 | 8-Me |
| 13-578 | 4-F-Ph | 2-NH₂-4-Pym | ring 23 | 8-Me |
| 13-579 | 4-F-Ph | 2-NH₂-4-Pym | ring 24 | 8-Me |
| 13-580 | 4-F-Ph | 2-NH₂-4-Pym | ring 25 | 8-Me |
| 13-581 | 4-F-Ph | 2-NH₂-4-Pym | ring 26 | 8-Me |
| 13-582 | 4-F-Ph | 2-NH₂-4-Pym | ring 27 | 8-Me |
| 13-583 | 4-F-Ph | 2-NH₂-4-Pym | ring 28 | 8-Me |
| 13-584 | 4-F-Ph | 2-NH₂-4-Pym | ring 29 | 8-Me |
| 13-585 | 4-F-Ph | 2-NH₂-4-Pym | ring 30 | 8-Me |
| 13-586 | 4-F-Ph | 2-NH₂-4-Pym | ring 31 | 8-Me |
| 13-587 | 4-F-Ph | 2-NH₂-4-Pym | ring 32 | 8-Me |
| 13-588 | 4-F-Ph | 2-NH₂-4-Pym | ring 33 | 8-Me |
| 13-589 | 4-F-Ph | 2-NH₂-4-Pym | ring 34 | 8-Me |
| 13-590 | 4-F-Ph | 2-NH₂-4-Pym | ring 35 | 8-Me |
| 13-591 | 4-F-Ph | 2-NH₂-4-Pym | ring 36 | 8-Me |
| 13-592 | 4-F-Ph | 2-NH₂-4-Pym | ring 37 | 8-Me |
| 13-593 | 4-F-Ph | 2-MeNH-4-Pym | ring 1 | — |
| 13-594 | 4-F-Ph | 2-MeNH-4-Pym | ring 2 | — |
| 13-595 | 4-F-Ph | 2-MeNH-4-Pym | ring 3 | — |
| 13-596 | 4-F-Ph | 2-MeNH-4-Pym | ring 4 | — |
| 13-597 | 4-F-Ph | 2-MeNH-4-Pym | ring 5 | — |
| 13-598 | 4-F-Ph | 2-MeNH-4-Pym | ring 6 | — |
| 13-599 | 4-F-Ph | 2-MeNH-4-Pym | ring 7 | — |
| 13-600 | 4-F-Ph | 2-MeNH-4-Pym | ring 8 | — |
| 13-601 | 4-F-Ph | 2-MeNH-4-Pym | ring 9 | — |
| 13-602 | 4-F-Ph | 2-MeNH-4-Pym | ring 10 | — |
| 13-603 | 4-F-Ph | 2-MeNH-4-Pym | ring 11 | — |
| 13-604 | 4-F-Ph | 2-MeNH-4-Pym | ring 12 | — |
| 13-605 | 4-F-Ph | 2-MeNH-4-Pym | ring 13 | — |
| 13-606 | 4-F-Ph | 2-MeNH-4-Pym | ring 14 | — |
| 13-607 | 4-F-Ph | 2-MeNH-4-Pym | ring 15 | — |
| 13-608 | 4-F-Ph | 2-MeNH-4-Pym | ring 16 | — |
| 13-609 | 4-F-Ph | 2-MeNH-4-Pym | ring 17 | — |
| 13-610 | 4-F-Ph | 2-MeNH-4-Pym | ring 18 | — |
| 13-611 | 4-F-Ph | 2-MeNH-4-Pym | ring 19 | — |
| 13-612 | 4-F-Ph | 2-MeNH-4-Pym | ring 20 | — |
| 13-613 | 4-F-Ph | 2-MeNH-4-Pym | ring 21 | — |
| 13-614 | 4-F-Ph | 2-MeNH-4-Pym | ring 22 | — |
| 13-615 | 4-F-Ph | 2-MeNH-4-Pym | ring 23 | — |
| 13-616 | 4-F-Ph | 2-MeNH-4-Pym | ring 24 | — |
| 13-617 | 4-F-Ph | 2-MeNH-4-Pym | ring 25 | — |
| 13-618 | 4-F-Ph | 2-MeNH-4-Pym | ring 26 | — |
| 13-619 | 4-F-Ph | 2-MeNH-4-Pym | ring 27 | — |
| 13-620 | 4-F-Ph | 2-MeNH-4-Pym | ring 28 | — |
| 13-621 | 4-F-Ph | 2-MeNH-4-Pym | ring 29 | — |
| 13-622 | 4-F-Ph | 2-MeNH-4-Pym | ring 30 | — |
| 13-623 | 4-F-Ph | 2-MeNH-4-Pym | ring 31 | — |
| 13-624 | 4-F-Ph | 2-MeNH-4-Pym | ring 32 | — |
| 13-625 | 4-F-Ph | 2-MeNH-4-Pym | ring 33 | — |
| 13-626 | 4-F-Ph | 2-MeNH-4-Pym | ring 34 | — |
| 13-627 | 4-F-Ph | 2-MeNH-4-Pym | ring 35 | — |
| 13-628 | 4-F-Ph | 2-MeNH-4-Pym | ring 36 | — |
| 13-629 | 4-F-Ph | 2-MeNH-4-Pym | ring 37 | — |
| 13-630 | 4-F-Ph | 2-MeNH-4-Pym | ring 1 | 2-Me |
| 13-631 | 4-F-Ph | 2-MeNH-4-Pym | ring 2 | 2-Me |
| 13-632 | 4-F-Ph | 2-MeNH-4-Pym | ring 3 | 2-Me |
| 13-633 | 4-F-Ph | 2-MeNH-4-Pym | ring 4 | 2-Me |
| 13-634 | 4-F-Ph | 2-MeNH-4-Pym | ring 5 | 2-Me |
| 13-635 | 4-F-Ph | 2-MeNH-4-Pym | ring 6 | 2-Me |
| 13-636 | 4-F-Ph | 2-MeNH-4-Pym | ring 7 | 2-Me |
| 13-637 | 4-F-Ph | 2-MeNH-4-Pym | ring 8 | 2-Me |
| 13-638 | 4-F-Ph | 2-MeNH-4-Pym | ring 9 | 2-Me |
| 13-639 | 4-F-Ph | 2-MeNH-4-Pym | ring 10 | 2-Me |
| 13-640 | 4-F-Ph | 2-MeNH-4-Pym | ring 11 | 2-Me |
| 13-641 | 4-F-Ph | 2-MeNH-4-Pym | ring 12 | 2-Me |
| 13-642 | 4-F-Ph | 2-MeNH-4-Pym | ring 13 | 2-Me |
| 13-643 | 4-F-Ph | 2-MeNH-4-Pym | ring 14 | 2-Me |
| 13-644 | 4-F-Ph | 2-MeNH-4-Pym | ring 15 | 2-Me |
| 13-645 | 4-F-Ph | 2-MeNH-4-Pym | ring 16 | 2-Me |
| 13-646 | 4-F-Ph | 2-MeNH-4-Pym | ring 17 | 2-Me |
| 13-647 | 4-F-Ph | 2-MeNH-4-Pym | ring 18 | 2-Me |
| 13-648 | 4-F-Ph | 2-MeNH-4-Pym | ring 19 | 2-Me |
| 13-649 | 4-F-Ph | 2-MeNH-4-Pym | ring 20 | 2-Me |
| 13-650 | 4-F-Ph | 2-MeNH-4-Pym | ring 21 | 2-Me |
| 13-651 | 4-F-Ph | 2-MeNH-4-Pym | ring 22 | 2-Me |
| 13-652 | 4-F-Ph | 2-MeNH-4-Pym | ring 23 | 2-Me |
| 13-653 | 4-F-Ph | 2-MeNH-4-Pym | ring 24 | 2-Me |
| 13-654 | 4-F-Ph | 2-MeNH-4-Pym | ring 25 | 2-Me |
| 13-655 | 4-F-Ph | 2-MeNH-4-Pym | ring 26 | 2-Me |
| 13-656 | 4-F-Ph | 2-MeNH-4-Pym | ring 27 | 2-Me |
| 13-657 | 4-F-Ph | 2-MeNH-4-Pym | ring 28 | 2-Me |
| 13-658 | 4-F-Ph | 2-MeNH-4-Pym | ring 29 | 2-Me |
| 13-659 | 4-F-Ph | 2-MeNH-4-Pym | ring 30 | 2-Me |
| 13-660 | 4-F-Ph | 2-MeNH-4-Pym | ring 31 | 2-Me |
| 13-661 | 4-F-Ph | 2-MeNH-4-Pym | ring 32 | 2-Me |
| 13-662 | 4-F-Ph | 2-MeNH-4-Pym | ring 33 | 2-Me |
| 13-663 | 4-F-Ph | 2-MeNH-4-Pym | ring 34 | 2-Me |
| 13-664 | 4-F-Ph | 2-MeNH-4-Pym | ring 35 | 2-Me |
| 13-665 | 4-F-Ph | 2-MeNH-4-Pym | ring 36 | 2-Me |
| 13-666 | 4-F-Ph | 2-MeNH-4-Pym | ring 37 | 2-Me |
| 13-667 | 4-F-Ph | 2-MeNH-4-Pym | ring 1 | 2-OH |
| 13-668 | 4-F-Ph | 2-MeNH-4-Pym | ring 2 | 2-OH |
| 13-669 | 4-F-Ph | 2-MeNH-4-Pym | ring 3 | 2-OH |
| 13-670 | 4-F-Ph | 2-MeNH-4-Pym | ring 4 | 2-OH |
| 13-671 | 4-F-Ph | 2-MeNH-4-Pym | ring 5 | 2-OH |
| 13-672 | 4-F-Ph | 2-MeNH-4-Pym | ring 6 | 2-OH |
| 13-673 | 4-F-Ph | 2-MeNH-4-Pym | ring 7 | 2-OH |
| 13-674 | 4-F-Ph | 2-MeNH-4-Pym | ring 8 | 2-OH |
| 13-675 | 4-F-Ph | 2-MeNH-4-Pym | ring 9 | 2-OH |
| 13-676 | 4-F-Ph | 2-MeNH-4-Pym | ring 10 | 2-OH |
| 13-677 | 4-F-Ph | 2-MeNH-4-Pym | ring 11 | 2-OH |
| 13-678 | 4-F-Ph | 2-MeNH-4-Pym | ring 12 | 2-OH |
| 13-679 | 4-F-Ph | 2-MeNH-4-Pym | ring 13 | 2-OH |
| 13-680 | 4-F-Ph | 2-MeNH-4-Pym | ring 14 | 2-OH |
| 13-681 | 4-F-Ph | 2-MeNH-4-Pym | ring 15 | 2-OH |
| 13-682 | 4-F-Ph | 2-MeNH-4-Pym | ring 16 | 2-OH |
| 13-683 | 4-F-Ph | 2-MeNH-4-Pym | ring 17 | 2-OH |

TABLE 13-continued

| Compound No. | R¹ | R² | A | R⁵ |
|---|---|---|---|---|
| 13-684 | 4-F-Ph | 2-MeNH-4-Pym | ring 18 | 2-OH |
| 13-685 | 4-F-Ph | 2-MeNH-4-Pym | ring 19 | 2-OH |
| 13-686 | 4-F-Ph | 2-MeNH-4-Pym | ring 20 | 2-OH |
| 13-687 | 4-F-Ph | 2-MeNH-4-Pym | nug 21 | 2-OH |
| 13-688 | 4-F-Ph | 2-MeNH-4-Pym | ring 22 | 2-OH |
| 13-689 | 4-F-Ph | 2-MeNH-4-Pym | ring 23 | 2-OH |
| 13-690 | 4-F-Ph | 2-MeNH-4-Pym | ring 24 | 2-OH |
| 13-691 | 4-F-Ph | 2-MeNH-4-Pym | ring 25 | 2-OH |
| 13-692 | 4-F-Ph | 2-MeNH-4-Pym | ring 26 | 2-OH |
| 13-693 | 4-F-Ph | 2-MeNH-4-Pym | ring 27 | 2-OH |
| 13-694 | 4-F-Ph | 2-MeNH-4-Pym | ring 28 | 2-OH |
| 13-695 | 4-F-Ph | 2-MeNH-4-Pym | ring 29 | 2-OH |
| 13-696 | 4-F-Ph | 2-MeNH-4-Pym | ring 30 | 2-OH |
| 13-697 | 4-F-Ph | 2-MeNH-4-Pym | ring 31 | 2-OH |
| 13-698 | 4-F-Ph | 2-MeNH-4-Pym | ring 32 | 2-OH |
| 13-699 | 4-F-Ph | 2-MeNH-4-Pym | ring 33 | 2-OH |
| 13-700 | 4-F-Ph | 2-MeNH-4-Pym | ring 34 | 2-OH |
| 13-701 | 4-F-Ph | 2-MeNH-4-Pym | ring 35 | 2-OH |
| 13-702 | 4-F-Ph | 2-MeNH-4-Pym | ring 36 | 2-OH |
| 13-703 | 4-F-Ph | 2-MeNH-4-Pym | ring 37 | 2-OH |
| 13-704 | 4-F-Ph | 2-MeNH-4-Pym | ring 1 | 2-MeO |
| 13-705 | 4-F-Ph | 2-MeNH-4-Pym | ring 2 | 2-MeO |
| 13-706 | 4-F-Ph | 2-MeNH-4-Pym | ring 3 | 2-MeO |
| 13-707 | 4-F-Ph | 2-MeNH-4-Pym | ring 4 | 2-MeO |
| 13-708 | 4-F-Ph | 2-MeNH-4-Pym | ring 5 | 2-MeO |
| 13-709 | 4-F-Ph | 2-MeNH-4-Pym | ring 6 | 2-MeO |
| 13-710 | 4-F-Ph | 2-MeNH-4-Pym | ring 7 | 2-MeO |
| 13-711 | 4-F-Ph | 2-MeNH-4-Pym | ring 8 | 2-MeO |
| 13-712 | 4-F-Ph | 2-MeNH-4-Pym | ring 9 | 2-MeO |
| 13-713 | 4-F-Ph | 2-MeNH-4-Pym | ring 10 | 2-MeO |
| 13-714 | 4-F-Ph | 2-MeNH-4-Pym | ring 11 | 2-MeO |
| 13-715 | 4-F-Ph | 2-MeNH-4-Pym | ring 12 | 2-MeO |
| 13-716 | 4-F-Ph | 2-MeNH-4-Pym | ring 13 | 2-MeO |
| 13-717 | 4-F-Ph | 2-MeNH-4-Pym | ring 14 | 2-MeO |
| 13-718 | 4-F-Ph | 2-MeNH-4-Pym | ring 15 | 2-MeO |
| 13-719 | 4-F-Ph | 2-MeNH-4-Pym | ring 16 | 2-MeO |
| 13-720 | 4-F-Ph | 2-MeNH-4-Pym | ring 17 | 2-MeO |
| 13-721 | 4-F-Ph | 2-MeNH-4-Pym | ring 18 | 2-MeO |
| 13-722 | 4-F-Ph | 2-MeNH-4-Pym | ring 19 | 2-MeO |
| 13-723 | 4-F-Ph | 2-MeNH-4-Pym | ring 20 | 2-MeO |
| 13-724 | 4-F-Ph | 2-MeNH-4-Pym | ring 21 | 2-MeO |
| 13-725 | 4-F-Ph | 2-MeNH-4-Pym | ring 22 | 2-MeO |
| 13-726 | 4-F-Ph | 2-MeNH-4-Pym | ring 23 | 2-MeO |
| 13-727 | 4-F-Ph | 2-MeNH-4-Pym | ring 24 | 2-MeO |
| 13-728 | 4-F-Ph | 2-MeNH-4-Pym | ring 25 | 2-MeO |
| 13-729 | 4-F-Ph | 2-MeNH-4-Pym | ring 26 | 2-MeO |
| 13-730 | 4-F-Ph | 2-MeNH-4-Pym | ring 27 | 2-MeO |
| 13-731 | 4-F-Ph | 2-MeNH-4-Pym | ring 28 | 2-MeO |
| 13-732 | 4-F-Ph | 2-MeNH-4-Pym | ring 29 | 2-MeO |
| 13-733 | 4-F-Ph | 2-MeNH-4-Pym | ring 30 | 2-MeO |
| 13-734 | 4-F-Ph | 2-MeNH-4-Pym | ring 31 | 2-MeO |
| 13-735 | 4-F-Ph | 2-MeNH-4-Pym | ring 32 | 2-MeO |
| 13-736 | 4-F-Ph | 2-MeNH-4-Pym | ring 33 | 2-MeO |
| 13-737 | 4-F-Ph | 2-MeNH-4-Pym | ring 34 | 2-MeO |
| 13-738 | 4-F-Ph | 2-MeNH-4-Pym | ring 35 | 2-MeO |
| 13-739 | 4-F-Ph | 2-MeNH-4-Pym | ring 36 | 2-MeO |
| 13-740 | 4-F-Ph | 2-MeNH-4-Pym | ring 37 | 2-MeO |
| 13-741 | 4-F-Ph | 2-MeNH-4-Pym | ring 1 | 2-F |
| 13-742 | 4-F-Ph | 2-MeNH-4-Pym | ring 2 | 2-F |
| 13-743 | 4-F-Ph | 2-MeNH-4-Pym | ring 3 | 2-F |
| 13-744 | 4-F-Ph | 2-MeNH-4-Pym | ring 4 | 2-F |
| 13-745 | 4-F-Ph | 2-MeNH-4-Pym | ring 5 | 2-F |
| 13-746 | 4-F-Ph | 2-MeNH-4-Pym | ring 6 | 2-F |
| 13-747 | 4-F-Ph | 2-MeNH-4-Pym | ring 7 | 2-F |
| 13-748 | 4-F-Ph | 2-MeNH-4-Pym | ring 8 | 2-F |
| 13-749 | 4-F-Ph | 2-MeNH-4-Pym | ring 9 | 2-F |
| 13-750 | 4-F-Ph | 2-MeNH-4-Pym | ring 10 | 2-F |
| 13-751 | 4-F-Ph | 2-MeNH-4-Pym | ring 11 | 2-F |
| 13-752 | 4-F-Ph | 2-MeNH-4-Pym | ring 12 | 2-F |
| 13-753 | 4-F-Ph | 2-MeNH-4-Pym | ring 13 | 2-F |
| 13-754 | 4-F-Ph | 2-MeNH-4-Pym | ring 14 | 2-F |
| 13-755 | 4-F-Ph | 2-MeNH-4-Pym | ring 15 | 2-F |
| 13-756 | 4-F-Ph | 2-MeNH-4-Pym | ring 16 | 2-F |
| 13-757 | 4-F-Ph | 2-MeNH-4-Pym | ring 17 | 2-F |
| 13-758 | 4-F-Ph | 2-MeNH-4-Pym | ring 18 | 2-F |
| 13-759 | 4-F-Ph | 2-MeNH-4-Pym | ring 19 | 2-F |
| 13-760 | 4-F-Ph | 2-MeNH-4-Pym | ring 20 | 2-F |
| 13-761 | 4-F-Ph | 2-MeNH-4-Pym | ring 21 | 2-F |
| 13-762 | 4-F-Ph | 2-MeNH-4-Pym | ring 22 | 2-F |
| 13-763 | 4-F-Ph | 2-MeNH-4-Pym | ring 23 | 2-F |
| 13-764 | 4-F-Ph | 2-MeNH-4-Pym | ring 24 | 2-F |
| 13-765 | 4-F-Ph | 2-MeNH-4-Pym | ring 25 | 2-F |
| 13-766 | 4-F-Ph | 2-MeNH-4-Pym | ring 26 | 2-F |
| 13-767 | 4-F-Ph | 2-MeNH-4-Pym | ring 27 | 2-F |
| 13-768 | 4-F-Ph | 2-MeNH-4-Pym | ring 28 | 2-F |
| 13-769 | 4-F-Ph | 2-MeNH-4-Pym | ring 29 | 2-F |
| 13-770 | 4-F-Ph | 2-MeNH-4-Pym | ring 30 | 2-F |
| 13-771 | 4-F-Ph | 2-MeNH-4-Pym | ring 31 | 2-F |
| 13-772 | 4-F-Ph | 2-MeNH-4-Pym | ring 32 | 2-F |
| 13-773 | 4-F-Ph | 2-MeNH-4-Pym | ring 33 | 2-F |
| 13-774 | 4-F-Ph | 2-MeNH-4-Pym | ring 34 | 2-F |
| 13-775 | 4-F-Ph | 2-MeNH-4-Pym | ring 35 | 2-F |
| 13-776 | 4-F-Ph | 2-MeNH-4-Pym | ring 36 | 2-F |
| 13-777 | 4-F-Ph | 2-MeNH-4-Pym | ring 37 | 2-F |
| 13-778 | 4-F-Ph | 2-MeNH-4-Pym | ring 1 | 2-Cl |
| 13-779 | 4-F-Ph | 2-MeNH-4-Pym | ring 2 | 2-Cl |
| 13-780 | 4-F-Ph | 2-MeNH-4-Pym | ring 3 | 2-Cl |
| 13-781 | 4-F-Ph | 2-MeNH-4-Pym | ring 4 | 2-Cl |
| 13-782 | 4-F-Ph | 2-MeNH-4-Pym | ring 5 | 2-Cl |
| 13-783 | 4-F-Ph | 2-MeNH-4-Pym | ring 6 | 2-Cl |
| 13-784 | 4-F-Ph | 2-MeNH-4-Pym | ring 7 | 2-Cl |
| 13-785 | 4-F-Ph | 2-MeNH-4-Pym | ring 8 | 2-Cl |
| 13-786 | 4-F-Ph | 2-MeNH-4-Pym | ring 9 | 2-Cl |
| 13-787 | 4-F-Ph | 2-MeNH-4-Pym | ring 10 | 2-Cl |
| 13-788 | 4-F-Ph | 2-MeNH-4-Pym | ring 11 | 2-Cl |
| 13-789 | 4-F-Ph | 2-MeNH-4-Pym | ring 12 | 2-Cl |
| 13-790 | 4-F-Ph | 2-MeNH-4-Pym | ring 13 | 2-Cl |
| 13-791 | 4-F-Ph | 2-MeNH-4-Pym | ring 14 | 2-Cl |
| 13-792 | 4-F-Ph | 2-MeNH-4-Pym | ring 15 | 2-Cl |
| 13-793 | 4-F-Ph | 2-MeNH-4-Pym | ring 16 | 2-Cl |
| 13-794 | 4-F-Ph | 2-MeNH-4-Pym | ring 17 | 2-Cl |
| 13-795 | 4-F-Ph | 2-MeNH-4-Pym | ring 18 | 2-Cl |
| 13-796 | 4-F-Ph | 2-MeNH-4-Pym | ring 19 | 2-Cl |
| 13-797 | 4-F-Ph | 2-MeNH-4-Pym | ring 20 | 2-Cl |
| 13-798 | 4-F-Ph | 2-MeNH-4-Pym | ring 21 | 2-Cl |
| 13-799 | 4-F-Ph | 2-MeNH-4-Pym | ring 22 | 2-Cl |
| 13-800 | 4-F-Ph | 2-MeNH-4-Pym | ring 23 | 2-Cl |
| 13-801 | 4-F-Ph | 2-MeNH-4-Pym | ring 24 | 2-Cl |
| 13-802 | 4-F-Ph | 2-MeNH-4-Pym | ring 25 | 2-Cl |
| 13-803 | 4-F-Ph | 2-MeNH-4-Pym | ring 26 | 2-Cl |
| 13-804 | 4-F-Ph | 2-MeNH-4-Pym | ring 27 | 2-Cl |
| 13-805 | 4-F-Ph | 2-MeNH-4-Pym | ring 28 | 2-Cl |
| 13-806 | 4-F-Ph | 2-MeNH-4-Pym | ring 29 | 2-Cl |
| 13-807 | 4-F-Ph | 2-MeNH-4-Pym | ring 30 | 2-Cl |
| 13-808 | 4-F-Ph | 2-MeNH-4-Pym | ring 31 | 2-Cl |
| 13-809 | 4-F-Ph | 2-MeNH-4-Pym | ring 32 | 2-Cl |
| 13-810 | 4-F-Ph | 2-MeNH-4-Pym | ring 33 | 2-Cl |
| 13-811 | 4-F-Ph | 2-MeNH-4-Pym | ring 34 | 2-Cl |
| 13-812 | 4-F-Ph | 2-MeNH-4-Pym | ring 35 | 2-Cl |
| 13-813 | 4-F-Ph | 2-MeNH-4-Pym | ring 36 | 2-Cl |

TABLE 13-continued

| Compound No. | R¹ | R² | A | R⁵ |
|---|---|---|---|---|
| 13-814 | 4-F-Ph | 2-MeNH-4-Pym | ring 37 | 2-Cl |
| 13-815 | 4-F-Ph | 2-MeNH-4-Pym | ring 1 | 2,2-diF |
| 13-816 | 4-F-Ph | 2-MeNH-4-Pym | ring 2 | 2,2-diF |
| 13-817 | 4-F-Ph | 2-MeNH-4-Pym | ring 3 | 2,2-diF |
| 13-818 | 4-F-Ph | 2-MeNH-4-Pym | ring 4 | 2,2-diF |
| 13-819 | 4-F-Ph | 2-MeNH-4-Pym | ring 5 | 2,2-diF |
| 13-820 | 4-F-Ph | 2-MeNH-4-Pym | ring 6 | 2,2-diF |
| 13-821 | 4-F-Ph | 2-MeNH-4-Pym | ring 7 | 2,2-diF |
| 13-822 | 4-F-Ph | 2-MeNH-4-Pym | ring 8 | 2,2-diF |
| 13-823 | 4-F-Ph | 2-MeNH-4-Pym | ring 9 | 2,2-diF |
| 13-824 | 4-F-Ph | 2-MeNH-4-Pym | ring 10 | 2,2-diF |
| 13-825 | 4-F-Ph | 2-MeNH-4-Pym | ring 11 | 2,2-diF |
| 13-826 | 4-F-Ph | 2-MeNH-4-Pym | ring 12 | 2,2-diF |
| 13-827 | 4-F-Ph | 2-MeNH-4-Pym | ring 13 | 2,2-diF |
| 13-828 | 4-F-Ph | 2-MeNH-4-Pym | ring 14 | 2,2-diF |
| 13-829 | 4-F-Ph | 2-MeNH-4-Pym | ring 15 | 2,2-diF |
| 13-830 | 4-F-Ph | 2-MeNH-4-Pym | ring 16 | 2,2-diF |
| 13-831 | 4-F-Ph | 2-MeNH-4-Pym | ring 17 | 2,2-diF |
| 13-832 | 4-F-Ph | 2-MeNH-4-Pym | ring 18 | 2,2-diF |
| 13-833 | 4-F-Ph | 2-MeNH-4-Pym | ring 19 | 2,2-diF |
| 13-834 | 4-F-Ph | 2-MeNH-4-Pym | ring 20 | 2,2-diF |
| 13-835 | 4-F-Ph | 2-MeNH-4-Pym | ring 21 | 2,2-diF |
| 13-836 | 4-F-Ph | 2-MeNH-4-Pym | ring 22 | 2,2-diF |
| 13-837 | 4-F-Ph | 2-MeNH-4-Pym | ring 23 | 2,2-diF |
| 13-838 | 4-F-Ph | 2-MeNH-4-Pym | ring 24 | 2,2-diF |
| 13-839 | 4-F-Ph | 2-MeNH-4-Pym | ring 25 | 2,2-diF |
| 13-840 | 4-F-Ph | 2-MeNH-4-Pym | ring 26 | 2,2-diF |
| 13-841 | 4-F-Ph | 2-MeNH-4-Pym | ring 27 | 2,2-diF |
| 13-842 | 4-F-Ph | 2-MeNH-4-Pym | ring 28 | 2,2-diF |
| 13-843 | 4-F-Ph | 2-MeNH-4-Pym | ring 29 | 2,2-diF |
| 13-844 | 4-F-Ph | 2-MeNH-4-Pym | ring 30 | 2,2-diF |
| 13-845 | 4-F-Ph | 2-MeNH-4-Pym | ring 31 | 2,2-diF |
| 13-846 | 4-F-Ph | 2-MeNH-4-Pym | ring 32 | 2,2-diF |
| 13-847 | 4-F-Ph | 2-MeNH-4-Pym | ring 33 | 2,2-diF |
| 13-848 | 4-F-Ph | 2-MeNH-4-Pym | ring 34 | 2,2-diF |
| 13-849 | 4-F-Ph | 2-MeNH-4-Pym | ring 35 | 2,2-diF |
| 13-850 | 4-F-Ph | 2-MeNH-4-Pym | ring 36 | 2,2-diF |
| 13-851 | 4-F-Ph | 2-MeNH-4-Pym | ring 37 | 2,2-diF |
| 13-852 | 4-F-Ph | 2-MeNH-4-Pym | ring 1 | 8-Me |
| 13-853 | 4-F-Ph | 2-MeNH-4-Pym | ring 2 | 8-Me |
| 13-854 | 4-F-Ph | 2-MeNH-4-Pym | ring 3 | 8-Me |
| 13-855 | 4-F-Ph | 2-MeNH-4-Pym | ring 4 | 8-Me |
| 13-856 | 4-F-Ph | 2-MeNH-4-Pym | ring 5 | 8-Me |
| 13-857 | 4-F-Ph | 2-MeNH-4-Pym | ring 6 | 8-Me |
| 13-858 | 4-F-Ph | 2-MeNH-4-Pym | ring 7 | 8-Me |
| 13-859 | 4-F-Ph | 2-MeNH-4-Pym | ring 8 | 8-Me |
| 13-860 | 4-F-Ph | 2-MeNH-4-Pym | ring 9 | 8-Me |
| 13-861 | 4-F-Ph | 2-MeNH-4-Pym | ring 10 | 8-Me |
| 13-862 | 4-F-Ph | 2-MeNH-4-Pym | ring 11 | 8-Me |
| 13-863 | 4-F-Ph | 2-MeNH-4-Pym | ring 12 | 8-Me |
| 13-864 | 4-F-Ph | 2-MeNH-4-Pym | ring 13 | 8-Me |
| 13-865 | 4-F-Ph | 2-MeNH-4-Pym | ring 14 | 8-Me |
| 13-866 | 4-F-Ph | 2-MeNH-4-Pym | ring 15 | 8-Me |
| 13-867 | 4-F-Ph | 2-MeNH-4-Pym | ring 16 | 8-Me |
| 13-868 | 4-F-Ph | 2-MeNH-4-Pym | ring 17 | 8-Me |
| 13-869 | 4-F-Ph | 2-MeNH-4-Pym | ring 18 | 8-Me |
| 13-870 | 4-F-Ph | 2-MeNH-4-Pym | ring 19 | 8-Me |
| 13-871 | 4-F-Ph | 2-MeNH-4-Pym | ring 20 | 8-Me |
| 13-872 | 4-F-Ph | 2-MeNH-4-Pym | ring 21 | 8-Me |
| 13-873 | 4-F-Ph | 2-MeNH-4-Pym | ring 22 | 8-Me |
| 13-874 | 4-F-Ph | 2-MeNH-4-Pym | ring 23 | 8-Me |
| 13-875 | 4-F-Ph | 2-MeNH-4-Pym | ring 24 | 8-Me |
| 13-876 | 4-F-Ph | 2-MeNH-4-Pym | ring 25 | 8-Me |
| 13-877 | 4-F-Ph | 2-MeNH-4-Pym | ring 26 | 8-Me |
| 13-878 | 4-F-Ph | 2-MeNH-4-Pym | ring 27 | 8-Me |
| 13-879 | 4-F-Ph | 2-MeNH-4-Pym | ring 28 | 8-Me |
| 13-880 | 4-F-Ph | 2-MeNH-4-Pym | ring 29 | 8-Me |
| 13-881 | 4-F-Ph | 2-MeNH-4-Pym | ring 30 | 8-Me |
| 13-882 | 4-F-Ph | 2-MeNH-4-Pym | ring 31 | 8-Me |
| 13-883 | 4-F-Ph | 2-MeNH-4-Pym | ring 32 | 8-Me |
| 13-884 | 4-F-Ph | 2-MeNH-4-Pym | ring 33 | 8-Me |
| 13-885 | 4-F-Ph | 2-MeNH-4-Pym | ring 34 | 8-Me |
| 13-886 | 4-F-Ph | 2-MeNH-4-Pym | ring 35 | 8-Me |
| 13-887 | 4-F-Ph | 2-MeNH-4-Pym | ring 36 | 8-Me |
| 13-888 | 4-F-Ph | 2-MeNH-4-Pym | ring 37 | 8-Me |
| 13-889 | 4-F-Ph | 2-(α-Me-BnNH)-4-Pym | ring 1 | — |
| 13-890 | 4-F-Ph | 2-(α-Me-BnNH)-4-Pym | ring 2 | — |
| 13-891 | 4-F-Ph | 2-(α-Me-BnNH)-4-Pym | ring 3 | — |
| 13-892 | 4-F-Ph | 2-(α-Me-BnNH)-4-Pym | ring 4 | — |
| 13-893 | 4-F-Ph | 2-(α-Me-BnNH)-4-Pym | ring 5 | — |
| 13-894 | 4-F-Ph | 2-(α-Me-BnNH)-4-Pym | ring 6 | — |
| 13-895 | 4-F-Ph | 2-(α-Me-BnNH)-4-Pym | ring 7 | — |
| 13-896 | 4-F-Ph | 2-(α-Me-BnNH)-4-Pym | ring 8 | — |
| 13-897 | 4-F-Ph | 2-(α-Me-BnNH)-4-Pym | ring 9 | — |
| 13-898 | 4-F-Ph | 2-(α-Me-BnNH)-4-Pym | ring 10 | — |
| 13-899 | 4-F-Ph | 2-(α-Me-BnNH)-4-Pym | ring 11 | — |
| 13-900 | 4-F-Ph | 2-(α-Me-BnNH)-4-Pym | ring 12 | — |
| 13-901 | 4-F-Ph | 2-(α-Me-BnNH)-4-Pym | ring 13 | — |
| 13-902 | 4-F-Ph | 2-(α-Me-BnNH)-4-Pym | ring 14 | — |
| 13-903 | 4-F-Ph | 2-(α-Me-BnNH)-4-Pym | ring 15 | — |
| 13-904 | 4-F-Ph | 2-(α-Me-BnNH)-4-Pym | ring 16 | — |
| 13-905 | 4-F-Ph | 2-(α-Me-BnNH)-4-Pym | ring 17 | — |
| 13-906 | 4-F-Ph | 2-(α-Me-BnNH)-4-Pym | ring 18 | — |
| 13-907 | 4-F-Ph | 2-(α-Me-BnNH)-4-Pym | ring 19 | — |
| 13-908 | 4-F-Ph | 2-(α-Me-BnNH)-4-Pym | ring 20 | — |
| 13-909 | 4-F-Ph | 2-(α-Me-BnNH)-4-Pym | ring 21 | — |
| 13-910 | 4-F-Ph | 2-(α-Me-BnNH)-4-Pym | ring 22 | — |
| 13-911 | 4-F-Ph | 2-(α-Me-BnNH)-4-Pym | ring 23 | — |
| 13-912 | 4-F-Ph | 2-(α-Me-BnNH)-4-Pym | ring 24 | — |
| 13-913 | 4-F-Ph | 2-(α-Me-BnNH)-4-Pym | ring 25 | — |
| 13-914 | 4-F-Ph | 2-(α-Me-BnNH)-4-Pym | ring 26 | — |
| 13-915 | 4-F-Ph | 2-(α-Me-BnNH)-4-Pym | ring 27 | — |
| 13-916 | 4-F-Ph | 2-(α-Me-BnNH)-4-Pym | ring 28 | — |
| 13-917 | 4-F-Ph | 2-(α-Me-BnNH)-4-Pym | ring 29 | — |
| 13-918 | 4-F-Ph | 2-(α-Me-BnNH)-4-Pym | ring 30 | — |
| 13-919 | 4-F-Ph | 2-(α-Me-BnNH)-4-Pym | ring 31 | — |
| 13-920 | 4-F-Ph | 2-(α-Me-BnNH)-4-Pym | ring 32 | — |
| 13-921 | 4-F-Ph | 2-(α-Me-BnNH)-4-Pym | ring 33 | — |
| 13-922 | 4-F-Ph | 2-(α-Me-BnNH)-4-Pym | ring 34 | — |
| 13-923 | 4-F-Ph | 2-(α-Me-BnNH)-4-Pym | ring 35 | — |
| 13-924 | 4-F-Ph | 2-(α-Me-BnNH)-4-Pym | ring 36 | — |
| 13-925 | 4-F-Ph | 2-(α-Me-BnNH)-4-Pym | ring 37 | — |
| 13-926 | 4-F-Ph | 2-(α-Me-BnNH)-4-Pym | ring 1 | 2-Me |
| 13-927 | 4-F-Ph | 2-(α-Me-BnNH)-4-Pym | ring 2 | 2-Me |
| 13-928 | 4-F-Ph | 2-(α-Me-BnNH)-4-Pym | ring 3 | 2-Me |
| 13-929 | 4-F-Ph | 2-(α-Me-BnNH)-4-Pym | ring 4 | 2-Me |
| 13-930 | 4-F-Ph | 2-(α-Me-BnNH)-4-Pym | ring 5 | 2-Me |
| 13-931 | 4-F-Ph | 2-(α-Me-BnNH)-4-Pym | ring 6 | 2-Me |
| 13-932 | 4-F-Ph | 2-(α-Me-BnNH)-4-Pym | ring 7 | 2-Me |
| 13-933 | 4-F-Ph | 2-(α-Me-BnNH)-4-Pym | ring 8 | 2-Me |
| 13-934 | 4-F-Ph | 2-(α-Me-BnNH)-4-Pym | ring 9 | 2-Me |
| 13-935 | 4-F-Ph | 2-(α-Me-BnNH)-4-Pym | ring 10 | 2-Me |
| 13-936 | 4-F-Ph | 2-(α-Me-BnNH)-4-Pym | ring 11 | 2-Me |
| 13-937 | 4-F-Ph | 2-(α-Me-BnNH)-4-Pym | ring 12 | 2-Me |
| 13-938 | 4-F-Ph | 2-(α-Me-BnNH)-4-Pym | ring 13 | 2-Me |
| 13-939 | 4-F-Ph | 2-(α-Me-BnNH)-4-Pym | ring 14 | 2-Me |
| 13-940 | 4-F-Ph | 2-(α-Me-BnNH)-4-Pym | ring 15 | 2-Me |
| 13-941 | 4-F-Ph | 2-(α-Me-BnNH)-4-Pym | ring 16 | 2-Me |
| 13-942 | 4-F-Ph | 2-(α-Me-BnNH)-4-Pym | ring 17 | 2-Me |
| 13-943 | 4-F-Ph | 2-(α-Me-BnNH)-4-Pym | ring 18 | 2-Me |

TABLE 13-continued

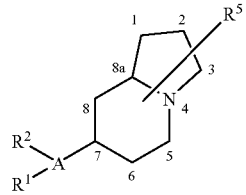

| Compound No. | R¹ | R² | A | R⁵ |
|---|---|---|---|---|
| 13-944 | 4-F-Ph | 2-(α-Me-BnNH)-4-Pym | ring 19 | 2-Me |
| 13-945 | 4-F-Ph | 2-(α-Me-BnNH)-4-Pym | ring 20 | 2-Me |
| 13-946 | 4-F-Ph | 2-(α-Me-BnNH)-4-Pym | ring 21 | 2-Me |
| 13-947 | 4-F-Ph | 2-(α-Me-BnNH)-4-Pym | ring 22 | 2-Me |
| 13-948 | 4-F-Ph | 2-(α-Me-BnNH)-4-Pym | ring 23 | 2-Me |
| 13-949 | 4-F-Ph | 2-(α-Me-BnNH)-4-Pym | ring 24 | 2-Me |
| 13-950 | 4-F-Ph | 2-(α-Me-BnNH)-4-Pym | ring 25 | 2-Me |
| 13-951 | 4-F-Ph | 2-(α-Me-BnNH)-4-Pym | ring 26 | 2-Me |
| 13-952 | 4-F-Ph | 2-(α-Me-BnNH)-4-Pym | ring 27 | 2-Me |
| 13-953 | 4-F-Ph | 2-(α-Me-BnNH)-4-Pym | ring 28 | 2-Me |
| 13-954 | 4-F-Ph | 2-(α-Me-BnNH)-4-Pym | ring 29 | 2-Me |
| 13-955 | 4-F-Ph | 2-(α-Me-BnNH)-4-Pym | ring 30 | 2-Me |
| 13-956 | 4-F-Ph | 2-(α-Me-BnNH)-4-Pym | ring 31 | 2-Me |
| 13-957 | 4-F-Ph | 2-(α-Me-BnNH)-4-Pym | ring 32 | 2-Me |
| 13-958 | 4-F-Ph | 2-(α-Me-BnNH)-4-Pym | ring 33 | 2-Me |
| 13-959 | 4-F-Ph | 2-(α-Me-BnNH)-4-Pym | ring 34 | 2-Me |
| 13-960 | 4-F-Ph | 2-(α-Me-BnNH)-4-Pym | ring 35 | 2-Me |
| 13-961 | 4-F-Ph | 2-(α-Me-BnNH)-4-Pym | ring 36 | 2-Me |
| 13-962 | 4-F-Ph | 2-(α-Me-BnNH)-4-Pym | ring 37 | 2-Me |
| 13-963 | 4-F-Ph | 2-(α-Me-BnNH)-4-Pym | ring 1 | 2-OH |
| 13-964 | 4-F-Ph | 2-(α-Me-BnNH)-4-Pym | ring 2 | 2-OH |
| 13-965 | 4-F-Ph | 2-(α-Me-BnNH)-4-Pym | ring 3 | 2-OH |
| 13-966 | 4-F-Ph | 2-(α-Me-BnNH)-4-Pym | ring 4 | 2-OH |
| 13-967 | 4-F-Ph | 2-(α-Me-BnNH)-4-Pym | ring 5 | 2-OH |
| 13-968 | 4-F-Ph | 2-(α-Me-BnNH)-4-Pym | ring 6 | 2-OH |
| 13-969 | 4-F-Ph | 2-(α-Me-BnNH)-4-Pym | ring 7 | 2-OH |
| 13-970 | 4-F-Ph | 2-(α-Me-BnNH)-4-Pym | ring 8 | 2-OH |
| 13-971 | 4-F-Ph | 2-(α-Me-BnNH)-4-Pym | ring 9 | 2-OH |
| 13-972 | 4-F-Ph | 2-(α-Me-BnNH)-4-Pym | ring 10 | 2-OH |
| 13-973 | 4-F-Ph | 2-(α-Me-BnNH)-4-Pym | ring 11 | 2-OH |
| 13-974 | 4-F-Ph | 2-(α-Me-BnNH)-4-Pym | ring 12 | 2-OH |
| 13-975 | 4-F-Ph | 2-(α-Me-BnNH)-4-Pym | ring 13 | 2-OH |
| 13-976 | 4-F-Ph | 2-(α-Me-BnNH)-4-Pym | ring 14 | 2-OH |
| 13-977 | 4-F-Ph | 2-(α-Me-BnNH)-4-Pym | ring 15 | 2-OH |
| 13-978 | 4-F-Ph | 2-(α-Me-BnNH)-4-Pym | ring 16 | 2-OH |
| 13-979 | 4-F-Ph | 2-(α-Me-BnNH)-4-Pym | ring 17 | 2-OH |
| 13-980 | 4-F-Ph | 2-(α-Me-BnNH)-4-Pym | ring 18 | 2-OH |
| 13-981 | 4-F-Ph | 2-(α-Me-BnNH)-4-Pym | ring 19 | 2-OH |
| 13-982 | 4-F-Ph | 2-(α-Me-BnNH)-4-Pym | ring 20 | 2-OH |
| 13-983 | 4-F-Ph | 2-(α-Me-BnNH)-4-Pym | ring 21 | 2-OH |
| 13-984 | 4-F-Ph | 2-(α-Me-BnNH)-4-Pym | ring 22 | 2-OH |
| 13-985 | 4-F-Ph | 2-(α-Me-BnNH)-4-Pym | ring 23 | 2-OH |
| 13-986 | 4-F-Ph | 2-(α-Me-BnNH)-4-Pym | ring 24 | 2-OH |
| 13-987 | 4-F-Ph | 2-(α-Me-BnNH)-4-Pym | ring 25 | 2-OH |
| 13-988 | 4-F-Ph | 2-(α-Me-BnNH)-4-Pym | ring 26 | 2-OH |
| 13-989 | 4-F-Ph | 2-(α-Me-BnNH)-4-Pym | ring 27 | 2-OH |
| 13-990 | 4-F-Ph | 2-(α-Me-BnNH)-4-Pym | ring 28 | 2-OH |
| 13-991 | 4-F-Ph | 2-(α-Me-BnNH)-4-Pym | ring 29 | 2-OH |
| 13-992 | 4-F-Ph | 2-(α-Me-BnNH)-4-Pym | ring 30 | 2-OH |
| 13-993 | 4-F-Ph | 2-(α-Me-BnNH)-4-Pym | ring 31 | 2-OH |
| 13-994 | 4-F-Ph | 2-(α-Me-BnNH)-4-Pym | ring 32 | 2-OH |
| 13-995 | 4-F-Ph | 2-(α-Me-BnNH)-4-Pym | ring 33 | 2-OH |
| 13-996 | 4-F-Ph | 2-(α-Me-BnNH)-4-Pym | ring 34 | 2-OH |
| 13-997 | 4-F-Ph | 2-(α-Me-BnNH)-4-Pym | ring 35 | 2-OH |
| 13-998 | 4-F-Ph | 2-(α-Me-BnNH)-4-Pym | ring 36 | 2-OH |
| 13-999 | 4-F-Ph | 2-(α-Me-BnNH)-4-Pym | ring 37 | 2-OH |
| 13-1000 | 4-F-Ph | 2-(α-Me-BnNH)-4-Pym | ring 1 | 2-MeO |
| 13-1001 | 4-F-Ph | 2-(α-Me-BnNH)-4-Pym | ring 2 | 2-MeO |
| 13-1002 | 4-F-Ph | 2-(α-Me-BnNH)-4-Pym | ring 3 | 2-MeO |
| 13-1003 | 4-F-Ph | 2-(α-Me-BnNH)-4-Pym | ring 4 | 2-MeO |
| 13-1004 | 4-F-Ph | 2-(α-Me-BnNH)-4-Pym | ring 5 | 2-MeO |
| 13-1005 | 4-F-Ph | 2-(α-Me-BnNH)-4-Pym | ring 6 | 2-MeO |
| 13-1006 | 4-F-Ph | 2-(α-Me-BnNH)-4-Pym | ring 7 | 2-MeO |
| 13-1007 | 4-F-Ph | 2-(α-Me-BnNH)-4-Pym | ring 8 | 2-MeO |
| 13-1008 | 4-F-Ph | 2-(α-Me-BnNH)-4-Pym | ring 9 | 2-MeO |

TABLE 13-continued

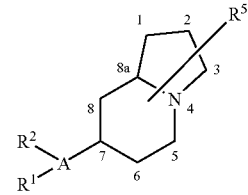

| Compound No. | R¹ | R² | A | R⁵ |
|---|---|---|---|---|
| 13-1009 | 4-F-Ph | 2-(α-Me-BnNH)-4-Pym | ring 10 | 2-MeO |
| 13-1010 | 4-F-Ph | 2-(α-Me-BnNH)-4-Pym | ring 11 | 2-MeO |
| 13-1011 | 4-F-Ph | 2-(α-Me-BnNH)-4-Pym | ring 12 | 2-MeO |
| 13-1012 | 4-F-Ph | 2-(α-Me-BnNH)-4-Pym | ring 13 | 2-MeO |
| 13-1013 | 4-F-Ph | 2-(α-Me-BnNH)-4-Pym | ring 14 | 2-MeO |
| 13-1014 | 4-F-Ph | 2-(α-Me-BnNH)-4-Pym | ring 15 | 2-MeO |
| 13-1015 | 4-F-Ph | 2-(α-Me-BnNH)-4-Pym | ring 16 | 2-MeO |
| 13-1016 | 4-F-Ph | 2-(α-Me-BnNH)-4-Pym | ring 17 | 2-MeO |
| 13-1017 | 4-F-Ph | 2-(α-Me-BnNH)-4-Pym | ring 18 | 2-MeO |
| 13-1018 | 4-F-Ph | 2-(α-Me-BnNH)-4-Pym | ring 19 | 2-MeO |
| 13-1019 | 4-F-Ph | 2-(α-Me-BnNH)-4-Pym | ring 20 | 2-MeO |
| 13-1020 | 4-F-Ph | 2-(α-Me-BnNH)-4-Pym | ring 21 | 2-MeO |
| 13-1021 | 4-F-Ph | 2-(α-Me-BnNH)-4-Pym | ring 22 | 2-MeO |
| 13-1022 | 4-F-Ph | 2-(α-Me-BnNH)-4-Pym | ring 23 | 2-MeO |
| 13-1023 | 4-F-Ph | 2-(α-Me-BnNH)-4-Pym | ring 24 | 2-MeO |
| 13-1024 | 4-F-Ph | 2-(α-Me-BnNH)-4-Pym | ring 25 | 2-MeO |
| 13-1025 | 4-F-Ph | 2-(α-Me-BnNH)-4-Pym | ring 26 | 2-MeO |
| 13-1026 | 4-F-Ph | 2-(α-Me-BnNH)-4-Pym | ring 27 | 2-MeO |
| 13-1027 | 4-F-Ph | 2-(α-Me-BnNH)-4-Pym | ring 28 | 2-MeO |
| 13-1028 | 4-F-Ph | 2-(α-Me-BnNH)-4-Pym | ring 29 | 2-MeO |
| 13-1029 | 4-F-Ph | 2-(α-Me-BnNH)-4-Pym | ring 30 | 2-MeO |
| 13-1030 | 4-F-Ph | 2-(α-Me-BnNH)-4-Pym | ring 31 | 2-MeO |
| 13-1031 | 4-F-Ph | 2-(α-Me-BnNH)-4-Pym | ring 32 | 2-MeO |
| 13-1032 | 4-F-Ph | 2-(α-Me-BnNH)-4-Pym | ring 33 | 2-MeO |
| 13-1033 | 4-F-Ph | 2-(α-Me-BnNH)-4-Pym | ring 34 | 2-MeO |
| 13-1034 | 4-F-Ph | 2-(α-Me-BnNH)-4-Pym | ring 35 | 2-MeO |
| 13-1035 | 4-F-Ph | 2-(α-Me-BnNH)-4-Pym | ring 36 | 2-MeO |
| 13-1036 | 4-F-Ph | 2-(α-Me-BnNH)-4-Pym | ring 37 | 2-MeO |
| 13-1037 | 4-F-Ph | 2-(α-Me-BnNH)-4-Pym | ring 1 | 2-F |
| 13-1038 | 4-F-Ph | 2-(α-Me-BnNH)-4-Pym | ring 2 | 2-F |
| 13-1039 | 4-F-Ph | 2-(α-Me-BnNH)-4-Pym | ring 3 | 2-F |
| 13-1040 | 4-F-Ph | 2-(α-Me-BnNH)-4-Pym | ring 4 | 2-F |
| 13-1041 | 4-F-Ph | 2-(α-Me-BnNH)-4-Pym | ring 5 | 2-F |
| 13-1042 | 4-F-Ph | 2-(α-Me-BnNH)-4-Pym | ring 6 | 2-F |
| 13-1043 | 4-F-Ph | 2-(α-Me-BnNH)-4-Pym | ring 7 | 2-F |
| 13-1044 | 4-F-Ph | 2-(α-Me-BnNH)-4-Pym | ring 8 | 2-F |
| 13-1045 | 4-F-Ph | 2-(α-Me-BnNH)-4-Pym | ring 9 | 2-F |
| 13-1046 | 4-F-Ph | 2-(α-Me-BnNH)-4-Pym | ring 10 | 2-F |
| 13-1047 | 4-F-Ph | 2-(α-Me-BnNH)-4-Pym | ring 11 | 2-F |
| 13-1048 | 4-F-Ph | 2-(α-Me-BnNH)-4-Pym | ring 12 | 2-F |
| 13-1049 | 4-F-Ph | 2-(α-Me-BnNH)-4-Pym | ring 13 | 2-F |
| 13-1050 | 4-F-Ph | 2-(α-Me-BnNH)-4-Pym | ring 14 | 2-F |
| 13-1051 | 4-F-Ph | 2-(α-Me-BnNH)-4-Pym | ring 15 | 2-F |
| 13-1052 | 4-F-Ph | 2-(α-Me-BnNH)-4-Pym | ring 16 | 2-F |
| 13-1053 | 4-F-Ph | 2-(α-Me-BnNH)-4-Pym | ring 17 | 2-F |
| 13-1054 | 4-F-Ph | 2-(α-Me-BnNH)-4-Pym | ring 18 | 2-F |
| 13-1055 | 4-F-Ph | 2-(α-Me-BnNH)-4-Pym | ring 19 | 2-F |
| 13-1056 | 4-F-Ph | 2-(α-Me-BnNH)-4-Pym | ring 20 | 2-F |
| 13-1057 | 4-F-Ph | 2-(α-Me-BnNH)-4-Pym | ring 21 | 2-F |
| 13-1058 | 4-F-Ph | 2-(α-Me-BnNH)-4-Pym | ring 22 | 2-F |
| 13-1059 | 4-F-Ph | 2-(α-Me-BnNH)-4-Pym | ring 23 | 2-F |
| 13-1060 | 4-F-Ph | 2-(α-Me-BnNH)-4-Pym | ring 24 | 2-F |
| 13-1061 | 4-F-Ph | 2-(α-Me-BnNH)-4-Pym | ring 25 | 2-F |
| 13-1062 | 4-F-Ph | 2-(α-Me-BnNH)-4-Pym | ring 26 | 2-F |
| 13-1063 | 4-F-Ph | 2-(α-Me-BnNH)-4-Pym | ring 27 | 2-F |
| 13-1064 | 4-F-Ph | 2-(α-Me-BnNH)-4-Pym | ring 28 | 2-F |
| 13-1065 | 4-F-Ph | 2-(α-Me-BnNH)-4-Pym | ring 29 | 2-F |
| 13-1066 | 4-F-Ph | 2-(α-Me-BnNH)-4-Pym | ring 30 | 2-F |
| 13-1067 | 4-F-Ph | 2-(α-Me-BnNH)-4-Pym | ring 31 | 2-F |
| 13-1068 | 4-F-Ph | 2-(α-Me-BnNH)-4-Pym | ring 32 | 2-F |
| 13-1069 | 4-F-Ph | 2-(α-Me-BnNH)-4-Pym | ring 33 | 2-F |
| 13-1070 | 4-F-Ph | 2-(α-Me-BnNH)-4-Pym | ring 34 | 2-F |
| 13-1071 | 4-F-Ph | 2-(α-Me-BnNH)-4-Pym | ring 35 | 2-F |
| 13-1072 | 4-F-Ph | 2-(α-Me-BnNH)-4-Pym | ring 36 | 2-F |
| 13-1073 | 4-F-Ph | 2-(α-Me-BnNH)-4-Pym | ring 37 | 2-F |

TABLE 13-continued

| Compound No. | R¹ | R² | A | R⁵ |
|---|---|---|---|---|
| 13-1074 | 4-F-Ph | 2-(α-Me-BnNH)-4-Pym | ring 1 | 2-Cl |
| 13-1075 | 4-F-Ph | 2-(α-Me-BnNH)-4-Pym | ring 2 | 2-Cl |
| 13-1076 | 4-F-Ph | 2-(α-Me-BnNH)-4-Pym | ring 3 | 2-Cl |
| 13-1077 | 4-F-Ph | 2-(α-Me-BnNH)-4-Pym | ring 4 | 2-Cl |
| 13-1078 | 4-F-Ph | 2-(α-Me-BnNH)-4-Pym | ring 5 | 2-Cl |
| 13-1079 | 4-F-Ph | 2-(α-Me-BnNH)-4-Pym | ring 6 | 2-Cl |
| 13-1080 | 4-F-Ph | 2-(α-Me-BnNH)-4-Pym | ring 7 | 2-Cl |
| 13-1081 | 4-F-Ph | 2-(α-Me-BnNH)-4-Pym | ring 8 | 2-Cl |
| 13-1082 | 4-F-Ph | 2-(α-Me-BnNH)-4-Pym | ring 9 | 2-Cl |
| 13-1083 | 4-F-Ph | 2-(α-Me-BnNH)-4-Pym | ring 10 | 2-Cl |
| 13-1084 | 4-F-Ph | 2-(α-Me-BnNH)-4-Pym | ring 11 | 2-Cl |
| 13-1085 | 4-F-Ph | 2-(α-Me-BnNH)-4-Pym | ring 12 | 2-Cl |
| 13-1086 | 4-F-Ph | 2-(α-Me-BnNH)-4-Pym | ring 13 | 2-Cl |
| 13-1087 | 4-F-Ph | 2-(α-Me-BnNH)-4-Pym | ring 14 | 2-Cl |
| 13-1088 | 4-F-Ph | 2-(α-Me-BnNH)-4-Pym | ring 15 | 2-Cl |
| 13-1089 | 4-F-Ph | 2-(α-Me-BnNH)-4-Pym | ring 16 | 2-Cl |
| 13-1090 | 4-F-Ph | 2-(α-Me-BnNH)-4-Pym | ring 17 | 2-Cl |
| 13-1091 | 4-F-Ph | 2-(α-Me-BnNH)-4-Pym | ring 18 | 2-Cl |
| 13-1092 | 4-F-Ph | 2-(α-Me-BnNH)-4-Pym | ring 19 | 2-Cl |
| 13-1093 | 4-F-Ph | 2-(α-Me-BnNH)-4-Pym | ring 20 | 2-Cl |
| 13-1094 | 4-F-Ph | 2-(α-Me-BnNH)-4-Pym | ring 21 | 2-Cl |
| 13-1095 | 4-F-Ph | 2-(α-Me-BnNH)-4-Pym | ring 22 | 2-Cl |
| 13-1096 | 4-F-Ph | 2-(α-Me-BnNH)-4-Pym | ring 23 | 2-Cl |
| 13-1097 | 4-F-Ph | 2-(α-Me-BnNH)-4-Pym | ring 24 | 2-Cl |
| 13-1098 | 4-F-Ph | 2-(α-Me-BnNH)-4-Pym | ring 25 | 2-Cl |
| 13-1099 | 4-F-Ph | 2-(α-Me-BnNH)-4-Pym | ring 26 | 2-Cl |
| 13-1100 | 4-F-Ph | 2-(α-Me-BnNH)-4-Pym | ring 27 | 2-Cl |
| 13-1101 | 4-F-Ph | 2-(α-Me-BnNH)-4-Pym | ring 28 | 2-Cl |
| 13-1102 | 4-F-Ph | 2-(α-Me-BnNH)-4-Pym | ring 29 | 2-Cl |
| 13-1103 | 4-F-Ph | 2-(α-Me-BnNH)-4-Pym | ring 30 | 2-Cl |
| 13-1104 | 4-F-Ph | 2-(α-Me-BnNH)-4-Pym | ring 31 | 2-Cl |
| 13-1105 | 4-F-Ph | 2-(α-Me-BnNH)-4-Pym | ring 32 | 2-Cl |
| 13-1106 | 4-F-Ph | 2-(α-Me-BnNH)-4-Pym | ring 33 | 2-Cl |
| 13-1107 | 4-F-Ph | 2-(α-Me-BnNH)-4-Pym | ring 34 | 2-Cl |
| 13-1108 | 4-F-Ph | 2-(α-Me-BnNH)-4-Pym | ring 35 | 2-Cl |
| 13-1109 | 4-F-Ph | 2-(α-Me-BnNH)-4-Pym | ring 36 | 2-Cl |
| 13-1110 | 4-F-Ph | 2-(α-Me-BnNH)-4-Pym | ring 37 | 2-Cl |
| 13-1111 | 4-F-Ph | 2-(α-Me-BnNH)-4-Pym | ring 1 | 2,2-diF |
| 13-1112 | 4-F-Ph | 2-(α-Me-BnNH)-4-Pym | ring 2 | 2,2-diF |
| 13-1113 | 4-F-Ph | 2-(α-Me-BnNH)-4-Pym | ring 3 | 2,2-diF |
| 13-1114 | 4-F-Ph | 2-(α-Me-BnNH)-4-Pym | ring 4 | 2,2-diF |
| 13-1115 | 4-F-Ph | 2-(α-Me-BnNH)-4-Pym | ring 5 | 2,2-diF |
| 13-1116 | 4-F-Ph | 2-(α-Me-BnNH)-4-Pym | ring 6 | 2,2-diF |
| 13-1117 | 4-F-Ph | 2-(α-Me-BnNH)-4-Pym | ring 7 | 2,2-diF |
| 13-1118 | 4-F-Ph | 2-(α-Me-BnNH)-4-Pym | ring 8 | 2,2-diF |
| 13-1119 | 4-F-Ph | 2-(α-Me-BnNH)-4-Pym | ring 9 | 2,2-diF |
| 13-1120 | 4-F-Ph | 2-(α-Me-BnNH)-4-Pym | ring 10 | 2,2-diF |
| 13-1121 | 4-F-Ph | 2-(α-Me-BnNH)-4-Pym | ring 11 | 2,2-diF |
| 13-1122 | 4-F-Ph | 2-(α-Me-BnNH)-4-Pym | ring 12 | 2,2-diF |
| 13-1123 | 4-F-Ph | 2-(α-Me-BnNH)-4-Pym | ring 13 | 2,2-diF |
| 13-1124 | 4-F-Ph | 2-(α-Me-BnNH)-4-Pym | ring 14 | 2,2-diF |
| 13-1125 | 4-F-Ph | 2-(α-Me-BnNH)-4-Pym | ring 15 | 2,2-diF |
| 13-1126 | 4-F-Ph | 2-(α-Me-BnNH)-4-Pym | ring 16 | 2,2-diF |
| 13-1127 | 4-F-Ph | 2-(α-Me-BnNH)-4-Pym | ring 17 | 2,2-diF |
| 13-1128 | 4-F-Ph | 2-(α-Me-BnNH)-4-Pym | ring 18 | 2,2-diF |
| 13-1129 | 4-F-Ph | 2-(α-Me-BnNH)-4-Pym | ring 19 | 2,2-diF |
| 13-1130 | 4-F-Ph | 2-(α-Me-BnNH)-4-Pym | ring 20 | 2,2-diF |
| 13-1131 | 4-F-Ph | 2-(α-Me-BnNH)-4-Pym | ring 21 | 2,2-diF |
| 13-1132 | 4-F-Ph | 2-(α-Me-BnNH)-4-Pym | ring 22 | 2,2-diF |
| 13-1133 | 4-F-Ph | 2-(α-Me-BnNH)-4-Pym | ring 23 | 2,2-diF |
| 13-1134 | 4-F-Ph | 2-(α-Me-BnNH)-4-Pym | ring 24 | 2,2-diF |
| 13-1135 | 4-F-Ph | 2-(α-Me-BnNH)-4-Pym | ring 25 | 2,2-diF |
| 13-1136 | 4-F-Ph | 2-(α-Me-BnNH)-4-Pym | ring 26 | 2,2-diF |
| 13-1137 | 4-F-Ph | 2-(α-Me-BnNH)-4-Pym | ring 27 | 2,2-diF |
| 13-1138 | 4-F-Ph | 2-(α-Me-BnNH)-4-Pym | ring 28 | 2,2-diF |
| 13-1139 | 4-F-Ph | 2-(α-Me-BnNH)-4-Pym | ring 29 | 2,2-diF |
| 13-1140 | 4-F-Ph | 2-(α-Me-BnNH)-4-Pym | ring 30 | 2,2-diF |
| 13-1141 | 4-F-Ph | 2-(α-Me-BnNH)-4-Pym | ring 31 | 2,2-diF |
| 13-1142 | 4-F-Ph | 2-(α-Me-BnNH)-4-Pym | ring 32 | 2,2-diF |
| 13-1143 | 4-F-Ph | 2-(α-Me-BnNH)-4-Pym | ring 33 | 2,2-diF |
| 13-1144 | 4-F-Ph | 2-(α-Me-BnNH)-4-Pym | ring 34 | 2,2-diF |
| 13-1145 | 4-F-Ph | 2-(α-Me-BnNH)-4-Pym | ring 35 | 2,2-diF |
| 13-1146 | 4-F-Ph | 2-(α-Me-BnNH)-4-Pym | ring 36 | 2,2-diF |
| 13-1147 | 4-F-Ph | 2-(α-Me-BnNH)-4-Pym | ring 37 | 2,2-diF |
| 13-1148 | 4-F-Ph | 2-(α-Me-BnNH)-4-Pym | ring 1 | 8-Me |
| 13-1149 | 4-F-Ph | 2-(α-Me-BnNH)-4-Pym | ring 2 | 8-Me |
| 13-1150 | 4-F-Ph | 2-(α-Me-BnNH)-4-Pym | ring 3 | 8-Me |
| 13-1151 | 4-F-Ph | 2-(α-Me-BnNH)-4-Pym | ring 4 | 8-Me |
| 13-1152 | 4-F-Ph | 2-(α-Me-BnNH)-4-Pym | ring 5 | 8-Me |
| 13-1153 | 4-F-Ph | 2-(α-Me-BnNH)-4-Pym | ring 6 | 8-Me |
| 13-1154 | 4-F-Ph | 2-(α-Me-BnNH)-4-Pym | ring 7 | 8-Me |
| 13-1155 | 4-F-Ph | 2-(α-Me-BnNH)-4-Pym | ring 8 | 8-Me |
| 13-1156 | 4-F-Ph | 2-(α-Me-BnNH)-4-Pym | ring 9 | 8-Me |
| 13-1157 | 4-F-Ph | 2-(α-Me-BnNH)-4-Pym | ring 10 | 8-Me |
| 13-1158 | 4-F-Ph | 2-(α-Me-BnNH)-4-Pym | ring 11 | 8-Me |
| 13-1159 | 4-F-Ph | 2-(α-Me-BnNH)-4-Pym | ring 12 | 8-Me |
| 13-1160 | 4-F-Ph | 2-(α-Me-BnNH)-4-Pym | ring 13 | 8-Me |
| 13-1161 | 4-F-Ph | 2-(α-Me-BnNH)-4-Pym | ring 14 | 8-Me |
| 13-1162 | 4-F-Ph | 2-(α-Me-BnNH)-4-Pym | ring 15 | 8-Me |
| 13-1163 | 4-F-Ph | 2-(α-Me-BnNH)-4-Pym | ring 16 | 8-Me |
| 13-1164 | 4-F-Ph | 2-(α-Me-BnNH)-4-Pym | ring 17 | 8-Me |
| 13-1165 | 4-F-Ph | 2-(α-Me-BnNH)-4-Pym | ring 18 | 8-Me |
| 13-1166 | 4-F-Ph | 2-(α-Me-BnNH)-4-Pym | ring 19 | 8-Me |
| 13-1167 | 4-F-Ph | 2-(α-Me-BnNH)-4-Pym | ring 20 | 8-Me |
| 13-1168 | 4-F-Ph | 2-(α-Me-BnNH)-4-Pym | ring 21 | 8-Me |
| 13-1169 | 4-F-Ph | 2-(α-Me-BnNH)-4-Pym | ring 22 | 8-Me |
| 13-1170 | 4-F-Ph | 2-(α-Me-BnNH)-4-Pym | ring 23 | 8-Me |
| 13-1171 | 4-F-Ph | 2-(α-Me-BnNH)-4-Pym | ring 24 | 8-Me |
| 13-1172 | 4-F-Ph | 2-(α-Me-BnNH)-4-Pym | ring 25 | 8-Me |
| 13-1173 | 4-F-Ph | 2-(α-Me-BnNH)-4-Pym | ring 26 | 8-Me |
| 13-1174 | 4-F-Ph | 2-(α-Me-BnNH)-4-Pym | ring 27 | 8-Me |
| 13-1175 | 4-F-Ph | 2-(α-Me-BnNH)-4-Pym | ring 28 | 8-Me |
| 13-1176 | 4-F-Ph | 2-(α-Me-BnNH)-4-Pym | ring 29 | 8-Me |
| 13-1177 | 4-F-Ph | 2-(α-Me-BnNH)-4-Pym | ring 30 | 8-Me |
| 13-1178 | 4-F-Ph | 2-(α-Me-BnNH)-4-Pym | ring 31 | 8-Me |
| 13-1179 | 4-F-Ph | 2-(α-Me-BnNH)-4-Pym | ring 32 | 8-Me |
| 13-1180 | 4-F-Ph | 2-(α-Me-BnNH)-4-Pym | ring 33 | 8-Me |
| 13-1181 | 4-F-Ph | 2-(α-Me-BnNH)-4-Pym | ring 34 | 8-Me |
| 13-1182 | 4-F-Ph | 2-(α-Me-BnNH)-4-Pym | ring 35 | 8-Me |
| 13-1183 | 4-F-Ph | 2-(α-Me-BnNH)-4-Pym | ring 36 | 8-Me |
| 13-1184 | 4-F-Ph | 2-(α-Me-BnNH)-4-Pym | ring 37 | 8-Me |

In the above tables, the following abbreviations are used:
Allyl represents allyl,
Bn represents benzyl,
Bu represents butyl,
Et represents ethyl,
Me represents methyl,
Ph represents phenyl,
Phet represents phenethyl,
Pr represents propyl,
Pym represents pyrimidinyl
Pyr represents pyridyl,
>CH$_2$ represents methylidenyl,
>CHMe represents ethylidenyl,
>CHEt represents propylidenyl,
>C(Me)$_2$ represents isopropylidenyl,
>CHPr represents butylidenyl, and
>CHPh represents benzylidenyl.

In the case where column R⁵ of Table 1, Table 2, Table 5, Table 6, Table 7, Table 8, Table 11 and Table 12 represents only "—", this means that R⁵ is a hydrogen atom.
In addition, "ring 1" to "ring 37" in colunm A of Table 11, Table 12 and Table 13 indicates the following ring.
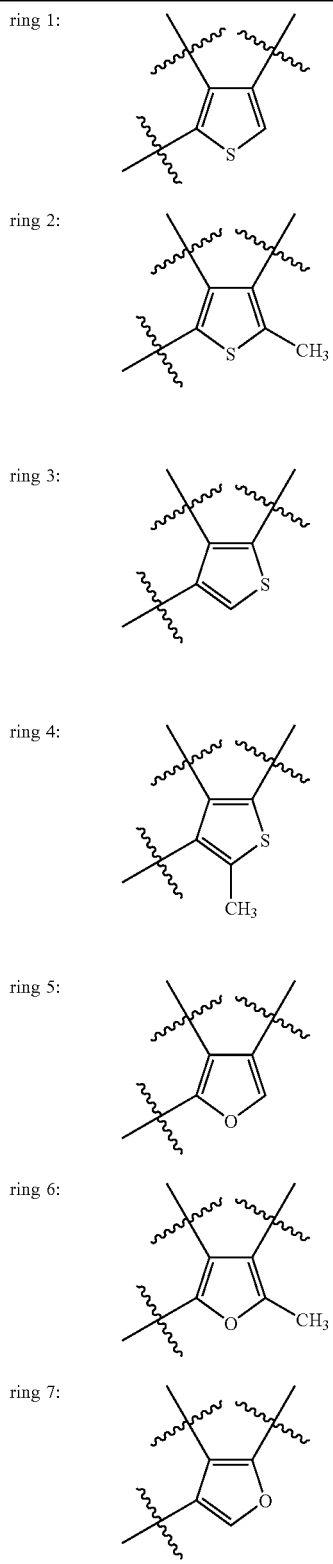
In addition, "ring 1" to "ring 37" in colunm A of Table 11, Table 12 and Table 13 indicates the following ring.
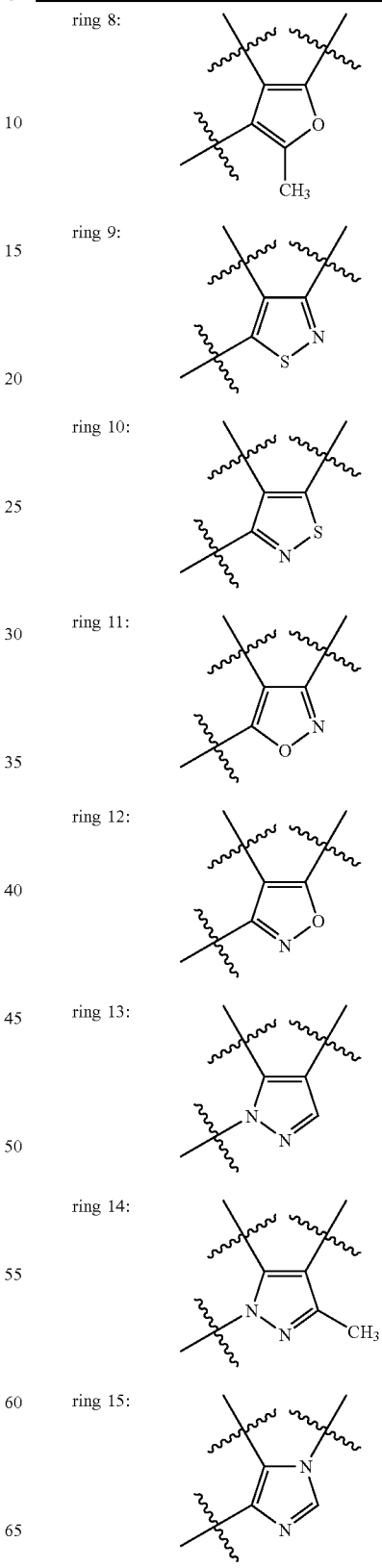

-continued
In addition, "ring 1" to "ring 37" in column A of Table 11, Table 12 and Table 13 indicates the following ring.
ring 16: 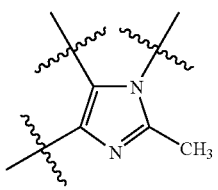
ring 17: 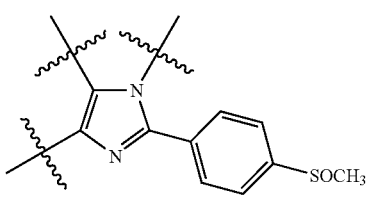
ring 18: 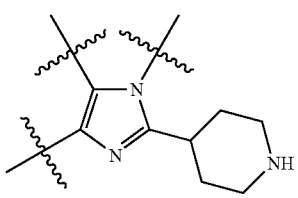
ring 19: 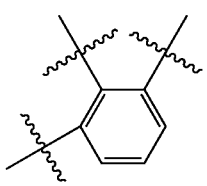
ring 20: 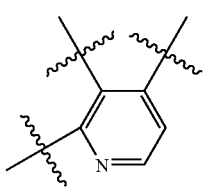
ring 21: 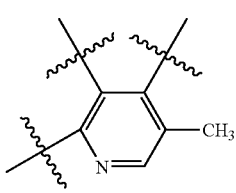
ring 22: 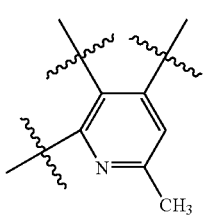
-continued
In addition, "ring 1" to "ring 37" in column A of Table 11, Table 12 and Table 13 indicates the following ring.
ring 23: 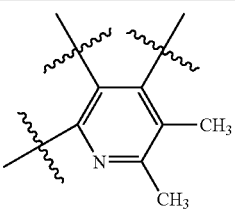
ring 24: 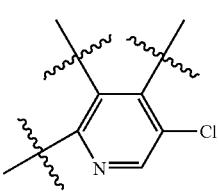
ring 25: 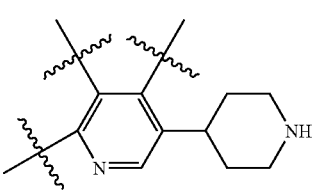
ring 26: 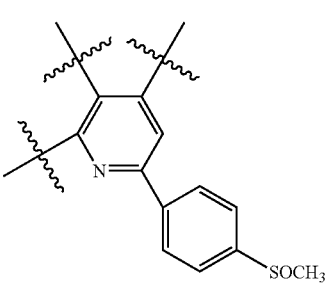
ring 27: 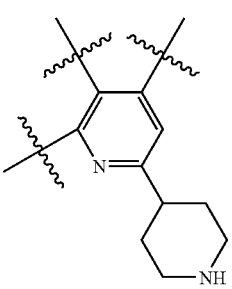
ring 28: 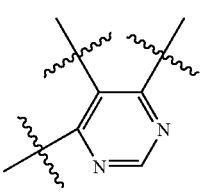
ring 29: 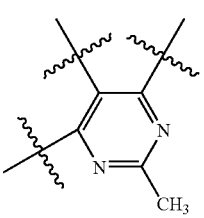

In addition, "ring 1" to "ring 37" in colunm A of Table 11, Table 12 and Table 13 indicates the following ring.

ring 30: 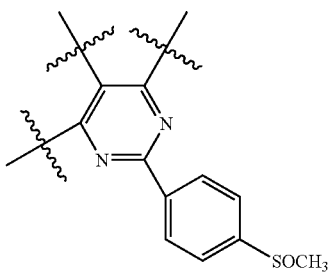

ring 31: 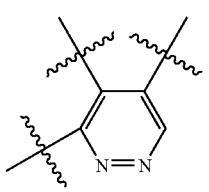

ring 32: 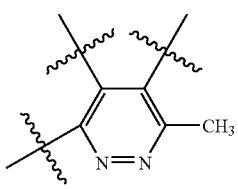

ring 33: 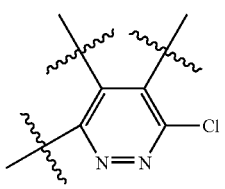

ring 34: 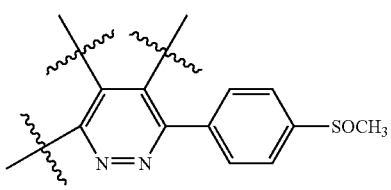

ring 35: 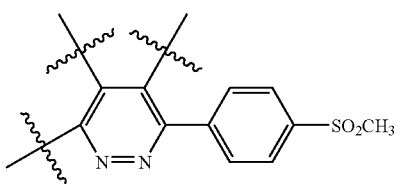

ring 36: 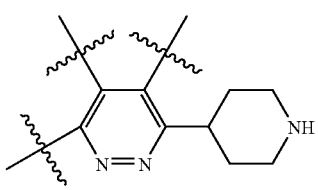

In addition, "ring 1" to "ring 37" in colunm A of Table 11, Table 12 and Table 13 indicates the following ring.

ring 37: 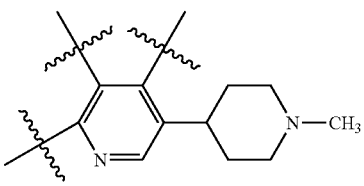

In the above Tables 1 to 13, examples of preferred compounds include the compounds of Compound Nos.:
1-1, 1-6 to 1-8, 1-11, 1-15 to 1-24, 1-27, 1-38, 1-41 to 1-43, 1-45 to 1-47, 1-154, 1-159 to 1-161, 1-164, 1-168 to 1-177, 1-180, 1-191, 1-194 to 1-196, 1-198 to 1-200, 1-307, 1-312 to 1-314, 1-317, 1-321 to 1-330, 1-333, 1-344, 1-347 to 1-349, 1-351 to 1-353, 1-358, 1-363, 1-368, 1-372 to 1-374, 1-376, 1-378 to 1-380, 1-384, 1-395, 1-398 to 1-400, 1-402, 1-409, 1-414, 1-419, 1-423 to 1-425, 1-427, 1-429 to 1-431, 1-435, 1-446, 1-449 to 1-451, 1-453, 1-460, 1-465 to 1-467, 1-470, 1-474 to 1-483, 1-486, 1-497, 1-500 to 1-502, 1-504 to 1-506, 1-613, 1-618 to 1-620, 1-623, 1-627 to 1-636, 1-639, 1-650, 1-653 to 1-655, 1-657 to 1-659, 1-766, 1-771 to 1-773, 1-776, 1-780 to 1-789, 1-792, 1-803, 1-806 to 1-808, 1-810 to 1-812, 1-919, 1-924 to 1-926, 1-929, 1-933 to 1-942, 1-945, 1-956, 1-959 to 1-961, 1-963 to 1-965, 1-970, 1-975, 1-980, 1-984, 1-985, 1-990 to 1-992, 1-996, 1-1010 to 1-1012, 1-1014, 1-1021, 1-1026, 1-1031, 1-1035, 1-1036, 1-1041 to 1-1043, 1-1047, 1-1072, 1-1082, 1-1092, 1-1102, 1-1112, 1-1122, 1-1132, 1-1142, 1-1152, 1-1162, 1-1172, 1-1182, 1-1192, 1-1202, 1-1212, 1-1222, 1-1232, 1-1242, 1-1252 to 1-1268, 1-1275 to 1-1280, 1-1283 to 1-1290, 1-1292, 1-1293, 1-1321 to 1-1325, 1-1328 to 1-1337, 1-1340 to 1-1351, 1-1452 to 1-1456, 1-1459 to 1-1468, 1-1475 to 1-1480, 1-1483 to 1-1490, 1-1492, 1-1493, 1-1521 to 1-1525, 1-1528 to 1-1537, 1-1540 to 1-1551, 1-1652 to 1-1666,
2-1, 2-6 to 2-8, 2-11, 2-15 to 2-24, 2-27, 2-38, 2-41 to 2-43, 2-45 to 2-47, 2-52, 2-57, 2-62, 2-66 to 2-68, 2-72 to 2-74, 2-78, 2-89, 2-92 to 2-94, 2-96, 2-103, 2-108, 2-113, 2-117 to 2-119, 2-121, 2-123 to 2-125, 2-129, 2-140, 2-143 to 2-145, 2-147, 2-154, 2-164, 2-174, 2-184, 2-194, 2-204, 2-214, 2-224, 2-234, 2-244 to 2-248, 2-251 to 2-260, 2-267 to 2-272, 2-275 to 2-282, 2-284, 2-285, 2-313 to 2-317, 2-320 to 2-329, 2-332 to 2-343, 2-444 to 2-450,
3-5 to 3-7, 3-10, 3-14 to 3-23, 3-26, 3-37, 3-40 to 3-42, 3-51 to 3-53, 3-56, 3-60 to 3-69, 3-72, 3-83, 3-86 to 3-88,
4-5 to 4-7, 4-10, 4-14 to 4-23, 4-26, 4-37, 4-40 to 4-42,
5-2 to 5-4, 5-7, 5-18, 5-21 to 5-23, 5-25 to 5-27, 5-33 to 5-35, 5-38, 5-49, 5-52 to 5-58, 5-63, 5-64,
6-2 to 6-4, 6-7, 6-18, 6-21 to 6-27, 6-32,
7-1, 7-15, 7-16, 7-23, 7-27, 7-52, 7-66, 7-67, 7-74, 7-78, 7-503 to 7-516,
8-1, 8-15, 8-16, 8-23, 8-27, 8-252 to 8-258,
9-1 to 9-7, 9-12 to 9-18, 9-23, 9-24,
10-1 to 10-7,
11-13 to 11-18, 11-87 to 11-92, 11-124 to 11-129, 11-161 to 11-166, 11-198 to 11-203, 11-235 to 11-240, 11-272 to 11-277, 11-309 to 11-314, 11-346 to 11-351, 11-383 to 11-388, 11-420 to 11-425, 11-457 to 11-462, 11-494 to 11-499, 11-531 to 11-536, 11-568 to 11-573, 11-605 to 11-610, 11-642 to 11-647, 11-679 to 11-684, 11-716 to 11-721, 11-753 to 11-758, 11-790 to 11-795, 11-827 to 11-832, 11-864 to 11-869, 11-901 to 11-906, 11-938 to 11-943, 11-975 to 11-980, 11-1012 to 11-1017, 11-1049 to 11-1054, 11-1086 to 11-1091, 11-1123 to 11-1128, 11-1160 to 11-1165, 12-13 to 12-18, 12-87 to 12-92, 12-124 to 12-129, 12-161 to 12-166, 12-198 to 12-203, 12-235 to 12-240, 12-272 to 12-277, 12-309 to 12-314, 12-346 to 12-351, 12-383 to 12-388, 12-420 to 12-425, 12-457 to 12-462, 12-494 to 12-499, 12-531 to 12-536, 12-568 to 12-573, 12-605 to 12-610, 12-642 to 12-647, 12-679 to 12-684, 12-716 to 12-721, 12-753 to 12-758, 12-790 to 12-795, 12-827 to 12-832, 12-864 to 12-869, 12-901 to 12-906, 12-938 to 12-943, 12-975 to 12-980, 12-1012 to 12-1017, 12-1049 to 12-1054, 12-1086 to 12-1091, 12-1123 to 12-1128, 12-1160 to 12-1165, 13-13 to 13-18, 13-87 to 13-92, 13-124 to 13-129, 13-161 to 13-166, 13-198 to 13-203, 13-235 to 13-240, 13-272 to 13-277, 13-309 to 13-314, 13-346 to 13-351, 13-383 to 13-388, 13-420 to 13-425, 13-457 to 13-462, 13-494 to 13-499, 13-531 to 13-536, 13-568 to 13-573, 13-605 to 13-610, 13-642 to 13-647, 13-679 to 13-684, 13-716 to 13-721, 13-753 to 13-758, 13-790 to 13-795, 13-827 to 13-832, 13-864 to 13-869, 13-901 to 13-906, 13-938 to 13-943, 13-975 to 13-980, 13-1012 to 13-1017, 13-1049 to 13-1054, 13-1086 to 13-1091, 13-1123 to 13-1128 and 13-1160 to 13-1165.

Examples of more preferred compounds include the compounds of Compound Nos.:

1-1, 1-6 to 1-8, 1-11, 1-15, 1-16, 1-21 to 1-23, 1-27, 1-41 to 1-43, 1-45, 1-154, 1-159 to 1-161, 1-164, 1-168, 1-169, 1-174 to 1-176, 1-180, 1-194 to 1-196, 1-198, 1-307, 1-312 to 1-314, 1-317, 1-321, 1-322, 1-327 to 1-329, 1-333, 1-347 to 1-349, 1-351, 1-358, 1-409, 1-460, 1-465 to 1-467, 1-470, 1-474, 1-475, 1-480 to 1-482, 1-486, 1-500 to 1-502, 1-504, 1-613, 1-618 to 1-620, 1-623, 1-627, 1-628, 1-633 to 1-635, 1-639, 1-653 to 1-655, 1-657, 1-766, 1-771 to 1-773, 1-776, 1-780, 1-781, 1-786 to 1-788, 1-792, 1-806 to 1-808, 1-810, 1-919, 1-924 to 1-926, 1-929, 1-933, 1-934, 1-939 to 1-941, 1-945, 1-959 to 1-961, 1-963, 1-1252 to 1-1268, 1-1275 to 1-1280, 1-1321 to 1-1325, 1-1340 to 1-1351, 1-1452 to 1-1456, 1-1459 to 1-1468, 1-1475 to 1-1480, 1-1521 to 1-1525, 1-1540 to 1-1551, 1-1652 to 1-1666, 2-1, 2-6 to 2-8, 2-11, 2-15, 2-16, 2-21 to 2-23, 2-27, 2-41 to 2-43, 2-45, 2-52, 2-103, 2-154, 2-164, 2-174, 2-184, 2-194, 2-204, 2-214, 2-224, 2-234, 2-244 to 2-248, 2-251 to 2-260, 2-267 to 2-272, 2-313 to 2-317, 2-332 to 2-343, 2-444 to 2-450, 3-5 to 3-7, 3-10, 3-14, 3-15, 3-20 to 3-22, 3-26, 3-40 to 3-42, 3-51 to 3-53, 3-56, 3-60, 3-61, 3-66 to 3-68, 3-72, 3-86 to 3-88, 4-5 to 4-7, 4-10, 4-14, 4-15, 4-20 to 4-22, 4-26, 4-40 to 4-42, 5-2 to 5-4, 5-7, 5-21 to 5-23, 5-25, 5-33 to 5-35, 5-38, 5-52 to 5-54, 5-56, 5-63, 5-64, 6-2 to 6-4, 6-7, 6-21 to 6-23, 6-25, 6-32, 7-1, 7-52, 7-503 to 7-516, 8-1, 8-252 to 8-258, 9-1, 9-2, 9-6, 9-7, 9-12, 9-13, 9-17, 9-18, 9-23, 9-24, 10-1, 10-2, 10-6, 10-7, 11-13 to 11-15, 11-87, 11-88, 11-124, 11-125, 11-161, 11-162, 11-198, 11-199, 11-235, 11-236, 11-272, 11-273, 11-309, 11-310, 11-346, 11-347, 11-383, 11-384, 11-420, 11-421, 11-457, 11-458, 11-494, 11-495, 11-531, 11-532, 11-568, 11-569, 11-605, 11-606, 11-642, 11-643, 11-679, 11-680, 11-716, 11-717, 11-753, 11-754, 11-790, 11-791, 11-827, 11-828, 11-864, 11-865, 11-901, 11-902, 11-938, 11-939, 11-975, 11-976, 11-1012, 11-1013, 11-1049, 11-1050, 11-1086, 11-1087, 11-1123, 11-1124, 11-1160, 11-1161, 12-13 to 12-15, 12-87, 12-88, 12-124, 12-125, 12-161, 12-162, 12-198, 12-199, 12-235, 12-236, 12-272, 12-273, 12-309, 12-310, 12-346, 12-347, 12-383, 12-384, 12-420, 12-421, 12-457, 12-458, 12-494, 12-495, 12-531, 12-532, 12-568, 12-569, 12-605, 12-606, 12-642, 12-643, 12-679, 12-680, 12-716, 12-717, 12-753, 12-754, 12-790, 12-791, 12-827, 12-828, 12-864, 12-865, 12-901, 12-902, 12-938, 12-939, 12-975, 12-976, 12-1012, 12-1013, 12-1049, 12-1050, 12-1086, 12-1087, 12-1123, 12-1124, 12-1160, 12-1161, 13-13 to 13-15, 13-87, 13-88, 13-124, 13-125, 13-161, 13-162, 13-198, 13-199, 13-235, 13-236, 13-272, 13-273, 13-309, 13-310, 13-346, 13-347, 13-383, 13-384, 13-420, 13-421, 13-457, 13-458, 13-494, 13-495, 13-531, 13-532, 13-568, 13-569, 13-605, 13-606, 13-642, 13-643, 13-679, 13-680, 13-716, 13-717, 13-753, 13-754, 13-790, 13-791, 13-827, 13-828, 13-864, 13-865, 13-901, 13-902, 13-938, 13-939, 13-975, 13-976, 13-1012, 13-1013, 13-1049, 13-1050, 13-1086, 13-1087, 13-1123, 13-1124, 13-1160 and 13-1161.

Examples of still preferred compounds include the compounds of Compound Nos.:

1-1, 1-6 to 1-8, 1-11, 1-154, 1-159 to 1-161, 1-164, 1-168, 1-169, 1-176, 1-180, 1-198, 1-307, 1-312 to 1-314, 1-317, 1-321, 1-322, 1-329, 1-333, 1-351, 1-460, 1-465 to 1-467, 1-470, 1-474, 1-475, 1-482, 1-486, 1-504, 1-613, 1-618 to 1-620, 1-623, 1-627, 1-628, 1-635, 1-639, 1-657, 1-766, 1-771 to 1-773, 1-776, 1-780, 1-781, 1-788, 1-792, 1-810, 1-919, 1-924 to 1-926, 1-929, 1-933, 1-934, 1-941, 1-945, 1-963, 1-1252 to 1-1256, 1-1340 to 1-1351, 1-1452 to 1-1456, 1-1540 to 1-1551, 1-1652 to 1-1666, 2-1, 2-6 to 2-8, 2-11, 2-15, 2-16, 2-23, 2-27, 2-45, 2-244 to 2-248, 2-332 to 2-343, 2-444 to 2-450, 3-5 to 3-7, 3-10, 3-14, 3-15, 3-22, 3-26, 3-51 to 3-53, 3-56, 3-60, 3-61, 3-68, 3-72, 4-5 to 4-7, 4-10, 4-14, 4-15, 4-22, 4-26, 5-2 to 5-4, 5-7, 5-25, 5-33 to 5-35, 5-38, 5-56, 5-63, 5-64, 6-2 to 6-4, 6-7, 6-25, 6-32, 7-1, 7-503 to 7-516, 8-252 to 8-258, 9-23, 9-24, 11-15, 12-15 and 13-15.

Of the above, preferred compounds are as follows:

3-(1,2,3,5,6,8a-hexahydroindolizin-7-yl)-5-phenyl-4-(pyridin-4-yl)pyrazole, 5-(3-fluorophenyl)-3-(1,2,3,5,6,8a-hexahydroindolizin-7-yl)-4-(pyridin-4-yl)pyrazole, 5-(4-fluorophenyl)-3-(1,2,3,5,6,8a-hexahydroindolizin-7-yl)-4-(pyridin-4-yl)pyrazole, 5-(4-fluorophenyl)-3-(2-methyl-1,2,3,5,6,8a-hexahydroindolizin-7-yl)-4-(pyridin-4-yl)pyrazole, 5-(4-fluorophenyl)-3-(2-phenyl-1,2,3,5,6,8a-hexahydroindolizin-7-yl)-4-(pyridin-4-yl)pyrazole, 5-(4-fluorophenyl)-3-(2-hydroxy-1,2,3,5,6,8a-hexahydroindolizin-7-yl)-4-(pyridin-4-yl)pyrazole, 5-(4-fluorophenyl)-3-(2-methoxy-1,2,3,5,6,8a-hexahydroindolizin-7-yl)-4-(pyridin-4-yl)pyrazole, 3-(2-fluoro-1,2,3,5,6,8a-hexahydroindolizin-7-yl)-5-(4-fluorophenyl)-4-(pyridin-4-yl)pyrazole, 3-(2,2-difluoro-1,2,3,5,6,8a-hexahydroindolizin-7-yl)-5-(4-fluorophenyl)-4-(pyridin-4-yl)pyrazole, 5-(4-fluorophenyl)-3-(8-methyl-1,2,3,5,6,8a-hexahydroindolizin-7-yl)-4-(pyridin-4-yl)pyrazole,
5-(3-chlorophenyl)-3-(1,2,3,5,6,8a-hexahydroindolizin-7-yl)-4-(pyridin-4-yl)pyrazole,
3-(1,2,3,5,6,8a-hexahydroindolizin-7-yl)-4-(pyridin-4-yl)-5-(3-trifluoromethylphenyl)pyrazole,
5-(3,4-difluorophenyl)-3-(1,2,3,5,6,8a-hexahydroindolizin-7-yl)-4-(pyridin-4-yl)pyrazole,
5-(4-fluorophenyl)-3-(1,2,3,5,6,8a-hexahydroindolizin-7-yl)-1-methyl-4-(pyridin-4-yl)pyrazole,
3-(4-fluorophenyl)-5-(1,2,3,5,6,8a-hexahydroindolizin-7-yl)-1-methyl-4-(pyridin-4-yl)pyrazole,
3-(4-fluorophenyl)-1-methyl-5-(2-methyl-1,2,3,5,6,8a-hexahydroindolizin-7-yl)-4-(pyridin-4-yl)pyrazole,
3-(4-fluorophenyl)-1-methyl-5-(2-phenyl-1,2,3,5,6,8a-hexahydroindolizin-7-yl)-4-(pyridin-4-yl)pyrazole,
3-(4-fluorophenyl)-5-(2-hydroxy-1,2,3,5,6,8a-hexahydroindolizin-7-yl)-1-methyl-4-(pyridin-4-yl)pyrazole,
3-(4-fluorophenyl)-5-(2-methoxy-1,2,3,5,6,8a-hexahydroindolizin-7-yl)-1-methyl-4-(pyridin-4-yl)pyrazole,
5-(2-fluoro-1,2,3,5,6,8a-hexahydroindolizin-7-yl)-3-(4-fluorophenyl)-1-methyl-4-(pyridin-4-yl)pyrazole,
5-(2,2-difluoro-1,2,3,5,6,8a-hexahydroindolizin-7-yl)-3-(4-fluorophenyl)-1-methyl-4-(pyridin-4-yl)pyrazole,
3-(4-fluorophenyl)-1-methyl-5-(8-methyl-1,2,3,5,6,8a-hexahydroindolizin-7-yl)-4-(pyridin-4-yl)pyrazole,
5-(4-fluorophenyl)-4-(pyridin-4-yl)-3-(3,5,6,8a-tetrahydroindolizin-7-yl)pyrazole,
5-(4-fluorophenyl)-3-(1,2,3,5,8,8a-hexahydroindolizin-7-yl)-4-(pyridin-4-yl)pyrazole,
5-(4-fluorophenyl)-3-(7-hydroxy-1,2,3,5,6,7,8,8a-octahydroindolizin-7-yl)-4-(pyridin-4-yl)pyrazole,
5-(4-fluorophenyl)-3-(1,2,3,5,6,7,8,8a-octahydroindolizin-7-yl)-4-(pyridin-4-yl)pyrazole,
4-(4-fluorophenyl)-1-(1,2,3,5,6,7,8,8a-octahydroindolizin-7-yl)-5-(pyridin-4-yl)imidazole,
5-(4-chlorophenyl)-3-(1,2,3,5,6,8a-hexahydroindolizin-7-yl)-4-(pyridin-4-yl)pyrazole,
3-(2-ethyl-1,2,3,5,6,8a-hexahydroindolizin-7-yl)-5-(4-fluorophenyl)-4-(pyridin-4-yl)pyrazole,
5-(4-fluorophenyl)-3-(2-propyl-1,2,3,5,6,8a-hexahydroindolizin-7-yl)-4-(pyridin-4-yl)pyrazole,
5-(4-fluorophenyl)-3-(2-methyliden-1,2,3,5,6,8a-hexahydroindolizin-7-yl)-4-(pyridin-4-yl)pyrazole,
3-(2-ethyliden-1,2,3,5,6,8a-hexahydroindolizin-7-yl)-5-(4-fluorophenyl)-4-(pyridin-4-yl)pyrazole,
5-(4-fluorophenyl)-3-(2-propyliden-1,2,3,5,6,8a-hexahydroindolizin-7-yl)-4-(pyridin-4-yl)pyrazole,
5-(4-fluorophenyl)-1-methyl-3-(2-methyl-1,2,3,5,6,8a-hexahydroindolizin-7-yl)-4-(pyridin-4-yl)pyrazole,
5-(4-fluorophenyl)-1-methyl-3-(2-phenyl-1,2,3,5,6,8a-hexahydroindolizin-7-yl)-4-(pyridin-4-yl)pyrazole,
5-(4-fluorophenyl)-3-(2-hydroxy-1,2,3,5,6,8a-hexahydroindolizin-7-yl)-1-methyl-4-(pyridin-4-yl)pyrazole,
5-(4-fluorophenyl)-3-(2-methoxy-1,2,3,5,6,8a-hexahydroindolizin-7-yl)-1-methyl-4-(pyridin-4-yl)pyrazole,
3-(2-fluoro-1,2,3,5,6,8a-hexahydroindolizin-7-yl)-5-(4-fluorophenyl)-1-methyl-4-(pyridin-4-yl)pyrazole,
5-(4-fluorophenyl)-1-methyl-3-(8-methyl-1,2,3,5,6,8a-hexahydroindolizin-7-yl)-4-(pyridin-4-yl)pyrazole,
5-(4-fluorophenyl)-3-(2-methyl-3,5,6,8a-tetrahydroindolizin-7-yl)-4-(pyridin-4-yl)pyrazole,
3-(2-ethyl-3,5,6,8a-tetrahydroindolizin-7-yl)-5-(4-fluorophenyl)-4-(pyridin-4-yl)pyrazole,
5-(4-fluorophenyl)-3-(2-propyl-3,5,6,8a-tetrahydroindolizin-7-yl)-4-(pyridin-4-yl)pyrazole, and
5-(4-fluorophenyl)-3-(2-phenyl-3,5,6,8a-tetrahydroindolizin-7-yl)-4-(pyridin-4-yl)pyrazole.

In Table 1, Table 3, Table 5, Table 7 and Table 9, there are described compounds wherein $R^4$ is a hydrogen atom. These compounds have tautomers as shown below.

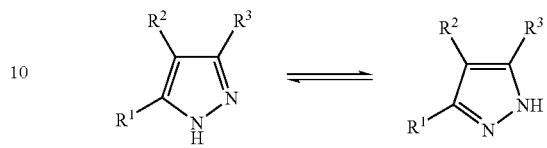

Examples of compounds shown In Table 1, Table 3, Table 5, Table 7 and Table 9 above intend to encompass both compounds.

[Best Mode for Carrying Out the Invention]

The compounds (I) of the present invention can be prepared by methods described below.

<Method A>

Method A is a method for preparing a compound of general formula (I) wherein $R^3$ is bonded to a carbon atom of the cyclic group A.

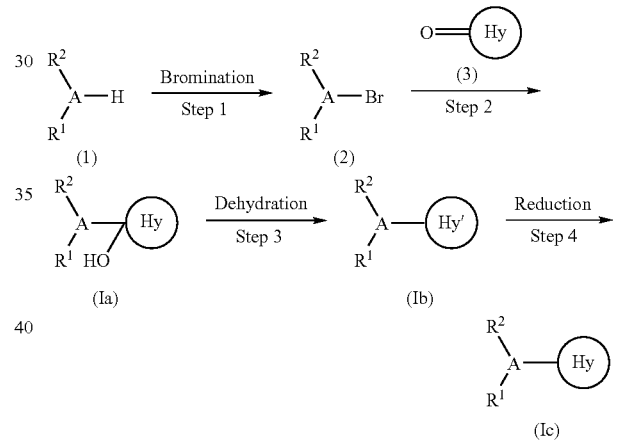

In the above formulae, A, $R^1$ and $R^2$ are as defined above, cyclic group Hy represents a group of the general formula (IIa), (IIb) or (IIc) wherein the dotted line is a single bond, and cyclic group Hy' represents a group of the general formula (IIa), (IIb) or (IIc) wherein the dotted line is a double bond.

In Step 1, a brominated cyclic compound (2) is prepared by brominating a cyclic compound (1) with a bromination reagent (for example, N-bromosuccinimide, etc.).

In Step 2, a compound (Ia) of the present invention is prepared by lithiating the brominated cyclic compound (2) and then reacting it with a heterocyclyl ketone (3).

Each of the reactions in Step 1 and Step 2 can be carried out according to the method described in detail in Brian L. Bray et al., J. Org. Chem., 55, 6317–6318 (1990).

Alternatively, the compound (Ia) can be prepared by lithiating the cyclic compound (1) directly in a similar manner to the procedure described in L. Revesz et al., Bioorg. Med. Chem. Lett., 10, 1261–1264 (2000) and the compound thus obtained is reacted with the heterocyclyl ketone (3).

In Step 3, a compound (Ib) of the present invention is prepared by subjecting the compound (Ia) of the present invention to a dehydration reaction.

The dehydration reaction can usually be carried out in the presence of an acid catalyst such as sulfuric acid, a solid catalyst such as alumina or a halogenation reagent such as thionyl chloride [these reactions are described in detail, for example, in G. H. Coleman & H. F. Johnstone, Org. Synth., I, 183 (1941), R. L. Sawyer & D. W. Andrus, Org. Synth., III, 276 (1955) and J. S. Lomas et al., Tetrahedron Lett., 599 (1971)].

Alternatively, the dehydration reaction of this step can be accomplished by a reaction using a trialkylsilane, such as triethylsilane, tripropylsilane or tributylsilane, and trifluoroacetic acid, for example in accordance with the method described in Francis A. Carey & Henry S. Tremper, J. Am. Chem. Soc., 91, 2967–2972 (1969).

In Step 4, a compound (Ic) of the present invention is prepared by reduction of the double bond of the compound (Ib) of the present invention.

The reduction reaction can be carried out, for example according to a method similar to that described in detail in S. M. Kerwin et al., J. Org. Chem., 52, 1686 (1987) and T. Hudlicky et al., J. Org. Chem., 52, 4641 (1987).

<Method B>

Method B is a method for preparing a compound wherein cyclic group A is a pyrazole or an imidazole group in which $R^3$ is bonded to the nitrogen atom.

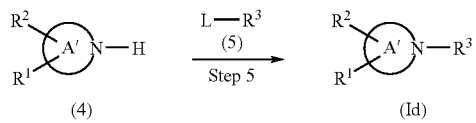

In the above formulae, $R^1$, $R^2$ and $R^3$ are as defined above, and cyclic group A' represents a pyrazole having one substituent $R^4$ or an imidazole group having one substituent $R^4$ as described in the definition of A and L represents a leaving group.

The leaving group in the definition of L is a group which is capable of leaving as a nucleophilic residue. Examples include halogen atoms such as fluorine, chlorine, bromine and iodine, lower alkanesulfonyloxy groups such as methanesulfonyloxy and ethanesulfonyloxy groups, halogeno lower alkane sulfonyloxy groups such as trifluoromethanesulfonyloxy and pentafluoroethanesulfonyloxy groups, and arylsulfonyloxy groups such as benzenesulfonyloxy, p-toluenesulfonyloxy and p-nitrobenzenesulfonyloxy groups. Of these, halogen atoms are preferred, and bromine atoms are particularly preferred.

In Step 5, a compound (Id) of the present invention is prepared by reacting a compound (4) with a heterocyclyl compound (5). This reaction is usually carried out in a solvent in the presence or absence of a base.

There is no particular restriction on the nature of the solvent to be employed, provided that it has no adverse effect on the reaction. Examples of suitable solvents which can be used include: alcohols such as methanol, ethanol, propanol and isopropanol; ethers such as diethyl ether, diisopropyl ether, tetrahydrofuran and dioxane; aprotic polar solvents such as dimethylformamide, dimethylacetamide and dimethyl sulfoxide; nitriles such as acetonitrile; esters such as methyl acetate and ethyl acetate; aromatic hydrocarbons such as benzene, toluene and xylene; and aliphatic hydrocarbons such as pentane, hexane and heptane, of which alcohols are preferred and methanol and ethanol are more preferred.

Examples of the base which can be used include: alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]-7-undecene, of which amines are preferred, and triethylamine, pyridine and 1,8-diazabicyclo[5.4.0]undec-7-ene are more preferred.

The reaction temperature is from −20° C. to 150° C., and preferably from 0° C. to 100° C.

The time required for the reaction is from 10 minutes to 48 hours, and preferably from 30 minutes to 12 hours is usually sufficient.

Alternatively, as cyclic group A is a pyrazole or an imidazole group, when the nitrogen atom thereof is substituted with a substituent (the substituent is a group as defined in $R^1$, $R^2$ and $R^3$ except a hydrogen atom), the desired substituent can be introduced according to a reaction similar to that described in Method B above.

<Method C>

Method C is an another method for preparing a compound of general formula (Id) wherein cyclic group A' is an imidazole group.

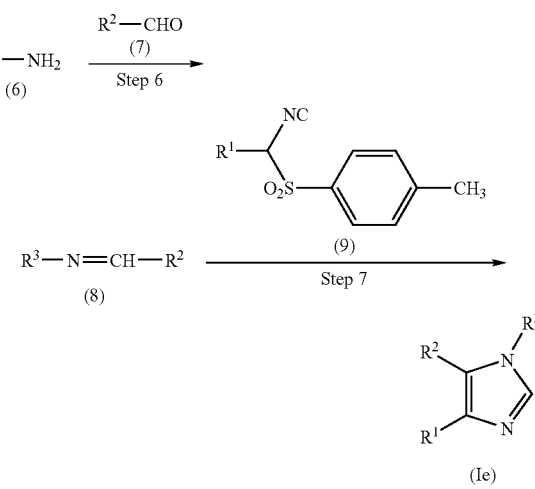

In the above formulae, $R^1$, $R^2$ and $R^3$ are as defined above.

In Step 6, an imine compound (8) is prepared by a dehydration condensation reaction of an amino compound (6) and an aldehyde compound (7).

In Step 7, a compound (Ie) of the present invention is prepared by reacting the imine compound (8) with an isocyanide compound (9).

Each of the reactions in Step 6 and Step 7 can be carried out according to the methods described in detail in WO 97/23479, WO 97/25046, WO 97/25047, WO 97/25048, WO 95/02591 and J. L. Adams et al., Bioorg. Med. Chem. Lett., 8, 3111–3116 (1998).

In the compound (I) of the present invention, a compound (If) wherein $R^2$ is a heteroaryl group containing at least one nitrogen atom and is substituted with a group of formula —$NR^aR^b$ can be prepared by Method D below.

<Method D>

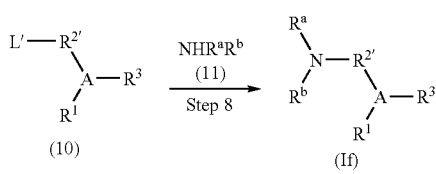

In the above formulae, A, $R^1$, $R^3$, $R^a$ and $R^b$ are as defined above,

L' represents a leaving group, the group —$R^{2'}$-L' is a group consisting of a heteroaryl group, wherein said heteroaryl group has at least one nitrogen atom, and a leaving group (group L')(for example, 2-methanesulfonylpyrimidin-4-yl, 2-methanesulfonylpyridin-4-yl, etc.) and said heteroaryl group having at least one nitrogen atom is the same group defined in $R^2$ as a heteroaryl group having at least one nitrogen atom.

The leaving group as defined for L' is a similar group to the leaving groups defined and exemplified above in the definition of L; a lower alkylsulfonyl group such as a methanesulfonyl, ethanesulfonyl, propanesulfonyl or butanesulfonyl group; or an arylsulfonyl group such as a benzenesulfonyl, p-toluenesulfonyl and p-nitrobenzenesulfonyl groups. Of these, preferred is a lower alkylsulfonyl group, and more preferred is a methanesulfonyl group.

In Step 8, the compound (If) of the present invention is prepared by reacting a compound (10) with an amine compound (11) to replace the leaving group with a group of formula —$NR^aR^b$. This step is carried out using a procedure similar to that used in Step 5 above.

The compounds which can be used as starting materials in Method A to Method D above, that is, the compounds (1), (3), (4), (5), (6), (7), (9) and (11), are either known compounds themselves or are compounds which are easily obtainable by treating known compounds according to known methods. The compound (10) can be easily synthesized from known compounds by carrying out similar reactions to those described in Method A to Method D above.

For example, concerning a compound (1):

a compound wherein A is a benzene ring having three substituents $R^4$ can be synthesized according to the methods described in D. J. P. Pinto et al., Bioorg. Med. Chem. Lett., 6, 2907–2912 (1996), D. J. P. Pinto et al., Bioorg. Med. Chem. Lett., 9, 919–924 (1999), M. B. Norton et al., J. Med. Chem., 39, 1846–1856 (1996), WO 96/10012, WO 96/26921, WO 96/16934 and the like, a compound wherein A is a pyridine ring having two substituents $R^4$ can be synthesized according to the methods described in R. W. Friesen et al., Bioorg. Med. Chem. Lett., 8, 2777–2782 (1998) and the like, a compound wherein A is a pyridazine ring having one substituent $R^4$ or a pyrimidine ring having one substituent $R^4$ can be synthesized according to the methods described in WO 00/31065 and the like, a compound wherein A is a furan ring having one substituent $R^4$ can be synthesized according to the methods described U.S. Pat. No. 6,048,880 and the like, a compound wherein A is a thiophene ring having one substituent $R^4$ can be synthesized according to the methods described in WO 94/26731, Y. Leblanc et al., Bioorg. Med. Chem. Lett., 5, 2123–2128 (1995), S. R. Bertenshaw et al., Bioorg. Med. Chem. Lett., 5, 2919–2922 (1995), D. J. P. Pinto et al., Bioorg. Med. Chem. Lett., 6, 2907–2912 (1996), WO 95/00501 and the like, a compound wherein A is a pyrazole ring having one substituent $R^4$ can be synthesized according to the methods described in WO 00/31063, WO 99/58523, WO 00/39116, WO 95/31451 and the like, a compound wherein A is an imidazole ring having one substituent $R^4$ can be synthesized according to the methods described in I. K. Khanna et al., J. Med. Chem., 40, 1634–1647 (1997), WO 93/14081, WO 97/23479, WO 97/25046, WO 97/25047, WO 97/25048, WO 95/02591, J. L. Adams et al., Bioorg. Med. Chem. Lett., 8, 3111–3116 (1998), and the like, a compound wherein A is an isoxazole ring can be synthesized according to the methods described in Japanese Patent Application Publication Number 2000-86657 and the like, and a compound wherein A is an isothiazole ring can be synthesized according to the methods described in WO 95/00501 and the like.

Alternatively, the compound (3) can be prepared according to Methods E to I described below and the compound (5) can be prepared according to Method L described below.

<Method E>

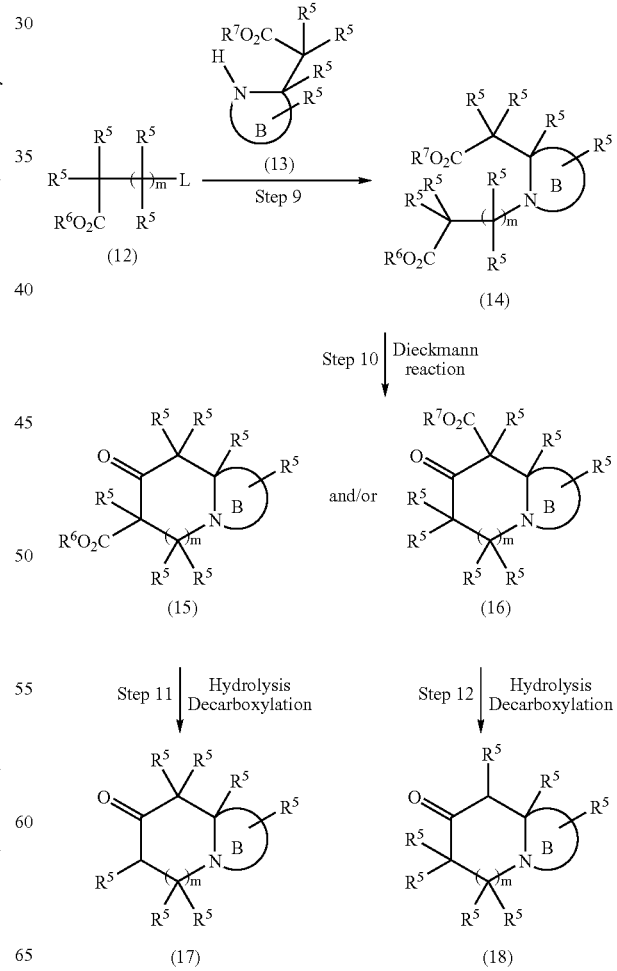

In the above formulae, B, L, $R^5$ and m are as defined above, and $R^6$ and $R^7$ are the same or different from each other, and each represents a lower alkyl group as defined above or an aralkyl group as defined above.

In Step 9, a cyclic amine diester compound (14) is prepared by the condensation of a cyclic amino acid ester compound (13) with a carboxylic acid ester compound (12) which has a leaving group (L).

This reaction is usually carried out in a solvent in the presence or absence of a base.

There is no particular restriction on the nature of the solvent to be employed, provided that it has no adverse effect on the reaction. Examples of suitable solvents which can be used include: alcohols such as methanol, ethanol, propanol and isopropanol; ethers such as diethyl ether, diisopropyl ether, tetrahydrofuran and dioxane; aprotic polar solvents such as dimethylformamide, dimethylacetamide and dimethyl sulfoxide; nitriles such as acetonitrile; esters such as methyl acetate and ethyl acetate; aromatic hydrocarbons such as benzene, toluene and xylene; and aliphatic hydrocarbons such as pentane, hexane and heptane.

Examples of the base which can be used include: alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]-7-undecene.

The reaction temperature is from −20° C. to 150° C., and preferably from 0° C. to 100° C.

The time required for the reaction is from 10 minutes to 48 hours, and preferably from 30 minutes to 12 hours is usually sufficient.

Then, the cyclic amine diester compound (14) is converted into a keto ester compound(s) (compound (15) and/or compound (16)) using a Dieckmann reaction (in Step 10), and the product(s) thus obtained is/are then hydrolyzed and decarboxylated successively to prepare the desired cyclic aminoketone compound(s) (compound (17) and compound (18)) (in Steps 11 and 12).

The reactions in Steps 10 to 12 can be carried out according to the procedures described in J. R. Harrison et al., J. Chem. Soc., Perkin Trans. 1, 1999, 3623–3631, and for example, Steps 11 and 12 can be carried out as follows.

The reactions of Steps 11 and 12 are usually carried out in the presence or absence of a solvent in the presence or absence of an acid or base.

There is no particular restriction on the nature of the solvent to be employed, provided that it has no adverse effect on the reaction. Examples of suitable solvents include water, or a mixture of water and an organic solvent (examples of which include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate), of which water, a mixture of water and an alcohol and a mixture of water and an ether are preferred.

The acid to be used is not particularly limited provided that it is one that is usually used as an acid in hydrolysis reactions, and examples thereof include mineral acids such as hydrochloric acid, sulfuric acid and phosphoric acid; carboxylic acids such as formic acid, acetic acid, propionic acid and trifluoroacetic acid; and sulfonic acids such as methanesulfonic acid and ethanesulfonic acid, of which mineral acids and carboxylic acids are preferred, and hydrochloric acid, sulfuric acid, formic acid and acetic acid are more preferred. The hydrolysis reaction is accelerated by the addition of an acid.

The base to be used is not particularly limited provided that it is one that is usually used as a base in hydrolysis reactions, and examples thereof include alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0] undec-7-ene. of which alkali metal hydroxides are preferred, and sodium hydroxide and potassium hydroxide are more preferred.

The reaction temperature is from −20° C. to 150° C., and preferably from 0° C. to 100° C.

The time required for the reaction is from 10 minutes to 48 hours, and preferably from 30 minutes to 12 hours is usually sufficient.

<Method F>

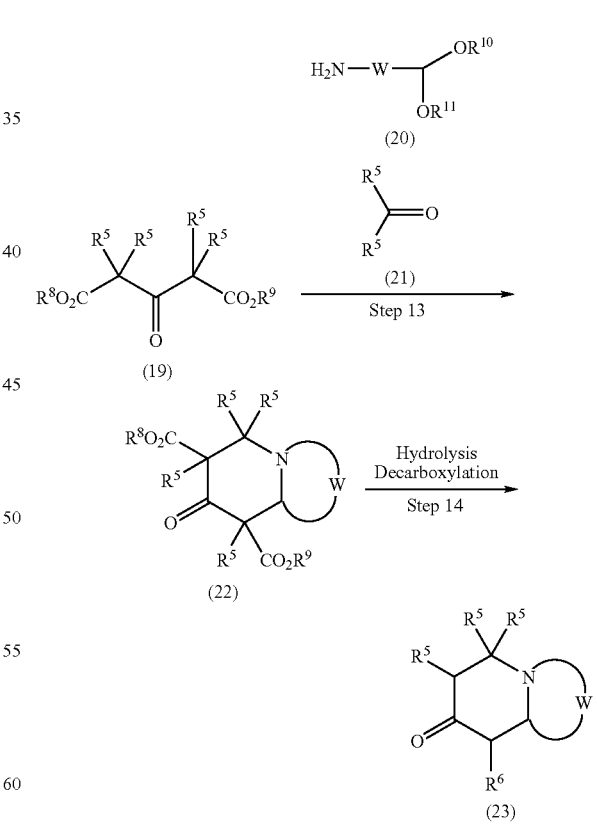

In the above formulae, $R^5$ is as defined above, $R^8$ and $R^9$ are the same or different from each other, and each represents a lower alkyl group as defined above or an aralkyl group as defined above, $R^{10}$ and $R^{11}$ are the same or different from each other, and each represents a lower alkyl group as defined above or $R^{10}$ and $R^{11}$ together form a lower alkylene group as defined above, W represents a lower alkylene group which is substituted with from 1 to 3 groups $R^5$, said alkylene group optionally being interrupted by one or two atoms or groups selected from the group consisting of nitrogen atoms, oxygen atoms, sulfur atoms, >SO groups and >SO$_2$ groups, and the cyclic group containing W shown in general formulae (22) and (23) is a group which corresponds to the cyclic group B which is unsubstitited or is substituted with from 1 to 3 groups $R^5$.

Step 13 and Step 14 can be conducted in a manner similar to the reactions described in detail in O. Pollet et al., Heterocycles, 43, 1391 (1996) or Anet et al., Austral. J. Scient. Res., <A>3, 635–640 (1950).

<Method G>

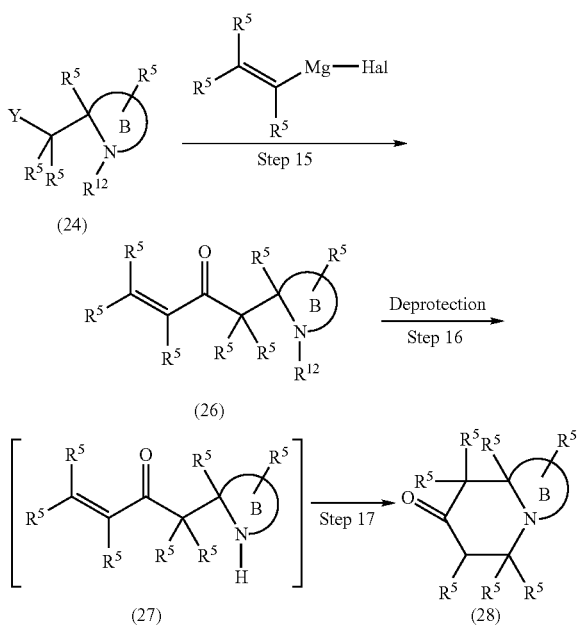

In the above formulae, B and $R^5$ are as defined above, $R^{12}$ represents an amino protecting group, Hal represents a halogen atom (preferably, it is a chlorine atom, bromine atom or iodine atom), and Y represents a halogenocarbonyl group (for example, —CO—Cl, —CO—Br or —CO—I), a N-(lower alkoxy)-N-(lower alkyl)carbamoyl group (examples of such groups include N-methoxy-N-methylcarbamoyl, N-ethoxy-N-methylcarbamoyl and N-ethyl-N-methoxycarbamoyl groups) or a cyano group.

The amino protecting group in the definition of $R^{12}$ can be any protecting group for an amino group which is commonly used in organic synthesis. Examples of suitable amino protecting groups include aliphatic acyl groups as defined and exemplified above, aromatic acyl groups as defined and exemplified above, silyl groups as defined and exemplified above, aralkyl groups as defined and exemplified above, alkoxycarbonyl groups as defined and exemplified above, alkenyloxycarbonyl groups as defined and exemplified above and aralkyloxycarbonyl groups as defined and exemplified above.

In Step 15, an α,β-unsaturated ketone derivative (26) is prepared by reacting a cyclic amino acid derivative (24) with a Grignard reagent of an olefin compound (25). Reactions of this type are well known for the preparation of ketones from carboxylic acid derivatives and Grignard reagents, and any such reaction known can be employed; for example, it can be carried out using the procedures described in detail in H. R. Snyder et al., Org. Synth., III, 798 (1955); J. Cason et al., J. Org. Chem., 26, 1768 (1961); G. H. Posner et al., J. Am. Chem. Soc., 94, 5106 (1972); and G. H. Posner, Org. React., 19, 1 (1972).

Then, the nitrogen protecting group ($R^{12}$) in the α,β-unsaturated ketone derivative (26) is removed to afford a deprotected intermediate (27) (in Step 16), which is then cyclized (in Step 17) to give the desired cyclic aminoketone compound (28). In Step 16, the deprotection reaction employed can be any which is conventionally used in organic synthesis (examples of which are described in T. W. Greene et al., Protective Groups in Organic Synthesis, John Willey & Sons, Inc.). Preferably, the deprotection reaction is conducted under neutral or acidic conditions. After the deprotection reaction, the resulting product (27) cyclizes immediately to give the desired aminoketone compound (28). In Step 16, when the deprotection reaction is conducted under acidic conditions, then the aminoketone compound (28) is prepared without further reaction by neutralizing the reaction mixture.

<Method H>

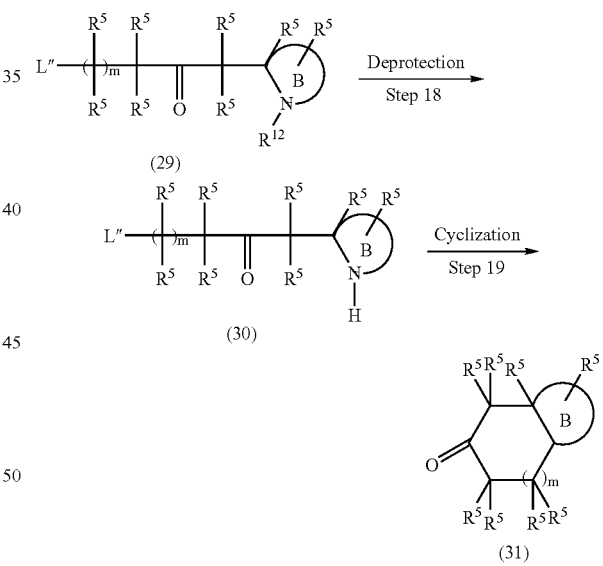

In the above formulae, B, $R^5$, $R^{12}$ and m are as defined above, and

L" represents a leaving group as defined for L, a lower alkylsulfonyl group as defined and exemplified above, an arylsulfonyl group as defined and exemplified above or a halogeno lower alkylsulfonyl group (examples of said group including trifluoromethanesulfonyl and pentafluoroethanesulfonyl groups).

Steps 18 and 19 involve first removing the amino protecting group ($R^{12}$) from a ketone compound (29) having the leaving group to afford a deprotected intermediate (30), and then cyclizing said intermediate to produce the desired aminoketone compound (31). These steps can be carried out in a manner similar to the reactions described in Steps 16 and 17 above.

The compound (29) used as the starting material in this method is either a known compound or it can be prepared from a known compound using known methods [for example, the methods described in S. W. Goldstein et al., J. Org. Chem., 57, 1179–1190 (1992); and B. Achille et al., J. Comb. Chem., 2, 337–340 (2000)].

<Method I>

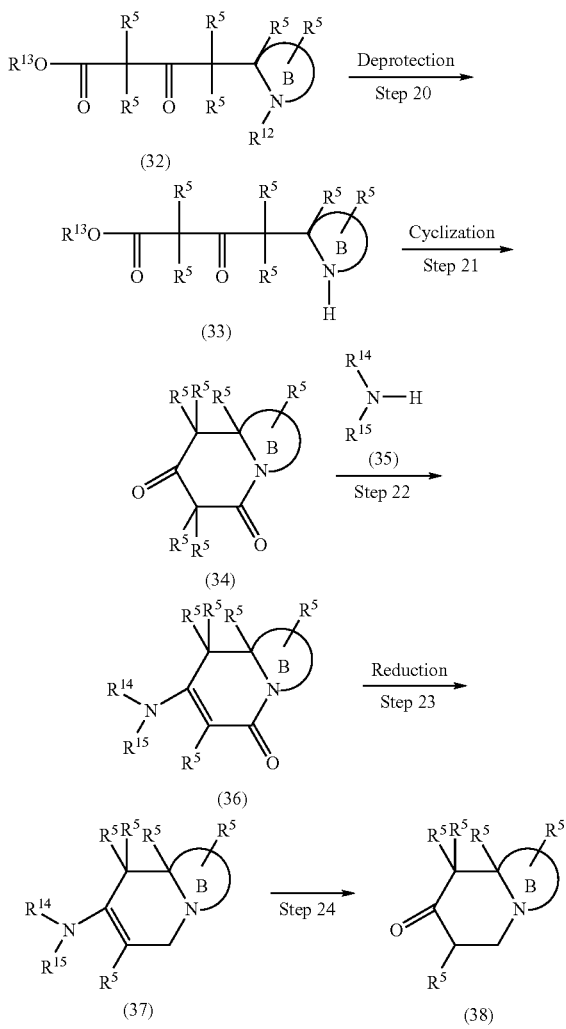

In the above formulae, $R^5$, $R^{12}$ and B are as defined above, $R^{13}$ represents a hydrogen atom or a carboxylprotecting group, and $R^{14}$ and $R^{15}$ are the same or different from each other, and each represents a hydrogen atom, a lower alkyl group as defined above or an aralkyl group as defined above, or $R^{14}$ and $R^{15}$, together with the nitrogen atom to which they are attached, form a 5- or 6-membered heterocyclyl group which includes one ring nitrogen atom and which may optionally include one further heteroatom selected from oxygen, sulfur and nitrogen atoms; examples of such groups include piperidyl, piperazinyl, morpholinyl and thiomorpholinyl.

The carboxylprotecting group in the definition of $R^{13}$ can be any protecting group for a carboxyl group which is commonly used in organic synthesis. Examples of suitable carboxylprotecting groups include lower alkyl groups as defined and exemplified above, lower alkenyl groups as defined and exemplified above, and aralkyl groups as defined and exemplified above; preferred are lower alkyl groups as defined and exemplified above and aralkyl groups as defined and exemplified above.

Steps 20 and 21 comprise first removing the protecting group ($R^{12}$) from a α-ketoacid compound (32) having a leaving group to afford a deprotected intermediate (33), and then cyclizing said intermediate to produce the desired ketolactam compound (34). These steps can be carried out in a manner similar to the reactions described in Steps 16 and 17 above.

In Step 22, a cyclic enaminolactam compound (36) is prepared by reacting the ketolactam compound (34) with a secondary amine compound (35). Any of the techniques conventionally used in the field of organic synthetic chemistry for the preparation of enamine derivatives can be employed. For example, the step can be carried out according to the procedure described in G. Stork et al., J. Am, Chem. Soc., 85, 207 (1963) or as described below.

The reaction is usually carried out in a solvent in the presence or absence of an acid.

There is no particular restriction on the nature of the solvent to be employed, provided that it has no adverse effect on the reaction. Examples of suitable solvents include aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate, of which ethers are preferred.

The acid to be used is not particularly limited, and examples thereof include mineral acids such as hydrochloric acid, sulfuric acid, perchloric acid and phosphoric acid; and organic acids such as acetic acid, formic acid, oxalic acid, methanesulfonic acid, p-toluenesulfonic acid, trifluoroacetic acid and trifluoromethanesulfonic acid. Of these, sulfuric acid, hydrochloric acid and p-toluensulfonic acid are preferred.

The reaction of this step can be carried out efficiently by removing water produced during the reaction by using molecular sieves or a water separator (for example, a Dean Stark Water Separator which can be obtained from Aldrich).

The reaction temperature is from −20° C. to 150° C., and preferably from 0° C. to 100° C.

The time required for the reaction is from 10 minutes to 48 hours, and preferably from 30 minutes to 12 hours is usually sufficient.

In Step 23, a cyclic enamine compound (37) is produced by reducing the cyclic enaminolactam compound (36). Any of the techniques conventionally used in the field of organic synthetic chemistry for performing reduction reactions can be employed. For example, the reduction can be carried out according to the procedures described in S. Cortes et al., J. Org. Chem., 48, 2246 (1983); Y. Tsuda et al., Synthesis, 652 (1977); H. C. Brown et al., J. Am. Chem. Soc., 86, 3566 (1964) and R. J. Sundberg et al., J. Org. Chem., 46, 3730 (1981), or alternatively, can be performed as described below.

This reaction is usually carried out in a solvent in the presence of a reducing reagent.

Examples of the reducing reagent to be employed include hydride reagents such as alkali metal borohydrides e.g. sodium borohydride and lithium borohydride, and aluminum hydrides e.g. lithium aluminum hydride and lithium triethoxyalumino hydride; a combination of a Lewis acid such as aluminum chloride, tin tetrachloride or titanium tetrachloride and a hydride reagent as defined above; and boron compounds such as diborane, of which lithium aluminium hydride is preferred.

In the reduction reaction, non-polar solvents can be used, preferred examples of which include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; and ethers such as diethyl ether, diisopropyl ether, tetrahydrofuran and dioxane, of which ethers are preferred.

The reaction temperature is from –20° C. to 150° C., and preferably from 0° C. to 100° C.

The time required for the reaction is from 10 minutes to 48 hours, and preferably from 30 minutes to 12 hours is usually sufficient.

In Step 24, the desired cyclic aminoketone compound (38) is obtained by hydrolizing the cyclic enamine compound (37). This reaction is performed by bringing the cyclic enamine compound (37) into contact with water in the presence or absence of a solvent with or without the addition of an acid or base.

There is no particular restriction on the nature of the solvent to be employed, provided that it has no adverse effect on the reaction. Examples of suitable solvents include water, or a mixture of water and an organic solvent (examples of which include: aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; and esters such as methyl acetate and ethyl acetate), of which water, a mixture of water and an alcohol and a mixture of water and an ether are preferred.

The acid to be used is not particularly limited provided that it is one that is usually used as an acid in hydrolysis reactions, and examples thereof include mineral acids such as hydrochloric acid, sulfuric acid and phosphoric acid; carboxylic acids such as formic acid, acetic acid, propionic acid and trifluoroacetic acid; and sulfonic acids such as methanesulfonic acid and ethanesulfonic acid. The hydrolysis reaction is accelerated by the addition of an acid. Of these, hydrochloric acid, sulfuric acid and acetic acid are more preferred.

The base to be used is not particularly limited provided that it is one that is usually used as a base in hydrolysis reactions, and examples thereof include alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene. Of these, sodium hydroxide and potassium hydroxide are preferred.

The reaction temperature is from –20° C. to 150° C., and preferably from 0° C. to 100° C.

The time required for the reaction is from 10 minutes to 48 hours, and preferably from 30 minutes to 12 hours is usually sufficient.

The compound (36), which is an intermediate in the preparation of the cyclic aminoketone compound (38) can also be produced by Method J below.

<Method J>

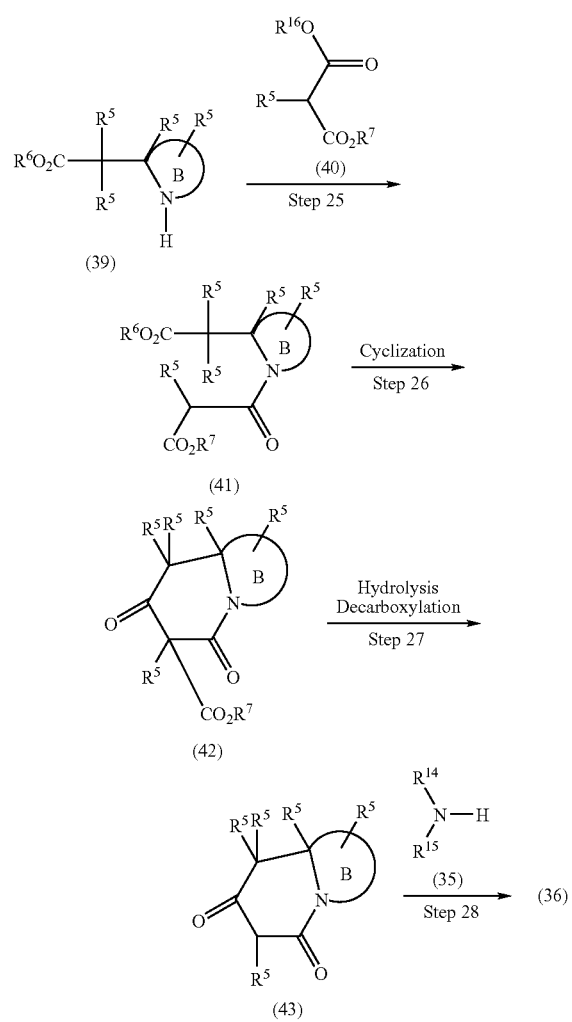

In the above formulae, B, $R^5$, $R^6$, $R^7$, $R^{14}$ and $R^{15}$ are as defined above, and $R^{16}$ represents a hydrogen atom or a carboxylprotecting group.

The carboxylprotecting group in the definition of $R^{16}$ can be any protecting group for a carboxyl group which is commonly used in organic synthesis. Examples of suitable carboxylprotecting groups include lower alkyl groups as defined and exemplified above and aralkyl groups as defined and exemplified above.

In Step 25, an aminodiester compound (41) is produced by the reaction of a cyclic amino acid ester compound (39) with a malonic acid derivative (40) or a reactive derivative thereof.

Any of the techniques conventionally used in the field of organic synthetic chemistry for amidation reactions can be employed, and this step can, for example, be carried out in the manner described in (a), (b) and (c) below.

(a) When $R^{16}$ is a hydrogen atom, the reaction is conducted in a solvent in the presence of a condensing agent and in the presence or absence of a base.

There is no particular restriction on the nature of the solvent to be employed, provided that it has no adverse effect on the reaction. Examples of suitable solvents include aliphatic hydrocarbons such as pentane, hexane and heptane; aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; esters such as methyl acetate and ethyl acetate; water; or a mixture of these solvents described above, of which halogenated hydrocarbons, ethers and esters are preferred and dichloromethane, tetrahydrofuran and ethyl acetate are more preferred.

Any suitable condensing agent that is conventionally employed in such reactions can be employed, and examples include dicyclohexylcarbodiimide, 1-ethyl-3-(3-dimethylaminopropyl)carbodiimide, N,N'-carbonyldiimidazole and the like.

The base to be used is not particularly limited, and examples thereof include alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which amines are preferred, and triethylamine, pyridine and 1,8-diazabicyclo-[5.4.0]undec-7-ene are more preferred.

The reaction temperature is from −20° C. to 150° C., and preferably from 0° C. to 100° C.

The time required for the reaction is from 10 minutes to 48 hours, and preferably from 30 minutes to 12 hours is usually sufficient.

Alternatively, where $R^{16}$ is a hydrogen atom, the reaction can also be carried out by converting the compound (40) into a reactive derivative thereof followed by the procedure described in (c) below.

(b) When $R^{16}$ is a carboxylprotecting group (preferably a lower alkyl group as defined above or an aralkyl group as defined above), the reaction is performed by heating in the presence or absence of a solvent.

When the reaction is conducted in a solvent, the same solvent as that described in (a) can be used. The temperature for the reaction is between 30° C. and 100° C., preferably between the range of ±5° C. of the boiling point of the solvent that is employed. Most preferably, the reaction is carried out by heating the reaction mixture under reflux.

When a solvent is not used in this reaction, the desired compound is prepared by heating a mixture of the compounds (39) and (40).

The reaction temperature is from 30° C. to 150° C., and preferably from 50° C. to 120° C.

The time required for the reaction is from 10 minutes to 48 hours, and preferably from 30 minutes to 12 hours is usually sufficient.

(c) When a reactive derivative of a compound (40) is used, the reactive derivative can be an acid halide, a mixed acid anhydride, an activated ester, an active amide or the like, and the reaction is conducted in a solvent in the presence of a condensing agent and in the presence or absence of a base.

The acid halide is prepared by the reaction of a compound (40) wherein $R^{16}$ is a hydrogen atom with a halogenation reagent (for example, thionyl chloride, oxalyl chloride or the like); the mixed acid anhydride is prepared by the reaction of a compound (40) wherein $R^{16}$ is a hydrogen atom with an acid halide (for example, methyl chlorocarbonate, ethyl chlorocarbonate or the like); the activated ester is prepared by the reaction of a compound (40) wherein $R^{16}$ is a hydrogen atom with a compound containing a hydroxyl group (for example, N-hydroxysuccinimide, N-hydroxyphthalimide or the like) in the presence of a condensing agent such as those described in (a) above; and the active amide (for example, a Weinreb amide) is prepared by the reaction of a compound (40) wherein $R^{16}$ is a hydrogen atom with an N-(lower alkoxy)-N-(lower alkyl)hydroxylamine (for example, N-methoxy-N-methylhydroxylamine or the like) in the presence of a condensing agent such as those described in (a) above. Each of these reactions described can be conducted under reaction conditions usually used in organic synthetic chemistry for such reactions.

With regard to the solvent, condensing agent and base, the solvents, condensing agents and bases described in (a) above can be used.

The reaction temperature is from −20° C. to 150° C., and preferably from 0° C. to 100° C.

The time required for the reaction is from 10 minutes to 48 hours, and preferably from 30 minutes to 12 hours is usually sufficient.

In Steps 26 and 27, a ketolactam compound (43) is prepared by first executing a Dieckman reaction on the amido diester compound (41) to afford a ketolactam ester compound (42), followed by the performance of hydrolysis and decarboxylation reactions on the product thus obtained. These steps can be conducted in a manner similar to that described in Steps 10 and 11 above.

In step 28, the cyclic enaminolactam compound (36) is prepared by the reaction of the ketolactam compound (43) with the secondary amine compound (35), and the reaction is carried out in a manner similar to that described in Step 22 above.

The compound (42), which is an intermediate in Method J described above, can also be synthesized by Method K below.

<Method K>

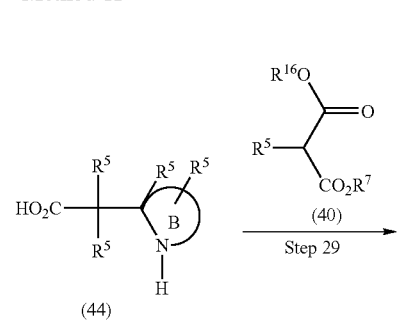

-continued

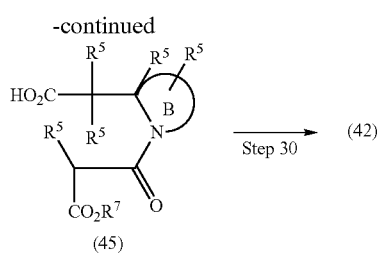

In the above formulae, B, $R^5$, $R^7$ and $R^{16}$ are as defined above.

In Step 29, an amido monoester compound (45) is prepared by the reaction of a cyclic amino acid compound (44) with a malonic acid derivative (40) or a reactive derivative thereof. This step is carried out in a manner similar to that described in (a), (b) and (c) of Step 25 above.

In Step 30, the ketolactam ester compound (42) is prepared by the intramolecular condensation of a carboxyl group and an active methylene group of the amido monoester compound (45). In this step, the compound (45) is either used in underivatised form or after first being converted into a reactive derivative thereof.
(a) When the compound (45) is used in underivatised form, the reaction is conducted in a solvent in the presence of a condensing agent and with or without a base.

There is no particular restriction on the nature of the solvent to be employed, provided that it has no adverse effect on the reaction. Examples of suitable solvents include halogenated hydrocarbons such as dichloromethane, chloroform, carbon tetrachloride and dichloroethane; ethers such as diethyl ether, diisopropyl ether, tetrahydrofuran and dioxane; alcohols such as methanol, ethanol, propanol, isopropanol, butanol, s-butanol, isobutanol and t-butanol; aprotic polar solvents such as N,N-dimethylformamide, N,N-dimethylacetamide and dimethyl sulfoxide; nitriles such as acetonitrile; esters such as methyl acetate and ethyl acetate; water; or a mixture of these solvents described above, of which halogenated hydrocarbons, ethers and esters are preferred and dichloromethane, tetrahydrofuran and ethyl acetate are more preferred.

Any suitable condensing agent that is conventionally employed in such reactions can be employed, and examples include dicyclohexylcarbodiimide, 1-ethyl-3-(3-dimethylaminopropyl)carbodiimide, N,N'-carbonyldiimidazole and the like.

The base to be used is not particularly limited, and examples thereof include alkali metal alkoxides such as sodium methoxide, sodium ethoxide and potassium t-butoxide; alkali metal hydrides such as sodium hydride and lithium hydride; alkali metal hydroxides such as sodium hydroxide and potassium hydroxide; alkali metal carbonates such as sodium carbonate and potassium carbonate; and amines such as triethylamine, tributylamine, pyridine, picoline and 1,8-diazabicyclo[5.4.0]undec-7-ene, of which amines are preferred, and triethylamine, pyridine and 1,8-diazabicyclo-[5.4.0]undec-7-ene are more preferred.

The reaction temperature is from –20° C. to 150° C., and preferably from 0° C. to 100° C.

The time required for the reaction is from 10 minutes to 48 hours, and preferably from 30 minutes to 12 hours is usually sufficient.
(b) When the compound (45) is used after first being converted into a reactive derivative, examples of the reactive derivative include acid halides, mixed acid anhydrides, activated esters, active amides and the like.

The acid halides are prepared by the reaction of the compound (45) with a halogenation reagent (for example, thionyl chloride, oxalyl chloride or the like); the mixed acid anhydride is prepared by the reaction of the compound (45) with an acid halide (for example, methyl chlorocarbonate, ethyl chlorocarbonate or the like); the activated ester is prepared by the reaction of the compound (45) with a compound containing a hydroxyl group (for example, N-hydroxysuccinimide, N-hydroxyphthalimide or the like) in the presence of a condensing agent such as those described in (a) above; and the active amide (for example, Weinreb amide) is prepared by the reaction of the compound (45) with a N-(lower alkoxy)-N-(lower alkyl)hydroxylamine (for example, N-methoxy-N-methylhydroxylamine or the like) in the presence of a condensing agent such as those described in (a) above. Each of these reactions described above can be conducted employing reaction conditions conventionally employed in organic synthetic chemistry for such reactions.

The cyclization of said reactive derivative is usually carried out in a solvent in the presence or absence of a base.

With regard to the solvent, condensing agent and base, the solvents, condensing agents and bases described in (a) above can be used.

The reaction temperature is from –20° C. to 150° C., and preferably from 0° C. to 100° C.

The time required for the reaction is from 10 minutes to 48 hours, and preferably from 30 minutes to 12 hours is usually sufficient.

<Method L>

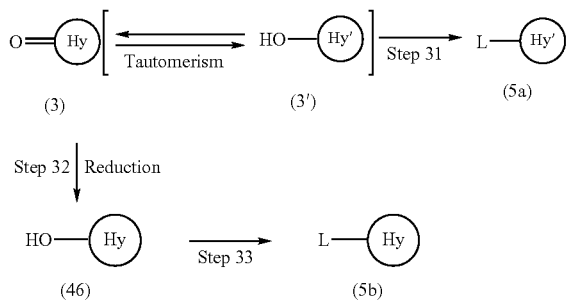

In the above formulae, Hy, Hy' and L are as defined above.

In Step 31, a compound (5a) is prepared by converting a hydroxyl group of a compound (3'), which is a tautomer of the heterocyclyl (3), into a leaving group. This step is carried out by reacting the compound (3') with a halogenation reagent (for example, a fluorination reagent such as (diethylamino)sulfur trifluoride (DAST); a chlorination reagent such as thionyl chloride, phosphorus trichloride, phosphorus pentachloride, phosphorus oxychloride and triphenylphosphine/carbon tetrachloride; a bromination reagent such as hydrobromic acid, thionyl bromide, phosphorus tribromide and triphenylphosphine/carbon tetrabromide; or an iodination reagent such as hydriodic acid and phosphorus triiodide), a sulfonyl halide (for example, methanesulfonyl chloride and p-toluenesulfonyl chloride) or a sulfonic anhydride (for example, trifluoromethanesulfonic anhydride).

In Step 32, a heterocyclyl alcohol (46) is produced by reducing the heterocyclyl ketone (3). The reaction is carried out by a reduction reaction using a reducing reagent (examples of the reducing reagent to be employed include hydride reagents such as alkali metal borohydrides e.g. sodium borohydride and lithium borohydride; aluminum hydrides e.g. lithium aluminum hydride and lithium triethoxyalumino hydride; sodium telluride hydride; and organic aluminium hydrides e.g. diisobutylaluminum hydride and di(methoxyethoxy)aluminum sodium dihydride) or catalytic reduction.

The reaction can be carried out according to the methods described in detail in J. Dale, J. Chem. Soc., 910 (1961) and F. G. Bordwell et al., J. Org. Chem., 33, 3385 (1968).

In Step 33, the compound (5b) is prepared by converting a hydroxyl group of the heterocyclyl alcohol (46) into a leaving group. This step is carried out in a manner similar to that described in Step 31.

The substituent $R^3$, which is one of the components of the compound of general formula (I), can be substituted with various substituents ($R^5$). The substituents $R^5$ can be converted into other substituents in each of the steps described above. The substituent $R^5$ can, for example, be converted as illustrated below employing conventional organic synthetic methods.

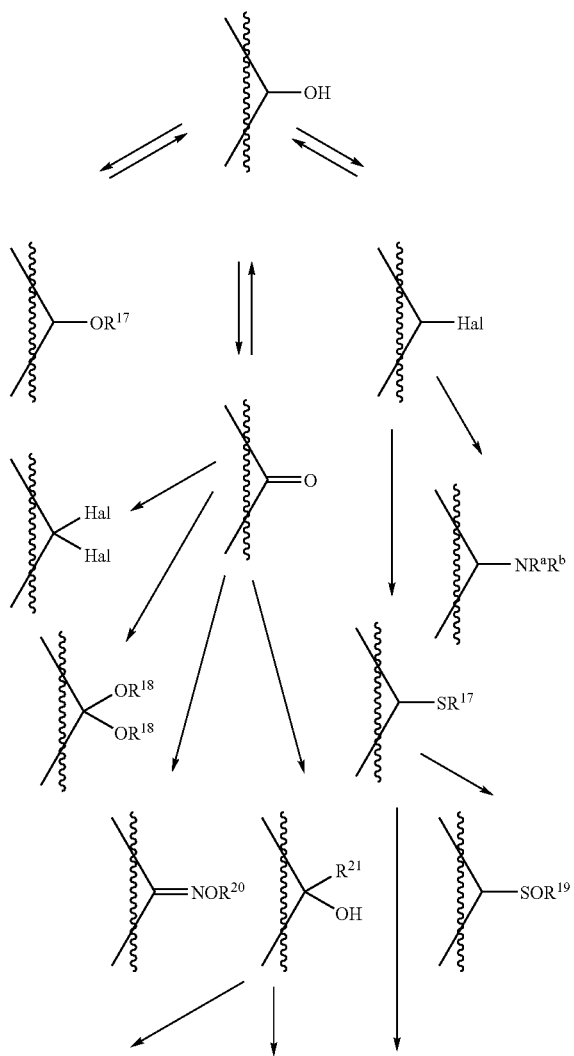

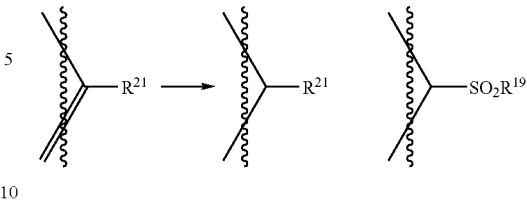

In the above formulae, $R^a$, $R^b$ and Hal have the same meanings as defined above, $R^{17}$ represents a lower alkyl group as defined above, a halogeno lower alkyl group as defined above, an aryl group or an aryl group which is substituted with one or more substituents selected from Substituent group α and Substituent group β, groups $R^{18}$ are the same or different from each other, and each represents a lower alkyl group as defined above or a halogeno lower alkyl group as defined above, or the two groups $R^{18}$ can together form a lower alkylene group, $R^{19}$ represents a lower alkyl group as defined above, $R^{20}$ represents a hydrogen atom or a lower alkyl group as defined above, and $R^{21}$ represents a lower alkyl group, a lower alkenyl group, a lower alkynyl group, an aralkyl group, a cycloalkyl group, a lower alkyl group which is substituted with one or more substituents selected from Substituent group α, a lower alkenyl group which is substituted with one or more substituents selected from Substituent group α or a lower alkynyl group which is substituted with one or more substituents selected from Substituent group α, as defined in the definition of Substituent group β, or an aryl group or an aryl group which is substituted with one or more substituents selected from Substituent group α and Substituent group β.

Furthermore, when $R^5$ is a halogen atom, a hydroxyl group, a cyano group or a lower alkylsulfonyl group, $R^5$ can be converted into a hydrogen atom by the formation of a double bond, followed by the reduction of said double bond using conventional methods as illustrated below.

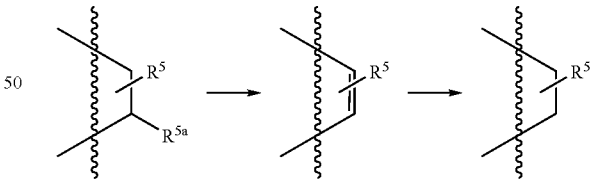

In the above formulae, $R^5$ has the same meaning as defined above, and $R^{5a}$ represents a halogen atom, a hydroxyl group, a cyano group or a lower alkylsulfonyl group.

Where $R^5$ represents a lower alkylidenyl group or an aralkylidenyl group, such a compound can be prepared from the corresponding oxo derivative as shown below. Subsequently, the alkylidenyl or aralkylidenyl compound can be converted to the corresponding alkyl-substituted compound or aralkyl-substituted compound:

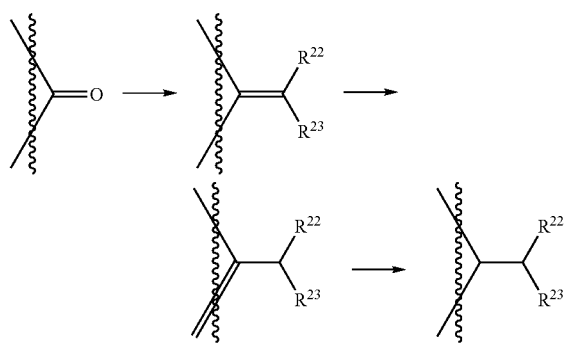

In the above formulae, $R^{22}$ and $R^{23}$ are the same or different from each other, and each represents a hydrogen atom, a lower alkyl group as defined above, an aryl group as defined above or an aralkyl group as defined above.

Alternatively, for the cyclic aminoketone compounds (38) obtained according to Method I, cyclic aminoketone compounds having optical activity are preferably prepared by Method M described below.

<Method M>

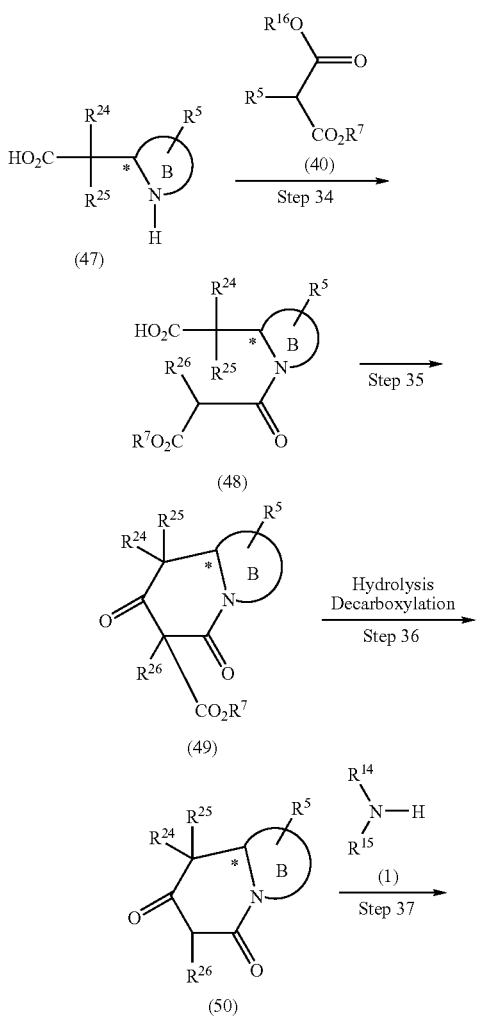

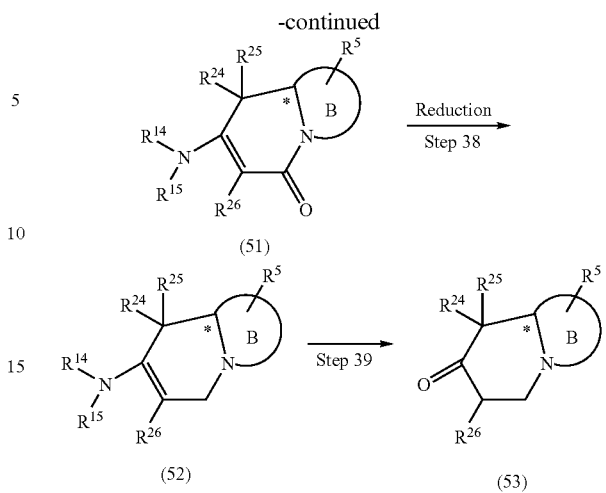

In the above formulae, $R^5$, $R^7$, $R^{14}$, $R^{15}$, $R^{16}$ and B have the same meanings as defined above, $R^{24}$, $R^{25}$ and $R^{26}$ are the same or different from each other and each represents one group selected from the groups defined in $R^5$, and the configuration based on carbon atom which is marked by * represents S or R, and the configuration based on the carbon atom which is marked by * in compound (47) is retained through all the Steps (namely in Steps 34 to 39).

Each of Steps 34, 35, 36, 37, 38 and 39 can be carried out according to Steps 25, 30, 11, 22, 23 and 24 described above.

By the reaction according to the present Method, substantially pure optically active substance (optical activity is about 99% ee to 100% ee) of general formula (53) is prepared.

The cyclic aminoketone compound (53) having optical activity is used as the heterocyclyl ketone (3) in Method A above in the preparation of compounds of general formula (I), and also is used as a synthetic intermediate of compounds which are disclosed in WO 00/00490. Alternatively, compounds disclosed in EP 1070711 can be prepared by using pyrrole derivatives which correspond to brominated cyclic compounds (2) and cyclic aminoketone compounds (53) having optical activity according to a reaction similar to that described in Step 2 (if desired, in Steps 3 and/or 4) above.

After completion of each of the reactions, the desired compound may be isolated from the reaction mixture in a conventional manner. For example, it can be obtained by neutralizing the reaction mixture as needed, removing insoluble matters by filtration, if any are present, adding organic solvents which are not miscible with each other, such as water and ethyl acetate, washing with water or the like, separating the organic layer containing the desired compound, drying it over anhydrous magnesium sulfate or the like and then distilling off the solvent.

The compound thus obtained can, if necessary, be isolated and purified by a conventional method such as recrystallization or reprecipitation or procedures that are usually used for the isolation and purification of the organic compounds. Examples of the procedures mentioned above include adsorption column chromatography using a carrier such as silica gel, alumina or magnesium-silica gel type Florisil, chromatography using a synthetic adsorbent, for example, partition column chromatography using a carrier such as Sephadex LH-20 (product of Pharmacia Co., Ltd.), Amberlite XAD-11 (product of Rohm & Haas Co., Ltd.) or Diaion HP-20 (product of Mitsubishi Chemical Corporation), ion exchange chromatography and normal-phase reverse-phase column chromatography (high-performance liquid chromatography is preferred) using a silica gel or alkylated silica gel. If necessary, these techniques can be used in combination to isolate and purify the desired compound by elution with appropriate solvent.

The compounds of the present invention exhibit excellent inhibitory activity against the production of inflammatory cytokines. Consequently, they are effective as a medicament, particularly as an agent for the prophylaxis or treatment of diseases mediated by inflammatory cytokines. Examples of such a medicament include analgesics, anti-inflammatory drugs and virucides, and agents for the prophylaxis or treatment of chronic rheumatoid arthritis, osteoarthritis, allergic diseases, asthma, septicaemia, psoriasis, osteoporosis, autoimmune diseases (e.g. systemic lupus erythematosus, ulcerative colitis and Crohn's disease), diabetes, nephritis, hepatitis, cancer, ischemic heart disease, Alzheimer's disease and arteriosclerosis. Of these, the compounds of the present invention are particularly useful as analgesics and anti-inflammatory drugs and as agents for the prophylaxis or treatment of chronic rheumatism, osteoarthritis, allergic diseases, septicaemia, psoriasis, osteoporosis, ulcerative colitis, diabetes, hepatitis and arteriosclerosis.

The compounds of formula (I) and pharmacologically acceptable salts, esters and other derivatives thereof according to the present invention can be administered by a number of different routes. Examples of these administration routes include oral administration in the form of tablets, capsules, granules, powders or syrups and parenteral administration in the form of injections or suppositories. Such formulations can be prepared in a known manner by using additives (i.e., carriers) such as excipients, lubricants, binders, disintegrators, stabilizers, corrigents and diluents.

Examples of suitable excipients include: organic excipients, examples of which include sugar derivatives such as lactose, sucrose, dextrose, mannitol and sorbitol, starch derivatives such as corn starch, potato starch, α-starch, dextrin and carboxymethyl starch, cellulose derivatives such as crystalline cellulose, low-substituted hydroxypropylcellulose, hydroxypropylmethylcellulose, carboxymethylcellulose, calcium carboxymethylcellulose and sodium internally-crosslinked carboxymethylcellulose, gum arabic, dextran and pullulan; and inorganic excipients, examples of which include silicate derivatives such as soft silicic acid anhydride, synthetic aluminum silicate and magnesium aluminometasilicate, phosphates such as calcium phosphate, carbonates such as calcium carbonate, and sulfates such as calcium sulfate.

Examples of suitable lubricants include: stearic acid; metal salts of stearic acid such as calcium stearate and magnesium stearate; talc; colloidal silica; waxes such as bee gum and spermaceti; boric acid; adipic acid; sulfates such as sodium sulfate; glycol; fumaric acid; sodium benzoate; DL-leucine; sodium salts of an aliphatic acid; lauryl sulfates such as sodium lauryl sulfate and magnesium lauryl sulfate; silicic acid derivatives such as silicic anhydride and silicic acid hydrate; and starch derivatives exemplified above as examples of suitable excipients.

Examples of suitable binders include polyvinylpyrrolidone, Macrogol™ and compounds similar to those exemplified above as suitable excipients.

Examples of suitable disintegrators include compounds similar to those exemplified above as suitable excipients and chemically modified starch or cellulose derivatives such as sodium cross carmellose, sodium carboxymethyl starch and crosslinked polyvinylpyrrolidone.

Examples of suitable stabilizers include: paraoxybenzoate esters such as methylparaben and propylparaben; alcohols such as chlorobutanol, benzyl alcohol and phenylethyl alcohol; benzalkonium chloride; phenol derivatives such as phenol and cresol; thimerosal; dehydroacetic acid; and sorbic acid.

Examples of suitable corrigents include sweeteners, acidifiers and flavors commonly employed for this purpose.

The dose of the compound of formula (I) or a pharmacologically acceptable salt, ester or other derivative thereof according to the present invention will vary depending on a variety of factors including the condition to be treated, the age of the patient (human) and the administration route. When administered orally, it is administered to an adult (human) in an amount of 0.1 mg (preferably 0.5 mg) a day as a lower limit and 2000 mg (preferably 500 mg) a day as an upper limit. It can be administered in from one to several portions depending on the condition of the patient. When administered intravenously, it is administered to an adult (human) in an amount of 0.01 mg (preferably 0.05 mg) a day as a lower limit and 200 mg (preferably 50 mg) a day as an upper limit. It can be administered in from one to several portions depending on the condition of the patient. The above dosage ranges are based on an adult human. The dosage range for mammals who differ in weight from an adult human would be proportional to the respective average weight of an adult human and a non-human mammal.

The present invention is further illustrated in detail by the following Examples, Reference examples and test examples. The scope of the present invention is not limited by these examples.

EXAMPLE

Example 1

(±)-4-(4-Fluorophenyl)-5-(pyridin-4-yl)-1-(1,2,3,5,6,7,8,8a-octahydroindolizin-7-yl)imidazole (Exemplification Compound Number 13-15)

1) (±)-7-Amino-1,2,3,5,6,7,8,8a-octahydroindolizine (±)-1,2,3,5,6,7,8,8a-octahydroindolizin-7-one (5.0 g, 35.9 mmol) was dissolved in a solution of 2M ammonia/ethanol (54 ml, 108 mmol calculated in terms of ammonia). The resulting solution was stirred at room temperature in an atmosphere of hydrogen in the presence of 10% palladium on charcoal (500 mg) for 4 hours. At the end of this time, the reaction mixture was filtered to remove the catalyst and the filtrate was concentrated by evaporation under reduced pressure, to give the title compound (4.91 g) as a colorless oil (yield 98%).

$^1$H-Nuclear magnetic resonance spectrum (500 MHz, CDCl$_3$) δ ppm: 3.15–3.04 (2H, m), 2.72–2.64 (1H, m), 2.10–2.00 (3H, m), 1.91–1.49 (6H, m), 1.47–1.33 (3H, m), 1.06–0.99 (1H, m).

2) (±)-7-(Pyridin-4-yl)methyleneamino-1,2,3,5,6,7,8,8a-octahydroindolizine (±)-7-Amino-1,2,3,5,6,7,8,8a-octahydroindolizine (4.91 g (35.0 mmol), prepared as described in 1)) was dissolved in toluene (95 ml). To the solution were added 4-formylpyridine (3.34 ml, 35.0 mmol) and anhydrous magnesium sulfate (3.75 g, 31.2 mmol), and the resulting mixture was stirred at 70° C. for 3 hours. At the end of this time, the reaction mixture was filtered to remove the catalyst and the filtrate was concentrated by evaporation under reduced pressure, to give the title compound (8.08 g) as a pale yellow oil (yield quantitative).

¹H-Nuclear magnetic resonance spectrum (400 MHz, CDCl₃) δ ppm: 8.90 (2H, d, J=6 Hz), 8.32 (1H, s), 7.71 (2H, d, J=6 Hz), 3.15–3.02 (3H, m), 2.71–2.62 (1H, m), 2.18–1.34 (9H, m), 1.08–0.98 (1H, m).

3) (±)-4-(4-Fluorophenyl)-5-(pyridin-4-yl)-1-(1,2,3,5,6,7,8,8a-octahydroindolizin-7-yl)imidazole α-(p-Toluenesulfonyl)-4-fluorobenzylisocyanide (10.1 g, 34.9 mmol) and (±)-7-(4-pyridylmethyleneamino)-1,2,3,5,6,7,8,8a-octahydroindolizine (8.0 g (34.9 mmol), prepared as described in 2)) were dissolved in dichloromethane (150 ml). To the solution was added 1,8-diazabicyclo[5.4.0]-7-undecene (5.22 ml, 34.9 mmol), and the resulting mixture was stirred at room temperature for 2 hours. At the end of this time, the reaction mixture was concentrated by evaporation under reduced pressure. To the residue was added a saturated aqueous solution of sodium hydrogencarbonate and this was extracted with ethyl acetate. The organic layer was washed with water, dried over anhydrous sodium sulfate and the solvent was removed by distillation under reduced pressure. The residue was purified by column chromatography through silica gel (eluent, ethyl acetate:methanol:isopropylamine=20:1:1), to give the title compound (1.87 g) as a pale yellow powder (yield 14%).

m.p. 187–189° C.

¹H-Nuclear magnetic resonance spectrum (500 MHz, CDCl₃) δ ppm: 8.73 (2H, d, J=3 Hz), 7.78 (1H, s), 7.35 (2H, dd, J=9 Hz, 5 Hz), 7.24 (2H, d, J=3 Hz), 6.92 (2H, t, J=9 Hz), 3.82–3.73 (1H, m), 3.18–3.14 (1H, m), 3.08–3.05 (1H, m), 2.18–1.96 (5H, m), 1.90–1.82 (3H, m), 1.77–1.71 (2H, m), 1.53–1.44 (1H, m).

Example 2

(±)-5-(4-Fluorophenyl)-3-(7-hydroxy-1,2,3,5,6,7,8,8a-octahydroindolizin-7-yl)-4-(pyridin-4-yl)pyrazole (Exemplification Compound Number 9-23)

1) 3-Bromo-5-(4-fluorophenyl)-4-(pyridin-4-yl)pyrazole 5-(4-Fluorophenyl)-4-(pyridin-4-yl)pyrazole (6.0 g (25 mmol), prepared as described in WO 00/31063) was dissolved in dimethylformamide (60 ml). To the solution was added N-bromosuccinimide (8.93 g, 50 mmol), and the resulting mixture was stirred at room temperature for 3 days. At the end of this time, water was added to the reaction mixture, and the precipitated crystals were collected by filtration and washed with diethyl ether, to give the title compound (5.73 g) as a white powder (yield 72%).

¹H-Nuclear magnetic resonance spectrum (400 MHz, CDCl₃-DMSO-d₆) δ ppm: 8.56 (2H, d, J=5 Hz), 7.33 (2H, dd, J=8 Hz, 5 Hz), 7.24 (2H, d, J=5 Hz), 7.05 (2H, t, J=8 Hz).

2) (±)-5-(4-Fluorophenyl)-3-(7-hydroxy-1,2,3,5,6,7,8,8a-octahydroindolizin-7-yl)-4-(pyridin-4-yl)pyrazole 3-Bromo-5-(4-fluorophenyl)-4-(pyridin-4-yl)pyrazole (3.18 g (10 mmol), prepared as described in 1)) was dissolved in tetrahydrofuran (32 ml). To the solution was added a solution of 1.6 M butyl lithium/hexane (13.75 ml, 13.75 mmol) at −78° C., and the resulting mixture was stirred for 10 minutes. To the mixture was added 1,2,3,5,6,7,8,8a-octahydroindolizin-7-one (1.53 g, 11 mmol) at −78° C., and the resulting mixture was stirred first at −78° C. for 2 hours, then at room temperature for 1 hour. At the end of this time, the reaction mixture was added to a saturated aqueous solution of sodium hydrogencarbonate and extracted with ethyl acetate. The organic layer was washed with water, dried over anhydrous sodium sulfate and the solvent was removed by distillation under reduced pressure. The residue was purified by column chromatography through silica gel (eluent, ethyl acetate:methanol:isopropylamine=20:1:1), to give the title compound (830 mg) as a pale yellow powder (yield 22%).

m.p. 180–181° C.

¹H-Nuclear magnetic resonance spectrum (500 MHz, CDCl₃) δ ppm: 8.57 (2H, d, J=6 Hz), 7.23 (2H, d, J=6 Hz), 7.19 (2H, dd, J=9 Hz, 5 Hz), 6.94 (2H, t, J=9 Hz), 3.04–2.99 (1H, m), 2.96–2.90 (1H, m), 2.42–2.36 (1H, m), 2.31–2.24 (1H, m), 2.28–1.99 (3H, m), 1.84–1.65 (6H, m), 1.36–1.30 (1H, m).

Example 3

(±)-5-(4-Fluorophenyl)-3-(1,2,3,5,8,8a-hexahydroindolizin-7-yl)-4-(pyridin-4-yl)pyrazole (Exemplification Compound Number 7-1)

The compound prepared as described in Example 2 (720 mg, 1.90 mmol) was dissolved in concentrated hydrochloric acid (14 ml). The resulting solution was heated under reflux for 8 hours. At the end of this time, the reaction mixture was neutralized with an aqueous solution of 1 N sodium hydroxide, and extracted with ethyl acetate. The organic layer was washed with water, dried over anhydrous sodium sulfate and the solvent was removed by distillation under reduced pressure. The residue was purified by column chromatography through silica gel (eluent, ethyl acetate:methanol:isopropylamine=10:1:1), to give the title compound (Rf=0.45, 255 mg) as a white powder (yield 37%).

m.p. 225–230° C.

¹H-Nuclear magnetic resonance spectrum (500 MHz, CDCl₃) δ ppm: 8.54 (2H, d, J=6 Hz), 7.29 (2H, dd, J=9 Hz, 5 Hz), 7.15 (2H, d, J=6 Hz), 6.99 (2H, t, J=9 Hz), 5.90 (1H, s), 3.64–3.59 (1H, m), 3.28–3.24 (1H, m), 2.90–2.85 (1H, m), 2.40–2.35 (1H, m), 2.28–2.15 (3H, m), 2.02–1.89 (2H, m), 1.82–1.75 (1H, m), 1.49–1.41 (1H, m).

Example 4

(±)-5-(4-Fluorophenyl)-3-(1,2,3,5,6,8a-hexahydroindolizin-7-yl)-4-(pyridin-4-yl)pyrazole (Exemplification Compound Number 1-307)

The title compound (Rf=0.30 mg) was obtained as a pale yellow powder (yield 27%) by column chromatography through silica gel carried out in Example 3.

m.p. 204–208° C.

¹H-Nuclear magnetic resonance spectrum (500 MHz, CDCl₃) δ ppm: 8.54 (2H, d, J=6 Hz), 7.28 (2H, dd, J=9 Hz, 5 Hz), 7.15 (2H, d, J=6 Hz), 7.00 (2H, t, J=9 Hz), 5.87 (1H, s), 3.32–3.26 (1H, m), 3.02–2.98 (1H, m), 2.92–2.88 (1H, m), 2.78–2.68 (2H, m), 2.46–2.38 (1H, m), 2.23–2.17 (1H, m), 2.01–1.74 (3H, m), 1.50–1.41 (1H, m).

Example 5

(±)-5-(4-Fluorophenyl)-3-(1,2,3,5,6,7,8,8a-octahydroindolizin-7-yl)-4-(pyridin-4-yl)pyrazole The compound (50 mg (0.14 mmol), prepared as described in Example 3) was dissolved in methanol (4 ml). The resulting solution was stirred at 50° C. in an atmosphere of hydrogen in the presence of 10% palladium hydroxide on charcoal (40 mg) for 4 hours. At the end of this time, the reaction mixture was filtered to remove the catalyst and the filtrate was concentrated by evaporation under reduced pressure. The residue was washed with diethyl ether, to give the title compound (27 mg) as a white powder (yield 53%).

m.p. 242–243° C.

$^1$H-Nuclear magnetic resonance spectrum (500 MHz, CDCl$_3$) δ ppm: 8.59 (2H, d, J=6 Hz), 7.31 (2H, dd, J=9 Hz, 5 Hz), 7.11 (2H, d, J=6 Hz), 6.99 (2H, t, J=9 Hz), 3.23–3.18 (1H, m), 3.15–3.08 (1H, m), 2.88–2.79 (1H, m), 2.17–1.42 (11H, m).

Example 6

(S)-5-(4-Fluorophenyl)-3-(1,2,3,5,8,8a-hexahydroindolizin-7-yl)-4-(pyridin-4-yl)pyrazole (Exemplification Compound Number 7-1)

Following a procedure similar to that described in Example 2-2), but using (S)-1,2,3,5,6,7,8,8a-octahydroindolizin-7-one instead of (±)-1,2,3,5,6,7,8,8a-octahydroindolizin-7-one, the resulting product was subjected to a dehydration reaction as described in Example 3 and then treated by column chromatography through silica gel (eluent, ethyl acetate:methanol:isopropylamine=10:1:1), to give the title compound (Rf=0.45, 980 mg) as a pale yellow powder (yield 6%).

m.p. 209–214° C.

$^1$H-Nuclear magnetic resonance spectrum (400 MHz, DMSO-d$_6$) δ ppm: 13.40–13.10 (1H, br.s), 8.52 (2H, m), 7.28 (2H, m), 7.24–7.16 (4H, m), 5.79–5.50 (1H, br.s), 3.44–3.29 (2H, m), 3.05 (1H, m), 2.72–2.62 (1H, br.s), 2.51–1.90 (4H, m), 1.73–1.64 (2H, m), 1.34–1.25 (1H, m).

Example 7

(S)-5-(4-Fluorophenyl)-3-(1,2,3,5,6,8a-hexahydroindolizin-7-yl)-4-(pyridin-4-yl)pyrazole (Exemplification Compound Number 1-307)

The title compound (Rf=0.30 mg, 830 mg) was obtained as a pale yellow powder (yield 5%) during the column chromatography through silica gel carried out in Example 6.

m.p. 198–202° C.

$^1$H-Nuclear magnetic resonance spectrum (400 MHz, DMSO-d$_6$) δ ppm: 13.23 (1H, br.s), 8.52–8.51 (2H, m), 7.31–7.27 (2H, m), 7.19–7.14 (4H, m), 5.63–5.62 (1H, br.s), 3.17–3.16 (1H, br.s), 2.93–2.87 (1H, m), 2.80–2.74 (1H, m), 2.68–2.61 (1H, m), 2.57–2.50 (1H, m), 2.38–2.33 (1H, m), 2.16–2.08 (1H, m), 1.85–1.57 (3H, m), 1.28–1.19 (1H, br.s).

Example 8

(S)-2-(4-Fluorophenyl)-4-(1,2,3,5,8,8a-hexahydroindolizin-7-yl)-3-(pyridin-4-yl)thiophene (Exemplification Compound Number 12-1)

1) 5-Ethoxycarbonyl-2-(4-fluorophenyl)-3-(pyridin-4-yl)thiophene

Phosphorus oxychloride (7.9 ml, 85 mmol) was added to dimethylformamide (17.04 ml, 220 mmol) dropwise under ice cooling. The resulting mixture was stirred at room temperature for 1 hour. The mixture was then added dropwise under ice cooling to a solution of 1-(4-fluorophenyl)-2-(pyridin-4-yl)ethanone (21.5 g (100 mmol), prepared as described in T. F. Gallagher et al., Bioorg. Med. Chem., 5, 49–64 (1997)) dissolved in a mixed solution of dimethylformamide (140 ml) and dichloromethane (280 ml). The resulting mixture was stirred at 50° C. for 2 hours. At the end of this time, the reaction mixture was cooled to room temperature, water was added, adjusted to pH 9 to 10 by adding an aqueous solution of 6 N sodium hydroxide and then extracted with dichloromethane. The organic layer was washed with water, dried over anhydrous magnesium sulfate and the solvent was removed by distillation under reduced pressure. The residue was dissolved in a mixed solution of dichloroethane (100 ml) and pyridine (15 ml). To the resulting solution was added ethyl thioacetate (11 ml, 100 mmol), and then triethylamine (25 ml, 180 mmol) with stirring under ice cooling. The resulting mixture was stirred at room temperature for 1 hour, then 80° C. for 3 hours. The resulting mixture was cooled to room temperature and partitioned between water and dichloromethane. The organic layer was washed with water, dried over anhydrous magnesium sulfate and the solvent was removed by distillation under reduced pressure. The residue was purified by column chromatography through silica gel (eluent, hexane:ethyl acetate=2:3), to give the title compound (18.11 g) as a brown viscous oil (yield 55%).

$^1$H-Nuclear magnetic resonance spectrum (500 MHz, CDCl$_3$) δ ppm: 8.54 (2H, d, J=6 Hz), 7.85 (1H, s), 7.28 (2H, dd, J=9 Hz, 5 Hz), 7.14 (2H, d, J=6 Hz), 7.04 (2H, t, J=9 Hz), 4.39 (2H, q, J=7 Hz), 1.40 (2H, t, J=7 Hz).

2) 5-Carboxy-2-(4-fluorophenyl)-3-(pyridin-4-yl)thiophene

5-Ethoxycarbonyl-2-(4-fluorophenyl)-3-(pyridin-4-yl)thiophene (15.17 g (46.3 mmol), prepared as described in 1)) was dissolved in ethanol (150 ml). To the solution was added an aqueous solution of 1 N sodium hydroxide (93 ml, 93 mmol), and the resulting mixture was stirred at 100° C. for 30 minutes. At the end of this time, ethanol was removed by distillation under reduced pressure. To the reaction residue was added water, and then an aqueous solution of 1 N hydrochloric acid (93 ml). The precipitated crystals were collected by filtration, to give the title compound (12.64 g) as a pale brown powder (yield 91%).

$^1$H-Nuclear magnetic resonance spectrum (500 MHz, CDCl$_3$) δ ppm: 8.52 (2H, d, J=6 Hz), 7.90 (1H, s), 7.38 (2H, dd, J=9 Hz, 5 Hz), 7.26 (2H, t, J=9 Hz), 7.25 (2H, d, J=6 Hz).

3) 2-(4-Fluorophenyl)-3-(pyridin-4-yl)thiophene

Quinoline (42 ml) and copper powder (2.95 g, 46.4 mmol) were added to 5-carboxy-2-(4-fluorophenyl)-3-(pyridin-4-yl)thiophene (12.64 g (42.2 mmol), prepared as described in 2))), and the resulting mixture was stirred at 240° C. for 2.5 hours. At the end of this time, the reaction mixture was cooled to room temperature and was filtered off. The filtrate was partitioned between ethyl acetate and a saturated aqueous solution of ammonium chloride. The organic layer was washed with water, dried over anhydrous magnesium sulfate and the solvent was removed by distillation under reduced pressure. The residue was purified by column chromatography through silica gel (eluent, hexane:ethyl acetate=1:1), to give the title compound (11.81 g) as a brown powder (yield quantitative).

$^1$H-Nuclear magnetic resonance spectrum (500 MHz, CDCl$_3$) δ ppm: 8.58–8.43 (2H, m), 7.38 (1H, d, J=5 Hz), 7.26 (2H, dd, J=9 Hz, 5 Hz), 7.19 (1H, d, J=5 Hz), 7.16 (2H, d, J=6 Hz), 7.01 (2H, t, J=9 Hz).

4) 4,5-Dibromo-2-(4-fluorophenyl)-3-(pyridin-4-yl)thiophene 2-(4-Fluorophenyl)-3-(pyridin-4-yl)thiophene (10.70 g (41.9 mmol), prepared as described in 3)) was dissolved in acetic acid (100 ml). To the solution was added bromine (8.6 ml, 167.6 mmol), and the resulting mixture was stirred at 60°

C. for 5 hours. The resulting mixture was cooled to room temperature, then made basic by the addition of an aqueous solution of 28% ammonia, and extracted with ethyl acetate. The organic layer was washed with water, dried over anhydrous magnesium sulfate and the solvent was removed by distillation under reduced pressure. The residue was purified by column chromatography through silica gel (eluent, hexane:ethyl acetate=5:2), to give the title compound (14.29 g) as a pale brown powder (yield 83%).

$^1$H-Nuclear magnetic resonance spectrum (500 MHz, CDCl$_3$) δ ppm: 8.61 (2H, d, J=6 Hz), 7.15 (2H, d, J=6 Hz), 7.09 (2H, dd, J=9 Hz, 5 Hz), 6.95 (2H, t, J=9 Hz).

5) 4-Bromo-2-(4-fluorophenyl)-3-(pyridin-4-yl) thiophene 4,5-Dibromo-2-(4-fluorophenyl)-3-(pyridin-4-yl) thiophene (13.88 g (33.6 mmol), prepared as described in 4)) was dissolved in tetrahydrofuran (140 ml). To the solution was added dropwise at −78° C. a solution of 1.59 M butyl lithium/hexane (23.3 ml, 37 mmol). The resulting mixture was stirred at −78° C. for 15 minutes. At the end of this time, water (24 ml) was added to the reaction mixture and it was allowed to warm to room temperature. The reaction mixture was partitioned between a saturated aqueous solution of ammonium chloride and ethyl acetate. The organic layer was washed with water, dried over anhydrous magnesium sulfate and the solvent was removed by distillation under reduced pressure. The residue (solid) was washed with diethyl ether, to give the title compound (11.20 g) as a pale brown powder (yield quantitative).

$^1$H-Nuclear magnetic resonance spectrum (500 MHz, CDCl$_3$) δ ppm: 8.60 (2H, d, J=6 Hz), 7.39 (1H, s), 7.16 (2H, d, J=6 Hz), 7.13 (2H, dd, J=9 Hz, 5 Hz), 6.95 (2H, t, J=9 Hz).

6) (S)-2-(4-Fluorophenyl)-4-(1,2,3,5,8,8a-hexahydroindolizin-7-yl)-3-(pyridin-4-yl)thiophene Following a procedure similar to that described in Example 2-2), but using 4-bromo-2-(4-fluorophenyl)-3-(pyridin-4-yl)thiophene prepared as described in 5) instead of 3-bromo-5-(4-fluorophenyl)-4-(pyridin-4-yl)pyrazole, and using (S)-1,2,3,5,6,7,8,8a-octahydroindolizin-7-one instead of (±)-1,2,3,5,6,7,8,8a-octahydroindolizin-7-one, the resulting product was subjected to a dehydration reaction as described in Example 3 and then treated by column chromatography through silica gel (eluent, ethyl acetate:methanol:isopropylamine=10:10:1), to give the title compound (Rf=0.50, 263 mg) as a brown amorphous solid (yield 23%).

$^1$H-Nuclear magnetic resonance spectrum (500 MHz, CDCl$_3$) δ ppm: 8.50 (2H, d, J=6 Hz), 7.24 (2H, dd, J=9 Hz, 5 Hz), 7.15 (2H, d, J=6 Hz), 7.02 (1H, s), 6.99 (2H, t, J=9 Hz), 6.20–6.16 (1H, m), 3.73–3.66 (1H, m), 3.25 (1H, dt, J=8 Hz, 2 Hz), 3.00–2.92 (1H, m), 2.77–2.68 (1H, m), 2.42–2.28 (2H, m), 2.22 (1H, dd, J=18 Hz, 9 Hz), 2.14–2.03 (1H, m), 1.98–1.88 (1H, m), 1.86–1.77 (1H, m), 1.63–1.50 (1H, m).

Example 9

(S)-2-(4-Fluorophenyl)-4-(1,2,3,5,6,8a-hexahydroindolizin-7-yl)-3-(pyridin-4-yl)thiophene (Exemplification Compound Number 11-1)

The title compound (Rf=0.40, 307 mg) was obtained as a brown amorphous solid (yield 27%) during the column chromatography through silica gel carried out in Example 8.

$^1$H-Nuclear magnetic resonance spectrum (500 MHz, CDCl$_3$) δ ppm: 8.50 (2H, d, J=6 Hz), 7.24 (2H, dd, J=9 Hz, 5 Hz), 7.15 (2H, d, J=6 Hz), 7.03 (1H, s), 6.99 (2H, t, J=9 Hz), 6.20–6.17 (1H, m), 3.43–3.37 (1H, m), 3.16 (1H, ddd, J=12 Hz, 5 Hz, 2 Hz), 2.99–2.92 (1H, m), 2.86 (1H, ddd, J=18 Hz, 7 Hz, 5 Hz), 2.74–2.63 (2H, m), 2.48–2.39 (1H, m), 2.12–2.03 (1H, m), 1.96–1.77 (2H, m), 1.66–1.55 (1H, m).

Example 10

(S)-5-(4-Chlorophenyl)-3-(1,2,3,5,8,8a-hexahydroindolizin-7-yl)-4-(pyridin-4-yl)pyrazole (Exemplification Compound Number 7-503)

1) 5-(4-Chlorophenyl)-4-(pyridin-4-yl)-1-(2-trimethylsilylethoxy)methylpyrazole

55% Sodium hydride (1.41 g, 32.1 mmol) was suspended in tetrahydrofuran (300 ml). To the suspension was added 5-(4-chlorophenyl)-4-(pyridin-4-yl)pyrazole (8.21 g, 32.1 mmol), and the resulting mixture was stirred at room temperature for 1 hour. To the resulting mixture was added (2-trimethylsilylethoxy)methyl chloride (5.68 ml, 32.1 mmol) dropwise under ice cooling, and the mixture was stirred at room temperature overnight. At the end of this time, water was added to the mixture and the mixture was extracted with ethyl acetate. The organic layer was washed with water, dried over anhydrous sodium sulfate and the solvent was removed by distillation under reduced pressure. The residue was purified by column chromatography through silica gel (eluent, hexane:ethyl acetate=3:1), to give the title compound (11.12 g) as a pale brown oil (yield 90%).

$^1$H-Nuclear magnetic resonance spectrum (500 MHz, CDCl$_3$) δ ppm: 8.45 (2H, d, J=6 Hz), 7.79 (1H, s), 7.42 (2H, d, J=8 Hz), 7.34 (2H, d, J=8 Hz), 7.07 (2H, d, J=6 Hz), 5.31 (2H, s), 3.69 (2H, t, J=8 Hz), 0.94 (2H, t, J=8 Hz), 0.00 (9H, s).

2) (S)-5-(4-Chlorophenyl)-3-(1,2,3,5,8,8a-hexahydroindolizin-7-yl)-4-(pyridin-4-yl)pyrazole Following a procedure similar to that described in Example 2-2), but using 5-(4-chlorophenyl)-4-(pyridin-4-yl)-1-(2-trimethylsilylethoxy)methylpyrazole prepared as described in 1) instead of 3-bromo-5-(4-fluorophenyl)-4-(pyridin-4-yl)pyrazole, and using (S)-1,2,3,5,6,7,8,8a-octahydroindolizin-7-one instead of (±)-1,2,3,5,6,7,8,8a-octahydroindolizin-7-one, the resulting product was subjected to a dehydration reaction as described in Example 3 and then treated by column chromatography through silica gel (eluent, ethyl acetate:methanol:isopropylamine=10:1:1), to give the title compound (Rf=0.50, 357 mg) as a pale brown powder (yield 4%).

m.p. 211–212° C.

$^1$H-Nuclear magnetic resonance spectrum (500 MHz, CDCl$_3$) δ ppm: 8.54 (2H, d, J=6 Hz), 7.26 (4H, s), 7.15 (2H, d, J=6 Hz), 5.98–5.86 (1H, m), 3.67–3.57 (1H, m), 3.33–3.23 (1H, m), 2.97–2.87 (1H, m), 2.40–2.08 (4H, m), 2.06–1.93 (2H, m), 1.86–1.72 (1H, m), 1.53–1.40 (1H, m).

Example 11

(S)-5-(4-Chlorophenyl)-3-(1,2,3,5,6,8a-hexahydroindolizin-7-yl)-4-(pyridin-4-yl)pyrazole (Exemplification Compound Number 1-1652)

The title compound (Rf=0.20, 454 mg) was obtained as a pale brown powder (yield 5%) during the column chromatography through silica gel carried out in Example 10.

m.p. 180–181° C.

$^1$H-Nuclear magnetic resonance spectrum (500 MHz, CDCl$_3$) δ ppm: 8.54 (2H, d, J=6 Hz), 7.26 (4H, s), 7.15 (2H, d, J=6 Hz), 5.95–5.85 (1H, m), 3.33–3.28 (1H, m), 3.00–2.90 (2H, m), 2.81–2.71 (2H, m), 2.40–2.30 (1H, m), 2.44–2.14 (1H, m), 2.03–1.86 (2H, m), 1.85–1.74 (1H, m), 1.54–1.44 (1H, m).

Example 12

5-(4-Fluorophenyl)-3-[(8aS)-2-methyl-1,2,3,5,6,8a-hexahydroindolizin-7-yl]-4-(pyridin-4-yl)pyrazole (Exemplification Compound Number 1-312)

Following a procedure similar to that described in Example 2-2), but using (8aS)-2-methyl-1,2,3,5,6,7,8,8a-octahydroindolizin-7-one instead of (±)-1,2,3,5,6,7,8,8a-octahydroindolizin-7-one, the resulting product was subjected to a dehydration reaction as described in Example 3 and then treated by column chromatography through silica gel (eluent, ethyl acetate:methanol:isopropylamine=10:1:1), to give the title compound (Rf=0.30, 190 mg) as a white powder (yield 4%).

m.p. 173–175° C. (with decomposition)

$^1$H-Nuclear magnetic resonance spectrum (400 MHz, CDCl$_3$) δ ppm: 8.54 (2H, d, J=6 Hz), 7.28 (2H, dd, J=9 Hz, 5 Hz), 7.15 (2H, d, J=6 Hz), 7.00 (2H, t, J=9 Hz), 5.82 (1H, s), 3.60–3.48 (1H, m), 3.07–2.98 (1H, m), 2.96–2.80 (2H, m), 2.49–2.00 (5H, m), 1.10–1.00 (1H, m), 1.07 (3H, d, J=7 Hz).

REFERENCE EXAMPLE

Reference Example 1

(±)-1,2,3,5,6,7,8,8a-octahydroindolizin-7-one 1) (±)-1-(t-Butoxycarbonyl)-N-methoxy-N-methylhomoprolinamide (±)-1-(t-Butoxycarbonyl)homoproline (5.03 g, 21.94 mmol) was dissolved in dichloromethane (100 ml). To the solution were added N-methoxy-N-methylhydroxylamine hydrochloride (2.57 g, 26.33 mmol), 1-ethyl-3-(3'-dimethylaminopropyl)carbodiimide (5.05 g, 26.33 mmol) and triethylamine (7.65 ml, 54.85 mmol), and the resulting mixture was stirred at room temperature for 1 hour. At the end of this time, the reaction mixture was partitioned with a saturated aqueous solution of ammonium chloride. The organic layer was washed with water, dried over anhydrous magnesium sulfate and the solvent was removed by distillation under reduced pressure. The residue was purified by column chromatography through silica gel (eluent, hexane:ethyl acetate=1:2), to give the title compound (4.00 g) as a colorless oil (yield 67%).

$^1$H-Nuclear magnetic resonance spectrum (400 MHz, CDCl$_3$) δ ppm: 4.28–4.12 (1H, br.s), 3.69 (3H, s), 3.45–3.25 (2H, br.s), 3.23–3.10 (3H, br.s), 3.09–2.83 (1H, m), 2.51–2.35 (1H, m), 2.14–1.98 (1H, m), 1.92–1.72 (3H, m), 1.46 (9H, s).

2) (±)-1-(t-Butoxycarbonyl)-2-(2-oxo-3-butenyl)pyrrolidine (±)-1-(t-Butoxycarbonyl)-N-methoxy-N-methylhomoprolinamide (4.00 g, 14.69 mmol), prepared as described in 1)) was dissolved in tetrahydrofuran (40 ml). To the solution was added a solution of 0.95 M vinylmagnesium bromide/tetrahydrofuran (23.2 ml, 22.04 mmol) at −78° C., whilst stirring, and the resulting mixture was stirred until the reaction mixture was allowed to warm to room temperature. At the end of this time, to the reaction mixture was added a saturated aqueous solution of ammonium chloride and the resulting mixture was extracted with ethyl acetate. The organic layer was washed with water, dried over anhydrous magnesium sulfate and the solvent was removed by distillation under reduced pressure. The residue was purified by column chromatography through silica gel (eluent, hexane:ethyl acetate=3:1), to give the title compound (1.48 g) as a colorless oil (yield 42%).

$^1$H-Nuclear magnetic resonance spectrum (500 MHz, CDCl$_3$) δ ppm: 6.42–6.20 (2H, m), 5.88 (1H, dd, J=9 Hz, 2 Hz), 4.24–4.14 (1H, m), 3.47–3.23 (2.5H, m), 3.15–3.04 (0.5H, m), 2.60–2.44 (1H, m), 2.11–1.97 (1H, m), 1.90–1.77 (2H, m), 1.74–1.64 (1H, m), 1.46 (9H, s).

3) (±)-1,2,3,5,6,7,8,8a-Octahydroindolizin-7-one (±)-1-(t-Butoxycarbonyl)-2-(2-oxo-3-butenyl)pyrrolidine (140 mg (0.59 mmol), prepared as described in 2)) was dissolved in tetrahydrofuran (2 ml). To the solution was added an aqueous solution of 1N hydrochloric acid (1.76 ml, 1.76 mmol), and the resulting mixture was stirred at 70° C. for 4 hours. At the end of this time, to the reaction mixture was added a saturated aqueous solution of sodium hydrogencarbonate and the resulting mixture was extracted with dichloromethane. The organic layer was washed with water, dried over anhydrous magnesium sulfate and the solvent was removed by distillation under reduced pressure, to give the title compound (76 mg) as a light brown oil (yield 93%).

$^1$H-Nuclear magnetic resonance spectrum (500 MHz, CDCl$_3$) δ ppm: 3.36–3.30 (1H, m), 3.19–3.13 (1H, m), 2.69–2.58 (1H, m), 2.55–2.50 (1H, m), 2.38–2.19 (5H, m), 2.02–1.93 (2H, m), 1.87–1.80 (1H, m), 1.59–1.50 (1H, m).

Reference Example 2

(±)-1,2,3,5,6,7,8,8a-octahydroindolizin-7-one 1) (±)-1-(t-Butoxycarbonyl)-2-[4-(p-toluenesulfonyl)-2-oxobutyl]pyrrolidine (±)-1-(t-Butoxycarbonyl)-2-(2-oxo-3-butenyl)pyrrolidine (206 mg (10.86 mmol), prepared as described in Reference example 1–2)) was dissolved in tetrahydrofuran (2 ml). To the solution was added 4-methylthiophenol (107 mg, 0.86 mmol), and the resulting mixture was stirred at room temperature for 2 hours. At the end of this time, the reaction mixture was concentrated by evaporation under reduced pressure, and the resulting residue was dissolved in dichloromethane (2 ml). To the resulting mixture was added 70 wt % m-chloroperbenzoic acid (468 mg, 1.894 mmol) by portions under ice cooling, and the resulting mixture was stirred at room temperature for 2 hours. To the mixture were added an aqueous solution of 10% sodium thiosulfate and a saturated aqueous solution of sodium hydrogencarbonate in that order, and the resulting mixture was stirred and extracted with dichloromethane. The organic layer was washed with water, dried over anhydrous magnesium sulfate and the solvent was removed by distillation under reduced pressure, to give the title compound (322 mg) as a colorless oil (yield 94%).

$^1$H-Nuclear magnetic resonance spectrum (500 MHz, CDCl$_3$) δ ppm: 7.78 (2H, d, J=8 Hz), 7.37 (2H, br.d, J=8 Hz), 4.14–4.04 (1H, m), 3.48–3.22 (4H, m), 3.00–2.77 (3H, m), 2.49–2.35 (4H, m), 2.10–1.98 (1H, m), 1.86–1.74 (2H, m), 1.43 (9H, br.s), 1.33–1.22 (1H, m).

2) (±)-1,2,3,5,6,7,8,8a-Octahydroindolizin-7-one (±)-1-(t-Butoxycarbonyl)-2-[4-(p-toluenesulfonyl)-2-oxobutyl]pyrrolidine (322 mg (0.814 mmol), prepared as described in 1)) was dissolved in methanol (3.2 ml). To the solution was added a solution of 4N hydrochloric acid/dioxane (0.61 ml, 2.44 mmol), and the resulting mixture was stirred at 50° C. for 30 minutes. At the end of this time, the reaction mixture was concentrated by evaporation under reduced pressure to remove solvents and any excess of hydrochloric acid. To the residue was added a saturated aqueous solution of sodium hydrogencarbonate and this was extracted with dichloromethane. The organic layer was washed with water, dried over anhydrous magnesium sulfate and the solvent was removed by distillation under reduced pressure. The residue was purified by column chromatography through alumina (eluent, ethyl acetate), to give the title compound (74 mg) as a light brown oil (yield 65%).

The oil was determined as (±)-1,2,3,5,6,7,8,8a-octahydroindolizin-7-one by
$^1$H-nuclear magnetic resonance spectrum.

Reference Example 3

(S)-1,2,3,5,6,7,8,8a-octahydroindolizin-7-one 1) (S)-1-Methylmalonyl homoproline

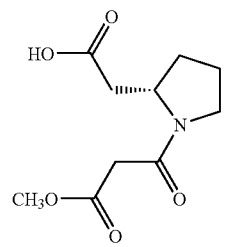

(S)-Homoproline (1.00 g, 7.74 mmol) was suspended in dichloromethane (30 ml). To the suspension was added triethylamine (1.08 ml, 7.74 mmol), and then methylmalonyl chloride (0.83 ml, 7.74 mmol) was added dropwise under ice cooling. The resulting mixture was stirred under ice cooling for 15 minutes and a further 30 minutes at room temperature. The reaction mixture was partitioned with a saturated solution of sodium hydrogencarbonate. A solution of concentrated hydrogen chloride was added to the aqueous layer to adjust the pH to 2, and this was then extracted with a mixed solution of dichloromethane and isopropanol (4:1). The organic layer was washed with water, dried over anhydrous magnesium sulfate and the solvent was removed by distillation under reduced pressure. The resulting residue was washed with diisopropyl ether, to give the title compound (1.42 g) as a pale yellow powder (yield 80%).

m.p. 142–144° C.

$^1$H-Nuclear magnetic resonance spectrum (500 MHz, CDCl$_3$) δ ppm: 4.40–4.38 (0.8H, m), 4.35–4.29 (0.2H, m), 3.76 (2.4H, s), 3.57–3.43 (3H, m), 3.42 (1.6H, s), 3.00 (0.8H, dd, J=16 Hz, 4 Hz), 2.65 (0.2H, dd, J=16 Hz, 4 Hz), 2.52 (0.2H, dd, J=16 Hz, 8 Hz), 2.46 (0.8H, dd, J=16 Hz, 8 Hz), 2.20–2.08 (1H, m), 2.07–1.92 (2H, m), 1.90–1.83 (1H, m).

2) (8aS)-6-Methoxycarbonyl-1,2,3,5,6,7,8,8a-octahydroindolizin-5,7-dione

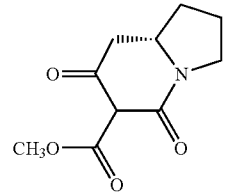

(S)-1-Methylmalonyl homoproline (200 mg (0.87 mmol), prepared as described in 1)) was suspended in tetrahydrofuran (6 ml). To the suspension was added carbonyldiimidazole (156 mg, 0.96 mmol), and the resulting mixture was stirred at room temperature for 30 minutes. To the mixture was added 1,8-diazabicyclo[5.4.0]-7-undecene (143 μl, 0.96 mmol), and the resulting mixture was stirred at room temperature for 1 hour. The reaction mixture was evaporated by distillation under reduced pressure, and the residue was partitioned between dichloromethane and an aqueous solution of 1N hydrochloric acid. The organic layer was washed with water, dried over anhydrous magnesium sulfate and the solvent was removed by distillation under reduced pressure, to give the title compound (183 mg) as a pale yellow powder (yield quantitative).

$^1$H-Nuclear magnetic resonance spectrum (500 MHz, CDCl$_3$) δ ppm: 3.90 (3H, s), 3.76–3.69 (1H, m), 3.67–3.60 (1H, m), 3.53–3.44 (1H, m), 2.68 (1H, dd, J=17 Hz, 4 Hz), 2.54 (1H, dd, J=17 Hz, 13 Hz), 2.30–2.23 (1H, m), 2.08–2.00 (1H, m), 1.88–1.76 (1H, m), 1.70–1.56 (2H, m).

3) (S)-1,2,3,5,6,7,8,8a-Octahydroindolizin-5,7-dione

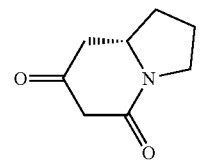

(8aS)-6-Methoxycarbonyl-1,2,3,5,6,7,8,8a-octahydroindolizin-5,7-dione (183 mg (0.87 mmol), prepared as described in 2)) was dissolved in an aqueous solution of 10% acetic acid (2 ml). The resulting mixture was stirred at 110° C. for 30 minutes, and then cooled to room temperature. To the reaction mixture was added a saturated aqueous solution of sodium hydrogencarbonate and the mixture was made alkaline. The mixture was extracted with a solution of dichloromethane and isopropanol (4:1). The organic layer was washed with water, dried over anhydrous magnesium sulfate and the solvent was removed by distillation under reduced pressure, to give the title compound (117 mg) as a pale brown oil (yield 87%).

$^1$H-Nuclear magnetic resonance spectrum (500 MHz, CDCl$_3$) δ ppm: 3.89–3.81 (1H, m), 3.72–3.64 (1H, m), 3.60–3.53 (1H, m), 3.27 (2H, dd, J=24 Hz, 20 Hz), 2.85 (1H, dd, J=17 Hz, 3 Hz), 2.36–2.30 (1H, m), 2.29 (1H, dd, J=17 Hz, 12 Hz), 2.13–2.04 (1H, m), 1.97–1.86 (1H, m), 1.72–1.62 (1H, m).-

4) (S)-7-(1-Pyrrolidinyl)-1,2,3,5,8,8a-hexahydroindolizin-5-one

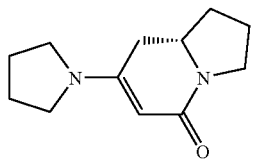

(S)-1,2,3,5,6,7,8,8a-octahydroindolizin-5,7-dione (117 mg (0.76 mmol), prepared as described in 3)) was dissolved in ethanol (1.2 ml). To the solution was added pyrrolidine (128 μl, 1.53 mmol), and the resulting mixture was allowed to stand at room temperature for 5 minutes. At the end of this time, the reaction mixture was concentrated by distillation under reduced pressure to remove solvents and any excess of pyrrolidine, to give the title compound (160 mg) as a light yellow powder (yield quantitative).

$^1$H-Nuclear magnetic resonance spectrum (500 MHz, CDCl$_3$) δ ppm: 4.60 (1H, s), 3.70–3.58 (2H, m), 3.50–3.41 (1H, m), 3.37–3.11 (4H, br.m), 2.62 (1H, dd, J=16 Hz, 5 Hz), 2.30–2.14 (2H, m), 2.05–1.57 (7H, m).

In the HPLC measurement of the above powder, R-isomer was not detected under the conditions described below, then it was determined that the optical purity of the powder was more than 99% ee.

HPLC conditions:
Column: CHIRALPAK OD (a trade mark for a product of Daiseru Chemical Industry Co., Ltd., column diameter 0.46 cm, length 25 cm)
Mobile phase: n-hexane/isopropanol=90/10
Flow rate: 1.0 ml/minute
Temperature: 40° C.
Detection: 254 nm (UV)
Retention time: S-isomer 27.23 minutes
R-isomer 32.30 minutes 5) (S)-1,2,3,5,6,7,8,8a-Octahydroindolizin-7-one

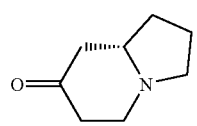

(S)-7-(1-Pyrrolidinyl)-1,2,3,5,8,8a-hexahydroindolizin-5-one (645 mg (3.13 mmol), prepared as described in 4)) was dissolved in tetrahydrofuran (10 ml). To the solution was added lithium aluminum hydride (356 mg, 9.39 mmol) under ice cooling, and the resulting mixture was stirred at room temperature overnight. To the reaction mixture were added an aqueous solution of 1N sodium hydroxide (1.44 ml) and ethanol, and insoluble material was filtered off. The filtrate was concentrated by distillation under reduced pressure and the resulting residue was purified by column chromatography through alumina (eluent, ethyl acetate), to give the title compound (236 mg) as a light brown oil (yield 54%).

b.p. 75–78° C./6 mmHg $^1$H-Nuclear magnetic resonance spectrum (500 MHz, CDCl$_3$) δ ppm: 3.36–3.30 (1H, m), 3.19–3.13 (1H, m), 2.67–2.58 (1H, m), 2.55–2.50 (1H, m), 2.38–2.19 (5H, m), 2.02–1.93 (2H, m), 1.87–1.80 (1H, m), 1.59–1.50 (1H, m).

By the $^1$H-Nuclear magnetic resonance spectrum measurement (described in W. H. Pirkle and D. J. Hoover, Top. Stereochem., 13, 263 (1982) fully) using shift reagents, R-isomer was not detected from the above powder, then it was determined that the optical purity of the powder was more than 99% ee.

Reference Example 4

(8aS)-2-Methyl-1,2,3,5,6,7,8,8a-octahydroindolizin-7-one 1) (S)-1-Benzyloxycarbonyl-4-methylideneproline methyl ester Potassium t-butoxide (1.41 g, 12.6 mmol) was suspended in diethyl ether (100 ml). To the suspension was added methyltriphenylphosphonium bromide (4.80 g, 13.4 mmol), and the resulting mixture was stirred at 5° C. for 15 minutes. To the mixture was added (S)-1-benzyloxycarbonyl-4-oxoproline methyl ester (2.50 g, 9.0 mmol) in diethyl ether (30 ml), and the resulting mixture was stirred at 35° C. for 3 hours. At the end of this time, the reaction mixture was added to a saturated solution of ammonium chloride (50 ml) under ice cooling, and then partitioned. The organic layer was washed with water, dried over anhydrous magnesium sulfate and the solvent was removed by distillation under reduced pressure. The residue was purified by column chromatography through silica gel (eluent, ethyl acetate:hexane=1:3), to give the title compound (1.80 g) as a pale yellow oil (yield 72%).

$^1$H-Nuclear magnetic resonance spectrum (400 MHz, CDCl$_3$) δ ppm: 7.40–7.23 (5H, m), 5.21–4.95 (4H, m), 4.60–4.50 (1H, m), 4.20–4.09 (2H, m), 3.74 (1.5H, s), 3.60 (1.5H, s), 3.07–2.91 (1H, m), 2.65 (1H, d, J=16 Hz).

2) (2S)-4-methylproline methyl ester (S)-1-Benzyloxycarbonyl-4-methylideneproline methyl ester (1.80 g (6.5 mmol), prepared as described in 1)) was dissolved in methanol (50 ml). The resulting solution was stirred at room temperature in an atmosphere of hydrogen in the presence of 10% palladium on charcoal (180 mg) for 2 hours. At the end of this time, the reaction mixture was filtered to remove the catalyst and the filtrate was concentrated by evaporation under reduced pressure, to give the title compound (0.93 g) as a pale yellow oil (yield quantitative).

$^1$H-Nuclear magnetic resonance spectrum (400 MHz, CDCl$_3$) δ ppm: 3.82 (1H, t, J=8 Hz), 3.74 (3H, s), 3.08 (1H, dd, J=10 Hz, 7 Hz), 2.60 (1H, dd, J=10 Hz, 8 Hz), 2.33 (1H, dt, J=12 Hz, 8 Hz), 2.28–2.15 (1H, m), 1.44–1.37 (1H, m), 1.27 (1H, dd, J=14 Hz, 7 Hz), 1.02 (3H, d, J=7 Hz).

3) (2S)-1-Benzyloxycarbonyl-2-hydroxymethyl-4-methylpyrrolidine (2S)-4-Methylproline methyl ester (0.93 g (6.5 mmol), prepared as described in 2)) was dissolved in toluene (20 ml). To the solution were added an aqueous solution (20 ml) of sodium hydrogencarbonate (1.89 g, 22.5 mmol) and benzyl chloroformate (1.54 ml, 10.8 mmol), and the resulting mixture was stirred at room temperature overnight. The reaction mixture was extracted with ethyl acetate. The organic layer was washed with water and the solvent was removed by distillation under reduced pressure, to give (2S)-1-benzyloxycarbonyl-4-methylproline methyl ester (1.78 g) as a pale yellow oil (yield 99%). All of the compound obtained above was dissolved in tetrahydrofuran (30 ml). To the resulting solution was added lithium borohydride (0.28 g, 13 mmol) in three portions, and the resulting mixture was stirred at room temperature. Ice was added to the mixture and the mixture was stirred for 1 hour. The reaction mixture was extracted with ethyl acetate. The organic layer was washed with water, dried over anhydrous magnesium sulfate and the solvent was removed by distillation under reduced pressure. The residue was purified by column chromatography through silica gel (eluent, ethyl acetate:hexane=2:5), to give the title compound (1.07 g) as a pale yellow oil (yield 66%).

$^1$H-Nuclear magnetic resonance spectrum (400 MHz, CDCl$_3$) δ ppm: 7.42–7.29 (5H, m), 5.14 (2H, br.s), 5.07–4.90 (1H, m), 4.08–3.87 (1H, m), 3.86–3.40 (4H, m), 2.90–2.65 (1H, m), 2.40–2.05 (2H, m), 1.02 (3H, d, J=6 Hz).

4) (2S)-1-Benzyloxycarbonyl-2-cyanomethyl-4-methylpyrrolidine (2S)-1-Benzyloxycarbonyl-2-hydroxymethyl-4-methylpyrrolidine (1.07 g (4.29 mmol), prepared as described in 3)) was dissolved in dichloromethane (15 ml). To the solution were added triethylamine (0.68 ml, 4.90 mmol), and then methanesulfonyl chloride (0.35 ml, 4.46 mmol) under ice cooling. The resulting mixture was stirred at the same temperature for 30 minutes. To the reaction mixture was added a saturated aqueous solution of sodium hydrogencarbonate and the resulting mixture was extracted with dichloromethane. The organic layer was washed with water, dried over anhydrous magnesium sulfate and the solvent was removed by distillation under reduced pressure, to give a brown oil (1.26 g, mesylate). The oil was dissolved in dimethyl sulfoxide (15 ml). To the solution was added sodium cyanide (0.19 g, 3.87 mmol), and the resulting mixture was stirred at 100° C. for 30 minutes. To the reaction mixture was added a saturated aqueous solution of sodium hydrogencarbonate and this was extracted with dichloromethane. The organic layer was washed with water, dried over anhydrous magnesium sulfate and the solvent was removed by distillation under reduced pressure, to give the title compound (0.77 g) as a pale brown oil (yield 70%).

$^1$H-Nuclear magnetic resonance spectrum (400 MHz, CDCl$_3$) δ ppm: 7.50–7.30 (5H, m), 5.25–5.05 (2H, m), 4.20–3.78 (1.8H, m), 3.70–3.62 (0.2H, m), 3.15–2.88 (1.4H, m), 2.84–2.67 (1.2H, m), 2.62–2.50 (0.4H, m), 2.45–2.30 (0.8H, m), 2.23–2.00 (1H, m), 1.89–1.77 (0.2H, m), 1.60–1.49 (1H, m), 1.10–1.03 (3H, m).

5) (2S)-4-Methylhomoproline hydrochloride (2S)-1-Benzyloxycarbonyl-2-cyanomethyl-4-methylpyrrolidine (17.70 g (68.5 mmol), prepared as described in 4)) was dissolved in concentrated hydrochloric acid (100 ml), and the resulting solution was stirred at 80° C. overnight. The resulting reaction mixture was cooled to room temperature and the solvent was removed by distillation under reduced pressure. The resulting solid was washed with acetone and dissolved in ethanol (50 ml). The insoluble material was filtered off. The filtrate was concentrated by evaporation under reduced pressure, to give the title compound (11.44 g) as a white powder (yield 93%).

$^1$H-Nuclear magnetic resonance spectrum (400 MHz, DMSO-d$_6$) δ ppm: 3.90–3.60 (1H, m), 3.40–3.20 (1H, m), 2.90–2.63 (3H, m), 2.42–2.16 (2H, m), 1.29–1.13 (1H, m), 1.06–0.95 (3H, m), 6) (8aS)-2-Methyl-1,2,3,5,6,7,8,8a-octahydroindolizin-7-one Following a procedure similar to that described in Reference example 3-1), but using (2S)-4-Methylhomoproline hydrochloride prepared as described in 5) instead of (S)-homoproline, and using double the molar quantity of triethylamine, then the resulting product was subjected to procedures similar to that described in Reference example 3-2), 3), 4) and 5) in that order, to give the title compound as a yellow oil (yield 61%).

$^1$H-Nuclear magnetic resonance spectrum (400 MHz, CDCl$_3$) δ ppm: 3.34–3.22 (1.2H, m), 2.77 (0.8H, dd, J=9 Hz, 3 Hz), 2.68–2.55 (1H, m), 2.51–2.43 (2H, m), 2.39–2.24 (5H, m), 2.20–2.10 (1H, m), 1.87–1.75 (0.8H, m), 1.57–1.51 (0.2H, m), 1.14 (2.4H, d, J=7 Hz), 1.04 (0.6H, d, J=7 Hz).

FORMULATION EXAMPLES

The formulations containing a compound represented by the general formula (I) defined above, or a pharmacologically acceptable salt, ester or other derivative thereof of the present invention can be prepared by methods such as the following.

Formulation Example 1

Powder 5 g of the compound of Example 1, 895 g of lactose and 100 g of corn starch are mixed in a blender to provide the desired powder.

Formulation Example 2

Granules 5 g of the compound of Example 2, 865 g of lactose and 100 g of low-substituted hydroxypropylcellulose are mixed, 300 g of a 10% aqueous hydroxypropyl cellulose solution are added to the resulting mixture, and this is then kneaded. The product thus obtained is then granulated using an extrusion granulating machine and dried to provide the desired granules.

Formulation Example 3

Capsules 5 g of the compound of Example 3, 115 g of lactose, 58 g of corn starch and 2 g of magnesium stearate are mixed using a V-shaped mixer, No. 3 capsules are chosen and then each of said No. 3 capsules is filled with 180 mg of the resulting mixture to provide the desired capsules.

Formulation Example 4

Tablets 5 g of the compound of Example 4, 90 g of lactose, 34 g of corn starch, 20 g of crystalline cellulose and 1 g of magnesium stearate are mixed in a blender, and the resulting mixture is then formed into tablets with a tablet machine to provide the desired tablets.

TEST EXAMPLES

Test Example 1

Inhibition of the Production of the Cytokines IL-1β and TNFα In Vitro in Human Whole Blood This test was performed according to the method of Hartman, et al. [D. A. Hartman, S. J. Ochalski and R. P. Carlson; The effects of anti-inflammatory and antiallergic drugs on cytokine release after stimulation of human whole blood by lipopolysaccharide and zymosan A: Inflamm. Res., 44, 269 (1995)].

Peripheral blood samples were collected in the presence of heparin from healthy adult volunteers. 1000 µl of whole blood were added to an Eppendorf tube to which 2 µl of a dimethyl sulfoxide solution of the test compound had been added in advance, after which 10 µl of lipopolysaccharide (E. coli 026: B6 origin, Difco) were added as a stimulant (final concentration of said lipopolysaccharide: 10 µg/ml). This was mixed well and then incubated for 6 hours at 37° C. in the presence of 5% $CO_2$. At the end of the incubation, the mixture was cooled to 4° C. to stop the reaction, followed immediately by centrifuging for 5 minutes at 14,000 rpm to separate and collect the supernatant plasma. The IL-1β and TNFα produced and released into the plasma were measured using commercially available enzyme immunoassay (ELISA) kits [Cayman (IL-1β) and Genzyme (TNFα)]. The procedure was also repeated in the absence of test compound. The inhibitory effect [$IC_{50}$ (µM)] on the production of IL-1β and TNFα was determined by the method of least squares from the amounts of the cytokines produced in the presence and absence of the test compound. The results for the inhibitory effect on TNFα production are as shown in Table 14 below.

TABLE 14

Inhibitory Effect on TNFα Production and Inhibitory Effect on IL-1β Production

| Test compound | Inhibitory Effect on TNFα Production $IC_{50}$ [µM] | Inhibitory Effect on IL-1β Production $IC_{50}$ [µM] |
|---|---|---|
| Compound of Example 2 | 0.070 | 0.035 |
| Compound of Example 12 | 0.0026 | — |

As shown in Tables 14 above, in this test, the tested compounds of the present invention showed excellent inhibitory activity against the production of cytokines.

Test Example 2

Inhibition of the Production of TNFα In Vivo

This test was performed according to the method of Ochalski, et al. [S. J. Ochalski, D. A. Hartman, M. T. Belfast, T. L. Walter, K. B. Glaser and R. P. Carlson; Inhibition of endotoxin-induced hypothermia and serum TNF-α levels in CD-1 mice by various pharmacological agents: Agents Actions 39, C52-C54 (1993)].

The production of TNFα was induced in mice by the intravenous injection of lipopolysaccharide (E. coli O26: B6 origin, Difco) which was prepared to a concentration of 0.045 mg/ml using physiological saline. The saline preparation of lipopolysaccharide was administered at the rate of 10 ml/1 kg of body weight into the caudal vein of Balb/c mice (males, age 5–7 weeks, body weight: approx. 22 g, Japan Charles River) which had been fasted overnight starting on the day before the experiment. One hour after administration, the mice were laparotomized under ether anaesthesia and blood was collected from the abdominal vena cava. Blood collection was performed using a 1 ml volume disposable syringe equipped with a 23G needle which had been moistened with heparin on the inside wall. Following blood collection, the blood was immediately transferred to a 1.5 ml volume Eppendorf tube and centrifuged at 4° C. and 14,000 rpm to separate the plasma. This plasma was then stored at −20° C. until measurement of TNFα. The measurement of the amount of TNFα was performed with a commercially available enzyme immunoassay (ELISA) kit (Mouse TNFα ELISA KIT, Genzyme).

To determine the inhibitory activity of the test compounds, each test compound was suspended in a 0.5% tragacanth solution and then administered orally to the Balb/c mice at the rate of 10 ml/1 kg of body weight 30 minutes before injection of lipopolysaccharide. A minimum of 3 dose levels of the test compound was administered to groups of 5 test mice for each test compound. The inhibitory rate relative to the control group was calculated for each dose level.

In this test, the tested compounds of the present invention showed excellent inhibitory activity against the production of TNFα in vivo.

Test Example 3

Inhibition of the Production of IL-1β In Vivo

This test was performed according to the method of Griffiths, et al. [Richard J. Griffiths, Ethan J. Stam, James T. Downs and Ivan G. Otterness; ATP Induces the Release of IL-1 from LPS-Primed Cells In Vivo: J. Immunol., 154, 2821–2828 (1995)].

The production of IL-1β was induced in mice by the intraperitoneal injection of lipopolysaccharide followed by the intraperitoneal injection of adenosine triphosphate (ATP). This was achieved by first administering a solution of lipopolysaccharide (E. coli 026: B6 origin, Difco), which had been prepared to a concentration of 0.0045 mg/ml using physiological saline, at the rate of 10 ml of said saline solution/1 kg of body weight into the peritoneal cavity of Balb/c mice (males, age 5–7 weeks, body weight: approx. 22 g, Japan Charles River) which had been fasted overnight starting on the day before the experiment. Two hours later, 0.5 ml of ATP, which had been prepared to a concentration of 6.03 mg/ml using physiological saline, were administered into the peritoneal cavity. 0.5 hours after the administration of ATP, the mice were sacrificed by suffocation using dry ice followed immediately by intraperitoneal injection of 3 ml of washing phosphate buffer solution [containing heparin (10 U/ml), p-toluenesulfonyl fluoride (0.25 mM), leupepsin (1 µg/ml), pepstatin (1 µg/ml) and EDTA (1 mM)] to wash the peritoneal cavity. A 1 ml volume disposable syringe equipped with a 21G needle was then used to recover the washing liquid. After the recovery, the washing liquid from the peritoneal cavity was immediately transferred to a 1.5 ml volume Eppendorf tube and centrifuged at 4° C. and 7,500 rpm to separate the supernatant. This supernatant was then stored at −20° C. until measurement of IL-1β.

The measurement of the amount of IL-1β was performed with an enzyme immunoassay (ELISA) kit (Mouse IL-1β ELISA KIT, Genzyme).

To determine the inhibitory activity of the test compounds, each test compound was suspended in a 0.5% tragacanth solution and then administered orally to the Balb/c mice at the rate of 10 ml/1 kg of body weight 30 minutes before injection of lipopolysaccharide.

A minimum of 3 dose levels of the test compound was administered to groups of 5 test mice for each test compound. The mean inhibitory rate relative to the control group was calculated for each dose level.

In this test, the compounds of the present invention demonstrated an excellent inhibitory effect against the production of IL-1β in vivo.

Test Example 4

Activity in Preventing the Development of Adjuvant-Induced Arthritis In Vivo

The test was performed according to the method described by Winder et al. (Arthritis Rheum., 12, 472–482, 1969).

Heat-killed dried *Mycobacterium butyricum* (Difco Laboratories, Lot 679123) was ground on an agate mortar, and was then suspended in dry-sterilised liquid paraffin (first grade, Wako Pure Chemical Industries, Ltd.) to make a 2 mg/ml suspension. The resulting suspension was then sonicated and used as an adjuvant. Arthritis was induced by the intradermal injection of the adjuvant (100 μg of heat killed dried bacterium/0.05 ml of paraffin/paw) into the heel of the right hind paw of a Lewis rat (male, age 9 weeks, 190 g, Japan Charles River). The test compounds, which had been suspended in a 0.5% aqueous sodium carboxymethyl cellulose solution (CMC, Daiichi Pure Chemicals, Co., Ltd.), were administered orally at the rate of 5 ml/kg once a day from the day of injection of the adjuvant (day 0) to day 20.

The volumes of the right hind paw (adjuvant-injected paw) and left hind paw (non-injected paw) were measured on days 3, 5, 7, 10, 13, 15, 18 and 21 using a Plethysmometer™ (Ugo Basile), the hind paws being soaked from the toe to the hairline in the bath of the Plethysmometer™. The volumes of the swollen feet (adjuvant-injected right hind foot volume−non-injected left hind foot volume) were calculated. The percent inhibition of swelling of the injected foot of the treated animals as compared to that of the control animals on day 21 was calculated as follows.

Inhibition (%)={1−(swollen foot volume of compound-treated animals)/(swollen foot volume of control animals)}×100

In this test, the tested compounds of the present invention showed excellent activity in preventing the development of adjuvant-induced arthritis.

Test Example 5

Activity in Preventing the Development of Arthritis Induced by Anti-Collagen Antibody In Vivo In this test, an anti-collagen antibody-induced mouse arthritis model was employed.

0.5 ml of an anti-collagen antibody solution (4 mg/ml, Arthritogenic mAb Cocktail: product of Immuno-Biological Laboratories Co., Ltd) were injected into the caudal vein of Balb/c mice (males, age 5–6 weeks old, Japan Charles River). Three days after injection, 0.1 ml of a lipopolysaccharide solution (0.5 mg/ml, Arthritogenic mAb Cocktail: product of Immuno-Biological Laboratories Co., Ltd) were administered to the mice by intraperitoneal injection.

The test compounds, which had been suspended in 0.5% tragacanth were administered orally to the test animals at the rate of 10 ml/1 kg of body weight once per day for 7 days from the day when the anti-collagen antibody was administered. To the mice of the control group, 0.5% tragacanth solution was administered instead of solutions of the test compounds.

After the administration of the test compounds (or 0.5% tragacanth solution), the degree of edema in the 4 paws of each test mouse was scored according to the following basis:
 0: normal (edema is not observed);
 1: edema is observed in one of the five toes;
 2: edema is observed in two or more of the five toes;
 3: the whole of the paw is swollen.

The degree of arthritis in the test mouse was evaluated by the total of the edema scores in the 4 paws. The rate of suppression was calculated from the degrees of arthritis of the control animals and of the animals treated with the test compounds.

From the rates of suppression, the activity of suppression was judged.

In this test, the tested compounds of the present invention showed excellent activity in preventing the development of arthritis induced by anti-collagen antibody.

Test Example 6

Activity in Treating Arthritis Induced by Anti-Collagen Antibody In Vivo

In this test, an anti-collagen antibody-induced mouse arthritis model was employed.

0.5 ml of an anti-collagen antibody solution (4 mg/ml, Arthritogenic mAb Cocktail: product of Immuno-Biological Laboratories Co., Ltd) were injected into the caudal vein of Balb/c mice (males, age 5–6 weeks old, Japan Charles River). Three days after injection, 0.1 ml of a lipopolysaccharide solution (0.5 mg/ml, Arthritogenic mAb Cocktail: product of Immuno-Biological Laboratories Co., Ltd) were administered to the mice by intraperitoneal injection.

7 days after the administration of the anti-collagen antibody solution, the degree of edema in the 4 paws of each test mouse was scored according to the basis as shown in Test Example 5 above.

Those mice in which edema in both the hind paws had been scored as "3" were selected. Test compounds, which had been suspended in 0.5% tragacanth solution, were administered orally to the selected mice at the rate of 10 ml/kg of body weight once per day for 3 days. To the mice of the control group, 0.5% tragacanth solution was administered instead of solutions of the test compounds.

After the administration of the test compounds (or 0.5% tragacanth solution), the degree of arthritis in each test mouse was evaluated in the same manner as described in Test Example 5. The rates of treatment of arthritis induced by anti-collagen antibody were calculated from the degrees of arthritis of the control animals and of the compound-treated animals.

From the rates of suppression, the activity of suppression was judged.

In this test, the tested compounds of the present invention showed excellent activity in treating arthritis induced by anti-collagen antibody.

The compounds of the present invention exhibit excellent activity in inhibiting the production of inflammatory cytokines, particularly in inhibiting the production of IL-1β and TNFα. Furthermore, the compounds of the present invention have satisfactory oral absorptivity and a low level of toxicity.

Consequently, the compounds of the present invention are useful as pharmaceutical agents. They can, for example, be used as an analgesic, an anti-inflammatory agent and an antiviral agent as well as an agent for use in the prophylaxis and treatment of chronic rheumatoid arthritis, osteoarthritis, allergic diseases, asthma, septicaemia, psoriasis, osteoporosis, autoimmune diseases (e.g., systemic lupus erythematosus, ulcerative colitis, Crohn's disease and the like), diabetes, glomerular nephritis, hepatitis, cancer, ischemic heart disease, Alzheimer's disease and arteriosclerosis. Of these applications, the compounds of the present invention are particularly useful as an analgesic and an anti-inflammatory agent and as an agent for the prophlaxis and treatment of chronic rheumatoid arthritis, osteoarthritis, allergic diseases, septicaemia, psoriasis, osteoporosis, ulcerative colitis, diabetes, hepatitis and arteriosclerosis.

What is claimed is:

1. A compound of the formula (I) below, or a pharmacologically acceptable salt thereof:

(I)

wherein:
  A represents a pyrazole ring having one substituent $R^4$;
  $R^1$ represents a phenyl group, a 4-fluorophenyl group, a 3-fluorophenyl group, a 3-chlorophenyl group, a 3,4-difluorophenyl group, a 3,4,5-trifluorophenyl group, a 3-chloro-4-fluorophenyl group, a 3-difluoromethoxyphenyl group or a 3-trifluoromethylphenyl group;
  $R^2$ represents an unsubstituted 4-pyridyl group, an unsubstituted 4-pyrimidinyl group, a 4-pyridyl group which is substituted at the 2-position thereof with one substituent selected from the group consisting of methoxy, amino, methylamino, benzylamino and a-methylbenzylamino, or a 4-pyrimidinyl group which is substituted a the 2-position thereof with one substituent selected from the group consisting of methoxy, amino, methylamino, benzylamino and α-methylbenzylamino; and
  $R^3$ represents a group of formula (IIa), (IIb) or (IIc) shown below:

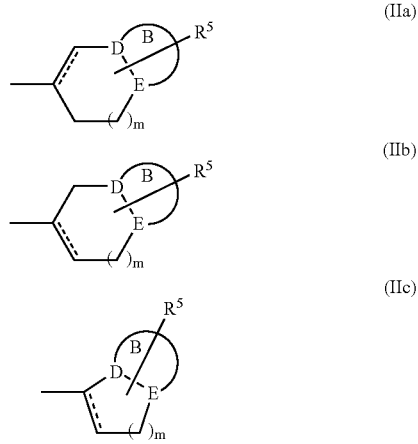

wherein
  a bond including a dotted line represents a single bond or a double bond,
  m represents 1 or 2,
  $R^5$ represents one substituent which is independently selected from the group consisting of a hydrogen atom, a methoxy group, a methyl group, an ethyl group, a propyl group and a phenyl group,
  one of D and E represents a nitrogen atom and the other represents a group of a formula $>C(R^6)$—, wherein $R^6$ is a substituent selected from the group consisting of a hydrogen atom, a Substituent group α and a Substituent group β, and
  B represents a, pyrrolidine ring or a pyrroline ring, and
  $R^4$ represents a hydrogen atom, a lower alkyl group, a halogeno lower alkyl group, or a phenyl group substituted with one or more substituents selected from the group consisting of Substituent group α, Substituent group β and Substituent group γ,
PROVIDED THAT said substituents $R^1$ and $R^3$ are bonded to the two atoms of said cyclic group A which are adjacent to the atom of the cyclic group A to which said substituent $R^2$ is bonded;
  Substituent group α is selected from the group consisting of hydroxyl groups, nitro groups, cyano groups, halogen atoms, lower alkoxy groups, halogeno lower alkoxy groups, lower alkylthio groups, halogeno lower alkylthio groups and groups of a formula $—NR^aR^b$, wherein $R^a$ and $R^b$ are the same or different from each other and each represents a hydrogen atom, a lower alkyl group, a lower alkenyl group, a lower alkynyl group, an aralkyl group or a lower alkylsulfonyl group, or $R^a$ and $R^b$, taken together with the nitrogen atom to which they are attached, form a heterocyclyl group;
  Substituent group β is selected from the group consisting of unsubstituted lower alkyl groups, unsubstituted lower alkenyl groups, unsubstituted lower alkynyl groups, aralkyl groups, cycloalkyl groups, lower alkyl groups which are substituted with one or more substituents from Substituent group α, lower alkenyl groups which are substituted with one or more substituents from Substituent group α, and lower alkynyl groups which are substituted with one or more substituents from Substituent group α;
  Substituents group γ is selected from the group consisting of oxo groups; hydroxyimino groups; lower alkoxyimino groups; lower alkylene groups; lower alkylenedioxy groups; lower alkylsulfinyl groups; lower alkylsulfonyl groups; unsubstituted aryl groups; aryl groups which are substituted with one or more substituents selected from the group consisting of Substituent group α and Substituent group β; unsubstituted aryloxy groups; aryloxy groups which are substituted with one or more substituents selected from the group consisting of Substituent group α and Substituent group β; lower alkylidenyl groups and aralkylidenyl groups.

2. The compound according to claim 1, or a pharmacologically acceptable salt thereof, wherein $R^3$ is a group of the formula (IIa).

3. The compound according to claim 1, or a pharmacologically acceptable salt thereof, wherein m is 1.

4. The compound according to claim 1, or a pharmacologically acceptable salt thereof, wherein the compound is 3-(1,2,3,5,6,8a-hexahydroindolizin-7-yl)-5-phenyl-4-(pyridin-4-yl)-pyrazole.

5. The compound according to claim 1, or a pharmacologically acceptable salt thereof, wherein the compound is 5-(3-fluorophenyl)-3-(1,2,3,5,6,8a-hexahydroindolizin-7-yl)-4-(pyridin-4-yl)pyrazole.

6. The compound according to claim 1, or a pharmacologically acceptable salt thereof, wherein the compound is 5-(4-fluorophenyl)-3-(1,2,3,5,6,8a-hexahydroindolizin-7-yl)-4-(pyridin-4-yl)pyrazole.

7. The compound according to claim 1, or a pharmacologically acceptable salt thereof, wherein the compound is 5-(4-fluorophenyl)-3-(2-methyl-1,2,3,5,6,8a-hexahydroindolizin-7-yl)-4-(pyridin-4-yl)pyrazole.

8. The compound according to claim 1, or a pharmacologically acceptable salt thereof, wherein the compound is 5-(4-fluorophenyl)-3-(2-phenyl-1,2,3,5,6,8a-hexahydroindolizin-7-yl)-4-(pyridin-4-yl)pyrazole.

9. The compound according to claim 1, or a pharmacologically acceptable salt thereof, wherein the compound is 5-(4-fluorophenyl)-3-(2-methoxy-1,2,3,5,6,8a-hexahydroindolizin-7-yl)-4-(pyridin-4-yl)pyrazole.

10. The compound according to claim 1, or a pharmacologically acceptable salt thereof, wherein the compound is 5-(3-chlorophenyl)-3-(1,2,3,5,6,8a-hexahydroindolizin-7-yl)-4-(pyridin-4-yl)pyrazole.

11. The compound according to claim 1, or a pharmacologically acceptable salt thereof, wherein the compound is 5-(3,4-difluorophenyl)-3-(1,2,3,5,6,8a-hexahydroindolizin-7-yl)-4-(pyridin-4-yl)pyrazole.

12. The compound according to claim 1, or a pharmacologically acceptable salt thereof, wherein the compound is 3-(2-ethyl-1,2,3,5,6,8a-hexahydroindolizin-7-yl)-5-(4-fluorophenyl)-4-(pyridin-4-yl)pyrazole.

13. The compound according to claim 1, or a pharmacologically acceptable salt thereof, wherein the compound is 5-(4-fluorophenyl)-3-(2-propyl-1,2,3,5,6,8a-hexahydroindolizin-7-yl)-4-(pyridin-4-yl)pyrazole.

14. The compound according to claim 1, or a pharmacologically acceptable salt thereof, selected from the group consisting of:
  5-(4-fluorophenyl)-3-(2-hydroxy-1,2,3,5,6,8a-hexahydroindolizin-7-yl)-4-(pyridin-4-yl)pyrazole,
  3-(2-fluoro-1,2,3,5,6,8a-hexahydroindolizin-7-yl)-5-(4-fluorophenyl)-4-(pyridin-4-yl)pyrazole,
  3-(2,2-difluoro-1,2,3,5,6,8a-hexahydroindolizin-7-yl)-5-(4-fluorophenyl)-4-(pyridin-4-yl)pyrazole,
  5-(4-fluorophenyl)-3-(8-methyl-1,2,3,5,6,8a-hexahydroindolizin-7-yl)-4-(pyridin-4-yl)pyrazole,
  3-(1,2,3,5,6,8a-hexahydroindolizin-7-yl)-4-(pyridin-4-yl)-5-(3-trifluoromethylphenyl)pyrazole,
  5-(4-fluorophenyl)-3-(1,2,3,5,6,8a-hexahydroindolizin-7-yl)-1-methyl-4-(pyridin-4-yl)pyrazole,
  3-(4-fluorophenyl)-5-(1,2,3,5,6,8a-hexahydroindolizin-7-yl)-1-methyl-4-(pyridin-4-yl)pyrazole,
  3-(4-fluorophenyl)-1-methyl-5-(2-methyl-1,2,3,5,6,8a-hexahydroindolizin-7-yl)-4-(pyridin-4-yl)pyrazole,
  3-(4-fluorophenyl)-1-methyl-5-(2-phenyl-1,2,3,5,6,8a-hexahydroindolizin-7-yl)-4-(pyridin-4-yl)pyrazole,
  3-(4-fluorophenyl)-5-(2-hydroxy-1,2,3,5,6,8a-hexahydroindolizin-7-yl)-1-methyl-4-(pyridin-4-yl)pyrazole,
  3-(4-fluorophenyl)-5-(2-methoxy-1,2,3,5,6,8a-hexahydroindolizin-7-yl)-1-methyl-4-(pyridin-4-yl)pyrazole,
  5-(2-fluoro-1,2,3,5,6,8a-hexahydroindolizin-7-yl)-3-(4-fluorophenyl)-1-methyl-4-(pyridin-4-yl)pyrazole,
  5-(2,2-difluoro-1,2,3,5,6,8a-hexahydroindolizin-7-yl)-3-(4-fluorophenyl)-1-methyl-4-(pyridin-4-yl)pyrazole,
  3-(4-fluorophenyl)-1-methyl-5-(8-methyl-1,2,3,5,6,8a-hexahydroindolizin-7-yl)-4-(pyridin-4-yl)pyrazole,
  5-(4-fluorophenyl)-4-(pyridin-4-yl)-3-(3,5,6,8a-tetrahydroindolizin-7-yl)pyrazole,
  5-(4-fluorophenyl)-3-(1,2,3,5,8,8a-hexahydroindolizin-7-yl)-4-(pyridin-4-yl)pyrazole,
  5-(4-fluorophenyl)-3-(7-hydroxy-1,2,3,5,6,7,8,8a-octahydroindolizin-7-yl)-4-(pyridin-4-yl)pyrazole,
  5-(4-fluorophenyl)-3-(1,2,3,5,6,7,8,8a-octahydroindolizin-7-yl)-4-(pyridin-4-yl)pyrazole,
  5-(4-chlorophenyl)-3-(1,2,3,5,6,8a-hexahydroindolizin-7-yl)-4-(pyridin-4-yl)pyrazole,
  5-(4-fluorophenyl)-3-(2-methyliden-1,2,3,5,6,8a-hexahydroindolizin-7-yl)-4-(pyridin-4-yl)pyrazole,
  3-(2-ethyliden-1,2,3,5,6,8a-hexahydroindolizin-7-yl)-5-(4-fluorophenyl)-4-(pyridin-4-yl)pyrazole,
  5-(4-fluorophenyl)-3-(2-propyliden-1,2,3,5,6,8a-hexahydroindolizin-7-yl)-4-(pyridin-4-yl)pyrazole,
  5-(4-fluorophenyl)-1-methyl-3-(2-methyl-1,2,3,5,6,8a-hexahydroindolizin-7-yl)-4-(pyridin-4-yl)pyrazole,
  5-(4-fluorophenyl)-1-methyl-3-(2-phenyl-1,2,3,5,6,8a-hexahydroindolizin-7-yl)-4-(pyridin-4-yl)pyrazole,
  5-(4-fluorophenyl)-3-(2-hydroxy-1,2,3,5,6,8a-hexahydroindolizin-7-yl)-1-methyl-4-(pyridin-4-yl)pyrazole,
  5-(4-fluorophenyl)-3-(2-methoxy-1,2,3,5,6,8a-hexahydroindolizin-7-yl)-1-methyl-4-(pyridin-4-yl)pyrazole,
  3-(2-fluoro-1,2,3,5,6,8a-hexahydroindolizin-7-yl)-5-(4-fluorophenyl)-1-methyl-4-(pyridin-4-yl)pyrazole,
  5-(4-fluorophenyl)-1-methyl-3-(8-methyl-1,2,3,5,6,8a-hexahydroindolizin-7-yl)-4-(pyridin-4-yl)pyrazole,
  5-(4-fluorophenyl)-3-(2-methyl-3,5,6,8a-tetrahydroindolizin-7-yl)-4-(pyridin-4-yl)pyrazole,
  3-(2-ethyl-3,5,6,8a-tetrahydroindolizin-7-yl)-5-(4-fluorophenyl)-4-(pyridin-4-yl)pyrazole,
  5-(4-fluorophenyl)-3-(2-propyl-3,5,6,8a-tetrahydroindolizin-7-yl)-4-(pyridin-4-yl)pyrazole, and
  5-(4-fluorophenyl)-3-(2-phenyl-3,5,6,8a-tetrahydroindolizin-7-yl)-4-(pyridin-4-yl)pyrazole.

15. A compound of the formula (I) below, or a pharmacologically acceptable salt thereof:

wherein:
  A represents a pyrazole ring having one substituent $R^4$;
  $R^1$ represents a phenyl group, a 4-fluorophenyl group, a 3-fluorophenyl group, a 3-chlorophenyl group, a 3,4-difluorophenyl group, a 3,4,5-trifluorophenyl group, a 3-chloro-4-fluorophenyl group, a 3-difluoromethoxyphenyl group or a 3-trifluoromethoxyphenyl group;
  $R^2$ represents an unsubstituted 4-pyridyl group; an unsubstituted 4-pyrimidinyl group; a 4-pyridyl group which is substituted at the 2-position thereof with one substituent selected from the group consisting of methoxy, amino, methylamino, benzylamino and a-methylbenzylamino; or a 4-pyrimidinyl group which is substituted at the 2-position thereof with one substituent selected from the group consisting of methoxy, amino, methylamino, benzylamino and α-methylbenzylamino; and
  $R^3$ represents a group of formula (IIa), (IIb) or (IIc) shown below:

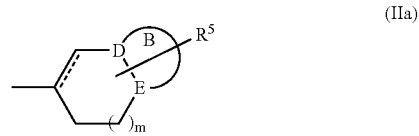

-continued

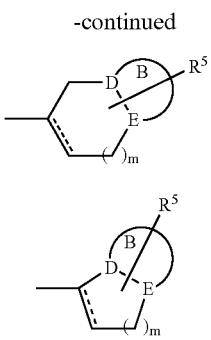

(IIb)

(IIc)

wherein
a bond including a dotted line represents a single bond or a double bond,
m represents 1 or 2,
$R^5$ represents one substituent which is independently selected from the group consisting of a hydrogen atom, a methoxy group, a methyl group, an ethyl group, a propyl group and a phenyl group,
one of D and E represents a nitrogen atom and the other represents a group of a formula $>C(R^6)$—, wherein $R^6$ is a substituent selected from the group consisting of a hydrogen atom, a Substituent group α and a Substituent group β, and
B represents a pyrrolidine ring or a pyrroline ring, and
$R^4$ represents a hydrogen atom; a lower alkyl group, a halogeno lower alkyl group, or a phenyl group substituted with one or more substituents selected from the group consisting of Substituent group α, Substituent group β and Substituent group γ,
PROVIDED THAT said substituents $R^1$ and $R^3$ are bonded to the two atoms of said cyclic group A which are adjacent to the atom of the cyclic group A to which said substituent $R^2$ is bonded;

Substituent group α is selected from the group consisting of hydroxyl groups, nitro groups, cyano groups, halogen atoms, lower alkoxy groups, halogeno lower alkoxy groups, lower alkylthio groups, halogeno lower alkylthio groups and groups of formula $-NR^aR^b$, wherein $R^a$ and $R^b$ are the same or different from each other and each represents a hydrogen atom, a lower alkyl group, a lower alkenyl group, a lower alkynyl group, an aralkyl group or a lower alkylsulfonyl group, or $R^a$ and $R^b$, taken together with the nitrogen atom to which they are attached, form a heterocyclyl group;

Substituent group β is selected from the group consisting of unsubstituted lower alkyl groups, unsubstituted lower alkenyl groups, unsubstituted lower alkynyl groups, aralkyl groups, cycloalkyl groups, lower alkyl groups which are substituted with groups from Substituent group α, lower alkenyl groups which are substituted with one or more groups from Substituent group α, and lower alkynyl which are substituted with one or more substituents which are substituted with groups from Substituent group α;

Substituents group γ is selected from the group consisting of oxo groups; hydroxyimino groups; lower alkoxyimino groups; lower alkylene groups; lower alkylenedioxy groups; lower alkylsulfinyl groups; lower alkylsulfonyl groups; unsubstituted aryl groups; and aryl groups which are substituted with groups selected from the group consisting of Substituent group α and Substituent group β.

16. A pharmaceutical composition comprising a pharmaceutically effective amount of the compound according to any one of claims 1, 2, 3, or 4 to 14, or a pharmacologically acceptable salt thereof, in combination with a pharmaceutically acceptable carrier.

17. The compound of claim 1, or a pharmaceutically acceptable salt thereof, wherein $R^3$ is a group of formula (IIb).

18. The compound of claim 1, or a pharmaceutically acceptable salt thereof, wherein $R^3$ is a group of the formula (IIc).

* * * * *

UNITED STATES PATENT AND TRADEMARK OFFICE
CERTIFICATE OF CORRECTION

| | |
|---|---|
| PATENT NO. | : 7,091,352 B2 |
| APPLICATION NO. | : 10/625024 |
| DATED | : August 15, 2006 |
| INVENTOR(S) | : Kimura et al. |

It is certified that error appears in the above-identified patent and that said Letters Patent is hereby corrected as shown below:

Column 21, line 25: delete "7" and insert -- $\gamma$ --.

Signed and Sealed this

First Day of July, 2008

JON W. DUDAS
*Director of the United States Patent and Trademark Office*